US009127274B2

(12) United States Patent
Akinc et al.

(10) Patent No.: US 9,127,274 B2
(45) Date of Patent: Sep. 8, 2015

(54) SERPINC1 IRNA COMPOSITIONS AND METHODS OF USE THEREOF

(71) Applicant: Alnylam Pharmaceuticals, Cambridge, MA (US)

(72) Inventors: Akin Akinc, Cambridge, MA (US); Alfica Sehgal, Cambridge, MA (US); Ivanka Toudjarska, Cambridge, MA (US); Donald Foster, Cambridge, MA (US); Stuart Milstein, Cambridge, MA (US); Brian Bettencourt, Cambridge, MA (US); Martin A. Maier, Cambridge, MA (US); Klaus Charisse, Cambridge, MA (US); Satyanarayana Kuchimanchi, Cambridge, MA (US); Kallanthottathil G. Rajeev, Cambridge, MA (US); Muthiah Monaharan, Cambridge, MA (US)

(73) Assignee: Alnylam Pharmaceuticals, Inc., Cambridge, MA (US)

(*) Notice: Subject to any disclaimer, the term of this patent is extended or adjusted under 35 U.S.C. 154(b) by 7 days.

(21) Appl. No.: 13/837,129

(22) Filed: Mar. 15, 2013

(65) Prior Publication Data

US 2013/0317081 A1 Nov. 28, 2013

Related U.S. Application Data

(60) Provisional application No. 61/638,952, filed on Apr. 26, 2012, provisional application No. 61/669,249, filed on Jul. 9, 2012, provisional application No. 61/734,573, filed on Dec. 7, 2012.

(51) Int. Cl.
*C12N 15/113* (2010.01)

(52) U.S. Cl.
CPC .......... *C12N 15/113* (2013.01); *C12N 2310/14* (2013.01); *C12N 2310/315* (2013.01); *C12N 2310/321* (2013.01); *C12N 2310/322* (2013.01); *C12N 2310/335* (2013.01); *C12N 2310/3515* (2013.01)

(58) Field of Classification Search
CPC ................. C12N 2310/321; C12N 2310/3521; C12N 2310/3533; C12N 15/133; C12N 2310/14; C12N 2310/315; C12N 2310/3515
See application file for complete search history.

(56) References Cited

U.S. PATENT DOCUMENTS

| | | | | |
|---|---|---|---|---|
| 8,071,291 | B2 | 12/2011 | Bare et al. | |
| 8,106,022 | B2 | 1/2012 | Manoharan et al. | |
| 2007/0031844 | A1* | 2/2007 | Khvorova et al. | 435/6 |
| 2008/0152661 | A1 | 6/2008 | Rozema et al. | |
| 2009/0239814 | A1* | 9/2009 | Manoharan et al. | 514/26 |
| 2011/0269823 | A1 | 11/2011 | Nakayama et al. | |

FOREIGN PATENT DOCUMENTS

WO 2010081878 A1 7/2010

OTHER PUBLICATIONS

International Search Report & Written Opinion issued in PCT/US13/38218, date of mailing Dec. 2, 2013.
Invitation to Pay Additional Fees, issued in PCT/US13/38218, date of mailing Sep. 5, 2013.

* cited by examiner

*Primary Examiner* — Jennifer McDonald
(74) *Attorney, Agent, or Firm* — McCarter & English, LLP; Maria Laccotripe Zacharakis; Deborah L. Nagle

(57) ABSTRACT

The invention relates to iRNA, e.g., double-stranded ribonucleic acid (dsRNA), compositions targeting the Serpinc1 gene, and methods of using such iRNA, e.g., dsRNA, compositions to inhibit expression of Serpinc1 and methods of treating subjects having a bleeding disorder, such as a hemophilia.

62 Claims, 47 Drawing Sheets

SEQ ID NO:1
>gi|254588059|ref|NM_000488.3| Homo sapiens serpin peptidase inhibitor, clade C
(antithrombin), member 1 (SERPINC1), mRNA
TCTGCCCCACCCTGTCCTCTGGAACCTCTGCGAGATTTAGAGGAAAGAACCAGTTTTCAGGCGGATTGCC
TCAGATCACACTATCTCCACTTGCCCAGCCCTGTGGAAGATTAGCGGCCATGTATTCCAATGTGATAGGA
ACTGTAACCTCTGGAAAAAGGAAGGTTTATCTTTTGTCCTTGCTGCTCATTGGCTTCTGGGACTGCGTGA
CCTGTCACGGGAGCCCTGTGGACATCTGCACAGCCAAGCCGCGGGACATTCCCATGAATCCCATGTGCAT
TTACCGCTCCCCGGAGAAGAAGGCAACTGAGGATGAGGGCTCAGAACAGAAGATCCCGGAGGCCACCAAC
CGGCGTGTCTGGGAACTGTCCAAGGCCAATTCCCGCTTTGCTACCACTTTCTATCAGCACCTGGCAGATT
CCAAGAATGACAATGATAACATTTTCCTGTCACCCCTGAGTATCTCCACGGCTTTTGCTATGACCAAGCT
GGGTGCCTGTAATGACACCCTCCAGCAACTGATGGAGGTATTTAAGTTTGACACCATATCTGAGAAAACA
TCTGATCAGATCCACTTCTTCTTTGCCAAACTGAACTGCCGACTCTATCGAAAAGCCAACAAATCCTCCA
AGTTAGTATCAGCCAATCGCCTTTTTGGAGACAAATCCCTTACCTTCAATGAGACCTACCAGGACATCAG
TGAGTTGGTATATGGAGCCAAGCTCCAGCCCCTGGACTTCAAGGAAAATGCAGAGCAATCCAGAGCGGCC
ATCAACAAATGGGTGTCCAATAAGACCGAAGGCCGAATCACCGATGTCATTCCCTCGGAAGCCATCAATG
AGCTCACTGTTCTGGTGCTGGTTAACACCATTTACTTCAAGGGCCTGTGGAAGTCAAAGTTCAGCCCTGA
GAACACAAGGAAGGAACTGTTCTACAAGGCTGATGGAGAGTCGTGTTCAGCATCTATGATGTACCAGGAA
GGCAAGTTCCGTTATCGGCGCGTGGCTGAAGGCACCCAGGTGCTTGAGTTGCCCTTCAAAGGTGATGACA
TCACCATGGTCCTCATCTTGCCCAAGCCTGAGAAGAGCCTGGCCAAGGTAGAGAAGGAACTCACCCCAGA
GGTGCTGCAAGAGTGGCTGGATGAATTGGAGGAGATGATGCTGGTGGTCCACATGCCCCGCTTCCGCATT
GAGGACGGCTTCAGTTTGAAGGAGCAGCTGCAAGACATGGGCCTTGTCGATCTGTTCAGCCCTGAAAAGT
CCAAACTCCCAGGTATTGTTGCAGAAGGCCGAGATGACCTCTATGTCTCAGATGCATTCCATAAGGCATT
TCTTGAGGTAAATGAAGAAGGCAGTGAAGCAGCTGCAAGTACCGCTGTTGTGATTGCTGGCCGTTCGCTA
AACCCCAACAGGGTGACTTTCAAGGCCAACAGGCCTTTCCTGGTTTTTATAAGAGAAGTTCCTCTGAACA
CTATTATCTTCATGGGCAGAGTAGCCAACCCTTGTGTTAAGTAAAATGTTCTTATTCTTTGCACCTCTTC
CTATTTTTGGTTTGTGAACAGAAGTAAAAATAAATACAAACTACTTCCATCTCACATTA

Figure 30A

SEQ ID NO:2
>gi|157167169|ref|NM_001104583.1| Macaca mulatta serpin peptidase inhibitor, clade C (antithrombin), member 1 (SERPINC1), mRNA
GGCACGAGGACCATCTCCACTTGCCCAGCCCTGTGGAAGATTAGCGACCATGTATTCCAATGTGATAGGA
ACCGTAGCCTCTGGAAAAAGGAAGGTTTATCTTCTGTCCTTGCTGCTCATTGGCCTCTGGGACTGTATGA
CCTGTCACGGGAGCCCTGTGGACATCTGCACAGCCAAGCCGCGGGACATTCCCATGAATCCCATGTGCAT
TTACCGCTCCCCGGAGAAGAAGGCAACTGAGGATGAGGGCTCAGAACAGAAGATCCCCGAGGCCACCAAC
CGGCGCGTCTGGGAACTGTCCAAGGCCAATTCCCGCTTTGCTACCACTTTCTATCAGCACCTGGCAGATT
CCAAGAACGACAAGGATAACATTTTCCTGTCACCCCTGAGTGTCTCCACGGCTTTTGCTATGACCAAGCT
GGGTGCCTGTAATGACACCCTCAAGCAACTGATGGAGGTATTTAAGTTTGACACCATATCTGAGAAAACA
TCTGATCAGATCCACTTCTTCTTTGCCAAACTGAACTGCCGACTCTATCGAAAAGCCAACAAATCCTCCA
AGTTAGTATCAGCCAATCGCCTTTTTGGAGACAAATCCCTTACCTTCAATGAGACCTACCAGGACATCAG
TGAGTTGGTATACGGAGCCAAGCTCCAGCCCCTGGACTTCAAGGAAAATGCAGAGCAATCCAGAGCGGCC
ATCAACAAATGGGTGTCCAATAAGACCGAAGGCCGAATCACCGATGTCATTCCCCCGGAAGCCATCAACG
AGCTCACTGTTCTGGTGCTGGTTAACACCATTTACTTCAAGGGCCTGTGGAAGTCAAAGTTTAGCCCTGA
GAACACAAGGATGGAACCGTTCTACAAGGCTGATGGAGAGTCGTGTTCAGCGTCTATGATGTACCAGGAA
GGCAAGTTCTGTTATCGGCGCGTGGCTGAAGGCACCCAGGTGCTTGAGTTGCCCTTCAAGGGTGATGACA
TCACCATGGTGCTCATCCTGCCCAAGCCTGAGAAGAGCCTGACCAAGGTGGAGCAGGAACTCACCCCAGA
GGTGCTGCAGGAGTGGCTGGATGAGTTGGAGGAGATGATGCTGGTGGTTCACATGCCCCGCTTCCGCATT
GAGGACGGCTTCAGTTTGAAGGAGCAGCTGCAAGACATGGGCCTTGTCGATCTGTTCAGCCCTGAAAAGT
CCAAACTCCCAGGTATTGTTGCAGAAGGCCGGGATGACCTCTATGTCTCCGATGCATTCCATAAGGCATT
TCTTGAGGTAAATGAAGAAGGCAGTGAAGCAGCTGCAAGTACCGCCATTGGGATTGCTGGCCGTTCGCTA
AACCCCAACAGGGTGACCTTCAAGGCCAACAGGCCTTTCCTGGTTTTTATAAGAGAAGTTCCTCTGAACA
CTATTATCTTCATGGGCAGAGTAGCCAACCCTTGTGTGAGCTAAACTGTTCTTATTCTTTGTACCTCTTC
CTATTTTGGTTTGTGAATAGAAGTAAAAATAAATACAACTACTCCCATCTTACATTAAAAAAAAAAAAAA
AAAAA

Figure 30B

SEQ ID NO:3
>gi|237874216|ref|NM_080844.4| Mus musculus serine (or cysteine) peptidase inhibitor, clade C (antithrombin), member 1 (Serpinc1), mRNA
ATAGGTAATTTTAGAAATAGATCTGATTTGTATCTGAGACATTTTAGTGAAGTGGTGAGATATAAGACAT
AATCAGAAGACATATCTACCTGAAGACTTTAAGGGGAGAGCTCCCTCCCCCACCTGGCCTCTGGACCTCT
CAGATTTAGGGGAAAGAACCAGTTTTCGGAGTGATCGTCTCAGTCAGCACCATCTCTGTAGGAGCATCGG
CCATGTATTCCCCTGGGGCAGGAAGTGGGGCTGCTGGTGAGAGGAAGCTTTGTCTCCTCTCTCTGCTCCT
CATCGGTGCCTTGGGCTGTGCTATCTGTCACGGAAACCCTGTGGACGACATCTGCATAGCGAAGCCCCGA
GACATCCCCGTGAATCCCTTGTGCATTTACCGCTCCCCTGGGAAGAAGGCCACCGAGGAGGATGGCTCAG
AGCAGAAGGTTCCAGAAGCCACCAACCGGCGGGTCTGGGAACTGTCCAAGGCCAATTCGCGATTTGCCAC
TAACTTCTACCAGCACCTGGCAGACTCCAAGAATGACAACGACAACATTTTCCTGTCACCCTTGAGCATC
TCCACTGCTTTTGCTATGACCAAGCTGGGTGCCTGTAACGACACTCTCAAGCAGCTGATGGAGGTTTTTA
AATTTGATACCATCTCCGAGAAGACATCCGACCAGATCCACTTCTTCTTTGCCAAACTGAACTGCCGACT
CTATCGAAAAGCCAACAAGTCCTCTGACTTGGTATCAGCCAACCGCCTTTTTGGAGACAAATCCCTCACC
TTCAACGAGAGCTATCAAGATGTTAGTGAGGTTGTCTATGGAGCCAAGCTCCAGCCCCTGGACTTCAAGG
AGAATCCGGAGCAATCCAGAGTGACCATCAACAACTGGGTAGCTAATAAGACTGAAGGCCGCATCAAAGA
TGTCATCCCACAGGGCGCCATTAACGAGCTCACTGCCCTGGTTCTGGTTAACACCATTTACTTCAAGGGC
CTGTGGAAGTCAAAGTTCAGCCCTGAGAACACAAGGAAGGAACCGTTCTATAAGGTCGATGGGCAGTCAT
GCCCAGTGCCTATGATGTACCAGGAAGGCAAATTCAAATACCGGCGCGTGGCAGAGGGCACCCAGGTGCT
AGAGCTGCCCTTCAAGGGGGATGACATCACCATGGTGCTCATCCTGCCCAAGCCTGAGAAGAGCCTGGCC
AAGGTGGAGCAGGAGCTCACCCCAGAGCTGCTGCAGGAGTGGCTGGATGAGCTGTCAGAGACTATGCTTG
TGGTCCACATGCCCCGCTTCCGCACCGAGGATGGCTTCAGTCTGAAGGAGCAGCTGCAAGACATGGGCCT
CATTGATCTCTTCAGCCCTGAAAAGTCCCAACTCCCAGGGATCGTTGCTGGAGGCAGGGACGACCTCTAT
GTCTCCGACGCATTCCACAAAGCATTTCTTGAGGTAAATGAGGAAGGCAGTGAAGCAGCAGCGAGTACTT
CTGTCGTGATTACTGGCCGGTCACTGAACCCCAATAGGGTGACCTTCAAGGCCAACAGGCCCTTCCTGGT
TCTTATAAGGGAAGTTGCACTGAACACTATTATATTCATGGGGAGAGTGGCTAATCCTTGTGTGAACTAA
AATATTCTTAATCTTTGCACCTTTTCCTACTTTGGTGTTTGTGAATAGAAGTAAAAATAAATACGACTGC
CACCTCACGAGAATGGACTTTTCCACTTGAAGACGAGAGACTGGAGTACAGATGCTACACCACTTTTGGG
CAAGTGAAGGGGGAGCAGCCAGCCACGGTGGCACAAACCTATATCCTGGTGCTTTTGAAGGTAGAAGCAG
GGCGGTCAGGAGTTAAGGCCAGTTGAGGCTGGGCTGCAGAGTGAAAGACCATGTCTCAAGATGGTCTTTC
TCCTCCCCAAAGTAGAAAAGAAAACCATAAAAACAAGAGGTAAATATATTACTATTTCATCTTAGAGGAT
AGCAGGCATCTTGAAAGGGTAGAGGGACCTTAAATTCTCATTATTGCCCCCATACTACAAACTAAAAAAC
AAACCCGAATCAATCTCCCATAAAGACAGAGATTCAAATAAGAGTATTAAACGTTTTATTTCTCAAACCA
CTCACATGCATAATGTTCTTATACACAGTGTCAAAATAAAGAGAAATGCATTTTTATACAAAAAAAAAAA
A

Figure 30C

SEQ ID NO:4
>gi|58865629|ref|NM_001012027.1| Rattus norvegicus serpin peptidase inhibitor, clade C (antithrombin), member 1 (Serpinc1), mRNA
CGGAGGGATTGCTCAGCACTGTCTCCACGGCTTCTCTGCAGAAGCGTCCACCATGTATTCCCCGGGAATA
GGAAGTGCGGTTGCTGGAGAGAGGAAGCTTTGTCTCCTCTCTCTGCTACTCATTGGTGCCTTGGGCTGTG
CTGTCTGTCATGGAAACCCTGTGGACGACATCTGCATAGCGAAGCCCCGAGACATCCCCGTGAACCCCAT
GTGCATTTACCGCTCCCCTGCGAAGAAGGCCACGGAGGAGGATGTCCTAGAGCAGAAGGTTCCGGAAGCC
ACCAACCGGCGGGTCTGGGAACTGTCCAAGGCCAATTCTCGATTTGCCACTAACTTCTATCAGCACCTGG
CAGACTCCAAGAACGACAACGACAACATTTTCCTGTCACCCTTGAGCATCTCCACGGCGTTTGCTATGAC
CAAGCTGGGTGCTTGTAATAACACCCTCAAGCAGCTGATGGAGGTTTTTAAATTTGATACCATCTCCGAG
AAGACATCCGACCAGATCCACTTCTTCTTTGCCAAACTGAACTGCCGACTCTATCGAAAAGCCAACAAGT
CCTCTAACTTGGTGTCAGCCAACCGCCTTTTTGGAGACAAATCCCTTACCTTCAATGAGAGCTATCAAGA
CGTTAGTGAGATTGTCTATGGAGCCAAGCTTCAGCCCCTGGACTTCAAGGAGAATCCGGAGCAATCCAGA
GTGACCATCAACAACTGGGTAGCTAATAAGACTGAAGGCCGCATCAAAGACGTCATCCCCCAAGGAGCCA
TTGATGAGCTCACTGCCCTGGTGCTGGTTAACACCATTTACTTCAAGGGCCTGTGGAAGTCAAAGTTCAG
CCCTGAGAACACAAGGAAGGAACCATTCCACAAAGTTGATGGGCAGTCATGCCTGGTGCCCATGATGTAC
CAGGAAGGCAAATTCAAATACAGGCGTGTGGGAGAGGGTACCCAGGTGCTAGAGATGCCCTTCAAGGGGG
ACGACATCACCATGGTGCTCATCCTGCCCAAGCCTGAGAAGAGCCTGGCTAAGGTGGAGCAGGAACTCAC
CCCGGAGCTGCTGCAGGAGTGGCTGGATGAGCTGTCGGAGGTCATGCTTGTGGTCCACGTGCCCCGCTTC
CGCATCGAGGACAGCTTCAGTCTGAAGGAGCAGCTGCAAGACATGGGCCTTGTTGATCTCTTCAGCCCTG
AGAAGTCCCAACTCCCAGGGATCATTGCTGAAGGCAGGGACGACCTCTTTGTCTCCGATGCATTCCACAA
AGCGTTTCTTGAGGTAAATGAGGAAGGCAGTGAAGCAGCAGCGAGTACTTCTGTCGTGATTACTGGCCGG
TCACTGAACCCCAGTAGGGTGACCTTCAAGGCCAACAGGCCCTTCCTGGTTCTTATAAGGGAAGTCGCAC
TGAACACTATTATATTCATGGGGAGAGTGTCTAATCCTTGTGTGAACTAAAATATTCTTAATCTTTGCAC
CTTTTCCTATCTCGGTGTTTGTTAATGGAAGTAAAAATAAATATGACTGCCACCTCAAAAAAAAAAAAAA
AAAAAAAAAAAAAAAAAAAA

Figure 30D

SEQ ID NO:5 Reverse Complement of SEQ ID NO:1
TAATGTGAGATGGAAGTAGTTTGTATTTATTTTTACTTCTGTTCACAAACCAAAAATAGGAAGAGGTGCAAAGAATAAGAACATTT
TACTTAACACAAGGGTTGGCTACTCTGCCCATGAAGATAATAGTGTTCAGAGGAACTTCTCTTATAAAAACCAGGAAAGGCCTGTT
GGCCTTGAAAGTCACCCTGTTGGGGTTTAGCGAACGGCCAGCAATCACAACAGCGGTACTTGCAGCTGCTTCACTGCCTTCTTCAT
TTACCTCAAGAAATGCCTTATGGAATGCATCTGAGACATAGAGGTCATCTCGGCCTTCTGCAACAATACCTGGGAGTTTGGACTTT
TCAGGGCTGAACAGATCGACAAGGCCCATGTCTTGCAGCTGCTCCTTCAAACTGAAGCCGTCCTCAATGCGGAAGCGGGGCATGTG
GACCACCAGCATCATCTCCTCCAATTCATCCAGCCACTCTTGCAGCACCTCTGGGGTGAGTTCCTTCTCTACCTTGGCCAGGCTCT
TCTCAGGCTTGGGCAAGATGAGGACCATGGTGATGTCATCACCTTTGAAGGGCAACTCAAGCACCTGGGTGCCTTCAGCCACGCGC
CGATAACGGAACTTGCCTTCCTGGTACATCATAGATGCTGAACACGACTCTCCATCAGCCTTGTAGAACAGTTCCTTCCTTGTGTT
CTCAGGGCTGAACTTTGACTTCCACAGGCCCTTGAAGTAAATGGTGTTAACCAGCACCAGAACAGTGAGCTCATTGATGGCTTCCG
AGGGAATGACATCGGTGATTCGGCCTTCGGTCTTATTGGACACCCATTTGTTGATGGCCGCTCTGGATTGCTCTGCATTTTCCTTG
AAGTCCAGGGGCTGGAGCTTGGCTCCATATACCAACTCACTGATGTCCTGGTAGGTCTCATTGAAGGTAAGGGATTTGTCTCCAAA
AAGGCGATTGGCTGATACTAACTTGGAGGATTTGTTGGCTTTTCGATAGAGTCGGCAGTTCAGTTTGGCAAAGAAGAAGTGGATCT
GATCAGATGTTTTCTCAGATATGGTGTCAAACTTAAATACCTCCATCAGTTGCTGGAGGGTGTCATTACAGGCACCCAGCTTGGTC
ATAGCAAAAGCCGTGGAGATACTCAGGGGTGACAGGAAAATGTTATCATTGTCATTCTTGGAATCTGCCAGGTGCTGATAGAAAGT
GGTAGCAAAGCGGGAATTGGCCTTGGACAGTTCCCAGACACGCCGGTTGGTGGCCTCCGGGATCTTCTGTTCTGAGCCCTCATCCT
CAGTTGCCTTCTTCTCCGGGGAGCGGTAAATGCACATGGGATTCATGGGAATGTCCCGCGGCTTGGCTGTGCAGATGTCCACAGGG
CTCCCGTGACAGGTCACGCAGTCCCAGAAGCCAATGAGCAGCAAGGACAAAAGATAAACCTTCCTTTTTCCAGAGGTTACAGTTCC
TATCACATTGGAATACATGGCCGCTAATCTTCCACAGGGCTGGGCAAGTGGAGATAGTGTGATCTGAGGCAATCCGCCTGAAAACT
GGTTCTTTCCTCTAAATCTCGCAGAGGTTCCAGAGGACAGGGTGGGGCAGA

Figure 30E

SEQ ID NO:6 Reverse Complement of SEQ ID NO:2

TTTTTTTTTTTTTTTTTTTTTAATGTAAGATGGGAGTAGTTGTATTTATTTTTACTTCTATTCACAAACCAAAATAGGAAGAGGTACA
AAGAATAAGAACAGTTTAGCTCACACAAGGGTTGGCTACTCTGCCCATGAAGATAATAGTGTTCAGAGGAACTTCTCTTATAAAAA
CCAGGAAAGGCCTGTTGGCCTTGAAGGTCACCCTGTTGGGGTTTAGCGAACGGCCAGCAATCCCAATGGCGGTACTTGCAGCTGCT
TCACTGCCTTCTTCATTTACCTCAAGAAATGCCTTATGGAATGCATCGGAGACATAGAGGTCATCCCGGCCTTCTGCAACAATACC
TGGGAGTTTGGACTTTTCAGGGCTGAACAGATCGACAAGGCCCATGTCTTGCAGCTGCTCCTTCAAACTGAAGCCGTCCTCAATGC
GGAAGCGGGGCATGTGAACCACCAGCATCATCTCCTCCAACTCATCCAGCCACTCCTGCAGCACCTCTGGGGTGAGTTCCTGCTCC
ACCTTGGTCAGGCTCTTCTCAGGCTTGGGCAGGATGAGCACCATGGTGATGTCATCACCCTTGAAGGGCAACTCAAGCACCTGGGT
GCCTTCAGCCACGCGCCGATAACAGAACTTGCCTTCCTGGTACATCATAGACGCTGAACACGACTCTCCATCAGCCTTGTAGAACG
GTTCCATCCTTGTGTTCTCAGGGCTAAACTTTGACTTCCACAGGCCCTTGAAGTAAATGGTGTTAACCAGCACCAGAACAGTGAGC
TCGTTGATGGCTTCCGGGGGAATGACATCGGTGATTCGGCCTTCGGTCTTATTGGACACCCATTTGTTGATGGCCGCTCTGGATTG
CTCTGCATTTTCCTTGAAGTCCAGGGGCTGGAGCTTGGCTCCGTATACCAACTCACTGATGTCCTGGTAGGTCTCATTGAAGGTAA
GGGATTTGTCTCCAAAAAGGCGATTGGCTGATACTAACTTGGAGGATTTGTTGGCTTTTCGATAGAGTCGGCAGTTCAGTTTGGCA
AAGAAGAAGTGGATCTGATCAGATGTTTTCTCAGATATGGTGTCAAACTTAAATACCTCCATCAGTTGCTTGAGGGTGTCATTACA
GGCACCCAGCTTGGTCATAGCAAAAGCCGTGGAGACACTCAGGGGTGACAGGAAAATGTTATCCTTGTCGTTCTTGGAATCTGCCA
GGTGCTGATAGAAAGTGGTAGCAAAGCGGGAATTGGCCTTGGACAGTTCCCAGACGCGCCGGTTGGTGGCCTCGGGGATCTTCTGT
TCTGAGCCCTCATCCTCAGTTGCCTTCTTCTCCGGGGAGCGGTAAATGCACATGGGATTCATGGGAATGTCCCGCGGCTTGGCTGT
GCAGATGTCCACAGGGCTCCCGTGACAGGTCATACAGTCCCAGAGGCCAATGAGCAGCAAGGACAGAAGATAAACCTTCCTTTTTC
CAGAGGCTACGGTTCCTATCACATTGGAATACATGGTCGCTAATCTTCCACAGGGCTGGGCAAGTGGAGATGGTCCTCGTGCC

Figure 30F

SEQ ID NO:7 Reverse Complement of SEQ ID NO:3
TTTTTTTTTTTTGTATAAAAATGCATTTCTCTTTATTTTGACACTGTGTATAAGAACATTATGCATGTGAGTGGTTTGAGAAATAA
AACGTTTAATACTCTTATTTGAATCTCTGTCTTTATGGGAGATTGATTCGGGTTTGTTTTTTAGTTTGTAGTATGGGGCAATAAT
GAGAATTTAAGGTCCCTCTACCCTTTCAAGATGCCTGCTATCCTCTAAGATGAAATAGTAATATATTTACCTCTTGTTTTTATGGT
TTTCTTTTCTACTTTGGGGAGGAGAAAGACCATCTTGAGACATGGTCTTTCACTCTGCAGCCCAGCCTCAACTGGCCTTAACTCCT
GACCGCCCTGCTTCTACCTTCAAAAGCACCAGGATATAGGTTTGTGCCACCGTGGCTGGCTGCTCCCCCTTCACTTGCCCAAAAGT
GGTGTAGCATCTGTACTCCAGTCTCTCGTCTTCAAGTGGAAAAGTCCATTCTCGTGAGGTGGCAGTCGTATTTATTTTTACTTCTA
TTCACAAACACCAAAGTAGGAAAAGGTGCAAAGATTAAGAATATTTTAGTTCACACAAGGATTAGCCACTCTCCCCATGAATATAA
TAGTGTTCAGTGCAACTTCCCTTATAAGAACCAGGAAGGGCCTGTTGGCCTTGAAGGTCACCCTATTGGGGTTCAGTGACCGGCCA
GTAATCACGACAGAAGTACTCGCTGCTGCTTCACTGCCTTCCTCATTTACCTCAAGAAATGCTTTGTGGAATGCGTCGGAGACATA
GAGGTCGTCCCTGCCTCCAGCAACGATCCCTGGGAGTTGGGACTTTTCAGGGCTGAAGAGATCAATGAGGCCCATGTCTTGCAGCT
GCTCCTTCAGACTGAAGCCATCCTCGGTGCGGAAGCGGGGCATGTGGACCACAAGCATAGTCTCTGACAGCTCATCCAGCCACTCC
TGCAGCAGCTCTGGGGTGAGCTCCTGCTCCACCTTGGCCAGGCTCTTCTCAGGCTTGGGCAGGATGAGCACCATGGTGATGTCATC
CCCCTTGAAGGGCAGCTCTAGCACCTGGGTGCCCTCTGCCACGCGCCGGTATTTGAATTTGCCTTCCTGGTACATCATAGGCACTG
GGCATGACTGCCCATCGACCTTATAGAACGGTTCCTTCCTTGTGTTCTCAGGGCTGAACTTTGACTTCCACAGGCCCTTGAAGTAA
ATGGTGTTAACCAGAACCAGGGCAGTGAGCTCGTTAATGGCGCCCTGTGGGATGACATCTTTGATGCGGCCTTCAGTCTTATTAGC
TACCCAGTTGTTGATGGTCACTCTGGATTGCTCCGGATTCTCCTTGAAGTCCAGGGGCTGGAGCTTGGCTCCATAGACAACCTCAC
TAACATCTTGATAGCTCTCGTTGAAGGTGAGGGATTTGTCTCCAAAAAGGCGGTTGGCTGATACCAAGTCAGAGGACTTGTTGGCT
TTTCGATAGAGTCGGCAGTTCAGTTTGGCAAAGAAGAAGTGGATCTGGTCGGATGTCTTCTCGGAGATGGTATCAAATTTAAAAAC
CTCCATCAGCTGCTTGAGAGTGTCGTTACAGGCACCCAGCTTGGTCATAGCAAAAGCAGTGGAGATGCTCAAGGGTGACAGGAAAA
TGTTGTCGTTGTCATTCTTGGAGTCTGCCAGGTGCTGGTAGAAGTTAGTGGCAAATCGCGAATTGGCCTTGGACAGTTCCCAGACC
CGCCGGTTGGTGGCTTCTGGAACCTTCTGCTCTGAGCCATCCTCCTCGGTGGCCTTCTTCCCAGGGGAGCGGTAAATGCACAAGGG
ATTCACGGGGATGTCTCGGGGCTTCGCTATGCAGATGTCGTCCACAGGGTTTCCGTGACAGATAGCACAGCCCAAGGCACCGATGA
GGAGCAGAGAGAGGAGACAAAGCTTCCTCTCACCAGCAGCCCCACTTCCTGCCCCAGGGGAATACATGGCCGATGCTCCTACAGAG
ATGGTGCTGACTGAGACGATCACTCCGAAAACTGGTTCTTTCCCCTAAATCTGAGAGGTCCAGAGGCCAGGTGGGGGAGGGAGCTC
TCCCCTTAAAGTCTTCAGGTAGATATGTCTTCTGATTATGTCTTATATCTCACCACTTCACTAAAATGTCTCAGATACAAATCAGA
TCTATTTCTAAAATTACCTAT

Figure 30G

SEQ ID NO:8 Reverse Complement of SEQ ID NO:4
TTTTTTTTTTTTTTTTTTTTTTTTTTTTTTTTTTTGAGGTGGCAGTCATATTTATTTTTACTTCCATTAACAAACACCGAGATAGG
AAAAGGTGCAAAGATTAAGAATATTTTAGTTCACACAAGGATTAGACACTCTCCCCATGAATATAATAGTGTTCAGTGCGACTTCC
CTTATAAGAACCAGGAAGGGCCTGTTGGCCTTGAAGGTCACCCTACTGGGGTTCAGTGACCGGCCAGTAATCACGACAGAAGTACT
CGCTGCTGCTTCACTGCCTTCCTCATTTACCTCAAGAAACGCTTTGTGGAATGCATCGGAGACAAAGAGGTCGTCCCTGCCTTCAG
CAATGATCCCTGGGAGTTGGGACTTCTCAGGGCTGAAGAGATCAACAAGGCCCATGTCTTGCAGCTGCTCCTTCAGACTGAAGCTG
TCCTCGATGCGGAAGCGGGGCACGTGGACCACAAGCATGACCTCCGACAGCTCATCCAGCCACTCCTGCAGCAGCTCCGGGGTGAG
TTCCTGCTCCACCTTAGCCAGGCTCTTCTCAGGCTTGGGCAGGATGAGCACCATGGTGATGTCGTCCCCCTTGAAGGGCATCTCTA
GCACCTGGGTACCCTCTCCCACACGCCTGTATTTGAATTTGCCTTCCTGGTACATCATGGGCACCAGGCATGACTGCCCATCAACT
TTGTGGAATGGTTCCTTCCTTGTGTTCTCAGGGCTGAACTTTGACTTCCACAGGCCCTTGAAGTAAATGGTGTTAACCAGCACCAG
GGCAGTGAGCTCATCAATGGCTCCTTGGGGGATGACGTCTTTGATGCGGCCTTCAGTCTTATTAGCTACCCAGTTGTTGATGGTCA
CTCTGGATTGCTCCGGATTCTCCTTGAAGTCCAGGGGCTGAAGCTTGGCTCCATAGACAATCTCACTAACGTCTTGATAGCTCTCA
TTGAAGGTAAGGGATTTGTCTCCAAAAAGGCGGTTGGCTGACACCAAGTTAGAGGACTTGTTGGCTTTTCGATAGAGTCGGCAGTT
CAGTTTGGCAAAGAAGAAGTGGATCTGGTCGGATGTCTTCTCGGAGATGGTATCAAATTTAAAAACCTCCATCAGCTGCTTGAGGG
TGTTATTACAAGCACCCAGCTTGGTCATAGCAAACGCCGTGGAGATGCTCAAGGGTGACAGGAAAATGTTGTCGTTGTCGTTCTTG
GAGTCTGCCAGGTGCTGATAGAAGTTAGTGGCAAATCGAGAATTGGCCTTGGACAGTTCCCAGACCCGCCGGTTGGTGGCTTCCGG
AACCTTCTGCTCTAGGACATCCTCCTCCGTGGCCTTCTTCGCAGGGGAGCGGTAAATGCACATGGGGTTCACGGGGATGTCTCGGG
GCTTCGCTATGCAGATGTCGTCCACAGGGTTTCCATGACAGACAGCACAGCCCAAGGCACCAATGAGTAGCAGAGAGAGGAGACAA
AGCTTCCTCTCTCCAGCAACCGCACTTCCTATTCCCGGGGAATACATGGTGGACGCTTCTGCAGAGAAGCCGTGGAGACAGTGCTG
AGCAATCCCTCCG

Figure 30H

SEQ ID NO: 9

AAVALLPAVLLALLAP

SEQ ID NO: 10

AALLPVLLAAP

SEQ ID NO: 11 HIV Tat peptide

GRKKRRQRRRPPQ

SEQ ID NO: 12 Drosophila Antennapedia peptide

RQIKIWFQNRRMKWKK

Peptide-based Cleavable Linking Group

NHCHRAC(O)NHCHRBC(O)-

Figure 30I

SERPINC1 IRNA COMPOSITIONS AND METHODS OF USE THEREOF

RELATED APPLICATIONS

This application claims priority to U.S. Provisional Application No. 61/638,952, filed on Apr. 26, 2012, to U.S. Provisional Application No. 61/669,249, filed on Jul. 9, 2012, and to U.S. Provisional Application No. 61/734,573, filed on Dec. 7, 2012. The entire contents of each of the foregoing applications are incorporated herein by reference.

SEQUENCE LISTING

The instant application contains a Sequence Listing which has been submitted in ASCII format via EFS-Web and is hereby incorporated by reference in its entirety. Said ASCII copy, created on Jul. 26, 2013, is named 12130100204SeqList.txt and is 458,189 bytes in size.

BACKGROUND OF THE INVENTION

Serpinc1 is a member of the serine proteinase inhibitor (serpin) superfamily. Serpinc1 is a plasma protease inhibitor that inhibits thrombin as well as other activated serine proteases of the coagulation system, such as factors X, IX, XI, XII and VII and, thus, regulates the blood coagulation cascade (see, e.g., FIG. 1). The anticoagulant activity of Serpinc1 is enhanced by the presence of heparin and other related glycosaminoglycans which catalyze the formation of a thrombin:antithrombin (TAT) complexes.

Bleeding disorders, either inherited or acquired, are conditions in which there is inadequate blood clotting. For example, hemophilia is a group of hereditary genetic bleeding disorders that impair the body's ability to control blood clotting or coagulation. Hemophilia A is a recessive X-linked genetic disorder involving a lack of functional clotting Factor VIII and represents 80% of hemophilia cases. Hemophilia B is a recessive X-linked genetic disorder involving a lack of functional clotting Factor IX. It comprises approximately 20% of haemophilia cases. Hemophilia C is an autosomal genetic disorder involving a lack of functional clotting Factor XI. Hemophilia C is not completely recessive, as heterozygous individuals also show increased bleeding.

Although, at present there is no cure for hemophilia, it can be controlled with regular infusions of the deficient clotting factor, e.g., factor VIII in hemophilia A. However, some hemophiliacs develop antibodies (inhibitors) against the replacement factors given to them and, thus, become refractory to replacement coagulation factor. Accordingly, bleeds in such subjects cannot be properly controlled.

The development of high-titer inhibitors to, for example, factor VIII and other coagulation factors, is the most serious complication of hemophilia therapy and makes treatment of bleeds very challenging. Currently, the only strategies to stop bleeds in such subjects are the use of "bypassing agents" such as factor eight inhibitor bypass activity (FEIBA) and activated recombinant factor VII (rFVIIa), plasmapheresis, continuous factor replacement, and immune tolerance therapy, none of which are completely effective. Accordingly, there is a need in the art for alternative treatments for subjects having a bleeding disorder, such as hemophilia.

SUMMARY OF THE INVENTION

The present invention provides iRNA compositions which effect the RNA-induced silencing complex (RISC)-mediated cleavage of RNA transcripts of a Serpinc1 gene. The Serpinc1 gene may be within a cell, e.g., a cell within a subject, such as a human. The present invention also provides methods of using and uses of the iRNA compositions of the invention for inhibiting the expression of a Serpinc1 gene and/or for treating a subject having a disorder that would benefit from inhibiting or reducing the expression of a Serpinc1 gene, e.g., a bleeding disorder, such as hemophilia.

Accordingly, in one aspect, the present invention provides double-stranded ribonucleic acids (dsRNAs) for inhibiting expression of Serpinc1. The dsRNAs comprise a sense strand and an antisense strand, wherein the sense strand comprises at least 15 contiguous nucleotides differing by no more than 3 nucleotides from the nucleotide sequence of SEQ ID NO:1 and the antisense strand comprises at least 15 contiguous nucleotides differing by no more than 3 nucleotides from the nucleotide sequence of SEQ ID NO:5.

In another aspect, the present invention provides double-stranded ribonucleic acids (dsRNAs) for inhibiting expression of Serpinc1. The dsRNAs comprise a sense strand and an antisense strand, the antisense strand comprising a region of complementarity which comprises at least 15 contiguous nucleotides differing by no more than 3 nucleotides from any one of the antisense sequences listed in any one of Tables 3, 4, 8, 11, 12, 14, 15, 20, and 21.

In one embodiment, the sense and antisense strands comprise sequences selected from the group consisting of AD-50487.1, AD-50477.1, AD-50483.1, AD-50475.1, AD-50495.1, AD-50476.1, AD-50499.1, AD-50478.1, AD-50489.1, AD-50501.1, AD-50507.1, AD-50484.1, AD-50515.1, AD-50540.1, AD-50528.1, AD-50549.1, AD-50539.1, AD-50534.1, AD-50527.1, AD-50514.1, AD-50509.1, AD-50529.1, AD-54944, AD-56813, AD-57205, AD-57214, and AD-57213 of any one of Tables 3, 4, 8, 11, 12, 14, 15, 20, and 21. In certain embodiments of the invention, the dsRNAs comprise at least one modified nucleotide. In one embodiment, at least one of the modified nucleotides is selected from the group consisting of a 2'-O-methyl modified nucleotide, a nucleotide comprising a 5'-phosphorothioate group, and a terminal nucleotide linked to a cholesteryl derivative or a dodecanoic acid bisdecylamide group. In another embodiment, the modified nucleotide is selected from the group consisting of a 2'-deoxy-2'-fluoro modified nucleotide, a 2'-deoxy-modified nucleotide, a locked nucleotide, an abasic nucleotide, a 2'-amino-modified nucleotide, a 2'-alkyl-modified nucleotide, a morpholino nucleotide, a phosphoramidate, and a non-natural base comprising nucleotide.

The region of complementarity of the dsRNAs may be at least 17 nucleotides in length, between 19 and 21 nucleotides in length, or 19 nucleotides in length.

In one embodiment, each strand of a dsRNA is no more than 30 nucleotides in length.

At least one strand of a dsRNA may comprise a 3' overhang of at least 1 nucleotide or at least 2 nucleotides.

In certain embodiments, a dsRNA further comprises a ligand. In one embodiment, the ligand is conjugated to the 3' end of the sense strand of the dsRNA.

In some embodiments, the ligand is one or more N-acetylgalactosamine (GalNAc) derivatives attached through a bivalent or trivalent branched linker. In particular embodiments, the ligand is

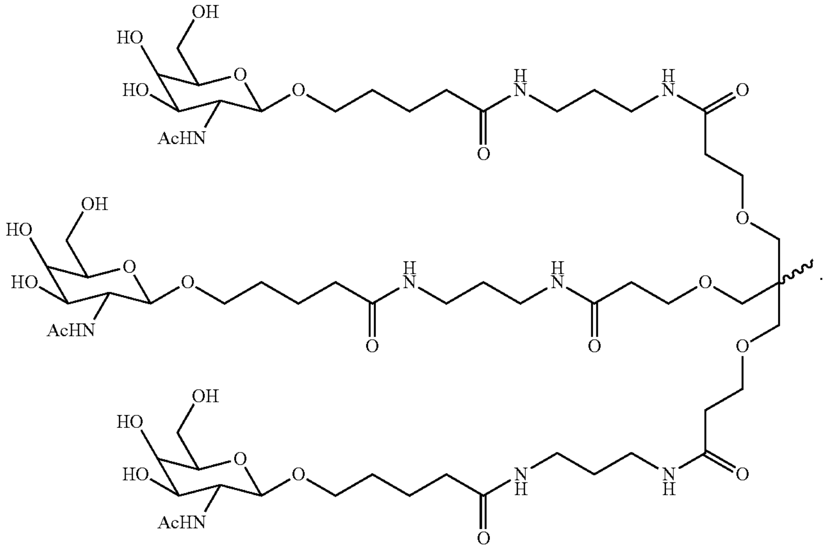 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]
In some embodiments, the RNAi agent is conjugated to the ligand as shown in the following schematic
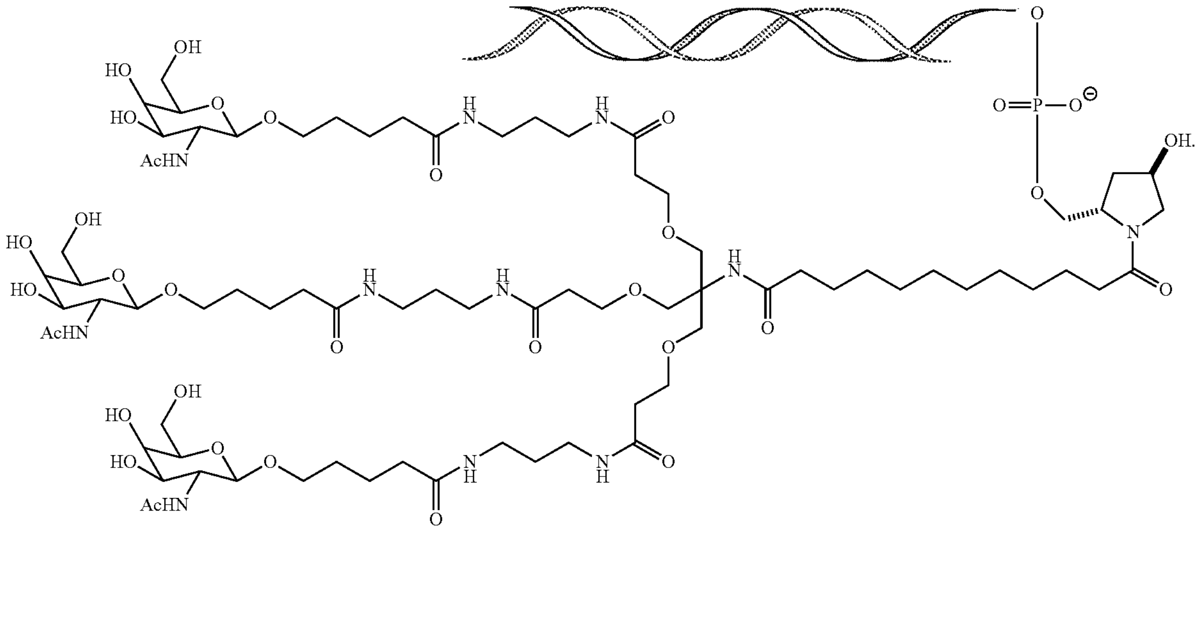 [SMILES: CC(=O)NC1C(OCCCCC(=O)NCCCNC(=O)CCOCC(COCCC(=O)NCCCNC(=O)CCCCOC2OC(CO)C(O)C(O)C2NC(C)=O)(COCCC(=O)NCCCNC(=O)CCCCOC2OC(CO)C(O)C(O)C2NC(C)=O)NC(=O)CCCCCCCCCCC(=O)N2C[C@H](O)C[C@H]2COP(=O)([O-])O)OC(CO)C(O)C1O]
In another embodiment, the RNAi agent is conjugated to the ligand as shown in the following schematic, wherein X is O or S.

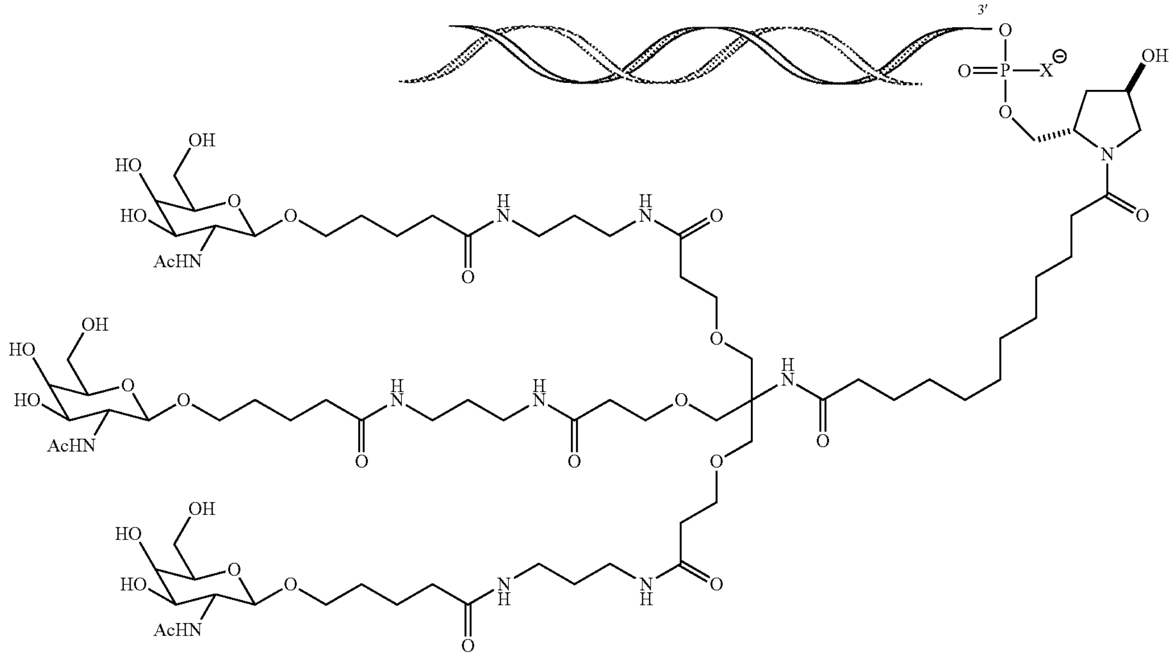

In one embodiment, the region of complementarity of a dsRNA consists of one of the antisense sequences of any one of Tables 3, 4, 8, 11, 12, 14, 15, 20, and 21.

In another embodiment, a dsRNA comprises a sense strand consisting of a sense strand sequence selected from the sequences of any one of Tables 3, 4, 8, 11, 12, 14, 15, 20, and 21, and an antisense strand consisting of an antisense sequence selected from the sequences of any one of Tables 3, 4, 8, 11, 12, 14, 15, 20, and 21.

In another aspect, the present invention provides a cell containing a dsRNA of the invention.

In yet another aspect, the present invention provides a vector encoding at least one strand of a dsRNA, wherein the dsRNA comprises a region of complementarity to at least a part of an mRNA encoding Serpinc1, wherein the dsRNA is 30 base pairs or less in length, and wherein the dsRNA targets the mRNA for cleavage.

The region of complementarity may be least 15 nucleotides in length or 19 to 21 nucleotides in length.

In a further aspect, the present invention provides a cell comprising a vector encoding at least one strand of a dsRNA, wherein the dsRNA comprises a region of complementarity to at least a part of an mRNA encoding Serpinc1, wherein the dsRNA is 30 base pairs or less in length, and wherein the dsRNA targets the mRNA for cleavage.

In one aspect, the present invention provides a pharmaceutical composition for inhibiting expression of a Serpinc1 gene comprising a dsRNA or vector of the invention.

In one embodiment, the pharmaceutical composition further comprises a lipid formulation, such as an MC3, SNALP, or XTC formulation.

In another aspect, the present invention provides methods of inhibiting Serpinc1 expression in a cell. The methods include contacting the cell with the dsRNA or a vector of the invention, and maintaining the cell produced for a time sufficient to obtain degradation of the mRNA transcript of a Serpinc1 gene, thereby inhibiting expression of the Serpinc1 gene in the cell.

The cell may be within a subject, such as a human subject, for example a human subject suffering from a bleeding disorder, e.g., a hemophilia.

In one embodiment of the methods of the invention, Serpinc1 expression is inhibited by at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%.

In another aspect, the present invention provides methods of treating a subject having a disorder that would benefit from reduction in Serpinc1 expression, e.g., a bleeding disorder, such as a hemophilia. The methods include administering to the subject a therapeutically effective amount of the dsRNA or vector of the invention, thereby treating the subject.

In one aspect, the invention provides methods of preventing at least one symptom, e.g., bleeding, in a subject having a disorder that would benefit from reduction in Serpinc1 expression, e.g., hemophilia. The methods include administering to the subject a therapeutically effective amount of the RNA, e.g., dsRNA, or vector of the invention, thereby preventing at least one symptom in the subject having a disorder that would benefit from reduction in Serpinc1 expression.

The disorder may be a bleeding disorder, such as a hemophilia.

In one embodiment, the administration of the dsRNA to the subject causes an increase in blood clotting and/or a decrease in Serpinc1 protein expression and/or accumulation.

In one embodiment, the dsRNA is conjugated to a ligand, e.g., at the 3'-end of the sense strand of the dsRNA. In one embodiment the ligand is an N-acetylgalactosamine (GalNAc) derivative.

In one embodiment, the dsRNA is administered at a dose of about 0.01 mg/kg to about 10 mg/kg, e.g., about 0.05 mg/kg to about 5 mg/kg, about 0.05 mg/kg to about 10 mg/kg, about 0.1 mg/kg to about 5 mg/kg, about 0.1 mg/kg to about 10 mg/kg, about 0.2 mg/kg to about 5 mg/kg, about 0.2 mg/kg to about 10 mg/kg, about 0.3 mg/kg to about 5 mg/kg, about 0.3 mg/kg to about 10 mg/kg, about 0.4 mg/kg to about 5 mg/kg, about 0.4 mg/kg to about 10 mg/kg, about 0.5 mg/kg to about 5 mg/kg, about 0.5 mg/kg to about 10 mg/kg, about 1 mg/kg to about 5 mg/kg, about 1 mg/kg to about 10 mg/kg, about 1.5 mg/kg to about 5 mg/kg, about 1.5 mg/kg to about 10 mg/kg, about 2 mg/kg to about 2.5 mg/kg, about 2 mg/kg to about 10 mg/kg, about 3 mg/kg to about 5 mg/kg, about 3 mg/kg to about 10 mg/kg, about 3.5 mg/kg to about 5 mg/kg, about 4 mg/kg to about 5 mg/kg, about 4.5 mg/kg to about 5 mg/kg, about 4 mg/kg to about 10 mg/kg, about 4.5 mg/kg to about 10 mg/kg, about 5 mg/kg to about 10 mg/kg, about 5.5 mg/kg to about 10 mg/kg, about 6 mg/kg to about 10 mg/kg, about 6.5 mg/kg to about 10 mg/kg, about 7 mg/kg to about 10 mg/kg, about 7.5 mg/kg to about 10 mg/kg, about 8 mg/kg to about 10 mg/kg, about 8.5 mg/kg to about 10 mg/kg, about 9 mg/kg to about 10 mg/kg, or about 9.5 mg/kg to about 10 mg/kg. Values and ranges intermediate to the recited values are also intended to be part of this invention.

For example, the dsRNA may be administered at a dose of about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or about 10 mg/kg. Values and ranges intermediate to the recited values are also intended to be part of this invention.

In another embodiment, the dsRNA is administered at a dose of about 0.5 to about 50 mg/kg, about 0.75 to about 50 mg/kg, about 1 to about 50 mg/mg, about 1.5 to about 50 mg/kb, about 2 to about 50 mg/kg, about 2.5 to about 50 mg/kg, about 3 to about 50 mg/kg, about 3.5 to about 50 mg/kg, about 4 to about 50 mg/kg, about 4.5 to about 50 mg/kg, about 5 to about 50 mg/kg, about 7.5 to about 50 mg/kg, about 10 to about 50 mg/kg, about 15 to about 50 mg/kg, about 20 to about 50 mg/kg, about 20 to about 50 mg/kg, about 25 to about 50 mg/kg, about 25 to about 50 mg/kg, about 30 to about 50 mg/kg, about 35 to about 50 mg/kg, about 40 to about 50 mg/kg, about 45 to about 50 mg/kg, about 0.5 to about 45 mg/kg, about 0.75 to about 45 mg/kg, about 1 to about 45 mg/mg, about 1.5 to about 45 mg/kb, about 2 to about 45 mg/kg, about 2.5 to about 45 mg/kg, about 3 to about 45 mg/kg, about 3.5 to about 45 mg/kg, about 4 to about 45 mg/kg, about 4.5 to about 45 mg/kg, about 5 to about 45 mg/kg, about 7.5 to about 45 mg/kg, about 10 to about 45 mg/kg, about 15 to about 45 mg/kg, about 20 to about 45 mg/kg, about 20 to about 45 mg/kg, about 25 to about 45 mg/kg, about 25 to about 45 mg/kg, about 30 to about 45 mg/kg, about 35 to about 45 mg/kg, about 40 to about 45 mg/kg, about 0.5 to about 40 mg/kg, about 0.75 to about 40 mg/kg, about 1 to about 40 mg/mg, about 1.5 to about 40 mg/kb, about 2 to about 40 mg/kg, about 2.5 to about 40 mg/kg, about 3 to about 40 mg/kg, about 3.5 to about 40 mg/kg, about 4 to about 40 mg/kg, about 4.5 to about 40 mg/kg, about 5 to about 40 mg/kg, about 7.5 to about 40 mg/kg, about 10 to about 40 mg/kg, about 15 to about 40 mg/kg, about 20 to about 40 mg/kg, about 20 to about 40 mg/kg, about 25 to about 40 mg/kg, about 25 to about 40 mg/kg, about 30 to about 40 mg/kg, about 35 to about 40 mg/kg, about 0.5 to about 30 mg/kg, about 0.75 to about 30 mg/kg, about 1 to about 30 mg/mg, about 1.5 to about 30 mg/kb, about 2 to about 30 mg/kg, about 2.5 to about 30 mg/kg, about 3 to about 30 mg/kg, about 3.5 to about 30 mg/kg, about 4 to about 30 mg/kg, about 4.5 to about 30 mg/kg, about 5 to about 30 mg/kg, about 7.5 to about 30 mg/kg, about 10 to about 30 mg/kg, about 15 to about 30 mg/kg, about 20 to about 30 mg/kg, about 20 to about 30 mg/kg, about 25 to about 30 mg/kg, about 0.5 to about 20 mg/kg, about 0.75 to about 20 mg/kg, about 1 to about 20 mg/mg, about 1.5 to about 20 mg/kb, about 2 to about 20 mg/kg, about 2.5 to about 20 mg/kg, about 3 to about 20 mg/kg, about 3.5 to about 20 mg/kg, about 4 to about 20 mg/kg, about 4.5 to about 20 mg/kg, about 5 to about 20 mg/kg, about 7.5 to about 20 mg/kg, about 10 to about 20 mg/kg, or about 15 to about 20 mg/kg. Values and ranges intermediate to the recited values are also intended to be part of this invention.

For example, subjects can be administered a therapeutic amount of iRNA, such as about 0.5, 0.6, 0.7. 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 31, 32, 33, 34, 34, 35, 36, 37, 38, 39, 40, 41, 42, 43, 44, 45, 46, 47, 48, 49, or about 50 mg/kg. Values and ranges intermediate to the recited values are also intended to be part of this invention.

The dsRNA, e.g., conjugated to a ligand, may be administered to the subject once a week or twice a month.

In another aspect, the present invention provides methods of inhibiting the expression of Serpinc1 in a subject. The methods include administering to the subject a therapeutically effective amount of the dsRNA or a vector of the invention, thereby inhibiting the expression of Serpinc1 in the subject.

In one embodiment, the dsRNA is conjugated to a ligand, e.g., at the 3'-end of the sense strand of the dsRNA. In one embodiment the ligand is an N-acetylgalactosamine (GalNAc) derivative.

In one embodiment, the dsRNA is administered at a dose of about 0.01 mg/kg to about 10 mg/kg, e.g., about 0.05 mg/kg to about 5 mg/kg, about 0.05 mg/kg to about 10 mg/kg, about 0.1 mg/kg to about 5 mg/kg, about 0.1 mg/kg to about 10 mg/kg, about 0.2 mg/kg to about 5 mg/kg, about 0.2 mg/kg to about 10 mg/kg, about 0.3 mg/kg to about 5 mg/kg, about 0.3 mg/kg to about 10 mg/kg, about 0.4 mg/kg to about 5 mg/kg, about 0.4 mg/kg to about 10 mg/kg, about 0.5 mg/kg to about 5 mg/kg, about 0.5 mg/kg to about 10 mg/kg, about 1 mg/kg to about 5 mg/kg, about 1 mg/kg to about 10 mg/kg, about 1.5 mg/kg to about 5 mg/kg, about 1.5 mg/kg to about 10 mg/kg, about 2 mg/kg to about 2.5 mg/kg, about 2 mg/kg to about 10 mg/kg, about 3 mg/kg to about 5 mg/kg, about 3 mg/kg to about 10 mg/kg, about 3.5 mg/kg to about 5 mg/kg, about 4 mg/kg to about 5 mg/kg, about 4.5 mg/kg to about 5 mg/kg, about 4 mg/kg to about 10 mg/kg, about 4.5 mg/kg to about 10 mg/kg, about 5 mg/kg to about 10 mg/kg, about 5.5 mg/kg to about 10 mg/kg, about 6 mg/kg to about 10 mg/kg, about 6.5 mg/kg to about 10 mg/kg, about 7 mg/kg to about 10 mg/kg, about 7.5 mg/kg to about 10 mg/kg, about 8 mg/kg to about 10 mg/kg, about 8.5 mg/kg to about 10 mg/kg, about 9 mg/kg to about 10 mg/kg, or about 9.5 mg/kg to about 10 mg/kg. Values and ranges intermediate to the recited values are also intended to be part of this invention.

For example, the dsRNA may be administered at a dose of about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or about 10 mg/kg. Values and ranges intermediate to the recited values are also intended to be part of this invention.

In another embodiment, the dsRNA is administered at a dose of about 0.5 to about 50 mg/kg, about 0.75 to about 50 mg/kg, about 1 to about 50 mg/mg, about 1.5 to about 50 mg/kb, about 2 to about 50 mg/kg, about 2.5 to about 50 mg/kg, about 3 to about 50 mg/kg, about 3.5 to about 50 mg/kg, about 4 to about 50 mg/kg, about 4.5 to about 50 mg/kg, about 5 to about 50 mg/kg, about 7.5 to about 50 mg/kg, about 10 to about 50 mg/kg, about 15 to about 50 mg/kg, about 20 to about 50 mg/kg, about 20 to about 50 mg/kg, about 25 to about 50 mg/kg, about 25 to about 50 mg/kg, about 30 to about 50 mg/kg, about 35 to about 50 mg/kg, about 40 to about 50 mg/kg, about 45 to about 50 mg/kg, about 0.5 to about 45 mg/kg, about 0.75 to about 45 mg/kg, about 1 to about 45 mg/mg, about 1.5 to about 45 mg/kb, about 2 to about 45 mg/kg, about 2.5 to about 45 mg/kg, about 3 to about 45 mg/kg, about 3.5 to about 45 mg/kg, about 4 to about 45 mg/kg, about 4.5 to about 45 mg/kg, about 5 to about 45 mg/kg, about 7.5 to about 45 mg/kg, about 10 to about 45 mg/kg, about 15 to about 45 mg/kg, about 20 to about 45 mg/kg, about 20 to about 45 mg/kg, about 25 to about 45 mg/kg, about 25 to about 45 mg/kg, about 30 to about 45 mg/kg, about 35 to about 45 mg/kg, about 40 to about 45 mg/kg, about 0.5 to about 40 mg/kg, about 0.75 to about 40 mg/kg, about 1 to about 40 mg/mg, about 1.5 to about 40 mg/kb, about 2 to about 40 mg/kg, about 2.5 to about 40 mg/kg, about 3 to about 40 mg/kg, about 3.5 to about 40 mg/kg, about 4 to about 40 mg/kg, about 4.5 to about 40 mg/kg, about 5 to about 40 mg/kg, about 7.5 to about 40 mg/kg, about 10 to about 40 mg/kg, about 15 to about 40 mg/kg, about 20 to about 40 mg/kg, about 20 to about 40 mg/kg, about 25 to about 40 mg/kg, about 25 to about 40 mg/kg, about 30 to about 40 mg/kg, about 35 to about 40 mg/kg, about 0.5 to about 30 mg/kg, about 0.75 to about 30 mg/kg, about 1 to about 30 mg/mg, about 1.5 to about 30 mg/kb, about 2 to about 30 mg/kg, about 2.5 to about 30 mg/kg, about 3 to about 30 mg/kg, about 3.5 to about 30 mg/kg, about 4 to about 30 mg/kg, about 4.5 to about 30 mg/kg, about 5 to about 30 mg/kg, about 7.5 to about 30 mg/kg, about 10 to about 30 mg/kg, about 15 to about 30 mg/kg, about 20 to about 30 mg/kg, about 20 to about 30 mg/kg, about 25 to about 30 mg/kg, about 0.5 to about 20 mg/kg, about 0.75 to about 20 mg/kg, about 1 to about 20 mg/mg, about 1.5 to about 20 mg/kb, about 2 to about 20 mg/kg, about 2.5 to about 20 mg/kg, about 3 to about 20 mg/kg, about 3.5 to about 20 mg/kg, about 4 to about 20 mg/kg, about 4.5 to about 20 mg/kg, about 5 to about 20 mg/kg, about 7.5 to about 20 mg/kg, about 10 to about 20 mg/kg, or about 15 to about 20 mg/kg. Values and ranges intermediate to the recited values are also intended to be part of this invention.

For example, subjects can be administered a therapeutic amount of iRNA, such as about 0.5, 0.6, 0.7. 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 31, 32, 33, 34, 34, 35, 36, 37, 38, 39, 40, 41, 42, 43, 44, 45, 46, 47, 48, 49, or about 50 mg/kg. Values and ranges intermediate to the recited values are also intended to be part of this invention.

The dsRNA, e.g., conjugated to a ligand, may be administered to the subject once a week or twice a month.

In yet another aspect, the invention provides kits for performing the methods of the invention. In one embodiment, the invention provides a kit for performing a method of inhibiting expression of Serpinc1 in a cell by contacting a cell with a double stranded RNAi agent in an amount effective to inhibit expression of the Serpinc1 gene in the cell. The kit comprises an RNAi agent and instructions for use and, optionally, means for administering the RNAi agent to a subject.

BRIEF DESCRIPTION OF THE DRAWINGS

FIG. 30A shows the nucleotide sequence of *Homo sapiens* serpin peptidase inhibitor, Glade C (antithrombin), member 1 (SERPINC1) (SEQ ID NO:1); FIG. 30B shows the nucleotide sequence of *Macaca mulatta* serpin peptidase inhibitor, Glade C (antithrombin), member 1 (SERPINC1) (SEQ ID NO:2); FIG. 30C shows the nucleotide sequence of *Mus musculus* serine (or cysteine) peptidase inhibitor, Glade C (antithrombin), member 1 (Serpinc1) (SEQ ID NO:3); FIG. 30D shows the nucleotide sequence of *Rattus norvegicus* serpin peptidase inhibitor, Glade C (antithrombin), member 1 (Serpinc1) (SEQ ID NO:4); FIG. 30E shows the reverse complement of SEQ ID NO:1 (SEQ ID NO:5); FIG. 30F shows the reverse complement of SEQ ID NO:2 (SEQ ID NO:6); FIG. 30G shows the reverse complement of SEQ ID NO:3 (SEQ ID NO:7); FIG. 30H shows the reverse complement of SEQ ID NO:4 (SEQ ID NO:8); and FIG. 30I shows the amino acid sequence of an exemplary hydrophobic MTS-containing peptide, RFGF (SEQ ID NO: 9); the amino acid sequence of an exemplary RFGF analogue (SEQ ID NO: 10); the amino acid sequence of the HIV Tat protein (SEQ ID NO: 11); the amino acid sequence of the *Drosophila* Antennapedia protein (SEQ ID NO: 12); and the amino acid sequence of an exemplary Peptide-based Cleavable Linking Group.

DETAILED DESCRIPTION OF THE INVENTION

Figure 1:
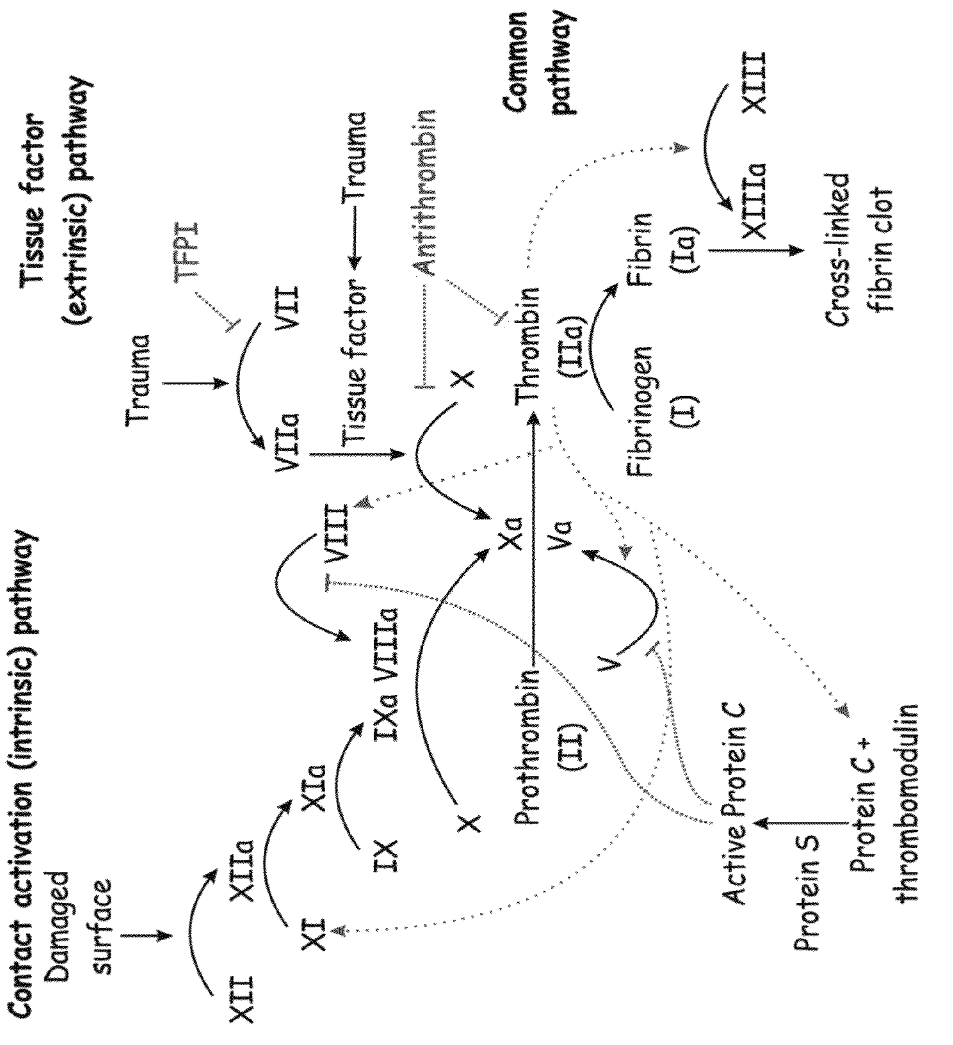
FIG. 1 is a schematic of the blood coagulation cascade.

The present invention provides iRNA compositions which effect the RNA-induced silencing complex (RISC)-mediated cleavage of RNA transcripts of a Serpinc1 gene. The Serpinc1 gene may be within a cell, e.g., a cell within a subject, such as a human. The present invention also provides methods of using the iRNA compositions of the invention for inhibiting the expression of a Serpinc1 gene and/or for treating a subject having a disorder that would benefit from inhibiting or reducing the expression of a Serpinc1 gene, e.g., a bleeding disorder, such as hemophilia. The present invention further provides methods for preventing at least one symptom, e.g., bleeding, in a subject having a disorder that would benefit from inhibiting or reducing the expression of a Serpinc1 gene, e.g., a bleeding disorder, such as hemophilia.

The iRNAs of the invention include an RNA strand (the antisense strand) having a region which is about 30 nucleotides or less in length, e.g., 15-30, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 nucleotides in length, which region is substantially complementary to at least part of an mRNA transcript of a Serpinc1 gene. The use of these iRNAs enables the targeted degradation of mRNAs of a Serpinc1 gene in mammals. Very low dosages of Serpinc1 iRNAs, in particular, can specifically and efficiently mediate RNA interference (RNAi), resulting in significant inhibition of expression of a Serpinc1 gene. The present inventors have demonstrated that iRNAs targeting Serpinc1 can mediate RNAi in vitro and in vivo, resulting in significant inhibition of expression of a Serpinc1 gene. Thus, methods and compositions including these iRNAs are useful for treating a subject who would benefit by a reduction in the levels and/or activity of a Serpinc1 protein, such as a subject having a bleeding disorder, e.g., hemophilia.

The following detailed description discloses how to make and use compositions containing iRNAs to inhibit the expression of a Serpinc1 gene, as well as compositions, uses, and methods for treating subjects having diseases and disorders that would benefit from inhibition and/or reduction of the expression of this gene.

I. DEFINITIONS

In order that the present invention may be more readily understood, certain terms are first defined. In addition, it should be noted that whenever a value or range of values of a parameter are recited, it is intended that values and ranges intermediate to the recited values are also intended to be part of this invention.

The articles "a" and "an" are used herein to refer to one or to more than one (i.e., to at least one) of the grammatical object of the article. By way of example, "an element" means one element or more than one element, e.g., a plurality of elements.

The term "including" is used herein to mean, and is used interchangeably with, the phrase "including but not limited to".

The term "or" is used herein to mean, and is used interchangeably with, the term "and/or," unless context clearly indicates otherwise.

As used herein, "Serpinc1" refers to a particular polypeptide expressed in a cell. Serpinc1 is also known as serpin peptidase inhibitor, Glade C (antithrombin), member 1; antithrombin III; AT3; antithrombin; and heparin cofactor 1. The sequence of a human Serpinc1 mRNA transcript can be found at, for example, GenBank Accession No. GI:254588059 (NM_000488; SEQ ID NO:1). The sequence of rhesus Serpinc1 mRNA can be found at, for example, GenBank Accession No. GI:157167169 (NM_001104583; SEQ ID NO:2). The sequence of mouse Serpinc1 mRNA can be found at, for example, GenBank Accession No. GI:237874216 (NM_080844; SEQ ID NO:3). The sequence of rat Serpinc1 mRNA can be found at, for example, GenBank Accession No. GI:58865629 (NM_001012027; SEQ ID NO:4).

The term"Serpinc1" as used herein also refers to a particular polypeptide expressed in a cell by naturally occurring DNA sequence variations of the Serpinc1 gene, such as a single nucleotide polymorphism in the Serpinc1 gene. Numerous SNPs within the Serpinc1 gene have been identified and may be found at, for example, NCBI dbSNP (see, e.g., www.ncbi.nlm.nih.gov/snp). Non-limiting examples of SNPs within the Serpinc1 gene may be found at, NCBI dbSNP Accession Nos. rs677; rs5877; rs5878; rs5879; rs941988; rs941989; rs1799876; rs19637711; rs2008946; and rs2227586. As used herein, "target sequence" refers to a contiguous portion of the nucleotide sequence of an mRNA molecule formed during the transcription of a Serpinc1 gene, including mRNA that is a product of RNA processing of a primary transcription product. In one embodiment, the target portion of the sequence will be at least long enough to serve as a substrate for iRNA-directed cleavage at or near that portion of the nucleotide sequence of an mRNA molecule formed during the transcription of a Serpinc1 gene.

The target sequence may be from about 9-36 nucleotides in length, e.g., about 15-30 nucleotides in length. For example, the target sequence can be from about 15-30 nucleotides, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 nucleotides in length. Ranges and lengths intermediate to the above recited ranges and lengths are also contemplated to be part of the invention.

As used herein, the term "strand comprising a sequence" refers to an oligonucleotide comprising a chain of nucleotides that is described by the sequence referred to using the standard nucleotide nomenclature.

"G," "C," "A," "T" and "U" each generally stand for a nucleotide that contains guanine, cytosine, adenine, thymidine and uracil as a base, respectively. However, it will be understood that the term "ribonucleotide" or "nucleotide" can also refer to a modified nucleotide, as further detailed below, or a surrogate replacement moiety (see, e.g., Table 2). The skilled person is well aware that guanine, cytosine, adenine, and uracil can be replaced by other moieties without substantially altering the base pairing properties of an oligonucleotide comprising a nucleotide bearing such replacement moiety. For example, without limitation, a nucleotide comprising inosine as its base can base pair with nucleotides containing adenine, cytosine, or uracil. Hence, nucleotides containing uracil, guanine, or adenine can be replaced in the nucleotide sequences of dsRNA featured in the invention by a nucleotide containing, for example, inosine. In another example, adenine and cytosine anywhere in the oligonucleotide can be replaced with guanine and uracil, respectively to form G-U Wobble base pairing with the target mRNA. Sequences containing such replacement moieties are suitable for the compositions and methods featured in the invention.

The terms "iRNA", "RNAi agent," "iRNA agent,", "RNA interference agent" as used interchangeably herein, refer to an agent that contains RNA as that term is defined herein, and which mediates the targeted cleavage of an RNA transcript via an RNA-induced silencing complex (RISC) pathway. iRNA directs the sequence-specific degradation of mRNA through a process known as RNA interference (RNAi). The iRNA modulates, e.g., inhibits, the expression of Serpinc1 in a cell, e.g., a cell within a subject, such as a mammalian subject.

In one embodiment, an RNAi agent of the invention includes a single stranded RNA that interacts with a target RNA sequence, e.g., a Serpinc1 target mRNA sequence, to direct the cleavage of the target RNA. Without wishing to be bound by theory it is believed that long double stranded RNA introduced into cells is broken down into siRNA by a Type III endonuclease known as Dicer (Sharp et al. (2001) *Genes Dev.* 15:485). Dicer, a ribonuclease-III-like enzyme, processes the dsRNA into 19-23 base pair short interfering RNAs with characteristic two base 3' overhangs (Bernstein, et al., (2001) *Nature* 409:363). The siRNAs are then incorporated into an RNA-induced silencing complex (RISC) where one or more helicases unwind the siRNA duplex, enabling the complementary antisense strand to guide target recognition (Nykanen, et al., (2001) *Cell* 107:309). Upon binding to the appropriate target mRNA, one or more endonucleases within the RISC cleave the target to induce silencing (Elbashir, et al., (2001) *Genes Dev.* 15:188). Thus, in one aspect the invention relates to a single stranded RNA (siRNA) generated within a cell and which promotes the formation of a RISC complex to effect silencing of the target gene, i.e., a Serpinc1 gene. Accordingly, the term "siRNA" is also used herein to refer to an RNAi as described above.

In another embodiment, the RNAi agent may be a single-stranded siRNA that is introduced into a cell or organism to inhibit a target mRNA. The single-stranded siRNAs are generally 15-30 nucleotides and are chemically modified. The design and testing of single-stranded siRNAs are described in U.S. Pat. No. 8,101,348 and in Lima et al., (2012) *Cell* 150: 883-894, the entire contents of each of which are hereby incorporated herein by reference. Any of the antisense nucleotide sequences described herein may be used as a single-stranded siRNA as described herein or as chemically modified by the methods described in Lima et al., (2012) *Cell* 150; 883-894.

In another aspect, the agent is a single-stranded antisense RNA molecule that inhibits a target via an antisense inhibition mechanism. The single-stranded antisense RNA molecule is complementary to a sequence within the target mRNA. Antisense RNA can inhibit translation in a stoichiometric manner by base pairing to the mRNA and physically obstructing the translation machinery, see Dias, N. et al., (2002) *Mol Cancer Ther* 1:347-355. Alternatively, the single-stranded antisense RNA molecule inhibits a target mRNA by hydridizing to the target and cleaving the target through an RNaseH cleavage event. The single-stranded antisense RNA molecule may be about 15 to about 30 nucleotides in length and have a sequence that is complementary to a target sequence. For example, the single-stranded antisense RNA molecule may comprise a sequence that is at least about 15, 16, 17, 18, 19, 20, or more contiguous nucleotides from any one of the antisense sequences in any one of Tables 3, 4, 8, 11, 12, 14, 15, 20, and 21.

In another embodiment, an "iRNA" for use in the compositions, uses, and methods of the invention is a double-stranded RNA and is referred to herein as a "double stranded RNAi agent," "double-stranded RNA (dsRNA) molecule," "dsRNA agent," or "dsRNA". The term "dsRNA", refers to a complex of ribonucleic acid molecules, having a duplex structure comprising two anti-parallel and substantially complementary nucleic acid strands, referred to as having "sense" and "antisense" orientations with respect to a target RNA, i.e., a Serpinc1 gene. In some embodiments of the invention, a double-stranded RNA (dsRNA) triggers the degradation of a target RNA, e.g., an mRNA, through a post-transcriptional gene-silencing mechanism referred to herein as RNA interference or RNAi.

The duplex region may be of any length that permits specific degradation of a desired target RNA through a RISC pathway, and may range from about 9 to 36 base pairs in length, e.g., about 15-30 base pairs in length, for example, about 9, 10, 11, 12, 13, 14, 15, 16, 17, 18, 19, 20, and 21, 22, 23, 24, 25, 26, 27, 28, 29, 30, 31, 32, 33, 34, 35, or 36 base pairs in length, such as about 15-30, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs in length. Ranges and lengths intermediate to the above recited ranges and lengths are also contemplated to be part of the invention.

The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5'-end of the respective other strand forming the duplex structure, the connecting RNA chain is referred to as a "hairpin loop." A hairpin loop can comprise at least one unpaired nucleotide. In some embodiments, the hairpin loop can comprise at least 2, at least 3, at least 4, at least 5, at least 6, at least 7, at least 8, at least 9, at least 10, at least 20, at least 23 or more unpaired nucleotides.

Where the two substantially complementary strands of a dsRNA are comprised by separate RNA molecules, those molecules need not, but can be covalently connected. Where the two strands are connected covalently by means other than an uninterrupted chain of nucleotides between the 3'-end of one strand and the 5'-end of the respective other strand forming the duplex structure, the connecting structure is referred to as a "linker." The RNA strands may have the same or a different number of nucleotides. The maximum number of base pairs is the number of nucleotides in the shortest strand of the dsRNA minus any overhangs that are present in the duplex. In addition to the duplex structure, an RNAi may comprise one or more nucleotide overhangs.

As used herein, the term "nucleotide overhang" refers to at least one unpaired nucleotide that protrudes from the duplex structure of an iRNA, e.g., a dsRNA. For example, when a 3'-end of one strand of a dsRNA extends beyond the 5'-end of the other strand, or vice versa, there is a nucleotide overhang. A dsRNA can comprise an overhang of at least one nucleotide; alternatively the overhang can comprise at least two nucleotides, at least three nucleotides, at least four nucleotides, at least five nucleotides or more. A nucleotide overhang can comprise or consist of a nucleotide/nucleoside analog, including a deoxynucleotide/nucleoside. The overhang(s) can be on the sense strand, the antisense strand or any combination thereof. Furthermore, the nucleotide(s) of an overhang can be present on the 5'-end, 3'-end or both ends of either an antisense or sense strand of a dsRNA.

In one embodiment, the antisense strand of a dsRNA has a 1-10 nucleotide, e.g., a 1, 2, 3, 4, 5, 6, 7, 8, 9, or 10 nucleotide, overhang at the 3'-end and/or the 5'-end. In one embodiment, the sense strand of a dsRNA has a 1-10 nucleotide, e.g., a 1, 2, 3, 4, 5, 6, 7, 8, 9, or 10 nucleotide, overhang at the 3'-end and/or the 5'-end. In another embodiment, one or more of the nucleotides in the overhang is replaced with a nucleoside thiophosphate.

The terms "blunt" or "blunt ended" as used herein in reference to a dsRNA mean that there are no unpaired nucleotides or nucleotide analogs at a given terminal end of a dsRNA, i.e., no nucleotide overhang. One or both ends of a dsRNA can be blunt. Where both ends of a dsRNA are blunt, the dsRNA is said to be blunt ended. To be clear, a "blunt ended" dsRNA is a dsRNA that is blunt at both ends, i.e., no nucleotide overhang at either end of the molecule. Most often such a molecule will be double-stranded over its entire length.

The term "antisense strand" or "guide strand" refers to the strand of an iRNA, e.g., a dsRNA, which includes a region that is substantially complementary to a target sequence, e.g., a Serpinc1 mRNA. As used herein, the term "region of complementarity" refers to the region on the antisense strand that is substantially complementary to a sequence, for example a target sequence, e.g., a Serpinc1 nucleotide sequence, as defined herein. Where the region of complementarity is not fully complementary to the target sequence, the mismatches can be in the internal or terminal regions of the molecule. Generally, the most tolerated mismatches are in the terminal regions, e.g., within 5, 4, 3, or 2 nucleotides of the 5'- and/or 3'-terminus of the iRNA.

The term "sense strand," or "passenger strand" as used herein, refers to the strand of an iRNA that includes a region that is substantially complementary to a region of the antisense strand as that term is defined herein.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions can include: 400 mM NaCl, 40 mM PIPES pH 6.4, 1 mM EDTA, 50° C. or 70° C. for 12-16 hours followed by washing (see, e.g., "Molecular Cloning: A Laboratory Manual, Sambrook, et al. (1989) Cold Spring Harbor Laboratory Press). Other conditions, such as physiologically relevant conditions as can be encountered inside an organism, can apply. The skilled person will be able to determine the set of conditions most appropriate for a test of complementarity of two sequences in accordance with the ultimate application of the hybridized nucleotides.

Complementary sequences within an iRNA, e.g., within a dsRNA as described herein, include base-pairing of the oligonucleotide or polynucleotide comprising a first nucleotide sequence to an oligonucleotide or polynucleotide comprising a second nucleotide sequence over the entire length of one or both nucleotide sequences. Such sequences can be referred to as "fully complementary" with respect to each other herein. However, where a first sequence is referred to as "substantially complementary" with respect to a second sequence herein, the two sequences can be fully complementary, or they can form one or more, but generally not more than 5, 4, 3 or 2 mismatched base pairs upon hybridization for a duplex up to 30 base pairs, while retaining the ability to hybridize under the conditions most relevant to their ultimate application, e.g., inhibition of gene expression via a RISC pathway. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, can yet be referred to as "fully complementary" for the purposes described herein.

"Complementary" sequences, as used herein, can also include, or be formed entirely from, non-Watson-Crick base pairs and/or base pairs formed from non-natural and modified nucleotides, in so far as the above requirements with respect to their ability to hybridize are fulfilled. Such non-Watson-Crick base pairs include, but are not limited to, G:U Wobble or Hoogstein base pairing.

The terms "complementary," "fully complementary" and "substantially complementary" herein can be used with respect to the base matching between the sense strand and the antisense strand of a dsRNA, or between the antisense strand of an iRNA agent and a target sequence, as will be understood from the context of their use.

As used herein, a polynucleotide that is "substantially complementary to at least part of" a messenger RNA (mRNA) refers to a polynucleotide that is substantially complementary to a contiguous portion of the mRNA of interest (e.g., an mRNA encoding Serpinc1). For example, a polynucleotide is complementary to at least a part of a Serpinc1 mRNA if the sequence is substantially complementary to a non-interrupted portion of an mRNA encoding Serpinc1.

In general, the majority of nucleotides of each strand are ribonucleotides, but as described in detail herein, each or both strands can also include one or more non-ribonucleotides, e.g., a deoxyribonucleotide and/or a modified nucleotide. In addition, an "iRNA" may include ribonucleotides with chemical modifications. Such modifications may include all types of modifications disclosed herein or known in the art. Any such modifications, as used in an iRNA molecule, are encompassed by "iRNA" for the purposes of this specification and claims.

The term "inhibiting," as used herein, is used interchangeably with "reducing," "silencing," "downregulating," "suppressing" and other similar terms, and includes any level of inhibition.

The phrase "inhibiting expression of a Serpinc1," as used herein, includes inhibition of expression of any Serpinc1 gene (such as, e.g., a mouse Serpinc1 gene, a rat Serpinc1 gene, a monkey Serpinc1 gene, or a human Serpinc1 gene) as well as variants or mutants of a Serpinc1 gene that encodes a Serpinc1 protein.

"Inhibiting expression of a Serpinc1 gene" includes any level of inhibition of a Serpinc1 gene, e.g., at least partial suppression of the expression of a Serpinc1 gene, such as an inhibition by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%.

The expression of a Serpinc1 gene may be assessed based on the level of any variable associated with Serpinc1 gene expression, e.g., Serpinc1 mRNA level, Serpinc1 protein level, or, for example, thrombin:antithrombin complex levels as a measure of thrombin generation potential, bleeding time, prothrombin time (PT), platelet count, and/or activated partial thromboplastin time (aPTT). Inhibition may be assessed by a decrease in an absolute or relative level of one or more of these variables compared with a control level. The control level may be any type of control level that is utilized in the art, e.g., a pre-dose baseline level, or a level determined from a similar subject, cell, or sample that is untreated or treated with a control (such as, e.g., buffer only control or inactive agent control).

In one embodiment, at least partial suppression of the expression of a Serpinc1 gene, is assessed by a reduction of the amount of Serpinc1 mRNA which can be isolated from or detected in a first cell or group of cells in which a Serpinc1 gene is transcribed and which has or have been treated such that the expression of a Serpinc1 gene is inhibited, as compared to a second cell or group of cells substantially identical to the first cell or group of cells but which has or have not been so treated (control cells). The degree of inhibition may be expressed in terms of $$\frac{(mRNA \text{ in control cells}) - (mRNA \text{ in treated cells})}{(mRNA \text{ in control cells})} \cdot 100\%$$

The phrase "contacting a cell with an RNAi agent," such as a dsRNA, as used herein, includes contacting a cell by any possible means. Contacting a cell with an RNAi agent includes contacting a cell in vitro with the iRNA or contacting a cell in vivo with the iRNA. The contacting may be done directly or indirectly. Thus, for example, the RNAi agent may be put into physical contact with the cell by the individual performing the method, or alternatively, the RNAi agent may be put into a situation that will permit or cause it to subsequently come into contact with the cell.

Contacting a cell in vitro may be done, for example, by incubating the cell with the RNAi agent. Contacting a cell in vivo may be done, for example, by injecting the RNAi agent into or near the tissue where the cell is located, or by injecting the RNAi agent into another area, e.g., the bloodstream or the subcutaneous space, such that the agent will subsequently reach the tissue where the cell to be contacted is located. For example, the RNAi agent may contain and/or be coupled to a ligand, e.g., GalNAc3, that directs the RNAi agent to a site of interest, e.g., the liver. Combinations of in vitro and in vivo methods of contacting are also possible. For example, a cell may also be contacted in vitro with an RNAi agent and subsequently transplanted into a subject.

In one embodiment, contacting a cell with an iRNA includes "introducing" or "delivering the iRNA into the cell" by facilitating or effecting uptake or absorption into the cell. Absorption or uptake of an iRNA can occur through unaided diffusive or active cellular processes, or by auxiliary agents or devices. Introducing an iRNA into a cell may be in vitro and/or in vivo. For example, for in vivo introduction, iRNA can be injected into a tissue site or administered systemically. In vivo delivery can also be done by a beta-glucan delivery system, such as those described in U.S. Pat. Nos. 5,032,401 and 5,607,677, and U.S. Publication No. 2005/0281781, the entire contents of which are hereby incorporated herein by reference. In vitro introduction into a cell includes methods known in the art such as electroporation and lipofection. Further approaches are described herein below and/or are known in the art.

The term "lipid nanoparticle" or "LNP" is a vesicle comprising a lipid layer encapsulating a pharmaceutically active molecule, such as a nucleic acid molecule, e.g., an iRNA or a plasmid from which an iRNA is transcribed. LNPs are described in, for example, U.S. Pat. Nos. 6,858,225, 6,815,432, 8,158,601, and 8,058,069, the entire contents of which are hereby incorporated herein by reference.

The term "SNALP" refers to a stable nucleic acid-lipid particle. A SNALP is a vesicle of lipids coating a reduced aqueous interior comprising a nucleic acid such as an iRNA or a plasmid from which an iRNA is transcribed. SNALPs are described, e.g., in U.S. Patent Application Publication Nos. 20060240093, 20070135372, and in International Application No. WO 2009082817, the entire contents of which are hereby incorporated herein by reference. Examples of "SNALP" formulations are described below.

As used herein, a "subject" is an animal, such as a mammal, including a primate (such as a human, a non-human primate, e.g., a monkey, and a chimpanzee), a non-primate (such as a cow, a pig, a camel, a llama, a horse, a goat, a rabbit, a sheep, a hamster, a guinea pig, a cat, a dog, a rat, a mouse, a horse, and a whale), or a bird (e.g., a duck or a goose). In an embodiment, the subject is a human, such as a human being treated or assessed for a disease, disorder or condition that would benefit from reduction in Serpinc1 expression; a human at risk for a disease, disorder or condition that would benefit from reduction in Serpinc1 expression; a human having a disease, disorder or condition that would benefit from reduction in Serpinc1 expression; and/or human being treated for a disease, disorder or condition that would benefit from reduction in Serpinc1 expression as described herein. As used herein, the terms "treating" or "treatment" refer to a beneficial or desired result including, but not limited to, alleviation or amelioration of one or more symptoms, diminishing the extent of bleeding, stabilized (i.e., not worsening) state of bleeding, amelioration or palliation of the bleeding, whether detectable or undetectable. "Treatment" can also mean prolonging survival as compared to expected survival in the absence of treatment.

By "lower" in the context of a disease marker or symptom is meant a statistically significant decrease in such level. The decrease can be, for example, at least 10%, at least 20%, at least 30%, at least 40% or more, and is preferably down to a level accepted as within the range of normal for an individual without such disorder.

As used herein, "prevention" or "preventing," when used in reference to a disease, disorder or condition thereof, that would benefit from a reduction in expression of a Serpinc1 gene, refers to a reduction in the likelihood that a subject will develop a symptom associated with a such a disease, disorder, or condition, e.g., a symptom such as a bleed. The likelihood of developing a bleed is reduced, for example, when an individual having one or more risk factors for a bleed either fails to develop a bleed or develops a bleed with less severity relative to a population having the same risk factors and not receiving treatment as described herein. The failure to develop a disease, disorder or condition, or the reduction in the development of a symptom associated with such a disease, disorder or condition (e.g., by at least about 10% on a clinically accepted scale for that disease or disorder), or the exhibition of delayed symptoms delayed (e.g., by days, weeks, months or years) is considered effective prevention.

As used herein, the term "bleeding disorder" is a disease or disorder that results in poor blood clotting and/or excessive bleeding. A bleeding disorder may be an inherited disorder, such as a hemophilia or von Willebrand's disease, or an acquired disorder, associated with, for example, disseminated intravascular coagulation, pregnancy-associated eclampsia, vitamin K deficiency, an autoimmune disorder, inflammatory bowel disease, ulcerative colitis, a dermatologic disorder (e.g., psoriasis, pemphigus), a respiratory disease (e.g., asthma, chronic obstructive pulmonary disease), an allergic drug reaction, e.g., the result of medications, such as aspirin, heparin, and warfarin, diabetes, acute hepatitis B infection, acute hepatitis C infection, a malignancy or solid tumor (e.g., prostate, lung, colon, pancreas, stomach, bile duct, head and neck, cervix, breast, melanoma, kidney, and/or a hematologic malignancy). In one embodiment, an inherited bleeding disorder is a hemophilia, e.g., hemophilia A, B, or C. In one embodiment, a subject having an inherited bleeding disorder, e.g., a hemophilia, has developed inhibitors, e.g., alloantibody inhibitors, to replacement coagulation therapies and is referred to herein as an "inhibitor subject." In one embodiment, the inhibitor subject has hemophilia A. In another embodiment, the inhibitor subject has hemophilia B. In yet another embodiment, the inhibitor subject has hemophilia C.

"Therapeutically effective amount," as used herein, is intended to include the amount of an RNAi agent that, when administered to a subject having a bleeding disorder and bleeding, is sufficient to effect treatment of the disease (e.g., by diminishing, ameliorating or maintaining the existing disease or one or more symptoms of disease). The "therapeutically effective amount" may vary depending on the RNAi agent, how the agent is administered, the disease and its severity and the history, age, weight, family history, genetic makeup, the types of preceding or concomitant treatments, if any, and other individual characteristics of the subject to be treated.

"Prophylactically effective amount," as used herein, is intended to include the amount of an iRNA that, when administered to a subject having a bleeding disorder but not bleeding, e.g., a subject having a bleeding disorder and scheduled for surgery, is sufficient to prevent or ameliorate the disease or one or more symptoms of the disease. Ameliorating the disease includes slowing the course of the disease or reducing the severity of later-developing disease. The "prophylactically effective amount" may vary depending on the iRNA, how the agent is administered, the degree of risk of disease, and the history, age, weight, family history, genetic makeup, the types of preceding or concomitant treatments, if any, and other individual characteristics of the patient to be treated.

A "therapeutically effective amount" or "prophylactically effective amount" also includes an amount of an RNAi agent that produces some desired local or systemic effect at a reasonable benefit/risk ratio applicable to any treatment. iRNA employed in the methods of the present invention may be administered in a sufficient amount to produce a reasonable benefit/risk ratio applicable to such treatment.

The phrase "pharmaceutically acceptable" is employed herein to refer to those compounds, materials, compositions, and/or dosage forms which are, within the scope of sound medical judgment, suitable for use in contact with the tissues of human subjects and animal subjects without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the subject being treated. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) lubricating agents, such as magnesium state, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; and (22) other non-toxic compatible substances employed in pharmaceutical formulations.

The term "sample," as used herein, includes a collection of similar fluids, cells, or tissues isolated from a subject, as well as fluids, cells, or tissues present within a subject. Examples of biological fluids include blood, serum and serosal fluids, plasma, cerebrospinal fluid, ocular fluids, lymph, urine, saliva, and the like. Tissue samples may include samples from tissues, organs or localized regions. For example, samples may be derived from particular organs, parts of organs, or fluids or cells within those organs. In certain embodiments, samples may be derived from the liver (e.g., whole liver or certain segments of liver or certain types of cells in the liver, such as, e.g., hepatocytes). In some embodiments, a "sample derived from a subject" refers to blood or plasma drawn from the subject.

II. iRNAs OF THE INVENTION

Described herein are iRNAs which inhibit the expression of a Serpinc1 gene. In one embodiment, the iRNA agent includes double-stranded ribonucleic acid (dsRNA) molecules for inhibiting the expression of a Serpinc1 gene in a cell, such as a cell within a subject, e.g., a mammal, such as a human having a bleeding disorder, e.g., an inherited bleeding disorder. The dsRNA includes an antisense strand having a region of complementarity which is complementary to at least a part of an mRNA formed in the expression of a Serpinc1 gene. The region of complementarity is about 30 nucleotides or less in length (e.g., about 30, 29, 28, 27, 26, 25, 24, 23, 22, 21, 20, 19, or 18 nucleotides or less in length). Upon contact with a cell expressing the Serpinc1 gene, the iRNA inhibits the expression of the Serpinc1 gene (e.g., a human, a primate, a non-primate, or a bird Serpinc1 gene) by at least about 10% as assayed by, for example, a PCR or branched DNA (bDNA)-based method, or by a protein-based method, such as by immunofluorescence analysis, using, for example, Western Blotting or flowcytometric techniques.

A dsRNA includes two RNA strands that are complementary and hybridize to form a duplex structure under conditions in which the dsRNA will be used. One strand of a dsRNA (the antisense strand) includes a region of complementarity that is substantially complementary, and generally fully complementary, to a target sequence. The target sequence can be derived from the sequence of an mRNA formed during the expression of a Serpinc1 gene. The other strand (the sense strand) includes a region that is complementary to the antisense strand, such that the two strands hybridize and form a duplex structure when combined under suitable conditions. As described elsewhere herein and as known in the art, the complementary sequences of a dsRNA can also be contained as self-complementary regions of a single nucleic acid molecule, as opposed to being on separate oligonucleotides.

Generally, the duplex structure is between 15 and 30 base pairs in length, e.g., between, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs in length. Ranges and lengths intermediate to the above recited ranges and lengths are also contemplated to be part of the invention.

Similarly, the region of complementarity to the target sequence is between 15 and 30 nucleotides in length, e.g., between 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 nucleotides in length. Ranges and lengths intermediate to the above recited ranges and lengths are also contemplated to be part of the invention.

In some embodiments, the dsRNA is between about 15 and about 20 nucleotides in length, or between about 25 and about 30 nucleotides in length. In general, the dsRNA is long enough to serve as a substrate for the Dicer enzyme. For example, it is well-known in the art that dsRNAs longer than about 21-23 nucleotides in length may serve as substrates for Dicer. As the ordinarily skilled person will also recognize, the region of an RNA targeted for cleavage will most often be part of a larger RNA molecule, often an mRNA molecule. Where relevant, a "part" of an mRNA target is a contiguous sequence of an mRNA target of sufficient length to allow it to be a substrate for RNAi-directed cleavage (i.e., cleavage through a RISC pathway).

One of skill in the art will also recognize that the duplex region is a primary functional portion of a dsRNA, e.g., a duplex region of about 9 to 36 base pairs, e.g., about 10-36, 11-36, 12-36, 13-36, 14-36, 15-36, 9-35, 10-35, 11-35, 12-35, 13-35, 14-35, 15-35, 9-34, 10-34, 11-34, 12-34, 13-34, 14-34, 15-34, 9-33, 10-33, 11-33, 12-33, 13-33, 14-33, 15-33, 9-32, 10-32, 11-32, 12-32, 13-32, 14-32, 15-32, 9-31, 10-31, 11-31, 12-31, 13-32, 14-31, 15-31, 15-30, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs. Thus, in one embodiment, to the extent that it becomes processed to a functional duplex, of e.g., 15-30 base pairs, that targets a desired RNA for cleavage, an RNA molecule or complex of RNA molecules having a duplex region greater than 30 base pairs is a dsRNA. Thus, an ordinarily skilled artisan will recognize that in one embodiment, a miRNA is a dsRNA. In another embodiment, a dsRNA is not a naturally occurring miRNA. In another embodiment, an iRNA agent useful to target Serpinc1 expression is not generated in the target cell by cleavage of a larger dsRNA.

A dsRNA as described herein can further include one or more single-stranded nucleotide overhangs e.g., 1, 2, 3, or 4 nucleotides. dsRNAs having at least one nucleotide overhang can have unexpectedly superior inhibitory properties relative to their blunt-ended counterparts. A nucleotide overhang can comprise or consist of a nucleotide/nucleoside analog, including a deoxynucleotide/nucleoside. The overhang(s) can be on the sense strand, the antisense strand or any combination thereof. Furthermore, the nucleotide(s) of an overhang can be present on the 5'-end, 3'-end or both ends of either an antisense or sense strand of a dsRNA.

A dsRNA can be synthesized by standard methods known in the art as further discussed below, e.g., by use of an automated DNA synthesizer, such as are commercially available from, for example, Biosearch, Applied Biosystems, Inc.

iRNA compounds of the invention may be prepared using a two-step procedure. First, the individual strands of the double-stranded RNA molecule are prepared separately. Then, the component strands are annealed. The individual strands of the siRNA compound can be prepared using solution-phase or solid-phase organic synthesis or both. Organic synthesis offers the advantage that the oligonucleotide strands comprising unnatural or modified nucleotides can be easily prepared. Single-stranded oligonucleotides of the invention can be prepared using solution-phase or solid-phase organic synthesis or both.

In one aspect, a dsRNA of the invention includes at least two nucleotide sequences, a sense sequence and an anti-sense sequence. The sense strand is selected from the group of sequences provided in any one of Tables 3, 4, 8, 11, 12, 14, 15, 20, and 21, and the corresponding antisense strand of the sense strand is selected from the group of sequences of any one of Tables 3, 4, 8, 11, 12, 14, 15, 20, and 21. In this aspect, one of the two sequences is complementary to the other of the two sequences, with one of the sequences being substantially complementary to a sequence of an mRNA generated in the expression of a Serpinc1 gene. As such, in this aspect, a dsRNA will include two oligonucleotides, where one oligonucleotide is described as the sense strand in any one of Tables 3, 4, 8, 11, 12, 14, 15, 20, and 21, and the second oligonucleotide is described as the corresponding antisense strand of the sense strand in any one of Tables 3, 4, 8, 11, 12, 14, 15, 20, and 21. In one embodiment, the substantially complementary sequences of the dsRNA are contained on separate oligonucleotides. In another embodiment, the substantially complementary sequences of the dsRNA are contained on a single oligonucleotide.

It will be understood that, although some of the sequences in Tables 3, 4, 8, 11, 12, 14, 15, 20, and 21 are described as modified and/or conjugated sequences, the RNA of the iRNA of the invention e.g., a dsRNA of the invention, may comprise any one of the sequences set forth in Tables 3, 4, 8, 11, 12, 14, 15, 20, and 21 that is un-modified, un-conjugated, and/or modified and/or conjugated differently than described therein.

The skilled person is well aware that dsRNAs having a duplex structure of between about 20 and 23 base pairs, e.g., 21, base pairs have been hailed as particularly effective in inducing RNA interference (Elbashir et al., *EMBO* 2001, 20:6877-6888). However, others have found that shorter or longer RNA duplex structures can also be effective (Chu and Rana (2007) *RNA* 14:1714-1719; Kim et al. (2005) *Nat Biotech* 23:222-226). In the embodiments described above, by virtue of the nature of the oligonucleotide sequences provided in any one of Tables 3, 4, 8, 11, 12, 14, 15, 20, and 21, dsRNAs described herein can include at least one strand of a length of minimally 21 nucleotides. It can be reasonably expected that shorter duplexes having one of the sequences of any one of Tables 3, 4, 8, 11, 12, 14, 15, 20, and 21 minus only a few nucleotides on one or both ends can be similarly effective as compared to the dsRNAs described above. Hence, dsRNAs having a sequence of at least 15, 16, 17, 18, 19, 20, or more contiguous nucleotides derived from one of the sequences of any one of Tables 3, 4, 8, 11, 12, 14, 15, 20, and 21, and differing in their ability to inhibit the expression of a Serpinc1 gene by not more than about 5, 10, 15, 20, 25, or 30% inhibition from a dsRNA comprising the full sequence, are contemplated to be within the scope of the present invention.

In addition, the RNAs provided in any one of Tables 3, 4, 8, 11, 12, 14, 15, 20, and 21 identify a site(s) in a Serpinc1 transcript that is susceptible to RISC-mediated cleavage. As such, the present invention further features iRNAs that target within one of these sites. As used herein, an iRNA is said to target within a particular site of an RNA transcript if the iRNA promotes cleavage of the transcript anywhere within that particular site. Such an iRNA will generally include at least about 15 contiguous nucleotides from one of the sequences provided in any one of Tables 3, 4, 8, 11, 12, 14, 15, 20, and 21 coupled to additional nucleotide sequences taken from the region contiguous to the selected sequence in a Serpinc1 gene.

While a target sequence is generally about 15-30 nucleotides in length, there is wide variation in the suitability of particular sequences in this range for directing cleavage of any given target RNA. Various software packages and the guidelines set out herein provide guidance for the identification of optimal target sequences for any given gene target, but an empirical approach can also be taken in which a "window" or "mask" of a given size (as a non-limiting example, 21 nucleotides) is literally or figuratively (including, e.g., in silico) placed on the target RNA sequence to identify sequences in the size range that can serve as target sequences. By moving the sequence "window" progressively one nucleotide upstream or downstream of an initial target sequence location, the next potential target sequence can be identified, until the complete set of possible sequences is identified for any given target size selected. This process, coupled with systematic synthesis and testing of the identified sequences (using assays as described herein or as known in the art) to identify those sequences that perform optimally can identify those RNA sequences that, when targeted with an iRNA agent, mediate the best inhibition of target gene expression. Thus, while the sequences identified, for example, in any one of Tables 3, 4, 8, 11, 12, 14, 15, 20, and 21 represent effective target sequences, it is contemplated that further optimization of inhibition efficiency can be achieved by progressively "walking the window" one nucleotide upstream or downstream of the given sequences to identify sequences with equal or better inhibition characteristics.

Further, it is contemplated that for any sequence identified, e.g., in any one of Tables 3, 4, 8, 11, 12, 14, 15, 20, and 21, further optimization could be achieved by systematically either adding or removing nucleotides to generate longer or shorter sequences and testing those sequences generated by walking a window of the longer or shorter size up or down the target RNA from that point. Again, coupling this approach to generating new candidate targets with testing for effectiveness of iRNAs based on those target sequences in an inhibition assay as known in the art and/or as described herein can lead to further improvements in the efficiency of inhibition. Further still, such optimized sequences can be adjusted by, e.g., the introduction of modified nucleotides as described herein or as known in the art, addition or changes in overhang, or other modifications as known in the art and/or discussed herein to further optimize the molecule (e.g., increasing serum stability or circulating half-life, increasing thermal stability, enhancing transmembrane delivery, targeting to a particular location or cell type, increasing interaction with silencing pathway enzymes, increasing release from endosomes) as an expression inhibitor.

An iRNA as described herein can contain one or more mismatches to the target sequence. In one embodiment, an iRNA as described herein contains no more than 3 mismatches. If the antisense strand of the iRNA contains mismatches to a target sequence, it is preferable that the area of mismatch is not located in the center of the region of complementarity. If the antisense strand of the iRNA contains mismatches to the target sequence, it is preferable that the mismatch be restricted to be within the last 5 nucleotides from either the 5'- or 3'-end of the region of complementarity. For example, for a 23 nucleotide iRNA agent the strand which is complementary to a region of a Serpinc1 gene, generally does not contain any mismatch within the central 13 nucleotides. The methods described herein or methods known in the art can be used to determine whether an iRNA containing a mismatch to a target sequence is effective in inhibiting the expression of a Serpinc1 gene. Consideration of the efficacy of iRNAs with mismatches in inhibiting expression of a Serpinc1 gene is important, especially if the particular region of complementarity in a Serpinc1 gene is known to have polymorphic sequence variation within the population.

III. MODIFIED iRNAs OF THE INVENTION

In one embodiment, the RNA of the iRNA of the invention e.g., a dsRNA, is un-modified, and does not comprise, e.g., chemical modifications and/or conjugations known in the art and described herein. In another embodiment, the RNA of an iRNA of the invention, e.g., a dsRNA, is chemically modified to enhance stability or other beneficial characteristics. The nucleic acids featured in the invention can be synthesized and/or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference. Modifications include, for example, end modifications, e.g., 5'-end modifications (phosphorylation, conjugation, inverted linkages) or 3'-end modifications (conjugation, DNA nucleotides, inverted linkages, etc.); base modifications, e.g., replacement with stabilizing bases, destabilizing bases, or bases that base pair with an expanded repertoire of partners, removal of bases (abasic nucleotides), or conjugated bases; sugar modifications (e.g., at the 2'-position or 4'-position) or replacement of the sugar; and/or backbone modifications, including modification or replacement of the phosphodiester linkages. Specific examples of iRNA compounds useful in the embodiments described herein include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In some embodiments, a modified iRNA will have a phosphorus atom in its internucleoside backbone.

Modified RNA backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5'-linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; 5,625,050; 6,028,188; 6,124,445; 6,160,109; 6,169,170; 6,172,209; 6,239,265; 6,277,603; 6,326,199; 6,346,614; 6,444,423; 6,531,590; 6,534,639; 6,608,035; 6,683,167; 6,858,715; 6,867,294; 6,878,805; 7,015,315; 7,041,816; 7,273,933; 7,321,029; and U.S. Pat. RE39464, the entire contents of each of which are hereby incorporated herein by reference.

Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, the entire contents of each of which are hereby incorporated herein by reference.

In other embodiments, suitable RNA mimetics are contemplated for use in iRNAs, in which both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, the entire contents of each of which are hereby incorporated herein by reference. Additional PNA compounds suitable for use in the iRNAs of the invention are described in, for example, in Nielsen et al., *Science,* 1991, 254, 1497-1500.

Some embodiments featured in the invention include RNAs with phosphorothioate backbones and oligonucleosides with heteroatom backbones, and in particular —$CH_2$—NH—$CH_2$—, —$CH_2$—N($CH_3$)—O—$CH_2$—[known as a methylene(methylimino) or MMI backbone], —$CH_2$—O—N($CH_3$)—$CH_2$—, —$CH_2$—N($CH_3$)—N($CH_3$)—$CH_2$— and —N($CH_3$)—$CH_2$—$CH_2$—[wherein the native phosphodiester backbone is represented as —O—P—O—$CH_2$—] of the above-referenced U.S. Pat. No. 5,489,677, and the amide backbones of the above-referenced U.S. Pat. No. 5,602,240. In some embodiments, the RNAs featured herein have morpholino backbone structures of the above-referenced U.S. Pat. No. 5,034,506.

Modified RNAs can also contain one or more substituted sugar moieties. The iRNAs, e.g., dsRNAs, featured herein can include one of the following at the 2'-position: OH; F; O-, S-, or N-alkyl; O-, S-, or N-alkenyl; O-, S- or N-alkynyl; or O-alkyl-O-alkyl, wherein the alkyl, alkenyl and alkynyl can be substituted or unsubstituted $C_1$ to $C_{10}$ alkyl or $C_2$ to $C_{10}$ alkenyl and alkynyl. Exemplary suitable modifications include $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nO[(CH_2)_nCH_3)]_2$, where n and m are from 1 to about 10. In other embodiments, dsRNAs include one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an iRNA, or a group for improving the pharmacodynamic properties of an iRNA, and other substituents having similar properties. In some embodiments, the modification includes a 2'-methoxyethoxy(2'-O—$CH_2CH_2OCH_3$, also known as 2'-O-(2-methoxyethyl) or 2'-MOE) (Martin et al., *Helv. Chim. Acta,* 1995, 78:486-504) i.e., an alkoxy-alkoxy group. Another exemplary modification is 2'-dimethylaminooxyethoxy, i.e., a $O(CH_2)_2ON(CH_3)_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_2$)$_2$.

Other modifications include 2'-methoxy(2'-$OCH_3$), 2'-aminopropoxy(2'-$OCH_2CH_2CH_2NH_2$) and 2'-fluoro (2'-F). Similar modifications can also be made at other positions on the RNA of an iRNA, particularly the 3' position of the sugar on the 3' terminal nucleotide or in 2'-5' linked dsRNAs and the 5' position of 5' terminal nucleotide. iRNAs can also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application. The entire contents of each of the foregoing are hereby incorporated herein by reference.

An iRNA can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazadenine and 3-deazaguanine and 3-deazaadenine. Further nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. L, ed. John Wiley & Sons, 1990, these disclosed by Englisch et al., Angewandte Chemie, International Edition, 1991, 30, 613, and those disclosed by Sanghvi, Y S., Chapter 15, dsRNA Research and Applications, pages 289-302, Crooke, S. T. and Lebleu, B., Ed., CRC Press, 1993. Certain of these nucleobases are particularly useful for increasing the binding affinity of the oligomeric compounds featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. Nos. 3,687,808, 4,845,205; 5,130,30; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; 5,750,692; 6,015,886; 6,147,200; 6,166,197; 6,222,025; 6,235,887; 6,380,368; 6,528,640; 6,639,062; 6,617,438; 7,045,610; 7,427,672; and 7,495,088, the entire contents of each of which are hereby incorporated herein by reference.

The RNA of an iRNA can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs has been shown to increase siRNA stability in serum, and to reduce off-target effects (Elmen, J. et al., (2005) *Nucleic Acids Research* 33(1):439-447; Mook, O R. et al., (2007) *Mol Canc Ther* 6(3):833-843; Grunweller, A. et al., (2003) *Nucleic Acids Research* 31(12):3185-3193).

Representative U.S. patents that teach the preparation of locked nucleic acid nucleotides include, but are not limited to, the following: U.S. Pat. Nos. 6,268,490; 6,670,461; 6,794,499; 6,998,484; 7,053,207; 7,084,125; and 7,399,845, the entire contents of each of which are hereby incorporated herein by reference.

Potentially stabilizing modifications to the ends of RNA molecules can include N-(acetylaminocaproyl)-4-hydroxyprolinol (Hyp-C6-NHAc), N-(caproyl-4-hydroxyprolinol (Hyp-C6), N-(acetyl-4-hydroxyprolinol (Hyp-NHAc), thymidine-2'-O-deoxythymidine (ether), N-(aminocaproyl)-4-hydroxyprolinol (Hyp-C6-amino), 2-docosanoyl-uridine-3"-phosphate, inverted base dT(idT) and others. Disclosure of this modification can be found in PCT Publication No. WO 2011/005861.

IV. iRNAs CONJUGATED TO LIGANDS

Another modification of the RNA of an iRNA of the invention involves chemically linking to the RNA one or more ligands, moieties or conjugates that enhance the activity, cellular distribution or cellular uptake of the iRNA. Such moieties include but are not limited to lipid moieties such as a cholesterol moiety (Letsinger et al., *Proc. Natl. Acid. Sci. USA,* 1989, 86: 6553-6556), cholic acid (Manoharan et al., *Biorg. Med. Chem. Let.,* 1994, 4:1053-1060), a thioether, e.g., beryl-5-tritylthiol (Manoharan et al., *Ann. N.Y. Acad. Sci.,* 1992, 660:306-309; Manoharan et al., *Biorg. Med. Chem. Let.,* 1993, 3:2765-2770), a thiocholesterol (Oberhauser et al., *Nucl. Acids Res.,* 1992, 20:533-538), an aliphatic chain, e.g., dodecandiol or undecyl residues (Saison-Behmoaras et al., *EMBO J,* 1991, 10:1111-1118; Kabanov et al., *FEBS Lett.,* 1990, 259:327-330; Svinarchuk et al., *Biochimie,* 1993, 75:49-54), a phospholipid, e.g., di-hexadecyl-rac-glycerol or triethyl-ammonium 1,2-di-O-hexadecyl-rac-glycero-3-phosphonate (Manoharan et al., *Tetrahedron Lett.,* 1995, 36:3651-3654; Shea et al., *Nucl. Acids Res.,* 1990, 18:3777-3783), a polyamine or a polyethylene glycol chain (Manoharan et al., *Nucleosides & Nucleotides,* 1995, 14:969-973), or adamantane acetic acid (Manoharan et al., *Tetrahedron Lett.,* 1995, 36:3651-3654), a palmityl moiety (Mishra et al., *Biochim. Biophys. Acta,* 1995, 1264:229-237), or an octadecylamine or hexylamino-carbonyloxycholesterol moiety (Crooke et al., *J. Pharmacol. Exp. Ther.,* 1996, 277:923-937).

In one embodiment, a ligand alters the distribution, targeting or lifetime of an iRNA agent into which it is incorporated. In preferred embodiments a ligand provides an enhanced affinity for a selected target, e.g., molecule, cell or cell type, compartment, e.g., a cellular or organ compartment, tissue, organ or region of the body, as, e.g., compared to a species absent such a ligand. Preferred ligands will not take part in duplex pairing in a duplexed nucleic acid.

Ligands can include a naturally occurring substance, such as a protein (e.g., human serum albumin (HSA), low-density lipoprotein (LDL), or globulin); carbohydrate (e.g., a dextran, pullulan, chitin, chitosan, inulin, cyclodextrin, N-acetylgalactosamine, or hyaluronic acid); or a lipid. The ligand can also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-gulucoseamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, vitamin A, biotin, or an RGD peptide or RGD peptide mimetic.

Other examples of ligands include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g., cholesterol, cholic acid, adamantane acetic acid, 1-pyrene butyric acid, dihydrotestosterone, 1,3-Bis-O (hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, $[MPEG]_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a hepatic cell. Ligands can also include hormones and hormone receptors. They can also include non-peptidic species, such as lipids, lectins, carbohydrates, vitamins, cofactors, multivalent lactose, multivalent galactose, N-acetyl-galactosamine, N-acetyl-gulucosamine multivalent mannose, or multivalent fucose. The ligand can be, for example, a lipopolysaccharide, an activator of p38 MAP kinase, or an activator of NF-κB.

The ligand can be a substance, e.g., a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

In some embodiments, a ligand attached to an iRNA as described herein acts as a pharmacokinetic modulator (PK modulator). PK modulators include lipophiles, bile acids, steroids, phospholipid analogues, peptides, protein binding agents, PEG, vitamins etc. Exemplary PK modulators include, but are not limited to, cholesterol, fatty acids, cholic acid, lithocholic acid, dialkylglycerides, diacylglyceride, phospholipids, sphingolipids, naproxen, ibuprofen, vitamin E, biotin etc. Oligonucleotides that comprise a number of phosphorothioate linkages are also known to bind to serum protein, thus short oligonucleotides, e.g., oligonucleotides of about 5 bases, 10 bases, 15 bases or 20 bases, comprising multiple of phosphorothioate linkages in the backbone are also amenable to the present invention as ligands (e.g. as PK modulating ligands). In addition, aptamers that bind serum components (e.g. serum proteins) are also suitable for use as PK modulating ligands in the embodiments described herein.

Ligand-conjugated oligonucleotides of the invention may be synthesized by the use of an oligonucleotide that bears a pendant reactive functionality, such as that derived from the attachment of a linking molecule onto the oligonucleotide (described below). This reactive oligonucleotide may be reacted directly with commercially-available ligands, ligands that are synthesized bearing any of a variety of protecting groups, or ligands that have a linking moiety attached thereto.

The oligonucleotides used in the conjugates of the present invention may be conveniently and routinely made through the well-known technique of solid-phase synthesis. Equipment for such synthesis is sold by several vendors including, for example, Applied Biosystems (Foster City, Calif.). Any other means for such synthesis known in the art may additionally or alternatively be employed. It is also known to use similar techniques to prepare other oligonucleotides, such as the phosphorothioates and alkylated derivatives.

In the ligand-conjugated oligonucleotides and ligand-molecule bearing sequence-specific linked nucleosides of the present invention, the oligonucleotides and oligonucleosides may be assembled on a suitable DNA synthesizer utilizing standard nucleotide or nucleoside precursors, or nucleotide or nucleoside conjugate precursors that already bear the linking moiety, ligand-nucleotide or nucleoside-conjugate precursors that already bear the ligand molecule, or non-nucleoside ligand-bearing building blocks.

When using nucleotide-conjugate precursors that already bear a linking moiety, the synthesis of the sequence-specific linked nucleosides is typically completed, and the ligand molecule is then reacted with the linking moiety to form the ligand-conjugated oligonucleotide. In some embodiments, the oligonucleotides or linked nucleosides of the present invention are synthesized by an automated synthesizer using phosphoramidites derived from ligand-nucleoside conjugates in addition to the standard phosphoramidites and non-standard phosphoramidites that are commercially available and routinely used in oligonucleotide synthesis.

A. Lipid Conjugates

In one embodiment, the ligand or conjugate is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, naproxen or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to inhibit, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In a preferred embodiment, the lipid based ligand binds HSA. Preferably, it binds HSA with a sufficient affinity such that the conjugate will be preferably distributed to a non-kidney tissue. However, it is preferred that the affinity not be so strong that the HSA-ligand binding cannot be reversed.

In another preferred embodiment, the lipid based ligand binds HSA weakly or not at all, such that the conjugate will be preferably distributed to the kidney. Other moieties that target to kidney cells can also be used in place of or in addition to the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by target cells such as liver cells. Also included are HSA and low density lipoprotein (LDL).

B. Cell Permeation Agents

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to iRNA agents can affect pharmacokinetic distribution of the iRNA, such as by enhancing cellular recognition and absorption. The peptide or peptidomimetic moiety can be about 5-50 amino acids long, e.g., about 5, 10, 15, 20, 25, 30, 35, 40, 45, or 50 amino acids long.

A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVLLALLAP (SEQ ID NO: 9). An RFGF analogue (e.g., amino acid sequence AALLPVLLAAP (SEQ ID NO: 10) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ (SEQ ID NO: 11) and the *Drosophila* Antennapedia protein (RQIKIWFQNRRMKWKK (SEQ ID NO: 12) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-84, 1991). Examples of a peptide or peptidomimetic tethered to a dsRNA agent via an incorporated monomer unit for cell targeting purposes is an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

An RGD peptide for use in the compositions and methods of the invention may be linear or cyclic, and may be modified, e.g., glycosylated or methylated, to facilitate targeting to a specific tissue(s). RGD-containing peptides and peptidiomimemtics may include D-amino acids, as well as synthetic RGD mimics. In addition to RGD, one can use other moieties that target the integrin ligand. Preferred conjugates of this ligand target PECAM-1 or VEGF.

A "cell permeation peptide" is capable of permeating a cell, e.g., a microbial cell, such as a bacterial or fungal cell, or a mammalian cell, such as a human cell. A microbial cell-permeating peptide can be, for example, a α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003).

C. Carbohydrate Conjugates

In some embodiments of the compositions and methods of the invention, an iRNA oligonucleotide further comprises a carbohydrate. The carbohydrate conjugated iRNA are advantageous for the in vivo delivery of nucleic acids, as well as compositions suitable for in vivo therapeutic use, as described herein. As used herein, "carbohydrate" refers to a compound which is either a carbohydrate per se made up of one or more monosaccharide units having at least 6 carbon atoms (which can be linear, branched or cyclic) with an oxygen, nitrogen or sulfur atom bonded to each carbon atom; or a compound having as a part thereof a carbohydrate moiety made up of one or more monosaccharide units each having at least six carbon atoms (which can be linear, branched or cyclic), with an oxygen, nitrogen or sulfur atom bonded to each carbon atom. Representative carbohydrates include the sugars (mono-, di-, tri- and oligosaccharides containing from about 4, 5, 6, 7, 8, or 9 monosaccharide units), and polysaccharides such as starches, glycogen, cellulose and polysaccharide gums. Specific monosaccharides include C5 and above (e.g., C5, C6, C7, or C8) sugars; di- and trisaccharides include sugars having two or three monosaccharide units (e.g., C5, C6, C7, or C8).

In one embodiment, a carbohydrate conjugate for use in the compositions and methods of the invention is a monosaccharide. In one embodiment, the monosaccharide is an N-acetylgalactosamine, such as Formula II

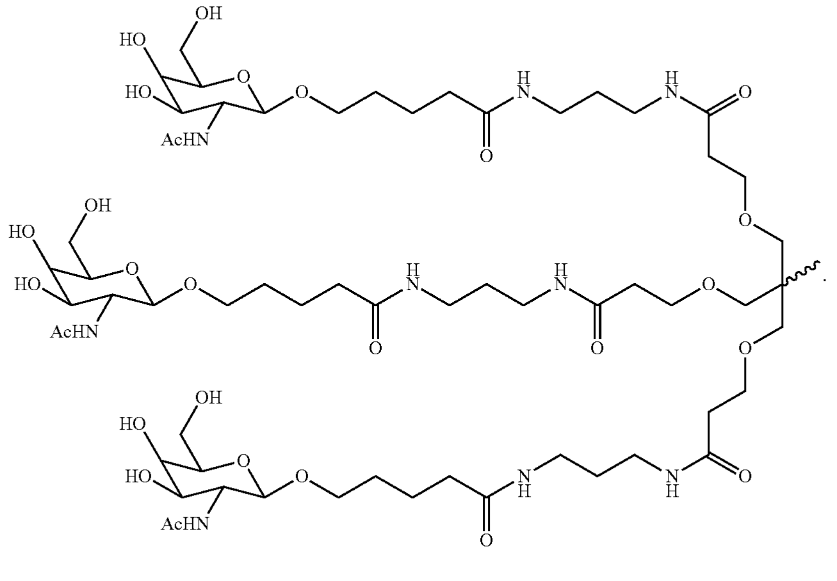

In another embodiment, a carbohydrate conjugate for use in the compositions and methods of the invention is selected from the group consisting of:
Formula II
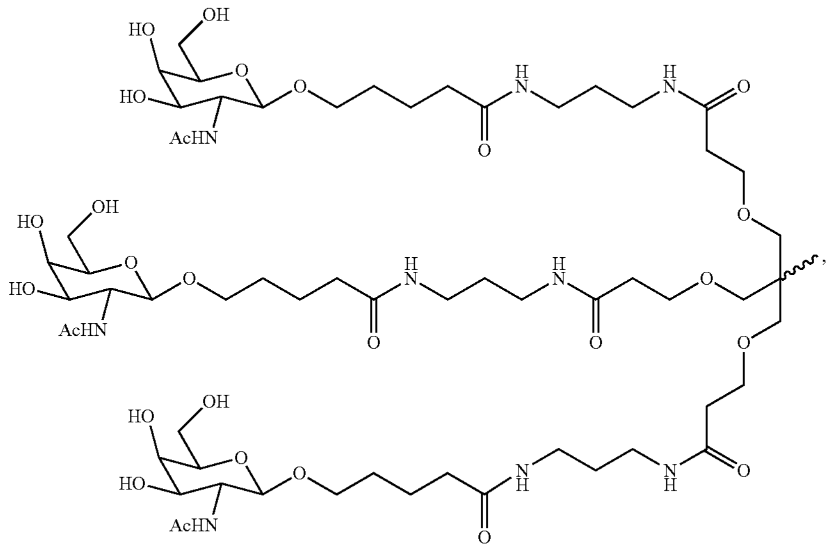
,
Formula III
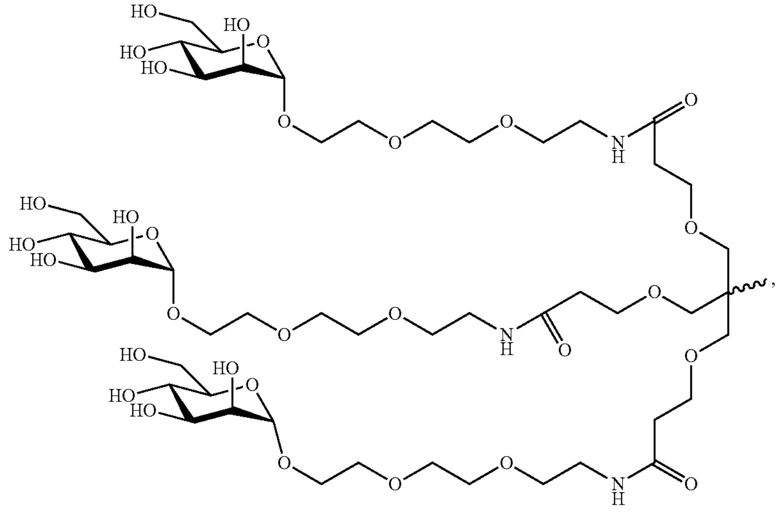
,
Formula IV
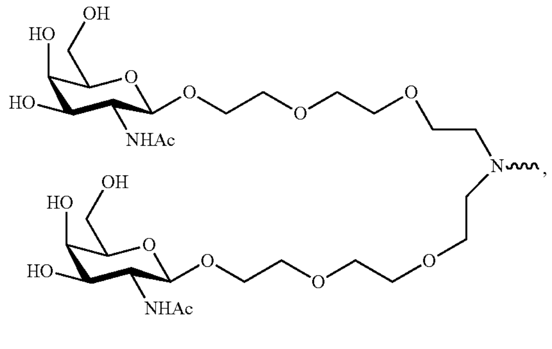
,
Formula V
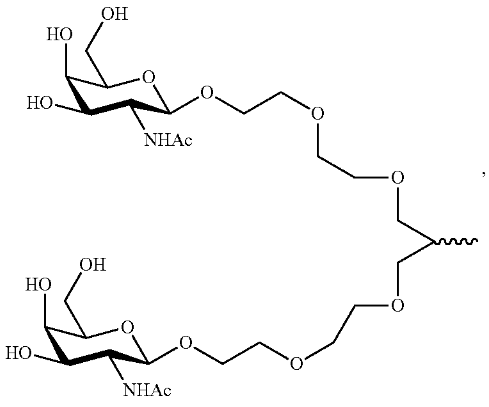
, -continued
Formula VI
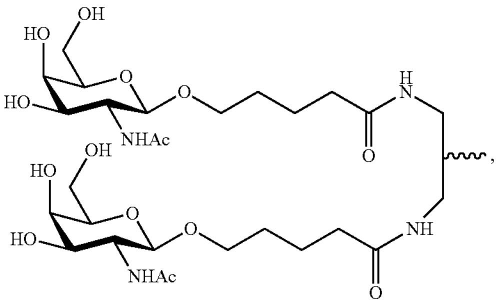
Formula VII
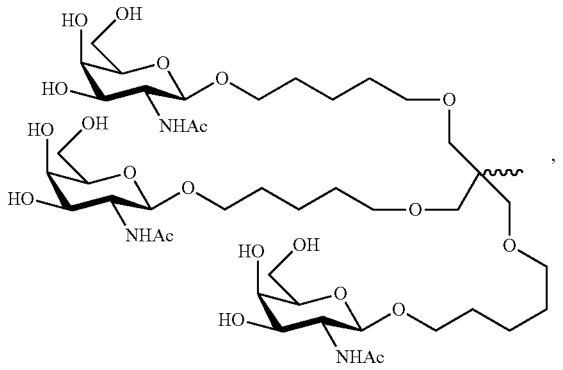
Formula VIII
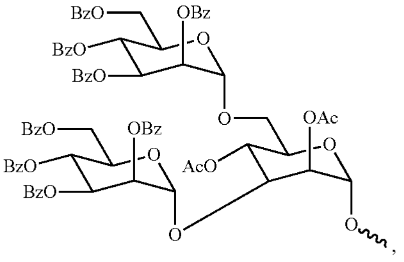
Formula IX
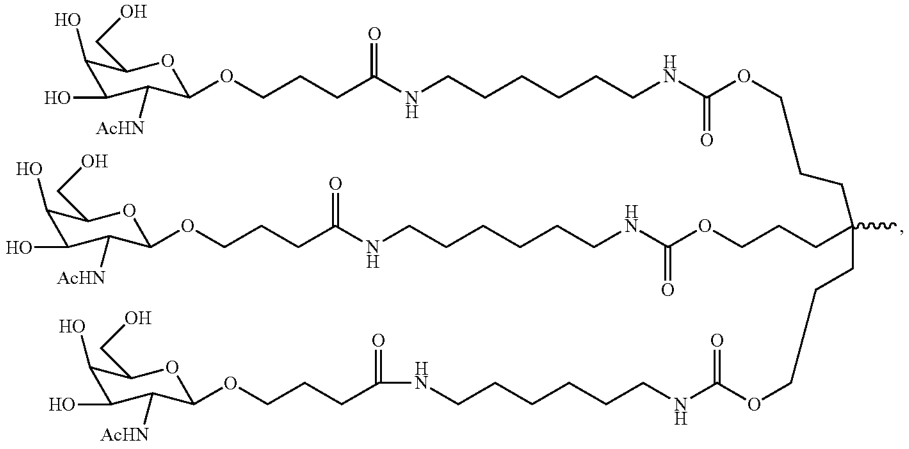
Formula X
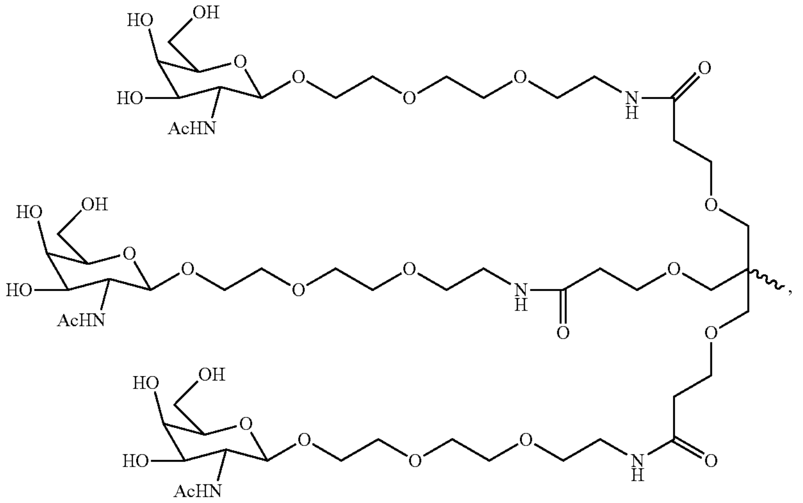

-continued
Formula XI
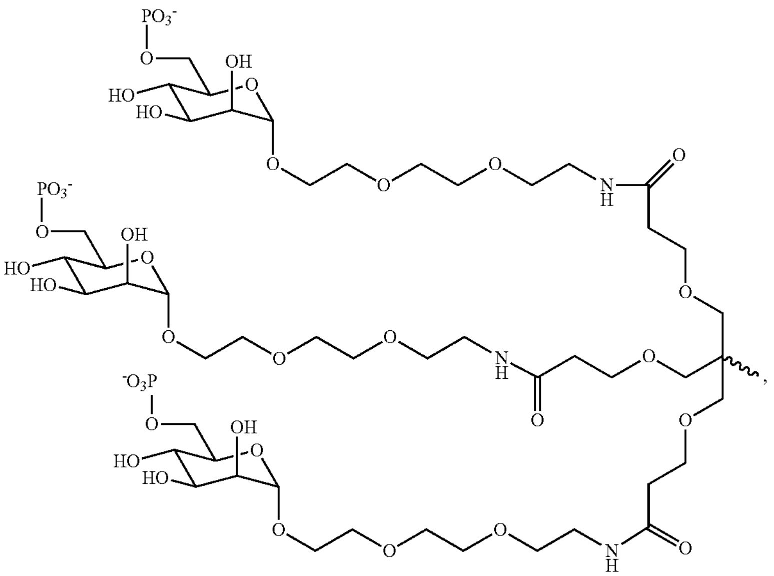
Formula XII
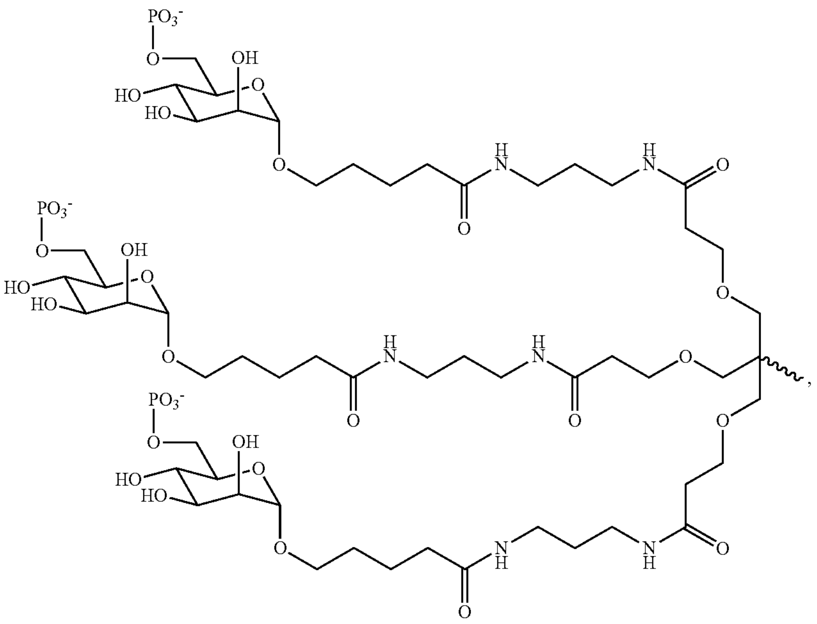
Formula XIII
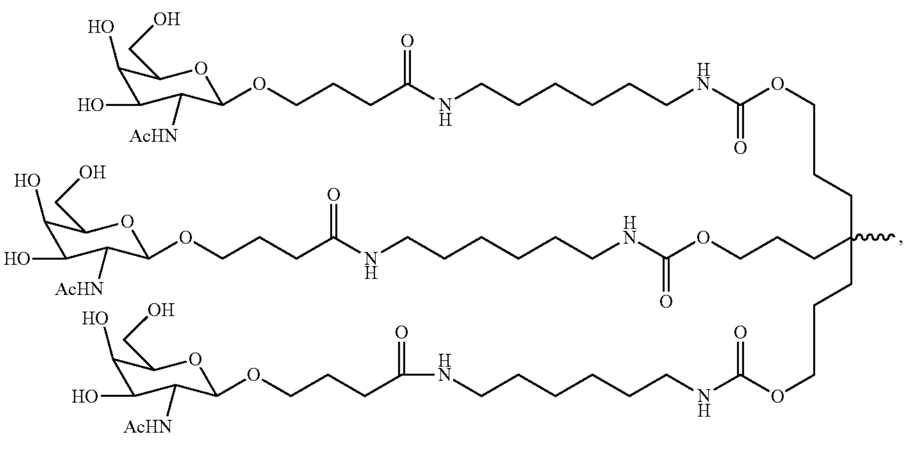

-continued
Formula XIV
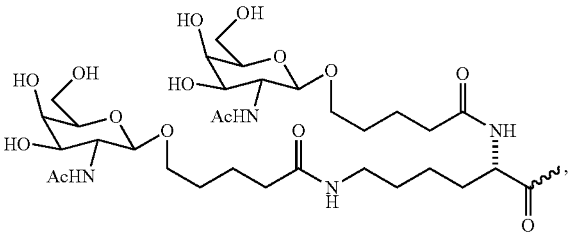
Formula XV
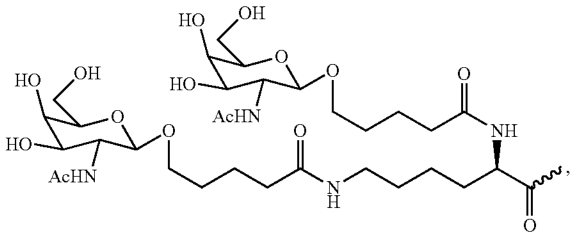
Formula XVI
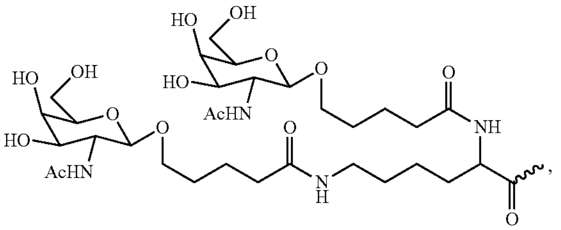
Formula XVII
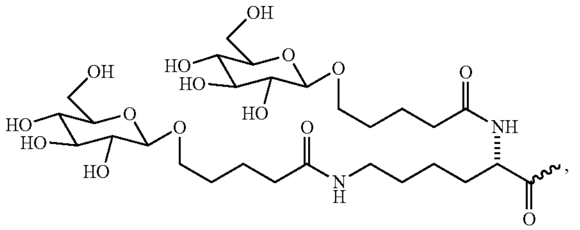
Formula XVIII
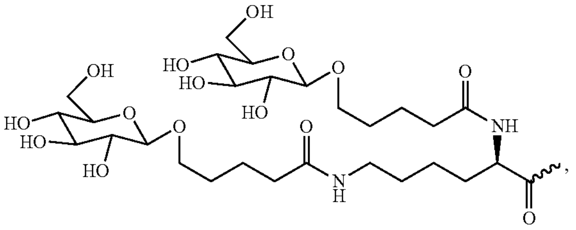
Formula XIX
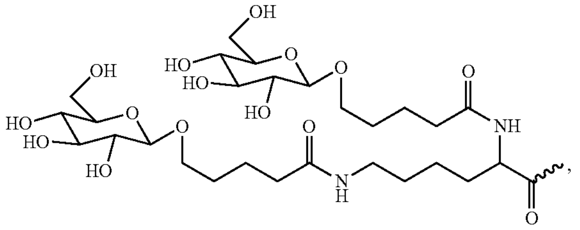
Formula XX
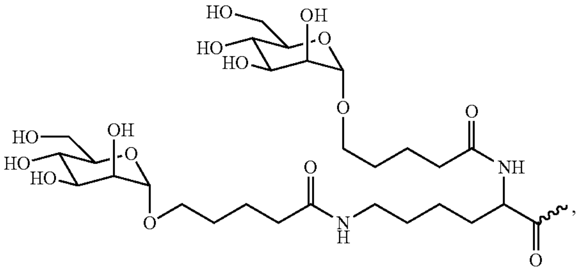
Formula XXI
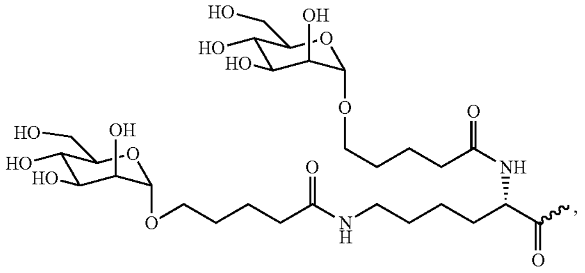
Forula XXII
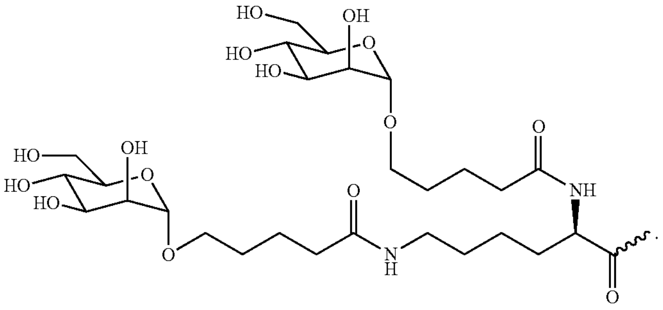
Another representative carbohydrate conjugate for use in the embodiments described herein includes, but is not limited to,

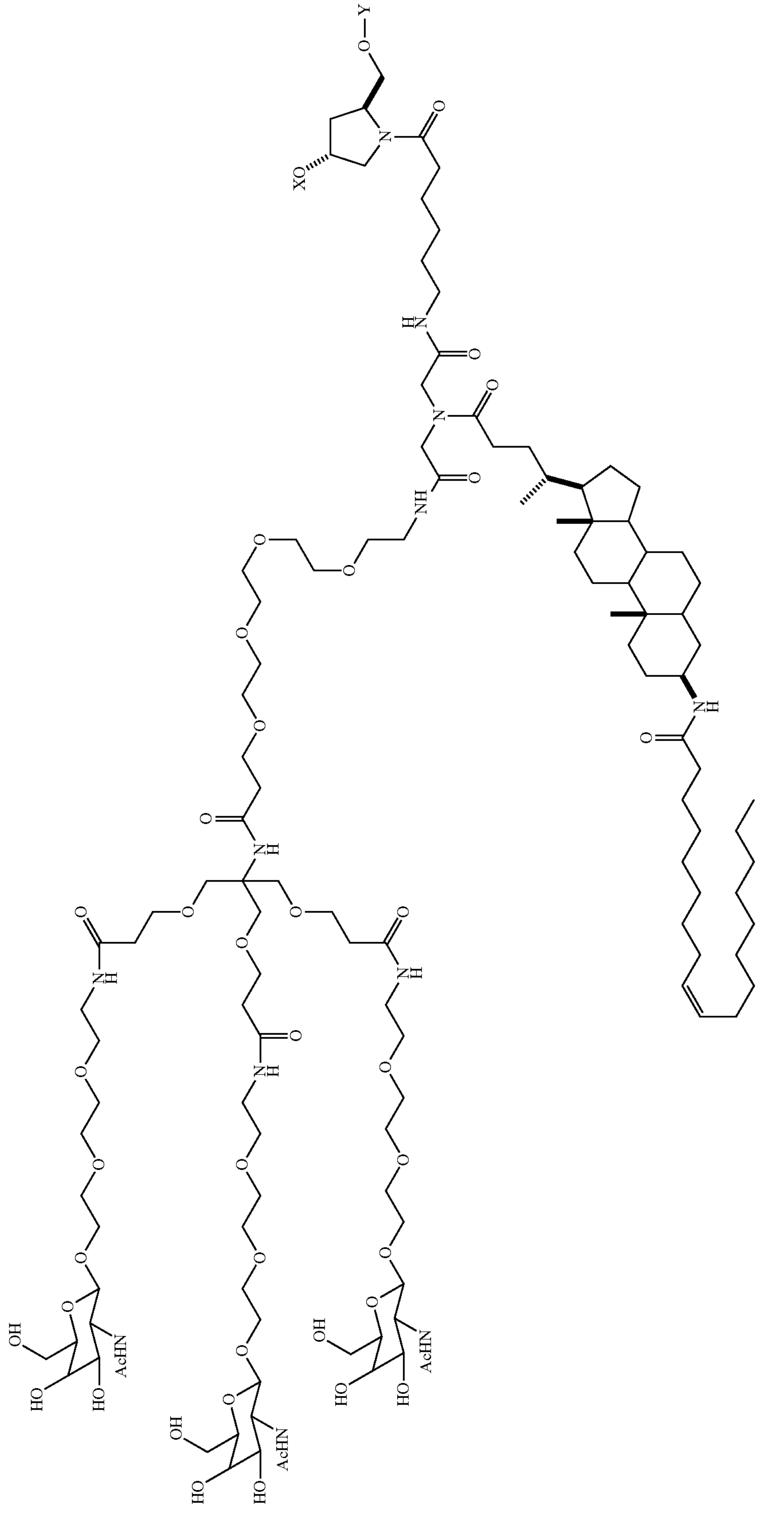

(Formula XXIII), when one of X or Y is an oligonucleotide, the other is a hydrogen.

In some embodiments, the carbohydrate conjugate further comprises one or more additional ligands as described above, such as, but not limited to, a PK modulator and/or a cell permeation peptide.

D. Linkers

In some embodiments, the conjugate or ligand described herein can be attached to an iRNA oligonucleotide with various linkers that can be cleavable or non-cleavable.

The term "linker" or "linking group" means an organic moiety that connects two parts of a compound, e.g., covalently attaches two parts of a compound. Linkers typically comprise a direct bond or an atom such as oxygen or sulfur, a unit such as NR8, C(O), C(O)NH, SO, $SO_2$, $SO_2NH$ or a chain of atoms, such as, but not limited to, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylherterocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, which one or more methylenes can be interrupted or terminated by O, S, S(O), $SO_2$, N(8), C(O), substituted or unsubstituted aryl, substituted or unsubstituted heteroaryl, substituted or unsubstituted heterocyclic; where R8 is hydrogen, acyl, aliphatic or substituted aliphatic. In one embodiment, the linker is between about 1-24 atoms, 2-24, 3-24, 4-24, 5-24, 6-24, 6-18, 7-18, 8-18 atoms, 7-17, 8-17, 6-16, 7-16, or 8-16 atoms.

A cleavable linking group is one which is sufficiently stable outside the cell, but which upon entry into a target cell is cleaved to release the two parts the linker is holding together. In a preferred embodiment, the cleavable linking group is cleaved at least about 10 times, 20, times, 30 times, 40 times, 50 times, 60 times, 70 times, 80 times, 90 times or more, or at least about 100 times faster in a target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred pH, thereby releasing a cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. For example, a liver-targeting ligand can be linked to a cationic lipid through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus, one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It can be useful to make initial evaluations in cell-free or culture conditions and to confirm by further evaluations in whole animals. In preferred embodiments, useful candidate compounds are cleaved at least about 2, 4, 10, 20, 30, 40, 50, 60, 70, 80, 90, or about 100 times faster in the cell (or under in vitro conditions selected to mimic intracellular conditions) as compared to blood or serum (or under in vitro conditions selected to mimic extracellular conditions).

i. Redox Cleavable Linking Groups

In one embodiment, a cleavable linking group is a redox cleavable linking group that is cleaved upon reduction or oxidation. An example of reductively cleavable linking group is a disulphide linking group (—S—S—). To determine if a candidate cleavable linking group is a suitable "reductively cleavable linking group," or for example is suitable for use with a particular iRNA moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In one, candidate compounds are cleaved by at most about 10% in the blood. In other embodiments, useful candidate compounds are degraded at least about 2, 4, 10, 20, 30, 40, 50, 60, 70, 80, 90, or about 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

ii. Phosphate-Based Cleavable Linking Groups

In another embodiment, a cleavable linker comprises a phosphate-based cleavable linking group. A phosphate-based cleavable linking group is cleaved by agents that degrade or hydrolyze the phosphate group. An example of an agent that cleaves phosphate groups in cells are enzymes such as phosphatases in cells. Examples of phosphate-based linking groups are —O—P(O)(ORk)-O—, —O—P(S)(ORk)-O—, —O—P(S)(SRk)-O—, —S—P(O)(ORk)-O—, —O—P(O)(ORk)-S—, —S—P(O)(ORk)-S—, —O—P(S)(ORk)-S—, —S—P(S)(ORk)-O—, —O—P(O)(Rk)-O—, —O—P(S)(Rk)-O—, —S—P(O)(Rk)-O—, —S—P(S)(Rk)-O—, —S—P(O)(Rk)-S—, —O—P(S)(Rk)-S—. Preferred embodiments are —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O, —S—P(S)(H)—O—, —S—P(O)(H)—S—, —O—P(S)(H)—S—. A preferred embodiment is —O—P(O)(OH)—O—. These candidates can be evaluated using methods analogous to those described above.

Iii. Acid Cleavable Linking Groups

In another embodiment, a cleavable linker comprises an acid cleavable linking group. An acid cleavable linking group is a linking group that is cleaved under acidic conditions. In preferred embodiments acid cleavable linking groups are cleaved in an acidic environment with a pH of about 6.5 or lower (e.g., about 6.0, 5.75, 5.5, 5.25, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C═NN—, C(O)O, or —OC(O). A preferred embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

iv. Ester-Based Linking Groups

In another embodiment, a cleavable linker comprises an ester-based cleavable linking group. An ester-based cleavable linking group is cleaved by enzymes such as esterases and amidases in cells. Examples of ester-based cleavable linking groups include but are not limited to esters of alkylene, alkenylene and alkynylene groups. Ester cleavable linking groups have the general formula —C(O)O—, or —OC(O)—. These candidates can be evaluated using methods analogous to those described above.

v. Peptide-Based Cleaving Groups

In yet another embodiment, a cleavable linker comprises a peptide-based cleavable linking group. A peptide-based cleavable linking group is cleaved by enzymes such as peptidases and proteases in cells. Peptide-based cleavable linking groups are peptide bonds formed between amino acids to yield oligopeptides (e.g., dipeptides, tripeptides etc.) and polypeptides. Peptide-based cleavable groups do not include the amide group (—C(O)NH—). The amide group can be formed between any alkylene, alkenylene or alkynelene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide-based cleavable linking groups have the general formula —NHCHRAC(O)NHCHRBC(O), where RA and RB are the R groups of the two adjacent amino acids. These candidates can be evaluated using methods analogous to those described above.

In one embodiment, an iRNA of the invention is conjugated to a carbohydrate through a linker. Non-limiting examples of iRNA carbohydrate conjugates with linkers of the compositions and methods of the invention include, but are not limited to, (Formula XXIV)

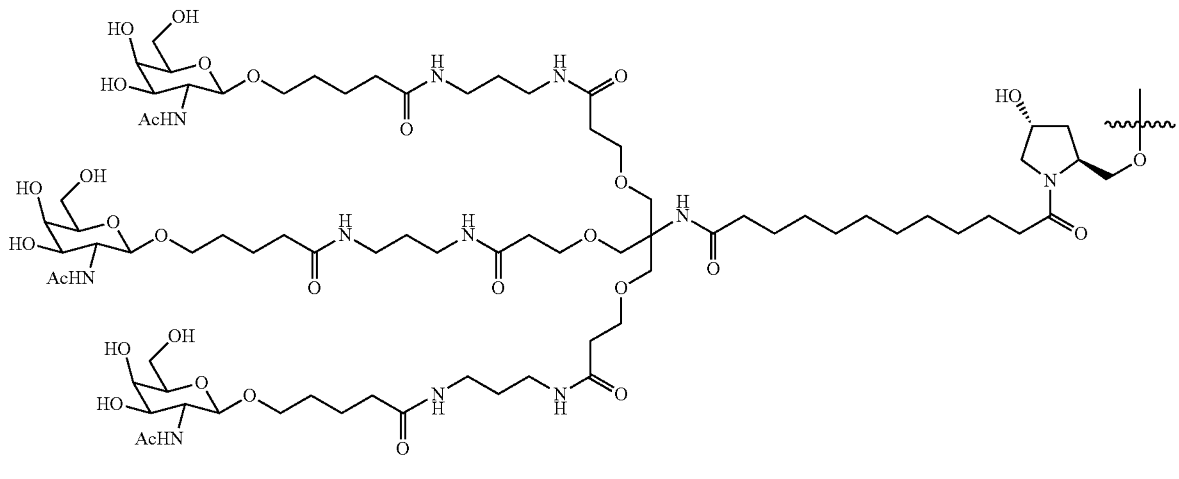
,

-continued
(Formula XXV)
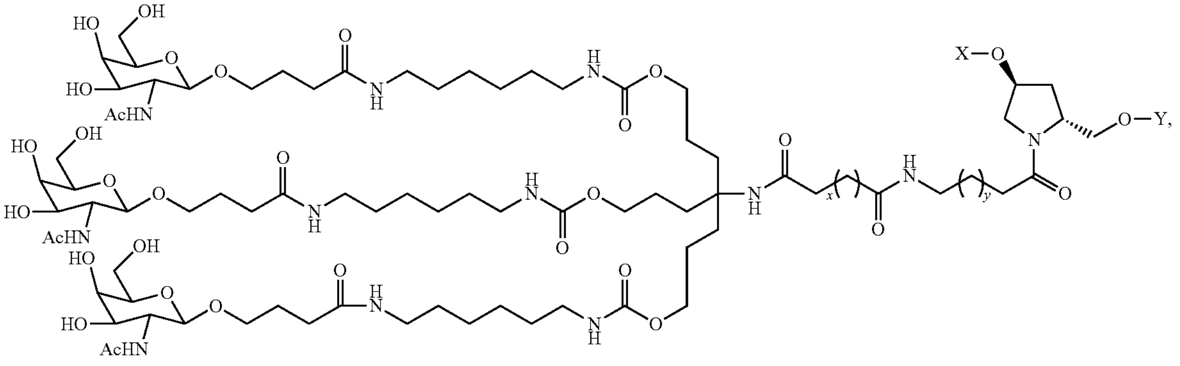
x = 1-30
y = 1-15
(Formula XXVI)
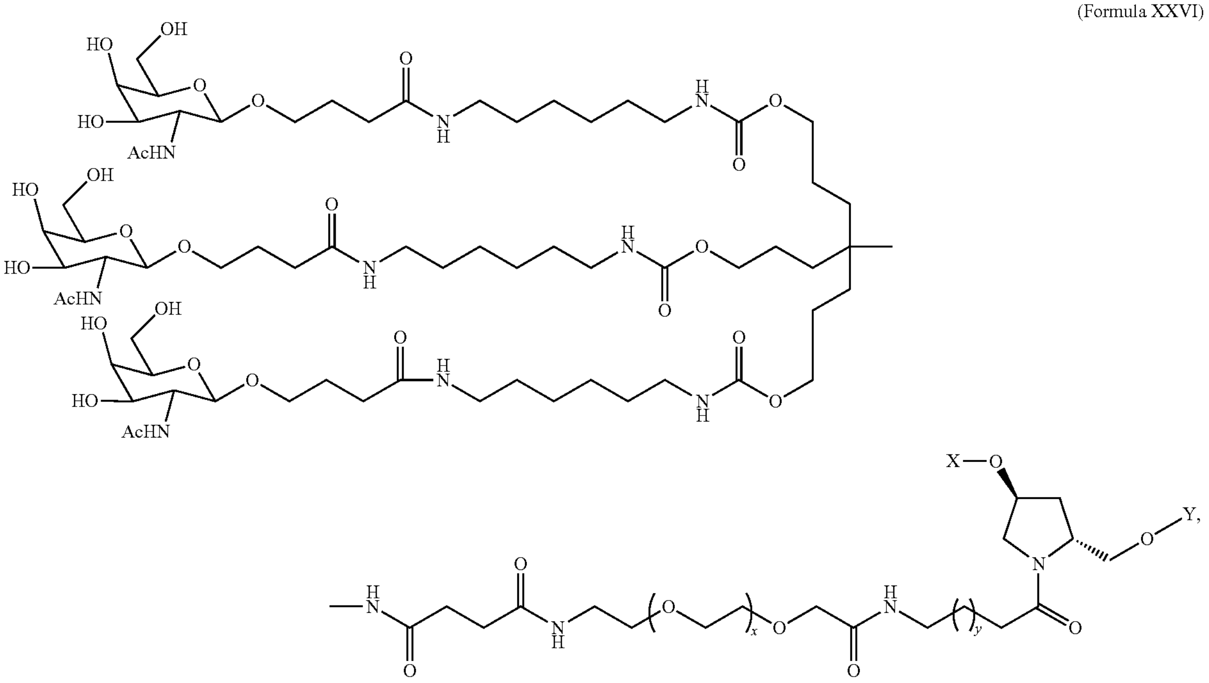
x = 1-30
y = 1-15
(Formula XXVII)
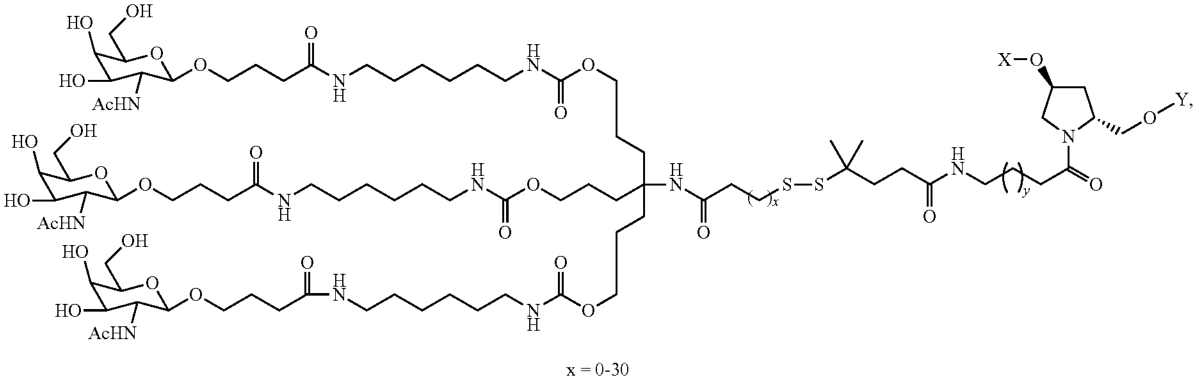
x = 0-30
y = 1-15

-continued
(Formula XXVIII)
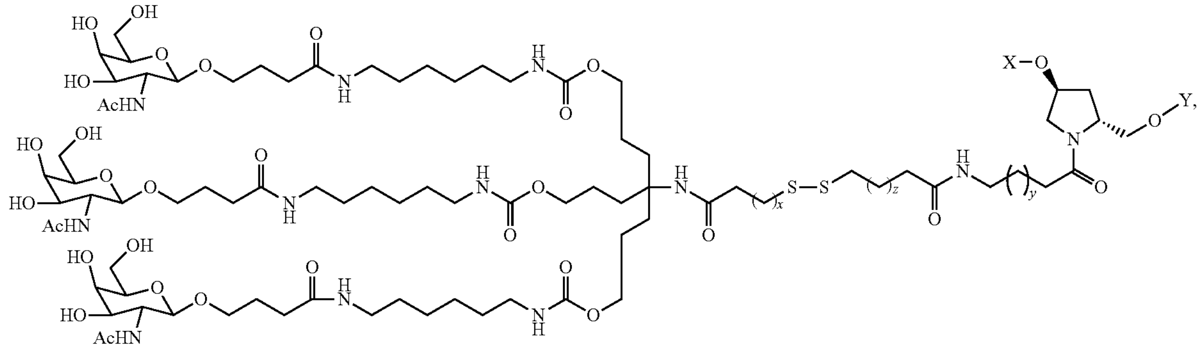
x = 0-30
y = 1-15
z = 1-20
(Formula XXIX)
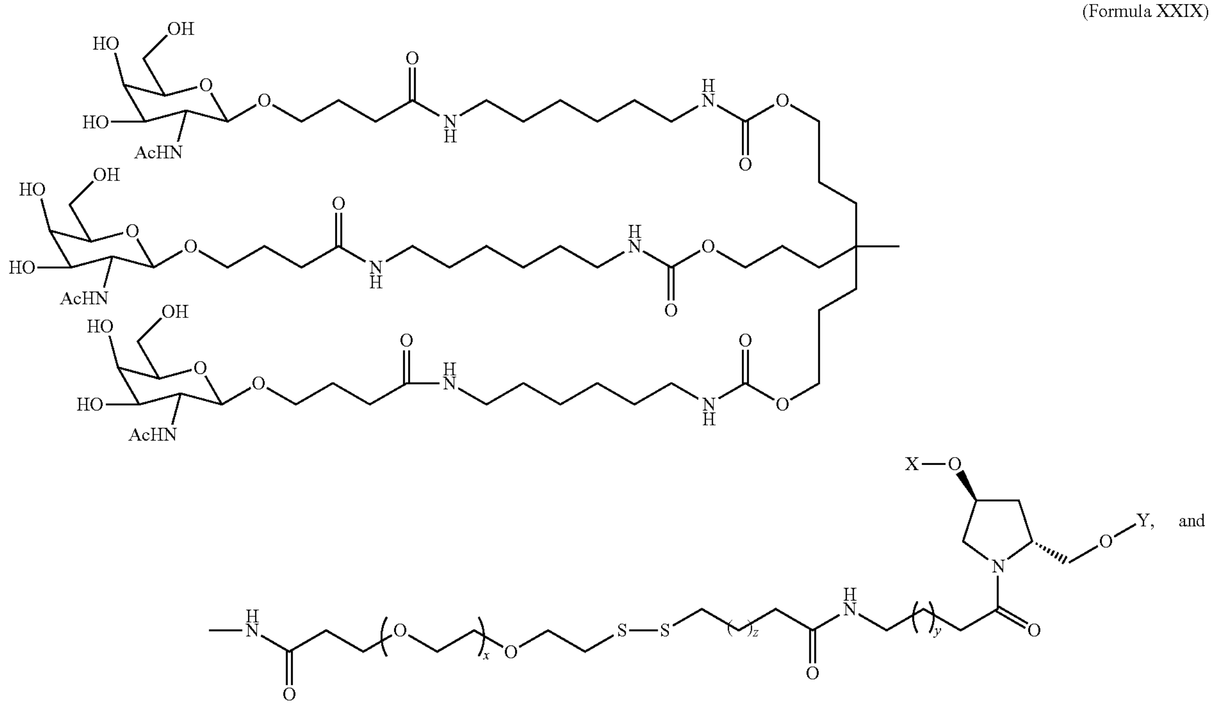
and
x = 1-30
y = 1-15
z = 1-20
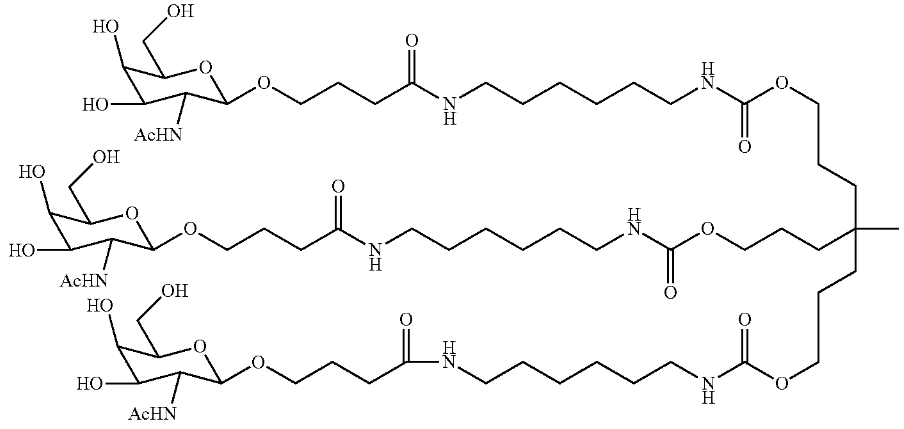

-continued

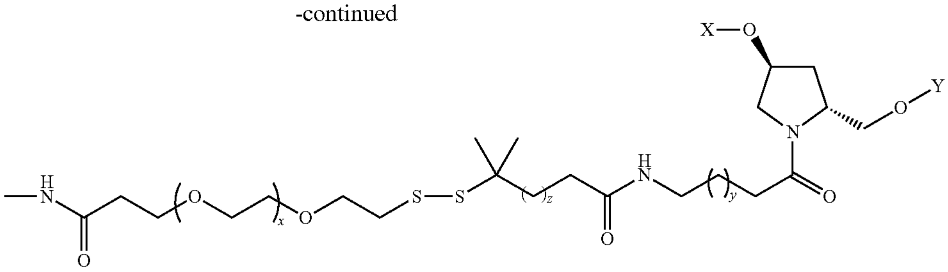

x = 1-30
y = 1-15
z = 1-20

(Formula XXX), when one of X or Y is an oligonucleotide, the other is a hydrogen.

In certain embodiments of the compositions and methods of the invention, a ligand is one or more "GalNAc" (N-acetylgalactosamine) derivatives attached through a bivalent or trivalent branched linker.

In one embodiment, a dsRNA of the invention is conjugated to a bivalent or trivalent branched linker selected from the group of structures shown in any of formula (XXXI)-(XXXIV):

Formula XXXI

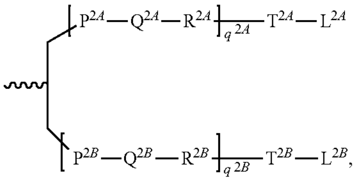

Formula XXXII

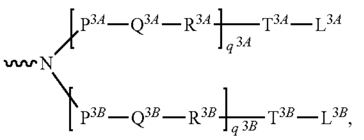

Formula XXXIII

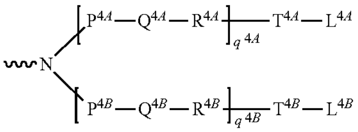

Formula XXXIV

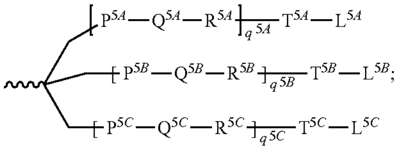

wherein:

q2A, q2B, q3A, q3B, q4A, q4B, q5A, q5B and q5C represent independently for each occurrence 0-20 and wherein the repeating unit can be the same or different;

$P^{2A}$, $P^{2B}$, $P^{3A}$, $P^{3B}$, $P^{4A}$, $P^{4B}$, $P^{5A}$, $P^{5B}$, $P^{5C}$, $T^{2A}$, $T^{2B}$, $T^{3A}$, $T^{3B}$, $T^{4A}$, $T^{4B}$, $T^{4A}$, $T^{5B}$, $T^{5C}$ are each independently for each occurrence absent, CO, NH, O, S, OC(O), NHC(O), $CH_2$, $CH_2NH$ or $CH_2O$;

$Q^{2A}$, $Q^{2B}$, $Q^{3A}$, $Q^{3B}$, $Q^{4A}$, $Q^{4B}$, $Q^{5A}$, $Q^{5B}$, $Q^{5C}$ are independently for each occurrence absent, alkylene, substituted alkylene wherein one or more methylenes can be interrupted or terminated by one or more of O, S, S(O), $SO_2$, $N(R^N)$, C(R')=C(R"), C≡C or C(O);

$R^{2A}$, $R^{2B}$, $R^{3A}$, $R^{3B}$, $R^{4A}$, $R^{4B}$, $R^{5A}$, $R^{5B}$, $R^{5C}$ are each independently for each occurrence absent, NH, O, S, $CH_2$, C(O)O, C(O)NH, $NHCH(R^a)C(O)$, $—C(O)—CH(R^a)—NH—$, CO, CH=N—O,

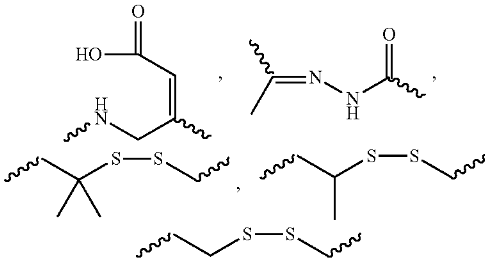

or heterocyclyl;

$L^{2A}$, $L^{2B}$, $L^{3A}$, $L^{3B}$, $L^{4A}$, $L^{4B}$, $L^{5A}$, $L^{5B}$ and $L^{5C}$ represent the ligand; i.e. each independently for each occurrence a monosaccharide (such as GalNAc), disaccharide, trisaccharide, tetrasaccharide, oligosaccharide, or polysaccharide; and $R^a$ is H or amino acid side chain. Trivalent conjugating GalNAc derivatives are particularly useful for use with RNAi agents for inhibiting the expression of a target gene, such as those of formula (XXXV):

Formula XXXV

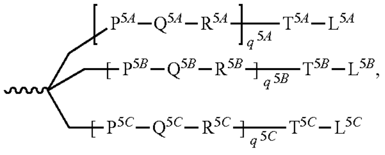

wherein $L^{5A}$, $L^{5B}$ and $L^{5C}$ represent a monosaccharide, such as GalNAc derivative. Examples of suitable bivalent and trivalent branched linker groups conjugating GalNAc derivatives include, but are not limited to, the structures recited above as formulas II, VII, XI, X, and XIII.

Representative U.S. patents that teach the preparation of RNA conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022;

5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941; 6,294,664; 6,320,017; 6,576,752; 6,783,931; 6,900,297; 7,037,646; 8,106,022, the entire contents of each of which are hereby incorporated herein by reference.

It is not necessary for all positions in a given compound to be uniformly modified, and in fact more than one of the aforementioned modifications can be incorporated in a single compound or even at a single nucleoside within an iRNA. The present invention also includes iRNA compounds that are chimeric compounds.

"Chimeric" iRNA compounds or "chimeras," in the context of this invention, are iRNA compounds, preferably dsRNAs, which contain two or more chemically distinct regions, each made up of at least one monomer unit, i.e., a nucleotide in the case of a dsRNA compound. These iRNAs typically contain at least one region wherein the RNA is modified so as to confer upon the iRNA increased resistance to nuclease degradation, increased cellular uptake, and/or increased binding affinity for the target nucleic acid. An additional region of the iRNA can serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of iRNA inhibition of gene expression. Consequently, comparable results can often be obtained with shorter iRNAs when chimeric dsRNAs are used, compared to phosphorothioate deoxy dsRNAs hybridizing to the same target region. Cleavage of the RNA target can be routinely detected by gel electrophoresis and, if necessary, associated nucleic acid hybridization techniques known in the art.

In certain instances, the RNA of an iRNA can be modified by a non-ligand group. A number of non-ligand molecules have been conjugated to iRNAs in order to enhance the activity, cellular distribution or cellular uptake of the iRNA, and procedures for performing such conjugations are available in the scientific literature. Such non-ligand moieties have included lipid moieties, such as cholesterol (Kubo, T. et al., *Biochem. Biophys. Res. Comm.,* 2007, 365(1):54-61; Letsinger et al., *Proc. Natl. Acad. Sci. USA,* 1989, 86:6553), cholic acid (Manoharan et al., *Bioorg. Med. Chem. Lett.,* 1994, 4:1053), a thioether, e.g., hexyl-5-tritylthiol (Manoharan et al., *Ann. N.Y. Acad. Sci.,* 1992, 660:306; Manoharan et al., *Bioorg. Med. Chem. Let.,* 1993, 3:2765), a thiocholesterol (Oberhauser et al., *Nucl. Acids Res.,* 1992, 20:533), an aliphatic chain, e.g., dodecandiol or undecyl residues (Saison-Behmoaras et al., *EMBO J.,* 1991, 10:111; Kabanov et al., *FEBS Lett.,* 1990, 259:327; Svinarchuk et al., *Biochimie,* 1993, 75:49), a phospholipid, e.g., di-hexadecyl-rac-glycerol or triethylammonium 1,2-di-O-hexadecyl-rac-glycero-3-H-phosphonate (Manoharan et al., *Tetrahedron Lett.,* 1995, 36:3651; Shea et al., *Nucl. Acids Res.,* 1990, 18:3777), a polyamine or a polyethylene glycol chain (Manoharan et al., *Nucleosides & Nucleotides,* 1995, 14:969), or adamantane acetic acid (Manoharan et al., *Tetrahedron Lett.,* 1995, 36:3651), a palmityl moiety (Mishra et al., *Biochim. Biophys. Acta,* 1995, 1264:229), or an octadecylamine or hexylamino-carbonyl-oxycholesterol moiety (Crooke et al., *J. Pharmacol. Exp. Ther.,* 1996, 277:923). Representative United States patents that teach the preparation of such RNA conjugates have been listed above. Typical conjugation protocols involve the synthesis of an RNAs bearing an aminolinker at one or more positions of the sequence. The amino group is then reacted with the molecule being conjugated using appropriate coupling or activating reagents. The conjugation reaction can be performed either with the RNA still bound to the solid support or following cleavage of the RNA, in solution phase. Purification of the RNA conjugate by HPLC typically affords the pure conjugate.

IV. DELIVERY OF AN iRNA OF THE INVENTION

The delivery of an iRNA of the invention to a cell e.g., a cell within a subject, such as a human subject (e.g., a subject in need thereof, such as a subject having a bleeding disorder) can be achieved in a number of different ways. For example, delivery may be performed by contacting a cell with an iRNA of the invention either in vitro or in vivo. In vivo delivery may also be performed directly by administering a composition comprising an iRNA, e.g., a dsRNA, to a subject. Alternatively, in vivo delivery may be performed indirectly by administering one or more vectors that encode and direct the expression of the iRNA. These alternatives are discussed further below.

In general, any method of delivering a nucleic acid molecule (in vitro or in vivo) can be adapted for use with an iRNA of the invention (see e.g., Akhtar S, and Julian R L. (1992) *Trends Cell. Biol.* 2(5):139-144 and WO94/02595, which are incorporated herein by reference in their entireties). For in vivo delivery, factors to consider in order to deliver an iRNA molecule include, for example, biological stability of the delivered molecule, prevention of non-specific effects, and accumulation of the delivered molecule in the target tissue. The non-specific effects of an iRNA can be minimized by local administration, for example, by direct injection or implantation into a tissue or topically administering the preparation. Local administration to a treatment site maximizes local concentration of the agent, limits the exposure of the agent to systemic tissues that can otherwise be harmed by the agent or that can degrade the agent, and permits a lower total dose of the iRNA molecule to be administered. Several studies have shown successful knockdown of gene products when an iRNA is administered locally. For example, intraocular delivery of a VEGF dsRNA by intravitreal injection in cynomolgus monkeys (Tolentino, M J., et al (2004) *Retina* 24:132-138) and subretinal injections in mice (Reich, S J., et al (2003) *Mol. Vis.* 9:210-216) were both shown to prevent neovascularization in an experimental model of age-related macular degeneration. In addition, direct intratumoral injection of a dsRNA in mice reduces tumor volume (Pille, J., et al (2005) *Mol. Ther.* 11:267-274) and can prolong survival of tumor-bearing mice (Kim, W J., et al (2006) *Mol. Ther.* 14:343-350; Li, S., et al (2007) *Mol. Ther.* 15:515-523). RNA interference has also shown success with local delivery to the CNS by direct injection (Dorn, G., et al. (2004) *Nucleic Acids* 32:e49; Tan, P H., et al (2005) *Gene Ther.* 12:59-66; Makimura, H., et al (2002) *BMC Neurosci.* 3:18; Shishkina, G T., et al (2004) *Neuroscience* 129:521-528; Thakker, E R., et al (2004) *Proc. Natl. Acad. Sci. U.S.A.* 101:17270-17275; Akaneya, Y., et al (2005) *J. Neurophysiol.* 93:594-602) and to the lungs by intranasal administration (Howard, K A., et al (2006) *Mol. Ther.* 14:476-484; Zhang, X., et al (2004) *J. Biol. Chem.* 279:10677-10684; Bitko, V., et al (2005) *Nat. Med.* 11:50-55). For administering an iRNA systemically for the treatment of a disease, the RNA can be modified or alternatively delivered using a drug delivery system; both methods act to prevent the rapid degradation of the dsRNA by endo- and exo-nucleases in vivo. Modification of the RNA or the pharmaceutical carrier can also permit targeting of the iRNA composition to the target tissue and avoid undesirable off-target effects. iRNA molecules can be modified by chemical conjugation to lipophilic groups such as cholesterol to enhance cellular uptake and prevent degradation. For example, an iRNA directed against ApoB conjugated to a lipophilic cholesterol moiety was injected systemically into mice and resulted in knockdown of apoB mRNA in both the liver and jejunum (Soutschek, J., et al (2004) *Nature* 432:173-178). Conjugation of an iRNA to an aptamer has been shown to inhibit tumor growth and mediate tumor regression in a mouse model of prostate cancer (McNamara, J O., et al (2006) *Nat. Biotechnol.* 24:1005-1015). In an alternative embodiment, the iRNA can be delivered using drug delivery systems such as a nanoparticle, a dendrimer, a polymer, liposomes, or a cationic delivery system. Positively charged cationic delivery systems facilitate binding of an iRNA molecule (negatively charged) and also enhance interactions at the negatively charged cell membrane to permit efficient uptake of an iRNA by the cell. Cationic lipids, dendrimers, or polymers can either be bound to an iRNA, or induced to form a vesicle or micelle (see e.g., Kim S H., et al (2008) *Journal of Controlled Release* 129(2):107-116) that encases an iRNA. The formation of vesicles or micelles further prevents degradation of the iRNA when administered systemically. Methods for making and administering cationic-iRNA complexes are well within the abilities of one skilled in the art (see e.g., Sorensen, D R., et al (2003) *J. Mol. Biol.* 327:761-766; Verma, U N., et al (2003) *Clin. Cancer Res.* 9:1291-1300; Arnold, A S et al (2007) *J. Hypertens.* 25:197-205, which are incorporated herein by reference in their entirety). Some non-limiting examples of drug delivery systems useful for systemic delivery of iRNAs include DOTAP (Sorensen, D R., et al (2003), supra; Verma, U N., et al (2003), supra), Oligofectamine, "solid nucleic acid lipid particles" (Zimmermann, T S., et al (2006) *Nature* 441:111-114), cardiolipin (Chien, P Y., et al (2005) *Cancer Gene Ther.* 12:321-328; Pal, A., et al (2005) *Int J. Oncol.* 26:1087-1091), polyethyleneimine (Bonnet M E., et al (2008) *Pharm. Res.* August 16 Epub ahead of print; Aigner, A. (2006) *J. Biomed. Biotechnol.* 71659), Arg-Gly-Asp (RGD) peptides (Liu, S. (2006) *Mol. Pharm.* 3:472-487), and polyamidoamines (Tomalia, D A., et al (2007) *Biochem. Soc. Trans.* 35:61-67; Yoo, H., et al (1999) *Pharm. Res.* 16:1799-1804). In some embodiments, an iRNA forms a complex with cyclodextrin for systemic administration. Methods for administration and pharmaceutical compositions of iRNAs and cyclodextrins can be found in U.S. Pat. No. 7,427,605, which is herein incorporated by reference in its entirety.

A. Vector Encoded iRNAs of the Invention iRNA targeting the Serpinc1 gene can be expressed from transcription units inserted into DNA or RNA vectors (see, e.g., Couture, A, et al., *TIG.* (1996), 12:5-10; Skillern, A., et al., International PCT Publication No. WO 00/22113, Conrad, International PCT Publication No. WO 00/22114, and Conrad, U.S. Pat. No. 6,054,299). Expression can be transient (on the order of hours to weeks) or sustained (weeks to months or longer), depending upon the specific construct used and the target tissue or cell type. These transgenes can be introduced as a linear construct, a circular plasmid, or a viral vector, which can be an integrating or non-integrating vector. The transgene can also be constructed to permit it to be inherited as an extrachromosomal plasmid (Gassmann, et al., *Proc. Natl. Acad. Sci. USA* (1995) 92:1292).

The individual strand or strands of an iRNA can be transcribed from a promoter on an expression vector. Where two separate strands are to be expressed to generate, for example, a dsRNA, two separate expression vectors can be co-introduced (e.g., by transfection or infection) into a target cell. Alternatively each individual strand of a dsRNA can be transcribed by promoters both of which are located on the same expression plasmid. In one embodiment, a dsRNA is expressed as inverted repeat polynucleotides joined by a linker polynucleotide sequence such that the dsRNA has a stem and loop structure.

iRNA expression vectors are generally DNA plasmids or viral vectors. Expression vectors compatible with eukaryotic cells, preferably those compatible with vertebrate cells, can be used to produce recombinant constructs for the expression of an iRNA as described herein. Eukaryotic cell expression vectors are well known in the art and are available from a number of commercial sources. Typically, such vectors are provided containing convenient restriction sites for insertion of the desired nucleic acid segment. Delivery of iRNA expressing vectors can be systemic, such as by intravenous or intramuscular administration, by administration to target cells ex-planted from the patient followed by reintroduction into the patient, or by any other means that allows for introduction into a desired target cell.

iRNA expression plasmids can be transfected into target cells as a complex with cationic lipid carriers (e.g., Oligofectamine) or non-cationic lipid-based carriers (e.g., Transit-TKO™). Multiple lipid transfections for iRNA-mediated knockdowns targeting different regions of a target RNA over a period of a week or more are also contemplated by the invention. Successful introduction of vectors into host cells can be monitored using various known methods. For example, transient transfection can be signaled with a reporter, such as a fluorescent marker, such as Green Fluorescent Protein (GFP). Stable transfection of cells ex vivo can be ensured using markers that provide the transfected cell with resistance to specific environmental factors (e.g., antibiotics and drugs), such as hygromycin B resistance.

Viral vector systems which can be utilized with the methods and compositions described herein include, but are not limited to, (a) adenovirus vectors; (b) retrovirus vectors, including but not limited to lentiviral vectors, moloney murine leukemia virus, etc.; (c) adeno-associated virus vectors; (d) herpes simplex virus vectors; (e) SV 40 vectors; (f) polyoma virus vectors; (g) papilloma virus vectors; (h) picornavirus vectors; (i) pox virus vectors such as an orthopox, e.g., vaccinia virus vectors or avipox, e.g. canary pox or fowl pox; and (j) a helper-dependent or gutless adenovirus. Replication-defective viruses can also be advantageous. Different vectors will or will not become incorporated into the cells' genome. The constructs can include viral sequences for transfection, if desired. Alternatively, the construct can be incorporated into vectors capable of episomal replication, e.g. EPV and EBV vectors. Constructs for the recombinant expression of an iRNA will generally require regulatory elements, e.g., promoters, enhancers, etc., to ensure the expression of the iRNA in target cells. Other aspects to consider for vectors and constructs are further described below.

Vectors useful for the delivery of an iRNA will include regulatory elements (promoter, enhancer, etc.) sufficient for expression of the iRNA in the desired target cell or tissue. The regulatory elements can be chosen to provide either constitutive or regulated/inducible expression.

Expression of the iRNA can be precisely regulated, for example, by using an inducible regulatory sequence that is sensitive to certain physiological regulators, e.g., circulating glucose levels, or hormones (Docherty et al., 1994, *FASEB J.* 8:20-24). Such inducible expression systems, suitable for the control of dsRNA expression in cells or in mammals include, for example, regulation by ecdysone, by estrogen, progesterone, tetracycline, chemical inducers of dimerization, and isopropyl-beta-D1-thiogalactopyranoside (IPTG). A person skilled in the art would be able to choose the appropriate regulatory/promoter sequence based on the intended use of the iRNA transgene.

Viral vectors that contain nucleic acid sequences encoding an iRNA can be used. For example, a retroviral vector can be used (see Miller et al., *Meth. Enzymol.* 217:581-599 (1993)). These retroviral vectors contain the components necessary for the correct packaging of the viral genome and integration into the host cell DNA. The nucleic acid sequences encoding an iRNA are cloned into one or more vectors, which facilitate delivery of the nucleic acid into a patient. More detail about retroviral vectors can be found, for example, in Boesen et al., *Biotherapy* 6:291-302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., *J. Clin. Invest.* 93:644-651 (1994); Kiem et al., *Blood* 83:1467-1473 (1994); Salmons and Gunzberg, *Human Gene Therapy* 4:129-141 (1993); and Grossman and Wilson, *Curr. Opin. in Genetics and Devel.* 3:110-114 (1993). Lentiviral vectors contemplated for use include, for example, the HIV based vectors described in U.S. Pat. Nos. 6,143,520; 5,665,557; and 5,981,276, which are herein incorporated by reference.

Adenoviruses are also contemplated for use in delivery of iRNAs of the invention. Adenoviruses are especially attractive vehicles, e.g., for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, *Current Opinion in Genetics and Development* 3:499-503 (1993) present a review of adenovirus-based gene therapy. Bout et al., *Human Gene Therapy* 5:3-10 (1994) demonstrated the use of adenovirus vectors to transfer genes to the respiratory epithelia of rhesus monkeys. Other instances of the use of adenoviruses in gene therapy can be found in Rosenfeld et al., *Science* 252:431-434 (1991); Rosenfeld et al., *Cell* 68:143-155 (1992); Mastrangeli et al., *J. Clin. Invest.* 91:225-234 (1993); PCT Publication WO94/12649; and Wang, et al., *Gene Therapy* 2:775-783 (1995). A suitable AV vector for expressing an iRNA featured in the invention, a method for constructing the recombinant AV vector, and a method for delivering the vector into target cells, are described in Xia H et al. (2002), *Nat. Biotech.* 20: 1006-1010.

Adeno-associated virus (AAV) vectors may also be used to delivery an iRNA of the invention (Walsh et al., Proc. Soc. Exp. Biol. Med. 204:289-300 (1993); U.S. Pat. No. 5,436,146). In one embodiment, the iRNA can be expressed as two separate, complementary single-stranded RNA molecules from a recombinant AAV vector having, for example, either the U6 or H1 RNA promoters, or the cytomegalovirus (CMV) promoter. Suitable AAV vectors for expressing the dsRNA featured in the invention, methods for constructing the recombinant AV vector, and methods for delivering the vectors into target cells are described in Samulski R et al. (1987), *J. Virol.* 61: 3096-3101; Fisher K J et al. (1996), *J. Virol,* 70: 520-532; Samulski R et al. (1989), *J. Virol.* 63: 3822-3826; U.S. Pat. No. 5,252,479; U.S. Pat. No. 5,139,941; International Patent Application No. WO 94/13788; and International Patent Application No. WO 93/24641, the entire disclosures of which are herein incorporated by reference.

Another viral vector suitable for delivery of an iRNA of the invention is a pox virus such as a vaccinia virus, for example an attenuated vaccinia such as Modified Virus Ankara (MVA) or NYVAC, an avipox such as fowl pox or canary pox.

The tropism of viral vectors can be modified by pseudotyping the vectors with envelope proteins or other surface antigens from other viruses, or by substituting different viral capsid proteins, as appropriate. For example, lentiviral vectors can be pseudotyped with surface proteins from vesicular stomatitis virus (VSV), rabies, Ebola, Mokola, and the like. AAV vectors can be made to target different cells by engineering the vectors to express different capsid protein serotypes; see, e.g., Rabinowitz J E et al. (2002), *J Virol* 76:791-801, the entire disclosure of which is herein incorporated by reference.

The pharmaceutical preparation of a vector can include the vector in an acceptable diluent, or can include a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

V. PHARMACEUTICAL COMPOSITIONS OF THE INVENTION

The present invention also includes pharmaceutical compositions and formulations which include the iRNAs of the invention. In one embodiment, provided herein are pharmaceutical compositions containing an iRNA, as described herein, and a pharmaceutically acceptable carrier. The pharmaceutical compositions containing the iRNA are useful for treating a disease or disorder associated with the expression or activity of a Serpinc1 gene, e.g. a bleeding disorder. Such pharmaceutical compositions are formulated based on the mode of delivery. One example is compositions that are formulated for systemic administration via parenteral delivery, e.g., by intravenous (IV) delivery. Another example is compositions that are formulated for direct delivery into the brain parenchyma, e.g., by infusion into the brain, such as by continuous pump infusion. The pharmaceutical compositions of the invention may be administered in dosages sufficient to inhibit expression of a Serpinc1 gene. In general, a suitable dose of an iRNA of the invention will be in the range of about 0.001 to about 200.0 milligrams per kilogram body weight of the recipient per day, generally in the range of about 1 to 50 mg per kilogram body weight per day. For example, the dsRNA can be administered at about 0.01 mg/kg, about 0.05 mg/kg, about 0.5 mg/kg, about 1 mg/kg, about 1.5 mg/kg, about 2 mg/kg, about 3 mg/kg, about 10 mg/kg, about 20 mg/kg, about 30 mg/kg, about 40 mg/kg, or about 50 mg/kg per single dose.

For example, the dsRNA may be administered at a dose of about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or about 10 mg/kg. Values and ranges intermediate to the recited values are also intended to be part of this invention.

In another embodiment, the dsRNA is administered at a dose of about 0.1 to about 50 mg/kg, about 0.25 to about 50 mg/kg, about 0.5 to about 50 mg/kg, about 0.75 to about 50 mg/kg, about 1 to about 50 mg/mg, about 1.5 to about 50 mg/kb, about 2 to about 50 mg/kg, about 2.5 to about 50 mg/kg, about 3 to about 50 mg/kg, about 3.5 to about 50 mg/kg, about 4 to about 50 mg/kg, about 4.5 to about 50 mg/kg, about 5 to about 50 mg/kg, about 7.5 to about 50 mg/kg, about 10 to about 50 mg/kg, about 15 to about 50 mg/kg, about 20 to about 50 mg/kg, about 20 to about 50 mg/kg, about 25 to about 50 mg/kg, about 25 to about 50 mg/kg, about 30 to about 50 mg/kg, about 35 to about 50 mg/kg, about 40 to about 50 mg/kg, about 45 to about 50 mg/kg, about 0.1 to about 45 mg/kg, about 0.25 to about 45 mg/kg, about 0.5 to about 45 mg/kg, about 0.75 to about 45 mg/kg, about 1 to about 45 mg/mg, about 1.5 to about 45 mg/kb, about 2 to about 45 mg/kg, about 2.5 to about 45 mg/kg, about 3 to about 45 mg/kg, about 3.5 to about 45 mg/kg, about 4 to about 45 mg/kg, about 4.5 to about 45 mg/kg, about 5 to about 45 mg/kg, about 7.5 to about 45 mg/kg, about 10 to about 45 mg/kg, about 15 to about 45 mg/kg, about 20 to about 45 mg/kg, about 20 to about 45 mg/kg, about 25 to about 45 mg/kg, about 25 to about 45 mg/kg, about 30 to about 45 mg/kg, about 35 to about 45 mg/kg, about 40 to about 45 mg/kg, about 0.1 to about 40 mg/kg, about 0.25 to about 40 mg/kg, about 0.5 to about 40 mg/kg, about 0.75 to about 40 mg/kg, about 1 to about 40 mg/mg, about 1.5 to about 40 mg/kb, about 2 to about 40 mg/kg, about 2.5 to about 40 mg/kg, about 3 to about 40 mg/kg, about 3.5 to about 40 mg/kg, about 4 to about 40 mg/kg, about 4.5 to about 40 mg/kg, about 5 to about 40 mg/kg, about 7.5 to about 40 mg/kg, about 10 to about 40 mg/kg, about 15 to about 40 mg/kg, about 20 to about 40 mg/kg, about 20 to about 40 mg/kg, about 25 to about 40 mg/kg, about 25 to about 40 mg/kg, about 30 to about 40 mg/kg, about 35 to about 40 mg/kg, about 0.1 to about 30 mg/kg, about 0.25 to about 30 mg/kg, about 0.5 to about 30 mg/kg, about 0.75 to about 30 mg/kg, about 1 to about 30 mg/mg, about 1.5 to about 30 mg/kb, about 2 to about 30 mg/kg, about 2.5 to about 30 mg/kg, about 3 to about 30 mg/kg, about 3.5 to about 30 mg/kg, about 4 to about 30 mg/kg, about 4.5 to about 30 mg/kg, about 5 to about 30 mg/kg, about 7.5 to about 30 mg/kg, about 10 to about 30 mg/kg, about 15 to about 30 mg/kg, about 20 to about 30 mg/kg, about 20 to about 30 mg/kg, about 25 to about 30 mg/kg, about 0.1 to about 20 mg/kg, about 0.25 to about 20 mg/kg, about 0.5 to about 20 mg/kg, about 0.75 to about 20 mg/kg, about 1 to about 20 mg/mg, about 1.5 to about 20 mg/kb, about 2 to about 20 mg/kg, about 2.5 to about 20 mg/kg, about 3 to about 20 mg/kg, about 3.5 to about 20 mg/kg, about 4 to about 20 mg/kg, about 4.5 to about 20 mg/kg, about 5 to about 20 mg/kg, about 7.5 to about 20 mg/kg, about 10 to about 20 mg/kg, or about 15 to about 20 mg/kg. Values and ranges intermediate to the recited values are also intended to be part of this invention.

For example, the dsRNA may be administered at a dose of about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or about 10 mg/kg. Values and ranges intermediate to the recited values are also intended to be part of this invention.

In another embodiment, the dsRNA is administered at a dose of about 0.5 to about 50 mg/kg, about 0.75 to about 50 mg/kg, about 1 to about 50 mg/mg, about 1.5 to about 50 mg/kb, about 2 to about 50 mg/kg, about 2.5 to about 50 mg/kg, about 3 to about 50 mg/kg, about 3.5 to about 50 mg/kg, about 4 to about 50 mg/kg, about 4.5 to about 50 mg/kg, about 5 to about 50 mg/kg, about 7.5 to about 50 mg/kg, about 10 to about 50 mg/kg, about 15 to about 50 mg/kg, about 20 to about 50 mg/kg, about 20 to about 50 mg/kg, about 25 to about 50 mg/kg, about 25 to about 50 mg/kg, about 30 to about 50 mg/kg, about 35 to about 50 mg/kg, about 40 to about 50 mg/kg, about 45 to about 50 mg/kg, about 0.5 to about 45 mg/kg, about 0.75 to about 45 mg/kg, about 1 to about 45 mg/mg, about 1.5 to about 45 mg/kb, about 2 to about 45 mg/kg, about 2.5 to about 45 mg/kg, about 3 to about 45 mg/kg, about 3.5 to about 45 mg/kg, about 4 to about 45 mg/kg, about 4.5 to about 45 mg/kg, about 5 to about 45 mg/kg, about 7.5 to about 45 mg/kg, about 10 to about 45 mg/kg, about 15 to about 45 mg/kg, about 20 to about 45 mg/kg, about 20 to about 45 mg/kg, about 25 to about 45 mg/kg, about 25 to about 45 mg/kg, about 30 to about 45 mg/kg, about 35 to about 45 mg/kg, about 40 to about 45 mg/kg, about 0.5 to about 40 mg/kg, about 0.75 to about 40 mg/kg, about 1 to about 40 mg/mg, about 1.5 to about 40 mg/kb, about 2 to about 40 mg/kg, about 2.5 to about 40 mg/kg, about 3 to about 40 mg/kg, about 3.5 to about 40 mg/kg, about 4 to about 40 mg/kg, about 4.5 to about 40 mg/kg, about 5 to about 40 mg/kg, about 7.5 to about 40 mg/kg, about 10 to about 40 mg/kg, about 15 to about 40 mg/kg, about 20 to about 40 mg/kg, about 20 to about 40 mg/kg, about 25 to about 40 mg/kg, about 25 to about 40 mg/kg, about 30 to about 40 mg/kg, about 35 to about 40 mg/kg, about 0.5 to about 30 mg/kg, about 0.75 to about 30 mg/kg, about 1 to about 30 mg/mg, about 1.5 to about 30 mg/kb, about 2 to about 30 mg/kg, about 2.5 to about 30 mg/kg, about 3 to about 30 mg/kg, about 3.5 to about 30 mg/kg, about 4 to about 30 mg/kg, about 4.5 to about 30 mg/kg, about 5 to about 30 mg/kg, about 7.5 to about 30 mg/kg, about 10 to about 30 mg/kg, about 15 to about 30 mg/kg, about 20 to about 30 mg/kg, about 20 to about 30 mg/kg, about 25 to about 30 mg/kg, about 0.5 to about 20 mg/kg, about 0.75 to about 20 mg/kg, about 1 to about 20 mg/mg, about 1.5 to about 20 mg/kb, about 2 to about 20 mg/kg, about 2.5 to about 20 mg/kg, about 3 to about 20 mg/kg, about 3.5 to about 20 mg/kg, about 4 to about 20 mg/kg, about 4.5 to about 20 mg/kg, about 5 to about 20 mg/kg, about 7.5 to about 20 mg/kg, about 10 to about 20 mg/kg, or about 15 to about 20 mg/kg. In one embodiment, the dsRNA is administered at a dose of about 10 mg/kg to about 30 mg/kg. Values and ranges intermediate to the recited values are also intended to be part of this invention.

For example, subjects can be administered a therapeutic amount of iRNA, such as about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 31, 32, 33, 34, 34, 35, 36, 37, 38, 39, 40, 41, 42, 43, 44, 45, 46, 47, 48, 49, or about 50 mg/kg. Values and ranges intermediate to the recited values are also intended to be part of this invention.

The pharmaceutical composition can be administered once daily, or the iRNA can be administered as two, three, or more sub-doses at appropriate intervals throughout the day or even using continuous infusion or delivery through a controlled release formulation. In that case, the iRNA contained in each sub-dose must be correspondingly smaller in order to achieve the total daily dosage. The dosage unit can also be compounded for delivery over several days, e.g., using a conventional sustained release formulation which provides sustained release of the iRNA over a several day period. Sustained release formulations are well known in the art and are particularly useful for delivery of agents at a particular site, such as could be used with the agents of the present invention. In this embodiment, the dosage unit contains a corresponding multiple of the daily dose.

In other embodiments, a single dose of the pharmaceutical compositions can be long lasting, such that subsequent doses are administered at not more than 3, 4, or 5 day intervals, or at not more than 1, 2, 3, or 4 week intervals. In some embodiments of the invention, a single dose of the pharmaceutical compositions of the invention is administered once per week. In other embodiments of the invention, a single dose of the pharmaceutical compositions of the invention is administered bi-monthly.

The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual iRNAs encompassed by the invention can be made using conventional methodologies or on the basis of in vivo testing using an appropriate animal model, as described elsewhere herein.

Advances in mouse genetics have generated a number of mouse models for the study of various human diseases, such as a bleeding disorder that would benefit from reduction in the expression of Serpinc1. Such models can be used for in vivo testing of iRNA, as well as for determining a therapeutically effective dose. Suitable mouse models are known in the art and include, for example, Hemophilia A mouse models and Hemophilia B mouse models, e.g., mice containing a knockout of a clotting factor gene, such as those described in Bolliger, et al. (2010) *Thromb Haemost* 103:1233-1238, Bi L, et al. (1995) *Nat Genet.* 10: 119-21, Lin et al. (1997) *Blood* 90: 3962-6, Kundu et al. (1998) *Blood* 92: 168-74, Wang et al. (1997) *Proc Natl Acad Sci USA* 94: 11563-6, and Jin, et al. (2004) *Blood* 104:1733.

The pharmaceutical compositions of the present invention can be administered in a number of ways depending upon whether local or systemic treatment is desired and upon the area to be treated. Administration can be topical (e.g., by a transdermal patch), pulmonary, e.g., by inhalation or insufflation of powders or aerosols, including by nebulizer; intratracheal, intranasal, epidermal and transdermal, oral or parenteral. Parenteral administration includes intravenous, intraarterial, subcutaneous, intraperitoneal or intramuscular injection or infusion; subdermal, e.g., via an implanted device; or intracranial, e.g., by intraparenchymal, intrathecal or intraventricular, administration. The iRNA can be delivered in a manner to target a particular tissue, such as the liver (e.g., the hepatocytes of the liver). Pharmaceutical compositions and formulations for topical administration can include transdermal patches, ointments, lotions, creams, gels, drops, suppositories, sprays, liquids and powders. Conventional pharmaceutical carriers, aqueous, powder or oily bases, thickeners and the like can be necessary or desirable. Coated condoms, gloves and the like can also be useful. Suitable topical formulations include those in which the iRNAs featured in the invention are in admixture with a topical delivery agent such as lipids, liposomes, fatty acids, fatty acid esters, steroids, chelating agents and surfactants. Suitable lipids and liposomes include neutral (e.g., dioleoylphosphatidyl DOPE ethanolamine, dimyristoylphosphatidyl choline DMPC, distearolyphosphatidyl choline) negative (e.g., dimyristoylphosphatidyl glycerol DMPG) and cationic (e.g., dioleoyltetramethylaminopropyl DOTAP and dioleoylphosphatidyl ethanolamine DOTMA). iRNAs featured in the invention can be encapsulated within liposomes or can form complexes thereto, in particular to cationic liposomes. Alternatively, iRNAs can be complexed to lipids, in particular to cationic lipids. Suitable fatty acids and esters include but are not limited to arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-20}$ alkyl ester (e.g., isopropylmyristate IPM), monoglyceride, diglyceride or pharmaceutically acceptable salt thereof). Topical formulations are described in detail in U.S. Pat. No. 6,747,014, which is incorporated herein by reference.

A. iRNA Formulations Comprising Membranous Molecular Assemblies

An iRNA for use in the compositions and methods of the invention can be formulated for delivery in a membranous molecular assembly, e.g., a liposome or a micelle. As used herein, the term "liposome" refers to a vesicle composed of amphiphilic lipids arranged in at least one bilayer, e.g., one bilayer or a plurality of bilayers. Liposomes include unilamellar and multilamellar vesicles that have a membrane formed from a lipophilic material and an aqueous interior. The aqueous portion contains the iRNA composition. The lipophilic material isolates the aqueous interior from an aqueous exterior, which typically does not include the iRNA composition, although in some examples, it may. Liposomes are useful for the transfer and delivery of active ingredients to the site of action. Because the liposomal membrane is structurally similar to biological membranes, when liposomes are applied to a tissue, the liposomal bilayer fuses with bilayer of the cellular membranes. As the merging of the liposome and cell progresses, the internal aqueous contents that include the iRNA are delivered into the cell where the iRNA can specifically bind to a target RNA and can mediate RNAi. In some cases the liposomes are also specifically targeted, e.g., to direct the iRNA to particular cell types.

A liposome containing a RNAi agent can be prepared by a variety of methods. In one example, the lipid component of a liposome is dissolved in a detergent so that micelles are formed with the lipid component. For example, the lipid component can be an amphipathic cationic lipid or lipid conjugate. The detergent can have a high critical micelle concentration and may be nonionic. Exemplary detergents include cholate, CHAPS, octylglucoside, deoxycholate, and lauroyl sarcosine. The RNAi agent preparation is then added to the micelles that include the lipid component. The cationic groups on the lipid interact with the RNAi agent and condense around the RNAi agent to form a liposome. After condensation, the detergent is removed, e.g., by dialysis, to yield a liposomal preparation of RNAi agent.

If necessary a carrier compound that assists in condensation can be added during the condensation reaction, e.g., by controlled addition. For example, the carrier compound can be a polymer other than a nucleic acid (e.g., spermine or spermidine). pH can also adjusted to favor condensation.

Methods for producing stable polynucleotide delivery vehicles, which incorporate a polynucleotide/cationic lipid complex as structural components of the delivery vehicle, are further described in, e.g., WO 96/37194, the entire contents of which are incorporated herein by reference. Liposome formation can also include one or more aspects of exemplary methods described in Felgner, P. L. et al., *Proc. Natl. Acad. Sci., USA* 8:7413-7417, 1987; U.S. Pat. No. 4,897,355; U.S. Pat. No. 5,171,678; Bangham, et al. *M. Mol. Biol.* 23:238, 1965; Olson, et al. *Biochim. Biophys. Acta* 557:9, 1979; Szoka, et al. *Proc. Natl. Acad. Sci.* 75: 4194, 1978; Mayhew, et al. *Biochim. Biophys. Acta* 775:169, 1984; Kim, et al. *Biochim. Biophys. Acta* 728:339, 1983; and Fukunaga, et al. *Endocrinol.* 115:757, 1984. Commonly used techniques for preparing lipid aggregates of appropriate size for use as delivery vehicles include sonication and freeze-thaw plus extrusion (see, e.g., Mayer, et al. *Biochim. Biophys. Acta* 858:161, 1986). Microfluidization can be used when consistently small (50 to 200 nm) and relatively uniform aggregates are desired (Mayhew, et al. *Biochim. Biophys. Acta* 775:169, 1984). These methods are readily adapted to packaging RNAi agent preparations into liposomes.

Liposomes fall into two broad classes. Cationic liposomes are positively charged liposomes which interact with the negatively charged nucleic acid molecules to form a stable complex. The positively charged nucleic acid/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun.,* 1987, 147, 980-985).

Liposomes which are pH-sensitive or negatively-charged, entrap nucleic acids rather than complex with it. Since both the nucleic acid and the lipid are similarly charged, repulsion rather than complex formation occurs. Nevertheless, some nucleic acid is entrapped within the aqueous interior of these liposomes. pH-sensitive liposomes have been used to deliver nucleic acids encoding the thymidine kinase gene to cell monolayers in culture. Expression of the exogenous gene was detected in the target cells (Zhou et al., *Journal of Controlled Release,* 1992, 19, 269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Examples of other methods to introduce liposomes into cells in vitro and in vivo include U.S. Pat. No. 5,283,185; U.S. Pat. No. 5,171,678; WO 94/00569; WO 93/24640; WO 91/16024; Felgner, *J. Biol. Chem.* 269:2550, 1994; Nabel, *Proc. Natl. Acad. Sci.* 90:11307, 1993; Nabel, *Human Gene Ther.* 3:649, 1992; Gershon, *Biochem.* 32:7143, 1993; and Strauss *EMBO J.* 11:417, 1992.

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporine A into different layers of the skin (Hu et al. *S.T.P. Pharma. Sci.,* 1994, 4(6) 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters,* 1987, 223, 42; Wu et al., *Cancer Research,* 1993, 53, 3765).

Various liposomes comprising one or more glycolipids are known in the art. Papahadjopoulos et al. (*Ann. N.Y. Acad. Sci.,* 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.,* 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al).

In one embodiment, cationic liposomes are used. Cationic liposomes possess the advantage of being able to fuse to the cell membrane. Non-cationic liposomes, although not able to fuse as efficiently with the plasma membrane, are taken up by macrophages in vivo and can be used to deliver RNAi agents to macrophages.

Further advantages of liposomes include: liposomes obtained from natural phospholipids are biocompatible and biodegradable; liposomes can incorporate a wide range of water and lipid soluble drugs; liposomes can protect encapsulated RNAi agents in their internal compartments from metabolism and degradation (Rosoff, in "Pharmaceutical Dosage Forms," Lieberman, Rieger and Banker (Eds.), 1988, volume 1, p. 245). Important considerations in the preparation of liposome formulations are the lipid surface charge, vesicle size and the aqueous volume of the liposomes.

A positively charged synthetic cationic lipid, N-[1-(2,3-dioleyloxy)propyl]-N,N,N-trimethylammonium chloride (DOTMA) can be used to form small liposomes that interact spontaneously with nucleic acid to form lipid-nucleic acid complexes which are capable of fusing with the negatively charged lipids of the cell membranes of tissue culture cells, resulting in delivery of RNAi agent (see, e.g., Felgner, P. L. et al., Proc. Natl. Acad. Sci., USA 8:7413-7417, 1987 and U.S. Pat. No. 4,897,355 for a description of DOTMA and its use with DNA).

A DOTMA analogue, 1,2-bis(oleoyloxy)-3-(trimethylammonia)propane (DOTAP) can be used in combination with a phospholipid to form DNA-complexing vesicles. Lipofectin™ Bethesda Research Laboratories, Gaithersburg, Md.) is an effective agent for the delivery of highly anionic nucleic acids into living tissue culture cells that comprise positively charged DOTMA liposomes which interact spontaneously with negatively charged polynucleotides to form complexes.

When enough positively charged liposomes are used, the net charge on the resulting complexes is also positive. Positively charged complexes prepared in this way spontaneously attach to negatively charged cell surfaces, fuse with the plasma membrane, and efficiently deliver functional nucleic acids into, for example, tissue culture cells. Another commercially available cationic lipid, 1,2-bis(oleoyloxy)-3,3-(trimethylammonia)propane ("DOTAP") (Boehringer Mannheim, Indianapolis, Ind.) differs from DOTMA in that the oleoyl moieties are linked by ester, rather than ether linkages.

Other reported cationic lipid compounds include those that have been conjugated to a variety of moieties including, for example, carboxyspermine which has been conjugated to one of two types of lipids and includes compounds such as 5-carboxyspermylglycine dioctaoleoylamide ("DOGS") (Transfectam™, Promega, Madison, Wis.) and dipalmitoylphosphatidylethanolamine 5-carboxyspermyl-amide ("DPPES") (see, e.g., U.S. Pat. No. 5,171,678).

Another cationic lipid conjugate includes derivatization of the lipid with cholesterol ("DC-Choi") which has been formulated into liposomes in combination with DOPE (See, Gao, X. and Huang, L., *Biochim. Biophys. Res. Commun.* 179:280, 1991). Lipopolylysine, made by conjugating polylysine to DOPE, has been reported to be effective for transfection in the presence of serum (Zhou, X. et al., *Biochim. Biophys. Acta* 1065:8, 1991). For certain cell lines, these liposomes containing conjugated cationic lipids, are said to exhibit lower toxicity and provide more efficient transfection than the DOTMA-containing compositions. Other commercially available cationic lipid products include DMRIE and DMRIE-HP (Vical, La Jolla, Calif.) and Lipofectamine (DOSPA) (Life Technology, Inc., Gaithersburg, Md.). Other cationic lipids suitable for the delivery of oligonucleotides are described in WO 98/39359 and WO 96/37194.

Liposomal formulations are particularly suited for topical administration, liposomes present several advantages over other formulations. Such advantages include reduced side effects related to high systemic absorption of the administered drug, increased accumulation of the administered drug at the desired target, and the ability to administer RNAi agent into the skin. In some implementations, liposomes are used for delivering RNAi agent to epidermal cells and also to enhance the penetration of RNAi agent into dermal tissues, e.g., into skin. For example, the liposomes can be applied topically. Topical delivery of drugs formulated as liposomes to the skin has been documented (see, e.g., Weiner et al., *Journal of Drug Targeting,* 1992, vol. 2, 405-410 and du Plessis et al., *Antiviral Research,* 18, 1992, 259-265; Mannino, R. J. and Fould-Fogerite, S., *Biotechniques* 6:682-690, 1988; Itani, T. et al. *Gene* 56:267-276. 1987; Nicolau, C. et al. *Meth. Enz.* 149:157-176, 1987; Straubinger, R. M. and Papahadjopoulos, D. *Meth. Enz.* 101:512-527, 1983; Wang, C. Y. and Huang, L., *Proc. Natl. Acad. Sci. USA* 84:7851-7855, 1987).

Non-ionic liposomal systems have also been examined to determine their utility in the delivery of drugs to the skin, in particular systems comprising non-ionic surfactant and cholesterol. Non-ionic liposomal formulations comprising Novasome I (glyceryl dilaurate/cholesterol/polyoxyethylene-10-stearyl ether) and Novasome II (glyceryl distearate/cholesterol/polyoxyethylene-10-stearyl ether) were used to deliver a drug into the dermis of mouse skin. Such formulations with RNAi agent are useful for treating a dermatological disorder.

Liposomes that include iRNA can be made highly deformable. Such deformability can enable the liposomes to penetrate through pore that are smaller than the average radius of the liposome. For example, transfersomes are a type of deformable liposomes. Transferosomes can be made by adding surface edge activators, usually surfactants, to a standard liposomal composition. Transfersomes that include RNAi agent can be delivered, for example, subcutaneously by infection in order to deliver RNAi agent to keratinocytes in the skin. In order to cross intact mammalian skin, lipid vesicles must pass through a series of fine pores, each with a diameter less than 50 nm, under the influence of a suitable transdermal gradient. In addition, due to the lipid properties, these transferosomes can be self-optimizing (adaptive to the shape of pores, e.g., in the skin), self-repairing, and can frequently reach their targets without fragmenting, and often self-loading.

Other formulations amenable to the present invention are described in U.S. provisional application Ser. Nos. 61/018,616, filed Jan. 2, 2008; 61/018,611, filed Jan. 2, 2008; 61/039,748, filed Mar. 26, 2008; 61/047,087, filed Apr. 22, 2008 and 61/051,528, filed May 8, 2008. PCT application no PCT/US2007/080331, filed Oct. 3, 2007 also describes formulations that are amenable to the present invention.

Transfersomes are yet another type of liposomes, and are highly deformable lipid aggregates which are attractive candidates for drug delivery vehicles. Transfersomes can be described as lipid droplets which are so highly deformable that they are easily able to penetrate through pores which are smaller than the droplet. Transfersomes are adaptable to the environment in which they are used, e.g., they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in Pharmaceutical Dosage Forms, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in Pharmaceutical Dosage Forms, Marcel Dekker, Inc., New York, N.Y., 1988, p. 285).

The iRNA for use in the methods of the invention can also be provided as micellar formulations. "Micelles" are defined herein as a particular type of molecular assembly in which amphipathic molecules are arranged in a spherical structure such that all the hydrophobic portions of the molecules are directed inward, leaving the hydrophilic portions in contact with the surrounding aqueous phase. The converse arrangement exists if the environment is hydrophobic.

A mixed micellar formulation suitable for delivery through transdermal membranes may be prepared by mixing an aqueous solution of the siRNA composition, an alkali metal $C_8$ to $C_{22}$ alkyl sulphate, and a micelle forming compounds. Exemplary micelle forming compounds include lecithin, hyaluronic acid, pharmaceutically acceptable salts of hyaluronic acid, glycolic acid, lactic acid, chamomile extract, cucumber extract, oleic acid, linoleic acid, linolenic acid, monoolein, monooleates, monolaurates, borage oil, evening of primrose oil, menthol, trihydroxy oxo cholanyl glycine and pharmaceutically acceptable salts thereof, glycerin, polyglycerin, lysine, polylysine, triolein, polyoxyethylene ethers and analogues thereof, polidocanol alkyl ethers and analogues thereof, chenodeoxycholate, deoxycholate, and mixtures thereof. The micelle forming compounds may be added at the same time or after addition of the alkali metal alkyl sulphate. Mixed micelles will form with substantially any kind of mixing of the ingredients but vigorous mixing in order to provide smaller size micelles.

In one method a first micellar composition is prepared which contains the siRNA composition and at least the alkali metal alkyl sulphate. The first micellar composition is then mixed with at least three micelle forming compounds to form a mixed micellar composition. In another method, the micellar composition is prepared by mixing the siRNA composition, the alkali metal alkyl sulphate and at least one of the micelle forming compounds, followed by addition of the remaining micelle forming compounds, with vigorous mixing.

Phenol and/or m-cresol may be added to the mixed micellar composition to stabilize the formulation and protect against bacterial growth. Alternatively, phenol and/or m-cresol may be added with the micelle forming ingredients. An isotonic agent such as glycerin may also be added after formation of the mixed micellar composition.

For delivery of the micellar formulation as a spray, the formulation can be put into an aerosol dispenser and the dispenser is charged with a propellant. The propellant, which is under pressure, is in liquid form in the dispenser. The ratios of the ingredients are adjusted so that the aqueous and propellant phases become one, i.e., there is one phase. If there are two phases, it is necessary to shake the dispenser prior to dispensing a portion of the contents, e.g., through a metered valve. The dispensed dose of pharmaceutical agent is propelled from the metered valve in a fine spray.

Propellants may include hydrogen-containing chlorofluorocarbons, hydrogen-containing fluorocarbons, dimethyl ether and diethyl ether. In certain embodiments, HFA 134a (1,1,1,2 tetrafluoroethane) may be used.

The specific concentrations of the essential ingredients can be determined by relatively straightforward experimentation. For absorption through the oral cavities, it is often desirable to increase, e.g., at least double or triple, the dosage for through injection or administration through the gastrointestinal tract.

B. Lipid Particles iRNAs, e.g., dsRNAs of in the invention may be fully encapsulated in a lipid formulation, e.g., a LNP, e.g., to form a SPLP, pSPLP, SNALP, or other nucleic acid-lipid particle.

As used herein, the term "SNALP" refers to a stable nucleic acid-lipid particle, including SPLP. As used herein, the term "SPLP" refers to a nucleic acid-lipid particle comprising plasmid DNA encapsulated within a lipid vesicle. SNALPs and SPLPs typically contain a cationic lipid, a non-cationic lipid, and a lipid that prevents aggregation of the particle (e.g., a PEG-lipid conjugate). SNALPs and SPLPs are extremely useful for systemic applications, as they exhibit extended circulation lifetimes following intravenous (i.v.) injection and accumulate at distal sites (e.g., sites physically separated from the administration site). SPLPs include "pSPLP," which include an encapsulated condensing agent-nucleic acid complex as set forth in PCT Publication No. WO 00/03683. The particles of the present invention typically have a mean diameter of about 50 nm to about 150 nm, more typically about 60 nm to about 130 nm, more typically about 70 nm to about 110 nm, most typically about 70 nm to about 90 nm, and are substantially nontoxic. In addition, the nucleic acids when present in the nucleic acid-lipid particles of the present invention are resistant in aqueous solution to degradation with a nuclease. Nucleic acid-lipid particles and their method of preparation are disclosed in, e.g., U.S. Pat. Nos. 5,976,567; 5,981,501; 6,534,484; 6,586,410; 6,815,432; U.S. Publication No. 2010/0324120 and PCT Publication No. WO 96/40964.

In one embodiment, the lipid to drug ratio (mass/mass ratio) (e.g., lipid to dsRNA ratio) will be in the range of from about 1:1 to about 50:1, from about 1:1 to about 25:1, from about 3:1 to about 15:1, from about 4:1 to about 10:1, from about 5:1 to about 9:1, or about 6:1 to about 9:1. Ranges intermediate to the above recited ranges are also contemplated to be part of the invention.

The cationic lipid can be, for example, N,N-dioleyl-N,N-dimethylammonium chloride (DODAC), N,N-distearyl-N,N-dimethylammonium bromide (DDAB), N-(1-(2,3-dioleoyloxy)propyl)-N,N,N-trimethylammonium chloride (DOTAP), N-(1-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-Dilinoleylcarbamoyloxy-3-dimethylaminopropane (DLin-C-DAP), 1,2-Dilinoleyoxy-3-(dimethylamino) acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.Cl), 1,2-Dilinoleoyl-3-trimethylaminopropane chloride salt (DLin-TAP.Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DMA), 1,2-Dilinolenyloxy-N,N-dimethylaminopropane (DLinDMA), 2,2-Dilinoleyl-4-dimethylaminomethyl-[1,3]-dioxolane (DLin-K-DMA) or analogs thereof, (3aR,5s,6aS)—N,N-dimethyl-2,2-di((9Z,12Z)-octadeca-9,12-dienyl)tetrahydro-3aH-cyclopenta[d][1,3]dioxol-5-amine (ALN100), (6Z,9Z,28Z,31Z)-heptatriaconta-6,9,28,31-tetraen-19-yl 4-(dimethylamino)butanoate (MC3), 1,1'-(2-(4-(2-((2-(bis (2-hydroxydodecyl)amino)ethyl)(2-hydroxydodecyl)amino) ethyl)piperazin-1-yl)ethylazanediyl)didodecan-2-ol (Tech G1), or a mixture thereof. The cationic lipid can comprise from about 20 mol % to about 50 mol % or about 40 mol % of the total lipid present in the particle.

In another embodiment, the compound 2,2-Dilinoleyl-4-dimethylaminoethyl-[1,3]-dioxolane can be used to prepare lipid-siRNA nanoparticles. Synthesis of 2,2-Dilinoleyl-4-dimethylaminoethyl-[1,3]-dioxolane is described in U.S. provisional patent application No. 61/107,998 filed on Oct. 23, 2008, which is herein incorporated by reference.

In one embodiment, the lipid-siRNA particle includes 40% 2,2-Dilinoleyl-4-dimethylaminoethyl-[1,3]-dioxolane: 10% DSPC: 40% Cholesterol: 10% PEG-C-DOMG (mole percent) with a particle size of 63.0±20 nm and a 0.027 siRNA/ Lipid Ratio.

The ionizable/non-cationic lipid can be an anionic lipid or a neutral lipid including, but not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof. The non-cationic lipid can be from about 5 mol % to about 90 mol %, about 10 mol %, or about 58 mol % if cholesterol is included, of the total lipid present in the particle.

The conjugated lipid that inhibits aggregation of particles can be, for example, a polyethyleneglycol (PEG)-lipid including, without limitation, a PEG-diacylglycerol (DAG), a PEG-dialkyloxypropyl (DAA), a PEG-phospholipid, a PEG-ceramide (Cer), or a mixture thereof. The PEG-DAA conjugate can be, for example, a PEG-dilauryloxypropyl ($Ci_2$), a PEG-dimyristyloxypropyl ($Ci_4$), a PEG-dipalmityloxypropyl ($Ci_6$), or a PEG-distearyloxypropyl ($C]_8$). The conjugated lipid that prevents aggregation of particles can be from 0 mol % to about 20 mol % or about 2 mol % of the total lipid present in the particle.

In some embodiments, the nucleic acid-lipid particle further includes cholesterol at, e.g., about 10 mol % to about 60 mol % or about 48 mol % of the total lipid present in the particle.

In one embodiment, the lipidoid ND98.4HCl (MW 1487) (see U.S. patent application Ser. No. 12/056,230, filed Mar. 26, 2008, which is incorporated herein by reference), Cholesterol (Sigma-Aldrich), and PEG-Ceramide C16 (Avanti Polar Lipids) can be used to prepare lipid-dsRNA nanoparticles (i.e., LNP01 particles). Stock solutions of each in ethanol can be prepared as follows: ND98, 133 mg/ml; Cholesterol, 25 mg/ml, PEG-Ceramide C16, 100 mg/ml. The ND98, Cholesterol, and PEG-Ceramide C16 stock solutions can then be combined in a, e.g., 42:48:10 molar ratio. The combined lipid solution can be mixed with aqueous dsRNA (e.g., in sodium acetate pH 5) such that the final ethanol concentration is about 35-45% and the final sodium acetate concentration is about 100-300 mM. Lipid-dsRNA nanoparticles typically form spontaneously upon mixing. Depending on the desired particle size distribution, the resultant nanoparticle mixture can be extruded through a polycarbonate membrane (e.g., 100 nm cut-off) using, for example, a thermobarrel extruder, such as Lipex Extruder (Northern Lipids, Inc). In some cases, the extrusion step can be omitted. Ethanol removal and simultaneous buffer exchange can be accomplished by, for example, dialysis or tangential flow filtration. Buffer can be exchanged with, for example, phosphate buffered saline (PBS) at about pH 7, e.g., about pH 6.9, about pH 7.0, about pH 7.1, about pH 7.2, about pH 7.3, or about pH 7.4.

Formula 1

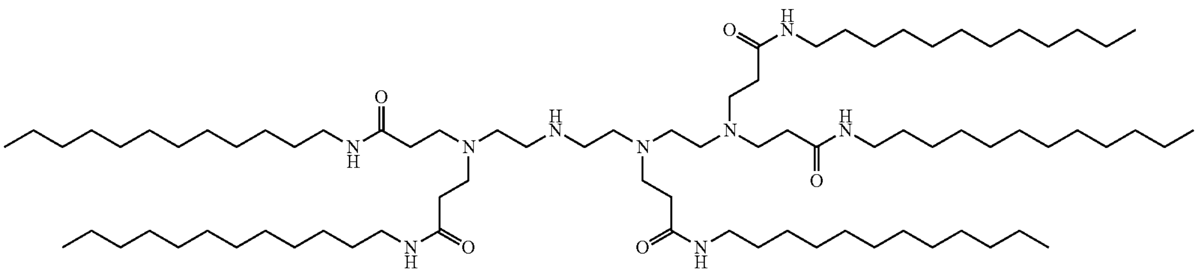

ND98 Isomer I

LNP01 formulations are described, e.g., in International Application Publication No. WO 2008/042973, which is hereby incorporated by reference.

Additional exemplary lipid-dsRNA formulations are described in Table 1.

TABLE 1

| | Ionizable/Cationic Lipid | cationic lipid/non-cationic lipid/cholesterol/PEG-lipid conjugate Lipid:siRNA ratio |
|---|---|---|
| SNALP-1 | 1,2-Dilinolenyloxy-N,N-dimethylaminopropane (DLinDMA) | DLinDMA/DPPC/Cholesterol/PEG-cDMA (57.1/7.1/34.4/1.4) lipid:siRNA ~7:1 |
| 2-XTC | 2,2-Dilinoleyl-4-dimethylaminoethyl-[1,3]-dioxolane (XTC) | XTC/DPPC/Cholesterol/PEG-cDMA 57.1/7.1/34.4/1.4 lipid:siRNA ~7:1 |
| LNP05 | 2,2-Dilinoleyl-4-dimethylaminoethyl-[1,3]-dioxolane (XTC) | XTC/DSPC/Cholesterol/PEG-DMG 57.5/7.5/31.5/3.5 lipid:siRNA ~6:1 |
| LNP06 | 2,2-Dilinoleyl-4-dimethylaminoethyl-[1,3]-dioxolane (XTC) | XTC/DSPC/Cholesterol/PEG-DMG 57.5/7.5/31.5/3.5 lipid:siRNA ~11:1 |
| LNP07 | 2,2-Dilinoleyl-4-dimethylaminoethyl-[1,3]-dioxolane (XTC) | XTC/DSPC/Cholesterol/PEG-DMG 60/7.5/31/1.5, lipid:siRNA ~6:1 |
| LNP08 | 2,2-Dilinoleyl-4-dimethylaminoethyl-[1,3]-dioxolane (XTC) | XTC/DSPC/Cholesterol/PEG-DMG 60/7.5/31/1.5, lipid:siRNA ~11:1 |
| LNP09 | 2,2-Dilinoleyl-4-dimethylaminoethyl-[1,3]-dioxolane (XTC) | XTC/DSPC/Cholesterol/PEG-DMG 50/10/38.5/1.5 Lipid:siRNA 10:1 |
| LNP10 | (3aR,5s,6aS)-N,N-dimethyl-2,2-di((9Z,12Z)-octadeca-9,12-dienyl)tetrahydro-3aH-cyclopenta[d][1,3]dioxol-5-amine (ALN100) | ALN100/DSPC/Cholesterol/PEG-DMG 50/10/38.5/1.5 Lipid:siRNA 10:1 |
| LNP11 | (6Z,9Z,28Z,31Z)-heptatriaconta-6,9,28,31-tetraen-19-yl 4-(dimethylamino)butanoate (MC3) | MC-3/DSPC/Cholesterol/PEG-DMG 50/10/38.5/1.5 Lipid:siRNA 10:1 |
| LNP12 | 1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol (Tech G1) | Tech G1/DSPC/Cholesterol/PEG-DMG 50/10/38.5/1.5 Lipid:siRNA 10:1 |
| LNP13 | XTC | XTC/DSPC/Chol/PEG-DMG 50/10/38.5/1.5 Lipid:siRNA: 33:1 |
| LNP14 | MC3 | MC3/DSPC/Chol/PEG-DMG 40/15/40/5 Lipid:siRNA: 11:1 |
| LNP15 | MC3 | MC3/DSPC/Chol/PEG-DSG/GalNAc-PEG-DSG 50/10/35/4.5/0.5 Lipid:siRNA: 11:1 |
| LNP16 | MC3 | MC3/DSPC/Chol/PEG-DMG 50/10/38.5/1.5 Lipid:siRNA: 7:1 |
| LNP17 | MC3 | MC3/DSPC/Chol/PEG-DSG 50/10/38.5/1.5 Lipid:siRNA: 10:1 |
| LNP18 | MC3 | MC3/DSPC/Chol/PEG-DMG 50/10/38.5/1.5 Lipid:siRNA: 12:1 |
| LNP19 | MC3 | MC3/DSPC/Chol/PEG-DMG 50/10/35/5 Lipid:siRNA: 8:1 |
| LNP20 | MC3 | MC3/DSPC/Chol/PEG-DPG 50/10/38.5/1.5 Lipid:siRNA: 10:1 |
| LNP21 | C12-200 | C12-200/DSPC/Chol/PEG-DSG 50/10/38.5/1.5 Lipid:siRNA: 7:1 |
| LNP22 | XTC | XTC/DSPC/Chol/PEG-DSG 50/10/38.5/1.5 Lipid:siRNA: 10:1 |

DSPC: distearoylphosphatidylcholine

DPPC: dipalmitoylphosphatidylcholine

PEG-DMG: PEG-didimyristoyl glycerol (C14-PEG, or PEG-C14) (PEG with avg mol wt of 2000)

PEG-DSG: PEG-distyryl glycerol (C18-PEG, or PEG-C18) (PEG with avg mol wt of 2000)

PEG-cDMA: PEG-carbamoyl-1,2-dimyristyloxypropylamine (PEG with avg mol wt of 2000)

SNALP (1,2-Dilinolenyloxy-N,N-dimethylaminopropane (DLinDMA)) comprising formulations are described in International Publication No. WO2009/127060, filed Apr. 15, 2009, which is hereby incorporated by reference.

XTC comprising formulations are described, e.g., in U.S. Provisional Ser. No. 61/148,366, filed Jan. 29, 2009; U.S. Provisional Ser. No. 61/156,851, filed Mar. 2, 2009; U.S. Provisional Serial No. filed Jun. 10, 2009; U.S. Provisional Ser. No. 61/228,373, filed Jul. 24, 2009; U.S. Provisional Ser. No. 61/239,686, filed Sep. 3, 2009, and International Application No. PCT/US2010/022614, filed Jan. 29, 2010, which are hereby incorporated by reference.

MC3 comprising formulations are described, e.g., in U.S. Publication No. 2010/0324120, filed Jun. 10, 2010, the entire contents of which are hereby incorporated by reference.

ALNY-100 comprising formulations are described, e.g., International patent application number PCT/US09/63933, filed on Nov. 10, 2009, which is hereby incorporated by reference.

C12-200 comprising formulations are described in U.S. Provisional Ser. No. 61/175,770, filed May 5, 2009 and International Application No. PCT/US10/33777, filed May 5, 2010, which are hereby incorporated by reference.

Synthesis of Ionizable/Cationic Lipids

Any of the compounds, e.g., cationic lipids and the like, used in the nucleic acid-lipid particles of the invention can be prepared by known organic synthesis techniques, including the methods described in more detail in the Examples. All substituents are as defined below unless indicated otherwise.

"Alkyl" means a straight chain or branched, noncyclic or cyclic, saturated aliphatic hydrocarbon containing from 1 to 24 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like.

"Alkenyl" means an alkyl, as defined above, containing at least one double bond between adjacent carbon atoms. Alkenyls include both cis and trans isomers. Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like.

"Alkynyl" means any alkyl or alkenyl, as defined above, which additionally contains at least one triple bond between adjacent carbons. Representative straight chain and branched alkynyls include acetylenyl, propynyl, 1-butynyl, 2-butynyl, 1-pentynyl, 2-pentynyl, 3-methyl-1 butynyl, and the like.

"Acyl" means any alkyl, alkenyl, or alkynyl wherein the carbon at the point of attachment is substituted with an oxo group, as defined below. For example, —C(═O)alkyl, —C(═O)alkenyl, and —C(═O)alkynyl are acyl groups.

"Heterocycle" means a 5- to 7-membered monocyclic, or 7- to 10-membered bicyclic, heterocyclic ring which is either saturated, unsaturated, or aromatic, and which contains from 1 or 2 heteroatoms independently selected from nitrogen, oxygen and sulfur, and wherein the nitrogen and sulfur heteroatoms can be optionally oxidized, and the nitrogen heteroatom can be optionally quaternized, including bicyclic rings in which any of the above heterocycles are fused to a benzene ring. The heterocycle can be attached via any heteroatom or carbon atom. Heterocycles include heteroaryls as defined below. Heterocycles include morpholinyl, pyrrolidinonyl, pyrrolidinyl, piperidinyl, piperizynyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The terms "optionally substituted alkyl", "optionally substituted alkenyl", "optionally substituted alkynyl", "optionally substituted acyl", and "optionally substituted heterocycle" means that, when substituted, at least one hydrogen atom is replaced with a substituent. In the case of an oxo substituent (═O) two hydrogen atoms are replaced. In this regard, substituents include oxo, halogen, heterocycle, —CN, —ORx, —NRxRy, —NRxC(═O)Ry, —NRxSO2Ry, —C(═O)Rx, —C(═O)ORx, —C(═O)NRxRy, —SOnRx and —SOnNR xRy, wherein n is 0, 1 or 2, Rx and Ry are the same or different and independently hydrogen, alkyl or heterocycle, and each of said alkyl and heterocycle substituents can be further substituted with one or more of oxo, halogen, —OH, —CN, alkyl, —ORx, heterocycle, —NR xRy, —NRxC(═O)Ry, —NRxSO2Ry, —C(═O)Rx, —C(═O)ORx, —C(═O)NRxRy, —S OnRx and —SOnNRxRy.

"Halogen" means fluoro, chloro, bromo and iodo.

In some embodiments, the methods of the invention can require the use of protecting groups. Protecting group methodology is well known to those skilled in the art (see, for example, Protective Groups in Organic Synthesis, Green, T. W. et al., Wiley-Interscience, New York City, 1999). Briefly, protecting groups within the context of this invention are any group that reduces or eliminates unwanted reactivity of a functional group. A protecting group can be added to a functional group to mask its reactivity during certain reactions and then removed to reveal the original functional group. In some embodiments an "alcohol protecting group" is used. An "alcohol protecting group" is any group which decreases or eliminates unwanted reactivity of an alcohol functional group. Protecting groups can be added and removed using techniques well known in the art.

Synthesis of Formula A

In some embodiments, nucleic acid-lipid particles of the invention are formulated using a cationic lipid of formula A:

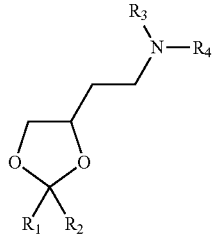

where R1 and R2 are independently alkyl, alkenyl or alkynyl, each can be optionally substituted, and R3 and R4 are independently lower alkyl or R3 and R4 can be taken together to form an optionally substituted heterocyclic ring. In some embodiments, the cationic lipid is XTC (2,2-Dilinoleyl-4-dimethylaminoethyl-[1,3]-dioxolane). In general, the lipid of formula A above can be made by the following Reaction Schemes 1 or 2, wherein all substituents are as defined above unless indicated otherwise.

Scheme 1

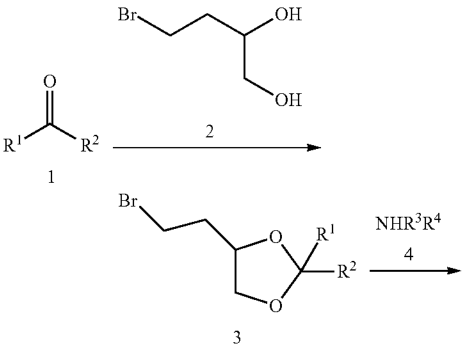

1

3

-continued

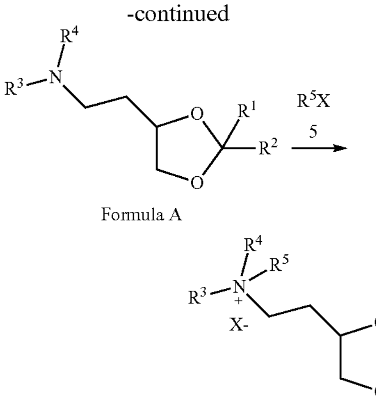

Lipid A, where R1 and R2 are independently alkyl, alkenyl or alkynyl, each can be optionally substituted, and R3 and R4 are independently lower alkyl or R3 and R4 can be taken together to form an optionally substituted heterocyclic ring, can be prepared according to Scheme 1. Ketone 1 and bromide 2 can be purchased or prepared according to methods known to those of ordinary skill in the art. Reaction of 1 and 2 yields ketal 3. Treatment of ketal 3 with amine 4 yields lipids of formula A. The lipids of formula A can be converted to the corresponding ammonium salt with an organic salt of formula 5, where X is anion counter ion selected from halogen, hydroxide, phosphate, sulfate, or the like.

Scheme 2

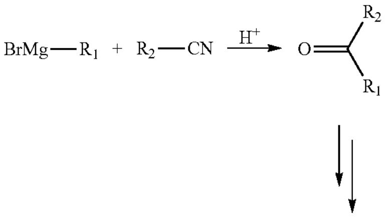

-continued

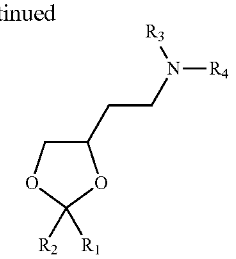

Alternatively, the ketone 1 starting material can be prepared according to Scheme 2. Grignard reagent 6 and cyanide 7 can be purchased or prepared according to methods known to those of ordinary skill in the art. Reaction of 6 and 7 yields ketone 1. Conversion of ketone 1 to the corresponding lipids of formula A is as described in Scheme 1.

Synthesis of MC3

Preparation of DLin-M-C3-DMA (i.e., (6Z,9Z,28Z,31Z)-heptatriaconta-6,9,28,31-tetraen-19-yl 4-(dimethylamino) butanoate) was as follows. A solution of (6Z,9Z,28Z,31Z)-heptatriaconta-6,9,28,31-tetraen-19-ol (0.53 g), 4-N,N-dimethylaminobutyric acid hydrochloride (0.51 g), 4-N,N-dimethylaminopyridine (0.61 g) and 1-ethyl-3-(3-dimethylaminopropyl)carbodiimide hydrochloride (0.53 g) in dichloromethane (5 mL) was stirred at room temperature overnight. The solution was washed with dilute hydrochloric acid followed by dilute aqueous sodium bicarbonate. The organic fractions were dried over anhydrous magnesium sulphate, filtered and the solvent removed on a rotovap. The residue was passed down a silica gel column (20 g) using a 1-5% methanol/dichloromethane elution gradient. Fractions containing the purified product were combined and the solvent removed, yielding a colorless oil (0.54 g).

Synthesis of ALNY-100

Synthesis of ketal 519 [ALNY-100] was performed using the following scheme 3:

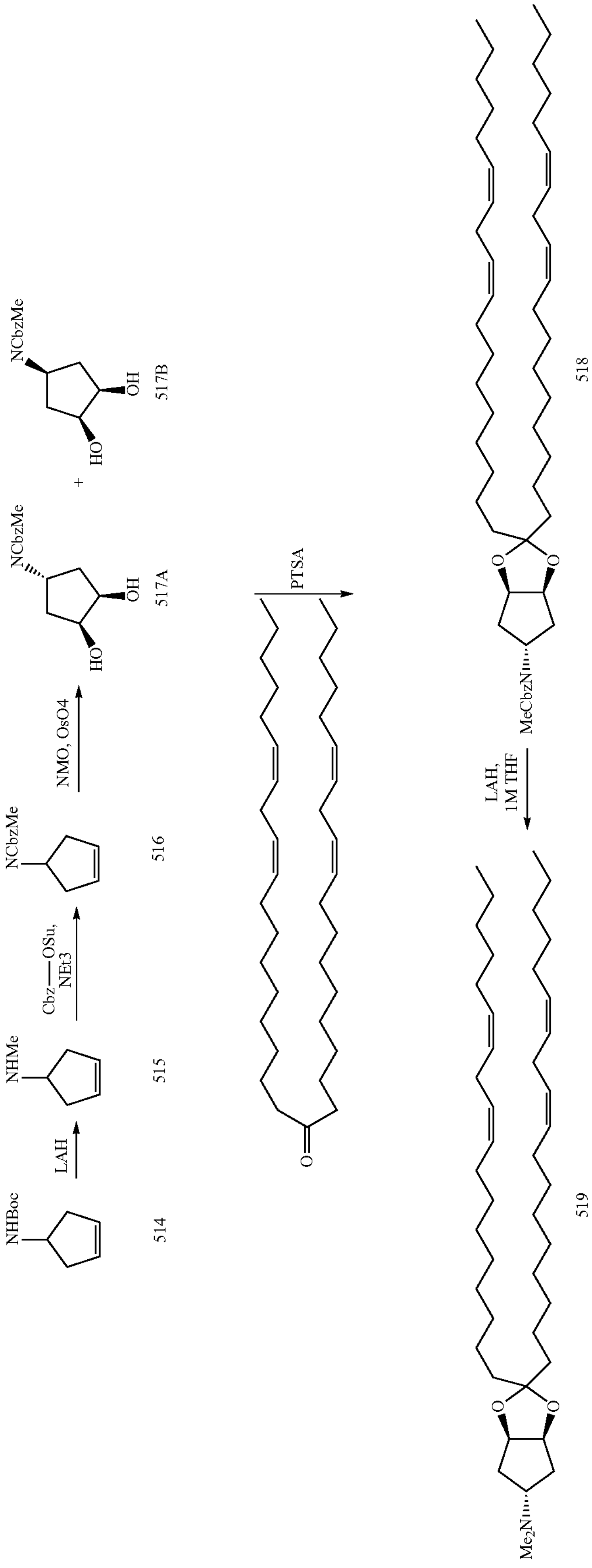
514 515 516 517A + 517B 518 519

Synthesis of 515

To a stirred suspension of $LiAlH_4$ (3.74 g, 0.09852 mol) in 200 ml anhydrous THF in a two neck RBF (1 L), was added a solution of 514 (10 g, 0.04926 mol) in 70 mL of THF slowly at 0° C. under nitrogen atmosphere. After complete addition, reaction mixture was warmed to room temperature and then heated to reflux for 4 h. Progress of the reaction was monitored by TLC. After completion of reaction (by TLC) the mixture was cooled to 0° C. and quenched with careful addition of saturated Na2SO4 solution. Reaction mixture was stirred for 4 h at room temperature and filtered off. Residue was washed well with THF. The filtrate and washings were mixed and diluted with 400 mL dioxane and 26 mL conc. HCl and stirred for 20 minutes at room temperature. The volatilities were stripped off under vacuum to furnish the hydrochloride salt of 515 as a white solid. Yield: 7.12 g $^1$H-NMR (DMSO, 400 MHz): δ=9.34 (broad, 2H), 5.68 (s, 2H), 3.74 (m, 1H), 2.66-2.60 (m, 2H), 2.50-2.45 (m, 5H).

Synthesis of 516

To a stirred solution of compound 515 in 100 mL dry DCM in a 250 mL two neck RBF, was added NEt3 (37.2 mL, 0.2669 mol) and cooled to 0° C. under nitrogen atmosphere. After a slow addition of N-(benzyloxy-carbonyloxy)-succinimide (20 g, 0.08007 mol) in 50 mL dry DCM, reaction mixture was allowed to warm to room temperature. After completion of the reaction (2-3 h by TLC) mixture was washed successively with 1N HCl solution (1×100 mL) and saturated NaHCO3 solution (1×50 mL). The organic layer was then dried over anhyd. Na2SO4 and the solvent was evaporated to give crude material which was purified by silica gel column chromatography to get 516 as sticky mass. Yield: 11 g (89%). $^1$H-NMR ($CDCl_3$, 400 MHz): δ=7.36-7.27 (m, 5H), 5.69 (s, 2H), 5.12 (s, 2H), 4.96 (br., 1H) 2.74 (s, 3H), 2.60 (m, 2H), 2.30-2.25 (m, 2H). LC-MS [M+H]-232.3 (96.94%).

Synthesis of 517A and 517E

The cyclopentene 516 (5 g, 0.02164 mol) was dissolved in a solution of 220 mL acetone and water (10:1) in a single neck 500 mL RBF and to it was added N-methyl morpholine-N-oxide (7.6 g, 0.06492 mol) followed by 4.2 mL of 7.6% solution of OsO4 (0.275 g, 0.00108 mol) in tert-butanol at room temperature. After completion of the reaction (~3 h), the mixture was quenched with addition of solid Na2SO3 and resulting mixture was stirred for 1.5 h at room temperature. Reaction mixture was diluted with DCM (300 mL) and washed with water (2×100 mL) followed by saturated NaHCO3 (1×50 mL) solution, water (1×30 mL) and finally with brine (lx 50 mL). Organic phase was dried over an .Na2SO4 and solvent was removed in vacuum. Silica gel column chromatographic purification of the crude material was afforded a mixture of diastereomers, which were separated by prep HPLC. Yield: −6 g crude 517A—Peak-1 (white solid), 5.13 g (96%). $^1$H-NMR (DMSO, 400 MHz): δ=7.39-7.31 (m, 5H), 5.04 (s, 2H), 4.78-4.73 (m, 1H), 4.48-4.47 (d, 2H), 3.94-3.93 (m, 2H), 2.71 (s, 3H), 1.72-1.67 (m, 4H). LC-MS-[M+H]-266.3, [M+NH4+]-283.5 present, HPLC-97.86%. Stereochemistry confirmed by X-ray.

Synthesis of 518

Using a procedure analogous to that described for the synthesis of compound 505, compound 518 (1.2 g, 41%) was obtained as a colorless oil. $^1$H-NMR ($CDCl_3$, 400 MHz): δ=7.35-7.33 (m, 4H), 7.30-7.27 (m, 1H), 5.37-5.27 (m, 8H), 5.12 (s, 2H), 4.75 (m, 1H), 4.58-4.57 (m, 2H), 2.78-2.74 (m, 7H), 2.06-2.00 (m, 8H), 1.96-1.91 (m, 2H), 1.62 (m, 4H), 1.48 (m, 2H), 1.37-1.25 (br m, 36H), 0.87 (m, 6H). HPLC-98.65%.

General Procedure for the Synthesis of Compound 519

A solution of compound 518 (1 eq) in hexane (15 mL) was added in a drop-wise fashion to an ice-cold solution of LAH in THF (1 M, 2 eq). After complete addition, the mixture was heated at 40° C. over 0.5 h then cooled again on an ice bath. The mixture was carefully hydrolyzed with saturated aqueous Na2SO4 then filtered through celite and reduced to an oil. Column chromatography provided the pure 519 (1.3 g, 68%) which was obtained as a colorless oil. $^{13}$C NMR δ=130.2, 130.1 (×2), 127.9 (×3), 112.3, 79.3, 64.4, 44.7, 38.3, 35.4, 31.5, 29.9 (×2), 29.7, 29.6 (×2), 29.5 (×3), 29.3 (×2), 27.2 (×3), 25.6, 24.5, 23.3, 226, 14.1; Electrospray MS (+ve): Molecular weight for C44H80NO2 (M+H)+ Calc. 654.6. Found 654.6.

Formulations prepared by either the standard or extrusion-free method can be characterized in similar manners. For example, formulations are typically characterized by visual inspection. They should be whitish translucent solutions free from aggregates or sediment. Particle size and particle size distribution of lipid-nanoparticles can be measured by light scattering using, for example, a Malvern Zetasizer Nano ZS (Malvern, USA). Particles should be about 20-300 nm, such as 40-100 nm in size. The particle size distribution should be unimodal. The total dsRNA concentration in the formulation, as well as the entrapped fraction, is estimated using a dye exclusion assay. A sample of the formulated dsRNA can be incubated with an RNA-binding dye, such as Ribogreen (Molecular Probes) in the presence or absence of a formulation disrupting surfactant, e.g., 0.5% Triton-X100. The total dsRNA in the formulation can be determined by the signal from the sample containing the surfactant, relative to a standard curve. The entrapped fraction is determined by subtracting the “free” dsRNA content (as measured by the signal in the absence of surfactant) from the total dsRNA content. Percent entrapped dsRNA is typically >85%. For SNALP formulation, the particle size is at least 30 nm, at least 40 nm, at least 50 nm, at least 60 nm, at least 70 nm, at least 80 nm, at least 90 nm, at least 100 nm, at least 110 nm, and at least 120 nm. The suitable range is typically about at least 50 nm to about at least 110 nm, about at least 60 nm to about at least 100 nm, or about at least 80 nm to about at least 90 nm.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders can be desirable. In some embodiments, oral formulations are those in which dsRNAs featured in the invention are administered in conjunction with one or more penetration enhancer surfactants and chelators. Suitable surfactants include fatty acids and/or esters or salts thereof, bile acids and/or salts thereof. Suitable bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate and sodium glycodihydrofusidate. Suitable fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g., sodium). In some embodiments, combinations of penetration enhancers are used, for example, fatty acids/salts in combination with bile acids/salts. One exemplary combination is the sodium salt of lauric acid, capric acid and UDCA. Further penetration enhancers include polyoxyethylene-9-lauryl ether, polyoxyethylene-20-cetyl ether. DsRNAs featured in the invention can be delivered orally, in granular form including sprayed dried particles, or complexed to form micro or nanoparticles. DsRNA complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Suitable complexing agents include chitosan, N-trimethylchitosan, poly-L-lysine, polyhistidine, polyornithine, polyspermines, protamine, polyvinylpyridine, polythiodiethylaminomethylethylene P(TDAE), polyaminostyrene (e.g., p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for dsRNAs and their preparation are described in detail in U.S. Pat. No. 6,887,906, US Publn. No. 20030027780, and U.S. Pat. No. 6,747,014, each of which is incorporated herein by reference.

Compositions and formulations for parenteral, intraparenchymal (into the brain), intrathecal, intraventricular or intrahepatic administration can include sterile aqueous solutions which can also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions can be generated from a variety of components that include, but are not limited to, preformed liquids, self-emulsifying solids and self-emulsifying semisolids. Particularly preferred are formulations that target the liver when treating hepatic disorders such as hepatic carcinoma.

The pharmaceutical formulations of the present invention, which can conveniently be presented in unit dosage form, can be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention can be formulated into any of many possible dosage forms such as, but not limited to, tablets, capsules, gel capsules, liquid syrups, soft gels, suppositories, and enemas. The compositions of the present invention can also be formulated as suspensions in aqueous, non-aqueous or mixed media. Aqueous suspensions can further contain substances which increase the viscosity of the suspension including, for example, sodium carboxymethylcellulose, sorbitol and/or dextran. The suspension can also contain stabilizers.

C. Additional Formulations i. Emulsions

The compositions of the present invention can be prepared and formulated as emulsions. Emulsions are typically heterogeneous systems of one liquid dispersed in another in the form of droplets usually exceeding 0.1 μm in diameter (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising two immiscible liquid phases intimately mixed and dispersed with each other. In general, emulsions can be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions can contain additional components in addition to the dispersed phases, and the active drug which can be present as a solution in either the aqueous phase, oily phase or itself as a separate phase. Pharmaceutical excipients such as emulsifiers, stabilizers, dyes, and anti-oxidants can also be present in emulsions as needed. Pharmaceutical emulsions can also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion can be a semisolid or a solid, as is the case of emulsion-style ointment bases and creams. Other means of stabilizing emulsions entail the use of emulsifiers that can be incorporated into either phase of the emulsion. Emulsifiers can broadly be classified into four categories: synthetic surfactants, naturally occurring emulsifiers, absorption bases, and finely dispersed solids (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants can be classified into different classes based on the nature of the hydrophilic group: non-ionic, anionic, cationic and amphoteric (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y. Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that can readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used can be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of ease of formulation, as well as efficacy from an absorption and bioavailability standpoint (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

ii. Microemulsions

In one embodiment of the present invention, the compositions of iRNAs and nucleic acids are formulated as microemulsions. A microemulsion can be defined as a system of water, oil and amphiphile which is a single optically isotropic and thermodynamically stable liquid solution (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington's Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245; Block, in Pharmaceutical Dosage Forms, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions can, however, be prepared without the use of cosurfactants and alcohol-free self-emulsifying microemulsion systems are known in the art. The aqueous phase can typically be, but is not limited to, water, an aqueous solution of the drug, glycerol, PEG300, PEG400, polyglycerols, propylene glycols, and derivatives of ethylene glycol. The oil phase can include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (see e.g., U.S. Pat. Nos. 6,191,105; 7,063,860; 7,070,802; 7,157,099; Constantinides et al., *Pharmaceutical Research,* 1994, 11, 1385-1390; Ritschel, *Meth. Find. Exp. Clin. Pharmacol.,* 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (see e.g., U.S. Pat. Nos. 6,191,105; 7,063,860; 7,070,802; 7,157,099; Constantinides et al., *Pharmaceutical Research,* 1994, 11, 1385; Ho et al., *J. Pharm. Sci.,* 1996, 85, 138-143). Often microemulsions can form spontaneously when their components are brought together at ambient temperature. This can be particularly advantageous when formulating thermolabile drugs, peptides or iRNAs. Microemulsions have also been effective in the transdermal delivery of active components in both cosmetic and pharmaceutical applications. It is expected that the microemulsion compositions and formulations of the present invention will facilitate the increased systemic absorption of iRNAs and nucleic acids from the gastrointestinal tract, as well as improve the local cellular uptake of iRNAs and nucleic acids.

Microemulsions of the present invention can also contain additional components and additives such as sorbitan monostearate (Grill 3), Labrasol, and penetration enhancers to improve the properties of the formulation and to enhance the absorption of the iRNAs and nucleic acids of the present invention. Penetration enhancers used in the microemulsions of the present invention can be classified as belonging to one of five broad categories—surfactants, fatty acids, bile salts, chelating agents, and non-chelating non-surfactants (Lee et al., *Critical Reviews in Therapeutic Drug Carrier Systems,* 1991, p. 92). Each of these classes has been discussed above.

iii. Microparticles an RNAi agent of the invention may be incorporated into a particle, e.g., a microparticle. Microparticles can be produced by spray-drying, but may also be produced by other methods including lyophilization, evaporation, fluid bed drying, vacuum drying, or a combination of these techniques.

iv. Penetration Enhancers

In one embodiment, the present invention employs various penetration enhancers to effect the efficient delivery of nucleic acids, particularly iRNAs, to the skin of animals. Most drugs are present in solution in both ionized and nonionized forms. However, usually only lipid soluble or lipophilic drugs readily cross cell membranes. It has been discovered that even non-lipophilic drugs can cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers can be classified as belonging to one of five broad categories, i.e., surfactants, fatty acids, bile salts, chelating agents, and non-chelating non-surfactants (see e.g., Malmsten, M. Surfactants and polymers in drug delivery, Informa Health Care, New York, N.Y., 2002; Lee et al., Critical Reviews in Therapeutic Drug Carrier Systems, 1991, p. 92). Each of the above mentioned classes of penetration enhancers are described below in greater detail.

Surfactants (or "surface-active agents") are chemical entities which, when dissolved in an aqueous solution, reduce the surface tension of the solution or the interfacial tension between the aqueous solution and another liquid, with the result that absorption of iRNAs through the mucosa is enhanced. In addition to bile salts and fatty acids, these penetration enhancers include, for example, sodium lauryl sulfate, polyoxyethylene-9-lauryl ether and polyoxyethylene-20-cetyl ether) (see e.g., Malmsten, M. Surfactants and polymers in drug delivery, Informa Health Care, New York, N.Y., 2002; Lee et al., Critical Reviews in Therapeutic Drug Carrier Systems, 1991, p. 92); and perfluorochemical emulsions, such as FC-43. Takahashi et al., *J. Pharm. Pharmacol.,* 1988, 40, 252).

Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-20}$ alkyl esters thereof (e.g., methyl, isopropyl and t-butyl), and mono- and di-glycerides thereof (i.e., oleate, laurate, caprate, myristate, palmitate, stearate, linoleate, etc.) (see e.g., Touitou, E., et al. Enhancement in Drug Delivery, CRC Press, Danvers, MA, 2006; Lee et al., Critical Reviews in Therapeutic Drug Carrier Systems, 1991, p. 92; Muranishi, Critical Reviews in Therapeutic Drug Carrier Systems, 1990, 7, 1-33; El Hariri et al., *J. Pharm. Pharmacol.,* 1992, 44, 651-654).

The physiological role of bile includes the facilitation of dispersion and absorption of lipids and fat-soluble vitamins (see e.g., Malmsten, M. Surfactants and polymers in drug delivery, Informa Health Care, New York, N.Y., 2002; Brunton, Chapter 38 in: Goodman & Gilman's The Pharmacological Basis of Therapeutics, 9th Ed., Hardman et al. Eds., McGraw-Hill, New York, 1996, pp. 934-935). Various natural bile salts, and their synthetic derivatives, act as penetration enhancers. Thus the term "bile salts" includes any of the naturally occurring components of bile as well as any of their synthetic derivatives. Suitable bile salts include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (see e.g., Malmsten, M. Surfactants and polymers in drug delivery, Informa Health Care, New York, N.Y., 2002; Lee et al., Critical Reviews in Therapeutic Drug Carrier Systems, 1991, page 92; Swinyard, Chapter 39 In: Remington's Pharmaceutical Sciences, 18th Ed., Gennaro, ed., Mack Publishing Co., Easton, Pa., 1990, pages 782-783; Muranishi, Critical Reviews in Therapeutic Drug Carrier Systems, 1990, 7, 1-33; Yamamoto et al., *J. Pharm. Exp. Ther.,* 1992, 263, 25; Yamashita et al., *J. Pharm. Sci.,* 1990, 79, 579-583).

Chelating agents, as used in connection with the present invention, can be defined as compounds that remove metallic ions from solution by forming complexes therewith, with the result that absorption of iRNAs through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.,* 1993, 618, 315-339). Suitable chelating agents include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(see e.g., Katdare, A. et al., Excipient development for pharmaceutical, biotechnology, and drug delivery, CRC Press, Danvers, Mass., 2006; Lee et al., Critical Reviews in Therapeutic Drug Carrier Systems, 1991, page 92; Muranishi, Critical Reviews in Therapeutic Drug Carrier Systems, 1990, 7, 1-33; Buur et al., *J. Control Rel.,* 1990, 14, 43-51).

As used herein, non-chelating non-surfactant penetration enhancing compounds can be defined as compounds that demonstrate insignificant activity as chelating agents or as surfactants but that nonetheless enhance absorption of iRNAs through the alimentary mucosa (see e.g., Muranishi, Critical Reviews in Therapeutic Drug Carrier Systems, 1990, 7, 1-33). This class of penetration enhancers includes, for example, unsaturated cyclic ureas, 1-alkyl- and 1-alkenylazacyclo-alkanone derivatives (Lee et al., Critical Reviews in Therapeutic Drug Carrier Systems, 1991, page 92); and non-steroidal anti-inflammatory agents such as diclofenac sodium, indomethacin and phenylbutazone (Yamashita et al., *J. Pharm. Pharmacol.,* 1987, 39, 621-626).

Agents that enhance uptake of iRNAs at the cellular level can also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of dsRNAs. Examples of commercially available transfection reagents include, for example Lipofectamine™ (Invitrogen; Carlsbad, Calif.), Lipofectamine 2000™ (Invitrogen; Carlsbad, Calif.), 293Fectin™ (Invitrogen; Carlsbad, Calif.), Cellfectin™ (Invitrogen; Carlsbad, Calif.), DMRIE-C™ (Invitrogen; Carlsbad, Calif.), FreeStyle™ MAX (Invitrogen; Carlsbad, Calif.), Lipofectamine™ 2000 CD (Invitrogen; Carlsbad, Calif.), Lipofectamine™ (Invitrogen; Carlsbad, Calif.), RNAiMAX (Invitrogen; Carlsbad, Calif.), Oligofectamine™ (Invitrogen; Carlsbad, Calif.), Optifect™ (Invitrogen; Carlsbad, Calif.), X-tremeGENE Q2 Transfection Reagent (Roche; Grenzacherstrasse, Switzerland), DOTAP Liposomal Transfection Reagent (Grenzacherstrasse, Switzerland), DOSPER Liposomal Transfection Reagent (Grenzacherstrasse, Switzerland), or Fugene (Grenzacherstrasse, Switzerland), Transfectam® Reagent (Promega; Madison, Wis.), TransFast™ Transfection Reagent (Promega; Madison, Wis.), Tfx™-20 Reagent (Promega; Madison, Wis.), Tfx™-50 Reagent (Promega; Madison, Wis.), DreamFect™ (OZ Biosciences; Marseille, France), EcoTransfect (OZ Biosciences; Marseille, France), TransPassa D1 Transfection Reagent (New England Biolabs; Ipswich, Mass., USA), LyoVec™/LipoGen™ (Invitrogen; San Diego, Calif., USA), PerFectin Transfection Reagent (Genlantis; San Diego, Calif., USA), NeuroPORTER Transfection Reagent (Genlantis; San Diego, Calif., USA), GenePORTER Transfection reagent (Genlantis; San Diego, Calif., USA), GenePORTER 2 Transfection reagent (Genlantis; San Diego, Calif., USA), Cytofectin Transfection Reagent (Genlantis; San Diego, Calif., USA), BaculoPORTER Transfection Reagent (Genlantis; San Diego, Calif., USA), TroganPORTER™ transfection Reagent (Genlantis; San Diego, Calif., USA), RiboFect (Bioline; Taunton, Mass., USA), PlasFect (Bioline; Taunton, Mass., USA), UniFECTOR (B-Bridge International; Mountain View, Calif., USA), SureFECTOR (B-Bridge International; Mountain View, Calif., USA), or HiFect™ (B-Bridge International, Mountain View, Calif., USA), among others.

Other agents can be utilized to enhance the penetration of the administered nucleic acids, including glycols such as ethylene glycol and propylene glycol, pyrrols such as 2-pyrrol, azones, and terpenes such as limonene and menthone.

v. Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate dsRNA in hepatic tissue can be reduced when it is coadministered with polyinosinic acid, dextran sulfate, polycytidic acid or 4-acetamido-4' isothiocyano-stilbene-2,2'-disulfonic acid (Miyao et al., DsRNA Res. Dev., 1995, 5, 115-121; Takakura et al., DsRNA & Nucl. Acid Drug Dev., 1996, 6, 177-183.

vi. Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient can be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc).

Pharmaceutically acceptable organic or inorganic excipients suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids can include sterile and non-sterile aqueous solutions, non-aqueous solutions in common solvents such as alcohols, or solutions of the nucleic acids in liquid or solid oil bases. The solutions can also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

vii. Other Components

The compositions of the present invention can additionally contain other adjunct components conventionally found in pharmaceutical compositions, at their art-established usage levels. Thus, for example, the compositions can contain additional, compatible, pharmaceutically-active materials such as, for example, antipruritics, astringents, local anesthetics or anti-inflammatory agents, or can contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions can contain substances which increase the viscosity of the suspension including, for example, sodium carboxymethylcellulose, sorbitol and/or dextran. The suspension can also contain stabilizers.

In some embodiments, pharmaceutical compositions featured in the invention include (a) one or more iRNA compounds and (b) one or more agents which function by a non-RNAi mechanism and which are useful in treating a bleeding disorder. Examples of such agents include, but are not limited to an anti-inflammatory agent, anti-steatosis agent, anti-viral, and/or anti-fibrosis agent. In addition, other substances commonly used to protect the liver, such as silymarin, can also be used in conjunction with the iRNAs described herein. Other agents useful for treating liver diseases include telbivudine, entecavir, and protease inhibitors such as telaprevir and other disclosed, for example, in Tung et al., U.S. Application Publication Nos. 2005/0148548, 2004/0167116, and 2003/0144217; and in Hale et al., U.S. Application Publication No. 2004/0127488.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred.

The data obtained from cell culture assays and animal studies can be used in formulating a range of dosage for use in humans. The dosage of compositions featured herein in the invention lies generally within a range of circulating concentrations that include the ED50 with little or no toxicity. The dosage can vary within this range depending upon the dosage form employed and the route of administration utilized. For any compound used in the methods featured in the invention, the therapeutically effective dose can be estimated initially from cell culture assays. A dose can be formulated in animal models to achieve a circulating plasma concentration range of the compound or, when appropriate, of the polypeptide product of a target sequence (e.g., achieving a decreased concentration of the polypeptide) that includes the IC50 (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

In addition to their administration, as discussed above, the iRNAs featured in the invention can be administered in combination with other known agents effective in treatment of pathological processes mediated by Serpinc1 expression. In any event, the administering physician can adjust the amount and timing of iRNA administration on the basis of results observed using standard measures of efficacy known in the art or described herein.

VI. Methods of the Invention

The present invention also provides methods of using an iRNA of the invention and/or a composition containing an iRNA of the invention to reduce and/or inhibit Serpinc1 expression in a cell. In other aspects, the present invention provides an iRNA of the invention and/or a composition comprising an iRNA of the invention for use in reducing and/or inhibiting Serpinc1 expression in a cell. In yet other aspects, use of an iRNA of the invention and/or a composition comprising an iRNA of the invention for the manufacture of a medicament for reducing and/or inhibiting Serpinc1 expression in a cell are provided.

The methods and uses include contacting the cell with an iRNA, e.g., a dsRNA, of the invention and maintaining the cell for a time sufficient to obtain degradation of the mRNA transcript of a Serpinc1 gene, thereby inhibiting expression of the Serpinc1 gene in the cell.

Reduction in gene expression can be assessed by any methods known in the art. For example, a reduction in the expression of Serpinc1 may be determined by determining the mRNA expression level of Serpinc1 using methods routine to one of ordinary skill in the art, e.g., Northern blotting, qRT-PCR, by determining the protein level of Serpinc1 using methods routine to one of ordinary skill in the art, such as Western blotting, immunological techniques, and/or by determining a biological activity of Serpinc1, such as affecting one or more molecules associated with the cellular blood clotting mechanism (or in an in vivo setting, blood clotting itself).

In the methods and uses of the invention the cell may be contacted in vitro or in vivo, i.e., the cell may be within a subject.

A cell suitable for treatment using the methods of the invention may be any cell that expresses a Serpinc1 gene. A cell suitable for use in the methods and uses of the invention may be a mammalian cell, e.g., a primate cell (such as a human cell or a non-human primate cell, e.g., a monkey cell or a chimpanzee cell), a non-primate cell (such as a cow cell, a pig cell, a camel cell, a llama cell, a horse cell, a goat cell, a rabbit cell, a sheep cell, a hamster, a guinea pig cell, a cat cell, a dog cell, a rat cell, a mouse cell, a lion cell, a tiger cell, a bear cell, or a buffalo cell), a bird cell (e.g., a duck cell or a goose cell), or a whale cell. In one embodiment, the cell is a human cell, e.g., a human liver cell.

Serpinc1 expression may be inhibited in the cell by at least about 5, 6, 7, 8, 9, 10, 11, 12, 13, 14, 15, 16, 17, 18, 19, 20, and 21, 22, 23, 24, 25, 26, 27, 28, 29, 30, 31, 32, 33, 34, 35, 36, 37, 38, 39, 40, 41, 42, 43, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or about 100%.

The in vivo methods and uses of the invention may include administering to a subject a composition containing an iRNA, where the iRNA includes a nucleotide sequence that is complementary to at least a part of an RNA transcript of the Serpinc1 gene of the mammal to be treated. When the organism to be treated is a mammal such as a human, the composition can be administered by any means known in the art including, but not limited to oral, intraperitoneal, or parenteral routes, including intracranial (e.g., intraventricular, intraparenchymal and intrathecal), intravenous, intramuscular, subcutaneous, transdermal, airway (aerosol), nasal, rectal, and topical (including buccal and sublingual) administration. In certain embodiments, the compositions are administered by intravenous infusion or injection.

In some embodiments, the administration is via a depot injection. A depot injection may release the iRNA in a consistent way over a prolonged time period. Thus, a depot injection may reduce the frequency of dosing needed to obtain a desired effect, e.g., a desired inhibition of Serpinc1, or a therapeutic or prophylactic effect. A depot injection may also provide more consistent serum concentrations. Depot injections may include subcutaneous injections or intramuscular injections. In preferred embodiments, the depot injection is a subcutaneous injection.

In some embodiments, the administration is via a pump. The pump may be an external pump or a surgically implanted pump. In certain embodiments, the pump is a subcutaneously implanted osmotic pump. In other embodiments, the pump is an infusion pump. An infusion pump may be used for intravenous, subcutaneous, arterial, or epidural infusions. In preferred embodiments, the infusion pump is a subcutaneous infusion pump. In other embodiments, the pump is a surgically implanted pump that delivers the iRNA to the liver.

The mode of administration may be chosen based upon whether local or systemic treatment is desired and based upon the area to be treated. The route and site of administration may be chosen to enhance targeting.

In one aspect, the present invention also provides methods for inhibiting the expression of a Serpinc1 gene in a mammal, e.g., a human. The present invention also provides a composition comprising an iRNA, e.g., a dsRNA, that targets a Serpinc1 gene in a cell of a mammal for use in inhibiting expression of the Serpinc1 gene in the mammal. In another aspect, the present invention provides use of an iRNA, e.g., a dsRNA, that targets a Serpinc1 gene in a cell of a mammal in the manufacture of a medicament for inhibiting expression of the Serpinc1 gene in the mammal.

The methods and uses include administering to the mammal, e.g., a human, a composition comprising an iRNA, e.g., a dsRNA, that targets a Serpinc1 gene in a cell of the mammal and maintaining the mammal for a time sufficient to obtain degradation of the mRNA transcript of the Serpinc1 gene, thereby inhibiting expression of the Serpinc1 gene in the mammal.

Reduction in gene expression can be assessed by any methods known it the art and by methods, e.g. qRT-PCR, described herein. Reduction in protein production can be assessed by any methods known it the art and by methods, e.g. ELISA, described herein. In one embodiment, a puncture liver biopsy sample serves as the tissue material for monitoring the reduction in Serpinc1 gene and/or protein expression. In another embodiment, a blood sample serves as the tissue material for monitoring the reduction in Serpinc1 gene and/or protein expression. In other embodiments, inhibition of the expression of a Serpinc1 gene is monitored indirectly by, for example, determining the expression and/or activity of a gene in a Serpinc1 pathway (see, e.g., FIG. 1). For example, the activity of factor Xa may be monitored to determine the inhibition of expression of a Serpinc1 gene. Antithrombin levels, clot formation, and/or endogenous thrombin potential, in a sample, e.g., a blood or liver sample, may also be measured. Suitable assays are further described in the Examples section below.

The present invention further provides methods of treating a subject having a disorder that would benefit from reduction in Serpinc1 expression, e.g., hemophilia. The treatment methods (and uses) of the invention include administering to the subject, e.g., a human, a therapeutically effective amount of an iRNA targeting a Serpinc1 gene or a pharmaceutical composition comprising an iRNA targeting a Serpinc1 gene, thereby treating the subject having a disorder that would benefit from reduction in Serpinc1 expression.

In one aspect, the invention provides methods of preventing at least one symptom in a subject having a disorder that would benefit from reduction in Serpinc1 expression. The methods include administering to the subject a therapeutically effective amount of the iRNA, e.g., dsRNA, or vector of the invention, thereby preventing at least one symptom in the subject having a disorder that would benefit from reduction in Serpinc1 expression. For example, the invention provides methods for preventing bleeding in a subject suffering from a disorder that would benefit from reduction in Serpinc1 expression, e.g., a hemophilia In another aspect, the present invention provides use of a therapeutically effective amount of an iRNA of the invention for treating a subject, e.g., a subject that would benefit from a reduction and/or inhibition of Serpinc1 expression. The iRNA includes iRNA targeting a Serpinc1 gene or a pharmaceutical composition comprising an iRNA targeting a Serpinc1 gene.

In yet another aspect, the present invention provides use of an iRNA of the invention targeting a Serpinc1 gene or a pharmaceutical composition comprising an iRNA targeting a Serpinc1 gene in the manufacture of a medicament for treating a subject, e.g., a subject that would benefit from a reduction and/or inhibition of Serpinc1 expression.

In another aspect, the invention provides uses of an iRNA, e.g., a dsRNA, of the invention for preventing at least one symptom in a subject suffering from a disorder that would benefit from a reduction and/or inhibition of Serpinc1 expression, such as a bleeding disorder, e.g., a hemophilia.

In a further aspect, the present invention provides uses of an iRNA of the invention in the manufacture of a medicament for preventing at least one symptom in a subject suffering from a disorder that would benefit from a reduction and/or inhibition of Serpinc1 expression, such as a bleeding disorder, e.g., a hemophilia. An iRNA of the invention may be administered in "naked" form, or as a "free iRNA." A naked iRNA is administered in the absence of a pharmaceutical composition. The naked iRNA may be in a suitable buffer solution. The buffer solution may comprise acetate, citrate, prolamine, carbonate, or phosphate, or any combination thereof. In one embodiment, the buffer solution is phosphate buffered saline (PBS). The pH and osmolarity of the buffer solution containing the iRNA can be adjusted such that it is suitable for administering to a subject.

Alternatively, an iRNA of the invention may be administered as a pharmaceutical composition, such as a dsRNA liposomal formulation.

Subjects that would benefit from a reduction and/or inhibition of Serpinc1 gene expression are those having a bleeding disorder, e.g., an inherited bleeding disorder or an acquired bleeding disorder as described herein. In one embodiment, a subject having an inherited bleeding disorder has a hemophilia, e.g., hemophilia A, B, or C. In one embodiment, a subject having an inherited bleeding disorder, e.g., a hemophilia, is an inhibitor subject. In one embodiment, the inhibitor subject has hemophilia A. In another embodiment, the inhibitor subject has hemophilia B. In yet another embodiment, the inhibitor subject has hemophilia C. Treatment of a subject that would benefit from a reduction and/or inhibition of Serpinc1 gene expression includes therapeutic (e.g., on-demand, e.g., the subject is bleeding (spontaneous bleeding or bleeding as a result of trauma) and failing to clot) and prophylactic (e.g., the subject is not bleeding and/or is to undergo surgery) treatment.

The invention further provides methods and uses for the use of an iRNA or a pharmaceutical composition thereof, e.g., for treating a subject that would benefit from reduction and/or inhibition of Serpinc1 expression, e.g., a subject having a bleeding disorder, in combination with other pharmaceuticals and/or other therapeutic methods, e.g., with known pharmaceuticals and/or known therapeutic methods, such as, for example, those which are currently employed for treating these disorders. For example, in certain embodiments, an iRNA targeting Serpinc1 is administered in combination with, e.g., an agent useful in treating a bleeding disorder as described elsewhere herein. For example, additional therapeutics and therapeutic methods suitable for treating a subject that would benefit from reduction in Serpinc1 expression, e.g., a subject having a bleeding disorder, include fresh-frozen plasma (FFP); recombinant FVIIa; recombinant FIX; FXI concentrates; virus-inactivated, vWF-containing FVIII concentrates; desensitization therapy which may include large doses of FVIII or FIX, along with steroids or intravenous immunoglobulin (IVIG) and cyclophosphamide; plasmapheresis in conjunction with immunosuppression and infusion of FVIII or FIX, with or without antifibrinolytic therapy; immune tolerance induction (ITI), with or without immunosuppressive therapy (e.g., cyclophosphamide, prednisone, and/or anti-CD20); desmopressin acetate [DDAVP]; antifibrinolytics, such as aminocaproic acid and tranexamic acid; activated prothrombin complex concentrate (PCC); antihemophilic agents; corticosteroids; immunosuppressive agents; and estrogens. The iRNA and an additional therapeutic agent and/or treatment may be administered at the same time and/or in the same combination, e.g., parenterally, or the additional therapeutic agent can be administered as part of a separate composition or at separate times and/or by another method known in the art or described herein.

In one embodiment, the methods and uses include administering a composition featured herein such that expression of the target Serpinc1 gene is decreased, such as for about 1, 2, 3, 4, 5, 6, 7, 8, 12, 16, 18, 24, 28, 32, 36, 40, 44, 48, 52, 56, 60, 64, 68, 72, 76, or about 80 hours. In one embodiment, expression of the target Serpinc1 gene is decreased for an extended duration, e.g., at least about two, three, four, five, six, seven days or more, e.g., about one week, two weeks, three weeks, or about four weeks or longer.

Preferably, the iRNAs useful for the methods, uses, and compositions featured herein specifically target RNAs (primary or processed) of the target Serpinc1 gene. Compositions, uses, and methods for inhibiting the expression of these genes using iRNAs can be prepared and performed as described herein.

Administration of the dsRNA according to the methods and uses of the invention may result in a reduction of the severity, signs, symptoms, and/or markers of such diseases or disorders in a patient with a bleeding disorder. By "reduction" in this context is meant a statistically significant decrease in such level. The reduction can be, for example, at least about 5%, 10%, 15%, 20%, 25%, 30%, 35%, 40%, 45%, 50%, 55%, 60%, 65%, 70%, 75%, 80%, 85%, 90%, 95%, or about 100%.

Efficacy of treatment or prevention of disease can be assessed, for example by measuring disease progression, disease remission, symptom severity, frequency of bleeds, reduction in pain, quality of life, dose of a medication required to sustain a treatment effect, level of a disease marker or any other measurable parameter appropriate for a given disease being treated or targeted for prevention. It is well within the ability of one skilled in the art to monitor efficacy of treatment or prevention by measuring any one of such parameters, or any combination of parameters. For example, efficacy of treatment of a bleeding disorder may be assessed, for example, by periodic monitoring of thrombin:anti-thrombin levels. Comparisons of the later readings with the initial readings provide a physician an indication of whether the treatment is effective. It is well within the ability of one skilled in the art to monitor efficacy of treatment or prevention by measuring any one of such parameters, or any combination of parameters. In connection with the administration of an iRNA targeting Serpinc1 or pharmaceutical composition thereof, "effective against" a bleeding disorder indicates that administration in a clinically appropriate manner results in a beneficial effect for at least a statistically significant fraction of patients, such as a improvement of symptoms, a cure, a reduction in disease, extension of life, improvement in quality of life, or other effect generally recognized as positive by medical doctors familiar with treating bleeding disorders and the related causes.

A treatment or preventive effect is evident when there is a statistically significant improvement in one or more parameters of disease status, or by a failure to worsen or to develop symptoms where they would otherwise be anticipated. As an example, a favorable change of at least 10% in a measurable parameter of disease, and preferably at least 20%, 30%, 40%, 50% or more can be indicative of effective treatment. Efficacy for a given iRNA drug or formulation of that drug can also be judged using an experimental animal model for the given disease as known in the art. When using an experimental animal model, efficacy of treatment is evidenced when a statistically significant reduction in a marker or symptom is observed.

Alternatively, the efficacy can be measured by a reduction in the severity of disease as determined by one skilled in the art of diagnosis based on a clinically accepted disease severity grading scale, as but one example the Child-Pugh score (sometimes the Child-Turcotte-Pugh score). Any positive change resulting in e.g., lessening of severity of disease measured using the appropriate scale, represents adequate treatment using an iRNA or iRNA formulation as described herein.

Subjects can be administered a therapeutic amount of iRNA, such as about 0.01 mg/kg, 0.02 mg/kg, 0.03 mg/kg, 0.04 mg/kg, 0.05 mg/kg, 0.1 mg/kg, 0.15 mg/kg, 0.2 mg/kg, 0.25 mg/kg, 0.3 mg/kg, 0.35 mg/kg, 0.4 mg/kg, 0.45 mg/kg, 0.5 mg/kg, 0.55 mg/kg, 0.6 mg/kg, 0.65 mg/kg, 0.7 mg/kg, 0.75 mg/kg, 0.8 mg/kg, 0.85 mg/kg, 0.9 mg/kg, 0.95 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2.0 mg/kg, 2.1 mg/kg, 2.2 mg/kg, 2.3 mg/kg, 2.4 mg/kg, 2.5 mg/kg dsRNA, 2.6 mg/kg dsRNA, 2.7 mg/kg dsRNA, 2.8 mg/kg dsRNA, 2.9 mg/kg dsRNA, 3.0 mg/kg dsRNA, 3.1 mg/kg dsRNA, 3.2 mg/kg dsRNA, 3.3 mg/kg dsRNA, 3.4 mg/kg dsRNA, 3.5 mg/kg dsRNA, 3.6 mg/kg dsRNA, 3.7 mg/kg dsRNA, 3.8 mg/kg dsRNA, 3.9 mg/kg dsRNA, 4.0 mg/kg dsRNA, 4.1 mg/kg dsRNA, 4.2 mg/kg dsRNA, 4.3 mg/kg dsRNA, 4.4 mg/kg dsRNA, 4.5 mg/kg dsRNA, 4.6 mg/kg dsRNA, 4.7 mg/kg dsRNA, 4.8 mg/kg dsRNA, 4.9 mg/kg dsRNA, 5.0 mg/kg dsRNA, 5.1 mg/kg dsRNA, 5.2 mg/kg dsRNA, 5.3 mg/kg dsRNA, 5.4 mg/kg dsRNA, 5.5 mg/kg dsRNA, 5.6 mg/kg dsRNA, 5.7 mg/kg dsRNA, 5.8 mg/kg dsRNA, 5.9 mg/kg dsRNA, 6.0 mg/kg dsRNA, 6.1 mg/kg dsRNA, 6.2 mg/kg dsRNA, 6.3 mg/kg dsRNA, 6.4 mg/kg dsRNA, 6.5 mg/kg dsRNA, 6.6 mg/kg dsRNA, 6.7 mg/kg dsRNA, 6.8 mg/kg dsRNA, 6.9 mg/kg dsRNA, 7.0 mg/kg dsRNA, 7.1 mg/kg dsRNA, 7.2 mg/kg dsRNA, 7.3 mg/kg dsRNA, 7.4 mg/kg dsRNA, 7.5 mg/kg dsRNA, 7.6 mg/kg dsRNA, 7.7 mg/kg dsRNA, 7.8 mg/kg dsRNA, 7.9 mg/kg dsRNA, 8.0 mg/kg dsRNA, 8.1 mg/kg dsRNA, 8.2 mg/kg dsRNA, 8.3 mg/kg dsRNA, 8.4 mg/kg dsRNA, 8.5 mg/kg dsRNA, 8.6 mg/kg dsRNA, 8.7 mg/kg dsRNA, 8.8 mg/kg dsRNA, 8.9 mg/kg dsRNA, 9.0 mg/kg dsRNA, 9.1 mg/kg dsRNA, 9.2 mg/kg dsRNA, 9.3 mg/kg dsRNA, 9.4 mg/kg dsRNA, 9.5 mg/kg dsRNA, 9.6 mg/kg dsRNA, 9.7 mg/kg dsRNA, 9.8 mg/kg dsRNA, 9.9 mg/kg dsRNA, 9.0 mg/kg dsRNA, 10 mg/kg dsRNA, 15 mg/kg dsRNA, 20 mg/kg dsRNA, 25 mg/kg dsRNA, 30 mg/kg dsRNA, 35 mg/kg dsRNA, 40 mg/kg dsRNA, 45 mg/kg dsRNA, or about 50 mg/kg dsRNA. Values and ranges intermediate to the recited values are also intended to be part of this invention.

In certain embodiments, for example, when a composition of the invention comprises a dsRNA as described herein and a lipid, subjects can be administered a therapeutic amount of iRNA, such as about 0.01 mg/kg to about 5 mg/kg, about 0.01 mg/kg to about 10 mg/kg, about 0.05 mg/kg to about 5 mg/kg, about 0.05 mg/kg to about 10 mg/kg, about 0.1 mg/kg to about 5 mg/kg, about 0.1 mg/kg to about 10 mg/kg, about 0.2 mg/kg to about 5 mg/kg, about 0.2 mg/kg to about 10 mg/kg, about 0.3 mg/kg to about 5 mg/kg, about 0.3 mg/kg to about 10 mg/kg, about 0.4 mg/kg to about 5 mg/kg, about 0.4 mg/kg to about 10 mg/kg, about 0.5 mg/kg to about 5 mg/kg, about 0.5 mg/kg to about 10 mg/kg, about 1 mg/kg to about 5 mg/kg, about 1 mg/kg to about 10 mg/kg, about 1.5 mg/kg to about 5 mg/kg, about 1.5 mg/kg to about 10 mg/kg, about 2 mg/kg to about 2.5 mg/kg, about 2 mg/kg to about 10 mg/kg, about 3 mg/kg to about 5 mg/kg, about 3 mg/kg to about 10 mg/kg, about 3.5 mg/kg to about 5 mg/kg, about 4 mg/kg to about 5 mg/kg, about 4.5 mg/kg to about 5 mg/kg, about 4 mg/kg to about 10 mg/kg, about 4.5 mg/kg to about 10 mg/kg, about 5 mg/kg to about 10 mg/kg, about 5.5 mg/kg to about 10 mg/kg, about 6 mg/kg to about 10 mg/kg, about 6.5 mg/kg to about 10 mg/kg, about 7 mg/kg to about 10 mg/kg, about 7.5 mg/kg to about 10 mg/kg, about 8 mg/kg to about 10 mg/kg, about 8.5 mg/kg to about 10 mg/kg, about 9 mg/kg to about 10 mg/kg, or about 9.5 mg/kg to about 10 mg/kg. Values and ranges intermediate to the recited values are also intended to be part of this invention.

For example, the dsRNA may be administered at a dose of about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or about 10 mg/kg. Values and ranges intermediate to the recited values are also intended to be part of this invention.

In other embodiments, for example, when a composition of the invention comprises a dsRNA as described herein and an N-acetylgalactosamine, subjects can be administered a therapeutic amount of iRNA, such as a dose of about 0.1 to about 50 mg/kg, about 0.25 to about 50 mg/kg, about 0.5 to about 50 mg/kg, about 0.75 to about 50 mg/kg, about 1 to about 50 mg/mg, about 1.5 to about 50 mg/kb, about 2 to about 50 mg/kg, about 2.5 to about 50 mg/kg, about 3 to about 50 mg/kg, about 3.5 to about 50 mg/kg, about 4 to about 50 mg/kg, about 4.5 to about 50 mg/kg, about 5 to about 50 mg/kg, about 7.5 to about 50 mg/kg, about 10 to about 50 mg/kg, about 15 to about 50 mg/kg, about 20 to about 50 mg/kg, about 20 to about 50 mg/kg, about 25 to about 50 mg/kg, about 25 to about 50 mg/kg, about 30 to about 50 mg/kg, about 35 to about 50 mg/kg, about 40 to about 50 mg/kg, about 45 to about 50 mg/kg, about 0.1 to about 45 mg/kg, about 0.25 to about 45 mg/kg, about 0.5 to about 45 mg/kg, about 0.75 to about 45 mg/kg, about 1 to about 45 mg/mg, about 1.5 to about 45 mg/kb, about 2 to about 45 mg/kg, about 2.5 to about 45 mg/kg, about 3 to about 45 mg/kg, about 3.5 to about 45 mg/kg, about 4 to about 45 mg/kg, about 4.5 to about 45 mg/kg, about 5 to about 45 mg/kg, about 7.5 to about 45 mg/kg, about 10 to about 45 mg/kg, about 15 to about 45 mg/kg, about 20 to about 45 mg/kg, about 20 to about 45 mg/kg, about 25 to about 45 mg/kg, about 25 to about 45 mg/kg, about 30 to about 45 mg/kg, about 35 to about 45 mg/kg, about 40 to about 45 mg/kg, about 0.1 to about 40 mg/kg, about 0.25 to about 40 mg/kg, about 0.5 to about 40 mg/kg, about 0.75 to about 40 mg/kg, about 1 to about 40 mg/mg, about 1.5 to about 40 mg/kb, about 2 to about 40 mg/kg, about 2.5 to about 40 mg/kg, about 3 to about 40 mg/kg, about 3.5 to about 40 mg/kg, about 4 to about 40 mg/kg, about 4.5 to about 40 mg/kg, about 5 to about 40 mg/kg, about 7.5 to about 40 mg/kg, about 10 to about 40 mg/kg, about 15 to about 40 mg/kg, about 20 to about 40 mg/kg, about 20 to about 40 mg/kg, about 25 to about 40 mg/kg, about 25 to about 40 mg/kg, about 30 to about 40 mg/kg, about 35 to about 40 mg/kg, about 0.1 to about 30 mg/kg, about 0.25 to about 30 mg/kg, about 0.5 to about 30 mg/kg, about 0.75 to about 30 mg/kg, about 1 to about 30 mg/mg, about 1.5 to about 30 mg/kb, about 2 to about 30 mg/kg, about 2.5 to about 30 mg/kg, about 3 to about 30 mg/kg, about 3.5 to about 30 mg/kg, about 4 to about 30 mg/kg, about 4.5 to about 30 mg/kg, about 5 to about 30 mg/kg, about 7.5 to about 30 mg/kg, about 10 to about 30 mg/kg, about 15 to about 30 mg/kg, about 20 to about 30 mg/kg, about 20 to about 30 mg/kg, about 25 to about 30 mg/kg, about 0.1 to about 20 mg/kg, about 0.25 to about 20 mg/kg, about 0.5 to about 20 mg/kg, about 0.75 to about 20 mg/kg, about 1 to about 20 mg/mg, about 1.5 to about 20 mg/kb, about 2 to about 20 mg/kg, about 2.5 to about 20 mg/kg, about 3 to about 20 mg/kg, about 3.5 to about 20 mg/kg, about 4 to about 20 mg/kg, about 4.5 to about 20 mg/kg, about 5 to about 20 mg/kg, about 7.5 to about 20 mg/kg, about 10 to about 20 mg/kg, or about 15 to about 20 mg/kg. In one embodiment, when a composition of the invention comprises a dsRNA as described herein and an N-acetylgalactosamine, subjects can be administered a therapeutic amount of about 10 to about 30 mg/kg of dsRNA. Values and ranges intermediate to the recited values are also intended to be part of this invention.

For example, subjects can be administered a therapeutic amount of iRNA, such as about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 31, 32, 33, 34, 34, 35, 36, 37, 38, 39, 40, 41, 42, 43, 44, 45, 46, 47, 48, 49, or about 50 mg/kg. Values and ranges intermediate to the recited values are also intended to be part of this invention.

The iRNA can be administered by intravenous infusion over a period of time, such as over a 5, 6, 7, 8, 9, 10, 11, 12, 13, 14, 15, 16, 17, 18, 19, 20, and 21, 22, 23, 24, or about a 25 minute period. The administration may be repeated, for example, on a regular basis, such as weekly, biweekly (i.e., every two weeks) for one month, two months, three months, four months or longer. After an initial treatment regimen, the treatments can be administered on a less frequent basis. For example, after administration weekly or biweekly for three months, administration can be repeated once per month, for six months or a year or longer.

In one embodiment, the present invention provides methods for treating a subject suffering from a bleeding disorder, e.g., a hemophilia, by subcutaneously administering to said subject compound AD-57213 at a cumulative weekly dose of about 0.5 mg/kg to about 5 mg/kg, or about 1 mg/kg to about 3 mg/kg.

In one embodiment, the methods may include subcutaneously administering to the subject a cumulative weekly dose of about 0.5 mg/kg. For example, in one embodiment, the methods may include administering to the subject a cumulative weekly dose of about 0.5 mg/kg as 0.5 .mg/kg every week. In another embodiment, the methods may include administering to the subject a cumulative weekly dose of about 0.5 mg/kg as 1 mg/kg every two weeks.

In another embodiment, the methods may include subcutaneously administering to the subject a cumulative weekly dose of about 1.5 mg/kg. For example, in one embodiment, the methods may include administering to the subject a cumulative weekly dose of about 1.5 mg/kg as 1.5 .mg/kg every week. In another embodiment, the methods may include administering to the subject a cumulative weekly dose of about 1.5 mg/kg as 3 mg/kg every two weeks.

In another embodiment, the methods may include subcutaneously administering to the subject a cumulative weekly dose of about 2 mg/kg. For example, in one embodiment, the methods may include administering to the subject a cumulative weekly dose of about 2 mg/kg as 2 mg/kg every week. In another embodiment, the methods may include administering to the subject a cumulative weekly dose of about 2 mg/kg as 4 mg/kg every two weeks.

In yet another embodiment, the methods may include subcutaneously administering to the subject a cumulative weekly dose of about 3 mg/kg. For example, in one embodiment, the methods may include administering to the subject a cumulative weekly dose of about 3 mg/kg as 3 mg/kg every week. In another embodiment, the methods may include administering to the subject a cumulative weekly dose of about 3 mg/kg as 6 mg/kg every two weeks.

In another embodiment, the present invention provides methods for preventing in a subject at least one symptom of a bleeding disorder, e.g., a hemophilia, by subcutaneously administering to the subject compound AD-57213 at a cumulative weekly dose of about 0.5 mg/kg to about 5 mg/kgor about 1 mg/kg to about 3 mg/kg.

In one embodiment, the methods may include subcutaneously administering to the subject a cumulative weekly dose of about 0.5 mg/kg. For example, in one embodiment, the methods may include administering to the subject a cumulative weekly dose of about 0.5 mg/kg as 0.5 .mg/kg every week. In another embodiment, the methods may include administering to the subject a cumulative weekly dose of about 0.5 mg/kg as 1 mg/kg every two weeks.

In another embodiment, the methods may include subcutaneously administering to the subject a cumulative weekly dose of about 1.5 mg/kg. For example, in one embodiment, the methods may include administering to the subject a cumulative weekly dose of about 1.5 mg/kg as 1.5 .mg/kg every week. In another embodiment, the methods may include administering to the subject a cumulative weekly dose of about 1.5 mg/kg as 3 mg/kg every two weeks.

In another embodiment, the methods may include subcutaneously administering to the subject a cumulative weekly dose of about 2 mg/kg. For example, in one embodiment, the methods may include administering to the subject a cumulative weekly dose of about 2 mg/kg as 2 mg/kg every week. In another embodiment, the methods may include administering to the subject a cumulative weekly dose of about 2 mg/kg as 4 mg/kg every two weeks.

In yet another embodiment, the methods may include subcutaneously administering to the subject a cumulative weekly dose of about 3 mg/kg. For example, in one embodiment, the methods may include administering to the subject a cumulative weekly dose of about 3 mg/kg as 3 mg/kg every week. In another embodiment, the methods may include administering to the subject a cumulative weekly dose of about 3 mg/kg as 6 mg/kg every two weeks.

Administration of the iRNA can reduce Serpinc1 levels, e.g., in a cell, tissue, blood, urine or other compartment of the patient by at least about 5%, 6, 7, 8, 9, 10, 11, 12, 13, 14, 15, 16, 17, 18, 19, 20, and 21, 22, 23, 24, 25, 26, 27, 28, 29, 30, 31, 32, 33, 34, 35, 36, 37, 38, 39, 40, 41, 42, 43, 44, 45, 46, 47, 48, 39, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or at least about 99% or more.

In one embodiment, the treatment and/or preventive methods include subcutaneously administering to a subject compound AD-57213 at a dose sufficient to inhibit reduce Serpinc1 levels, e.g., in a cell, tissue, blood, urine or other compartment of the patient by at least about by about 40, 41, 42, 43, 44, 45, 46, 47, 48, 49, 50, 51, 52, 53, 54, 55, 56, 57, 58, 69, 60, 61, 62, 63, 64, 65, 66, 67, 68, 69, 70, 71, 72, 73, 74, 75, 76, 77, 78, 79, or about 80%.

Before administration of a full dose of the iRNA, patients can be administered a smaller dose, such as a 5% infusion reaction, and monitored for adverse effects, such as an allergic reaction. In another example, the patient can be monitored for unwanted immunostimulatory effects, such as increased cytokine (e.g., TNF-alpha or INF-alpha) levels.

Owing to the inhibitory effects on Serpinc1 expression, a composition according to the invention or a pharmaceutical composition prepared therefrom can enhance the quality of life.

Unless otherwise defined, all technical and scientific terms used herein have the same meaning as commonly understood by one of ordinary skill in the art to which this invention belongs. Although methods and materials similar or equivalent to those described herein can be used in the practice or testing of the iRNAs and methods featured in the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1 iRNA Synthesis

Source of Reagents

Where the source of a reagent is not specifically given herein, such reagent can be obtained from any supplier of reagents for molecular biology at a quality/purity standard for application in molecular biology.

Transcripts siRNA design was carried out to identify siRNAs targeting human, rhesus (*Macaca mulatta*), dog, mouse, and rat SERPINC1 transcripts annotated in the NCBI Gene database (http://www.ncbi.nlm.nih.gov/gene/). Design used the following transcripts from the NCBI RefSeq collection: Human—NM_000488.2, NM_000488.3; Rhesus—NM_001104583.1; Dog—XM_856414.1; Mouse—NM_080844.4; Rat—NM_001012027.1. Due to high primate/canine/rodent sequence divergence, siRNA duplexes were designed in several separate batches, including but not limited to batches containing duplexes matching human and rhesus transcripts only; human, rhesus, and dog transcripts only; human, rhesus, mouse, and rat transcripts only; and mouse and rat transcripts only. All siRNA duplexes were designed that shared 100% identity the listed human transcript and other species transcripts considered in each design batch (above).

siRNA Design, Specificity, and Efficacy Prediction

The predicted specificity of all possible 19mers was predicted from each sequence. Candidate 19mers were then selected that lacked repeats longer than 7 nucleotides. These 874 candidate human/rhesus, 67 human/rhesus/dog, 103 human/rhesus/mouse/rat, and 569 mouse/rat siRNAs were used in comprehensive searches against the appropriate transcriptomes (defined as the set of NM_ and XM_ records within the human, rhesus, dog, mouse, or rat NCBI Refseq sets) using an exhaustive "brute-force" algorithm implemented in the python script 'BruteForce.py'. The script next parsed the transcript-oligo alignments to generate a score based on the position and number of mismatches between the siRNA and any potential 'off-target' transcript. The off-target score is weighted to emphasize differences in the 'seed' region of siRNAs, in positions 2-9 from the 5'-end of the molecule.

Each oligo-transcript pair from the brute-force search was given a mismatch score by summing the individual mismatch scores; mismatches in the position 2-9 were counted as 2.8, mismatches in the cleavage site positions 10-11 were counted as 1.2, and mismatches in region 12-19 counted as 1.0. An additional off-target prediction was carried out by comparing the frequency of heptamers and octomers derived from 3 distinct, seed-derived hexamers of each oligo. The hexamers from positions 2-7 relative to the 5' start were used to create 2 heptamers and one octamer. 'Heptamer1' was created by adding a 3'-A to the hexamer; heptamer2 was created by adding a 5'-A to the hexamer; the octomer was created by adding an A to both 5'- and 3'-ends of the hexamer. The frequency of octamers and heptamers in the human, rhesus, mouse, or rat 3'-UTRome (defined as the subsequence of the transcriptome from NCBI's Refseq database where the end of the coding region, the 'CDS', is clearly defined) was pre-calculated. The octamer frequency was normalized to the heptamer frequency using the median value from the range of octamer frequencies. A 'mirSeedScore' was then calculated by calculating the sum of ((3×normalized octamer count)+(2×heptamer2 count)+(1×heptamer1 count)).

Both siRNAs strands were assigned to a category of specificity according to the calculated scores: a score above 3 qualifies as highly specific, equal to 3 as specific and between 2.2 and 2.8 as moderately specific. The duplexes were sorted by the specificity of the antisense strand and those duplexes whose antisense oligos lacked GC at the first position, lacked G at both positions 13 and 14, and had 3 or more Us or As in the seed region were selected.

siRNA Sequence Selection

A total of 66 sense and 66 antisense derived human/rhesus, 6 sense and 6 antisense derived human/rhesus/mouse, 12 human/rhesus/mouse/rat, and 21 sense and 21 antisense derived mouse/rat siRNA oligos were synthesized and formed into duplexes. A detailed list of Serpinc1 sense and antisense strand sequences is shown in Tables 3 and 4.

siRNA Synthesis

I. General Small and Medium Scale RNA Synthesis Procedure

RNA oligonucleotides were synthesized at scales between 0.2-500 μmol using commercially available 5'-O-(4,4'-dimethoxytrityl)-2'-O-t-butyldimethylsilyl-3'-O-(2-cyanoethyl-N,N-diisopropyl)phosphoramidite monomers of uridine, 4-N-acetylcytidine, 6-N-benzoyladenosine and 2-N-isobutyrylguanosine and the corresponding 2'-O-methyl and 2'-fluoro phosphoramidites according to standard solid phase oligonucleotide synthesis protocols. The amidite solutions were prepared at 0.1-0.15 M concentration and 5-ethylthio-1H-tetrazole (0.25-0.6 M in acetonitrile) was used as the activator. Phosphorothioate backbone modifications were introduced during synthesis using 0.2 M phenylacetyl disulfide (PADS) in lutidine:acetonitrile (1:1) (v; v) or 0.1 M 3-(dimethylaminomethylene)amino-3H-1,2,4-dithiazole-5-thione (DDTT) in pyridine for the oxidation step. After completion of synthesis, the sequences were cleaved from the solid support and deprotected using methylamine followed by triethylamine. 3HF to remove any 2'-O-t-butyldimethylsilyl protecting groups present.

For synthesis scales between 5-500 μmol and fully 2' modified sequences (2'-fluoro and/or 2'-O-methyl or combinations thereof) the oligonucleotides where deprotected using 3:1 (v/v) ethanol and concentrated (28-32%) aqueous ammonia either at 35° C. 16 h or 55° C. for 5.5 h. Prior to ammonia deprotection the oligonucleotides where treated with 0.5 M piperidine in acetonitrile for 20 min on the solid support. The crude oligonucleotides were analyzed by LC-MS and anion-exchange HPLC (IEX-HPLC). Purification of the oligonucleotides was carried out by IEX HPLC using: 20 mM phosphate, 10%-15% ACN, pH=8.5 (buffer A) and 20 mM phosphate, 10%-15% ACN, 1 M NaBr, pH=8.5 (buffer B). Fractions were analyzed for purity by analytical HPLC. The product-containing fractions with suitable purity were pooled and concentrated on a rotary evaporator prior to desalting. The samples were desalted by size exclusion chromatography and lyophilized to dryness. Equal molar amounts of sense and antisense strands were annealed in 1×PBS buffer to prepare the corresponding siRNA duplexes.

For small scales (0.2-1 μmol), synthesis was performed on a MerMade 192 synthesizer in a 96 well format. In case of fully 2'-modified sequences (2'-fluoro and/or 2'-O-methyl or combinations thereof) the oligonucleotides where deprotected using methylamine at room temperature for 30-60 min followed by incubation at 60° C. for 30 min or using 3:1 (v/v) ethanol and concentrated (28-32%) aqueous ammonia at room temperature for 30-60 min followed by incubation at 40° C. for 1.5 hours. The crude oligonucleotides were then precipitated in a solution of acetonitrile:acetone (9:1) and isolated by centrifugation and decanting the supernatant. The crude oligonucleotide pellet was re-suspended in 20 mM NaOAc buffer and analyzed by LC-MS and anion exchange HPLC. The crude oligonucleotide sequences were desalted in 96 deep well plates on a 5 mL HiTrap Sephadex G25 column (GE Healthcare). In each well about 1.5 mL samples corresponding to an individual sequence was collected. These purified desalted oligonucleotides were analyzed by LC-MS and anion exchange chromatography. Duplexes were prepared by annealing equimolar amounts of sense and antisense sequences on a Tecan robot. Concentration of duplexes was adjusted to 10 μM in 1×PBS buffer.

II. Synthesis of GalNAc-Conjugated Oligonucleotides for In Vivo Analysis

Oligonucleotides conjugated with GalNAc ligand at their 3'-terminus were synthesized at scales between 0.2-500 μmol using a solid support pre-loaded with a Y-shaped linker bearing a 4,4'-dimethoxytrityl (DMT)-protected primary hydroxy group for oligonucleotide synthesis and a GalNAc ligand attached through a tether.

For synthesis of GalNAc conjugates in the scales between 5-500 μmol, the above synthesis protocol for RNA was followed with the following adaptions: For polystyrene-based synthesis supports 5% dichloroacetic acid in toluene was used for DMT-cleavage during synthesis. Cleavage from the support and deprotection was performed as described above. Phosphorothioate-rich sequences (usually >5 phorphorothioates) were synthesized without removing the final 5'-DMT group ("DMT-on") and, after cleavage and deprotection as described above, purified by reverse phase HPLC using 50 mM ammonium acetate in water (buffer A) and 50 mM ammoniumacetate in 80% acetonitrile (buffer B). Fractions were analyzed for purity by analytical HPLC and/or LC-MS. The product-containing fractions with suitable purity were pooled and concentrated on a rotary evaporator. The DMT-group was removed using 20%-25% acetic acid in water until completion. The samples were desalted by size exclusion chromatography and lyophilized to dryness. Equal molar amounts of sense and antisense strands were annealed in 1×PBS buffer to prepare the corresponding siRNA duplexes.

For small scale synthesis of GalNAc conjugates (0.2-1 μmol), including sequences with multiple phosphorothioate linkages, the protocols described above for synthesis of RNA or fully 2'-F/2'-OMe-containing sequences on MerMade platform were applied. Synthesis was performed on pre-packed columns containing GalNAc-functionalized controlled pore glass support.

Example 2

In Vitro Screening

Cell Culture and Transfections

Figure 2A:
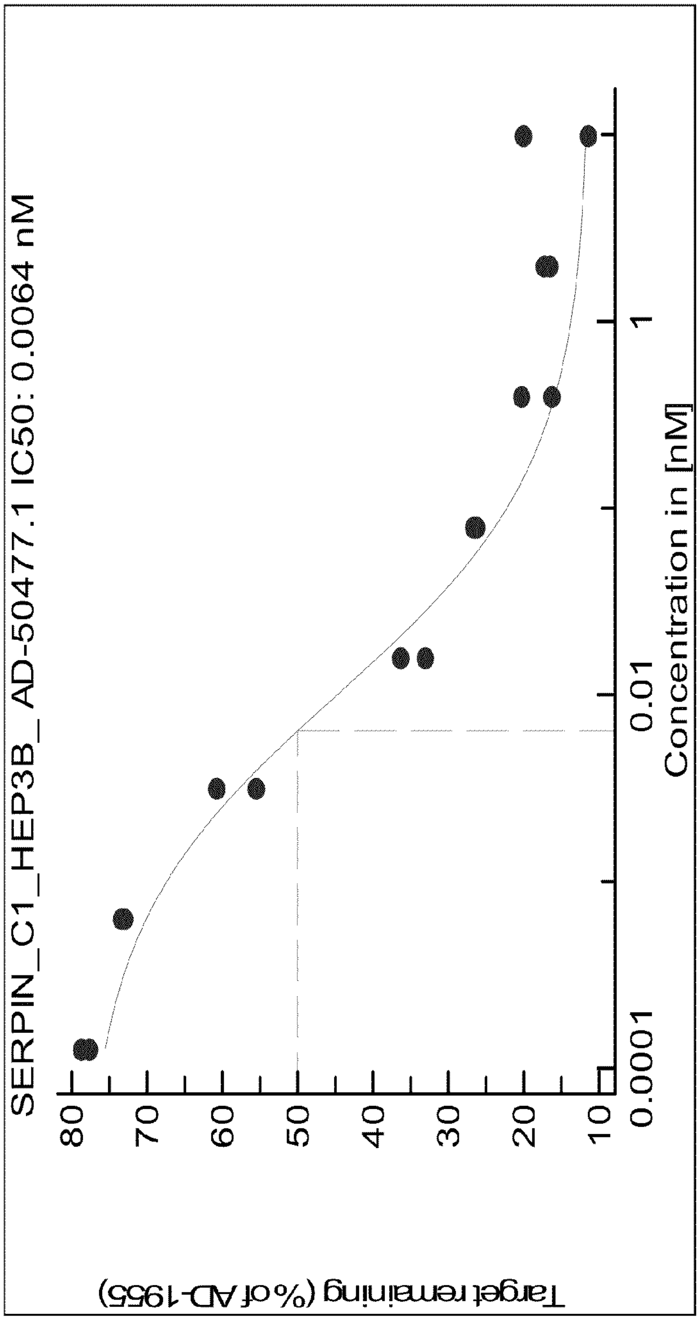
FIGS. 2A and 2B are graphs showing the inhibition of Serpinc1 expression in Hep3B cells following a single dose of the indicated iRNAs.
Figure 2B:
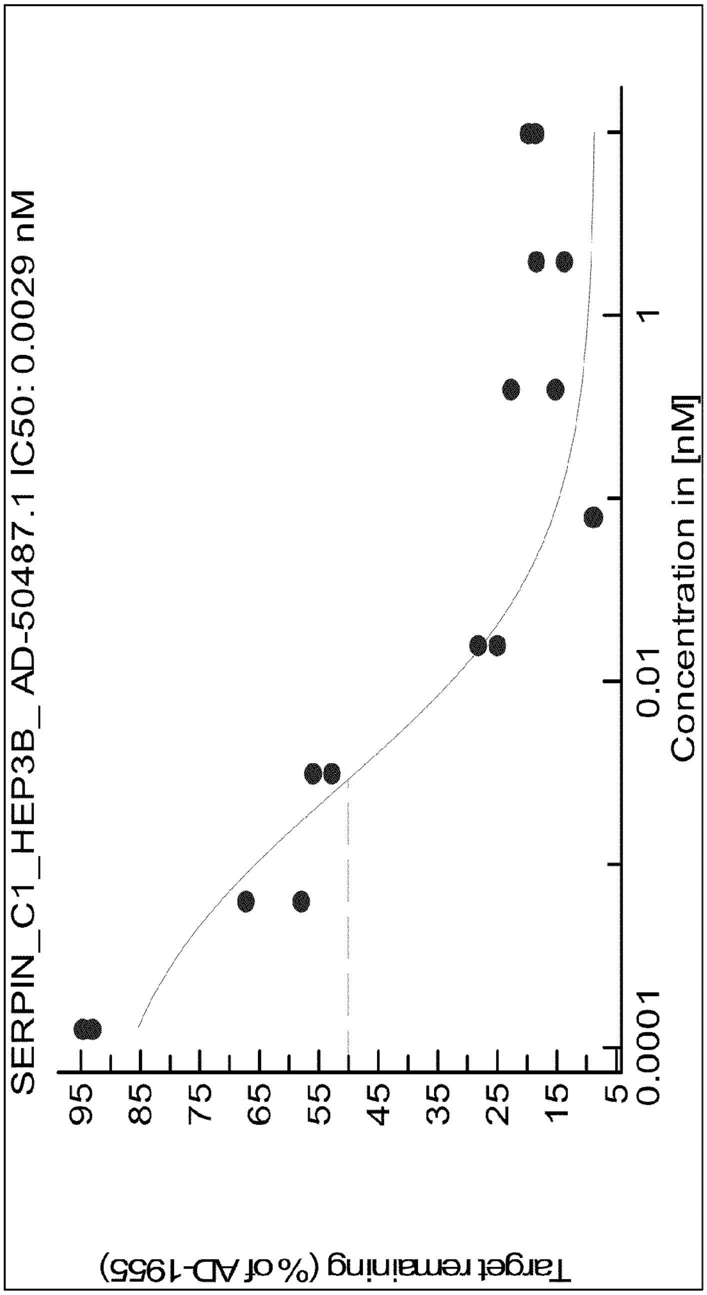

Hep3B cells (ATCC, Manassas, Va.) were grown to near confluence at 37° C. in an atmosphere of 5% CO2 in Eagle's Minimum Essential Medium (ATCC) supplemented with 10% FBS, streptomycin, and glutamine (ATCC) before being released from the plate by trypsinization. For mouse cross reactive duplexes, primary mouse hepatocytes (PMH) were freshly isolated less than 1 hour prior to transfections and grown in primary hepatocyte media. For both Hep3B and PMH, transfection was carried out by adding 14.8 μl of Opti-MEM plus 0.2 μl of Lipofectamine RNAiMax per well (Invitrogen, Carlsbad Calif. cat #13778-150) to 5 μl of each siRNA duplex to an individual well in a 96-well plate. The mixture was then incubated at room temperature for 15 minutes. Eighty μl of complete growth media without antibiotic containing ~$2\times10^4$ Hep3B cells were then added to the siRNA mixture. Cells were incubated for 24 hours prior to RNA purification. Single dose experiments were performed at 10 nM and 0.1 nM final duplex concentration and dose response experiments were done using 8×5-fold serial dilutions over the range of 10 nM to 128 pM (see FIGS. 2A and 2B).

Free Uptake Transfection

Five μl of each GalNac conjugated siRNA in PBS was combined with $4\times10^4$ freshly thawed cryopreserved Cynomolgus monkey hepatocytes resuspended in 95 μl of In Vitro Gro CP media (In Vitro Technologies-Celsis, Baltimore, Md.) in each well of a 96 well plate. The mixture was incubated for about 24 hrs at 37° C. in an atmosphere of 5% $CO_2$. siRNAs were tested at final concentrations of 100 nM, 10 nM and 0.1 nM for efficacy free uptake assays.

Total RNA Isolation using DYNABEADS mRNA Isolation Kit (Invitrogen, Part #: 610-12)

Cells were harvested and lysed in 150 μl of Lysis/Binding Buffer then mixed for 5 minutes at 850 rpm using an Eppendorf Thermomixer (the mixing speed was the same throughout the process). Ten microliters of magnetic beads and 80 μl Lysis/Binding Buffer mixture were added to a round bottom plate and mixed for 1 minute. Magnetic beads were captured using a magnetic stand and the supernatant was removed without disturbing the beads. After removing the supernatant, the lysed cells were added to the remaining beads and mixed for 5 minutes. After removing the supernatant, magnetic beads were washed 2 times with 150 Wash Buffer A and mixed for 1 minute. The beads were capturedagain and the supernatant was removed. The beads were then washed with 150 μl Wash Buffer B, captured and the supernatant was removed. The beads were next washed with 150 μl Elution Buffer, captured and the supernatant removed. Finally, the beads were allowed to dry for 2 minutes. After drying, 50 μl of Elution Buffer was added and mixed for 5 minutes at 70° C. The beads were captured on magnet for 5 minutes. 40 μl of supernatant was removed and added to another 96 well plate.

cDNA Synthesis Using ABI High Capacity cDNA Reverse Transcription Kit (Applied Biosystems, Foster City, Calif., Cat #4368813)

A master mix of 2 μl 10× Buffer, 0.8 μl 25×dNTPs, 2 μl Random primers, 1 μl Reverse Transcriptase, 1 μl RNase inhibitor and 3.2 μl of H2O per reaction were added into 10 μl total RNA. cDNA was generated using a Bio-Rad C-1000 or S-1000 thermal cycler (Hercules, Calif.) through the following steps: 25° C. for 10 minutes, 37° C. for 120 minutes, 85° C. for 5 seconds, and 4° C. hold.

Real Time PCR

Two μl of cDNA were added to a master mix containing 0.5 μl human GAPDH TaqMan Probe (Applied Biosystems Cat #4326317E), 0.5 μl human SERPINC1 TaqMan probe (Applied Biosystems cat #Hs00892758_ml) for human cells or 0.5 μl mouse GAPDH TaqMan Probe (Applied Biosystems Cat #4308313), 0.5 μl mouse SERPINC1 TaqMan probe (Applied Biosystems cat #Mm00446573_ml) for mouse cells and 50 Lightcycler 480 probe master mix (Roche Cat #04887301001) per well in a 384 well plates. Real time PCR was done in an ABI 7900HT Real Time PCR system (Applied Biosystems) using the ΔΔCt(RQ) assay. Each duplex was tested in two independent transfections and each transfection was assayed in duplicate, unless otherwise noted in the summary tables.

To calculate relative fold change in Serpinc1 mRNA levels, real time data were analyzed using the ΔΔCt method and normalized to assays performed with cells transfected with 10 nM AD-1955, or mock transfected cells. $IC_{50}$s were calculated using a 4 parameter fit model using XLFit and normalized to cells transfected with AD-1955 over the same dose range, or to its own lowest dose. Table 5 shows the results of a single dose screen in Hep3B cells and PMH cells transfected with the indicated iRNAs. Table 6 shows the results of dose response of the indicated iRNAs transfected into Hep3B and PMH cells.

The sense and antisense sequences of AD-1955 are:

```
SENSE:
                                    (SEQ ID NO: 13)
cuuAcGcuGAGuAcuucGAdTsdT

ANTISENSE:
                                    (SEQ ID NO: 14)
UCGAAGuACUcAGCGuAAGdTsdT.
```

TABLE 2

Abbreviations of nucleotide monomers used in nucleic acid sequence representation. It will be understood that these monomers, when present in an oligonucleotide, are mutually linked by 5'-3'-phosphodiester bonds.

| Abbreviation | Nucleotide(s) |
|---|---|
| A | Adenosine-3'-phosphate |
| Ab | beta-L-adenosine-3'-phosphate |
| Abs | beta-L-adenosine-3'-phosphorothioate |
| Af | 2'-fluoroadenosine-3'-phosphate |
| Afs | 2'-fluoroadenosine-3'-phosphorothioate |
| As | adenosine-3'-phosphorothioate |
| C | cytidine-3'-phosphate |
| Cb | beta-L-cytidine-3'-phosphate |
| Cbs | beta-L-cytidine-3'-phosphorothioate |
| Cf | 2'-fluorocytidine-3'-phosphate |
| Cfs | 2'-fluorocytidine-3'-phosphorothioate |

TABLE 2-continued

Abbreviations of nucleotide monomers used in nucleic acid sequence representation. It will be understood that these monomers, when present in an oligonucleotide, are mutually linked by 5'-3'-phosphodiester bonds.

| Abbreviation | Nucleotide(s) |
|---|---|
| (Chd) | 2'-O-hexadecyl-cytidine-3'-phosphate |
| (Chds) | 2'-O-hexadecyl-cytidine-3'-phosphorothioate |
| Cs | cytidine-3'-phosphorothioate |
| G | guanosine-3'-phosphate |
| Gb | beta-L-guanosine-3'-phosphate |
| Gbs | beta-L-guanosine-3'-phosphorothioate |
| Gf | 2'-fluoroguanosine-3'-phosphate |
| Gfs | 2'-fluoroguanosine-3'-phosphorothioate |
| Gs | guanosine-3'-phosphorothioate |
| T | 5'-methyluridine-3'-phosphate |
| Tb | beta-L-thymidine-3'-phosphate |
| Tbs | beta-L-thymidine-3'-phosphorothioate |
| Tf | 2'-fluoro-5-methyluridine-3'-phosphate |
| Tfs | 2'-fluoro-5-methyluridine-3'-phosphorothioate |
| Ts | 5-methyluridine-3'-phosphorothioate |
| U | Uridine-3'-phosphate |
| Ub | beta-L-uridine-3'-phosphate |
| Ubs | beta-L-uridine-3'-phosphorothioate |
| Uf | 2'-fluorouridine-3'-phosphate |
| Ufs | 2'-fluorouridine-3'-phosphorothioate |
| (Uhd) | 2'-O-hexadecyl-uridine-3'-phosphate |
| (Uhds) | 2'-O-hexadecyl-uridine-3'-phosphorothioate |
| Us | uridine-3'-phosphorothioate |
| N | any nucleotide (G, A, C, T or U) |
| a | 2'-O-methyladenosine-3'-phosphate |
| as | 2'-O-methyladenosine-3'-phosphorothioate |
| c | 2'-O-methylcytidine-3'-phosphate |
| cs | 2'-O-methylcytidine-3'-phosphorothioate |
| g | 2'-O-methylguanosine-3'-phosphate |
| gs | 2'-O-methylguanosine-3'-phosphorothioate |
| t | 2'-O-methyl-5-methyluridine-3'-phosphate |
| ts | 2'-O-methyl-5-methyluridine-3'-phosphorothioate |
| u | 2'-O-methyluridine-3'-phosphate |
| us | 2'-O-methyluridine-3'-phosphorothioate |
| dA | 2'-deoxyadenosine-3'-phosphate |
| dAs | 2'-deoxyadenosine-3'-phosphorothioate |
| dC | 2'-deoxycytidine-3'-phosphate |
| dCs | 2'-deoxycytidine-3'-phosphorothioate |
| dG | 2'-deoxyguanosine-3'-phosphate |
| dGs | 2'-deoxyguanosine-3'-phosphorothioate |
| dT | 2'-deoxythymidine |
| dTs | 2'-deoxythymidine-3'-phosphorothioate |
| dU | 2'-deoxyuridine |
| s | phosphorothioate linkage |
| L96 | N-[tris(GalNAc-alkyl)-amidodecanoyl)]-4-hydroxyprolinol Hyp-(GalNAc-alkyl)3 |
| (Aeo) | 2'-O-methoxyethyladenosine-3'-phosphate |
| (Aeos) | 2'-O-methoxyethyladenosine-3'-phosphorothioate |
| (Geo) | 2'-O-methoxyethylguanosine-3'-phosphate |
| (Geos) | 2'-O-methoxyethylguanosine-3'-phosphorothioate |
| (Teo) | 2'-O-methoxyethyl-5-methyluridine-3'-phosphate |
| (Teos) | 2'-O-methoxyethyl-5-methyluridine-3'-phosphorothioate |
| (m5Ceo) | 2'-O-methoxyethyl-5-methylcytidine-3'-phosphate |
| (m5Ceos) | 2'-O-methoxyethyl-5-methylcytidine-3'-phosphorothioate |

TABLE 3

Unmodified Sense and antisense strand sequences of Serpinc1 dsRNAs (The "Sense Sequence" column sequences are disclosed as SEQ ID NOS 15-71, respectively, in order of appearance, and the "Antisense Sequence" column sequences are disclosed as SEQ ID NOS 72-128, respectively, in order of appearance)

| Duplex Name | Sense Name | Sense Sequence | Antisense Name | Antisense Sequence |
|---|---|---|---|---|
| AD-50475.1-UM | A-104633.1 | CCCUGUGGACAUCUGCACA | A-104634.1 | UGUGCAGAUGUCCACAGGG |
| AD-50476.1-UM | A-104649.1 | CUACCACUUUCUAUCAGCA | A-104650.1 | UGCUGAUAGAAAGUGGUAG |

TABLE 3-continued

Unmodified Sense and antisense strand sequences of Serpinc1 dsRNAs (The "Sense Sequence" column sequences are disclosed as SEQ ID NOS 15-71, respectively, in order of appearance, and the "Antisense Sequence" column sequences are disclosed as SEQ ID NOS 72-128, respectively, in order of appearance)

| Duplex Name | Sense Name | Sense Sequence | Antisense Name | Antisense Sequence |
|---|---|---|---|---|
| AD-50477.1-UM | A-104665.1 | CUAUCGAAAAGCCAACAAA | A-104666.1 | UUUGUUGGCUUUUCGAUAG |
| AD-50478.1-UM | A-104681.1 | GGACUUCAAGGAAAAUGCA | A-104682.1 | UGCAUUUUCCUUGAAGUCC |
| AD-50479.1-UM | A-104697.1 | GUUAACACCAUUUACUUCA | A-104698.1 | UGAAGUAAAUGGUGUUAAC |
| AD-50480.1-UM | A-104713.1 | CCUGGUUUUUAUAAGAGAA | A-104714.1 | UUCUCUUAUAAAAACCAGG |
| AD-50481.1-UM | A-104635.1 | GACAUUCCCAUGAAUCCCA | A-104636.1 | UGGGAUUCAUGGGAAUGUC |
| AD-50482.1-UM | A-104651.1 | CACCUGGCAGAUUCCAAGA | A-104652.1 | UCUUGGAAUCUGCCAGGUG |
| AD-50483.1-UM | A-104667.1 | CGAAAAGCCAACAAAUCCU | A-104668.1 | AGGAUUUGUUGGCUUUUCG |
| AD-50484.1-UM | A-104683.1 | GAAAAUGCAGAGCAAUCCA | A-104684.1 | UGGAUUGCUCUGCAUUUUC |
| AD-50485.1-UM | A-104699.1 | GGCCUGUGGAAGUCAAAGU | A-104700.1 | ACUUUGACUUCCACAGGCC |
| AD-50486.1-UM | A-104715.1 | GAAGUUCCUCUGAACACUA | A-104716.1 | UAGUGUUCAGAGGAACUUC |
| AD-50487.1-UM | A-104637.1 | CCAUGAAUCCCAUGUGCAU | A-104638.1 | AUGCACAUGGGAUUCAUGG |
| AD-50488.1-UM | A-104653.1 | CAACUGAUGGAGGUAUUUA | A-104654.1 | UAAAUACCUCCAUCAGUUG |
| AD-50489.1-UM | A-104669.1 | CCAAGUUAGUAUCAGCCAA | A-104670.1 | UUGGCUGAUACUAACUUGG |
| AD-50490.1-UM | A-104685.1 | CGGCCAUCAACAAAUGGGU | A-104686.1 | ACCCAUUUGUUGAUGGCCG |
| AD-50491.1-UM | A-104701.1 | GAGGACGGCUUCAGUUUGA | A-104702.1 | UCAAACUGAAGCCGUCCUC |
| AD-50492.1-UM | A-104717.1 | CCUCUGAACACUAUUAUCU | A-104718.1 | AGAUAAUAGUGUUCAGAGG |
| AD-50493.1-UM | A-104639.1 | CAUGAAUCCCAUGUGCAUU | A-104640.1 | AAUGCACAUGGGAUUCAUG |
| AD-50494.1-UM | A-104655.1 | GAUGGAGGUAUUUAAGUUU | A-104656.1 | AAACUUAAAUACCUCCAUC |
| AD-50495.1 UM | A-104671.1 | GUAUCAGCCAAUCGCCUUU | A-104672.1 | AAAGGCGAUUGGCUGAUAC |
| AD-50496.1-UM | A-104687.1 | GGGUGUCCAAUAAGACCGA | A-104688.1 | UCGGUCUUAUUGGACACCC |
| AD-50497.1-UM | A-104703.1 | CAGCCCUGAAAAGUCCAAA | A-104704.1 | UUUGGACUUUUCAGGGCUG |
| AD-50498.1-UM | A-104641.1 | CCCAUGUGCAUUUACCGCU | A-104642.1 | AGCGGUAAAUGCACAUGGG |
| AD-50499.1-UM | A-104657.1 | GUAUUUAAGUUUGACACCA | A-104658.1 | UGGUGUCAAACUUAAAUAC |
| AD-50500.1-UM | A-104673.1 | GACAAAUCCCUUACCUUCA | A-104674.1 | UGAAGGUAAGGGAUUUGUC |
| AD-50501.1-UM | A-104689.1 | CUGUUCUGGUGCUGGUUAA | A-104690.1 | UUAACCAGCACCAGAACAG |
| AD-50502.1 UM | A-104705.1 | CCAAACUCCCAGGUAUUGU | A-104706.1 | ACAAUACCUGGGAGUUUGG |
| AD-50503.1-UM | A-104643.1 | CCCGCUUUGCUACCACUUU | A-104644.1 | AAAGUGGUAGCAAAGCGGG |
| AD-50505.1-UM | A-104675.1 | CUUACCUUCAAUGAGACCU | A-104676.1 | AGGUCUCAUUGAAGGUAAG |
| AD-50506.1-UM | A-104691.1 | CUGGUGCUGGUUAACACCA | A-104692.1 | UGGUGUUAACCAGCACCAG |
| AD-50507.1-UM | A-104707.1 | CAAACUCCCAGGUAUUGUU | A-104708.1 | AACAAUACCUGGGAGUUUG |
| AD-50508.1-UM | A-104645.1 | GCUUUGCUACCACUUUCUA | A-104646.1 | UAGAAAGUGGUAGCAAAGC |
| AD-50510.1-UM | A-104677.1 | CCUACCAGGACAUCAGUGA | A-104678.1 | UCACUGAUGUCCUGGUAGG |
| AD-50511.1-UM | A-104693.1 | GGUGCUGGUUAACACCAUU | A-104694.1 | AAUGGUGUUAACCAGCACC |
| AD-50512.1-UM | A-104709.1 | GCCGUUCGCUAAACCCCAA | A-104710.1 | UUGGGGUUUAGCGAACGGC |
| AD-50515.1-UM | A-104679.1 | GGACAUCAGUGAGUUGGUA | A-104680.1 | UACCAACUCACUGAUGUCC |
| AD-50516.1-UM | A-104695.1 | GUGCUGGUUAACACCAUUU | A-104696.1 | AAAUGGUGUUAACCAGCAC |

TABLE 3-continued

Unmodified Sense and antisense strand sequences of Serpinc1 dsRNAs (The "Sense Sequence" column sequences are disclosed as SEQ ID NOS 15-71, respectively, in order of appearance, and the "Antisense Sequence" column sequences are disclosed as SEQ ID NOS 72-128, respectively, in order of appearance)

| Duplex Name | Sense Name | Sense Sequence | Antisense Name | Antisense Sequence |
|---|---|---|---|---|
| AD-50517.1-UM | A-104711.1 | GCCUUUCCUGGUUUUUAUA | A-104712.1 | UAUAAAAACCAGGAAAGGC |
| AD-50518.1-UM | A-104719.1 | CUUUUGCUAUGACCAAGCU | A-104720.1 | AGCUUGGUCAUAGCAAAAG |
| AD-50523.1-UM | A-104721.1 | UGUACCAGGAAGGCAAGUU | A-104722.1 | AACUUGCCUUCCUGGUACA |
| AD-50528.1-UM | A-104723.1 | ACUAUUAUCUUCAUGGGCA | A-104724.1 | UGCCCAUGAAGAUAAUAGU |
| AD-50540.1-UM | A-104729.1 | UCAUGGGCAGAGUAGCCAA | A-104730.1 | UUGGCUACUCUGCCCAUGA |
| AD-50539.1-UM | A-104785.1 | CCAUUUACUUCAAGGGCCU | A-104786.1 | AGGCCCUUGAAGUAAAUGG |
| AD-50544.1-UM | A-104787.1 | UACUUCAAGGGCCUGUGGA | A-104788.1 | UCCACAGGCCCUUGAAGUA |
| AD-50549.1-UM | A-104789.1 | ACUUCAAGGGCCUGUGGAA | A-104790.1 | UUCCACAGGCCCUUGAAGU |
| AD-50514.1-UM | A-104663.1 | CGACUCUAUCGAAAAGCCA | A-104664.1 | UGGCUUUUCGAUAGAGUCG |
| AD-50522.1-UM | A-104779.1 | AACUGCCGACUCUAUCGAA | A-104780.1 | UUCGAUAGAGUCGGCAGUU |
| AD-50527.1-UM | A-104781.1 | ACUGCCGACUCUAUCGAAA | A-104782.1 | UUUCGAUAGAGUCGGCAGU |
| AD-50531.1-UM | A-104739.1 | GACUCUAUCGAAAAGCCAA | A-104740.1 | UUGGCUUUUCGAUAGAGUC |
| AD-50534.1-UM | A-104769.1 | UCUUCUUUGCCAAACUGAA | A-104770.1 | UUCAGUUUGGCAAAGAAGA |
| AD-50538.1-UM | A-104771.1 | UGCCAAACUGAACUGCCGA | A-104772.1 | UCGGCAGUUCAGUUUGGCA |
| AD-50543.1-UM | A-104773.1 | CCAAACUGAACUGCCGACU | A-104774.1 | AGUCGGCAGUUCAGUUUGG |
| AD-50553.1-UM | A-104777.1 | ACUGAACUGCCGACUCUAU | A-104778.1 | AUAGAGUCGGCAGUUCAGU |
| AD-50504.1-UM | A-104659.1 | GAACUGCCGACUCUAUCGA | A-104660.1 | UCGAUAGAGUCGGCAGUUC |
| AD-50509.1-UM | A-104661.1 | CUGCCGACUCUAUCGAAAA | A-104662.1 | UUUUCGAUAGAGUCGGCAG |
| AD-50529.1-UM | A-104751.1 | CUGGUUAACACCAUUUACU | A-104752.1 | AGUAAAUGGUGUUAACCAG |

TABLE 4

Modified Sense and antisense strand sequences of Serpinc1 dsRNAs (The "Sense Sequence" column sequences are disclosed as SEQ ID NOS 129-185, respectively, in order of appearance, and the "Antisense Sequence" column sequences are disclosed as SEQ ID NOS 186-242, respectively, in order of appearance)

| Duplex Name | Sense Name | Sense Sequence | Antisense Name | Antisense Sequence |
|---|---|---|---|---|
| AD-50475.1 | A-104633.1 | cccuGuGGAcAucuGcAcAdTsdT | A-104634.1 | UGUGcAGAUGUCcAcAGGGdTsdT |
| AD-50476.1 | A-104649.1 | cuAccAcuuucuAucAGcAdTsdT | A-104650.1 | UGCUGAuAGAAAGUGGuAGdTsdT |
| AD-50477.1 | A-104665.1 | cuAucGAAAAGccAAcAAAdTsdT | A-104666.1 | UUUGUUGGCUUUUCGAuAGdTsdT |
| AD-50478.1 | A-104681.1 | GGAcuucAAGGAAAAuGcAdTsdT | A-104682.1 | UGcAUUUUCCUUGAAGUCCdTsdT |
| AD-50479.1 | A-104697.1 | GuuAAcAccAuuuAcuucAdTsdT | A-104698.1 | UGAAGuAAAUGGUGUuAACdTsdT |
| AD-50480.1 | A-104713.1 | ccuGGuuuuuAuAAGAGAAdTsdT | A-104714.1 | UUCUCUuAuAAAAACcAGGdTsdT |
| AD-50481.1 | A-104635.1 | GAcAuucccAuGAAucccAdTsdT | A-104636.1 | UGGGAUUcAUGGGAAUGUCdTsdT |
| AD-50482.1 | A-104651.1 | cAccuGGcAGAuuccAAGAdTsdT | A-104652.1 | UCUUGGAAUCUGCcAGGUGdTsdT |
| AD-50483.1 | A-104667.1 | cGAAAAGccAAcAAAuccudTsdT | A-104668.1 | AGGAUUUGUUGGCUUUUCGdTsdT |
| AD-50484.1 | A-104683.1 | GAAAAuGcAGAGcAAuccAdTsdT | A-104684.1 | UGGAUUGCUCUGcAUUUUCdTsdT |
| AD-50485.1 | A-104699.1 | GGccuGuGGAAGucAAAGudTsdT | A-104700.1 | ACUUUGACUUCcAcAGGCCdTsdT |

TABLE 4-continued

Modified Sense and antisense strand sequences of Serpinc1 dsRNAs (The "Sense Sequence" column sequences are disclosed as SEQ ID NOS 129-185, respectively, in order of appearance, and the "Antisense Sequence" column sequences are disclosed as SEQ ID NOS 186-242, respectively, in order of appearance)

| Duplex Name | Sense Name | Sense Sequence | Antisense Name | Antisense Sequence |
|---|---|---|---|---|
| AD-50486.1 | A-104715.1 | GAAGuuccucuGAAcAcuAdTsdT | A-104716.1 | uAGUGUUcAGAGGAACUUCdTsdT |
| AD-50487.1 | A-104637.1 | ccAuGAAucccAuGuGcAudTsdT | A-104638.1 | AUGcAcAUGGGAUUcAUGGdTsdT |
| AD-50488.1 | A-104653.1 | cAAcuGAuGGAGGuAuuuAdTsdT | A-104654.1 | uAAAuACCUCcAUcAGUUGdTsdT |
| AD-50489.1 | A-104669.1 | ccAAGuuAGuAucAGccAAdTsdT | A-104670.1 | UUGGCUGAuACuAACUUGGdTsdT |
| AD-50490.1 | A-104685.1 | cGGccAucAAcAAAuGGGudTsdT | A-104686.1 | ACCcAUUUGUUGAUGGCCGdTsdT |
| AD-50491.1 | A-104701.1 | GAGGAcGGcuucAGuuuGAdTsdT | A-104702.1 | UcAAACUGAAGCCGUCCUCdTsdT |
| AD-50492.1 | A-104717.1 | ccucuGAAcAcuAuuAucudTsdT | A-104718.1 | AGAuAAuAGUGUUcAGAGGdTsdT |
| AD-50493.1 | A-104639.1 | cAuGAAucccAuGuGcAuudTsdT | A-104640.1 | AAUGcAcAUGGGAUUcAUGdTsdT |
| AD-50494.1 | A-104655.1 | GAuGGAGGuAuuuAAGuuudTsdT | A-104656.1 | AAACUuAAAuACCUCcAUCdTsdT |
| AD-50495.1 | A-104671.1 | GuAucAGccAAucGccuuudTsdT | A-104672.1 | AAAGGCGAUUGGCUGAuACdTsdT |
| AD-50496.1 | A-104687.1 | GGGuGuccAAuAAGAccGAdTsdT | A-104688.1 | UCGGUCUuAUUGGAcACCCdTsdT |
| AD-50497.1 | A-104703.1 | cAGcccuGAAAAGuccAAAdTsdT | A-104704.1 | UUUGGACUUUUcAGGGCUGdTsdT |
| AD-50498.1 | A-104641.1 | cccAuGuGcAuuuAccGcudTsdT | A-104642.1 | AGCGGuAAAUGcAcAUGGGdTsdT |
| AD-50499.1 | A-104657.1 | GuAuuuAAGuuuGAcAccAdTsdT | A-104658.1 | UGGUGUcAAACUuAAAuACdTsdT |
| AD-50500.1 | A-104673.1 | GAcAAAucccuuAccuucAdTsdT | A-104674.1 | UGAAGGuAAGGGAUUUGUCdTsdT |
| AD-50501.1 | A-104689.1 | cuGuucuGGuGcuGGuuAAdTsdT | A-104690.1 | UuAACcAGcACcAGAAcAGdTsdT |
| AD-50502.1 | A-104705.1 | ccAAAcucccAGGuAuuGudTsdT | A-104706.1 | AcAAuACCUGGGAGUUUGGdTsdT |
| AD-50503.1 | A-104643.1 | cccGcuuuGcuAccAcuuudTsdT | A-104644.1 | AAAGUGGuAGcAAAGCGGGdTsdT |
| AD-50505.1 | A-104675.1 | cuuAccuucAAuGAGAccudTsdT | A-104676.1 | AGGUCUcAUUGAAGGuAAGdTsdT |
| AD-50506.1 | A-104691.1 | cuGGuGcuGGuuAAcAccAdTsdT | A-104692.1 | UGGUGUuAACcAGcACcAGdTsdT |
| AD-50507.1 | A-104707.1 | cAAAcucccAGGuAuuGuudTsdT | A-104708.1 | AAcAAuACCUGGGAGUUUGdTsdT |
| AD-50508.1 | A-104645.1 | GcuuuGcuAccAcuuucuAdTsdT | A-104646.1 | uAGAAAGUGGuAGcAAAGCdTsdT |
| AD-50510.1 | A-104677.1 | ccuAccAGGAcAucAGuGAdTsdT | A-104678.1 | UcACUGAUGUCCUGGuAGGdTsdT |
| AD-50511.1 | A-104693.1 | GGuGcuGGuuAAcAccAuudTsdT | A-104694.1 | AAUGGUGUuAACcAGcACCdTsdT |
| AD-50512.1 | A-104709.1 | GccGuucGcuAAAccccAAdTsdT | A-104710.1 | UUGGGGUUuAGCGAACGGCdTsdT |
| AD-50515.1 | A-104679.1 | GGAcAucAGuGAGuuGGuAdTsdT | A-104680.1 | uACcAACUcACUGAUGUCCdTsdT |
| AD-50516.1 | A-104695.1 | GuGcuGGuuAAcAccAuuudTsdT | A-104696.1 | AAAUGGUGUuAACcAGcACdTsdT |
| AD-50517.1 | A-104711.1 | GccuuuccuGGuuuuuAuAdTsdT | A-104712.1 | uAuAAAAACcAGGAAAGGCdTsdT |
| AD-50518.1 | A-104719.1 | cuuuuGcuAuGAccAAGcudTsdT | A-104720.1 | AGCUUGGUcAuAGcAAAAGdTsdT |
| AD-50523.1 | A-104721.1 | uGuAccAGGAAGGcAAGuudTsdT | A-104722.1 | AACUUGCCUUCCUGGuAcAdTsdT |
| AD-50528.1 | A-104723.1 | AcuAuuAucuucAuGGGcAdTsdT | A-104724.1 | UGCCcAUGAAGAuAAuAGUdTsdT |
| AD-50540.1 | A-104729.1 | ucAuGGGcAGAGuAGccAAdTsdT | A-104730.1 | UUGGCuACUCUGCCcAUGAdTsdT |
| AD-50539.1 | A-104785.1 | ccAuuuAcuucAAGGGccudTsdT | A-104786.1 | AGGCCCUUGAAGuAAAUGGdTsdT |
| AD-50544.1 | A-104787.1 | uAcuucAAGGGccuGuGGAdTsdT | A-104788.1 | UCcAcAGGCCCUUGAAGuAdTsdT |
| AD-50549.1 | A-104789.1 | AcuucAAGGGccuGuGGAAdTsdT | A-104790.1 | UUCcAcAGGCCCUUGAAGUdTsdT |
| AD-50514.1 | A-104663.1 | cGAcucuAucGAAAAGccAdTsdT | A-104664.1 | UGGCUUUUCGAuAGAGUCGdTsdT |

TABLE 4-continued

Modified Sense and antisense strand sequences of Serpinc1 dsRNAs (The "Sense Sequence" column sequences are disclosed as SEQ ID NOS 129-185, respectively, in order of appearance, and the "Antisense Sequence" column sequences are disclosed as SEQ ID NOS 186-242, respectively, in order of appearance)

| Duplex Name | Sense Name | Sense Sequence | Antisense Name | Antisense Sequence |
|---|---|---|---|---|
| AD-50522.1 | A-104779.1 | AAcuGccGAcucuAucGAAdTsdT | A-104780.1 | UUCGAuAGAGUCGGcAGUUdTsdT |
| AD-50527.1 | A-104781.1 | AcuGccGAcucuAucGAAAdTsdT | A-104782.1 | UUUCGAuAGAGUCGGcAGUdTsdT |
| AD-50531.1 | A-104739.1 | GAcucuAucGAAAAGccAAdTsdT | A-104740.1 | UUGGCUUUUCGAuAGAGUCdTsdT |
| AD-50534.1 | A-104769.1 | ucuucuuuGccAAAcuGAAdTsdT | A-104770.1 | UUcAGUUUGGcAAAGAAGAdTsdT |
| AD-50538.1 | A-104771.1 | uGccAAAcuGAAcuGccGAdTsdT | A-104772.1 | UCGGcAGUUcAGUUUGGcAdTsdT |
| AD-50543.1 | A-104773.1 | ccAAAcuGAAcuGccGAcudTsdT | A-104774.1 | AGUCGGcAGUUcAGUUUGGdTsdT |
| AD-50553.1 | A-104777.1 | AcuGAAcuGccGAcucuAudTsdT | A-104778.1 | AuAGAGUCGGcAGUUcAGUdTsdT |
| AD-50504.1 | A-104659.1 | GAAcuGccGAcucuAucGAdTsdT | A-104660.1 | UCGAuAGAGUCGGcAGUUCdTsdT |
| AD-50509.1 | A-104661.1 | cuGccGAcucuAucGAAAAdTsdT | A-104662.1 | UUUUCGAuAGAGUCGGcAGdTsdT |
| AD-50529.1 | A-104751.1 | cuGGuuAAcAccAuuuAcudTsdT | A-104752.1 | AGuAAAUGGUGUuAACcAGdTsdT |

TABLE 5[1]

Serpinc1 single dose screen

| | Human (Hep3B) | | Mouse (PMH) | |
|---|---|---|---|---|
| Duplex Name | 10 nM Ave | 0.1 nM Ave | 10 nM Ave | 0.1 nM Ave |
| AD-50475.1 | 0.11 | 0.21 | | |
| AD-50476.1 | 0.08 | 0.43 | | |
| AD-50477.1 | 0.10 | 0.10 | | |
| AD-50478.1 | 0.12 | 0.36 | | |
| AD-50479.1 | 0.24 | 0.84 | | |
| AD-50480.1 | 0.31 | 0.73 | | |
| AD-50481.1 | 0.74 | 1.12 | | |
| AD-50482.1 | 0.61 | 0.89 | | |
| AD-50483.1 | 0.07 | 0.14 | | |
| AD-50484.1 | 0.12 | 0.33 | | |
| AD-50485.1 | 0.58 | 1.18 | | |
| AD-50486.1 | 0.79 | 0.94 | | |
| AD-50487.1 | 0.05 | 0.09 | | |
| AD-50488.1 | 0.83 | 1.07 | | |
| AD-50489.1 | 0.09 | 0.28 | | |
| AD-50490.1 | 0.04 | 0.78 | | |
| AD-50491.1 | 0.19 | 0.77 | | |
| AD-50492.1 | 0.16 | 0.84 | | |
| AD-50493.1 | 0.17 | 0.55 | | |
| AD-50494.1 | 0.16 | 0.59 | | |
| AD-50495.1 | 0.08 | 0.13 | | |
| AD-50496.1 | 0.57 | 0.94 | | |
| AD-50497.1 | 0.85 | 1.15 | | |
| AD-50498.1 | 0.16 | 1.02 | | |
| AD-50499.1 | 0.10 | 0.21 | | |
| AD-50500.1 | 0.22 | 0.58 | | |
| AD-50501.1 | 0.10 | 0.32 | | |
| AD-50502.1 | 0.76 | 1.07 | | |
| AD-50503.1 | 0.08 | 0.47 | | |
| AD-50505.1 | 0.74 | 0.77 | | |
| AD-50506.1 | 0.85 | 0.89 | | |
| AD-50507.1 | 0.03 | 0.37 | | |
| AD-50508.1 | 0.16 | 0.97 | | |
| AD-50510.1 | 0.09 | 0.89 | | |
| AD-50511.1 | 0.15 | 0.71 | | |
| AD-50512.1 | 0.88 | 1.19 | | |
| AD-50515.1 | 0.13 | 0.49 | | |
| AD-50516.1 | 0.85 | 0.95 | | |
| AD-50517.1 | 0.14 | 0.59 | | |
| AD-50518.1 | 0.36 | 1.05 | | |
| AD-50523.1 | 0.03 | 0.66 | | |
| AD-50528.1 | 0.04 | 0.27 | | |
| AD-50540.1 | 0.14 | 0.37 | | |
| AD-50539.1 | 0.09 | 0.46 | 0.39 | 1.10 |
| AD-50544.1 | 0.23 | 0.75 | 0.36 | 1.07 |
| AD-50549.1 | 0.10 | 0.19 | 0.17 | 0.71 |
| AD-50514.1 | 0.12 | 0.48 | 0.19 | 0.95 |
| AD-50522.1 | 0.61 | 1.02 | 0.46 | 1.32 |
| AD-50527.1 | 0.06 | 0.15 | 0.08 | 0.45 |
| AD-50531.1 | 0.09 | 0.47 | 0.24 | 1.04 |
| AD-50534.1 | 0.05 | 0.10 | 0.11 | 0.55 |
| AD-50538.1 | 0.61 | 0.86 | 0.79 | 1.23 |
| AD-50543.1 | 0.40 | 1.04 | 0.49 | 1.23 |
| AD-50553.1 | 0.40 | 0.93 | 0.72 | 1.25 |
| AD-50504.1 | ND | ND | 0.92 | 1.25 |
| AD-50509.1 | ND | ND | 0.12 | 0.37 |
| AD-50529.1 | ND | ND | 0.23 | 0.47 |

[1]Modified.

TABLE 6

Serpinc1 $IC_{50}$ Data

| Duplex Name | Hep3B $IC_{50}$ (nM) | PMH $IC_{50}$ (nM) |
|---|---|---|
| AD-50487.1 | 0.003 | — |
| AD-50477.1 | 0.006 | — |
| AD-50483.1 | 0.011 | — |
| AD-50475.1 | 0.011 | — |
| AD-50495.1 | 0.017 | — |
| AD-50476.1 | 0.026 | — |
| AD-50499.1 | 0.027 | — |
| AD-50478.1 | 0.028 | — |
| AD-50489.1 | 0.029 | — |
| AD-50501.1 | 0.045 | — |
| AD-50507.1 | 0.052 | — |
| AD-50484.1 | 0.081 | — |

TABLE 6-continued

| Serpinc1 $IC_{50}$ Data | | |
|---|---|---|
| Duplex Name | Hep3B $IC_{50}$ (nM) | PMH $IC_{50}$ (nM) |
| AD-50515.1 | 0.185 | — |
| AD-50540.1 | 0.023 | — |
| AD-50528.1 | 0.056 | — |
| AD-50549.1 | 0.053 | ND |
| AD-50539.1 | 0.170 | ND |
| AD-50534.1 | 0.007 | ND |
| AD-50527.1 | 0.028 | ND |
| AD-50514.1 | 0.085 | ND |
| AD-50527.1 | ND | 0.019 |
| AD-50534.1 | ND | 0.011 |
| AD-50509.1 | ND | 0.006 |
| AD-50529.1 | ND | 0.021 |

A subset of siRNAs were also synthesized with 2'-OMe modifications, and duplexes of these siRNAs in lipofectamine formulations were used to transfect Hep3B cells. The results of the single dose screen of the modified duplexes are shown in Table 7.

TABLE 7

| Lead Optimization (2'-OMe variants) | | | | |
|---|---|---|---|---|
| Parent | Duplex ID | Ave 1 nM | Ave 0.1 nM | Ave 0.01 nM |
| AD-50477 | AD-50477.1 | 0.22 | 0.33 | 0.53 |
| AD-50477 | AD-55025.1 | 0.29 | 0.68 | 0.86 |
| AD-50477 | AD-55031.1 | 0.42 | 0.74 | 0.93 |
| AD-50477 | AD-55037.1 | 0.52 | 0.73 | 0.95 |
| AD-50477 | AD-55043.1 | 0.45 | 0.70 | 0.94 |
| AD-50477 | AD-55049.1 | 0.24 | 0.47 | 0.95 |
| AD-50477 | AD-55055.1 | 0.37 | 0.68 | 0.99 |
| AD-50477 | AD-55061.1 | 0.43 | 0.66 | 0.85 |
| AD-50477 | AD-55067.1 | 0.56 | 0.72 | 0.92 |
| AD-50477 | AD-55026.1 | 0.28 | 0.59 | 0.87 |
| AD-50477 | AD-55032.1 | 0.49 | 0.76 | 0.86 |
| AD-50477 | AD-55038.1 | 0.52 | 0.75 | 0.93 |
| AD-50477 | AD-55044.1 | 0.84 | 0.77 | 1.06 |
| AD-50487 | AD-50487.1 | 0.21 | 0.50 | 0.76 |
| AD-50487 | AD-55050.1 | 0.24 | 0.53 | 0.75 |
| AD-50487 | AD-55056.1 | 0.27 | 0.50 | 0.84 |
| AD-50487 | AD-55062.1 | 0.30 | 0.61 | 0.84 |

TABLE 7-continued

| Lead Optimization (2'-OMe variants) | | | | |
|---|---|---|---|---|
| Parent | Duplex ID | Ave 1 nM | Ave 0.1 nM | Ave 0.01 nM |
| AD-50487 | AD-55068.1 | 0.20 | 0.37 | 0.66 |
| AD-50487 | AD-55027.1 | 0.18 | 0.36 | 0.67 |
| AD-50487 | AD-55033.1 | 0.22 | 0.43 | 0.70 |
| AD-50487 | AD-55039.1 | 0.19 | 0.38 | 0.67 |
| AD-50487 | AD-55045.1 | 0.18 | 0.29 | 0.57 |
| AD-50487 | AD-55051.1 | 0.17 | 0.29 | 0.60 |
| AD-50487 | AD-55057.1 | 0.21 | 0.37 | 0.65 |
| AD-50487 | AD-55063.1 | 0.19 | 0.33 | 0.63 |
| AD-50487 | AD-55069.1 | 0.16 | 0.26 | 0.51 |
| AD-50509 | AD-50509.1 | 0.15 | 0.31 | 0.57 |
| AD-50509 | AD-55029.1 | 0.17 | 0.26 | 0.49 |
| AD-50509 | AD-55028.1 | 0.17 | 0.35 | 0.54 |
| AD-50509 | AD-55052.1 | 0.21 | 0.32 | 0.59 |
| AD-50509 | AD-55035.1 | 0.19 | 0.31 | 0.62 |
| AD-50509 | AD-55047.1 | 0.19 | 0.35 | 0.66 |
| AD-50509 | AD-55058.1 | 0.21 | 0.40 | 0.66 |
| AD-50509 | AD-55046.1 | 0.18 | 0.37 | 0.66 |
| AD-50509 | AD-55070.1 | 0.17 | 0.40 | 0.68 |
| AD-50509 | AD-55034.1 | 0.19 | 0.37 | 0.69 |
| AD-50509 | AD-55041.1 | 0.20 | 0.28 | 0.63 |
| AD-50509 | AD-55064.1 | 0.19 | 0.34 | 0.65 |
| AD-50509 | AD-55040.1 | 0.18 | 0.34 | 0.69 |
| AD-50534 | AD-50534.1 | 0.19 | 0.42 | 0.83 |
| AD-50534 | AD-55053.1 | 0.24 | 0.38 | 0.59 |
| AD-50534 | AD-55030.1 | 0.15 | 0.33 | 0.64 |
| AD-50534 | AD-55054.1 | 0.18 | 0.40 | 0.69 |
| AD-50534 | AD-55059.1 | 0.18 | 0.33 | 0.56 |
| AD-50534 | AD-55036.1 | 0.22 | 0.37 | 0.61 |
| AD-50534 | AD-55060.1 | 0.19 | 0.42 | 0.62 |
| AD-50534 | AD-55071.1 | 0.29 | 0.56 | 0.81 |
| AD-50534 | AD-55048.1 | 0.26 | 0.56 | 0.83 |
| AD-50534 | AD-55066.1 | 0.30 | 0.49 | 0.76 |
| AD-50534 | AD-55042.1 | 0.25 | 0.47 | 0.79 |
| AD-50534 | AD-55065.1 | 0.24 | 0.50 | 0.83 |

Examples 3-4

Lead Optimization and In Vivo Testing

Table 8 is a detailed list of sequences of duplex siRNAs targeting Serpinc1 that were formulated as a lipid nanoparticle (LNP) (i.e., with MC3) or conjugated to GalNAc for lead optimization and in vivo delivery.

TABLE 8

Sense and antisense strand sequences of Serpinc1 dsRNAs for lead optimization (The "Sense Sequence" column sequences are disclosed as SEQ ID NOS 243-510, respectively, in order of appearance, and the "Antisense Sequence" column sequences are disclosed as SEQ ID NOS 511-778, respectively, in order of appearance)

| Duplex Name | Sense Name | Sense Sequence | Antisense Name | Antisense Sequences |
|---|---|---|---|---|
| AD-50477.1 | A-104665.1 | cuAucGAAAAGccAAcAAAdTsdT | A-104666.1 | UUUGUUGGCUUUUCGAuAGdTsdT |
| AD-55025.1 | A-113301.1 | cuAucGAAAAGccAAcAAAdTdT | A-113302.1 | UUUGUUGGCUUUUcGAuAGdTdT |
| AD-5503.1 | A-113301.2 | cuAucGAAAAGccAAcAAAdTdT | A-113303.1 | UUUGUUGGCUUuUcGAuAGdTdT |
| AD-55037.1 | A-113301.3 | cuAucGAAAAGccAAcAAAdTdT | A-113304.1 | UUUGUUGGcUUuUcGAuAGdTdT |
| AD-55043.1 | A-113301.4 | cuAucGAAAAGccAAcAAAdTdT | A-113305.1 | UUUGuUGGcUUuUcGAuAGdTdT |
| AD-55049.1 | A-113306.1 | cuAucGAAAAGcCAAcAAAdTdT | A-113302.2 | UUUGUUGGCUUUUcGAuAGdTdT |
| AD-55055.1 | A-113306.2 | cuAucGAAAAGcCAAcAAAdTdT | A-113303.2 | UUUGUUGGCUUuUcGAuAGdTdT |
| AD-55061.1 | A-113306.3 | cuAucGAAAAGcCAAcAAAdTdT | A-113304.2 | UUUGUUGGcUUuUcGAuAGdTdT |
| AD-55067.1 | A-113306.4 | cuAucGAAAAGcCAAcAAAdTdT | A-113305.2 | UUUGuUGGcUUuUcGAuAGdTdT |

TABLE 8-continued

Sense and antisense strand sequences of Serpinc1 dsRNAs for lead optimization (The "Sense Sequence" column sequences are disclosed as SEQ ID NOS 243-510, respectively, in order of appearance, and the "Antisense Sequence" column sequences are disclosed as SEQ ID NOS 511-778, respectively, in order of appearance)

| Duplex Name | Sense Name | Sense Sequence | Antisense Name | Antisense Sequences |
|---|---|---|---|---|
| AD-55026.1 | A-113307.1 | cuAucGAAAAGcCAACAAAdTdT | A-113302.3 | UUUGUUGGCUUUUcGAuAGdTdT |
| AD-55032.1 | A-113307.2 | cuAucGAAAAGcCAACAAAdTdT | A-113303.3 | UUUGUUGGCUUuUcGAuAGdTdT |
| AD-55038.1 | A-113307.3 | cuAucGAAAAGcCAACAAAdTdT | A-113304.3 | UUUGUUGGcUUuUcGAuAGdTdT |
| AD-55044.1 | A-113307.4 | cuAucGAAAAGcCAACAAAdTdT | A-113305.3 | UUUGuUGGcUUuUcGAuAGdTdT |
| AD-50487.1 | A-104637.1 | ccAuGAAucccAuGuGcAudTsdT | A-104638.1 | AUGcAcAUGGGAUUcAUGGdTsdT |
| AD-55050.1 | A-113308.1 | ccAuGAAucccAuGuGcAudTdT | A-113309.1 | AUGcAcAUGGGAUUcAuGGdTdT |
| AD-55056.1 | A-113308.2 | ccAuGAAucccAuGuGcAudTdT | A-113310.1 | AUGCAcAUGGGAUUcAuGGdTdT |
| AD-55062.1 | A-113308.3 | ccAuGAAucccAuGuGcAudTdT | A-113311.1 | AUGCAcAUGGGAuUcAuGGdTdT |
| AD-55068.1 | A-113308.4 | ccAuGAAucccAuGuGcAudTdT | A-113312.1 | AUGCACAUGGGAuUcAuGgdTdT |
| AD-55027.1 | A-113313.1 | ccAuGAAucccAuGUGcAUdTdT | A-113309.2 | AUGcAcAUGGGAUUcAuGGdTdT |
| AD-55033.1 | A-113313.2 | ccAuGAAucccAuGUGcAUdTdT | A-113310.2 | AUGCAcAUGGGAUUcAuGGdTdT |
| AD-55039.1 | A-113313.3 | ccAuGAAucccAuGUGcAUdTdT | A-113311.2 | AUGCAcAUGGGAuUcAuGGdTdT |
| AD-55045.1 | A-113313.4 | ccAuGAAucccAuGUGcAUdTdT | A-113312.2 | AUGCACAUGGGAuUcAuGgdTdT |
| AD-55055.1 | A-113314.1 | ccAuGAAucCcAuGUGcAUdTdT | A-113309.3 | AUGcAcAUGGGAUUcAuGGdTdT |
| AD-55057.1 | A-113341.2 | ccAuGAAucCcAuGUGcAUdTdT | A-113310.3 | AUGCAcAUGGGAUUcAuGGdTdT |
| AD-55063.1 | A-113314.3 | ccAuGAAucCcAuGUGcAUdTdT | A-113311.3 | AUGCAcAUGGGAuUcAuGGdTdT |
| AD-55069.1 | A-113314.4 | ccAuGAAucCcAuGUGcAUdTdT | A-113312.3 | AUGCACAUGGGAuUcAuGgdTdT |
| AD-50509.1 | A-104661.1 | cuGccGAcucuAucGAAAAdTsdT | A-104662.1 | UUUUCGAuAGAGUCGGcAGdTsdT |
| AD-55029.1 | A-113321.1 | cuGccGAcuCuAuCGAaAAdTdT | A-113316.3 | UUUUCGAuAGAGUCGGcAgdTdT |
| AD-55028.1 | A-113315.1 | cuGccGAcucuAucGAAAAdTdT | A-113316.1 | UUUUCGAuAGAGUCGGcAgdTdT |
| AD-55052.1 | A-113320.1 | cuGccGAcuCuAuCGAAAAdTdT | A-113316.2 | UUUUCGAuAGAGUCGGcAgdTdT |
| AD-55035.1 | A-113321.2 | cuGccGAcuCuAuCGAaAAdTdT | A-113317.3 | UUUUCGAuAGAGUCgGcAgdTdT |
| AD-55047.1 | A-113321.4 | cuGccGAcuCuAuCGAaAAdTdT | A-113319.3 | UUuUCGAUAGAGUCgGcAgdTdT |
| AD-55058.1 | A-113320.2 | ccGccGAcuCuAuCGAAAAdTdT | A-113317.2 | UUUUCGAuAGAGUCgGcAgdTdT |
| AD-55046.1 | A-113315.4 | cuGccGAcucuAucGAAAAdTdT | A-113319.1 | UUuUCGAUAGAGUCgGcAgdTdT |
| AD-55070.1 | A-113320.4 | cuGccGAcuCuAuCGAAAAdTdT | A-113319.2 | UUuUCGAUAGAGUCgGcAgdTdT |
| AD-55034.1 | A-113315.2 | cuGccGAcucuAucGAAAAdTdT | A-113317.1 | UUUUCGAuAGAGUCgGcAgdTdT |
| AD-55041.1 | A-113321.3 | cuGccGAcuCuAuCGAaAAdTdT | A-113318.3 | UUuUCGAuAGAGUCgGcAgdTdT |
| AD-55064.1 | A-113320.3 | cuGccGAcuCuAuCGAAAAdTdT | A-113318.2 | UUuUCGAuAGAGUCgGcAgdTdT |
| AD-55040.1 | A-113315.3 | cuGccGAcucuAucGAAAAdTdT | A-113318.1 | UUuUCGAuAGAGUCgGcAgdTdT |
| AD-50534.1 | A-104769.1 | ucuucuuuGccAAAcuGAAdTsdT | A-104770.1 | UUcAGUUUGGcAAAGAAGAdTsdT |
| AD-55053.1 | A-113322.1 | ucuucuuuGccAAAcuGAAdTdT | A-113323.1 | UUcAGUUUGGcAAAGAAGadTdT |
| AD-55030.1 | A-113327.1 | ucuucuuuGcCAAACuGAAdTdT | A-113323.2 | UUcAGUUUGGcAAAGAAGadTdT |
| AD-55054.1 | A-113327.5 | ucuucuuuGcCAAACuGAAdTdT | A-113328.1 | UUCAGUUuGGcAAAGAAGadTdT |
| AD-55059.1 | A-113322.2 | ucuucuuuGccAAAcuGAAdTdT | A-113324.1 | UUcAGUUUGGcAAAgAAGadTdT |
| AD-55036.1 | A-113327.2 | ucuucuuuGcCAAACuGAAdTdT | A-113324.2 | UUcAGUUUGGcAAAgAAGadTdT |

TABLE 8-continued

Sense and antisense strand sequences of Serpinc1 dsRNAs for lead optimization (The "Sense Sequence" column sequences are disclosed as SEQ ID NOS 243-510, respectively, in order of appearance, and the "Antisense Sequence" column sequences are disclosed as SEQ ID NOS 511-778, respectively, in order of appearance)

| Duplex Name | Sense Name | Sense Sequence | Antisense Name | Antisense Sequences |
|---|---|---|---|---|
| AD-55060.1 | A-113327.6 | ucuucuuuGcCAAACuGAAdTdT | A-113329.1 | UUCAGUUuGGcAAAgAAGadTdT |
| AD-55071.1 | A-113322.4 | ucuucuuuGccAAAcuGAAdTdT | A-113326.1 | UUcAGUUUGGCaAAgAAGadTdT |
| AD-55048.1 | A-113327.4 | ucuucuuuGcCAAACuGAAdTdT | A-113326.2 | UUcAGUUUGGCaAAgAAGadTdT |
| AD-55066.1 | A-113327.7 | ucuucuuuGcCAAACuGAAdTdT | A-113330.1 | UUCAGUUuGGcaAAgAAGadTdT |
| AD-55042.1 | A-113327.3 | ucuucuuuGcCAAACuGAAdTdT | A-113325.2 | UUcAGUUUGGcaAAgAAGadTdT |
| AD-55065.1 | A-113322.3 | ucuucuuuGccAAAcuGAAdTdT | A-113325.1 | UUcAGUUUGGcaAAgAAGadTdT |
| AD-54944.1 | A-113073.1 | GfgUfuAfaCfaCfCfAfuUfuAfcUfuCfaAf L96 | A-113074.1 | uUfgAfaGfuAfaAfuggUfgUfuAfaCfcsAfsg |
| AD-54951.1 | A-112997.1 | UfaGfuAfuCfaGfCfCfaAfuCfgCfcUfuUf L96 | A-112998.1 | aAfaGfgCfgAfuUfggcUfgAfuAfcUfasAfsc |
| AD-54942.1 | A-113041.1 | CfgCfuUfuGfcUfAfCfcAfcUfuUfcUfaUf L96 | A-113042.1 | aUfaGfaAfaGfuGfguaGfcAfaAfgCfgsGfsg |
| AD-54948.1 | A-113043.1 | CfuUfuGfcUfaCfCfAfcUfuUfcUfaUfcAf L96 | A-113044.1 | uGfaUfaGfaAfaGfuggUfaGfcAfaAfgsCfsg |
| AD-54957.1 | A-112999.1 | AfuCfgAfaAfaGfCfCfaAfcAfaAfuCfcUf L96 | A-113000.1 | aGfgAfuUfuGfuUfggcUfuUfuCfgAfusAfsg |
| AD-54933.1 | A-112991.1 | UfcCfcAfuGfaAfUfCfcCfaUfgUfgCfaUf L96 | A-112992.1 | aUfgCfaCfaUfgGfgauUfcAfuGfgGfasAfsu |
| AD-54962.1 | A-113079.1 | UfaAfgGfcAfuUfUfCfuUfgAfgGfuAfaAf L96 | A-113080.1 | uUfuAfcCfuCfaAfgaaAfuGfcCfuUfasUfsg |
| AD-54972.1 | A-113051.1 | GfcAfaCfuGfaUfGfGfaGfgUfaUfuUfaAf L96 | A-113052.1 | uUfaAfaUfaCfcUfccaufcAfgufuGfcsUfsg |
| AD-54949.1 | A-113059.1 | UfuUfaAfgUfuUfGfAfcAfcCfaUfaUfcUf L96 | A-113060.1 | aGfaUfaUfgGfuGfucaAfaCfuUfaAfasUfsa |
| AD-54936.1 | A-113039.1 | CfcAfuGfaAfuCfCfCfaUfgUfgCfaUfuUf L96 | A-113040.1 | aAfaUfgCfaCfaUfgggAfuUfcAfuGfgsGfsa |
| AD-54971.1 | A-113035.1 | UfgCfuGfgUfuAfAfCfaCfcAfuUfuAfcUf L96 | A-113036.1 | aGfuAfaAfuGfgUfguuAfaCfcAfgCfasCfsc |
| AD-54955.1 | A-113061.1 | UfcUfaUfcGfaAfAfAfgCfcAfaCfaAfaUf L96 | A-113062.1 | aUfuUfgUfuGfgCfuuuUfcGfaUfaGfasGfsu |
| AD-54953.1 | A-113029.1 | UfuCfcCfgCfuUfUfGfcUfaCfcAfcUfuUf L96 | A-113030.1 | aAfaGfuGfgUfaGfcaaAfgCfgGfgAfasUfsu |
| AD-54937.1 | A-113055.1 | GfaUfgGfaGfgUfAfUfuUfaAfgUfuUfgAf L96 | A-113056.1 | uCfaAfaCfuUfaAfauaCfcUfcCfaUfcsAfsg |
| AD-54967.1 | A-113065.1 | AfgAfcAfaAfuCfCfCfuUfaCfcUfuCfaAf L96 | A-113066.1 | uUfgAfaGfgUfaAfgggAfuUfuGfuCfusCfsc |
| AD-54935.1 | A-113023.1 | UfgCfuAfcCfaCfUfUfuCfuAfuCfaGfcAf L96 | A-113024.1 | uGfcUfgAfuAfgAfaagUfgGfuAfgCfasAfsa |
| AD-54976.1 | A-113037.1 | UfgUfaUfuCfcAfAfUfgUfgAfuAfgGfaAf L96 | A-113038.1 | uUfcCfuAfuCfaCfauuGfgAfaUfaCfasUfsg |
| AD-54965.1 | A-113033.1 | AfaCfuGfcCfgAfCfUfcUfaUfcGfaAfaAf L96 | A-113034.1 | uUfuUfcGfaUfaGfaguCfgGfcAfgUfusCfsa |
| AD-54959.1 | A-113031.1 | GfcCfgAfcUfcUfAfUfcGfaAfaAfgCfcAf L96 | A-113032.1 | uGfgCfuUfuUfcGfauaGfaGfuCfgGfcsAfsg |
| AD-54943.1 | A-113057.1 | UfaUfuUfaAfgUfUfUfgAfcAfcCfaUfaUf L96 | A-113058.1 | aUfaUfgGfuGfuCfaaaCfuUfaAfaUfasCfsc |

TABLE 8-continued

Sense and antisense strand sequences of Serpinc1 dsRNAs for lead optimization (The "Sense Sequence" column sequences are disclosed as SEQ ID NOS 243-510, respectively, in order of appearance, and the "Antisense Sequence" column sequences are disclosed as SEQ ID NOS 511-778, respectively, in order of appearance)

| Duplex Name | Sense Name | Sense Sequence | Antisense Name | Antisense Sequences |
|---|---|---|---|---|
| AD-54956.1 | A-113077.1 | UfgGfgCfcUfuGfUfCfgAfuCfuGfuUfcAf L96 | A-113078.1 | uGfaAfcAfgAfuCfgacAfaGfgCfcCfasUfsg |
| AD-54973.1 | A-113067.1 | CfaAfaUfcCfcUfUfAfcCfuUfcAfaUfgAf L96 | A-113068.1 | uCfaUfuGfaAfgGfuaaGfgGfaUfuUfgsUfsc |
| AD-54975.1 | A-113021.1 | UfcCfaAfaCfuCfCfCfaGfgUfaUfuGfuUf L96 | A-113022.1 | aAfcAfaUfaCfcUfgggAfgUfuUfgGfasCfsu |
| AD-54963.1 | A-113001.1 | GfaAfcUfgCfcGfAfCfuCfuAfuCfgAfaAf L96 | A-113002.1 | uUfuCfgAfuAfgAfgucGfgCfaGfuUfcsAfsg |
| AD-54978.1 | A-113069.1 | UfcAfaCfaAfaUfGfGfgUfgUfcCfaAfuAf L96 | A-113070.1 | uAfuUfgGfaCfaCfccaufuUfgUfuGfasUfsg |
| AD-54952.1 | A-113013.1 | CfaCfuGfuUfcUfGfGfuGfcUfgGfuUfaAf L96 | A-113014.1 | uUfaAfcCfaGfcAfccaGfaAfcAfgUfgsAfsg |
| AD-54950.1 | A-113075.1 | GfgAfcGfgCfuUfCfAfgUfuUfgAfaGfgAf L96 | A-113076.1 | uCfcUfuCfaAfaCfugaAfgCfcGfuCfcsUfsc |
| AD-54964.1 | A-113017.1 | CfuGfgAfcUfuCfAfAfgGfaAfaAfuGfcAf L96 | A-113018.1 | uGfcAfuUfuUfcCfuugAfaGfuCfcAfgsGfsg |
| AD-54974.1 | A-113005.1 | AfgGfuAfuUfuAfAfGfuUfuGfaCfaCfcAf L96 | A-113006.1 | uGfgUfgUfcAfaAfcuuAfaAfuAfcCfusCfsc |
| AD-54969.1 | A-113003.1 | UfuAfcUfuCfaAfGfGfgCfcUfgUfgGfaAf L96 | A-113004.1 | uUfcCfaCfaGfgCfccuUfgAfaGfuAfasAfsu |
| AD-54961.1 | A-113063.1 | UfuUfuUfgGfaGfAfCfaAfaUfcCfcUfuAf L96 | A-113064.1 | uAfaGfgGfaUfuUfgucUfcCfaAfaAfasGfsg |
| AD-54968.1 | A-113081.1 | GfaUfuGfcUfgGfCfCfgUfuCfgCfuAfaAf L96 | A-113082.1 | uUfuAfgCfgAfaCfggcCfaGfcAfaUfcsAfsc |
| AD-54947.1 | A-113027.1 | CfcGfaCfuCfuAfUfCfgAfaAfaGfcCfaAf L96 | A-113028.1 | uUfgGfcUfuUfuCfgauAfgAfgUfcGfgsCfsa |
| AD-54941.1 | A-113025.1 | CfaCfcAfuufuAfCfUfuCfaAfgGfgCfcUf L96 | A-113026.1 | aGfgCfcCfuUfgAfaguAfaAfuGfgUfgsUfsu |
| AD-54966.1 | A-113049.1 | CfaAfgCfuGfgGfUfGgcCfuGfuAfaUfgAf L96 | A-113050.1 | uCfaUfuAfcAfgGfcacCfcAfgCfuUfgsGfsu |
| AD-54940.1 | A-113009.1 | AfcAfcUfaUfuAfUfCfuUfcAfuGfgGfcAf L96 | A-113010.1 | uGfcCfcAfuGfaAfgauAfaUfaGfuGfusUfsc |
| AD-54958.1 | A-113015.1 | AfgGfaAfaAfuGfCfAfgAfgCfaAfuCfcAf L96 | A-113016.1 | uGfgAfuUfgCfuCfugcAfuUfuUfcCfusUfsg |
| AD-54938.1 | A-113071.1 | UfcUfgGfuGfcUfGfGfuUfaAfcAfcCfaUf L96 | A-113072.1 | aUfgGfuGfuUfaAfccaGfcAfcCfaGfasAfsc |
| AD-54934.1 | A-113007.1 | AfgCfcCfuGfuGfGfAfcAfuCfuGfcAfcAf L96 | A-113008.1 | uGfuGfcAfgAfuGfuccAfcAfgGfgCfusCfsc |
| AD-54939.1 | A-112993.1 | CfuUfcUfuCfuUfUfGfcCfaAfaCfuGfaAf L96 | A-112994.1 | uUfcAfgUfuUfgGfcaaAfgAfaGfaAfgsUfsg |
| AD-54960.1 | A-113047.1 | UfcUfcCfaCfgGfCfUfuUfuGfcUfaUfgAf L96 | A-113048.1 | uCfaUfaGfcAfaAfagcCfgUfgGfaGfasUfsa |
| AD-54954.1 | A-113045.1 | GfcAfcCfuGfgCfAfGfaUfuCfcAfaGfaAf L96 | A-113046.1 | uUfcUfuGfgAfaUfcugCfcAfgGfuGfcsUfsg |
| AD-54970.1 | A-113019.1 | CfuUfcAfuGfgGfCfAfgAfgUfaGfcCfaAf L96 | A-113020.1 | uUfgGfcUfaCfuCfugcCfcAfuGfaAfgsAfsu |
| AD-54946.1 | A-113011.1 | CfuCfcAfaGfuUfAfGfuAfuCfaGfcCfaAf L96 | A-113012.1 | uUfgGfcUfgAfuAfcuaAfcUfuGfgAfgsGfsa |

TABLE 8-continued

Sense and antisense strand sequences of Serpinc1 dsRNAs for lead optimization (The "Sense Sequence" column sequences are disclosed as SEQ ID NOS 243-510, respectively, in order of appearance, and the "Antisense Sequence" column sequences are disclosed as SEQ ID NOS 511-778, respectively, in order of appearance)

| Duplex Name | Sense Name | Sense Sequence | Antisense Name | Antisense Sequences |
|---|---|---|---|---|
| AD-56331.1 | A-113073.4 | GfgUfuAfaCfaCfCfAfuUfuAfcUfuCfaAfL96 | A-115852.1 | UUfgAfaGfuAfaAfuggUfgUfuAfaCfcsAfsg |
| AD-56337.1 | A-115853.1 | GfguuAfaCfaCfCfAfuUfuAfcUfuCfaAfL96 | A-113074.4 | uUfgAfaGfuAfaAfuggUfgUfuAfaCfcsAfsg |
| AD-56343.1 | A-115854.1 | GfguuAfaCfaCfCfAfuUfuAfcUfuCfaaL96 | A-113074.5 | uUfgAfaGfuAfaAfuggUfgUfuAfaCfcsAfsg |
| AD-56349.1 | A-115855.1 | GfguuAfaCfaCfCfAfuUfuacUfuCfaaL96 | A-113074.6 | uUfgAfaGfuAfaAfuggUfgUfuAfaCfcsAfsg |
| AD-56355.1 | A-115856.1 | GfguuAfaCfaCfCfAfuUfuAfcuucaaL96 | A-113074.7 | uUfgAfaGfuAfaAfuggUfgUfuAfaCfcsAfsg |
| AD-56361.1 | A-115857.1 | GfguuAfacaCfCfAfuUfuacUfucaaL96 | A-113074.8 | uUfgAfaGfuAfaAfuggUfgUfuAfaCfcsAfsg |
| AD-56367.1 | A-115858.1 | GfguuAfacaCfCfAfuuuacUfucaaL96 | A-113074.9 | uUfgAfaGfuAfaAfuggUfgUfuAfaCfcsAfsg |
| AD-56326.1 | A-115859.1 | GfguuAfacaCfCfAfuuuacuucaaL96 | A-113074.10 | uUfgAfaGfuAfaAfuggUfgUfuAfaCfcsAfsg |
| AD-56321.1 | A-115860.1 | GfguuaacaCfCfAfuuuacuucaaL96 | A-113074.11 | uUfgAfaGfuAfaAfuggUfgUfuAfaCfcsAfsg |
| AD-56338.1 | A-113073.5 | GfgUfuAfaCfaCfCfAfuUfuAfcUfuCfaAfL96 | A-115861.1 | uUfgaaGfuAfaAfuggUfgUfuAfaCfcsasg |
| AD-56344.1 | A-115853.2 | GfguuAfaCfaCfCfAfuUfuAfcUfuCfaAfL96 | A-115861.2 | uUfgaaGfuAfaAfuggUfgUfuAfaCfcsasg |
| AD-56350.1 | A-115854.2 | GfguuAfaCfaCfCfAfuUfuAfcUfuCfaaL96 | A-115861.3 | uUfgaaGfuAfaAfuggUfgUfuAfaCfcsasg |
| AD-56356.1 | A-115855.2 | GfguuAfaCfaCfCfAfuUfuacUfuCfaaL96 | A-115861.4 | uUfgaaGfuAfaAfuggUfgUfuAfaCfcsasg |
| AD-56362.1 | A-115856.2 | GfguuAfaCfaCfCfAfuUfuAfcuucaaL96 | A-115861.5 | uUfgaaGfuAfaAfuggUfgUfuAfaCfcsasg |
| AD-56368.1 | A-115857.2 | GfguuAfacaCfCfAfuUfuacUfucaaL96 | A-115861.6 | uUfgaaGfuAfaAfuggUfgUfuAfaCfcsasg |
| AD-56327.1 | A-115858.2 | GfguuAfacaCfCfAfuuuacUfucaaL96 | A-115861.7 | uUfgaaGfuAfaAfuggUfgUfuAfaCfcsasg |
| AD-56333.1 | A-115859.2 | GfguuAfacaCfCfAfuuuacuucaaL96 | A-115861.8 | uUfgaaGfuAfaAfuggUfgUfuAfaCfcsasg |
| AD-56339.1 | A-115860.2 | GfguuaacaCfCfAfuuuacuucaaL96 | A-115861.9 | uUfgaaGfuAfaAfuggUfgUfuAfaCfcsasg |
| AD-56345.1 | A-113073.6 | GfgUfuAfaCfaCfCfAfuUfuAfcUfuCfaAfL96 | A-115862.1 | uUfgaaGfuAfaAfuggUfguuAfaCfcsasg |
| AD-56351.1 | A-115853.3 | GfguuAfaCfaCfCfAfuUfuAfcUfuCfaAfL96 | A-115862.2 | uUfgaaGfuAfaAfuggUfguuAfaCfcsasg |
| AD-56357.1 | A-115854.3 | GfguuAfaCfaCfCfAfuUfuAfcUfuCfaaL96 | A-115862.3 | uUfgaaGfuAfaAfuggUfguuAfaCfcsasg |
| AD-56363.1 | A-115855.3 | GfguuAfaCfaCfCfAfuUfuacUfuCfaaL96 | A-115862.4 | uUfgaaGfuAfaAfuggUfguuAfaCfcsasg |
| AD-56369.1 | A-115856.3 | GfguuAfaCfaCfCfAfuUfuAfcuucaaL96 | A-115862.5 | uUfgaaGfuAfaAfuggUfguuAfaCfcsasg |
| AD-56328.1 | A-115857.3 | GfguuAfacaCfCfAfuUfuacUfucaaL96 | A-115862.6 | uUfgaaGfuAfaAfuggUfguuAfaCfcsasg |
| AD-56334.1 | A-115858.3 | GfguuAfacaCfCfAfuuuacUfucaaL96 | A-115862.7 | uUfgaaGfuAfaAfuggUfguuAfaCfcsasg |
| AD-56340.1 | A-115859.3 | GfguuAfacaCfCfAfuuuacuucaaL96 | A-115862.8 | uUfgaaGfuAfaAfuggUfguuAfaCfcsasg |
| AD-56346.1 | A-115860.3 | GfguuaacaCfCfAfuuuacuucaaL96 | A-115862.9 | uUfgaaGfuAfaAfuggUfguuAfaCfcsasg |
| AD-56352.1 | A-115863.1 | GfgUfUfAfaCfaCfCfAfuUfuAfcUfuCfaAfL96 | A-113074.12 | uUfgAfaGfuAfaAfuggUfgUfuAfaCfcsAfsg |
| AD-56358.1 | A-115864.1 | GfgUfUfAfaCfaCfCfAfUfUfAfcUfuCfaAfL96 | A-113074.13 | uUfgAfaGfuAfaAfuggUfgUfuAfaCfcsAfsg |
| AD-56364.1 | A-115865.1 | GfgUfUfAfaCfaCfCfAfuUfUfAfcUfUfCfaAfL96 | A-113074.14 | uUfgAfaGfuAfaAfuggUfgUfuAfaCfcsAfsg |

TABLE 8-continued

Sense and antisense strand sequences of Serpinc1 dsRNAs for lead optimization (The "Sense Sequence" column sequences are disclosed as SEQ ID NOS 243-510, respectively, in order of appearance, and the "Antisense Sequence" column sequences are disclosed as SEQ ID NOS 511-778, respectively, in order of appearance)

| Duplex Name | Sense Name | Sense Sequence | Antisense Name | Antisense Sequences |
|---|---|---|---|---|
| AD-56370.1 | A-115866.1 | GfgUfUfAfAfCfaCfCfAfuUfUfAfcUfUfCfAfAfL96 | A-113074.15 | uUfgAfaGfuAfaAfuggUfgUfuAfaCfcsAfsg |
| AD-56329.1 | A-115867.1 | GfGfUfUfAfAfCfaCfCfAfuUfUfAfcUfUfCfAfAfL96 | A-113074.16 | uUfgAfaGfuAfaAfuggUfgUfuAfaCfcsAfsg |
| AD-56335.1 | A-115868.1 | GfGfUfUfAfAfCfaCfCfAfuUfUfAfCfUfUfCfAfAfL96 | A-113074.17 | uUfgAfaGfuAfaAfuggUfgUfuAfaCfcsAfsg |
| AD-56341.1 | A-115869.1 | GfGfUfUfAfAfCfAfCfCfAfuUfUfAfCfUfUfCfAfAfL96 | A-113074.18 | uUfgAfaGfuAfaAfuggUfgUfuAfaCfcsAfsg |
| AD-56347.1 | A-115868.2 | GfGfUfUfAfAfCfaCfCfAfuUfUfAfCfUfUfCfAfAfL96 | A-115870.1 | uUfgaaGfuAfaAfuggUfgUfuaaCfcsasg |
| AD-56353.1 | A-115868.3 | GfGfUfUfAfAfCfaCfCfAfuUfUfAfCfUfUfCfAfAfL96 | A-115871.1 | uUfgAaGfuAfaAfuggUfgUfuaaCfcsasg |
| AD-56359.1 | A-115868.4 | GfGfUfUfAfAfCfaCfCfAfuUfUfAfCfUfUfCfAfAfL96 | A-115872.1 | uUfgAaGfuaaAfuggUfgUfuaaCfcsasg |
| AD-56365.1 | A-115868.5 | GfGfUfUfAfAfCfaCfCfAfuUfUfAfCfUfUfCfAfAfL96 | A-115873.1 | uUfgAaGfuAaAfuggUfgUfuaaCfcsasg |
| AD-56371.1 | A-115868.6 | GfGfUfUfAfAfCfaCfCfAfuUfUfAfCfUfUfCfAfAfL96 | A-115874.1 | uUfgAaguAaAfuggUfgUfuaaCfcsasg |
| AD-56330.1 | A-115868.7 | GfGfUfUfAfAfCfaCfCfAfuUfUfAfCfUfUfCfAfAfL96 | A-115875.1 | uUfgAaGuAaAfuggUfgUfuaaCfcsasg |
| AD-56336.1 | A-115868.8 | GfGfUfUfAfAfCfaCfCfAfuUfUfAfCfUfUfCfAfAfL96 | A-115876.1 | uUgAaguAaAfuggUfgUfuaaCfcsasg |
| AD-56342.1 | A-115868.9 | GfGfUfUfAfAfCfaCfCfAfuUfUfAfCfUfUfCfAfAfL96 | A-115877.1 | uUgAaGuAaAfuggUfgUfuaaCfcsasg |
| AD-56348.1 | A-115868.10 | GfGfUfUfAfAfCfaCfCfAfuUfUfAfCfUfUfCfAfAfL96 | A-115861.10 | uUfgaaGfuAfaAfuggUfgUfuAfaCfcsasg |
| AD-56354.1 | A-115868.11 | GfGfUfUfAfAfCfaCfCfAfuUfUfAfCfUfUfCfAfAfL96 | A-115878.1 | uUfgAaGfuAfaAfuggUfgUfuAfaCfcsasg |
| AD-56360.1 | A-115868.12 | GfGfUfUfAfAfCfaCfCfAfuUfUfAfCfUfUfCfAfAfL96 | A-115879.1 | uUfgAaGfuaaAfuggUfgUfuAfaCfcsasg |
| AD-56366.1 | A-115868.13 | GfGfUfUfAfAfCfaCfCfAfuUfUfAfCfUfUfCfAfAfL96 | A-115880.1 | uUfgAaGfuAaAfuggUfgUfuAfaCfcsasg |
| AD-56372.1 | A-115868.14 | GfGfUfUfAfAfCfaCfCfAfuUfUfAfCfUfUfCfAfAfL96 | A-115881.1 | uUfgAaguAaAfuggUfgUfuAfaCfcsasg |
| AD-56378.1 | A-115868.15 | GfGfUfUfAfAfCfaCfCfAfuUfUfAfCfUfUfCfAfAfL96 | A-115882.1 | uUfgAaGuAaAfuggUfgUfuAfaCfcsasg |
| AD-56384.1 | A-115868.16 | GfGfUfUfAfAfCfaCfCfAfuUfUfAfCfUfUfCfAfAfL96 | A-115883.1 | uUgAaGuAaAfuggUfgUfuAfaCfcsasg |
| AD-56390.1 | A-115868.17 | GfGfUfUfAfAfCfaCfCfAfuUfUfAfCfUfUfCfAfAfL96 | A-115884.1 | uUgaAguAaAfuggUfgUfuAfaCfcsasg |
| AD-56396.1 | A-113073.7 | GfgUfuAfaCfaCfCfAfuUfuAfcUfuCfaAfL96 | A-115885.1 | uUfgAfAfGfuAfaAfuggUfgUfUfAfaCfcsAfsg |
| AD-56402.1 | A-115863.2 | GfgUfUfAfaCfaCfCfAfuUfuAfcUfuCfaAfL96 | A-115885.2 | uUfgAfAfGfuAfaAfuggUfgUfUfAfaCfcsAfsg |
| AD-56408.1 | A-115864.2 | GfgUfUfAfaCfaCfCfAfuUfUfAfcUfuCfaAfL96 | A-115885.3 | uUfgAfAfGfuAfaAfuggUfgUfUfAfaCfcsAfsg |
| AD-56414.1 | A-115865.2 | GfgufUfAfaCfaCfCfAfuUfUfAfcUfUfCfaAfL96 | A-115885.4 | uUfgAfAfGfuAfaAfuggUfgUfUfAfaCfcsAfsg |

TABLE 8-continued

Sense and antisense strand sequences of Serpinc1 dsRNAs for lead optimization (The "Sense Sequence" column sequences are disclosed as SEQ ID NOS 243-510, respectively, in order of appearance, and the "Antisense Sequence" column sequences are disclosed as SEQ ID NOS 511-778, respectively, in order of appearance)

| Duplex Name | Sense Name | Sense Sequence | Antisense Name | Antisense Sequences |
|---|---|---|---|---|
| AD-56373.1 | A-115886.1 | GfgUfUfAfaCfaCfCfAfuUfUfAfcUfUfCfAfAfL96 | A-115885.5 | uUfgAfAfGfuAfaAfuggUfgUfUfAfaCfcsAfsg |
| AD-56379.1 | A-115866.2 | GfgufUfAfAfCfaCfCfAfuUfUfAfcUfUfCfAfAfL96 | A-115885.6 | uUfgAfAfGfuAfaAfuggUfgUfUfAfaCfcsAfsg |
| AD-56385.1 | A-115867.2 | GfGfUfUfAfAfCfaCfCfAfuUfUfAfcUfUfCfAfAfL96 | A-115885.7 | uUfgAfAfGfuAfaAfuggUfgUfUfAfaCfcsAfsg |
| AD-56391.1 | A-115868.18 | GfGfUfUfAfAfCfaCfCfAfuUfUfAfCfUfUfCfAfAfL96 | A-115885.8 | uUfgAfAfGfuAfaAfuggUfgUfUfAfaCfcsAfsg |
| AD-56397.1 | A-115869.2 | GfGfUfUfAfAfCfAfCfCfAfuUfUfAfCfUfUfCfAfAfL96 | A-115885.9 | uUfgAfAfGfuAfaAfuggUfgUfUfAfaCfcsAfsg |
| AD-56403.1 | A-113073.8 | GfgUfuAfaCfaCfCfAfuUfuAfcUfuCfaAfL96 | A-115887.1 | uUfgAfAfGfUfAfaAfuggUfgUfUfAfaCfcsAfsg |
| AD-56409.1 | A-115863.3 | GfgUfUfAfaCfaCfCfAfuUfuAfcUfuCfaAfL96 | A-115887.2 | uUfgAfAfGfUfAfaAfuggUfgUfUfAfaCfcsAfsg |
| AD-56415.1 | A-115864.3 | GfgufUfAfaCfaCfCfAfuUfUfAfcUfuCfaAfL96 | A-115887.3 | uUfgAfAfGfUfAfaAfuggUfgUfUfAfaCfcsAfsg |
| AD-56374.1 | A-115865.3 | GfgUfUfAfaCfaCfCfAfuUfUfAfcUfUfCfaAfL96 | A-115887.4 | uUfgAfAfGfUfAfaAfuggUfgUfUfAfaCfcsAfsg |
| AD-56380.1 | A-115886.2 | GfgUfUfAfaCfaCfCfAfuUfUfAfcUfUfCfAfAfL96 | A-115887.5 | uUfgAfAfGfUfAfaAfuggUfgUfUfAfaCfcsAfsg |
| AD-56386.1 | A-115866.3 | GfgUfUfAfAfCfaCfCfAfuUfUfAfcUfUfCfAfAfL96 | A-115887.6 | uUfgAfAfGfUfAfaAfuggUfgUfUfAfaCfcsAfsg |
| AD-56392.1 | A-115867.3 | GfGfUfUfAfAfCfaCfCfAfuUfUfAfcUfUfCfAfAfL96 | A-115887.7 | uUfgAfAfGfUfAfaAfuggUfgUfUfAfaCfcsAfsg |
| AD-56398.1 | A-115868.19 | GfGfUfUfAfAfCfaCfCfAfuUfUfAfCfUfUfCfAfAfL96 | A-115887.8 | uUfgAfAfGfUfAfaAfuggUfgUfUfAfaCfcsAfsg |
| AD-56404.1 | A-115869.3 | GfGfUfUfAfAfCfAfCfCaAfuUfUfAfCfUfUfCfAfAfL96 | A-115887.9 | uUfgAfAfGfUfAfaAfuggUfgUfUfAfaCfcsAfsg |
| AD-56410.1 | A-115881.1 | GfgUfuAfaCfaCfCfAfuUfuAfcUfUfCfAfAfL96 | A-113074.19 | uUfgAfaGfuAfaAfuggUfgUfuAfaCfcsAfsg |
| AD-56416.1 | A-115889.1 | GfgUfuAfaCfaCfCfAfuUfuAfCfUfUfCfaAfL96 | A-113074.20 | uUfgAfaGfuAfaAfuggUfgUfuAfaCfcsAfsg |
| AD-56375.1 | A-115890.1 | GfgUfuAfaCfaCfCfAfuUfUfAfCfUfuCfaAfL96 | A-113074.21 | uUfgAfaGfuAfaAfuggUfgUfuAfaCfcsAfsg |
| AD-56381.1 | A-115891.1 | GfgUfuAfaCfaCfCfAfUfUfUfAfcUfuCfaAfL96 | A-113074.22 | uUfgAfaGfuAfaAfuggUfgUfuAfaCfcsAfsg |
| AD-56387.1 | A-115892.1 | GfgUfuAfaCfAfCfCfAfUfUfuAfcUfuCfaAfL96 | A-113074.23 | uUfgAfaGfuAfaAfuggUfgUfuAfaCfcsAfsg |
| AD-56393.1 | A-115893.1 | GfgUfuAfAfCfAfCfCfAfuUfuAfcUfuCfaAfL96 | A-113074.24 | uUfgAfaGfuAfaAfuggUfgUfuAfaCfcsAfsg |
| AD-56399.1 | A-115894.1 | GfgUfUfAfAfCfaCfCfAfuUfuAfcUfuCfaAfL96 | A-113074.25 | uUfgAfaGfuAfaAfuggUfgUfuAfaCfcsAfsg |
| AD-56405.1 | A-115895.1 | GfGfUfUfAfaCfaCfCfAfuUfuAfcUfuCfaAfL96 | A-113074.26 | uUfgAfaGfuAfaAfuggUfgUfuAfaCfcsAfsg |
| AD-56411.1 | A-115896.1 | GfgUfuAfaCfaCfCfAfuUfuAfcUfucaaL96 | A-113074.27 | uUfgAfaGfuAfaAfuggUfgUfuAfaCfcsAfsg |
| AD-56417.1 | A-115897.1 | GfgUfuAfaCfaCfCfAfuUfuAfcuucaAfL96 | A-113074.28 | uUfgAfaGfuAfaAfuggUfgUfuAfaCfcsAfsg |
| AD-56376.1 | A-115898.1 | GfgUfuAfaCfaCfCfAfuUfuacuuCfaAfL96 | A-113074.29 | uUfgAfaGfuAfaAfuggUfgUfuAfaCfcsAfsg |

TABLE 8-continued

Sense and antisense strand sequences of Serpinc1 dsRNAs for lead optimization (The "Sense Sequence" column sequences are disclosed as SEQ ID NOS 243-510, respectively, in order of appearance, and the "Antisense Sequence" column sequences are disclosed as SEQ ID NOS 511-778, respectively, in order of appearance)

| Duplex Name | Sense Name | Sense Sequence | Antisense Name | Antisense Sequences |
|---|---|---|---|---|
| AD-56382.1 | A-115899.1 | GfgUfuAfaCfaCfCfAfuuuacufuCfaAfL96 | A-113074.30 | uUfgAfaGfuAfaAfuggUfgUfuAfaCfcsAfsg |
| AD-56388.1 | A-115900.1 | GfgUfuAfaCfaCfcauuuAfcUfuCfaAfL96 | A-113074.31 | uUfgAfaGfuAfaAfuggUfgUfuAfaCfcsAfsg |
| AD-56394.1 | A-115901.1 | gfgUfuAfaCfaccauUfuAfcUfuCfaAfL96 | A-113074.32 | uUfgAfaGfuAfaAfuggUfgUfuAfaCfcsAfsg |
| AD-56400.1 | A-115902.1 | GfgUfuAfacaccAfuUfuAfcufuCfaAfL96 | A-113074.33 | uUfgAfaGfuAfaAfuggUfgUfuAfaCfcsAfsg |
| AD-56406.1 | A-115903.1 | GfgUfuAfacaCfCfAfuuuAfcUfuCfaAfL96 | A-113074.34 | uUfgAfaGfuAfaAfuggUfgUfuAfaCfcsAfsg |
| AD-56412.1 | A-115904.1 | GfgUfuaacaCfCfAfuUfuAfcUfuCfaAfL96 | A-113074.35 | uUfgAfaGfuAfaAfuggUfgUfuAfaCfcsAfsg |
| AD-56418.1 | A-115905.1 | GfguuaaCfaCfCfAfuUfuAfcUfuCfaAfL96 | A-113074.36 | uUfgAfaGfuAfaAfuggUfgUfuAfaCfcsAfsg |
| AD-56377.1 | A-115906.1 | gguuAfaCfaCfCfAfuUfuAfcUfuCfaAfL96 | A-113074.37 | uUfgAfaGfuAfaAfuggUfgUfuAfaCfcsAfsg |
| AD-56383.1 | A-113073.9 | GfgUfuAfaCfaCfCfAfuUfuAfcUfuCfaAf L96 | A-115907.1 | UfUfGfAfaGfuAfaAfuggUfgUfuAfaCfcsAf sg |
| AD-56389.1 | A-113073.10 | GfgUfuAfaCfaCfCfAfuUfuAfcUfuCfaAf L96 | A-115908.1 | uUfGfAfAfGfuAfaAfuggUfgUfuAfaCfcsAf sg |
| AD-56395.1 | A-113073.11 | GfgUfuAfaCfaCfCfAfuUfuAfcUfuCfaAf L96 | A-115909.1 | uUfgAfAfGfUfAfaAfuggUfgUfuAfaCfcsAf sg |
| AD-56401.1 | A-113073.12 | GfgUfuAfaCfaCfCfAfuUfuAfcUfuCfaAf L96 | A-115910.1 | uUfgAfaGfUfAfAfAfuggUfgUfuAfaCfcsAf sg |
| AD-56407.1 | A-113073.13 | GfgUfuAfaCfaCfCfAfuUfuAfcUfuCfaAf L96 | A-115911.1 | uUfgAfaGfuAfAfAfUfGfgUfgUfuAfaCfcsA fsg |
| AD-56413.1 | A-113073.14 | GfgUfuAfaCfaCfCfAfuUfuAfcUfuCfaAf L96 | A-115912.1 | uUfgAfaGfuAfaAfUfGfGfUfgUfuAfaCfcsA fsg |
| AD-56419.2 | A-113073.15 | GfgUfuAfaCfaCfCfAfuUfuAfcUfuCfaAf L96 | A-115913.1 | uUfgAfaGfuAfaAfuGfGfUfGfUfuAfaCfcsA fsg |
| AD-56425.2 | A-113073.16 | GfgUfuAfaCfaCfCfAfuUfuAfcUfuCfaAf L96 | A-115914.1 | uUfgAfaGfuAfAfAfuggUfGfUfuAfaCfcsAf sg |
| AD-56431.2 | A-113073.17 | GfgUfuAfaCfaCfCfAfuUfuAfcUfuCfaAf L96 | A-115915.1 | uUfgAfaGfuAfaAfuggUfGfUfUfAfaCfcsAf sg |
| AD-56436.2 | A-113073.18 | GfgUfuAfaCfaCfCfAfuUfuAfcUfuCfaAf L96 | A-115916.1 | uUfgAfaGfuAfaAfuggUfgUfUfAfAfCfcsAf sg |
| AD-56442.2 | A-113073.19 | GfgUfuAfaCfaCfCfAfuUfuAfcUfuCfaAf L96 | A-115917.1 | uUfgAfaGfuAfaAfuggUfgUfuAfAfCfCfsAf sg |
| AD-56448.2 | A-113073.20 | GfgUfuAfaCfaCfCfAfuUfuAfcUfuCfaAf L96 | A-115918.1 | uUfgAfaGfuAfaAfuggUfgUfuAfaCfCfsAfs Gf |
| AD-56454.2 | A-113073.21 | GfgUfuAfaCfaCfCfAfuUfuAfcUfuCfaAf L96 | A-115919.1 | uugaaGfuAfaAfuggUfgUfuAfaCfcsAfsg |
| AD-56460.2 | A-113073.22 | GfgUfuAfaCfaCfCfAfuUfuAfcUfuCfaAf L96 | A-115920.1 | uUfgaaguAfaAfuggUfgUfuAfaCfcsAfsg |
| AD-56420.2 | A-113073.23 | GfgUfuAfaCfaCfCfAfuUfuAfcUfuCfaAf L96 | A-115921.1 | uUfgAfaguaaAfuggUfgUfuAfaCfcsAfsg |
| AD-56426.2 | A-113073.24 | GfgUfuAfaCfaCfCfAfuUfuAfcUfuCfaAf L96 | A-115922.1 | uUfgAfaGfuaaauggUfgUfuAfaCfcsAfsg |
| AD-56432.2 | A-113073.25 | GfgUfuAfaCfaCfCfAfuUfuAfcUfuCfaAf L96 | A-115923.1 | uUfgAfaGfuAfaauggugUfuAfaCfcsAfsg |
| AD-56437.2 | A-113073.26 | GfgUfuAfaCfaCfCfAfuUfuAfcUfuCfaAf L96 | A-115924.1 | uUfgAfaGfuAfaAfugguguuAfaCfcsAfsg |
| AD-56443.2 | A-113073.27 | GfgUfuAfaCfaCfCfAfuUfuAfcUfuCfaAf L96 | A-115925.1 | uUfgAfaGfuAfaAfuggUfguuaaCfcsAfsg |

TABLE 8-continued

Sense and antisense strand sequences of Serpinc1 dsRNAs for lead optimization (The "Sense Sequence" column sequences are disclosed as SEQ ID NOS 243-510, respectively, in order of appearance, and the "Antisense Sequence" column sequences are disclosed as SEQ ID NOS 511-778, respectively, in order of appearance)

| Duplex Name | Sense Name | Sense Sequence | Antisense Name | Antisense Sequences |
|---|---|---|---|---|
| AD-56449.2 | A-113073.28 | GfgUfuAfaCfaCfCfAfuUfuAfcUfuCfaAf L96 | A-115926.1 | uUfgAfaGfuAfaAfuggUfgUfuaaccsAfsg |
| AD-56455.2 | A-113073.29 | GfgUfuAfaCfaCfCfAfuUfuAfcUfuCfaAf L96 | A-115927.1 | uUfgAfaGfuAfaAfuggUfgUfuAfaccsasg |
| AD-56461.2 | A-115888.2 | GfgUfuAfaCfaCfCfAfuUfuAfcUfUfCfAf AfL96 | A-115919.2 | uugaaGfuAfaAfuggUfgUfuAfaCfcsAfsg |
| AD-56421.2 | A-115889.2 | GfgUfuAfaCfaCfCfAfuUfuAfCfUfUfCfa AfL96 | A-115920.2 | uUfgaaguAfaAfuggUfgUfuAfaCfcsAfsg |
| AD-56427.2 | A-115890.2 | GfgUfuAfaCfaCfCfAfuUfUfAfCfUfuCfa AfL96 | A-115921.2 | uUfgAfaguaaAfuggUfgUfuAfaCfcsAfsg |
| AD-56433.2 | A-115891.2 | GfgUfuAfaCfaCfCfAfUfUfUfAfcUfuCfa AfL96 | A-115922.2 | uUfgAfaGfuaaauggUfgUfuAfaCfcsAfsg |
| AD-56438.2 | A-115892.2 | GfgUfuAfaCfAfCfCfAfUfUfuAfcUfuCfa AfL96 | A-115923.2 | uUfgAfaGfuAfaauggugUfuAfaCfcsAfsg |
| AD-56444.2 | A-115893.2 | GfgUfuAfAfCfAfCfCfAfuUfuAfcUfuCfa AfL96 | A-115924.2 | uUfgAfaGfuAfaAfugguguuAfaCfcsAfsg |
| AD-56450.2 | A-115894.2 | GfgUfUfAfAfCfaCfCfAfuUfuAfcUfuCfa AfL96 | A-115925.2 | uUfgAfaGfuAfaAfuggUfguuaaCfcsAfsg |
| AD-56456.2 | A-115895.2 | GfGfUfUfAfaCfaCfCfAfuUfuAfcUfuCfa AfL96 | A-115926.2 | uUfgAfaGfuAfaAfuggUfgUfuaaccsAfsg |
| AD-56462.2 | A-115896.2 | GfgUfuAfaCfaCfCfAfuUfuAfcUfucaaL96 | A-115907.2 | UfUfGfAfaGfuAfaAfuggUfgUfuAfaCfcsAf sg |
| AD-56422.2 | A-115897.2 | GfgUfuAfaCfaCfCfAfuUfuAfcuucaAfL96 | A-115908.2 | uUfGfAfAfGfuAfaAfuggUfgUfuAfaCfcsAf sg |
| AD-56428.2 | A-115898.2 | GfgUfuAfaCfaCfCfAfuUfuacuuCfaAfL96 | A-115909.2 | uUfgAfAfGfUfAfaAfuggUfgUfuAfaCfcsAf sg |
| AD-56434.2 | A-115899.2 | GfgUfuAfaCfaCfCfAfuuuacUfuCfaAfL96 | A-115910.2 | uUfgAfaGfUfAfAfAfuggUfgUfuAfaCfcsAf sg |
| AD-56439.2 | A-115900.2 | GfgUfuAfaCfaCfcauuuAfcUfuCfaAfL96 | A-115911.2 | uUfgAfaGfuAfAfAfUfGfgUfgUfuAfaCfcsA fsg |
| AD-56445.2 | A-115901.2 | GfgUfuAfaCfaccauUfuAfcUfuCfaAfL96 | A-115912.2 | uUfgAfaGfuAfaAfUfGfGfUfgUfuAfaCfcsA fsg |
| AD-56451.2 | A-115902.2 | GfgUfuAfacaccAfuUfuAfcUfuCfaAfL96 | A-115913.2 | uUfgAfaGfuAfaAfuGfGfUfGfUfuAfaCfcsA fsg |
| AD-56457.2 | A-115903.2 | GfgUfuAfacaCfCfAfuuuAfcUfuCfaAfL96 | A-115914.2 | uUfgAfaGfuAfAfAfuggUfGfUfuAfaCfcsA fsg |
| AD-56463.2 | A-115904.2 | GfgUfuaacaCfCfAfuUfuAfcUfuCfaAfL96 | A-115915.2 | uUfgAfaGfuAfaAfuggUfGfUfUfAfaCfcsA fsg |
| AD-56423.2 | A-115905.2 | GfguuaaCfaCfCfAfuUfuAfcUfuCfaAfL96 | A-115916.2 | uUfgAfaGfuAfaAfuggUfgUfUfAfAfCfcsA fsg |
| AD-56429.2 | A-115906.2 | gguuAfaCfaCfCfAfuUfuAfcUfuCfaAfL96 | A-115917.2 | uUfgAfaGfuAfaAfuggUfgUfuAfAfCfCfsA fsg |
| AD-56440.2 | A-113073.31 | GfgUfuAfaCfaCfCfAfuUfuAfcUfuCfaAf L96 | A-115928.1 | uUfgAfaGfuAfaAfugGfUfgUfuAfaCfcsAf sg |
| AD-56446.2 | A-115929.1 | GfgUfuAfaCfacCfAfuUfuAfcUfuCfaAf L96 | A-115928.2 | uUfgAfaGfuAfaAfugGfUfgUfuAfaCfcsAf sg |
| AD-56452.2 | A-113073.32 | GfgUfuAfaCfaCfCfAfuUfuAfcUfuCfaAf L96 | A-115930.1 | UUfgAfaGfuAfaAfugGfUfgUfuAfaCfcsAf sg |

TABLE 8-continued

Sense and antisense strand sequences of Serpinc1 dsRNAs for lead optimization (The "Sense Sequence" column sequences are disclosed as SEQ ID NOS 243-510, respectively, in order of appearance, and the "Antisense Sequence" column sequences are disclosed as SEQ ID NOS 511-778, respectively, in order of appearance)

| Duplex Name | Sense Name | Sense Sequence | Antisense Name | Antisense Sequences |
|---|---|---|---|---|
| AD-56458.2 | A-115929.2 | GfgUfuAfaCfacCfAfuUfuAfcUfuCfaAf L96 | A-115930.2 | UUfgAfaGfuAfaAfugGfUfgUfuAfaCfcsAf sg |
| AD-56464.2 | A-113073.33 | GfgUfuAfaCfaCfCfAfuUfuAfcUfuCfaAf L96 | A-115931.1 | uUfgAfaGfuAfaAfugGUfgUfuAfaCfcsAfsg |
| AD-56424.2 | A-115929.3 | GfgUfuAfaCfacCfAfuUfuAfcUfuCfaAf L96 | A-115931.2 | uUfgAfaGfuAfaAfugGUfgUfuAfaCfcsAfsg |
| AD-56430.2 | A-115932.1 | GfgUfuAfaCfaCCfAfuUfuAfcUfuCfaAf L96 | A-115931.3 | uUfgAfaGfuAfaAfugGUfgUfuAfaCfcsAfsg |
| AD-56435.2 | A-113073.34 | GfgUfuAfaCfaCfCfAfuUfuAfcUfuCfaAf L96 | A-115933.1 | UUfgAfaGfuAfaAfugGUfgUfuAfaCfcsAfsg |
| AD-56441.2 | A-115929.4 | GfgUfuAfaCfacCfAfuUfuAfcUfuCfaAf L96 | A-115933.2 | UUfgAfaGfuAfaAfugGUfgUfuAfaCfcsAfsg |
| AD-56447.2 | A-115932.2 | GfgUfuAfaCfaCCfAfuUfuAfcUfuCfaAf L96 | A-115933.3 | UUfgAfaGfuAfaAfugGUfgUfuAfaCfcsAfsg |
| AD-56453.2 | A-115934.1 | GfgUfuAfaCfaUfCfAfuUfuAfcUfuCfaAf L96 | A-113074.39 | uUfgAfaGfuAfaAfuggUfgUfuAfaCfcsAfsg |
| AD-56459.2 | A-115935.1 | GfgUfuAfaCfaAfCfAfuUfuAfcUfuCfaAf L96 | A-113074.40 | uUfgAfaGfuAfaAfuggUfgUfuAfaCfcsAfsg |
| AD-56465.2 | A-115936.1 | GfgUfuAfaCfaCfUfAfuUfuAfcUfuCfaAf L96 | A-113074.41 | uUfgAfaGfuAfaAfuggUfgUfuAfaCfcsAfsg |
| AD-56471.2 | A-115937.1 | GfgUfuAfaCfaCfAfAfuUfuAfcUfuCfaAf L96 | A-113074.42 | uUfgAfaGfuAfaAfuggUfgUfuAfaCfcsAfsg |
| AD-56477.2 | A-113073.35 | GfgUfuAfaCfaCfCfAfuUfuAfcUfuCfaAf L96 | A-115938.1 | uUfgAfaGfuAfaAfuggUfgUfuAfaCfc |
| AD-56483.3 | A-113073.36 | GfgUfuAfaCfaCfCfAfuUfuAfcUfuCfaAf L96 | A-115939.1 | uUfgAfaGfuAfaAfuggUfgUfuAfaCfsc |
| AD-56488.2 | A-113073.37 | GfgUfuAfaCfaCfCfAfuUfuAfcUfuCfaAf L96 | A-115940.1 | uUfgAfaGfuAfaAfuggUfgUfuAfasCfsc |
| AD-56483.4 | A-113073.38 | GfgUfuAfaCfaCfCfAfuUfuAfcUfuCfaAf L96 | A-115939.2 | uUfgAfaGfuAfaAfuggUfgUfuAfaCfsc |
| AD-56497.2 | A-115941.1 | UfuAfaCfaCfCfAfuUfuAfcUfuCfaAfL96 | A-115940.2 | uUfgAfaGfuAfaAfuggUfgUfuAfasCfsc |
| AD-56502.2 | A-115941.2 | UfuAfaCfaCfCfAfuUfuAfcUfuCfaAfL96 | A-115942.1 | uUfgAfaGfuAfaAfuggUfgUfuAfa |
| AD-56466.2 | A-115941.3 | UfuAfaCfaCfCfAfuUfuAfcUfuCfaAfL96 | A-115943.1 | uUfgAfaGfuAfaAfuggUfgUfuAfsa |
| AD-56472.2 | A-115941.4 | UfuAfaCfaCfCfAfuUfuAfcUfuCfaAfL96 | A-115944.1 | uUfgAfaGfuAfaAfuggUfgUfusAfsa |
| AD-56478.2 | A-115945.1 | AfaCfaCfCfAfuUfuAfcUfuCfaAfL96 | A-115943.2 | uUfgAfaGfuAfaAfuggUfgUfuAfsa |
| AD-56484.2 | A-115945.2 | AfaCfaCfCfAfuUfuAfcUfuCfaAfL96 | A-115944.2 | uUfgAfaGfuAfaAfuggUfgUfusAfsa |
| AD-56493.2 | A-113073.39 | GfgUfuAfaCfaCfCfAfuUfuAfcUfuCfaAf L96 | A-115948.1 | uUfgAf(Aeo)GfuAfaAfuggUfgUfuA faCfcsAfsg |
| AD-56498.2 | A-113073.40 | GfgUfuAfaCfaCfCfAfuUfuAfcUfuCfaAf L96 | A-115949.1 | uUfgAfa(Geo)uAfaAfuggUfgUfuAf aCfcsAfsg |
| AD-56467.2 | A-113073.42 | GfgUfuAfaCfaCfCfAfuUfuAfcUfuCfaAf L96 | A-115951.1 | uUfgAfaGfu(Aeo)aAfuggUfgUfuAf aCfcsAfsg |
| AD-56473.2 | A-113073.43 | GfgUfuAfaCfaCfCfAfuUfuAfcUfuCfaAf L96 | A-115952.1 | uUfgAfaGfuAf(Aeo)AfuggUfgUfuA faCfcsAfsg |
| AD-56479.2 | A-113073.44 | GfgUfuAfaCfaCfCfAfuUfuAfcUfuCfaAf L96 | A-115953.1 | uUfgAfaGfuAfa(Aeo)uggUfgUfuAf aCfcsAfsg |

TABLE 8-continued

Sense and antisense strand sequences of Serpinc1 dsRNAs for lead optimization (The "Sense Sequence" column sequences are disclosed as SEQ ID NOS 243-510, respectively, in order of appearance, and the "Antisense Sequence" column sequences are disclosed as SEQ ID NOS 511-778, respectively, in order of appearance)

| Duplex Name | Sense Name | Sense Sequence | Antisense Name | Antisense Sequences |
|---|---|---|---|---|
| AD-56485.2 | A-113073.45 | GfgUfuAfaCfaCfCfAfuUfuAfcUfuCfaAfL96 | A-115954.1 | uUfgAfaGfuAfaAfugg(Teo)gUfuAfaCfcsAfsg |
| AD-56490.2 | A-113073.46 | GfgUfuAfaCfaCfCfAfuUfuAfcUfuCfaAfL96 | A-115955.1 | uUfgAfaGfuAfaAfuggUf(Geo)UfuAfaCfcsAfsg |
| AD-56494.2 | A-113073.47 | GfgUfuAfaCfaCfCfAfuUfuAfcUfuCfaAfL96 | A-115956.1 | uUfgAfaGfuAfaAfuggUfg(Teo)uAfaCfcsAfsg |
| AD-56499.2 | A-113073.48 | GfgUfuAfaCfaCfCfAfuUfuAfcUfuCfaAfL96 | A-115957.1 | uUfgAfaGfuAfaAfuggUfgUf(Teo)AfaCfcsAfsg |
| AD-56504.2 | A-113073.49 | GfgUfuAfaCfaCfCfAfuUfuAfcUfuCfaAfL96 | A-115958.1 | uUfgAfaGfuAfaAfuggUfgUfu(Aeo)aCfcsAfsg |
| AD-56468.2 | A-113073.50 | GfgUfuAfaCfaCfCfAfuUfuAfcUfuCfaAfL96 | A-115959.1 | uUfgAfaGfuAfaAfuggUfgUfuAf(Aeo)CfcsAfsg |
| AD-56474.2 | A-113073.51 | GfgUfuAfaCfaCfCfAfuUfuAfcUfuCfaAfL96 | A-115960.1 | uUfgAfaGfuAfaAfuggUfgUfuAfa(m5Ceo)csAfsg |
| AD-56480.2 | A-113073.52 | GfgUfuAfaCfaCfCfAfuUfuAfcUfuCfaAfL96 | A-115961.1 | uUfgAfaGfuAfaAfuggUfgUfuAfaCf(m5Ceos)Afsg |
| AD-56486.2 | A-113073.53 | GfgUfuAfaCfaCfCfAfuUfuAfcUfuCfaAfL96 | A-115962.1 | uUfgAfaGfuAfaAfuggUfgUfuAfaCfcs(Aeos)(Geo) |
| AD-56491.2 | A-113073.54 | GfgUfuAfaCfaCfCfAfuUfuAfcUfuCfaAfL96 | A-115963.1 | uUfgAfaGfuAfaAf(Teo)(Geo)(Geo)UfgUfusAfsa |
| AD-56495.2 | A-115964.1 | GfgUfuAfaCfaCfCfAfuUfuAfcUf(Teo)Cf(Aeo)AfL96 | A-113074.43 | uUfgAfaGfuAfaAfuggUfgUfuAfaCfcsAfsg |
| AD-56500.2 | A-115965.1 | Gf(Geo)UfuAfaCfaCfCfAfuUfuAfcUf(Teo)Cf(Aeo)AfL96 | A-113074.44 | uUfgAfaGfuAfaAfuggUfgUfuAfaCfcsAfsg |
| AD-56505.2 | A-115966.1 | Gf(Geo)Uf(Teo)AfaCfaCfCfAfuUfuAfcUf(Teo)Cf(Aeo)AfL96 | A-113074.45 | uUfgAfaGfuAfaAfuggUfgUfuAfaCfcsAfsg |
| AD-56469.2 | A-115967.1 | Gf(Geo)Uf(Teo)AfaCfaCfCfAfuUfuAf(m5Ceo)Uf(Teo)Cf(Aeo)AfL96 | A-113074.46 | uUfgAfaGfuAfaAfuggUfgUfuAfaCfcsAfsg |
| AD-56475.2 | A-115968.1 | Gf(Geo)Uf(Teo)AfaCfaCfCfAfuUf(Teo)Af(m5Ceo)Uf(Teo)Cf(Aeo)AfL96 | A-113074.47 | uUfgAfaGfuAfaAfuggUfgUfuAfaCfcsAfsg |
| AD-56481.2 | A-115969.1 | Gf(Geo)Uf(Teo)AfaCfaCfCfAf(Teo)Uf(Teo)Af(m5Ceo)Uf(Teo)Cf(Aeo)AfL96 | A-113074.48 | uUfgAfaGfuAfaAfuggUfgUfuAfaCfcsAfsg |
| AD-56487.2 | A-115970.1 | Gf(Geo)Uf(Teo)Af(Aeo)Cf(Aeo)CfCfAf(Teo)Uf(Teo)Af(m5Ceo)Uf(Teo)Cf(Aeo)AfL96 | A-113074.49 | uUfgAfaGfuAfaAfuggUfgUfuAfaCfcsAfsg |

Example 3

LNP-Mediated Delivery of siRNAs

Figure 3A:
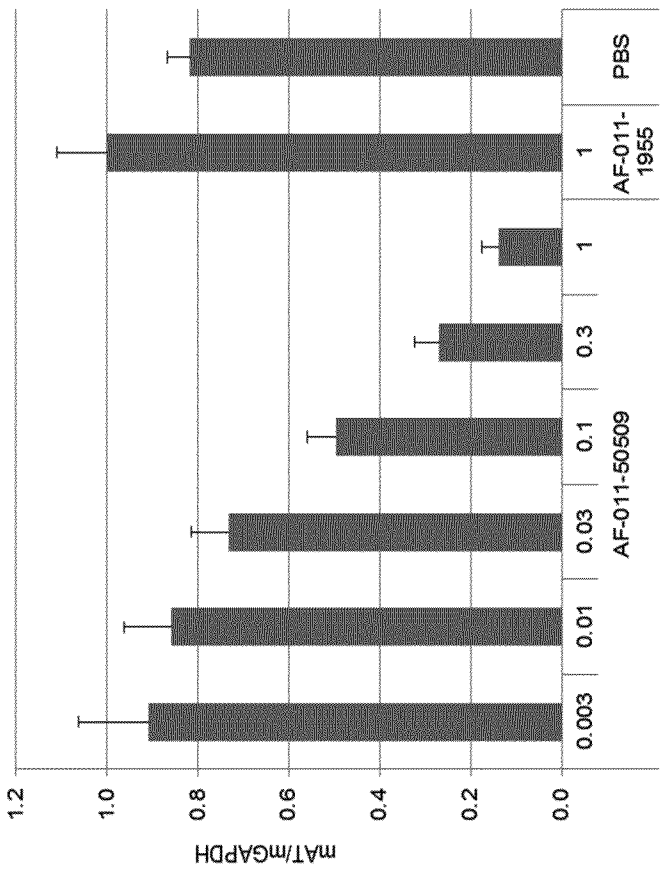
FIGS. 3A and 3B are graphs showing the inhibition of Serpinc1 mRNA (A) and protein (B) expression in CD-1 mice following a single dose, as indicated, of an LNP formulation of AD-50509 or AD-1955.
Figure 3B:
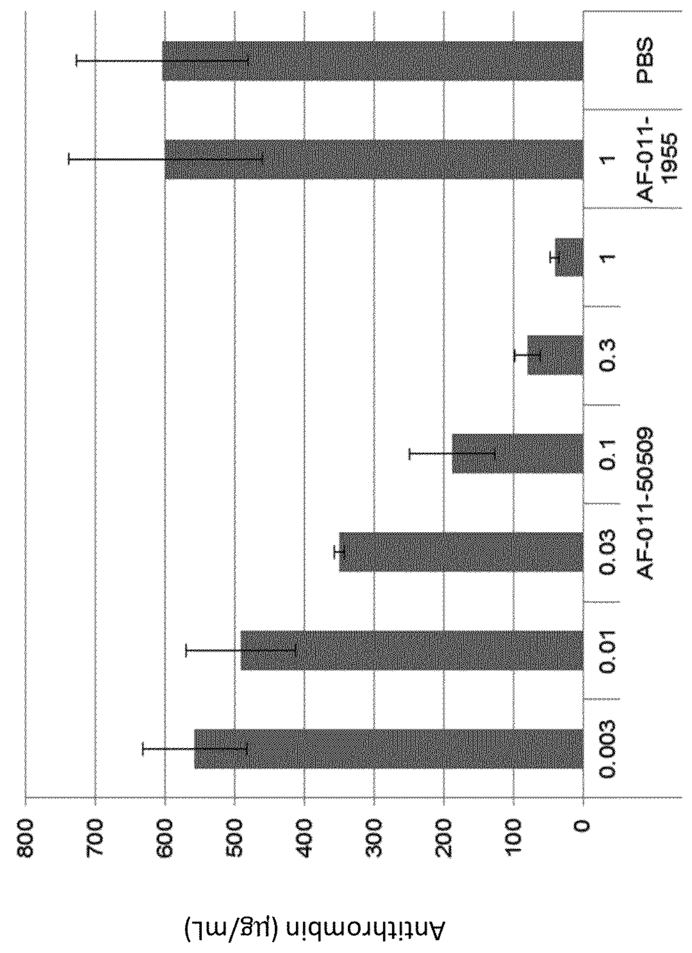

Based on the in vitro single dose and $IC_{50}$ results described above, modified AD-50509 was selected for formulation in a lipid nanoparticle (LNP). In order to determine an effective dose for LNP-mediated delivery of AD-50509, CD1 mice were intravenously injected with a single dose of an LNP formulation (AF-011) of AD-50509 siRNA at 0.003, 0.01, 0.03, 0.1, 0.3, or 1.0 mg/kg. Animals were sacrificied 48 hours later and the level of Serpinc1 mRNA relative to GAPDH and the level of Serpinc1 protein were determined as described herein. As shown in FIGS. 3A and 3B, the maximum Serpinc1 mRNA silencing of 85% with AF-011-AD-50509 was achieved with an $ED_{50}$ of about 0.1 mg/kg (FIG. 3A) and the maximum Serpinc1 protein silencing of 90% was achieved with an $ED_{50}$ of about 0.05 mg/kg (FIG. 3B).

Figure 4A:
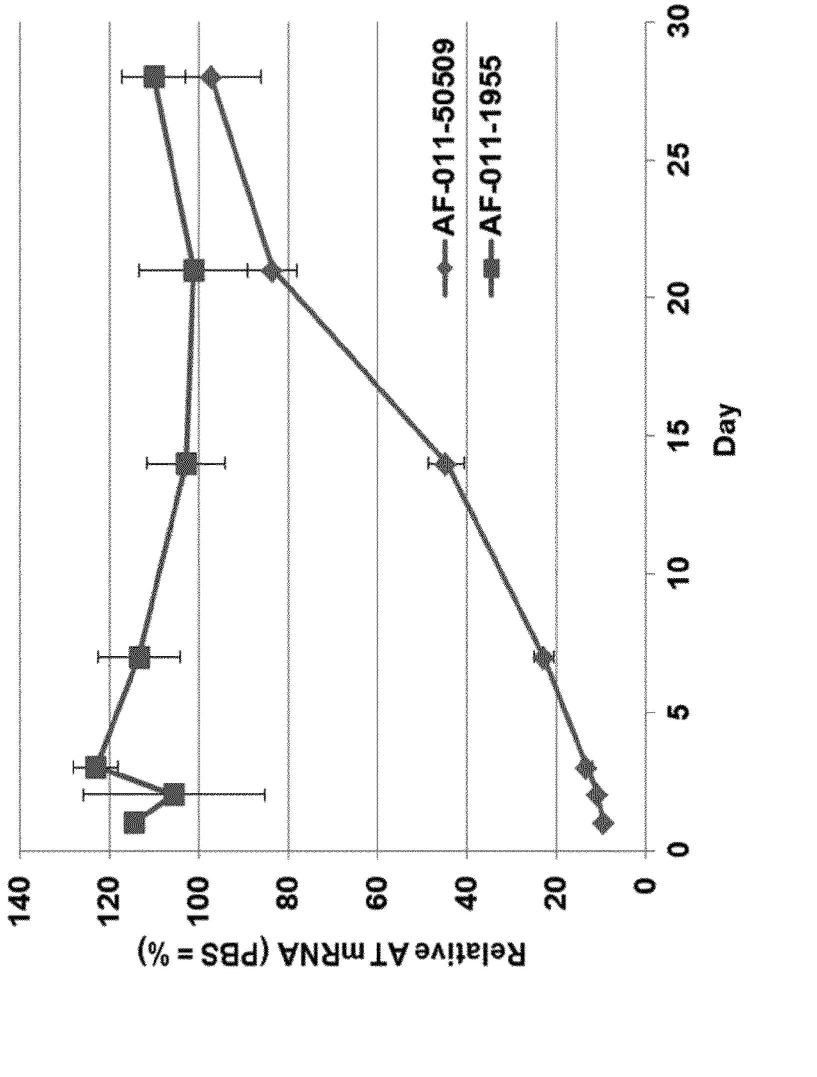
FIGS. 4A and 4B are graphs showing the duration of inhibition of Serpinc1 mRNA (A) and protein (B) expression in CD-1 mice following a single 1 mg/kg dose of an LNP formulation of AD-50509 or AD-1955.
Figure 4B:
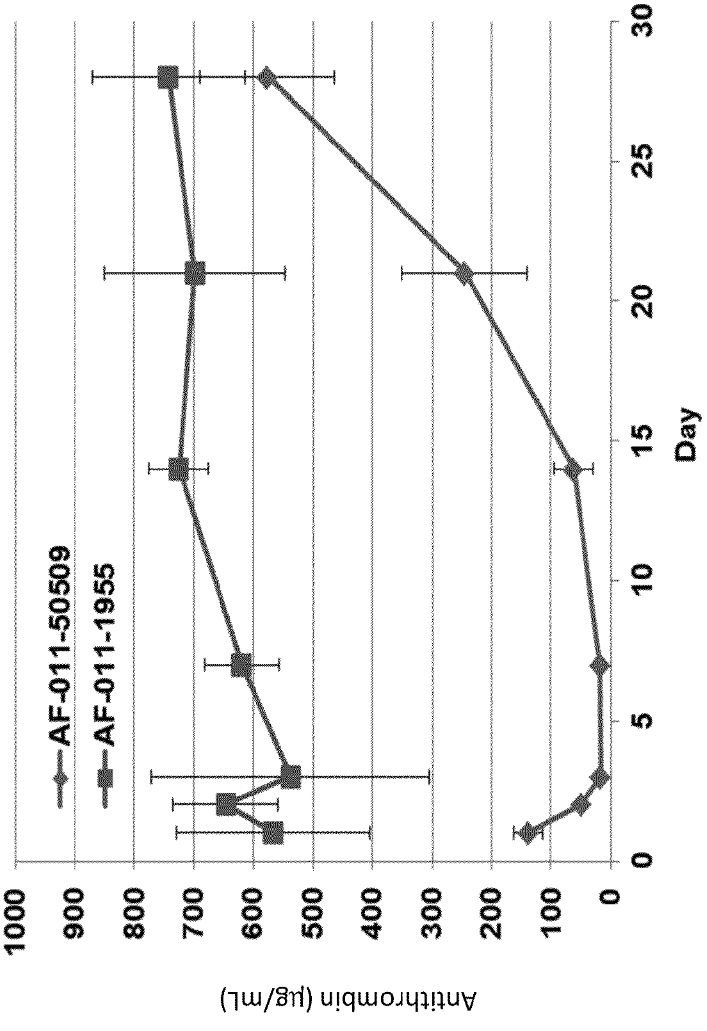
Figure 4C:
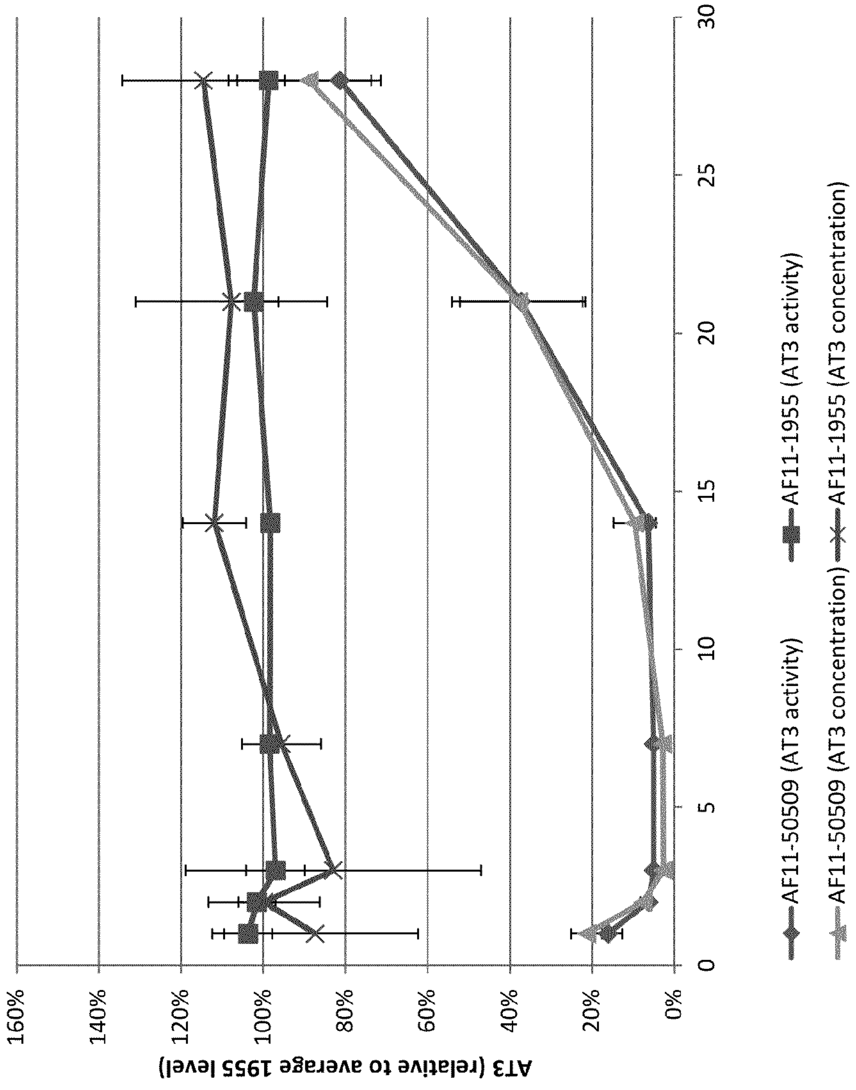
FIG. 4C is a graph showing the inhibition of Serpinc1 activity and Serpinc1 protein expression in CD1 mice following a single 1 mg/kg dose of an LNP formulation of AD-50509 or AD-1955.

The duration of silencing of an LNP formulation of AD-50509 siRNA (AF-011-50509) was determined in CD1 mice following a single 1 mg/kg intravenous injection of the siRNA. Animals were sacrificed at Day 1, 2, 3, 7, 14, 21, or 28 after administration and the relative level of Serpinc1 mRNA and the level of Serpinc1 protein were determined. FIG. 4A demonstrates that AF-011 formulated AD-50509 achieved Serpinc1 mRNA silencing of about 90% within 24 hours of administration and that there was approximately a 50% recovery in the relative amount of Serpinc1 mRNA by about two weeks after administration. FIG. 4B demonstrates that AF-011 formulated AD-50509 achieved Serpinc1 protein silencing of about 90% within about 72 hours of administration and that there was approximately a 50% recovery in the relative amount of Serpinc1 protein by about two weeks after administration. Serpinc1 activity was also determined by measuring Factor Xa activity using a commercially available kit (Aniara) in CD1 mice following a single 1 mg/kg intravenous injection of the LNP formulated AD-50509 siRNA. Animals were sacrificed at Day 1, 2, 3, 7, 14, 21, or 28 after administration and the relative activity level of Serpinc1 protein and the relative Serpinc1 protein level were determined. FIG. 4C shows that there is good correlation between the level of Serpinc1 protein level and Serpinc1 activity.

Example 4

GalNAc-Conjugated siRNAs

Forty-four modified Serpinc1 siRNA duplexes were conjugated with a trivalent GALNAc at the 3-end of the sense strand. These duplexes were assayed for efficacy in single dose free uptake of the conjugated duplexes in Cynomolgus monkey hepatocytes. Table 9 shows the results of these assays.

TABLE 9

| GalNAc Free-Uptake Single Dose | | | |
|---|---|---|---|
| Duplex ID | Ave 100 nM | Ave 10 nM | Ave 0.1 nM |
| AD-54944.1 | 0.4 | 0.53 | 0.94 |
| AD-54951.1 | 0.37 | 0.56 | 1 |
| AD-54942.1 | 0.38 | 0.58 | 1.01 |
| AD-54948.1 | 0.36 | 0.6 | 0.96 |
| AD-54957.1 | 0.47 | 0.61 | 1 |
| AD-54933.1 | 0.51 | 0.65 | 0.96 |
| AD-54962.1 | 0.48 | 0.66 | 0.95 |
| AD-54972.1 | 0.49 | 0.66 | 1.05 |
| AD-54949.1 | 0.49 | 0.71 | 0.96 |
| AD-54936.1 | 0.54 | 0.72 | 1.07 |
| AD-54971.1 | 0.49 | 0.72 | 1 |
| AD-54955.1 | 0.52 | 0.74 | 0.98 |
| AD-54953.1 | 0.63 | 0.76 | 1.07 |
| AD-54937.1 | 0.64 | 0.81 | 0.94 |
| AD-54967.1 | 0.74 | 0.82 | 1.02 |
| AD-54935.1 | 0.68 | 0.83 | 0.99 |
| AD-54976.1 | 0.7 | 0.85 | 1.04 |
| AD-54965.1 | 0.7 | 0.86 | 0.97 |
| AD-54959.1 | 0.79 | 0.86 | 0.95 |
| AD-54943.1 | 0.75 | 0.86 | 0.94 |
| AD-54956.1 | 0.86 | 0.87 | 0.95 |
| AD-54973.1 | 0.96 | 0.89 | 1 |
| AD-54975.1 | 0.67 | 0.89 | 0.99 |
| AD-54963.1 | 0.73 | 0.9 | 0.96 |
| AD-54978.1 | 0.85 | 0.9 | 0.98 |
| AD-54952.1 | 0.59 | 0.91 | 1.11 |
| AD-54950.1 | 0.89 | 0.91 | 0.95 |
| AD-54964.1 | 0.87 | 0.93 | 1.01 |
| AD-54974.1 | 0.83 | 0.93 | 0.96 |
| AD-54969.1 | 0.87 | 0.94 | 0.94 |
| AD-54961.1 | 0.74 | 0.94 | 1.07 |
| AD-54968.1 | 0.89 | 0.95 | 0.91 |
| AD-54947.1 | 0.92 | 0.96 | 0.94 |
| AD-54941.1 | 0.91 | 0.96 | 1 |
| AD-54966.1 | 0.93 | 0.97 | 1.06 |
| AD-54940.1 | 0.86 | 0.99 | 1.03 |
| AD-54958.1 | 0.97 | 0.99 | 1.06 |
| AD-54938.1 | 0.93 | 0.99 | 1.05 |
| AD-54934.1 | 0.92 | 1 | 0.96 |
| AD-54939.1 | 0.84 | 1.02 | 1.02 |
| AD-54960.1 | 0.98 | 1.03 | 1.02 |
| AD-54954.1 | 1.04 | 1.03 | 1.01 |

TABLE 9-continued

| GalNAc Free-Uptake Single Dose | | | |
|---|---|---|---|
| Duplex ID | Ave 100 nM | Ave 10 nM | Ave 0.1 nM |
| AD-54970.1 | 1.03 | 1.06 | 1.01 |
| AD-54946.1 | 0.83 | 1.17 | 1.1 |

These duplexes were also assayed for dose response in free uptake and transfection assays.

Table 10 shows the results of these assays and the rank order of the duplexes for both free uptake and transfection. The 5 duplexes with the best $IC_{50}$ are shaded in light gray and the bottom 5 duplexes are shaded in dark gray. The $IC_{50}$ rank order of the duplexes is well conserved between free uptake and transfection-mediated uptake of GalNAc conjugates.

TABLE 10

Dose Response of GalNAc-conjugated duplexes: Free uptake and Transfection

| | Free Uptake (nM) | Free Uptake Rank | Transfection (nM) | Transfection Rank |
|---|---|---|---|---|
| AD-54948.1 | 8.2 | 1 | 0.018 | 3 |
| AD-54951.1 | 10.1 | 2 | 0.009 | 1 |
| AD-54942.1 | 10.8 | 3 | 0.024 | 6 |
| AD-54957.1 | 17.8 | 4 | 0.012 | 2 |
| AD-54944.1 | 19.3 | 5 | 0.019 | 4 |
| AD-54933.1 | 33.2 | 6 | 0.031 | 7 |
| AD-54936.1 | 43.2 | 7 | 0.032 | 9 |
| AD-54971.1 | 44.7 | 8 | 0.041 | 11 |
| AD-54962.1 | 80.2 | 9 | 0.032 | 8 |
| AD-54972.1 | 101.4 | 10 | 0.035 | 10 |
| AD-54955.1 | 148.1 | 11 | 0.022 | 5 |
| AD-54949.1 | No IC50 | 12 | 0.302 | 13 |
| AD-54953.1 | No IC50 | 13 | 0.058 | 12 |

Example 5

AD-54944 Optimization

As described in Example 4 above, AD-54944 was among the most active GalNAc-conjugated siRNA duplex as determined by both free uptake and transfection assays and was, thus, selected for further optimization and in vivo testing.

Figure 5:
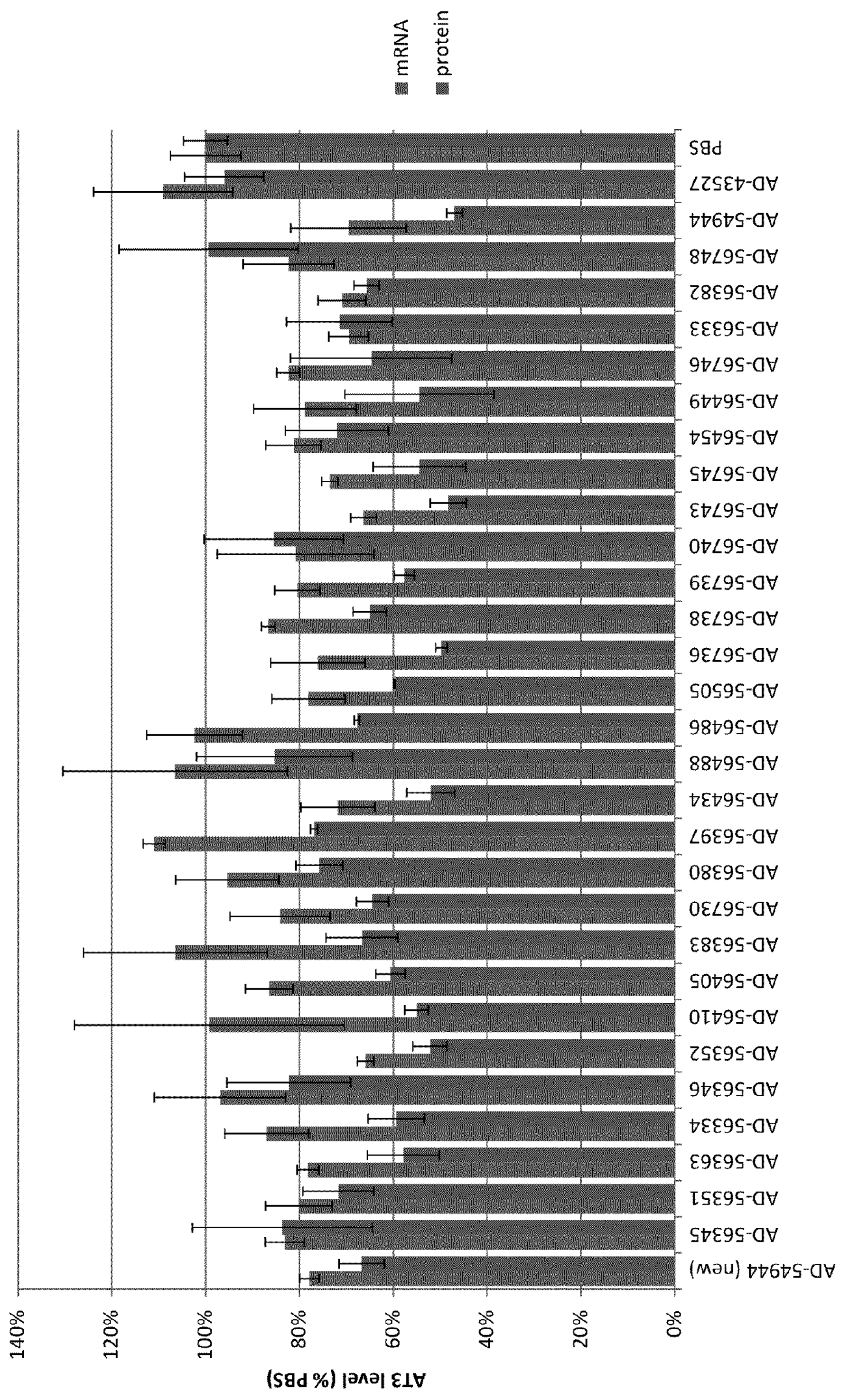
FIG. 5 is a graph showing the percent knock-down of Serpinc1 mRNA and protein levels following a single 10 mg/kg dose of the indicated iRNA conjugated to GalNAc.

Twenty-nine compounds were prepared based on the same AD-54944 parent sequence and screened for in vivo efficacy using a single 10 mg/kg dose. Animals (C57BL/6) were injected subcutaneously at Day 0 and sacrificed at Day 3. Serum Serpinc1 protein levels were determined by ELISA assay and the level of Serpinc1 mRNA was determined by QRT-PCR using liver samples from the animals. Tables 11 and 12 show the sequences of the duplexes and the results of the single dose screen with these duplexes as a percent knock-down of Serpinc1 protein levels from PBS. FIG. 5 shows the results of the single dose screen as a percent knock-down of Serpince mRNA and protein levels from PBS.

TABLE 11

AD-54944 optimized sequences and protein levels. (The "Sense Sequence" column sequences are disclosed as SEQ ID NOS 779-808, respectively, in order of appearance, and the "Antisense Sequence" column sequences are disclosed as SEQ ID NOS 809-838, respectively, in order of appearance)

| Duplex Name | Sense Sequence | Antisense Sequence | % PBS | Std Dev |
|---|---|---|---|---|
| AD-54944 (new) | GfgUfuAfaCfaCfCfAfuUfuAfcUfuCfaAfL96 | uUfgAfaGfuAfaAfuggUfgUfuAfaCfcsAfsg | 66.8 | 4.8 |
| AD-56345 | GfgUfuAfaCfaCfCfAfuUfuAfcUfuCfaAfL96 | uUfgaaGfuAfaAfuggUfguuAfaCfcsasg | 83.6 | 19.2 |
| AD-56351 | GfguuAfaCfaCfCfAfuUfuAfcUfuCfaAfL96 | uUfgaaGfuAfaAfuggUfguuAfaCfcsasg | 71.7 | 7.5 |
| AD-56363 | GfguuAfaCfaCfCfAfuUfuacUfuCfaaL96 | uUfgaaGfuAfaAfuggUfguuAfaCfcsasg | 57.9 | 7.6 |
| AD-56334 | GfguuAfacaCfCfAfuuuacUfucaaL96 | uUfgaaGfuAfaAfuggUfguuAfaCfcsasg | 59.4 | 6.0 |
| AD-56346 | GfguuaacaCfCfAfuuuacuucaaL96 | uUfgaaGfuAfaAfuggUfguuAfaCfcsasg | 82.3 | 13.2 |
| AD-56352 | GfgUfUfAfaCfaCfCfAfuUfuAfcUfuCfaAf L96 | uUfgAfaGfuAfaAfuggUfgUfuAfaCfcsAfsg | 52.2 | 3.6 |
| AD-56410 | GfgUfuAfaCfaCfCfAfuUfuAfcUfUfCfAfA fL96 | uUfgAfaGfuAfaAfuggUfgUfuAfaCfcsAfsg | 55.0 | 2.5 |
| AD-56405 | GfGfUfUfAfaCfaCfCfAfuUfuAfcUfuCfaA fL96 | uUfgAfaGfuAfaAfuggUfgUfuAfaCfcsAfsg | 60.6 | 3.1 |
| AD-56383 | GfgUfuAfaCfaCfCfAfuUfuAfcUfuCfaAfL 96 | UfUfGfAfaGfuAfaAfuggUfgUfuAfaCfcsAfsg | 66.7 | 7.6 |
| AD-56730 | GfgUfuAfaCfaCfCfAfuUfuAfcUfUfCfAfA fL96 | uUfgAfaGfuAfaAfuggUfgUfuAfaCfCfsAfsGf | 64.4 | 3.4 |
| AD-56380 | GfgUfUfAfaCfaCfCfAfuUfUfAfcUfUfCfA fAfL96 | uUfgAfAfGfUfAfaAfuggUfgUfUfAfaCfcsAfsg | 75.7 | 5.0 |
| AD-56397 | GfGfUfUfAfAfCfAfCfCfAfuUfUfAfCfUfU fCfAfAfL96 | uUfgAfAfGfuAfaAfuggUfgUfUfAfaCfcsAfsg | 76.9 | 0.8 |
| AD-56434 | GfgUfuAfaCfaCfCfAfuuuacUfuCfaAfL96 | uUfgAfaGfUfAfAfAfuggUfgUfuAfaCfcsAfsg | 52.0 | 5.1 |
| AD-56488 | GfgUfuAfaCfaCfCfAfuUfuAfcUfuCfaAfL 96 | uUfgAfaGfuAfaAfuggUfgUfuAfasCfsc | 85.3 | 16.6 |
| AD-56486 | GfgUfuAfaCfaCfCfAfuUfuAfcUfuCfaAfL 96 | uUfgAfaGfuAfaAfuggUfgUfuAfaCfcs(Aeos) (Geo) | 67.7 | 0.5 |
| AD-56505 | Gf(Geo)Uf(Teo)AfaCfaCfCfAfuUfuAfcU f(Teo)Cf(Aeo)AfL96 | uUfgAfaGfuAfaAfuggUfgUfuAfaCfcsAfsg | 59.7 | 0.2 |
| AD-56736 | Gf(Geo)Uf(Teo)AfaCfaCfCfAfuUf(Teo) Af(m5Ceo)Uf(Teo)Cf(Aeo)AfL96 | uUfgAfaGfuAfaAfuggUf(Geo)UfuAfaCfc-sAfsg | 49.7 | 1.2 |
| AD-56738 | Gf(Geo)Uf(Teo)AfaCfaCfCfAfuUfuAfcU f(Teo)Cf(Aeo)AfL96 | uUfgaaGfuAfaAfuggUfguuAfaCfcsasg | 65.0 | 3.6 |
| AD-56739 | Gf(Geo)Uf(Teo)AfaCfaCfCfAfuUf(Teo) Af(m5Ceo)Uf(Teo)Cf(Aeo)AfL96 | uUfgaaGfuAfaAfuggUfguuAfaCfcsasg | 57.6 | 2.1 |
| AD-56740 | Gf(Geo)Uf(Teo)AfaCfaCfCfAfuUfuAfcU f(Teo)Cf(Aeo)AfL96 | uUfgaaGfuAfaAfuggUfgUfuAfaCfcsasg | 85.5 | 14.8 |
| AD-56743 | Gf(Geo)UfuAfaCfaCfCfAfuUfuAfcUf (Teo)Cf(Aeo)AfL96 | uUfgaaGfuAfaAfuggUfgUfuAfaCfcsasg | 48.3 | 3.9 |
| AD-56745 | Gf(Geo)Uf(Teo)AfaCfaCfCfAfuUfuAf (m5Ceo)Uf(Teo)Cf(Aeo)AfL96 | uUfgaaGfuAfaAfuggUfgUfuAfaCfcsasg | 54.4 | 9.9 |
| AD-56454 | GfgUfuAfaCfaCfCfAfuUfuAfcUfuCfaA fL96 | uugaaGfuAfaAfuggUfgUfuAfaCfcsAfsg | 72.0 | 11.0 |
| AD-56449 | GfgUfuAfaCfaCfCfAfuUfuAfcUfuCfaA fL96 | uUfgAfaGfuAfaAfuggUfgUfuaaccsAfsg | 54.4 | 15.9 |
| AD-56746 | Gf(Geo)UfuAfaCfaCfCfAfuUfuAfcUf (Teo)Cf(Aeo)AfL96 | uUfgAfaGfuAfaAfuggUfgUfuaaccsAfsg | 64.7 | 17.2 |

TABLE 11-continued

AD-54944 optimized sequences and protein levels. (The "Sense Sequence" column sequences are disclosed as SEQ ID NOS 779-808, respectively, in order of appearance, and the "Antisense Sequence" column sequences are disclosed as SEQ ID NOS 809-838, respectively, in order of appearance)

| Duplex Name | Sense Sequence | Antisense Sequence | % PBS | Std Dev |
|---|---|---|---|---|
| AD-56333 | GfguuAfacaCfCfAfuuuacuucaaL96 | uUfgaaGfuAfaAfuggUfgUfuAfaCfcsasg | 71.5 | 11.3 |
| AD-56382 | GfgUfuAfaCfaCfCfAfuuuacUfuCfaAf L96 | uUfgAfaGfuAfaAfuggUfgUfuAfaCfcsAfsg | 65.7 | 2.7 |
| AD-56748 | GfgUfuAfaCfaCfCfAfuuuacUfuCfaAf L96 | uUfgaaGfuAfaAfuggUfguuAfaCfcsasg | 99.4 | 19.1 |
| AD-54944 (original) | GfgUfuAfaCfaCfCfAfuUfuAfcUfuCfa AfL96 | uUfgAfaGfuAfaAfuggUfgUfuAfaCfcsAfsg | 46.9 | 1.7 |
| control | | | 96.0 | 8.5 |
| PBS | | | 100.0 | 4.7 |

TABLE 12

AD-54944 optimized sequences and protein levels. (The "Sense Sequence" column sequences are disclosed as SEQ ID NOS 839-868, respectively, in order of appearance, and the "Antisense Sequence" column sequences are disclosed as SEQ ID NOS 869-898, respectively, in order of appearance)

| Duplex Name | Sense Sequence | Antisense Sequence | % PBS | Std Dev |
|---|---|---|---|---|
| AD-54944 (original) | GfgUfuAfaCfaCfCfAfuUfuAfcUfuCfaAfL96 | uUfgAfaGfuAfaAfuggUfgUfuAfaCfcsAfsg | 46.9 | 1.7 |
| AD-56743 | Gf(Geo)UfuAfaCfaCfCfAfuUfuAfcUf(Teo) Cf(Aeo)AfL96 | uUfgaaGfuAfaAfuggUfgUfuAfaCfcsasg | 48.3 | 3.9 |
| AD-56736 | Gf(Geo)Uf(Teo)AfaCfaCfCfAfuUf(Teo)Af (m5Ceo)Uf(Teo)Cf(Aeo)AfL96 | uUfgAfaGfuAfaAfuggUf(Geo)UfuAfaCfcsAfsg | 49.7 | 1.2 |
| AD-56434 | GfgUfuAfaCfaCfCfAfuuuacUfuCfaAfL96 | uUfgAfaGfUfAfAfAfuggUfgUfuAfaCfcsAfsg | 52.0 | 5.1 |
| AD-56352 | GfgUfUfAfaCfaCfCfAfuUfuAfcUfuCfaAfL96 | uUfgAfaGfuAfaAfuggUfgUfuAfaCfcsAfsg | 52.2 | 3.6 |
| AD-56745 | Gf(Geo)Uf(Teo)AfaCfaCfCfAfuUfuAf (m5Ceo)Uf(Teo)Cf(Aeo)AfL96 | uUfgaaGfuAfaAfuggUfgUfuAfaCfcsasg | 54.4 | 9.9 |
| AD-56449 | GfgUfuAfaCfaCfCfAfuUfuAfcUfuCfaAfL96 | uUfgAfaGfuAfaAfuggUfgUfuaaccsAfsg | 54.4 | 15.9 |
| AD-56410 | GfgUfuAfaCfaCfCfAfuUfuAfcUfUfCfAfAfL96 | uUfgAfaGfuAfaAfuggUfgUfuAfaCfcsAfsg | 55.0 | 2.5 |
| AD-56739 | Gf(Geo)Uf(Teo)AfaCfaCfCfAfuUf(Teo)Af (m5Ceo)Uf(Teo)Cf(Aeo)AfL96 | uUfgaaGfuAfaAfuggUfguuAfaCfcsasg | 57.6 | 2.1 |
| AD-56363 | GfguuAfaCfaCfCfAfuUfuacUfuCfaaL96 | uUfgaaGfuAfaAfuggUfguuAfaCfcsasg | 57.9 | 7.6 |
| AD-56334 | GfguuAfacaCfCfAfuuuacUfucaaL96 | uUfgaaGfuAfaAfuggUfguuAfaCfcsasg | 59.4 | 6.0 |
| AD-56505 | Gf(Geo)Uf(Teo)AfaCfaCfCfAfuUfuAfcUf (Teo)Cf(Aeo)AfL96 | uUfgAfaGfuAfaAfuggUfgUfuAfaCfcsAfsg | 59.7 | 0.2 |
| AD-56405 | GfGfUfUfAfaCfaCfCfAfuUfuAfcUfuCfaAfL96 | uUfgAfaGfuAfaAfuggUfgUfuAfaCfcsAfsg | 60.6 | 3.1 |
| AD-56730 | GfgUfuAfaCfaCfCfAfuUfuAfcUfUfCfAfAfL96 | uUfgAfaGfuAfaAfuggUfgUfuAfaCfCfsAfsGf | 64.4 | 3.4 |
| AD-56746 | Gf(Geo)UfuAfaCfaCfCfAfuUfuAfcUf(Teo) Cf(Aeo)AfL96 | uUfgAfaGfuAfaAfuggUfgUfuaaccsAfsg | 64.7 | 17.2 |
| AD-56738 | Gf(Geo)Uf(Teo)AfaCfaCfCfAfuUfuAfcUf (Teo)Cf(Aeo)AfL96 | uUfgaaGfuAfaAfuggUfguuAfaCfcsasg | 65.0 | 3.6 |
| AD-56382 | GfgUfuAfaCfaCfCfAfuuuacUfuCfaAfL96 | uUfgAfaGfuAfaAfuggUfgUfuAfaCfcsAfsg | 65.7 | 2.7 |
| AD-56383 | GfgUfuAfaCfaCfCfAfuUfuAfcUfuCfaAfL96 | UfUfGfAfaGfuAfaAfuggUfgUfuAfaCfcsAfsg | 66.7 | 7.6 |

TABLE 12-continued

AD-54944 optimized sequences and protein levels. (The "Sense Sequence" column sequences are disclosed as SEQ ID NOS 839-868, respectively, in order of appearance, and the "Antisense Sequence" column sequences are disclosed as SEQ ID NOS 869-898, respectively, in order of appearance)

| Duplex Name | Sense Sequence | Antisense Sequence | % PBS | Std Dev |
|---|---|---|---|---|
| AD-54944 (new) | GfgUfuAfaCfaCfCfAfuUfuAfcUfuCfaAfL96 | uUfgAfaGfuAfaAfuggUfgUfuAfaCfcsAfsg | 66.8 | 4.8 |
| AD-56486 | GfgUfuAfaCfaCfCfAfuUfuAfcUfuCfaAfL96 | uUfgAfaGfuAfaAfuggUfgUfuAfaCfcs(Aeos)(Geo) | 67.7 | 0.5 |
| AD-56333 | GfguuAfacaCfCfAfuuuacuucaaL96 | uUfgaaGfuAfaAfuggUfgUfuAfaCfcsasg | 71.5 | 11.3 |
| AD-56351 | GfguuAfaCfaCfCfAfuUfuAfcUfuCfaAfL96 | uUfgaaGfuAfaAfuggUfguuAfaCfcsasg | 71.7 | 7.5 |
| AD-56454 | GfgUfuAfaCfaCfCfAfuUfuAfcUfuCfaAfL96 | uugaaGfuAfaAfuggUfgUfuAfaCfcsAfsg | 72.0 | 11.0 |
| AD-56380 | GfgUfUfAfaCfaCfCfAfuUfUfAfcUfUfCfAfAfL96 | uUfgAfAfGfUfAfaAfuggUfgUfUfAfaCfcsAfsg | 75.7 | 5.0 |
| AD-56397 | GfGfUfUfAfAfCfAfCfCfAfuUfUfAfCfUfUfCfAfAfL96 | uUfgAfAfGfuAfaAfuggUfgUfUfAfaCfcsAfsg | 76.9 | 0.8 |
| AD-56346 | GfguuaacaCfCfAfuuuacuucaaL96 | uUfgaaGfuAfaAfuggUfguuAfaCfcsasg | 82.3 | 13.2 |
| AD-56345 | GfgUfuAfaCfaCfCfAfuUfuAfcUfuCfaAfL96 | uUfgaaGfuAfaAfuggUfguuAfaCfcsasg | 83.6 | 19.2 |
| AD-56488 | GfgUfuAfaCfaCfCfAfuUfuAfcUfuCfaAfL96 | uUfgAfaGfuAfaAfuggUfgUfuAfasCfsc | 85.3 | 16.6 |
| AD-56740 | Gf(Geo)Uf(Teo)AfaCfaCfCfAfuUfuAfcUf(Teo)Cf(Aeo)AfL96 | uUfgaaGfuAfaAfuggUfgUfuAfaCfcsasg | 85.5 | 14.8 |
| | | | 96.0 | 8.5 |
| AD-56748 | GfgUfuAfaCfaCfCfAfuuuacUfuCfaAfL96 | uUfgaaGfuAfaAfuggUfguuAfaCfcsasg | 99.4 | 19.1 |
| PBS | | | 100.0 | 4.7 |

The in vivo dose response of AD-54944 conjugated to GalNAc was determined by administering a single subcutaneous dose to C57BL/6J mice (n=5). AD-54944 conjugated to GalNAc was also administered subcutaneously as a repeat daily dose of 5 mg/kg to C57BL/6J mice (n=5) over a 5 day period. Animals were sacrificed 72 hours after administration and Serpinc1 protein and activity levels were determined in liver and serum samples as described above.

Figure 6:
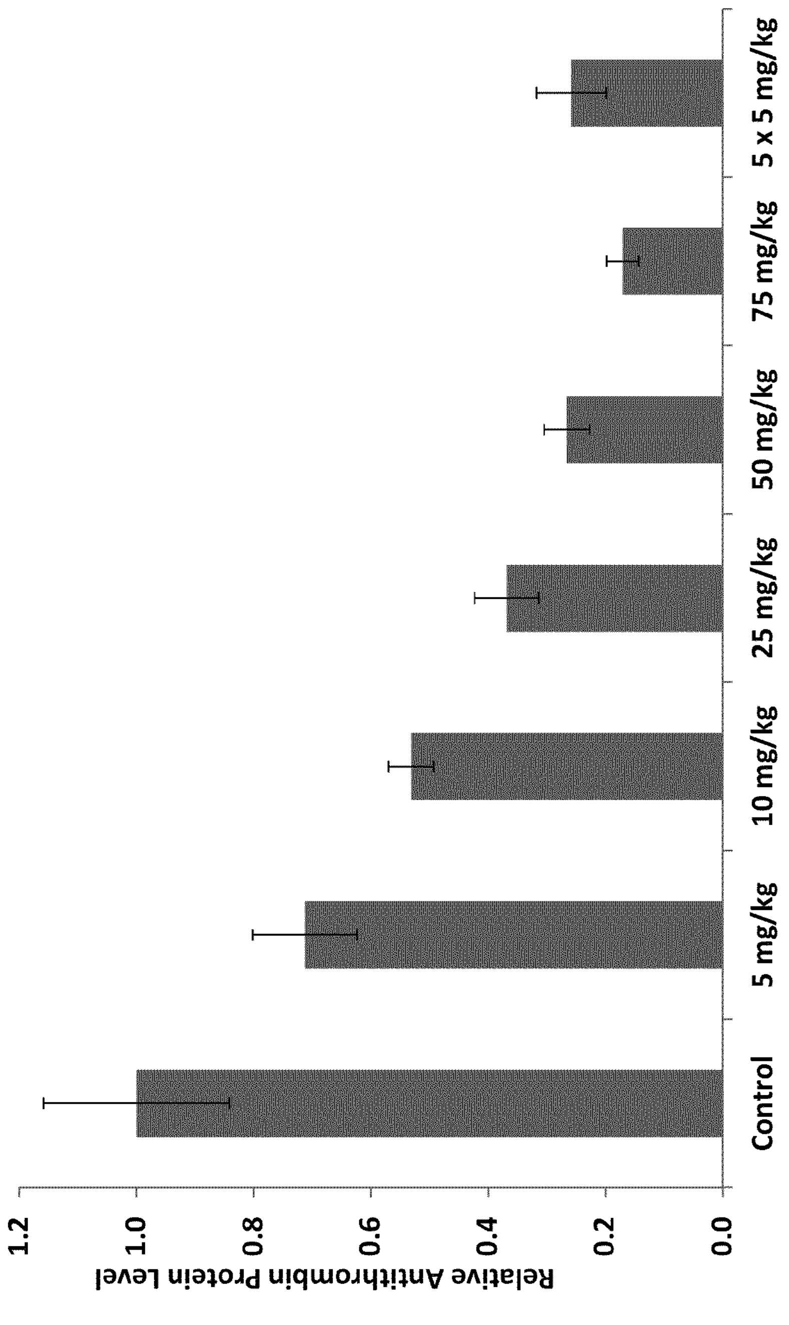
FIG. 6 is a graph showing the inhibition of Serpinc1 protein expression in C57BL/6 mice following a single 5 mg/kg, 10 mg/kg, 25 mg/kg, 50 mg/kg, and 75 mg/kg, and a repeat dose of 5×5 mg/kg of AD-54944 conjugated to GalNAc.

As shown in FIG. 6, a single subcutaneous dose of AD-54944 conjugated to GalNAc resulted in a protein $EC_{50}$ of about 10 mg/kg and a 5×5 mg/kg daily, repeat dose resulted in about a 75% protein silencing.

Figure 7A:
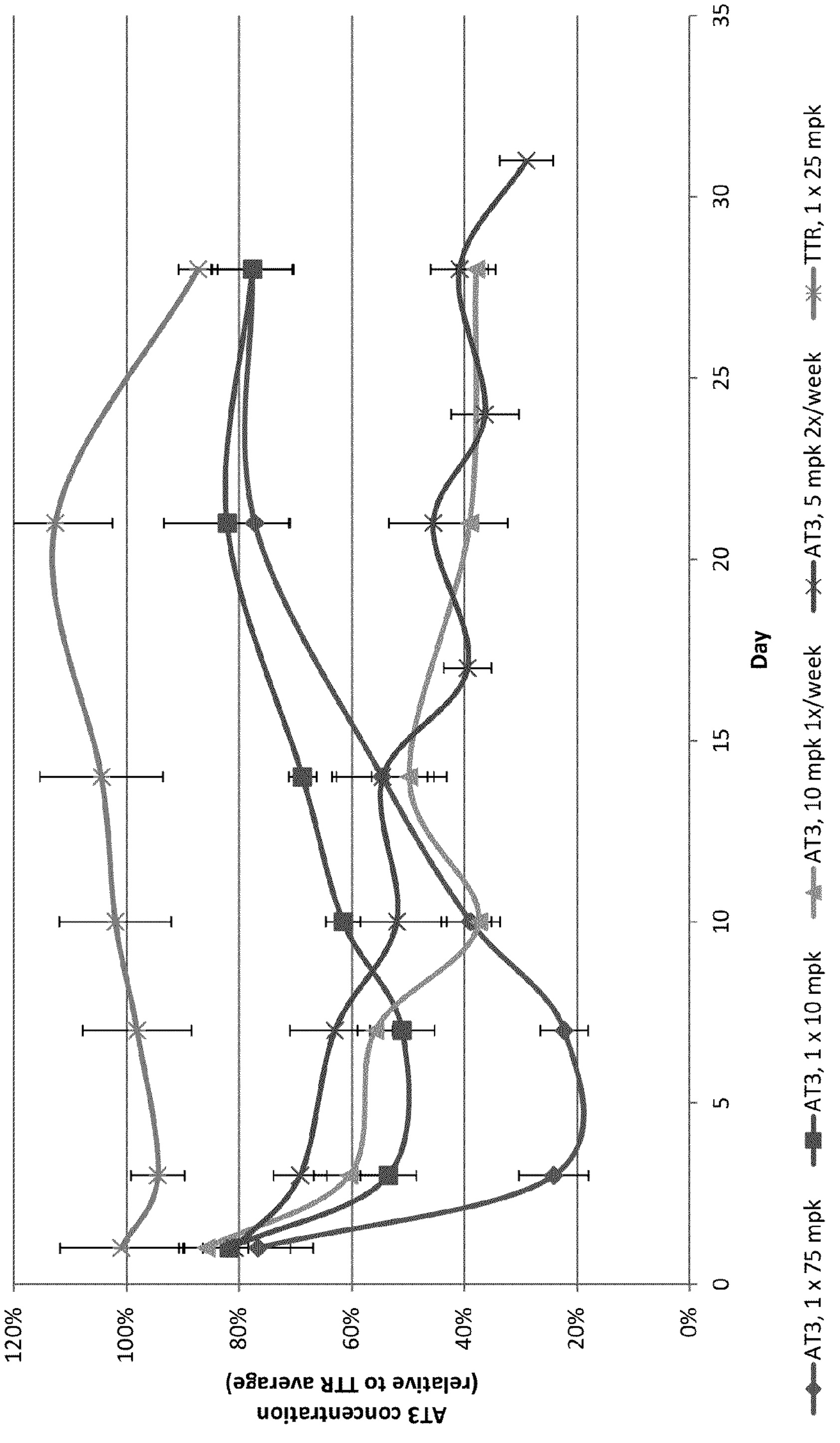
FIGS. 7A and 7B are graphs showing the effect of repeat-dosing on the duration of inhibition of Serpinc1 protein expression in C57BL/6 mice of GalNAc conjugated AD-54944.
Figure 7B:
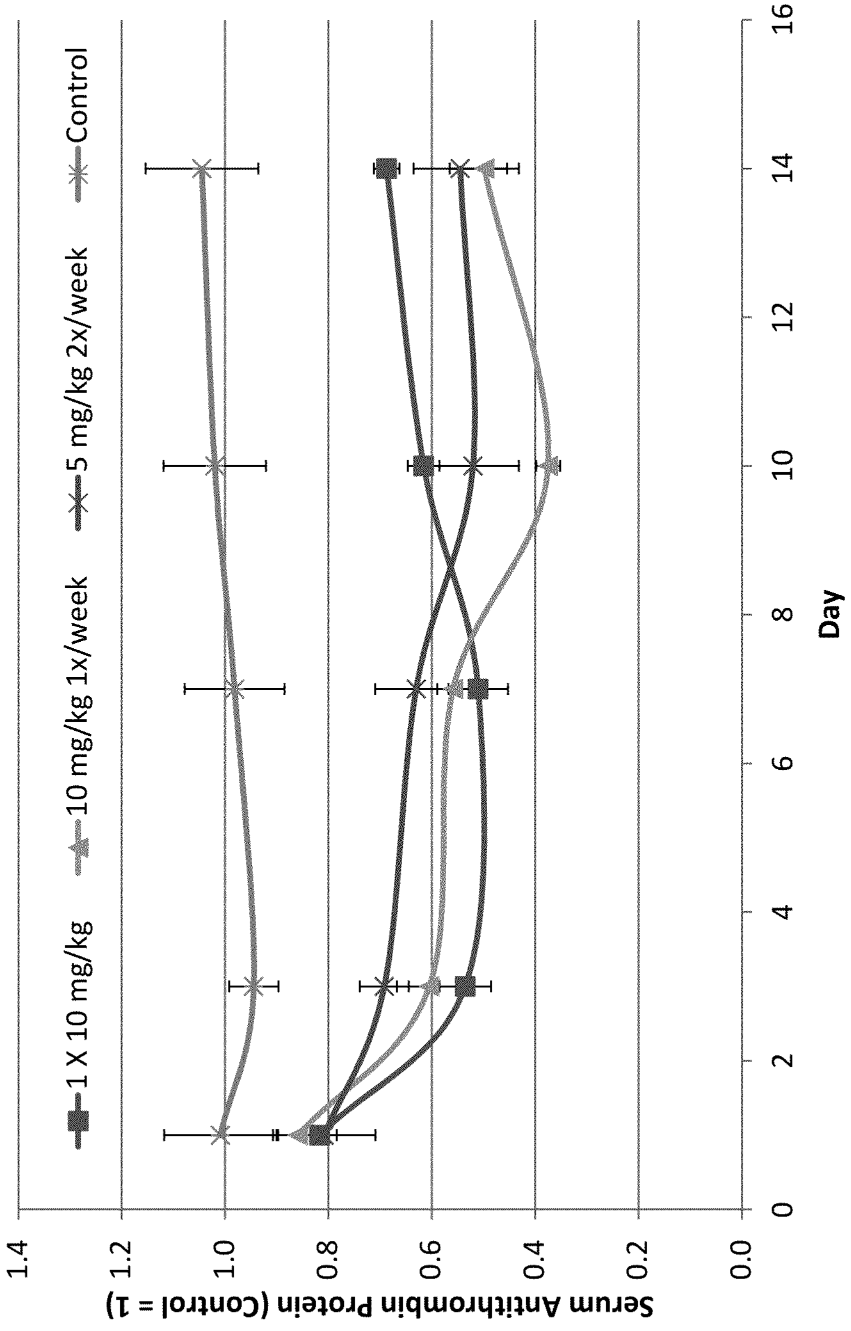

Additional repeat-dosing of AD-54944 conjugated to GalNAc in C57BL/6J mice was also performed over an 8 week period to determine the efficacy and duration of silencing. FIGS. 7A and 7B show the results of these studies.

Example 6

Dose Duration of a Split-Dose of AD-54944

In order to further evaluate compound AD-54944 knockdown of Serpinc1 expression and activity, a split-dosing experiment was performed. C57BL/6 mice were subcutaneously administered GalNAc-conjugated AD-54944 and the effect of a 3 times per week, ⅓ dose of AD-54944 was compared to the effect of a 1 time per week fully concentrated dose of AD-54944. A summary of the study design is presented in Table 13. Serum Serpinc1 protein levels were determined at Days 0, 3, 7, 10, 14, 17, 21, 24, 29, 31, and 35.

TABLE 13

Study Design of Split-Dosing Experiment

| Group | Test compound | Dose (mg/kg) | Frequency |
|---|---|---|---|
| 1 | AD-54944 | 1.25 | 3x/week (M, W, F) |
| 2 | | 2.5 | |
| 3 | | 5 | |
| 4 | | 10 | |
| 5 | | 3.75 | 1x/week (Monday) |
| 6 | | 7.5 | |
| 7 | | 15 | |
| 8 | | 30 | |
| 9 | PBS | — | |

Figure 8:
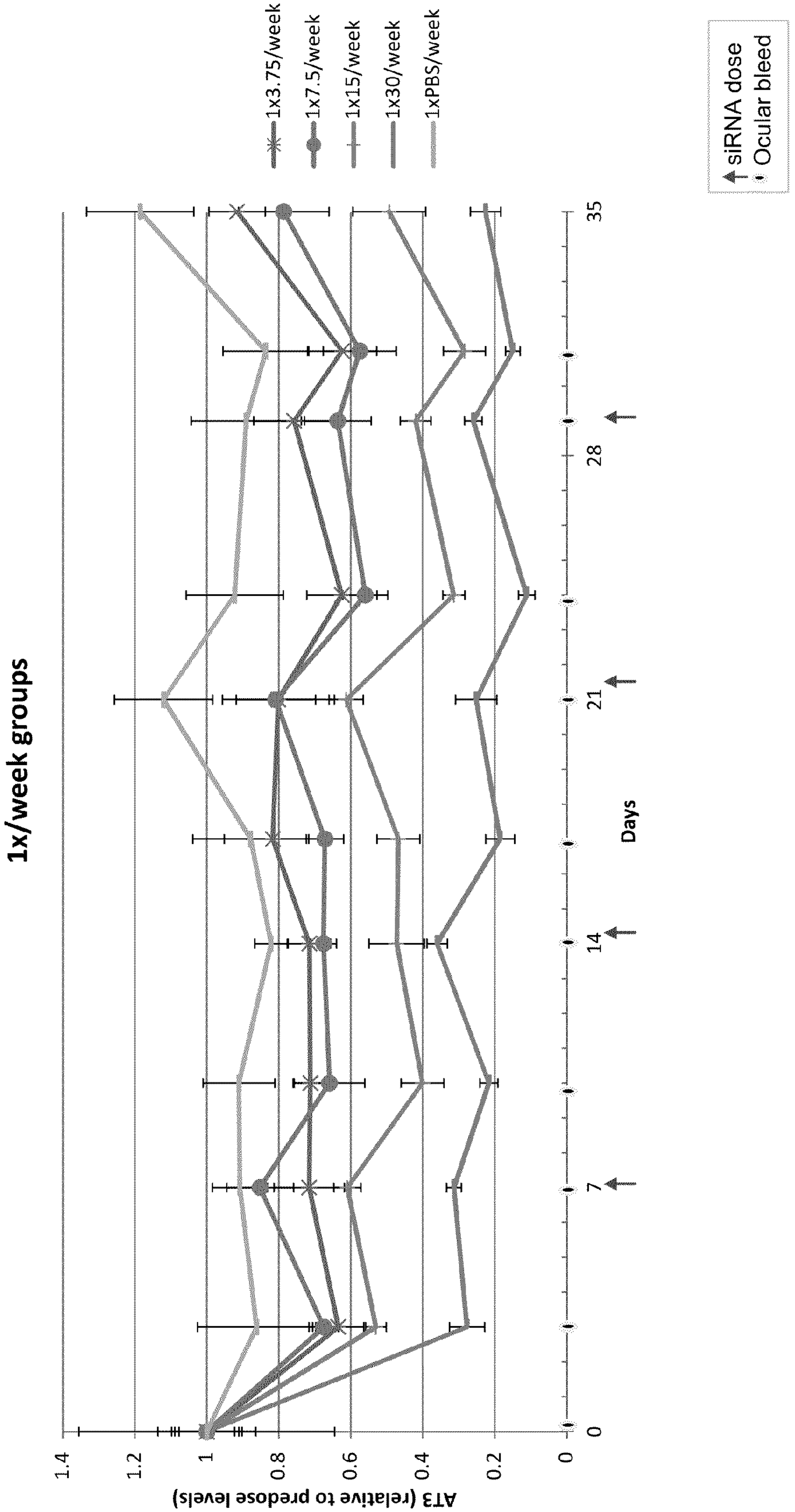
FIGS. 8 and 9 are graphs showing the effects of the indicated split-dosing regimens on the duration of silencing of Serpinc1 protein expression in C57BL/6 mice administered GalNAc conjugated AD-54944.
Figure 9:
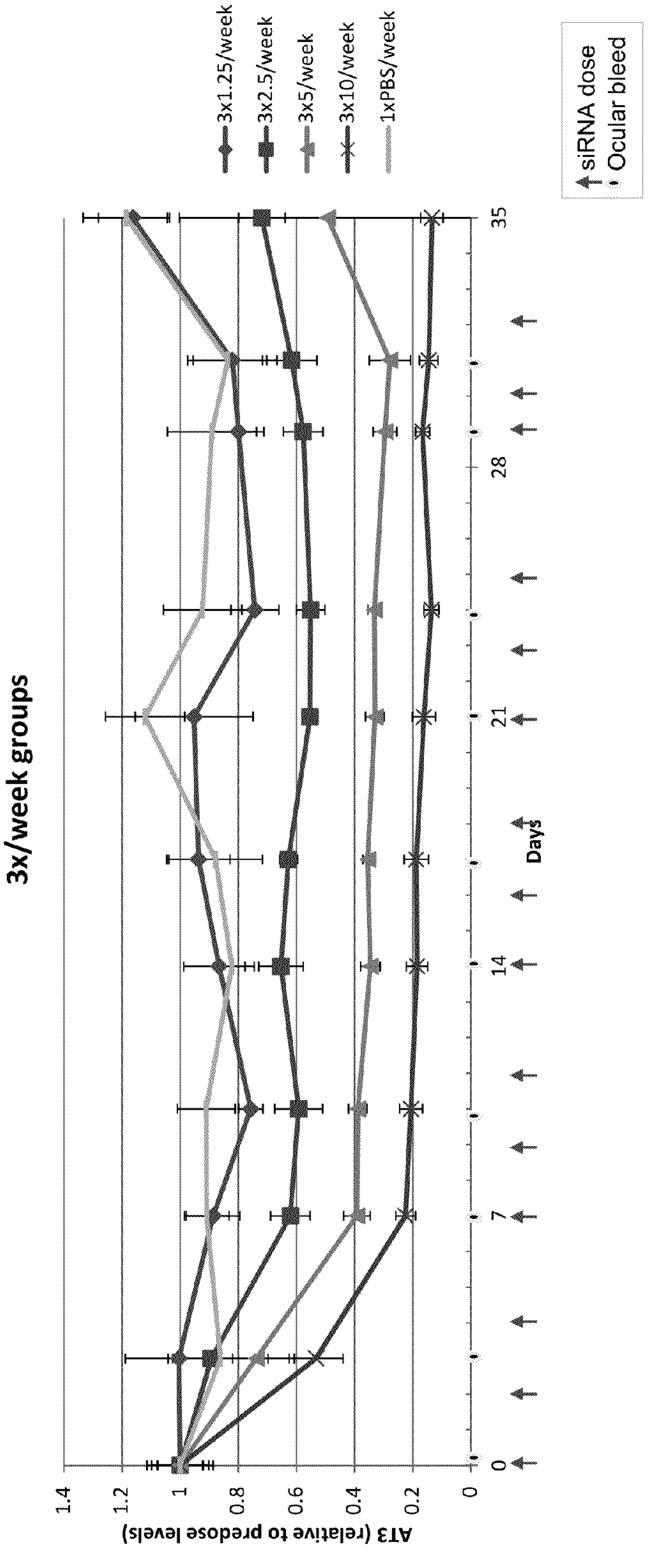

The results of the one-time per week split-dose screen as a percent knock-down of Serpinc1 protein levels from pre-dose levels are shown in FIG. 8 and the results of the three-time per week screen as a percent knock-down of Serpinc1 protein levels from pre-dose levels are shown in FIG. 9. The results demonstrate that there is a dose response effect with AD-54944 conjugated to GalNAc in both groups and that dosages at both 30 mg/kg one time per week and at 10 mg/kg three times per week lead to long-term silencing of Serpinc1.

Example 7

Further Optimization of AD-54944

In order to further improve the efficacy of AD-54944, additional compounds were prepared based on the AD-54944 parent sequence. In general, the modifications included the addition of phosphorothiate linkages, C16(hexadecyl) modifications, 5'-end-caps, and 2'-methyls. The new compounds were screened for in vivo efficacy using both a single 3 mg/mg dose and a single 10 mg/kg dose. Animals (C57BL/6) were injected subcutaneously at Day 0 and sacrificed at Day 3. Serum Serpinc1 protein levels were determined by ELISA assay. The ELISA assay was performed using an Antithrombin III Mouse ELISA kit purchased from Abcam. Briefly, serum was diluted (e.g., about 1:10,000) and used accordingly to manufacturers instructions. The plates were read at 450 nm at the end of the assay.

Figure 10:
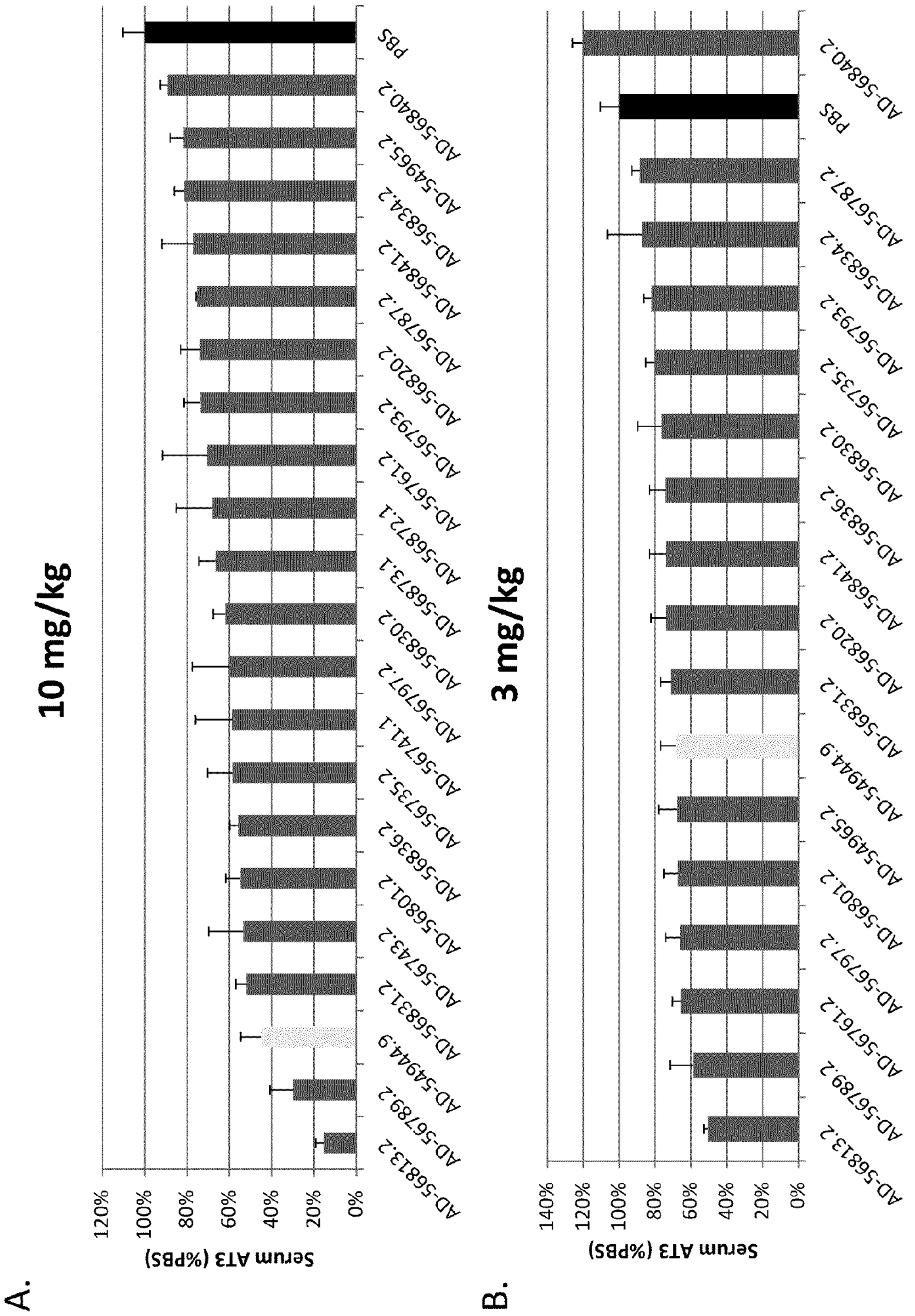
FIGS. 10A and 10B are graphs showing the percent knock-down of Serpinc1 protein levels following a single 10 mg/kg (A) or 3 mg/kg (B) dose of the indicated iRNA conjugated to GalNAc.

Table 14 shows the sequences of the duplexes and the results of the single dose screens with these duplexes as a percent knock-down of Serpinc1 protein levels from PBS. FIGS. 10A and 10B show the results of the single dose screen as a percent knock-down of Serpinc1 protein levels from PBS. As can be seen in Table 14 and FIG. 10, compound AD-56813 emerged as a new lead based on the level of knock-down of Serpinc1 protein levels.

Further compounds were prepared based on the AD-56813 parent sequence in which the number of 2'-methoxyethyl and phosphorothioate linkages were reduced in order to determine the minimum chemical modifications required for stability of the compounds which maintained activity of the compounds. The new compounds were screened for in vivo efficacy using both a single 3 mg/mg dose and a single 10 mg/kg dose. Animals (C57BL/6) were injected subcutaneously at Day 0 and sacrificed at Day 3. Serpinc1 (AT3) activity and serum Serpinc1 protein levels were determined by ELISA assay. The ELISA assay was performed as described above. Serpinc1 activity was determined using a BIOPHEN (anti-Factor Xa) activity assay kit. Briefly, serum samples were diluted from about 1:20 to about 1:60 and processed according to the manufacturers' instructions. The plates were read at 450 nm at the end of the assay.

Figure 11:
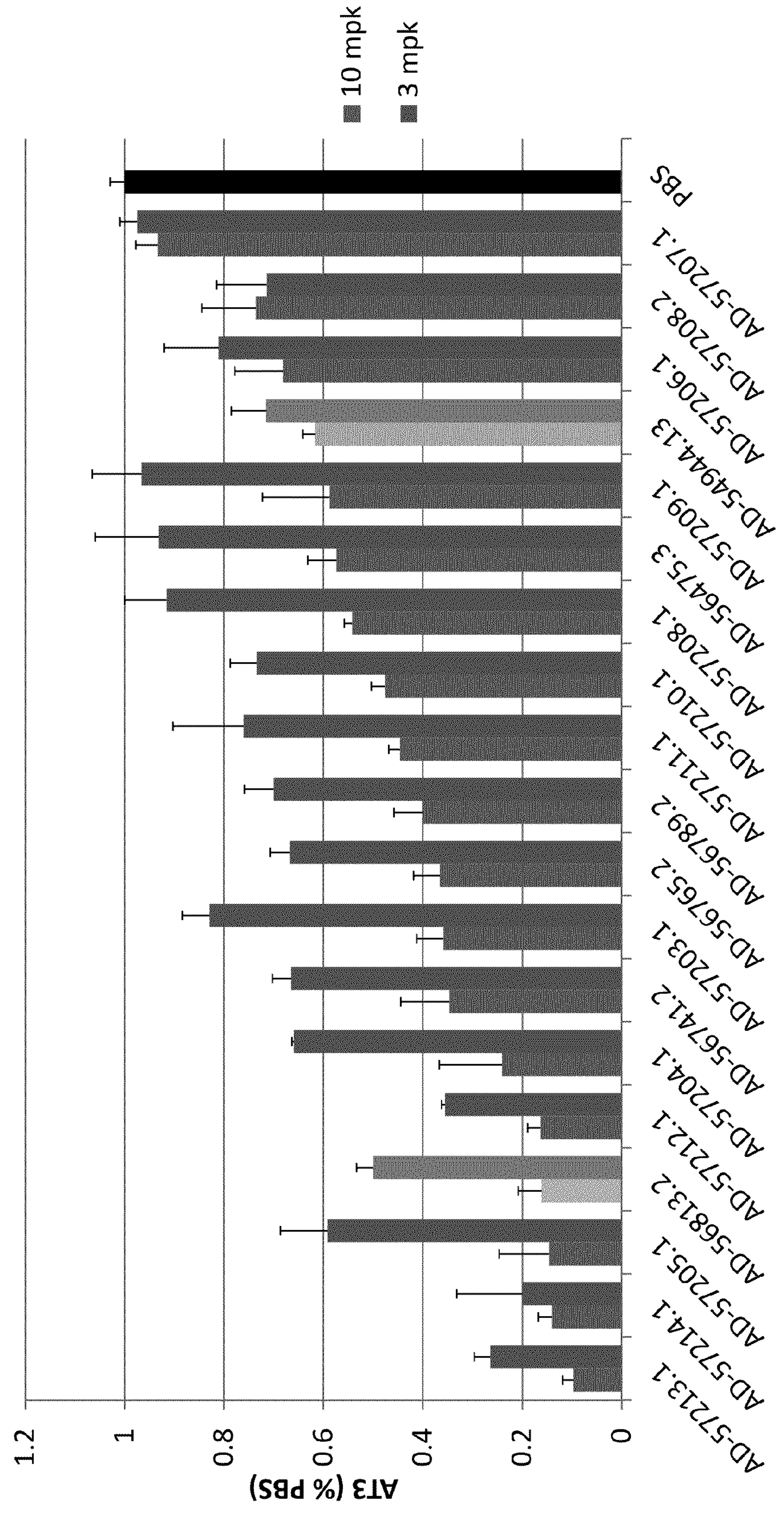
FIG. 11 is a graph showing the percent knock-down of Serpinc1 protein levels following a single 10 mg/kg or 3 mg/kg dose of the indicated iRNA conjugated to GalNAc.

The sequences of the duplexes that were newly prepared and the results of the single dose screens with these duplexes as a percent knock-down of Serpinc1 protein levels from PBS are shown in Table 15. FIG. 11 shows the results of the single dose screen as a percent knock-down of Serpinc1 protein levels from PBS and FIG. 12 shows the results of the single dose screen as a percent knock-down of Serpinc1 activity from PBS.

Figure 12:
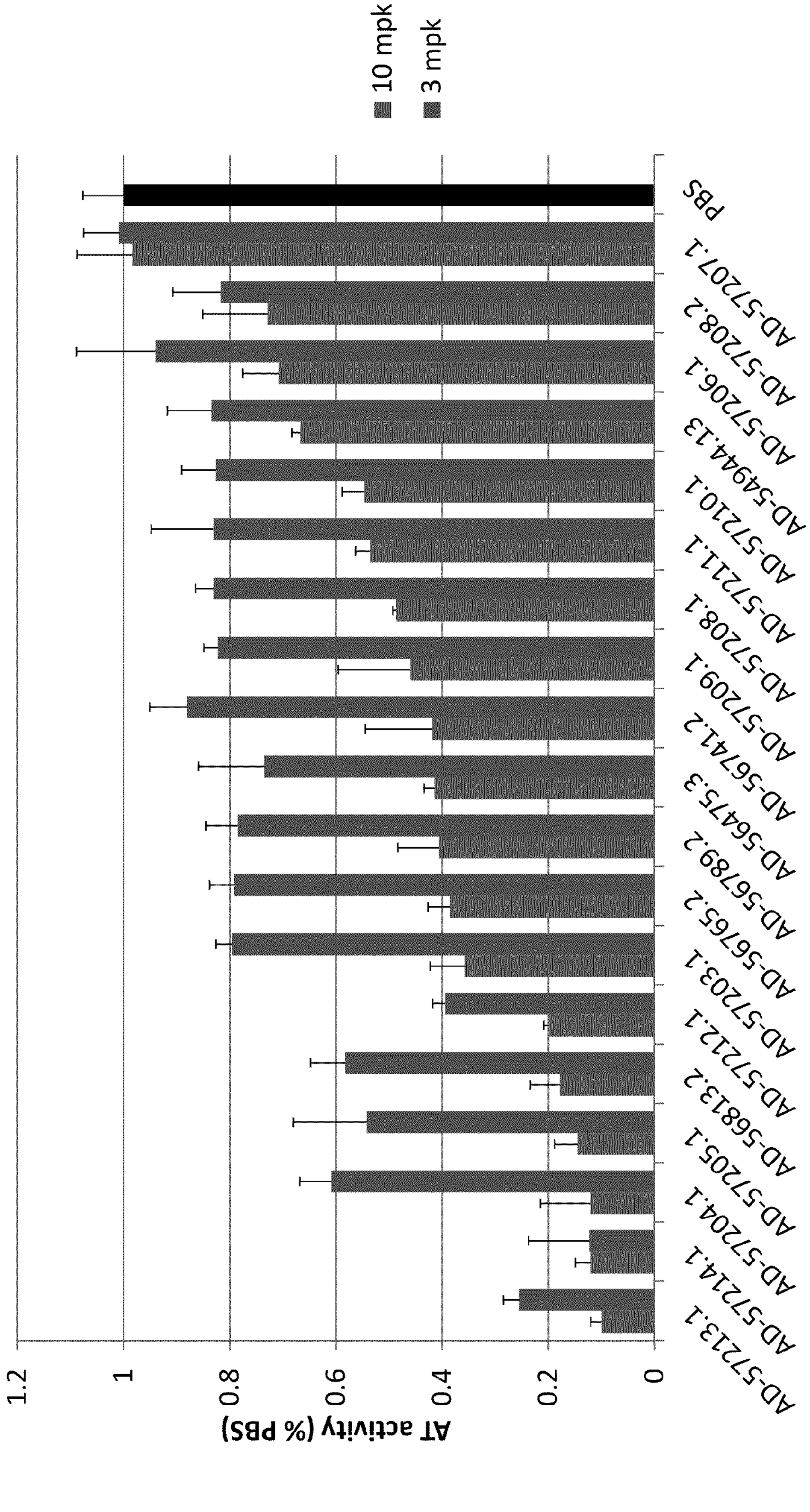
FIG. 12 is a graph showing the percent knock-down of Serpinc1 activity following a single 10 mg/kg or 3 mg/kg dose of the indicated iRNA conjugated to GalNAc.

As can be seen in Table 15 and FIGS. 11 and 12, although the number of modifications to the compound was dramatically reduced, compound AD-57213 maintained knockdown of Serpinc1 expression and activity and, thus, emerged as a new lead. A single 10 mg/kg dose of AD-57213 led to an $ED_{90}$ and a single 3 mg/kg dose led to an $ED_{50}$.

TABLE 14

AD-54944 optimized sequences and protein levels. (The "Sense Sequence" column sequences are disclosed as SEQ ID NOS 899-919, respectively, in order of appearance, and the "Antisense Sequence" column sequences are disclosed as SEQ ID NOS 920-940, respectively, in order of appearance)

| | | | | | 3 mpk | | 10 mpk | |
|---|---|---|---|---|---|---|---|---|
| Duplex ID | Sense strand | Sense sequence | Antisense | Antisense sequence | % PBS | stdev | % PBS | stdev |
| AD-56813.2 | A-116280.6 | Gfs(Geo)UfsuAfaCfsaCfsCfsAfuUfsuAfcUfsuCfs(Aeo)AfL96 | A-116278.6 | usUfsgAfaGfuAfaAfuggUfsgUfsuAfaCfscs(Aeos)(Geo) | 0.62 | 0.04 | 0.26 | 0.04 |
| AD-56789.2 | A-116276.12 | GfgUfsuAfaCfsaCfsCfsAfuUfsuAfcUfsuCfsaAfL96 | A-116275.7 | uUfsgAfaGfuAfaAfuggUfsgUfsuAfaCfscsAfsg | 0.74 | 0.11 | 0.44 | 0.11 |
| AD-56741 | A-115968.11 | Gf(Geo)Uf(Teo)AfaCfaCfCfAfuUf(Teo)Af(m5Ceo)Uf(Teo)Cf(Aeo)AfL96 | A-115861.11 | uUfgaaGfuAfaAfuggUfgUfuAfaCfcsasg | | | 0.52 | 0.09 |
| AD-54944/parent | A-113073.1 | GfgUfuAfaCfaCfCfAfuUfuAfcUfuCfaAfL96 | A-113074.1 | uUfgAfaGfuAfaAfuggUfgUfuAfaCfcsAfsg | 0.93 | 0.10 | 0.63 | 0.10 |
| AD-56743 | A-115965.5 | Gf(Geo)UfuAfaCfaCfCfAfuUfuAfcUf(Teo)Cf(Aeo)AfL96 | A-115861.11 | uUfgaaGfuAfaAfuggUfgUfuAfaCfcsasg | | | 0.71 | 0.24 |
| AD-56836.2 | A-115966.25 | Gf(Geo)Uf(Teo)AfaCfaCfCfAfuUfuAfcUf(Teo)Cf(Aeo)AfL96 | A-116284.3 | uUfgAfaGf(Uhd)AfaAfuggUfgUfuAfaCfcsasg | 1.01 | 0.11 | 0.73 | 0.11 |
| AD-56797.2 | A-115968.8 | Gf(Geo)Uf(Teo)AfaCfaCfCfAfuUf(Teo)Af(m5Ceo)Uf(Teo)Cf(Aeo)AfL96 | A-116250.6 | uUfgAfaGfuAfaAfuggUf(Geo)UfuAfaCfcs(Aeos)(Geo) | 0.87 | 0.25 | 0.74 | 0.25 |
| AD-56801.2 | A-116277.6 | Gf(Geo)UfsuAfaCfsaCfsCfsAfuUfsuAfcUfsuCfs(Aeo)AfL96 | A-116279.9 | uUfsgAfaGfuAfaAfuggUfsgUfsuAfaCfscs(Aeos)(Geo) | 0.83 | 0.08 | 0.77 | 0.08 |
| AD-56831.2 | A-116290.3 | Gf(Geo)Uf(Teo)AfaCfaCfCfAfuUf(Uhd)AfcUf(Teo)Cf(Aeo)AfL96 | A-115962.21 | uUfgAfaGfuAfaAfuggUfgUfuAfaCfcs(Aeos)(Geo) | 1.11 | 0.09 | 0.78 | 0.09 |
| AD-56830.2 | A-116283.3 | Gfs(Geo)UfsuAfaCfsaCfCfAfuUfsuAfcUfsuCfs(Aeo)AfL96 | A-116279.12 | uUfsgAfaGfuAfaAfuggUfsgUfsGuAfaCfscs(Aeos)(eo) | 1.01 | 0.13 | 0.79 | 0.13 |
| AD-56761.2 | A-116247.13 | gguuaacaCfCfAfuuuacu(Uhd)caaL96 | A-116244.6 | uUfgaaGfuAfaAfuggUfguuaaccsasg | 0.82 | 0.26 | 0.83 | 0.26 |
| AD- | A- | Gf(Geo)Uf(Teo)AfaCfaCfCfA | A- | uUfgAfaGfuAfaAfuggUfgUfuAf | 1.20 | 0.15 | 0.90 | 0.15 |

TABLE 14-continued

AD-54944 optimized sequences and protein levels. (The "Sense Sequence" column sequences are disclosed as SEQ ID NOS 899-919, respectively, in order of appearance, and the "Antisense Sequence" column sequences are disclosed as SEQ ID NOS 920-940, respectively, in order of appearance)

| | | | | | 3 mpk | | 10 mpk | |
|---|---|---|---|---|---|---|---|---|
| Duplex ID | Sense strand | Sense sequence | Antisense | Antisense sequence | % PBS | stdev | % PBS | stdev |
| 56735.2 | 115966.29 | fuUfuAfcUf(Teo)Cf(Aeo)AfL96 | 115962.18 | aCfcs(Aeos)(Geo) | | | | |
| AD-56872 | A-115965.5 | Gf(Geo)UfuAfaCfaCfCfAfuUfuAfcUf(Teo)Cf(Aeo)AfL96 | A-116392.1 | uUfgaaGfuAfaAfuggUfguuAfaCfcs(Aeos)(Geo) | | | 0.93 | 0.24 |
| AD-56820.2 | A-116317.4 | gUf(Uhd)AfaCfaCfCfAfuUfuAfcUfuCfaAfL96 | A-116297.10 | uUfgAfaGfuAfaAfuggUfgUfuAfaCfs(m5Ceos)(Aeo) | 1.05 | 0.10 | 0.94 | 0.10 |
| AD-56793.2 | A-116382.1 | gdGuudAdAcadCdCauudTdAcu(Uhd)dCadAL96 | A-1 116373.1 | udTdGadAgdTadAdAuggdTdGuudAdAcdCsasg | 0.98 | 0.08 | 0.99 | 0.08 |
| PBS/Control | | | | | 1.00 | 0.04 | 1.00 | 0.04 |
| AD-56873 | A-115968.11 | Gf(Geo)Uf(Teo)AfaCfaCfCfAfuUf(Teo)Af(m5Ceo)Uf(Teo)Cf(Aeo)AfL96 | A-116392.1 | uUfgaaGfuAfaAfuggUfguuAfaCfcs(Aeos)(Geo) | | | 1.01 | 0.18 |
| AD-54965 | A-113033.1 | AfaCfuGfcCfgAfCfUfcUfaUfcGfaAfaAfL96 | A-113034.1 | uUfuUfcGfaUfaGfaguCfgGfcAfgUfusCfsa | 0.89 | 0.07 | 1.03 | 0.07 |
| AD-56787.2 | A-116381.1 | gguuaacaccdAudTudAcdT(Uhd)dCasaL96 | A-116373.10 | udTdGadAgdTadAdAuggdTdGuudAdAcdCsasg | 1.03 | 0.18 | 1.04 | 0.18 |
| AD-56840.2 | A-116317.5 | gUf(Uhd)AfaCfaCfCfAfuUfuAfcUfuCfaAfL96 | A-116344.5 | uUfgAfaGfuAfaAfuggUfgUfuAfaCfs(Chds)(Aeo) | 1.38 | 0.14 | 1.05 | 0.14 |
| AD-56834.2 | A-116333.3 | GbguuAfaCfaCfCfAfuUfuAfcUfuCfaAfL96 | A-116334.3 | uUfgaaGfuAfaAfuggUfguuAfaCfcsasGb | 1.17 | 0.14 | 1.06 | 0.14 |
| AD-56841.2 | A-115966.26 | Gf(Geo)Uf(Teo)AfaCfaCfCfAfuUfuAfcUf(Teo)Cf(Aeo)AfL96 | A-116285.3 | uUfgAfaGf(Uhd)AfaAfuggUfgUfuAfaCfcs(Aeos)(Geo) | 1.15 | 0.21 | 1.09 | 0.21 |

TABLE 15

AD-56813 optimized sequences and protein and activity levels. (The "Sense Sequence" column sequences are disclosed as SEQ ID NOS 941-959, respectively, in order of appearance, and the "Antisense Sequence" column sequences are disclosed as SEQ ID NOS 960-978, respectively, in order of appearance)

| | | | | | ELISA | | | | Activity | | | |
|---|---|---|---|---|---|---|---|---|---|---|---|---|
| Duplex | Sense | | | Antisense | 10 mpk | | 3 mpk | | 10 mpk | | 3 mpk | |
| name | ID | Sense (5' to 3') | AS ID | (5' to 3') | Av | SD | Av | SD | Av | SD | Av | SD |
| AD-57213.1 | A-116858.1 | GfsgsUfuAfaCfaCfCfAfuUfuAfcUfuCfaAfL96 | A-116861.1 | usUfsgAfaGfuAfaAfuggUfgUfuAfaCfcsasg | 0.098 | 0.021 | 0.264 | 0.032 | 0.099 | 0.021 | 0.255 | 0.030 |
| AD-57214.1 | A-116859.1 | GfsgsUfuAfaCfaCfCfAfuUf(Uhd)AfcUfuCfaAfL96 | A-116861.1 | usUfsgAfaGfuAfaAfuggUfgUfuAfaCfcsasg | 0.140 | 0.027 | 0.200 | 0.132 | 0.121 | 0.028 | 0.123 | 0.114 |
| AD-57205.1 | A-113073.1 | GfgUfuAfaCfaCfCfAfuUfuAfcUfuCfaAfL96 | A-116861.1 | usUfsgAfaGfuAfaAfuggUfgUfuAfaCfcsasg | 0.147 | 0.100 | 0.592 | 0.094 | 0.145 | 0.043 | 0.542 | 0.139 |
| AD-56813.2 | A-116280.6 | Gfs(Geo)UfsuAfaCfsaCfsCfsAfuUfsuAfcUfsuCfs(Aeo)AfL96 | A-116278.6 | usUfsgAfaGfuAfaAfuggUfsgUfsuAfaCfscs(Aeos)(Geo) | 0.161 | 0.047 | 0.500 | 0.033 | 0.179 | 0.055 | 0.583 | 0.065 |

TABLE 15-continued

AD-56813 optimized sequences and protein and activity levels. (The "Sense Sequence" column sequences are disclosed as SEQ ID NOS 941-959, respectively, in order of appearance, and the "Antisense Sequence" column sequences are disclosed as SEQ ID NOS 960-978, respectively, in order of appearance)

| | | | | | ELISA | | | | Activity | | | |
|---|---|---|---|---|---|---|---|---|---|---|---|---|
| Duplex | Sense | | | Antisense | 10 mpk | | 3 mpk | | 10 mpk | | 3 mpk | |
| name | ID | Sense (5' to 3') | AS ID | (5' to 3') | Av | SD | Av | SD | Av | SD | Av | SD |
| AD-57212.1 | A-116276.12 | GfgUfsuAfaCfsaCfsCfsAfuUfsuAfcUfsuCfsaAfL96 | A-116860.1 | usUfsgAfaGfuAfaAfuggUfsgUfsuAfaCfscsasg | 0.164 | 0.026 | 0.355 | 0.007 | 0.198 | 0.011 | 0.395 | 0.023 |
| AD-57204.1 | A-113073.1 | GfgUfuAfaCfaCfCfAfuUfuAfcUfuCfaAfL96 | A-116860.1 | usUfsgAfaGfuAfaAfuggUfsgUfsuAfaCfscsasg | 0.170 | 0.127 | 0.659 | 0.004 | 0.121 | 0.094 | 0.608 | 0.060 |
| AD-56741.2 | A-115968 | Gf(Geo)Uf(Teo)AfaCfaCfCfAfuUf(Teo)Af(m5Ceo)Uf(Teo)Cf(Aeo)AfL96 | A-115861 | uUfgaaGfuAfaAfuggUfgUfuAfaCfcsasg | 0.347 | 0.098 | 0.666 | 0.036 | 0.419 | 0.126 | 0.880 | 0.070 |
| AD-57203.1 | A-113073.1 | GfgUfuAfaCfaCfCfAfuUfuAfcUfuCfaAfL96 | A-116278.6 | usUfsgAfaGfuAfaAfuggUfsgUfsuAfaCfscs(Aeos)(Geo) | 0.359 | 0.053 | 0.829 | 0.056 | 0.358 | 0.064 | 0.796 | 0.030 |
| AD-56765.2 | A-113073.1 | GfgUfuAfaCfaCfCffAuUfuAfcUfuCfaAfL96 | A-116275.7 | uUfsgAfaGfuAfaAfuggUfsgUfsuAfaCfscsAfsg | 0.366 | 0.053 | 0.668 | 0.040 | 0.385 | 0.041 | 0.791 | 0.047 |
| AD-56789.2 | A-116276.12 | GfgUfsuAfaCfsaCfsCfsAfuUfsuAfcUfsuCfsaAfL96 | A-116275.7 | uUfsgAfaGfuAfaAfuggUfsgUfsuAfaCfscsAfsg | 0.401 | 0.057 | 0.700 | 0.059 | 0.406 | 0.078 | 0.785 | 0.059 |
| AD-57211.1 | A-116858.1 | GfsgsUfuAfaCfaCfCfAfuUfuAfcUfuCfaAfL96 | A-113074.1 | uUfgAfaGfuAfaAfuggUfgUfuAfaCfcsAfsg | 0.446 | 0.023 | 0.760 | 0.142 | 0.536 | 0.027 | 0.831 | 0.117 |
| AD-57210.1 | A-116857.1 | GfsgsUfuAfaCfaCfsCfsAfuUfuAfcUfuCfaAfL96 | A-113074.1 | uUfgAfaGfuAfaAfuggUfgUfuAfaCfcsAfsg | 0.476 | 0.028 | 0.734 | 0.053 | 0.547 | 0.041 | 0.826 | 0.065 |
| AD-57208.1 | A-116276.12 | GfgUfsuAfaCfsaCfsCfsAfuUfsuAfcUfsuCfsaAfL96 | A-113074.1 | uUfgAfaGfuAfaAfuggUfgUfuAfaCfcsAfsg | 0.542 | 0.016 | 0.915 | 0.085 | 0.486 | 0.006 | 0.831 | 0.034 |
| AD-56475.3 | A-115968 | Gf(Geo)Uf(Teo)AfaCfaCfCfAfuUf(Teo)Af(m5Ceo)Uf(Teo)Cf(Aeo)AfL96 | A-113074.1 | uUfgAfaGfuAfaAfuggUfgUfuAfaCfcsAfsg | 0.574 | 0.058 | 0.932 | 0.127 | 0.415 | 0.019 | 0.735 | 0.123 |
| AD-57209.1 | A-116280.6 | Gfs(Geo)UfsuAfaCfsaCfsCfsAfuUfsuAfcUfsuCfs(Aeo)AfL96 | A-113074.1 | uUfgAfaGfuAfaAfuggUfgUfuAfaCfcsAfsg | 0.588 | 0.135 | 0.966 | 0.100 | 0.460 | 0.136 | 0.823 | 0.026 |
| AD-54944.13 | A-113073.1 | GfgUfuAfaCfaCfCfAfuUfuAfcUfuCfaAfL96 | A-113074.1 | uUfgAfaGfuAfaAfuggUfgUfuAfaCfcsAfsg | 0.617 | 0.025 | 0.715 | 0.071 | 0.667 | 0.016 | 0.835 | 0.083 |
| AD-57206.1 | A-113073.1 | GfgUfuAfaCfaCfCfAfuUfuAfcUfuCfaAfL96 | A-116870.1 | uUfgAfaGfuAfaAfuggUfgUfuAfaCfcAfsg | 0.681 | 0.097 | 0.811 | 0.110 | 0.707 | 0.068 | 0.940 | 0.149 |
| AD-57208.2 | A-116276.12 | GfgUfsuAfaCfsaCfsCfsAfuUfsuAfcUfsuCfsaAfL96 | A-113074.1 | uUfgAfaGfuAfaAfuggUfgUfuAfaCfcsAfsg | 0.736 | 0.109 | 0.714 | 0.101 | 0.729 | 0.122 | 0.817 | 0.090 |
| AD-57207.1 | A-113073.1 | GfgUfuAfaCfaCfCfAfuUfuAfcUfuCfaAfL96 | A-116871.1 | uUfgAfaGfuAfaAfuggUfgUfuAfaCfcAfg | 0.934 | 0.043 | 0.975 | 0.035 | 0.984 | 0.104 | 1.009 | 0.066 |
| | | | | | 1.000 | 0.029 | 1.000 | | 1.000 | 0.077 | 1.000 | |

Example 8

Serpinc1 Knock-Down in Hemophilic Mice

Figure 13:
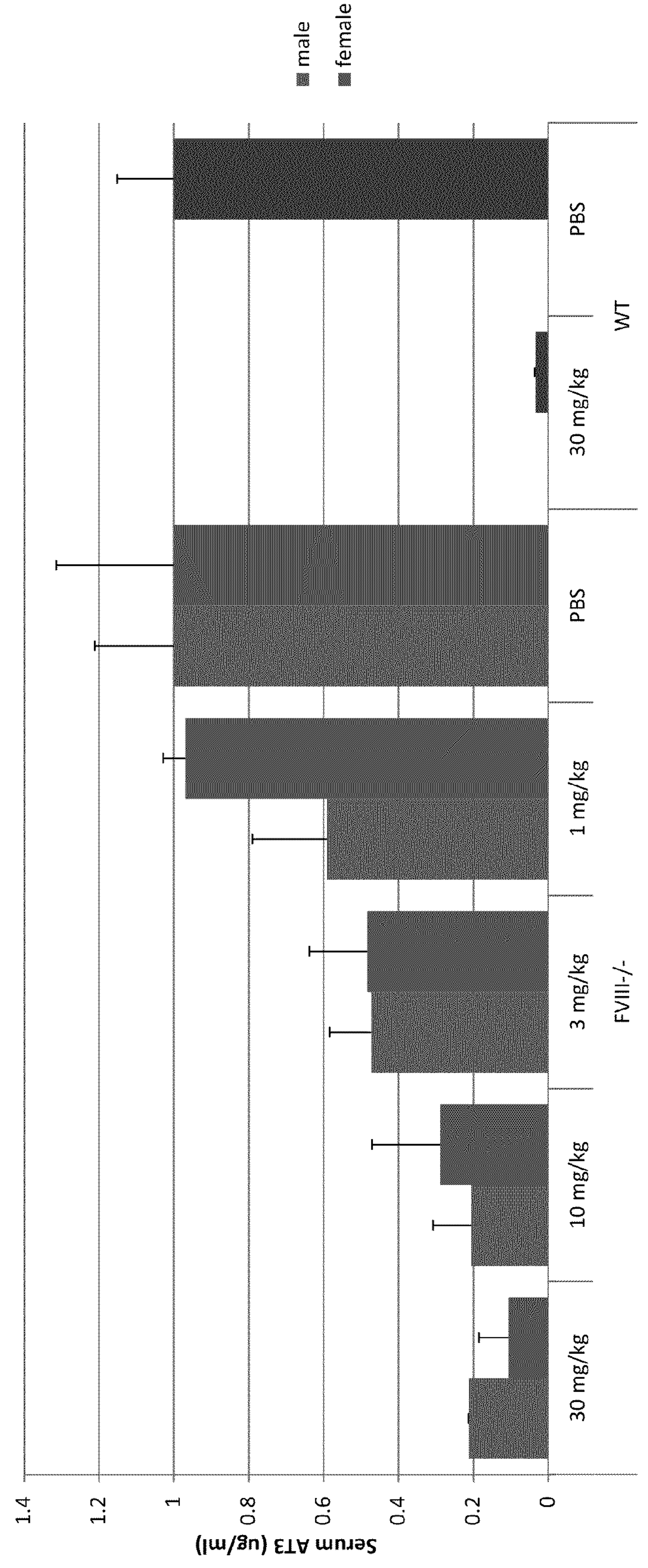
FIG. 13 is a graph showing a dose effect response to a single dose of AD-57213.

Male and female mice having a targeted deletion of Factor VIII (C57BL/6/129 hybrids) and recapitulating the hemophilia A phenotype and control or wild-type (C57BL/6 female) mice were subcutaneously injected with a single dose of compound AD-57213 conjugated to GalNAc at 30 mg/kg, 10 mg/kg, 3 mg/kg, or 1 mg/kg at Day 0, animals were sacrificed at Day 3 and Serpinc1 activity was determined as described above. FIG. 13 shows that, not only does a single dose of AD-57213 effectively knock-down Serpinc1 activity, but there is also a dose response to AD-57213.

Figure 31A:
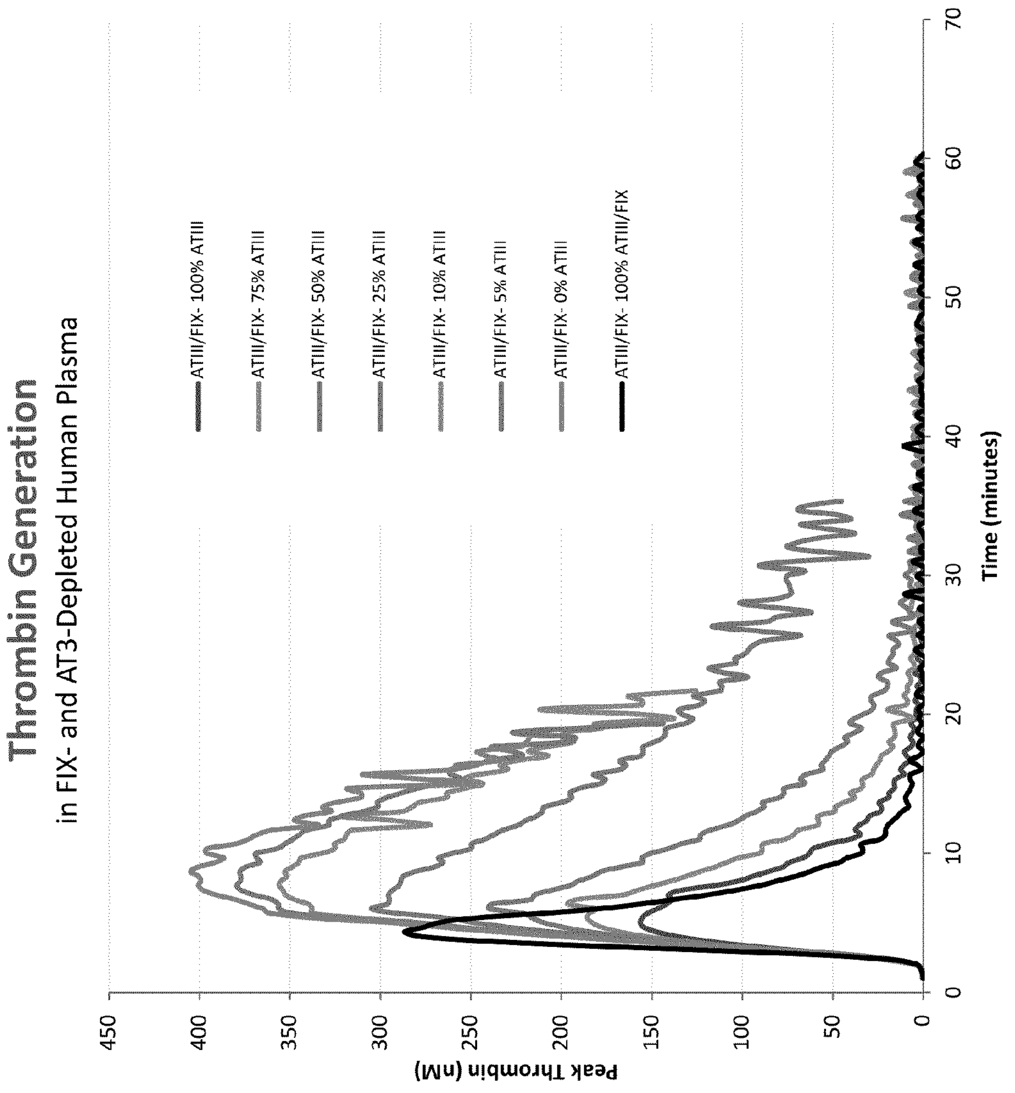
FIGS. 31A and 31B are graphs depicting that antithrombin reduction increases thrombin generation in Factor IX-depleted human plasma in vitro.
Figure 31B:
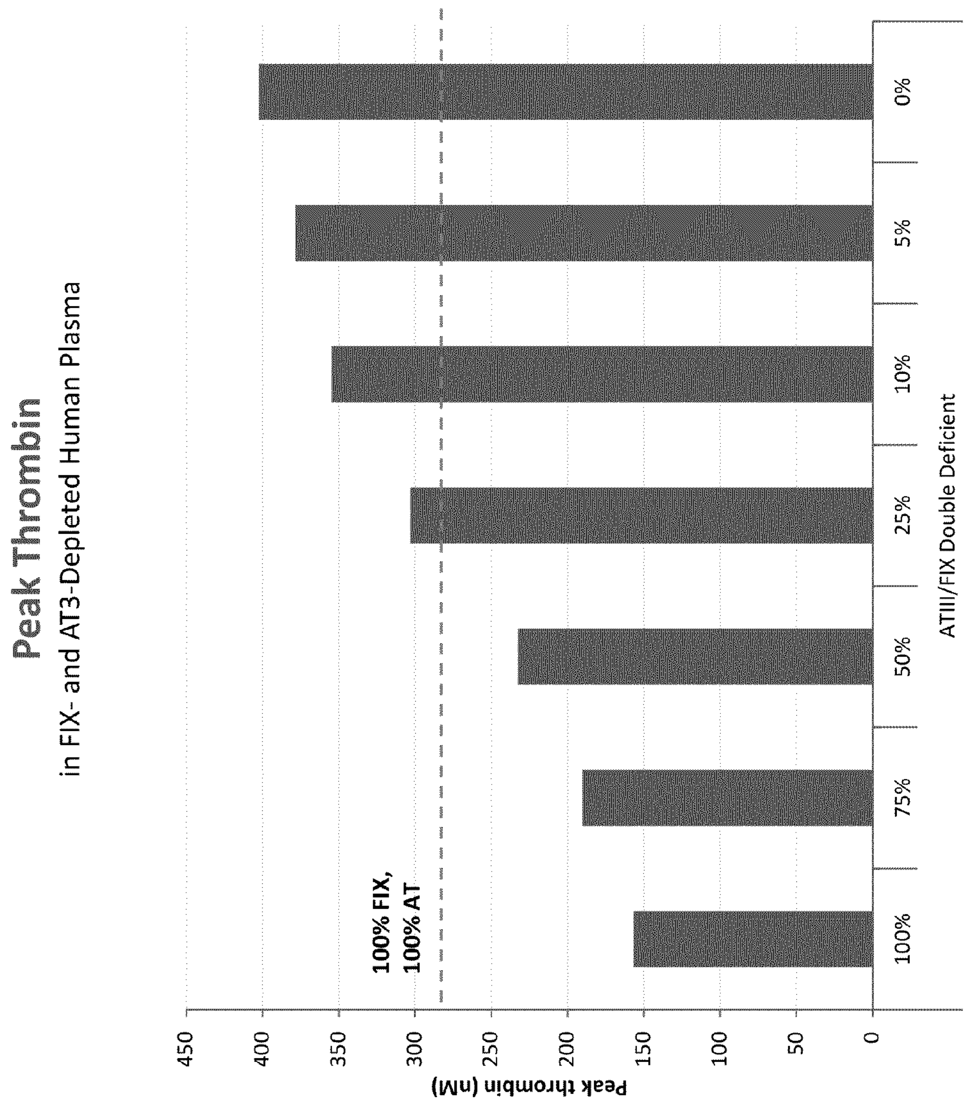

To investigate the impact of antithrombin reduction on thrombin generation in a hemophilia setting, thrombin generation studies were performed on Factor IX (FIX) and Anthithrombin- (AT-) depleted human plasma. FIX depletion recapitulates the hemophilia B phenotype AT was subsequently added back to the plasma samples at various levels (1 IU/ml=100%) to generate FIX-depleted plasma samples with different levels of antithrombin (0-100%). Control plasma was generated by adding back 1 IU/ml antithrombin and 5 μg/ml FIX (100%) to the double-depleted plasma. FIG. 31A depicts thrombin generation in FIX- and AT-depleted human plasma (tissue factor=5 pM). FIG. 31B depicts the peak thrombin in FIX- and AT-depleted human plasma (tissue factor=5 pM). Therefore, antithrombin reduction increases thrombin generation in Factor IX-depleted human plasma in vitro.

Example 9

Dose Duration of AD-57213

Figure 14:
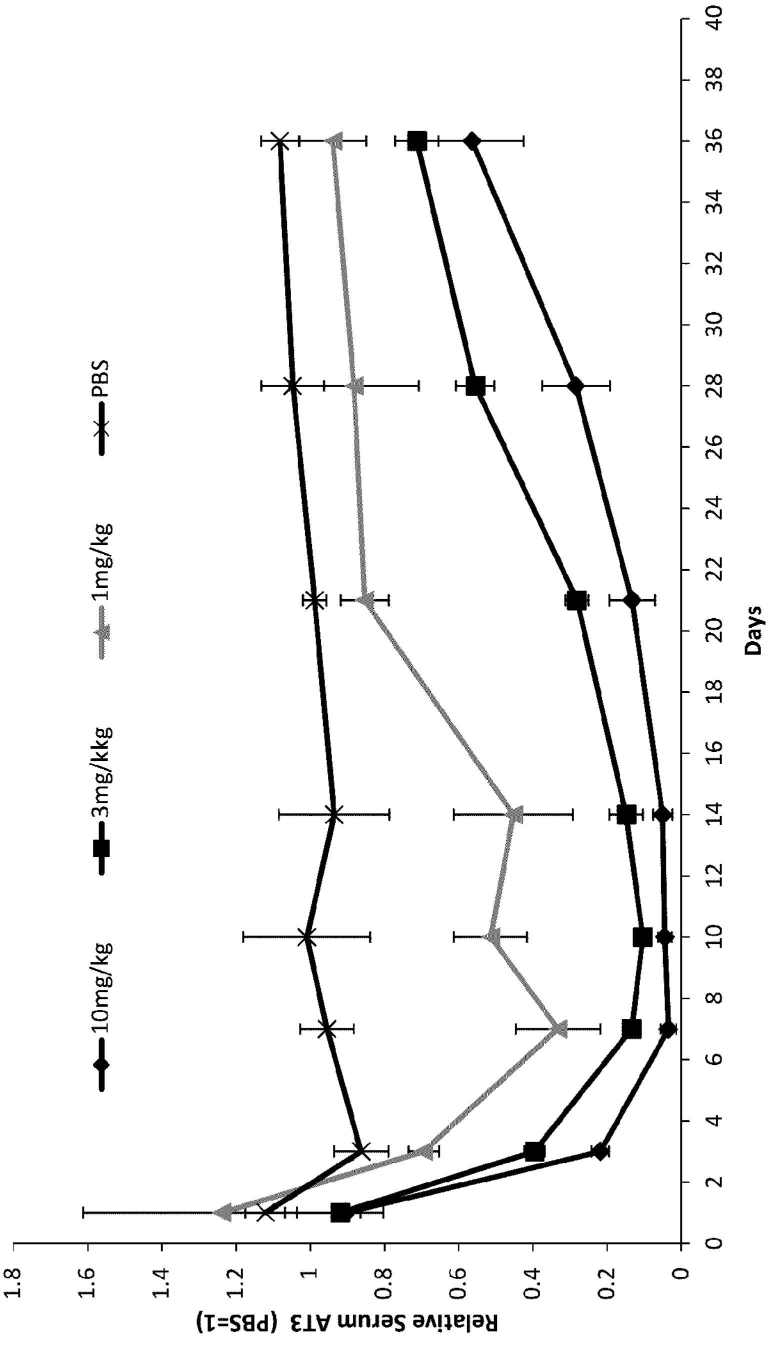
FIG. 14 is a graph showing the duration of silencing of Serpinc1 with AD-57213 following a single dose of 1 mg/kg, 3 mg/kg or 10 mg/kg in Hemophilia A mice.
Figure 16:
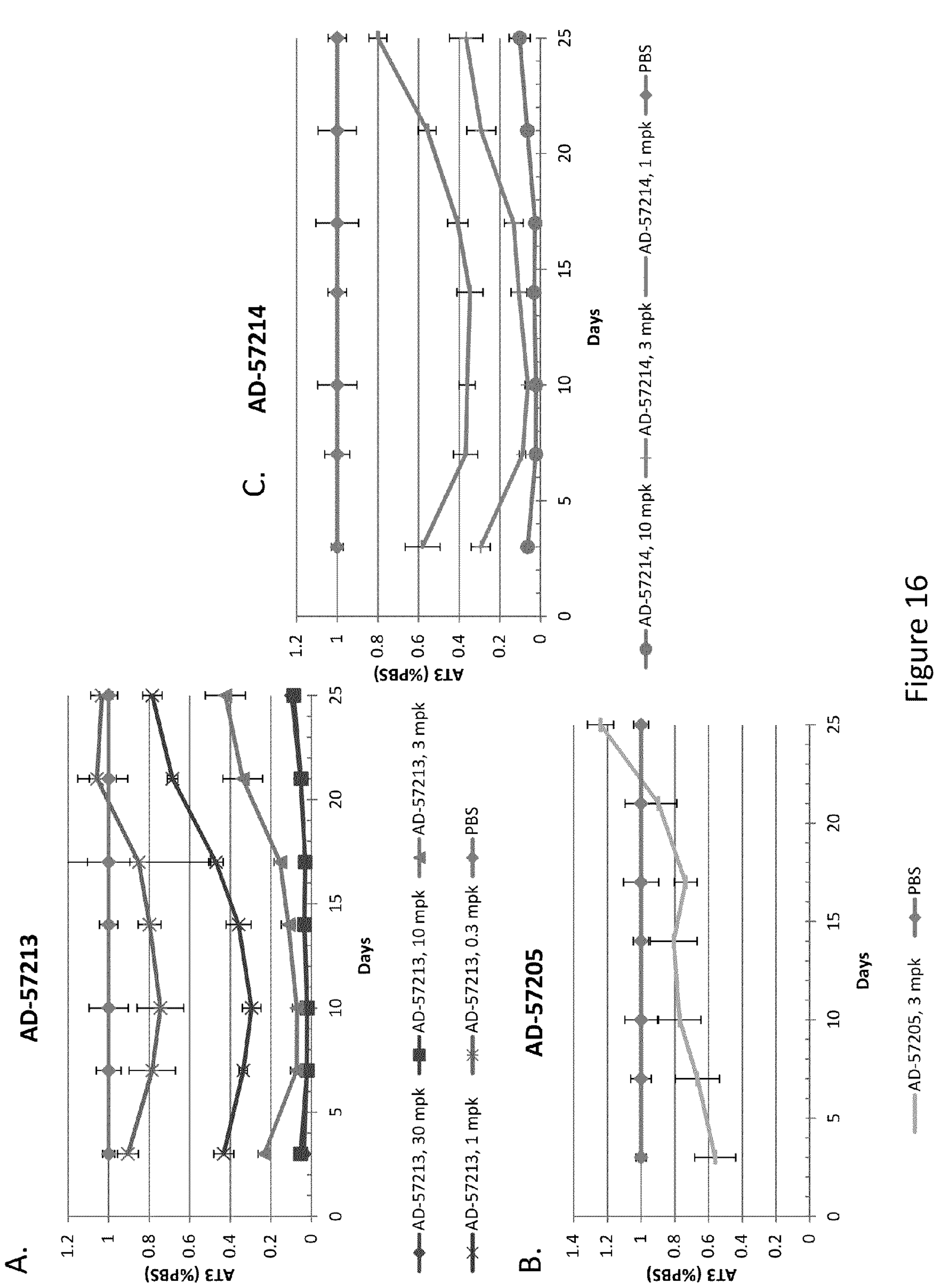
FIGS. 16A-16C are graphs showing the duration of silencing of Serpinc1 with AD-57213 (A), AD-57205 (B), and AD-57214 (C) following a single dose as indicated.

In order to evaluate the duration of anti-thrombin silencing in Hemophilia A mice (B6; 129S4-$F8^{tm1/Kaz/J}$; Jackson Labs) following a single dose of AD-57213 conjugated to GalNAc, mice were subcutaneously injected with compounds AD-57214, AD-57205, or AD-57213 or PBS. Whole blood was collected retroorbitally and assayed for Serpinc1 mRNA levels and Serpinc1 activity. The results of the single dose screen for compound AD-57213 administered at 10 mg/kg, 3 mg/kg, or 1 mg/kg as a percent knock-down of Serpinc1 activity from PBS at Days 3, 7, 10, 14, 17, 21, 28, and 36 are depicted in FIG. 14. FIG. 16 shows the results of the single dose screen for compounds AD-57213, AD-57205, and AD-57214 administered at the doses indicated in the Figures as a percent knock-down of Serpinc1 activity from PBS at Days 3, 7, 10, 14, 17, 21, and 25.

Figure 15:
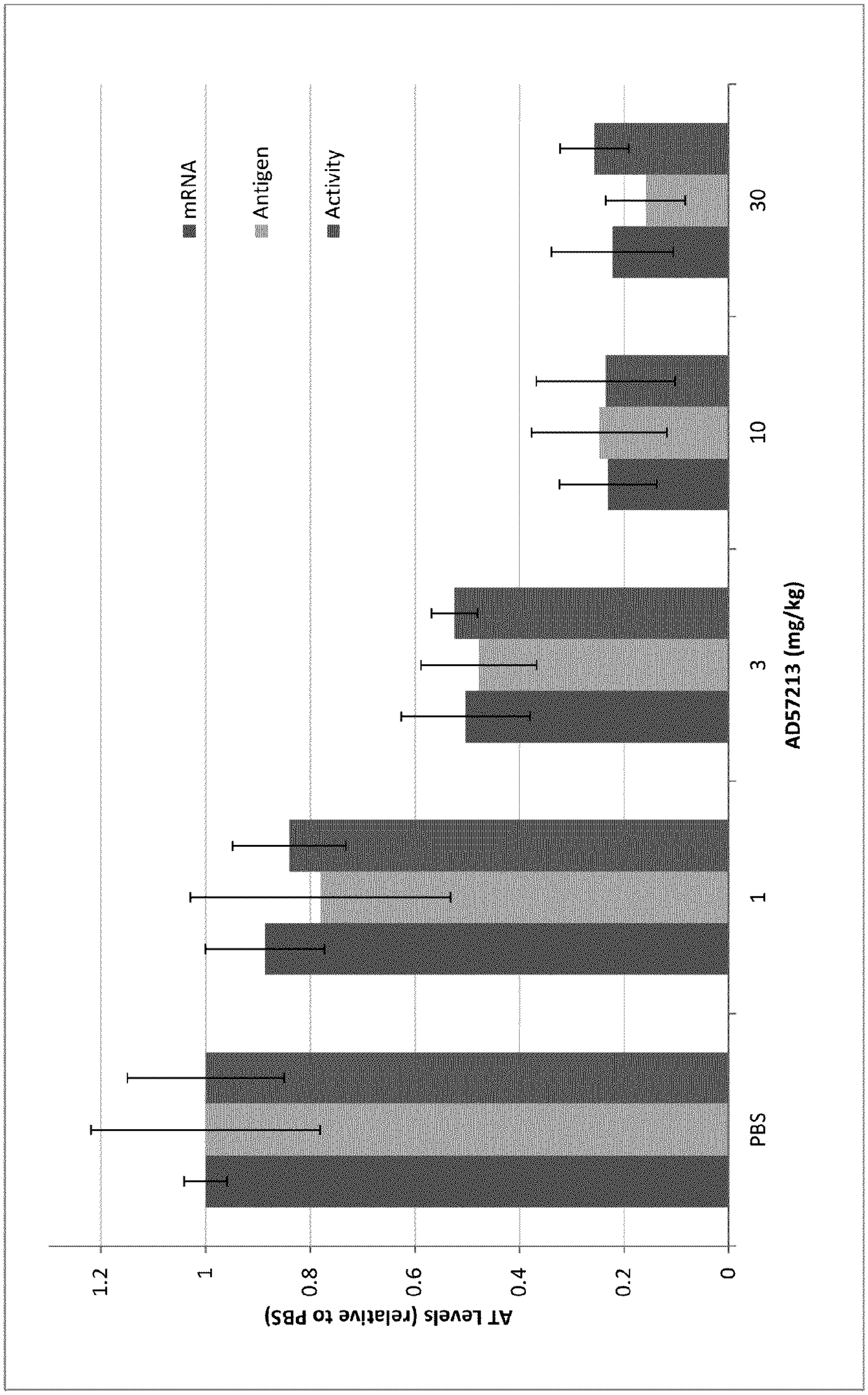
FIG. 15 is a graph showing the inhibition of Serpinc1 mRNA expression in C57BL/6 mice following a single 30 mg/kg, 10 mg/kg, 3 mg/kg, 1 mg/kg, and 0.3 mg/kg dose of AD-57213.

Liver mRNA, AT antigen in serum and AT activity were measured in hemophilia A mice (B6; 129S4-$F8^{tm1/Kaz/J}$; Jackson labs) injected subcutaneously with AD-57213 at a dose of 30 mg/kg, 10 mg/kg, 3 mg/kg, 1 mg/kg, or PBS at Day 0. Animals were sacrificed on Day 3 post-injection as described above. FIG. 15 shows the results of the single dose screen as a percent knock-down of Serpinc1 mRNA levels from PBS, as a percent knock-down of Serpinc1 antigen levels from PBS, and as a percent knock-down of Serpinc1 activity from PBS at Day 3 for AD-57213.

As evidenced by FIGS. 14-16, administration of compound AD-57213 leads to potent, dose-dependent suppression of Serpinc1 in HA mice with a single dose $ED_{50}$ of less than 1 mg/kg on Day 7. Serpinc1 suppression was durable and correlated with the maximal level of antithrombin suppression achieved. A single dose of 1 mg/kg led to the maintenance of 50% suppression for about 15 days, while a dose of 10 mg/kg led to greater than 80% suppression maintained for 28 days.

Example 10

Dose Duration of a Split-Dose of AD-57213

In order to further evaluate compound AD-57213 knock-down of Serpinc1 expression and activity, a split-dosing experiment was performed. C57BL/6 mice were subcutaneously administered GalNAc-conjugated AD-57213 and the effect of a 3 times per week, ⅓ dose of AD-57213 was compared to the effect of a 1 time per week fully concentrated dose of AD-57213. A summary of the study design is presented in Table 16. Serum Serpinc1 protein levels were determined.

TABLE 16

Study Design of Split-Dosing Experiment

| Group | Test compound | Dose (mg/kg) | Frequency |
|---|---|---|---|
| 1 | AD-57213 | 3 | q1w |
| 2 | | 1.5 | (Monday) |
| 3 | | 0.75 | |
| 4 | | 1 | t.i.w. |
| 5 | | 0.5 | (M, W, F) |
| 6 | | 0.25 | |
| 7 | PBS | — | q1w |

(q1w: Once a week)

Figure 17:
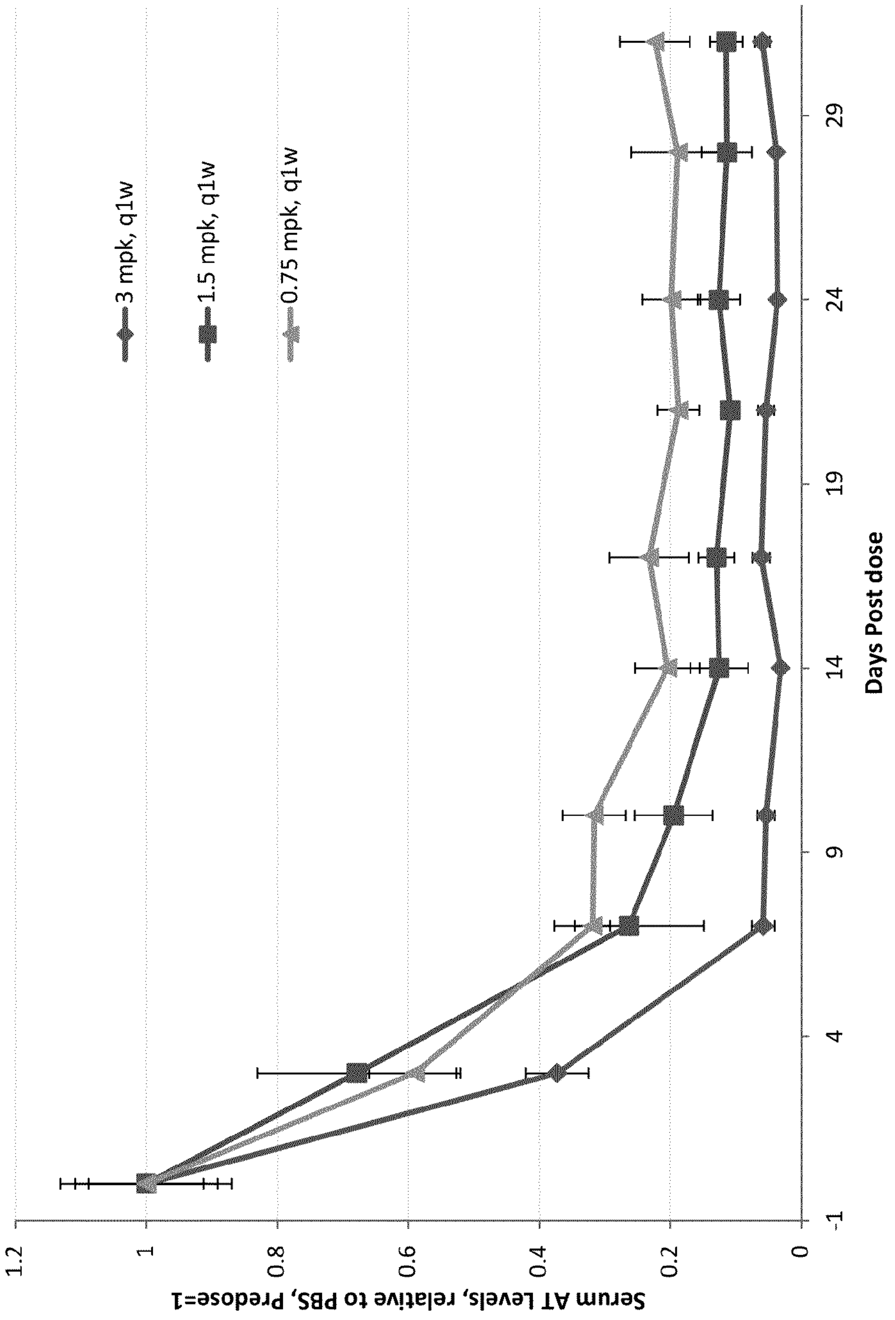
FIGS. 17-19 are graphs showing the effects of the indicated split-dosing regimens on the duration of silencing of Serpinc1 protein expression in C57BL/6 mice administered GalNAc conjugated AD-57213.
Figure 18:
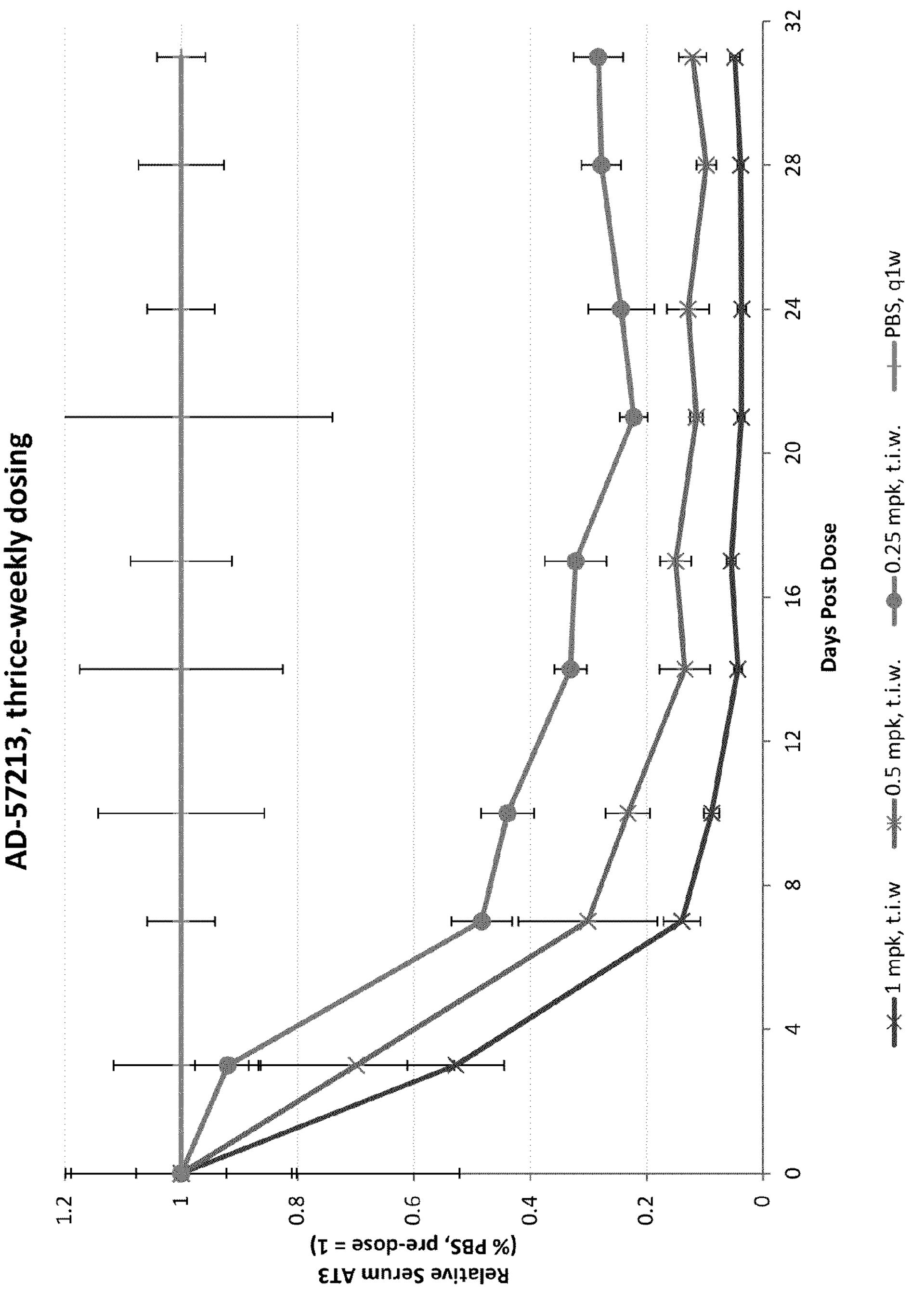

The results of the once a week (q1w) dosing as a percent knock-down of Serpinc1 protein levels from PBS are shown in FIG. 17 and the results of the three-time per week (t.i.w.) dosing as a percent knock-down of Serpinc1 protein levels from PBS are shown in FIG. 18.

Figure 19:
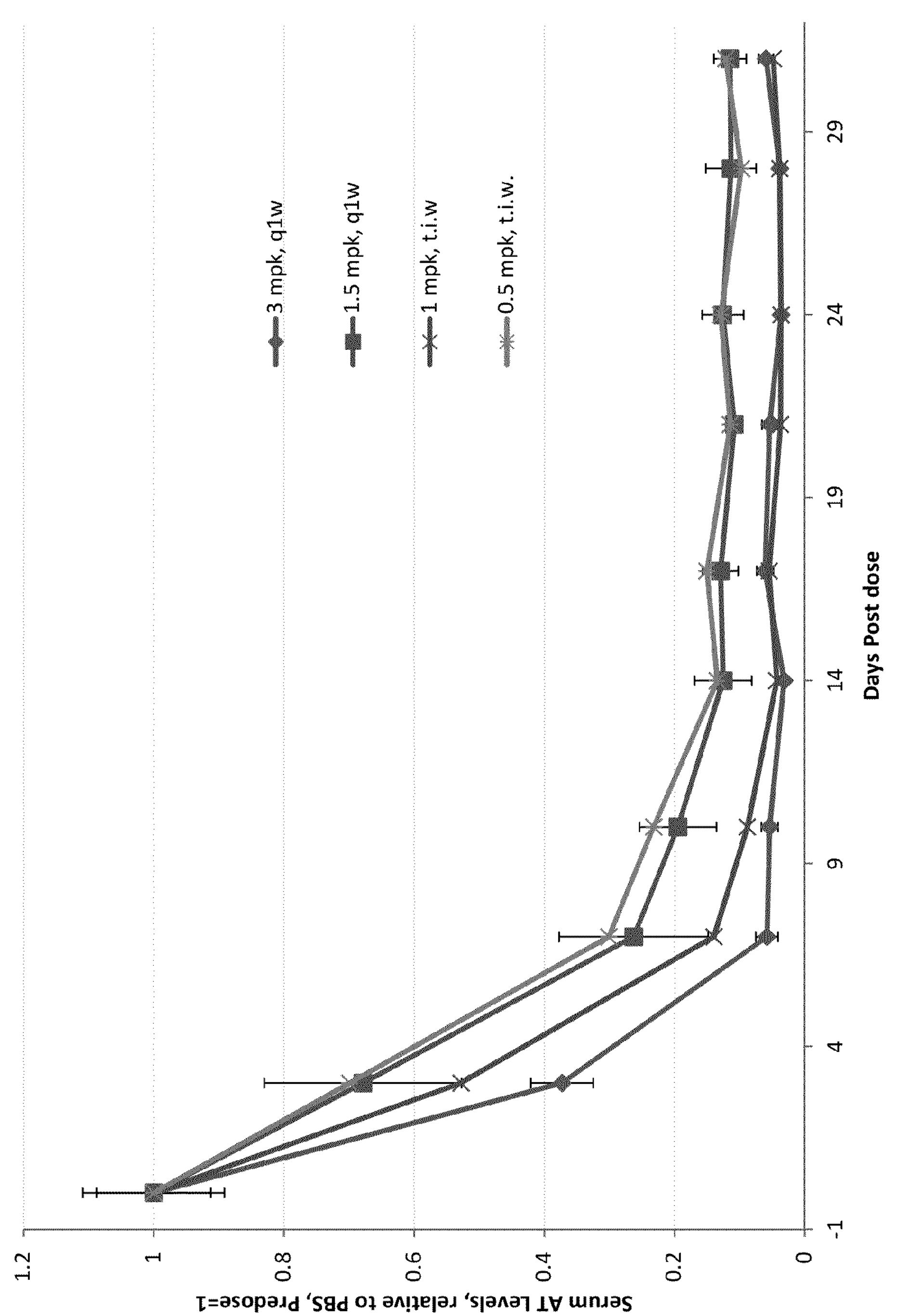

As shown in FIGS. 17 and 18, repeat dosing of compound AD-57213 led to a dose-dependent, durable response, with some additive effect. Animals dosed with 3 mg/kg reached the nadir levels of >95% knock-down after 2 weekly doses whereas the lower two dose groups attained nadir after 3 weekly doses (−90% knock-down for 1.5 mg/kg and ~80% for 0.75 mg/kg). To further study the different dosing regimens, in different groups, the same weekly dose was split and dosed three times a week, e.g., 1.5 mg/kg q1w was compared with 0.5 mg/kg tiw. As shown in FIG. 19, the cumulative weekly dose gave the same level of knock-down. For example, Serpinc1 levels achieved with 1.5 mg/kg (q1w) were equivalent to Serpinc1 levels achieved with 0.5 mg/kg administered three times a week.

Example 11

Non-Human Primate Dosing of Serpinc1 siRNAs

Compound AD-57213 was tested for efficacy in non-human primates as outlined in Table 17. Serum Serpinc1 protein levels were determined at Days −14, −8, −4, Day 1 at 4 hours post-dosing, Days 2, 4, 8, 11, 15, 22, 29, 37, 44, 51, and 58.

TABLE 17

| Non-Human Primate Dosing Experiment. | | | | | | |
|---|---|---|---|---|---|---|
| Test Article | Group Number | n | Dose level (mg/kg) | Route of administration | Rationale | |
| AD54944 | 1 | 3 | 10 | SC | Parent compound | |
| AD-57213 | 2* | 3 | 30 | SC | Dose response for the lead | Similar to 3 × 10 mpk |
| | 3 | 3 | 10 | SC | | Compare compounds at 10 mpk |
| | 4 | 3 | 3 | SC | | Dose curve |
| | 5 | 3 | 1 | SC | | |
| AD-57205 | 5 | 3 | 10 | SC | Same potency as 57213 at 10 mpk in mice | Has less PS |
| LNP-55029 | 7 | 3 | 0.3 | IV | Test target | Positive control for target knock-down and assays |

Figure 20:
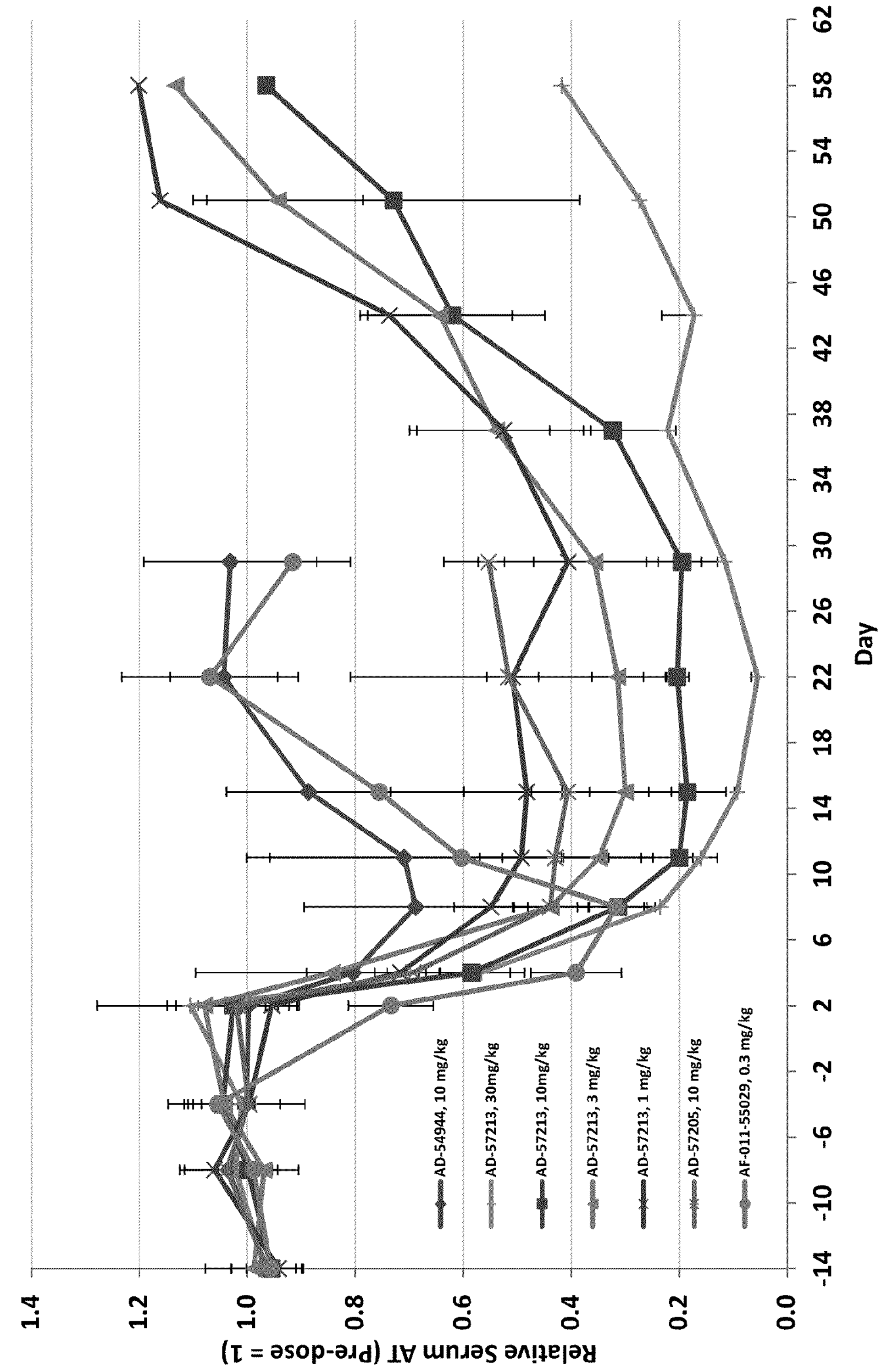
FIG. 20 is a graph showing the effects of the single dose screen of the indicated compounds on the duration of Serpinc1 protein expression in non-human primates.

FIG. 20 shows the results of the single dose screen for all compounds tested as a group average of the relative serum Serpinc1 levels compared to pre-dosing Serpinc1 levels and demonstrates that all of the siRNAs tested effectively knock-down Serpinc1 protein levels.

Figure 21:
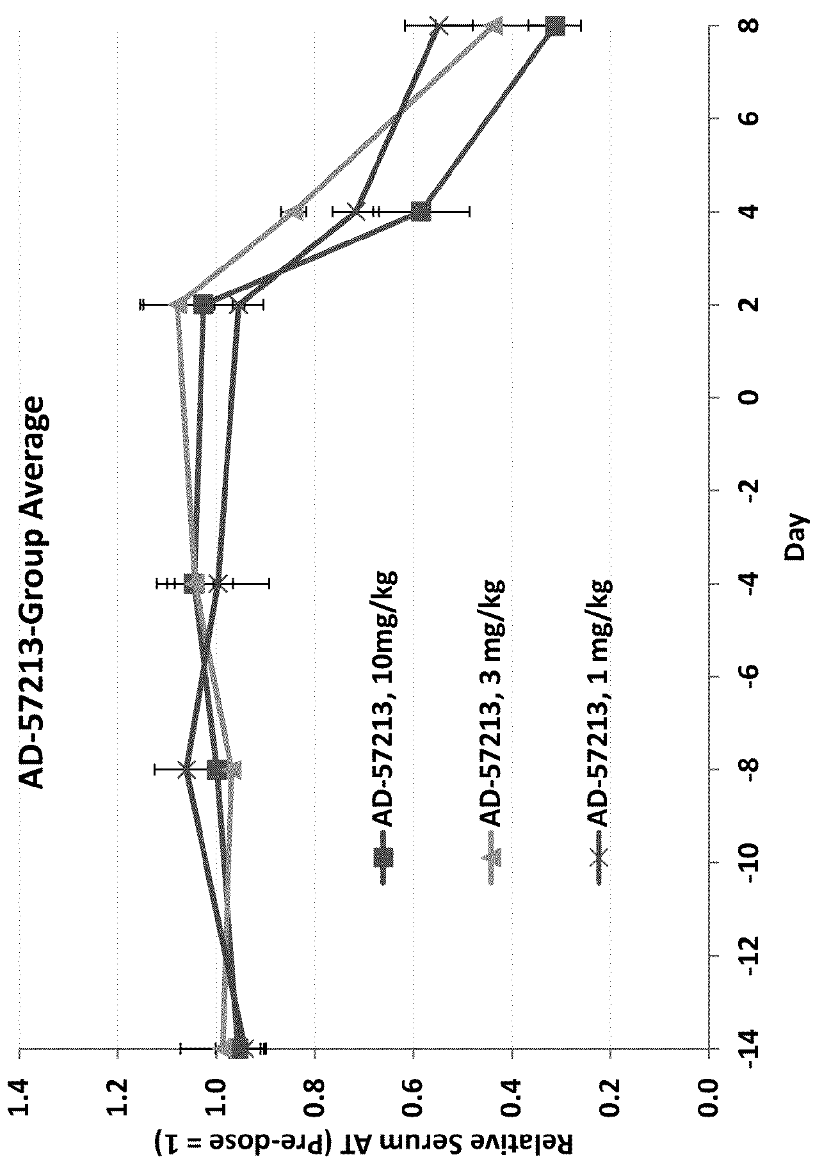
FIG. 21 is a graph showing the effects of the single dose screen of AD-57213 conjugated to GalNAc on the duration of Serpinc1 protein expression in non-human primates.

FIG. 21 shows the results of the single dose screen for compound AD-57213 as a group average of the relative serum Serpinc1 levels compared to pre-dosing Serpinc1 levels.

Figure 22:
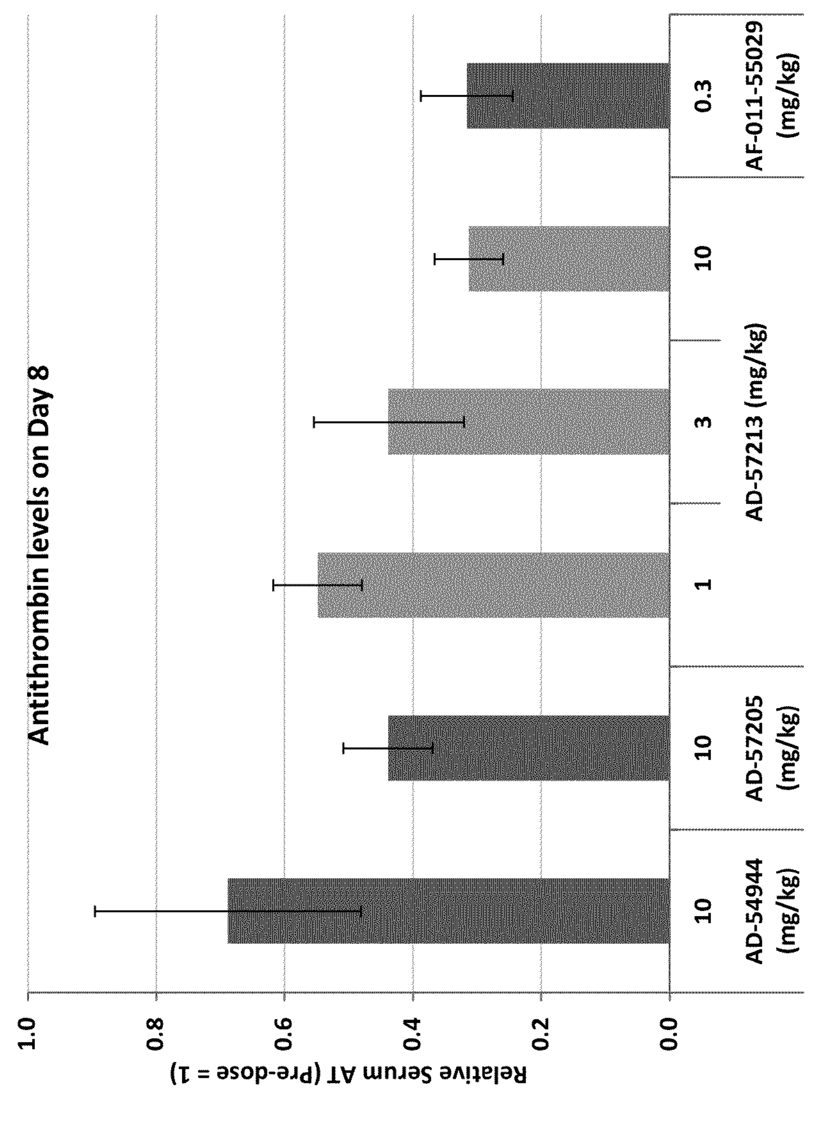
FIG. 22 is a graph showing the effects of the single dose screen of the indicated compounds on the duration of Serpinc1 protein expression in non-human primates.

FIG. 22 shows the results of the single dose screen for all compounds tested as a group average of the relative serum Serpinc1 levels compared to pre-dosing Serpinc1 levels on Day 8.

Overall, the results demonstrate that there is dose-dependent knock-down of Serpinc1 protein levels with AD-57213 in non-human primates and that both AD-57213 and AD-57205 show improved potency over the parent compound AD-52444.

Example 12

Non-Human Primate Dosing of a Therapeutic Serpinc1 siRNA

Compound AD-57213 was tested for efficacy in non-human primates. Cynomolgus monkeys were administered compound AD-57213 as outlined in Table 18 below. Plasma was collected at various time points after administration of AD-57213 and analyzed for antithrombin protein (Serpinc1) levels by ELISA.

TABLE 18

| Study Design: AD-57213 pharmacology in nonhuman primates | | | | | |
|---|---|---|---|---|---|
| Group Number | Test Article | N | Dose Level (mg/kg) | Route of Administration | Sample Collection |
| 1 | AD-57213 | 3 | 1 | SC | Plasma for AT protein and thrombin generation |
| 2 | | 3 | 3 | SC | |
| 3 | | 3 | 10 | SC | |
| 4 | | 3 | 30 | SC | |

Figure 23:
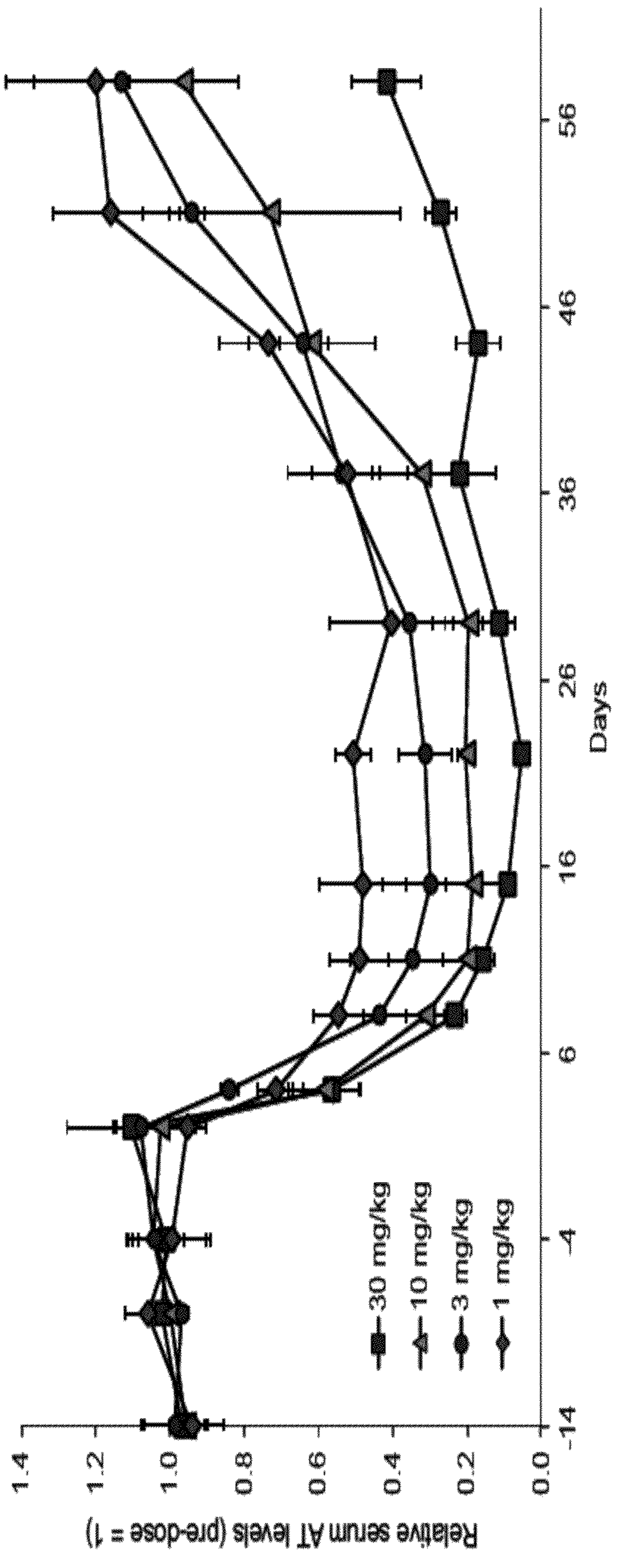
FIG. 23 is a graph showing the effects of the single dose of compound AD-57213 on serum antithrombin (Serpinc1) levels in non-human primates.
Figures 24A, 24B, 24C, 24D:
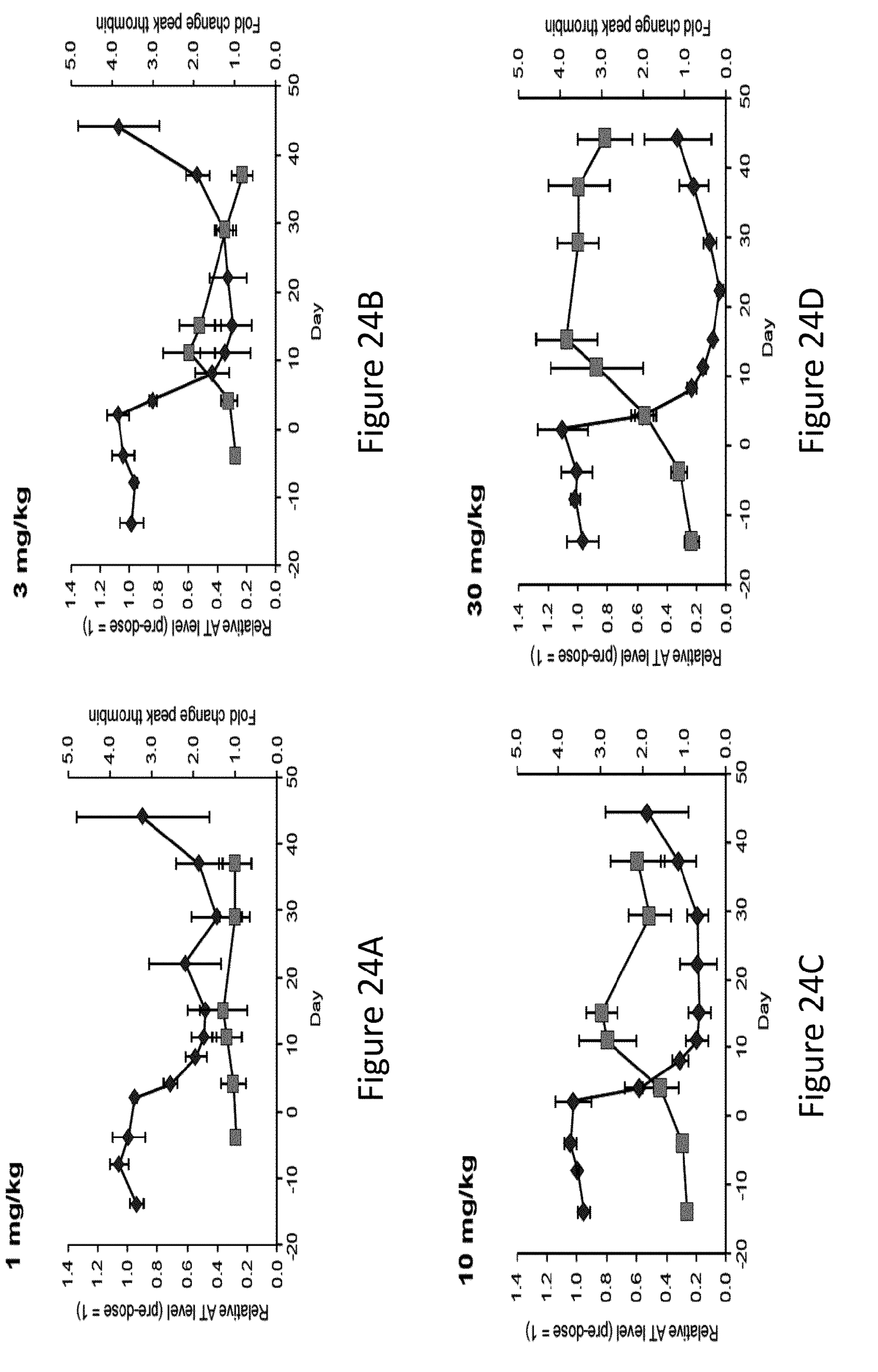
FIGS. 24A-24D are graphs showing the effects of the single dose of compound AD-57213 at A) 1 mg/kg, B) 3 mg/kg, C) 10 mg/kg, and D) 30 mg/kg on the relationship between serum antithrombin (Serpinc1) levels and fold change in peak plasma thrombin levels in non-human primates. Fold change in peak thrombin is depicted on the secondary y-axis (grey) and relative antithrombin level is depicted on the primary y-axis (black).

FIG. 23 shows the results of the single dose screen for compound AD-57213 as a group average of the relative serum Serpinc1 levels compared to the average of three pre-dose measurements. The results demonstrate dose dependent Serpinc1 silencing with approximately 50, 70, 80 and >90% silencing at 1, 3, 10 and 30 mg/kg, respectively. Data points represent group mean and error bars represent standard deviation.

Figure 25:
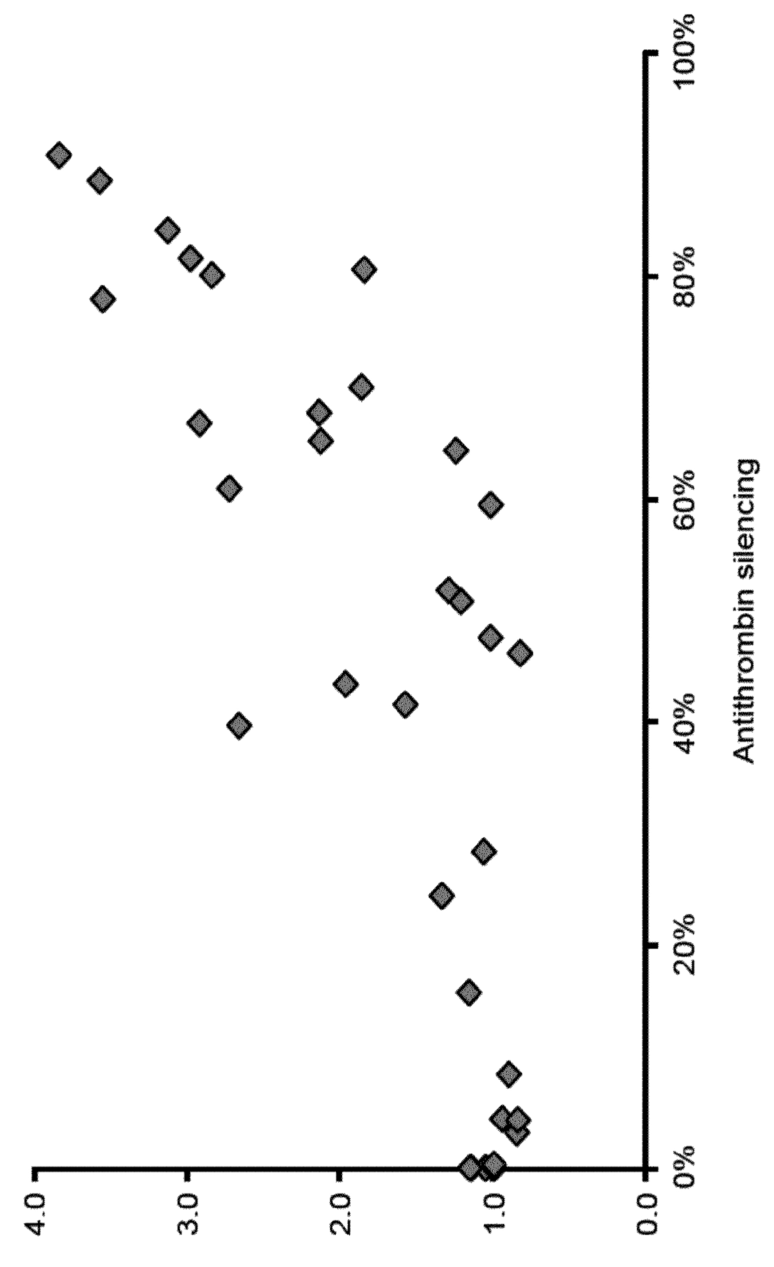
FIG. 25 is a graph showing the effects of AD-57213 as a fold change increase in peak thrombin as a function of relative antithrombin (Serpinc1) silencing.

FIGS. 24A-D show the relationship between relative serum Serpinc1 level and fold change in peak plasma thrombin level at a single A) 1 mg/kg, B) 3 mg/kg, C) 10 mg/kg, and D) 30 mg/kg dose of compound AD57213. Serpinc1 levels are represented relative to the average of three pre-dose measurements. Thrombin generation curves were generated from plasma samples collected at various time points using a Calibrated Automated Thrombinoscope (tissue factor=1 pM). Fold change in peak thrombin was calculated relative to the average peak thrombin value for two pre-dose values for each animal. Data points represent group mean and error bars represent standard deviation. FIG. 25 shows a consolidated scatterplot of fold change increase in peak thrombin as a function of relative Serpinc1 silencing.

Figure 26:
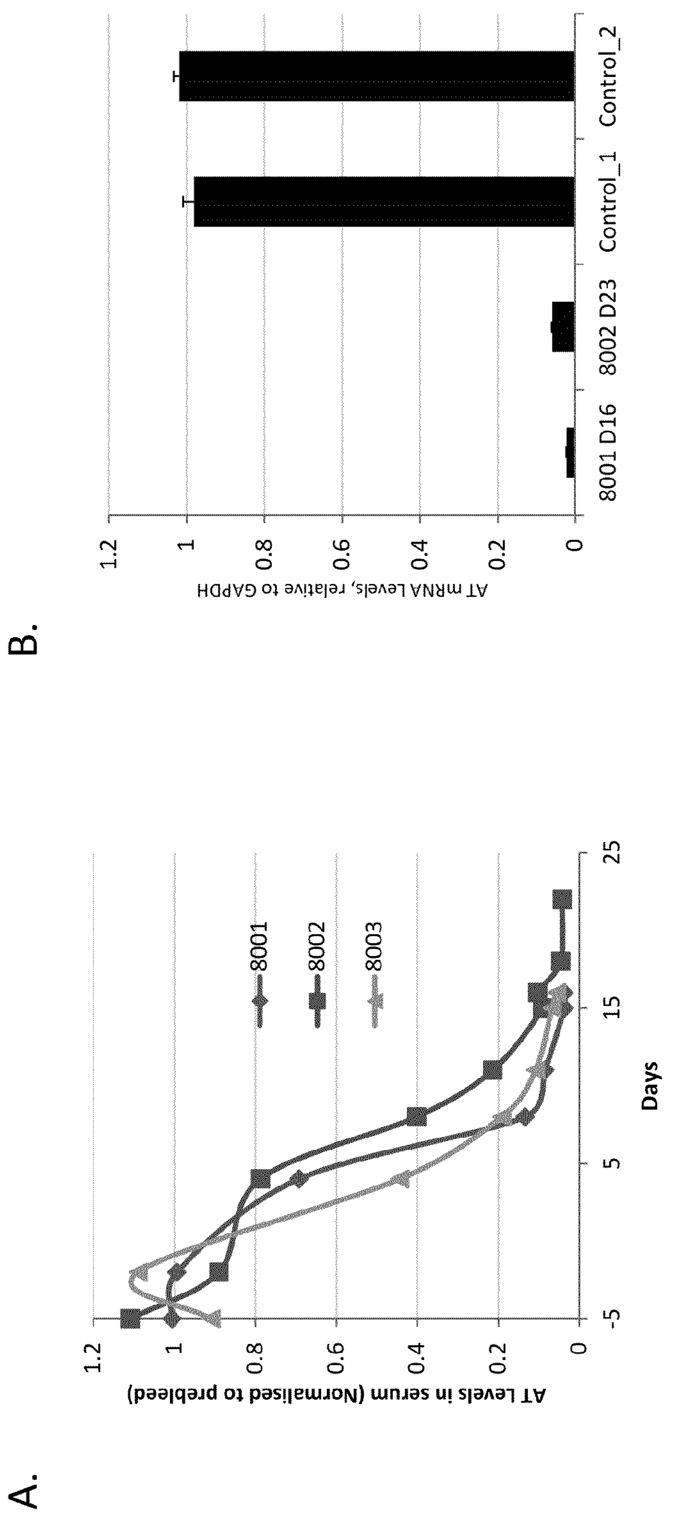
FIGS. 26A and 26B are graphs showing the cumulative effects of Serpinc1 silencing in non-human primates.

Animals were also administered three weekly AD-57213 doses of 30 mg/kg and the Serpinc1 protein and mRNA levels were determined in blood samples collected from the animals. The results of these studies are presented in FIG. 26A (Serpinc1 protein levels relative to prebleed levels) and 26B (Serpinc1 mRNA levels relative to GAPDH).

Overall, the results demonstrate that there is a durable, dose-dependent inhibition of Serpinc1 protein levels with compound AD-57213 in non-human primates that results in up to a 4-fold increase in thrombin generation.

Example 13

Repeat Administration of a Serpinc1 SiRNA in Non-Human Primate Dosing

Compound AD-57213 was tested for efficacy and to evaluate the cumulative effect of the compound in non-human primates with a repeat administration protocol. Cynomolgus monkeys were administered compound AD-57213 at 0.5 mg/kg q1w; 1 mg/kg q2w (every other week), for 2 months and 1.5 mg/kg q1w; 3 mg/kg q2w for 6 weeks. Serum was collected at various time points as illustrated in FIG. 27 and analyzed for antithrombin protein level (SerpinC1) by ELISA. Antithrombin levels were represented relative to the average of three pre-dose measurements.

Figure 27A:
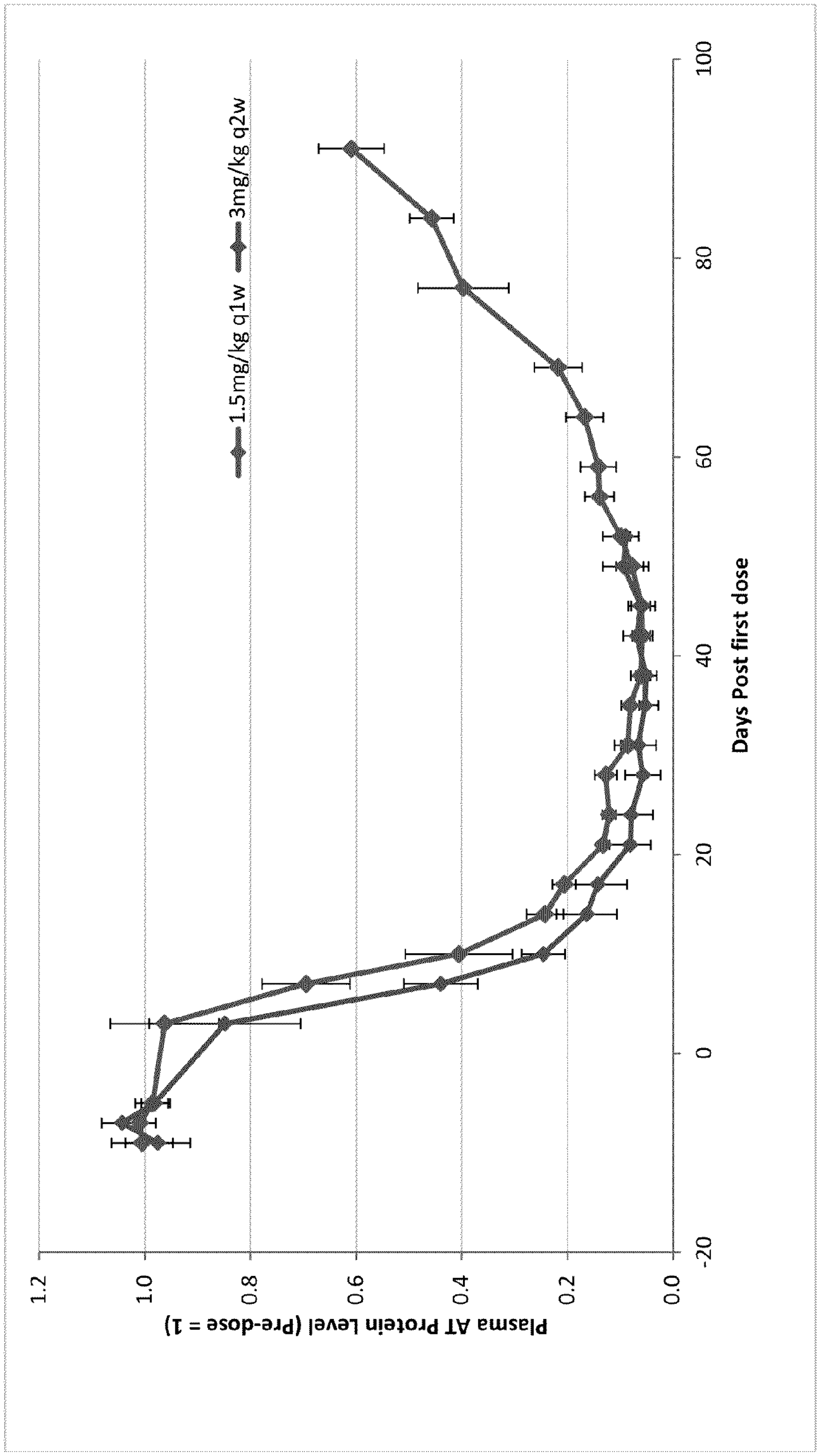
FIGS. 27A and 27B are graphs showing the effects of a multi-dose administration (0.5 mg/kg qw, 1 mg/kg q2w, 1.5 mg/kg qw, 3 mg/kg q2w) of a Serpinc1 siRNA on serum antithrombin levels in non-human primates. Data points represent group mean, error bars represent standard deviation (N=3). (qw=weekly; q2w=every other week).
Figure 27B:
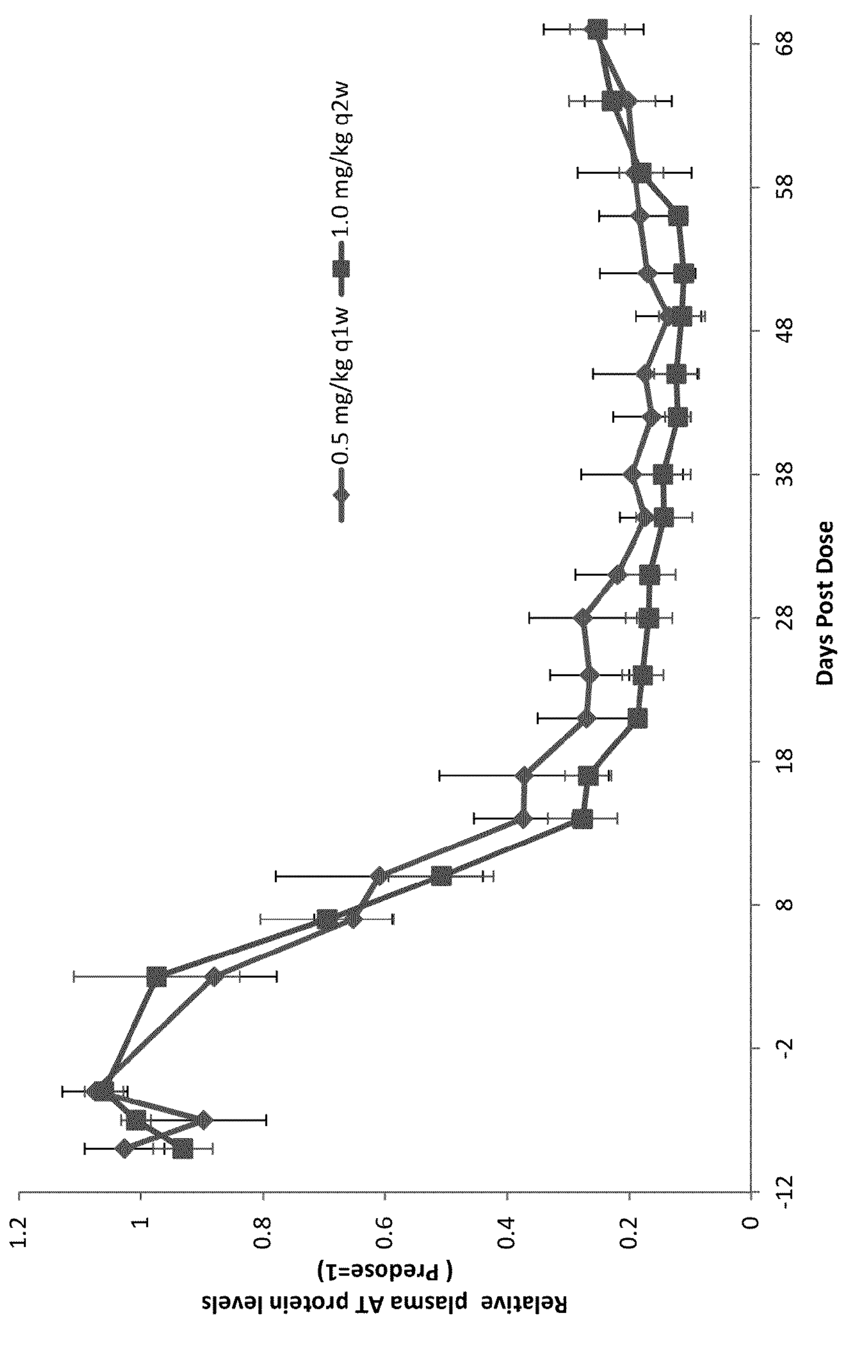

The first two dose groups with 0.5 mg/kg weekly cumulative dose led to 80% decrease in AT levels after 5 weeks. The latter two groups with 1.5 mg/kg the cumulative weekly dose led to >95% maximum knockdown. FIG. 27A shows the data from latter two groups. Animals receiving the 3 mg/kg dose were euthanized on Day 54 and animals receiving the 1.5 mg/kg q1w dose were administered an additional 6th weekly dose on day 36 and are being monitored for recovery to base line levels. FIG. 27B shows AT levels after 0.5 mg/kg cumulative weekly dose.

The data demonstrate that dose dependent antithrombin silencing was observed with all dosing regimens and achieved a steady-state level of suppression by day 25.

Example 14

Figure 28A:
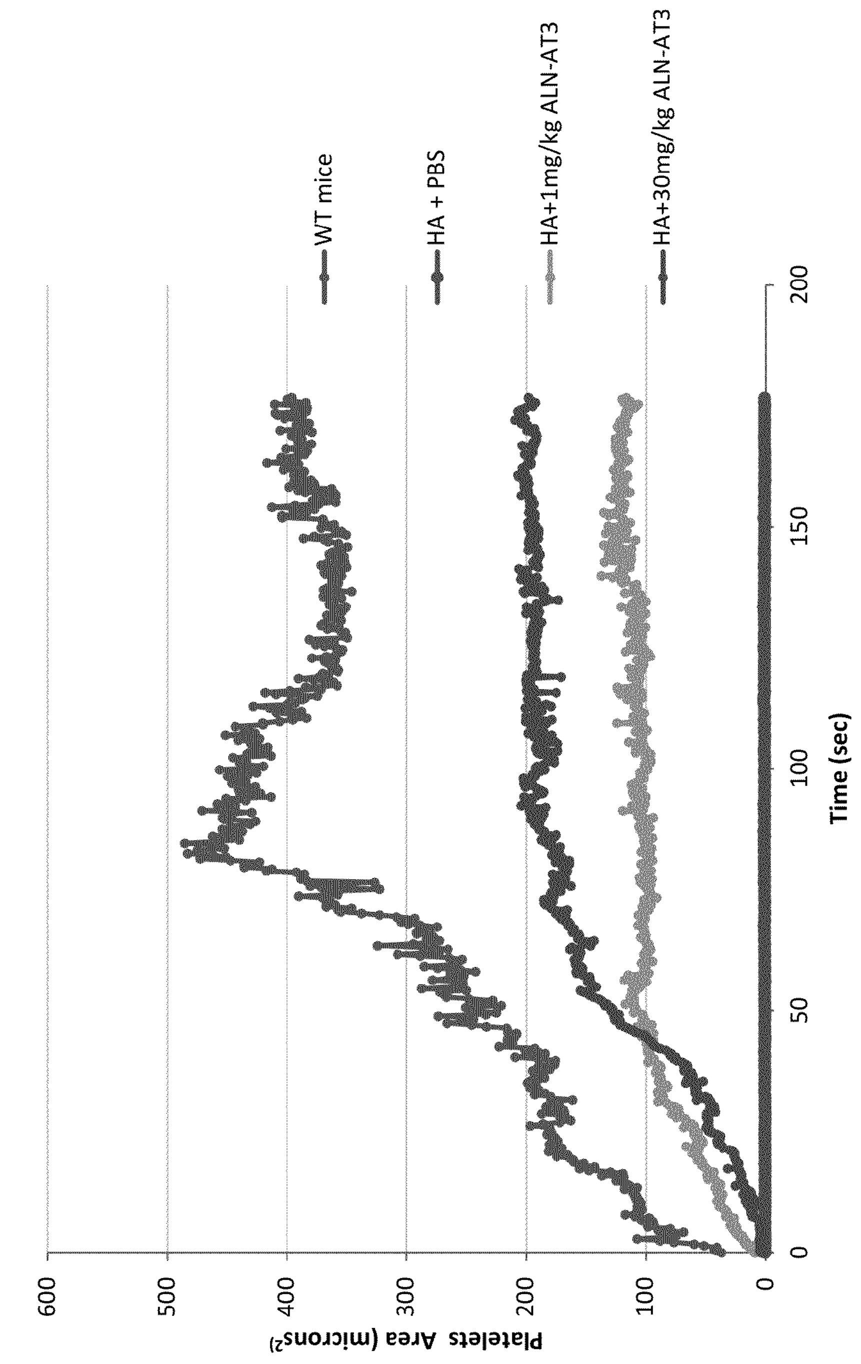
FIG. 28A is a graph showing the effect of Serpinc1 silencing on platelet accumulation following microvessel laser injury. The graph shows the median values from all inflicted injuriesigure 28B is a graph showing the effect of Serpinc1 silencing on fibrin area following microvessel laser injury. The graph shows the median values from all inflicted injuries.
Figure 28B:
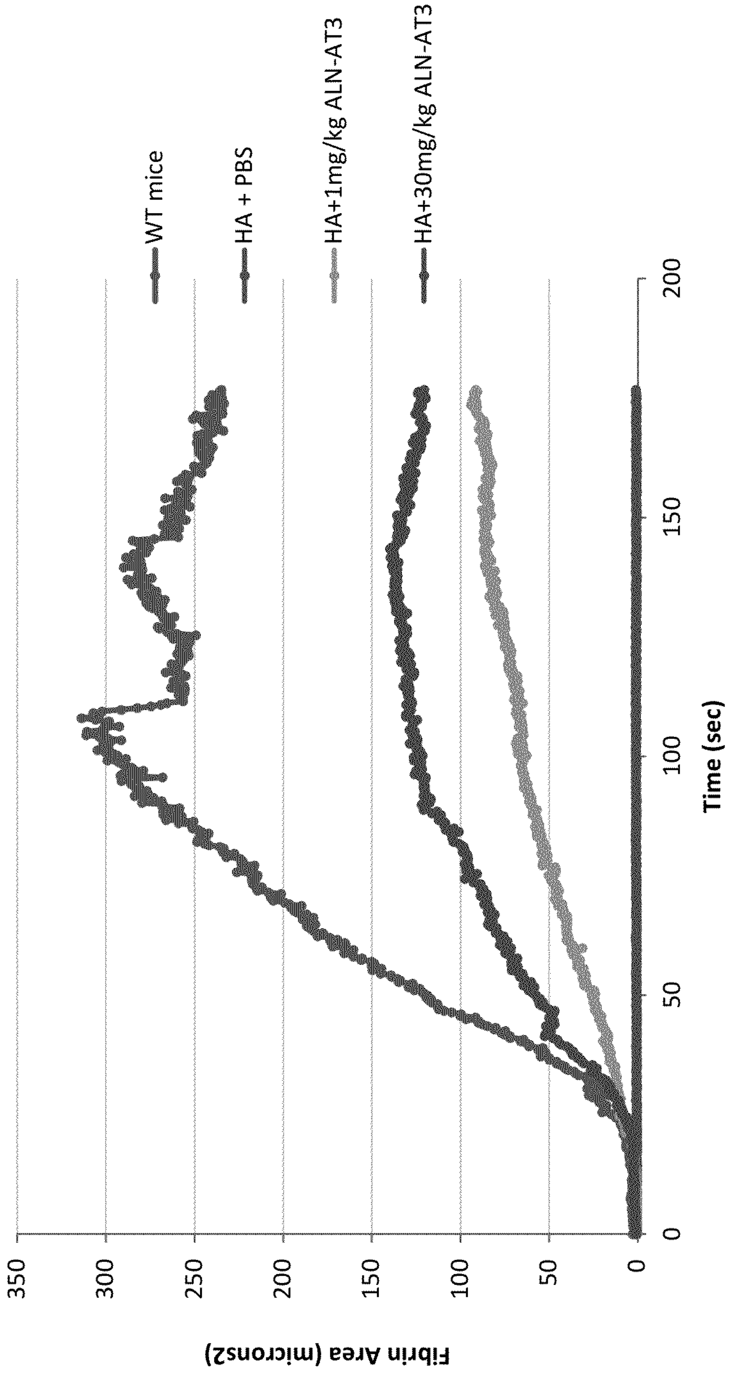

Correction in Hemostasis Following Administration of Compound AD-57213 in Hemophilic Mice Hemophilic animals have less thrombin generation potential and cannot form stable clots. Reduction of antithrombin protein in these animals should help rebalance the hemostasis, increase the endogenous thrombin generating potential, and enable clot formation. This hypothesis was tested in hemophilia A and hemophilia B mice in the microvessel laser injury model accompanied with intravital imaging. Mice were injected with compound AD-57213 and injury was induced 10 days post-treatment. Accumulation of platelets and fibrin at the site of injury were visualized, recorded and quantified. FIG. 28A shows the median values of platelet accumulation over time after laser surgery and FIG. 28B shows the median fibrin values from all inflicted injuries over time after laser surgery. As demonstrated by FIGS. 28A and 28B, compound AD-57213 injected at 1 mg/kg or 30 mg/kg led to platelet and fibrin deposition leading to clot formation in 100% of the injuries. Table 19 summarizes the results from two separate experiments with HA and HB animals.

TABLE 19

| Group | Animals (N) | Injuries (N) | Stable Thrombus (N) | Percent AT mRNA in liver |
|---|---|---|---|---|
| WT | 2 | 10 | 10 | 100% |
| HA + PBS | 2 | 13 | 0 | 100% |
| HA + 1 mg/kg ALN-AT3 | 4 | 20 | 20 | 50% |
| HA + 30 mg/kg ALN-AT3 | 4 | 20 | 20 | 5% |
| HB + PBS | 2 | 6 | 0 | 100% |
| HB + 30 mg/kg ALNAT3 | 2 | 6 | 6 | 5% |

Example 15

In Vivo Efficacy of AD-57213 LNP Formulation

Compounds AD-55029 (unconjugated) and AD-57213 (conjugated to GalNAc) were formulated in a lipid nucleic acid particle (AF-11) and wild-type animals were administered doses of 0.03 mg/kg, 0.1 mg/kg and 0.3 mg/kg of these LNP formulated compounds. Luciferase (AF11-1955) was used as control.

Figure 29:
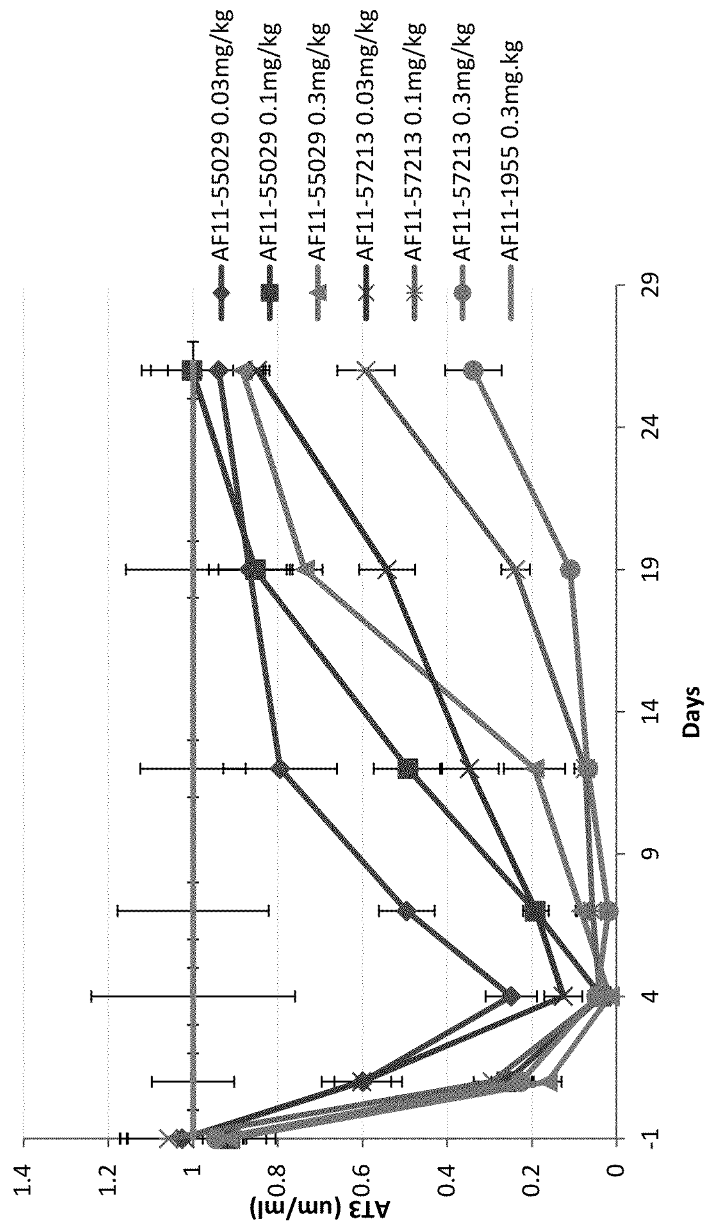
FIG. 29 is a graph showing the duration of silencing of Serpinc1 following administration of compound AD-57213 formulated in a lipid nucleic acid particle.

Both compounds led to >95% knock-down at 0.3 mg/kg but the levels were maintained by AF11-57213 for 15 days versus 8 days by AF11-55029 (see FIG. 29). A similar difference in duration of action between the two compounds was observed at the lower doses.

Example 16

Design, Synthesis, and in Vitro Screening of Additional siRNAs siRNA Design

SiRNA duplexes, 19 nucleotides long for both the sense and antisense strand, were designed using the human SERPINC1 mRNA sequence set forth in GenBank Accession No. NM_000488.3. One thousand five hundred and eighty-one duplexes were initially identified that did not contain repeats longer than 7 nucleotides, spanning the entire 1599 nucleotide transcript. All 1581 duplexes were then scored for predicted efficacy according to a linear model that evaluates the nucleotide pair at each duplex position, and the dose and cell line to be used for screening. The duplexes were also matched against all transcripts in the human RefSeq collection using a custom brute force algorithm, and scored for lowest numbers of mismatches (per strand) to transcripts other than SERPINC1. Duplexes to be synthesized and screened were then selected from the 1581, according to the following scheme: Beginning at the 5' end of the transcript, a duplex was selected within a "window" of every 10±2 nucleotides that 1) had the highest predicted efficacy, 2) had at least one mismatch in both strands to all transcripts other than SERPINC1, 3) had not already been synthesized and screened as part of other duplex sets.

If no duplex could be identified within a given window that satisfied all criteria, that window was skipped. One hundred and sixty-four duplexes were identified that satisfied these criteria.

A detailed list of Serpinc1 sense and antisense strand sequences is shown in Tables 20 and 21.

TABLE 20

AT3 (SERPINC1) unmodified sequences (The "Sense Sequence" column sequences are disclosed as SEQ ID NOS 979-1141, respectively, in order of appearance, and the "Antisense Sequence" column sequences are disclosed as SEQ ID NOS 1142-1304, respectively, in order of appearance)

| Duplex Name | Sense Oligo Name | Sense Sequence | Antis Oligo Name | Antisense Sequence | Position in NM_000488.3 |
|---|---|---|---|---|---|
| AD-59267.1 | A-120250.1 | GGAGAAGAAGGCAACUGAG | A-120251.1 | CUCAGUUGCCUUCUUCUCC | 293-311 |
| AD-59268.1 | A-120266.1 | UGACCAAGCUGGGUGCCUG | A-120267.1 | CAGGCACCCAGCUUGGUCA | 481-499 |
| AD-59269.1 | A-120282.1 | GGUUAACACCAUUUACUUC | A-120283.1 | GAAGUAAAUGGUGUUAACC | 860-878 |
| AD-59270.1 | A-120298.1 | GCUGGUUAACACCAUUUAC | A-120299.1 | GUAAAUGGUGUUAACCAGC | 857-875 |
| AD-59271.1 | A-120314.1 | UAAUGACACCCUCCAGCAA | A-120315.1 | UUGCUGGAGGGUGUCAUUA | 500-518 |
| AD-59272.1 | A-120330.1 | CGUGUUCAGCAUCUAUGAU | A-120331.1 | AUCAUAGAUGCUGAACACG | 952-970 |

TABLE 20-continued

AT3 (SERPINC1) unmodified sequences (The "Sense Sequence" column sequences are disclosed as SEQ ID NOS 979-1141, respectively, in order of appearance, and the "Antisense Sequence" column sequences are disclosed as SEQ ID NOS 1142-1304, respectively, in order of appearance)

| Duplex Name | Sense Oligo Name | Sense Sequence | Antis Oligo Name | Antisense Sequence | Position in NM_000488.3 |
|---|---|---|---|---|---|
| AD-59273.1 | A-120252.1 | UUGAGGACGGCUUCAGUUU | A-120253.1 | AAACUGAAGCCGUCCUCAA | 1189-1207 |
| AD-59274.1 | A-120268.1 | CGGCGUGUCUGGGAACUGU | A-120269.1 | ACAGUUCCCAGACACGCCG | 351-369 |
| AD-59275.1 | A-120284.1 | UUAACACCAUUUACUUCAA | A-120285.1 | UUGAAGUAAAUGGUGUUAA | 862-880 |
| AD-59276.1 | A-120300.1 | CCCUGAAAAGUCCAAACUC | A-120301.1 | GAGUUUGGACUUUUCAGGG | 1250-1268 |
| AD-59277.1 | A-120316.1 | CGAGAUGACCUCUAUGUCU | A-120317.1 | AGACAUAGAGGUCAUCUCG | 1290-1308 |
| AD-59278.1 | A-120332.1 | UCUACAAGGCUGAUGGAGA | A-120333.1 | UCUCCAUCAGCCUUGUAGA | 931-949 |
| AD-59279.1 | A-120254.1 | AGCUCACUGUUCUGGUGCU | A-120255.1 | AGCACCAGAACAGUGAGCU | 841-859 |
| AD-59280.1 | A-120270.1 | AGGAGCAGCUGCAAGACAU | A-120271.1 | AUGUCUUGCAGCUGCUCCU | 1210-1228 |
| AD-59281.1 | A-120286.1 | GCCACCAACCGGCGUGUCU | A-120287.1 | AGACACGCCGGUUGGUGGC | 342-360 |
| AD-59282.1 | A-120302.1 | CAGAACAGAAGAUCCCGGA | A-120303.1 | UCCGGGAUCUUCUGUUCUG | 322-340 |
| AD-59283.1 | A-120318.1 | CCUUGUCGAUCUGUUCAGC | A-120319.1 | GCUGAACAGAUCGACAAGG | 1232-1250 |
| AD-59284.1 | A-120334.1 | AGGCAAGUUCCGUUAUCGG | A-120335.1 | CCGAUAACGGAACUUGCCU | 980-998 |
| AD-59285.1 | A-120256.1 | UUUUGUCCUUGCUGCUCAU | A-120257.1 | AUGAGCAGCAAGGACAAAA | 172-190 |
| AD-59286.1 | A-120272.1 | AGACCUACCAGGACAUCAG | A-120273.1 | CUGAUGUCCUGGUAGGUCU | 682-700 |
| AD-59287.1 | A-120288.1 | AACUGAACUGCCGACUCUA | A-120289.1 | UAGAGUCGGCAGUUCAGUU | 589-607 |
| AD-59288.1 | A-120304.1 | CAUUUACUUCAAGGGCCUG | A-120305.1 | CAGGCCCUUGAAGUAAAUG | 869-887 |
| AD-59289.1 | A-120320.1 | CCCUGGACUUCAAGGAAAA | A-120321.1 | UUUUCCUUGAAGUCCAGGG | 730-748 |
| AD-59290.1 | A-120336.1 | AGCUGCAAGUACCGCUGUU | A-120337.1 | AACAGCGGUACUUGCAGCU | 1361-1379 |
| AD-59291.1 | A-120258.1 | ACACAAGGAAGGAACUGUU | A-120259.1 | AACAGUUCCUUCCUUGUGU | 913-931 |
| AD-59292.1 | A-120274.1 | GCAACUGAGGAUGAGGGCU | A-120275.1 | AGCCCUCAUCCUCAGUUGC | 303-321 |
| AD-59293.1 | A-120290.1 | GUAGCCAACCCUUGUGUUA | A-120291.1 | UAACACAAGGGUUGGCUAC | 1491-1509 |
| AD-59294.1 | A-120306.1 | GUUUGUGAACAGAAGUAAA | A-120307.1 | UUUACUUCUGUUCACAAAC | 1550-1568 |
| AD-59295.1 | A-120322.1 | GGGUGACUUUCAAGGCCAA | A-120323.1 | UUGGCCUUGAAAGUCACCC | 1411-1429 |
| AD-59296.1 | A-120338.1 | UUAUCGGCGCGUGGCUGAA | A-120339.1 | UUCAGCCACGCGCCGAUAA | 992-1010 |
| AD-59297.1 | A-120260.1 | CCACUUCUUCUUUGCCAAA | A-120261.1 | UUUGGCAAAGAAGAAGUGG | 572-590 |
| AD-59298.1 | A-120276.1 | AACACCAUUUACUUCAAGG | A-120277.1 | CCUUGAAGUAAAUGGUGUU | 864-882 |
| AD-59299.1 | A-120292.1 | GAUGGAGAGUCGUGUUCAG | A-120293.1 | CUGAACACGACUCUCCAUC | 942-960 |
| AD-59300.1 | A-120308.1 | CACCAUUUACUUCAAGGGC | A-120309.1 | GCCCUUGAAGUAAAUGGUG | 866-884 |
| AD-59301.1 | A-120324.1 | UUUACUUCAAGGGCCUGUG | A-120325.1 | CACAGGCCCUUGAAGUAAA | 871-889 |
| AD-59302.1 | A-120340.1 | UAAGAGAAGUUCCUCUGAA | A-120341.1 | UUCAGAGGAACUUCUCUUA | 1450-1468 |
| AD-59303.1 | A-120262.1 | GCGGGACAUUCCCAUGAAU | A-120263.1 | AUUCAUGGGAAUGUCCCGC | 251-269 |
| AD-59304.1 | A-120278.1 | UGCCCCACCCUGUCCUCUG | A-120279.1 | CAGAGGACAGGGUGGGGCA | 21-Mar |
| AD-59305.1 | A-120294.1 | UGGUUAACACCAUUUACUU | A-120295.1 | AAGUAAAUGGUGUUAACCA | 859-877 |
| AD-59306.1 | A-120310.1 | CGGAUUGCCUCAGAUCACA | A-120311.1 | UGUGAUCUGAGGCAAUCCG | 62-80 |
| AD-59307.1 | A-120326.1 | CCAGGACAUCAGUGAGUUG | A-120327.1 | CAACUCACUGAUGUCCUGG | 689-707 |

TABLE 20-continued

AT3 (SERPINC1) unmodified sequences (The "Sense Sequence" column sequences are disclosed as SEQ ID NOS 979-1141, respectively, in order of appearance, and the "Antisense Sequence" column sequences are disclosed as SEQ ID NOS 1142-1304, respectively, in order of appearance)

| Duplex Name | Sense Oligo Name | Sense Sequence | Antis Oligo Name | Antisense Sequence | Position in NM_000488.3 |
|---|---|---|---|---|---|
| AD-59308.1 | A-120342.1 | CCAGUUUUCAGGCGGAUUG | A-120343.1 | CAAUCCGCCUGAAAACUGG | 50-68 |
| AD-59309.1 | A-120264.1 | CACCAUAUCUGAGAAAACA | A-120265.1 | UGUUUUCUCAGAUAUGGUG | 542-560 |
| AD-59310.1 | A-120280.1 | AAGUAAAAAUAAAUACAAA | A-120281.1 | UUUGUAUUUAUUUUUACUU | 1562-1580 |
| AD-59311.1 | A-120296.1 | GCACCCAGGUGCUUGAGUU | A-120297.1 | AACUCAAGCACCUGGGUGC | 1012-1030 |
| AD-59312.1 | A-120312.1 | UAACACCAUUUACUUCAAG | A-120313.1 | CUUGAAGUAAAUGGUGUUA | 863-881 |
| AD-59313.1 | A-120328.1 | CCUUCAAAGGUGAUGACAU | A-120329.1 | AUGUCAUCACCUUUGAAGG | 1033-1051 |
| AD-59314.1 | A-120344.1 | CAAGGCCAAUUCCCGCUUU | A-120345.1 | AAAGCGGGAAUUGGCCUUG | 371-389 |
| AD-59315.1 | A-120360.1 | UCAGUUUGAAGGAGCAGCU | A-120361.1 | AGCUGCUCCUUCAAACUGA | 1201-1219 |
| AD-59316.1 | A-120376.1 | GGGACUGCGUGACCUGUCA | A-120377.1 | UGACAGGUCACGCAGUCCC | 199-217 |
| AD-59317.1 | A-120392.1 | UCAGCCAAUCGCCUUUUUG | A-120393.1 | CAAAAAGGCGAUUGGCUGA | 639-657 |
| AD-59318.1 | A-120408.1 | CCUCGGAAGCCAUCAAUGA | A-120409.1 | UCAUUGAUGGCUUCCGAGG | 823-841 |
| AD-59319.1 | A-120424.1 | GACAAUGAUAACAUUUUCC | A-120425.1 | GGAAAAUGUUAUCAUUGUC | 429-447 |
| AD-59320.1 | A-120346.1 | CUUAUUCUUUGCACCUCUU | A-120347.1 | AAGAGGUGCAAAGAAUAAG | 1521-1539 |
| AD-59321.1 | A-120362.1 | AUUGCUGGCCGUUCGCUAA | A-120363.1 | UUAGCGAACGGCCAGCAAU | 1383-1401 |
| AD-59322.1 | A-120378.1 | AAAUGAAGAAGGCAGUGAA | A-120379.1 | UUCACUGCCUUCUUCAUUU | 1340-1358 |
| AD-59323.1 | A-120394.1 | UGAGUUGGUAUAUGGAGCC | A-120395.1 | GGCUCCAUAUACCAACUCA | 701-719 |
| AD-59324.1 | A-120410.1 | UCCAGCAACUGAUGGAGGU | A-120411.1 | ACCUCCAUCAGUUGCUGGA | 511-529 |
| AD-59325.1 | A-120426.1 | AACUGUAACCUCUGGAAAA | A-120427.1 | UUUUCCAGAGGUUACAGUU | 140-158 |
| AD-59326.1 | A-120348.1 | UCAACAAAUGGGUGUCCAA | A-120349.1 | UUGGACACCCAUUUGUUGA | 772-790 |
| AD-59327.1 | A-120364.1 | GAUUAGCGGCCAUGUAUUC | A-120365.1 | GAAUACAUGGCCGCUAAUC | 109-127 |
| AD-59328.1 | A-120380.1 | GUGCUUGAGUUGCCCUUCA | A-120381.1 | UGAAGGGCAACUCAAGCAC | 1020-1038 |
| AD-59329.1 | A-120396.1 | UGCAGAAGGCCGAGAUGAC | A-120397.1 | GUCAUCUCGGCCUUCUGCA | 1280-1298 |
| AD-59330.1 | A-120412.1 | CUAUUUUUGGUUUGUGAAC | A-120413.1 | GUUCACAAACCAAAAAUAG | 1541-1559 |
| AD-59331.1 | A-120428.1 | CAGUGAAGCAGCUGCAAGU | A-120429.1 | ACUUGCAGCUGCUUCACUG | 1352-1370 |
| AD-59332.1 | A-120350.1 | GUGUCCAAUAAGACCGAAG | A-120351.1 | CUUCGGUCUUAUUGGACAC | 783-801 |
| AD-59333.1 | A-120366.1 | AUGAAUUGGAGGAGAUGAU | A-120367.1 | AUCAUCUCCUCCAAUUCAU | 1141-1159 |
| AD-59334.1 | A-120382.1 | AUCUAUGAUGUACCAGGAA | A-120383.1 | UUCCUGGUACAUCAUAGAU | 962-980 |
| AD-59335.1 | A-120398.1 | CCAUAAGGCAUUUCUUGAG | A-120399.1 | CUCAAGAAAUGCCUUAUGG | 1319-1337 |
| AD-59336.1 | A-120414.1 | AUGCAUUCCAUAAGGCAUU | A-120415.1 | AAUGCCUUAUGGAAUGCAU | 1312-1330 |
| AD-59337.1 | A-120430.1 | UGGUGCUGGUUAACACCAU | A-120431.1 | AUGGUGUUAACCAGCACCA | 853-871 |
| AD-59338.1 | A-120352.1 | AUCUGUUCAGCCCUGAAAA | A-120353.1 | UUUUCAGGGCUGAACAGAU | 1240-1258 |
| AD-59339.1 | A-120368.1 | AGAUGAUGCUGGUGGUCCA | A-120369.1 | UGGACCACCAGCAUCAUCU | 1153-1171 |
| AD-59340.1 | A-120384.1 | AUAUGGAGCCAAGCUCCAG | A-120385.1 | CUGGAGCUUGGCUCCAUAU | 710-728 |
| AD-59341.1 | A-120400.1 | CCGAAUCACCGAUGUCAUU | A-120401.1 | AAUGACAUCGGUGAUUCGG | 803-821 |
| AD-59342.1 | A-120416.1 | GCAGAGCAAUCCAGAGCGG | A-120417.1 | CCGCUCUGGAUUGCUCUGC | 750-768 |
| AD-59343.1 | A-120432.1 | ACACCAUUUACUUCAAGGG | A-120433.1 | CCCUUGAAGUAAAUGGUGU | 865-883 |

TABLE 20-continued

AT3 (SERPINC1) unmodified sequences (The "Sense Sequence" column sequences are disclosed as SEQ ID NOS 979-1141, respectively, in order of appearance, and the "Antisense Sequence" column sequences are disclosed as SEQ ID NOS 1142-1304, respectively, in order of appearance)

| Duplex Name | Sense Oligo Name | Sense Sequence | Antis Oligo Name | Antisense Sequence | Position in NM_000488.3 |
|---|---|---|---|---|---|
| AD-59344.1 | A-120354.1 | GUACCAGGAAGGCAAGUUC | A-120355.1 | GAACUUGCCUUCCUGGUAC | 971-989 |
| AD-59345.1 | A-120370.1 | UGCCCAAGCCUGAGAAGAG | A-120371.1 | CUCUUCUCAGGCUUGGGCA | 1069-1087 |
| AD-59346.1 | A-120386.1 | UUCUUUGCCAAACUGAACU | A-120387.1 | AGUUCAGUUUGGCAAAGAA | 579-597 |
| AD-59347.1 | A-120402.1 | UGGCCAAGGUAGAGAAGGA | A-120403.1 | UCCUUCUCUACCUUGGCCA | 1090-1108 |
| AD-59348.1 | A-120418.1 | UGCUGCAAGAGUGGCUGGA | A-120419.1 | UCCAGCCACUCUUGCAGCA | 1123-1141 |
| AD-59349.1 | A-120434.1 | CCAUGUGCAUUUACCGCUC | A-120435.1 | GAGCGGUAAAUGCACAUGG | 271-289 |
| AD-59350.1 | A-120356.1 | AGACAUGGGCCUUGUCGAU | A-120357.1 | AUCGACAAGGCCCAUGUCU | 1223-1241 |
| AD-59351.1 | A-120372.1 | UUUUGGAGACAAAUCCCUU | A-120373.1 | AAGGGAUUUGUCUCCAAAA | 653-671 |
| AD-59352.1 | A-120388.1 | GGAUGAGGGCUCAGAACAG | A-120389.1 | CUGUUCUGAGCCCUCAUCC | 311-329 |
| AD-59353.1 | A-120404.1 | CGGCUUUUGCUAUGACCAA | A-120405.1 | UUGGUCAUAGCAAAAGCCG | 469-487 |
| AD-59354.1 | A-120420.1 | AGCUCCAGCCCCUGGACUU | A-120421.1 | AAGUCCAGGGGCUGGAGCU | 721-739 |
| AD-59355.1 | A-120436.1 | CUGAUCAGAUCCACUUCUU | A-120437.1 | AAGAAGUGGAUCUGAUCAG | 562-580 |
| AD-59356.1 | A-120358.1 | UGCUGGUGGUCCACAUGCC | A-120359.1 | GGCAUGUGGACCACCAGCA | 1159-1177 |
| AD-59357.1 | A-120374.1 | GCGAGAUUUAGAGGAAAGA | A-120375.1 | UCUUUCCUCUAAAUCUCGC | 30-48 |
| AD-59358.1 | A-120390.1 | CUGCUCAUUGGCUUCUGGG | A-120391.1 | CCCAGAAGCCAAUGAGCAG | 183-201 |
| AD-59359.1 | A-120406.1 | CCUUCAAUGAGACCUACCA | A-120407.1 | UGGUAGGUCUCAUUGAAGG | 673-691 |
| AD-59360.1 | A-120422.1 | ACCAUUUACUUCAAGGGCC | A-120423.1 | GGCCCUUGAAGUAAAUGGU | 867-885 |
| AD-59587.1 | A-120438.1 | GCACCUCUUCCUAUUUUUG | A-120439.1 | CAAAAAUAGGAAGAGGUGC | 1531-1549 |
| AD-59588.1 | A-120454.1 | GUGGCUGAAGGCACCCAGG | A-120455.1 | CCUGGGUGCCUUCAGCCAC | 1002-1020 |
| AD-59589.1 | A-120470.1 | UCCGCAUUGAGGACGGCUU | A-120471.1 | AAGCCGUCCUCAAUGCGGA | 1183-1201 |
| AD-59590.1 | A-120486.1 | UGGACAUCUGCACAGCCAA | A-120487.1 | UUGGCUGUGCAGAUGUCCA | 229-247 |
| AD-59591.1 | A-120502.1 | GUCCAAACUCCCAGGUAUU | A-120503.1 | AAUACCUGGGAGUUUGGAC | 1259-1277 |
| AD-59592.1 | A-120518.1 | AGAAGGAACUCACCCCAGA | A-120519.1 | UCUGGGGUGAGUUCCUUCU | 1102-1120 |
| AD-59593.1 | A-120440.1 | UCUUGAGGUAAAUGAAGAA | A-120441.1 | UUCUUCAUUUACCUCAAGA | 1331-1349 |
| AD-59594.1 | A-120456.1 | AGCCCUGUGGACAUCUGCA | A-120457.1 | UGCAGAUGUCCACAGGGCU | 222-240 |
| AD-59595.1 | A-120472.1 | CAGAGCGGCCAUCAACAAA | A-120473.1 | UUUGUUGAUGGCCGCUCUG | 761-779 |
| AD-59596.1 | A-120488.1 | AUUUAAGUUUGACACCAUA | A-120489.1 | UAUGGUGUCAAACUUAAAU | 530-548 |
| AD-59597.1 | A-120504.1 | UGAGAAGAGCCUGGCCAAG | A-120505.1 | CUUGGCCAGGCUCUUCUCA | 1079-1097 |
| AD-59598.1 | A-120520.1 | UCACCAUGGUCCUCAUCUU | A-120521.1 | AAGAUGAGGACCAUGGUGA | 1051-1069 |
| AD-59599.1 | A-120442.1 | GGAAGGAACUGUUCUACAA | A-120443.1 | UUGUAGAACAGUUCCUUCC | 919-937 |
| AD-59600.1 | A-120458.1 | CUGGUUUUUAUAAGAGAAG | A-120459.1 | CUUCUCUUAUAAAAACCAG | 1440-1458 |
| AD-59601.1 | A-120474.1 | CUGGGUGCCUGUAAUGACA | A-120475.1 | UGUCAUUACAGGCACCCAG | 489-507 |
| AD-59602.1 | A-120490.1 | GUACCGCUGUUGUGAUUGC | A-120491.1 | GCAAUCACAACAGCGGUAC | 1369-1387 |
| AD-59603.1 | A-120506.1 | UCUAUCAGCACCUGGCAGA | A-120507.1 | UCUGCCAGGUGCUGAUAGA | 400-418 |
| AD-59604.1 | A-120522.1 | CUGGCAGAUUCCAAGAAUG | A-120523.1 | CAUUCUUGGAAUCUGCCAG | 411-429 |

TABLE 20-continued

AT3 (SERPINC1) unmodified sequences (The "Sense Sequence" column sequences are disclosed as SEQ ID NOS 979-1141, respectively, in order of appearance, and the "Antisense Sequence" column sequences are disclosed as SEQ ID NOS 1142-1304, respectively, in order of appearance)

| Duplex Name | Sense Oligo Name | Sense Sequence | Antis Oligo Name | Antisense Sequence | Position in NM_000488.3 |
|---|---|---|---|---|---|
| AD-59605.1 | A-120444.1 | CGAUGUCAUUCCCUCGGAA | A-120445.1 | UUCCGAGGGAAUGACAUCG | 812-830 |
| AD-59606.1 | A-120460.1 | GCUUCUGGGACUGCGUGAC | A-120461.1 | GUCACGCAGUCCCAGAAGC | 193-211 |
| AD-59607.1 | A-120476.1 | CCUGUCACGGGAGCCCUGU | A-120477.1 | ACAGGGCUCCCGUGACAGG | 211-229 |
| AD-59608.1 | A-120492.1 | AUUUACUUCAAGGGCCUGU | A-120493.1 | ACAGGCCCUUGAAGUAAAU | 870-888 |
| AD-59609.1 | A-120508.1 | UGCUACCACUUUCUAUCAG | A-120509.1 | CUGAUAGAAAGUGGUAGCA | 389-407 |
| AD-59610.1 | A-120524.1 | GGAACUGUCCAAGGCCAAU | A-120525.1 | AUUGGCCUUGGACAGUUCC | 362-380 |
| AD-59611.1 | A-120446.1 | ACAAAUCCUCCAAGUUAGU | A-120447.1 | ACUAACUUGGAGGAUUUGU | 619-637 |
| AD-59612.1 | A-120462.1 | AUUUACCGCUCCCCGGAGA | A-120463.1 | UCUCCGGGGAGCGGUAAAU | 279-297 |
| AD-59613.1 | A-120478.1 | ACCCCUGAGUAUCUCCACG | A-120479.1 | CGUGGAGAUACUCAGGGGU | 452-470 |
| AD-59614.1 | A-120494.1 | CACUAUCUCCACUUGCCCA | A-120495.1 | UGGGCAAGUGGAGAUAGUG | 79-97 |
| AD-59615.1 | A-120510.1 | AAAUACAAACUACUUCCAU | A-120511.1 | AUGGAAGUAGUUUGUAUUU | 1572-1590 |
| AD-59616.1 | A-120526.1 | CUGGUUAACACCAUUUACU | A-120527.1 | AGUAAAUGGUGUUAACCAG | 858-876 |
| AD-59617.1 | A-120448.1 | UCAUCUUGCCCAAGCCUGA | A-120449.1 | UCAGGCUUGGGCAAGAUGA | 1063-1081 |
| AD-59618.1 | A-120464.1 | CCUCAGAUCACACUAUCUC | A-120465.1 | GAGAUAGUGUGAUCUGAGG | 69-87 |
| AD-59619.1 | A-120480.1 | CUGUCCUCUGGAACCUCUG | A-120481.1 | CAGAGGUUCCAGAGGACAG | 30-Dec |
| AD-59620.1 | A-120496.1 | CCCUGUGGAAGAUUAGCGG | A-120497.1 | CCGCUAAUCUUCCACAGGG | 99-117 |
| AD-59621.1 | A-120512.1 | AUCUCCACGGCUUUUGCUA | A-120513.1 | UAGCAAAAGCCGUGGAGAU | 462-480 |
| AD-59622.1 | A-120528.1 | GUGGCUGGAUGAAUUGGAG | A-120529.1 | CUCCAAUUCAUCCAGCCAC | 1133-1151 |
| AD-59623.1 | A-120450.1 | CAAGUUAGUAUCAGCCAAU | A-120451.1 | AUUGGCUGAUACUAACUUG | 629-647 |
| AD-59624.1 | A-120466.1 | GUGAUGACAUCACCAUGGU | A-120467.1 | ACCAUGGUGAUGUCAUCAC | 1042-1060 |
| AD-59625.1 | A-120482.1 | UUCCAAGAAUGACAAUGAU | A-120483.1 | AUCAUUGUCAUUCUUGGAA | 419-437 |
| AD-59626.1 | A-120498.1 | UGAUGGAGGUAUUUAAGUU | A-120499.1 | AACUUAAAUACCUCCAUCA | 520-538 |
| AD-59627.1 | A-120514.1 | GUAUUCCAAUGUGAUAGGA | A-120515.1 | UCCUAUCACAUUGGAAUAC | 122-140 |
| AD-59628.1 | A-120530.1 | CAGCCAAGCCGCGGGACAU | A-120531.1 | AUGUCCCGCGGCUUGGCUG | 241-259 |
| AD-59629.1 | A-120452.1 | CAUGCCCCGCUUCCGCAUU | A-120453.1 | AAUGCGGAAGCGGGGCAUG | 1172-1190 |
| AD-59630.1 | A-120468.1 | AUGUGAUAGGAACUGUAAC | A-120469.1 | GUUACAGUUCCUAUCACAU | 130-148 |
| AD-59631.1 | A-120484.1 | ACAAAUCCCUUACCUUCAA | A-120485.1 | UUGAAGGUAAGGGAUUUGU | 661-679 |
| AD-59632.1 | A-120500.1 | AGGUUUAUCUUUUGUCCUU | A-120501.1 | AAGGACAAAAGAUAAACCU | 163-181 |
| AD-59633.1 | A-120516.1 | AGAUCCCGGAGGCCACCAA | A-120517.1 | UUGGUGGCCUCCGGGAUCU | 331-349 |
| AD-59634.1 | A-120532.1 | ACAUUUUCCUGUCACCCCU | A-120533.1 | AGGGGUGACAGGAAAAUGU | 439-457 |
| AD-59635.1 | A-120548.1 | GGCCUUUCCUGGUUUUUAU | A-120549.1 | AUAAAAACCAGGAAAGGCC | 1432-1450 |
| AD-59636.1 | A-120564.1 | UUGUGUUAAGUAAAAUGUU | A-120565.1 | AACAUUUUACUUAACACAA | 1502-1520 |
| AD-59637.1 | A-120534.1 | CAAGGAAAAUGCAGAGCAA | A-120535.1 | UUGCUCUGCAUUUUCCUUG | 740-758 |
| AD-59638.1 | A-120550.1 | CUGAGAAAACAUCUGAUCA | A-120551.1 | UGAUCAGAUGUUUUCUCAG | 550-568 |
| AD-59639.1 | A-120566.1 | UUACUUCAAGGGCCUGUGG | A-120567.1 | CCACAGGCCCUUGAAGUAA | 872-890 |
| AD-59640.1 | A-120536.1 | ACCCCAACAGGGUGACUUU | A-120537.1 | AAAGUCACCCUGUUGGGGU | 1402-1420 |

TABLE 20-continued

AT3 (SERPINC1) unmodified sequences (The "Sense Sequence" column sequences are disclosed as SEQ ID NOS 979-1141, respectively, in order of appearance, and the "Antisense Sequence" column sequences are disclosed as SEQ ID NOS 1142-1304, respectively, in order of appearance)

| Duplex Name | Sense Oligo Name | Sense Sequence | Antis Oligo Name | Antisense Sequence | Position in NM_000488.3 |
|---|---|---|---|---|---|
| AD-59641.1 | A-120552.1 | CCAGGUAUUGUUGCAGAAG | A-120553.1 | CUUCUGCAACAAUACCUGG | 1269-1287 |
| AD-59642.1 | A-120568.1 | GCCUGUGGAAGUCAAAGUU | A-120569.1 | AACUUUGACUUCCACAGGC | 883-901 |
| AD-59643.1 | A-120538.1 | UGGAACCUCUGCGAGAUUU | A-120539.1 | AAAUCUCGCAGAGGUUCCA | 20-38 |
| AD-59644.1 | A-120554.1 | AGCCCUGAGAACACAAGGA | A-120555.1 | UCCUUGUGUUCUCAGGGCU | 903-921 |
| AD-59645.1 | A-120570.1 | CUCUAUGUCUCAGAUGCAU | A-120571.1 | AUGCAUCUGAGACAUAGAG | 1299-1317 |
| AD-59646.1 | A-120540.1 | AAGACCGAAGGCCGAAUCA | A-120541.1 | UGAUUCGGCCUUCGGUCUU | 792-810 |
| AD-59647.1 | A-120556.1 | UAAAAUGUUCUUAUUCUUU | A-120557.1 | AAAGAAUAAGAACAUUUUA | 1512-1530 |
| AD-59648.1 | A-120572.1 | UCUGGAAAAAGGAAGGUUU | A-120573.1 | AAACCUUCCUUUUUCCAGA | 150-168 |
| AD-59649.1 | A-120542.1 | UUCAAGGCCAACAGGCCUU | A-120543.1 | AAGGCCUGUUGGCCUUGAA | 1419-1437 |
| AD-59650.1 | A-120558.1 | GAAGUCAAAGUUCAGCCCU | A-120559.1 | AGGGCUGAACUUUGACUUC | 890-908 |
| AD-59651.1 | A-120574.1 | CCAUCAAUGAGCUCACUGU | A-120575.1 | ACAGUGAGCUCAUUGAUGG | 832-850 |
| AD-59652.1 | A-120544.1 | CUCUGAACACUAUUAUCUU | A-120545.1 | AAGAUAAUAGUGUUCAGAG | 1462-1480 |
| AD-59653.1 | A-120560.1 | UGCUGGUUAACACCAUUUA | A-120561.1 | UAAAUGGUGUUAACCAGCA | 856-874 |
| AD-59654.1 | A-120546.1 | AGAGGAAAGAACCAGUUUU | A-120547.1 | AAAACUGGUUCUUUCCUCU | 39-57 |
| AD-59655.1 | A-120562.1 | UGCCCAGCCCUGUGGAAGA | A-120563.1 | UCUUCCACAGGGCUGGGCA | 92-110 |

TABLE 21

AT3 (SERPINC1) modified sequences (The "Sense Sequence" column sequences are disclosed as SEQ ID NOS 1305-1467, respectively, in order of appearance, and the "Antisense Sequence" column sequences are disclosed as SEQ ID NOS 1468-1630, respectively, in order of appearance)

| Duplex Name | Sense Oligo Name | oligoSeq | Antis Oligo Name | oligoSeq |
|---|---|---|---|---|
| AD-59267.1 | A-120250.1 | GGAGAAGAAGGCAACUGAGdTdT | A-120251.1 | CUCAGUUGCCUUCUUCUCCdTdT |
| AD-59268.1 | A-120266.1 | UGACCAAGCUGGGUGCCUGdTdT | A-120267.1 | CAGGCACCCAGCUUGGUCAdTdT |
| AD-59269.1 | A-120282.1 | GGUUAACACCAUUUACUUCdTdT | A-120283.1 | GAAGUAAAUGGUGUUAACCdTdT |
| AD-59270.1 | A-120298.1 | GCUGGUUAACACCAUUUACdTdT | A-120299.1 | GUAAAUGGUGUUAACCAGCdTdT |
| AD-59271.1 | A-120314.1 | UAAUGACACCCUCCAGCAAdTdT | A-120315.1 | UUGCUGGAGGGUGUCAUUAdTdT |
| AD-59272.1 | A-120330.1 | CGUGUUCAGCAUCUAUGAUdTdT | A-120331.1 | AUCAUAGAUGCUGAACACGdTdT |
| AD-59273.1 | A-120252.1 | UUGAGGACGGCUUCAGUUUdTdT | A-120253.1 | AAACUGAAGCCGUCCUCAAdTdT |
| AD-59274.1 | A-120268.1 | CGGCGUGUCUGGGAACUGUdTdT | A-120269.1 | ACAGUUCCCAGACACGCCGdTdT |
| AD-59275.1 | A-120284.1 | UUAACACCAUUUACUUCAAdTdT | A-120285.1 | UUGAAGUAAAUGGUGUUAAdTdT |
| AD-59276.1 | A-120300.1 | CCCUGAAAAGUCCAAACUCdTdT | A-120301.1 | GAGUUUGGACUUUUCAGGGdTdT |
| AD-59277.1 | A-120316.1 | CGAGAUGACCUCUAUGUCUdTdT | A-120317.1 | AGACAUAGAGGUCAUCUCGdTdT |
| AD-59278.1 | A-120332.1 | UCUACAAGGCUGAUGGAGAdTdT | A-120333.1 | UCUCCAUCAGCCUUGUAGAdTdT |
| AD-59279.1 | A-120254.1 | AGCUCACUGUUCUGGUGCUdTdT | A-120255.1 | AGCACCAGAACAGUGAGCUdTdT |

TABLE 21-continued

AT3 (SERPINC1) modified sequences (The "Sense Sequence" column sequences are disclosed as SEQ ID NOS 1305-1467, respectively, in order of appearance, and the "Antisense Sequence" column sequences are disclosed as SEQ ID NOS 1468-1630, respectively, in order of appearance)

| Duplex Name | Sense Oligo Name | oligoSeq | Antis Oligo Name | oligoSeq |
|---|---|---|---|---|
| AD-59280.1 | A-120270.1 | AGGAGCAGCUGCAAGACAUdTdT | A-120271.1 | AUGUCUUGCAGCUGCUCCUdTdT |
| AD-59281.1 | A-120286.1 | GCCACCAACCGGCGUGUCUdTdT | A-120287.1 | AGACACGCCGGUUGGUGGCdTdT |
| AD-59282.1 | A-120302.1 | CAGAACAGAAGAUCCCGGAdTdT | A-120303.1 | UCCGGGAUCUUCUGUUCUGdTdT |
| AD-59283.1 | A-120318.1 | CCUUGUCGAUCUGUUCAGCdTdT | A-120319.1 | GCUGAACAGAUCGACAAGGdTdT |
| AD-59284.1 | A-120334.1 | AGGCAAGUUCCGUUAUCGGdTdT | A-120335.1 | CCGAUAACGGAACUUGCCUdTdT |
| AD-59285.1 | A-120256.1 | UUUUGUCCUUGCUGCUCAUdTdT | A-120257.1 | AUGAGCAGCAAGGACAAAAdTdT |
| AD-59286.1 | A-120272.1 | AGACCUACCAGGACAUCAGdTdT | A-120273.1 | CUGAUGUCCUGGUAGGUCUdTdT |
| AD-59287.1 | A-120288.1 | AACUGAACUGCCGACUCUAdTdT | A-120289.1 | UAGAGUCGGCAGUUCAGUUdTdT |
| AD-59288.1 | A-120304.1 | CAUUUACUUCAAGGGCCUGdTdT | A-120305.1 | CAGGCCCUUGAAGUAAAUGdTdT |
| AD-59289.1 | A-120320.1 | CCCUGGACUUCAAGGAAAAdTdT | A-120321.1 | UUUUCCUUGAAGUCCAGGGdTdT |
| AD-59290.1 | A-120336.1 | AGCUGCAAGUACCGCUGUUdTdT | A-120337.1 | AACAGCGGUACUUGCAGCUdTdT |
| AD-59291.1 | A-120258.1 | ACACAAGGAAGGAACUGUUdTdT | A-120259.1 | AACAGUUCCUUCCUUGUGUdTdT |
| AD-59292.1 | A-120274.1 | GCAACUGAGGAUGAGGGCUdTdT | A-120275.1 | AGCCCUCAUCCUCAGUUGCdTdT |
| AD-59293.1 | A-120290.1 | GUAGCCAACCCUUGUGUUAdTdT | A-120291.1 | UAACACAAGGGUUGGCUACdTdT |
| AD-59294.1 | A-120306.1 | GUUUGUGAACAGAAGUAAAdTdT | A-120307.1 | UUUACUUCUGUUCACAAACdTdT |
| AD-59295.1 | A-120322.1 | GGGUGACUUUCAAGGCCAAdTdT | A-120323.1 | UUGGCCUUGAAAGUCACCCdTdT |
| AD-59296.1 | A-120338.1 | UUAUCGGCGCGUGGCUGAAdTdT | A-120339.1 | UUCAGCCACGCGCCGAUAAdTdT |
| AD-59297.1 | A-120260.1 | CCACUUCUUCUUUGCCAAAdTdT | A-120261.1 | UUUGGCAAAGAAGAAGUGGdTdT |
| AD-59298.1 | A-120276.1 | AACACCAUUUACUUCAAGGdTdT | A-120277.1 | CCUUGAAGUAAAUGGUGUUdTdT |
| AD-59299.1 | A-120292.1 | GAUGGAGAGUCGUGUUCAGdTdT | A-120293.1 | CUGAACACGACUCUCCAUCdTdT |
| AD-59300.1 | A-120308.1 | CACCAUUUACUUCAAGGGCdTdT | A-120309.1 | GCCCUUGAAGUAAAUGGUGdTdT |
| AD-59301.1 | A-120324.1 | UUUACUUCAAGGGCCUGUGdTdT | A-120325.1 | CACAGGCCCUUGAAGUAAAdTdT |
| AD-59302.1 | A-120340.1 | UAAGAGAAGUUCCUCUGAAdTdT | A-120341.1 | UUCAGAGGAACUUCUCUUAdTdT |
| AD-59303.1 | A-120262.1 | GCGGGACAUUCCCAUGAAUdTdT | A-120263.1 | AUUCAUGGGAAUGUCCCGCdTdT |
| AD-59304.1 | A-120278.1 | UGCCCCACCCUGUCCUCUGdTdT | A-120279.1 | CAGAGGACAGGGUGGGGCAdTdT |
| AD-59305.1 | A-120294.1 | UGGUUAACACCAUUUACUUdTdT | A-120295.1 | AAGUAAAUGGUGUUAACCAdTdT |
| AD-59306.1 | A-120310.1 | CGGAUUGCCUCAGAUCACAdTdT | A-120311.1 | UGUGAUCUGAGGCAAUCCGdTdT |
| AD-59307.1 | A-120326.1 | CCAGGACAUCAGUGAGUUGdTdT | A-120327.1 | CAACUCACUGAUGUCCUGGdTdT |
| AD-59308.1 | A-120342.1 | CCAGUUUUCAGGCGGAUUGdTdT | A-120343.1 | CAAUCCGCCUGAAAACUGGdTdT |
| AD-59309.1 | A-120264.1 | CACCAUAUCUGAGAAAACAdTdT | A-120265.1 | UGUUUUCUCAGAUAUGGUGdTdT |
| AD-59310.1 | A-120280.1 | AAGUAAAAAUAAAUACAAAdTdT | A-120281.1 | UUUGUAUUUAUUUUUACUUdTdT |
| AD-59311.1 | A-120296.1 | GCACCCAGGUGCUUGAGUUdTdT | A-120297.1 | AACUCAAGCACCUGGGUGCdTdT |
| AD-59312.1 | A-120312.1 | UAACACCAUUUACUUCAAGdTdT | A-120313.1 | CUUGAAGUAAAUGGUGUUAdTdT |
| AD-59313.1 | A-120328.1 | CCUUCAAAGGUGAUGACAUdTdT | A-120329.1 | AUGUCAUCACCUUUGAAGGdTdT |
| AD-59314.1 | A-120344.1 | CAAGGCCAAUUCCCGCUUUdTdT | A-120345.1 | AAAGCGGGAAUUGGCCUUGdTdT |
| AD-59315.1 | A-120360.1 | UCAGUUUGAAGGAGCAGCUdTdT | A-120361.1 | AGCUGCUCCUUCAAACUGAdTdT |

TABLE 21-continued

AT3 (SERPINC1) modified sequences (The "Sense Sequence" column sequences are disclosed as SEQ ID NOS 1305-1467, respectively, in order of appearance, and the "Antisense Sequence" column sequences are disclosed as SEQ ID NOS 1468-1630, respectively, in order of appearance)

| Duplex Name | Sense Oligo Name | oligoSeq | Antis Oligo Name | oligoSeq |
|---|---|---|---|---|
| AD-59316.1 | A-120376.1 | GGGACUGCGUGACCUGUCAdTdT | A-120377.1 | UGACAGGUCACGCAGUCCCdTdT |
| AD-59317.1 | A-120392.1 | UCAGCCAAUCGCCUUUUUGdTdT | A-120393.1 | CAAAAAGGCGAUUGGCUGAdTdT |
| AD-59318.1 | A-120408.1 | CCUCGGAAGCCAUCAAUGAdTdT | A-120409.1 | UCAUUGAUGGCUUCCGAGGdTdT |
| AD-59319.1 | A-120424.1 | GACAAUGAUAACAUUUUCCdTdT | A-120425.1 | GGAAAAUGUUAUCAUUGUCdTdT |
| AD-59320.1 | A-120346.1 | CUUAUUCUUUGCACCUCUUdTdT | A-120347.1 | AAGAGGUGCAAAGAAUAAGdTdT |
| AD-59321.1 | A-120362.1 | AUUGCUGGCCGUUCGCUAAdTdT | A-120363.1 | UUAGCGAACGGCCAGCAAUdTdT |
| AD-59322.1 | A-120378.1 | AAAUGAAGAAGGCAGUGAAdTdT | A-120379.1 | UUCACUGCCUUCUUCAUUUdTdT |
| AD-59323.1 | A-120394.1 | UGAGUUGGUAUAUGGAGCCdTdT | A-120395.1 | GGCUCCAUAUACCAACUCAdTdT |
| AD-59324.1 | A-120410.1 | UCCAGCAACUGAUGGAGGUdTdT | A-120411.1 | ACCUCCAUCAGUUGCUGGAdTdT |
| AD-59325.1 | A-120426.1 | AACUGUAACCUCUGGAAAAdTdT | A-120427.1 | UUUUCCAGAGGUUACAGUUdTdT |
| AD-59326.1 | A-120348.1 | UCAACAAAUGGGUGUCCAAdTdT | A-120349.1 | UUGGACACCCAUUUGUUGAdTdT |
| AD-59327.1 | A-120364.1 | GAUUAGCGGCCAUGUAUUCdTdT | A-120365.1 | GAAUACAUGGCCGCUAAUCdTdT |
| AD-59328.1 | A-120380.1 | GUGCUUGAGUUGCCCUUCAdTdT | A-120381.1 | UGAAGGGCAACUCAAGCACdTdT |
| AD-59329.1 | A-120396.1 | UGCAGAAGGCCGAGAUGACdTdT | A-120397.1 | GUCAUCUCGGCCUUCUGCAdTdT |
| AD-59330.1 | A-120412.1 | CUAUUUUUGGUUUGUGAACdTdT | A-120413.1 | GUUCACAAACCAAAAAUAGdTdT |
| AD-59331.1 | A-120428.1 | CAGUGAAGCAGCUGCAAGUdTdT | A-120429.1 | ACUUGCAGCUGCUUCACUGdTdT |
| AD-59332.1 | A-120350.1 | GUGUCCAAUAAGACCGAAGdTdT | A-120351.1 | CUUCGGUCUUAUUGGACACdTdT |
| AD-59333.1 | A-120366.1 | AUGAAUUGGAGGAGAUGAUdTdT | A-120367.1 | AUCAUCUCCUCCAAUUCAUdTdT |
| AD-59334.1 | A-120382.1 | AUCUAUGAUGUACCAGGAAdTdT | A-120383.1 | UUCCUGGUACAUCAUAGAUdTdT |
| AD-59335.1 | A-120398.1 | CCAUAAGGCAUUUCUUGAGdTdT | A-120399.1 | CUCAAGAAAUGCCUUAUGGdTdT |
| AD-59336.1 | A-120414.1 | AUGCAUUCCAUAAGGCAUUdTdT | A-120415.1 | AAUGCCUUAUGGAAUGCAUdTdT |
| AD-59337.1 | A-120430.1 | UGGUGCUGGUUAACACCAUdTdT | A-120431.1 | AUGGUGUUAACCAGCACCAdTdT |
| AD-59338.1 | A-120352.1 | AUCUGUUCAGCCCUGAAAAdTdT | A-120353.1 | UUUUCAGGGCUGAACAGAUdTdT |
| AD-59339.1 | A-120368.1 | AGAUGAUGCUGGUGGUCCAdTdT | A-120369.1 | UGGACCACCAGCAUCAUCUdTdT |
| AD-59340.1 | A-120384.1 | AUAUGGAGCCAAGCUCCAGdTdT | A-120385.1 | CUGGAGCUUGGCUCCAUAUdTdT |
| AD-59341.1 | A-120400.1 | CCGAAUCACCGAUGUCAUUdTdT | A-120401.1 | AAUGACAUCGGUGAUUCGGdTdT |
| AD-59342.1 | A-120416.1 | GCAGAGCAAUCCAGAGCGGdTdT | A-120417.1 | CCGCUCUGGAUUGCUCUGCdTdT |
| AD-59343.1 | A-120432.1 | ACACCAUUUACUUCAAGGGdTdT | A-120433.1 | CCCUUGAAGUAAAUGGUGUdTdT |
| AD-59344.1 | A-120354.1 | GUACCAGGAAGGCAAGUUCdTdT | A-120355.1 | GAACUUGCCUUCCUGGUACdTdT |
| AD-59345.1 | A-120370.1 | UGCCCAAGCCUGAGAAGAGdTdT | A-120371.1 | CUCUUCUCAGGCUUGGGCAdTdT |
| AD-59346.1 | A-120386.1 | UUCUUUGCCAAACUGAACUdTdT | A-120387.1 | AGUUCAGUUUGGCAAAGAAdTdT |
| AD-59347.1 | A-120402.1 | UGGCCAAGGUAGAGAAGGAdTdT | A-120403.1 | UCCUUCUCUACCUUGGCCAdTdT |
| AD-59348.1 | A-120418.1 | UGCUGCAAGAGUGGCUGGAdTdT | A-120419.1 | UCCAGCCACUCUUGCAGCAdTdT |
| AD-59349.1 | A-120434.1 | CCAUGUGCAUUUACCGCUCdTdT | A-120435.1 | GAGCGGUAAAUGCACAUGGdTdT |
| AD-59350.1 | A-120356.1 | AGACAUGGGCCUUGUCGAUdTdT | A-120357.1 | AUCGACAAGGCCCAUGUCUdTdT |

TABLE 21-continued

AT3 (SERPINC1) modified sequences (The "Sense Sequence" column sequences are disclosed as SEQ ID NOS 1305-1467, respectively, in order of appearance, and the "Antisense Sequence" column sequences are disclosed as SEQ ID NOS 1468-1630, respectively, in order of appearance)

| Duplex Name | Sense Oligo Name | oligoSeq | Antis Oligo Name | oligoSeq |
|---|---|---|---|---|
| AD-59351.1 | A-120372.1 | UUUUGGAGACAAAUCCCUUdTdT | A-120373.1 | AAGGGAUUUGUCUCCAAAAdTdT |
| AD-59352.1 | A-120388.1 | GGAUGAGGGCUCAGAACAGdTdT | A-120389.1 | CUGUUCUGAGCCCUCAUCCdTdT |
| AD-59353.1 | A-120404.1 | CGGCUUUUGCUAUGACCAAdTdT | A-120405.1 | UUGGUCAUAGCAAAAGCCGdTdT |
| AD-59354.1 | A-120420.1 | AGCUCCAGCCCCUGGACUUdTdT | A-120421.1 | AAGUCCAGGGGCUGGAGCUdTdT |
| AD-59355.1 | A-120436.1 | CUGAUCAGAUCCACUUCUUdTdT | A-120437.1 | AAGAAGUGGAUCUGAUCAGdTdT |
| AD-59356.1 | A-120358.1 | UGCUGGUGGUCCACAUGCCdTdT | A-120359.1 | GGCAUGUGGACCACCAGCAdTdT |
| AD-59357.1 | A-120374.1 | GCGAGAUUUAGAGGAAAGAdTdT | A-120375.1 | UCUUUCCUCUAAAUCUCGCdTdT |
| AD-59358.1 | A-120390.1 | CUGCUCAUUGGCUUCUGGGdTdT | A-120391.1 | CCCAGAAGCCAAUGAGCAGdTdT |
| AD-59359.1 | A-120406.1 | CCUUCAAUGAGACCUACCAdTdT | A-120407.1 | UGGUAGGUCUCAUUGAAGGdTdT |
| AD-59360.1 | A-120422.1 | ACCAUUUACUUCAAGGGCCdTdT | A-120423.1 | GGCCCUUGAAGUAAAUGGUdTdT |
| AD-59587.1 | A-120438.1 | GCACCUCUUCCUAUUUUUGdTdT | A-120439.1 | CAAAAAUAGGAAGAGGUGCdTdT |
| AD-59588.1 | A-120454.1 | GUGGCUGAAGGCACCCAGGdTdT | A-120455.1 | CCUGGGUGCCUUCAGCCACdTdT |
| AD-59589.1 | A-120470.1 | UCCGCAUUGAGGACGGCUUdTdT | A-120471.1 | AAGCCGUCCUCAAUGCGGAdTdT |
| AD-59590.1 | A-120486.1 | UGGACAUCUGCACAGCCAAdTdT | A-120487.1 | UUGGCUGUGCAGAUGUCCAdTdT |
| AD-59591.1 | A-120502.1 | GUCCAAACUCCCAGGUAUUdTdT | A-120503.1 | AAUACCUGGGAGUUUGGACdTdT |
| AD-59592.1 | A-120518.1 | AGAAGGAACUCACCCCAGAdTdT | A-120519.1 | UCUGGGGUGAGUUCCUUCUdTdT |
| AD-59593.1 | A-120440.1 | UCUUGAGGUAAAUGAAGAAdTdT | A-120441.1 | UUCUUCAUUUACCUCAAGAdTdT |
| AD-59594.1 | A-120456.1 | AGCCCUGUGGACAUCUGCAdTdT | A-120457.1 | UGCAGAUGUCCACAGGGCUdTdT |
| AD-59595.1 | A-120472.1 | CAGAGCGGCCAUCAACAAAdTdT | A-120473.1 | UUUGUUGAUGGCCGCUCUGdTdT |
| AD-59596.1 | A-120488.1 | AUUUAAGUUUGACACCAUAdTdT | A-120489.1 | UAUGGUGUCAAACUUAAAUdTdT |
| AD-59597.1 | A-120504.1 | UGAGAAGAGCCUGGCCAAGdTdT | A-120505.1 | CUUGGCCAGGCUCUUCUCAdTdT |
| AD-59598.1 | A-120520.1 | UCACCAUGGUCCUCAUCUUdTdT | A-120521.1 | AAGAUGAGGACCAUGGUGAdTdT |
| AD-59599.1 | A-120442.1 | GGAAGGAACUGUUCUACAAdTdT | A-120443.1 | UUGUAGAACAGUUCCUUCCdTdT |
| AD-59600.1 | A-120458.1 | CUGGUUUUUAUAAGAGAAGdTdT | A-120459.1 | CUUCUCUUAUAAAAACCAGdTdT |
| AD-59601.1 | A-120474.1 | CUGGGUGCCUGUAAUGACAdTdT | A-120475.1 | UGUCAUUACAGGCACCCAGdTdT |
| AD-59602.1 | A-120490.1 | GUACCGCUGUUGUGAUUGCdTdT | A-120491.1 | GCAAUCACAACAGCGGUACdTdT |
| AD-59603.1 | A-120506.1 | UCUAUCAGCACCUGGCAGAdTdT | A-120507.1 | UCUGCCAGGUGCUGAUAGAdTdT |
| AD-59604.1 | A-120522.1 | CUGGCAGAUUCCAAGAAUGdTdT | A-120523.1 | CAUUCUUGGAAUCUGCCAGdTdT |
| AD-59605.1 | A-120444.1 | CGAUGUCAUUCCCUCGGAAdTdT | A-120445.1 | UUCCGAGGGAAUGACAUCGdTdT |
| AD-59606.1 | A-120460.1 | GCUUCUGGGACUGCGUGACdTdT | A-120461.1 | GUCACGCAGUCCCAGAAGCdTdT |
| AD-59607.1 | A-120476.1 | CCUGUCACGGGAGCCCUGUdTdT | A-120477.1 | ACAGGGCUCCCGUGACAGGdTdT |
| AD-59608.1 | A-120492.1 | AUUUACUUCAAGGGCCUGUdTdT | A-120493.1 | ACAGGCCCUUGAAGUAAAUdTdT |
| AD-59609.1 | A-120508.1 | UGCUACCACUUUCUAUCAGdTdT | A-120509.1 | CUGAUAGAAAGUGGUAGCAdTdT |
| AD-59610.1 | A-120524.1 | GGAACUGUCCAAGGCCAAUdTdT | A-120525.1 | AUUGGCCUUGGACAGUUCCdTdT |
| AD-59611.1 | A-120446.1 | ACAAAUCCUCCAAGUUAGUdTdT | A-120447.1 | ACUAACUUGGAGGAUUUGUdTdT |
| AD-59612.1 | A-120462.1 | AUUUACCGCUCCCCGGAGAdTdT | A-120463.1 | UCUCCGGGGAGCGGUAAAUdTdT |

TABLE 21-continued

AT3 (SERPINC1) modified sequences (The "Sense Sequence" column sequences are disclosed as SEQ ID NOS 1305-1467, respectively, in order of appearance, and the "Antisense Sequence" column sequences are disclosed as SEQ ID NOS 1468-1630, respectively, in order of appearance)

| Duplex Name | Sense Oligo Name | oligoSeq | Antis Oligo Name | oligoSeq |
|---|---|---|---|---|
| AD-59613.1 | A-120478.1 | ACCCCUGAGUAUCUCCACGdTdT | A-120479.1 | CGUGGAGAUACUCAGGGGUdTdT |
| AD-59614.1 | A-120494.1 | CACUAUCUCCACUUGCCCAdTdT | A-120495.1 | UGGGCAAGUGGAGAUAGUGdTdT |
| AD-59615.1 | A-120510.1 | AAAUACAAACUACUUCCAUdTdT | A-120511.1 | AUGGAAGUAGUUUGUAUUUdTdT |
| AD-59616.1 | A-120526.1 | CUGGUUAACACCAUUUACUdTdT | A-120527.1 | AGUAAAUGGUGUUAACCAGdTdT |
| AD-59617.1 | A-120448.1 | UCAUCUUGCCCAAGCCUGAdTdT | A-120449.1 | UCAGGCUUGGGCAAGAUGAdTdT |
| AD-59618.1 | A-120464.1 | CCUCAGAUCACACUAUCUCdTdT | A-120465.1 | GAGAUAGUGUGAUCUGAGGdTdT |
| AD-59619.1 | A-120480.1 | CUGUCCUCUGGAACCUCUGdTdT | A-120481.1 | CAGAGGUUCCAGAGGACAGdTdT |
| AD-59620.1 | A-120496.1 | CCCUGUGGAAGAUUAGCGGdTdT | A-120497.1 | CCGCUAAUCUUCCACAGGGdTdT |
| AD-59621.1 | A-120512.1 | AUCUCCACGGCUUUUGCUAdTdT | A-120513.1 | UAGCAAAAGCCGUGGAGAUdTdT |
| AD-59622.1 | A-120528.1 | GUGGCUGGAUGAAUUGGAGdTdT | A-120529.1 | CUCCAAUUCAUCCAGCCACdTdT |
| AD-59623.1 | A-120450.1 | CAAGUUAGUAUCAGCCAAUdTdT | A-120451.1 | AUUGGCUGAUACUAACUUGdTdT |
| AD-59624.1 | A-120466.1 | GUGAUGACAUCACCAUGGUdTdT | A-120467.1 | ACCAUGGUGAUGUCAUCACdTdT |
| AD-59625.1 | A-120482.1 | UUCCAAGAAUGACAAUGAUdTdT | A-120483.1 | AUCAUUGUCAUUCUUGGAAdTdT |
| AD-59626.1 | A-120498.1 | UGAUGGAGGUAUUUAAGUUdTdT | A-120499.1 | AACUUAAAUACCUCCAUCAdTdT |
| AD-59627.1 | A-120514.1 | GUAUUCCAAUGUGAUAGGAdTdT | A-120515.1 | UCCUAUCACAUUGGAAUACdTdT |
| AD-59628.1 | A-120530.1 | CAGCCAAGCCGCGGGACAUdTdT | A-120531.1 | AUGUCCCGCGGCUUGGCUGdTdT |
| AD-59629.1 | A-120452.1 | CAUGCCCCGCUUCCGCAUUdTdT | A-120453.1 | AAUGCGGAAGCGGGGCAUGdTdT |
| AD-59630.1 | A-120468.1 | AUGUGAUAGGAACUGUAACdTdT | A-120469.1 | GUUACAGUUCCUAUCACAUdTdT |
| AD-59631.1 | A-120484.1 | ACAAAUCCCUUACCUUCAAdTdT | A-120485.1 | UUGAAGGUAAGGGAUUUGUdTdT |
| AD-59632.1 | A-120500.1 | AGGUUUAUCUUUUGUCCUUdTdT | A-120501.1 | AAGGACAAAAGAUAAACCUdTdT |
| AD-59633.1 | A-120516.1 | AGAUCCCGGAGGCCACCAAdTdT | A-120517.1 | UUGGUGGCCUCCGGGAUCUdTdT |
| AD-59634.1 | A-120532.1 | ACAUUUUCCUGUCACCCCUdTdT | A-120533.1 | AGGGGUGACAGGAAAAUGUdTdT |
| AD-59635.1 | A-120548.1 | GGCCUUUCCUGGUUUUUAUdTdT | A-120549.1 | AUAAAAACCAGGAAAGGCCdTdT |
| AD-59636.1 | A-120564.1 | UUGUGUUAAGUAAAAUGUUdTdT | A-120565.1 | AACAUUUUACUUAACACAAdTdT |
| AD-59637.1 | A-120534.1 | CAAGGAAAAUGCAGAGCAAdTdT | A-120535.1 | UUGCUCUGCAUUUUCCUUGdTdT |
| AD-59638.1 | A-120550.1 | CUGAGAAAACAUCUGAUCAdTdT | A-120551.1 | UGAUCAGAUGUUUUCUCAGdTdT |
| AD-59639.1 | A-120566.1 | UUACUUCAAGGGCCUGUGGdTdT | A-120567.1 | CCACAGGCCCUUGAAGUAAdTdT |
| AD-59640.1 | A-120536.1 | ACCCCAACAGGGUGACUUUdTdT | A-120537.1 | AAAGUCACCCUGUUGGGGUdTdT |
| AD-59641.1 | A-120552.1 | CCAGGUAUUGUUGCAGAAGdTdT | A-120553.1 | CUUCUGCAACAAUACCUGGdTdT |
| AD-59642.1 | A-120568.1 | GCCUGUGGAAGUCAAAGUUdTdT | A-120569.1 | AACUUUGACUUCCACAGGCdTdT |
| AD-59643.1 | A-120538.1 | UGGAACCUCUGCGAGAUUUdTdT | A-120539.1 | AAAUCUCGCAGAGGUUCCAdTdT |
| AD-59644.1 | A-120554.1 | AGCCCUGAGAACACAAGGAdTdT | A-120555.1 | UCCUUGUGUUCUCAGGGCUdTdT |
| AD-59645.1 | A-120570.1 | CUCUAUGUCUCAGAUGCAUdTdT | A-120571.1 | AUGCAUCUGAGACAUAGAGdTdT |
| AD-59646.1 | A-120540.1 | AAGACCGAAGGCCGAAUCAdTdT | A-120541.1 | UGAUUCGGCCUUCGGUCUUdTdT |
| AD-59647.1 | A-120556.1 | UAAAAUGUUCUUAUUCUUUdTdT | A-120557.1 | AAAGAAUAAGAACAUUUUAdTdT |

TABLE 21-continued

AT3 (SERPINC1) modified sequences (The "Sense Sequence" column sequences are disclosed as SEQ ID NOS 1305-1467, respectively, in order of appearance, and the "Antisense Sequence" column sequences are disclosed as SEQ ID NOS 1468-1630, respectively, in order of appearance)

| Duplex Name | Sense Oligo Name | oligoSeq | Antis Oligo Name | oligoSeq |
|---|---|---|---|---|
| AD-59648.1 | A-120572.1 | UCUGGAAAAAGGAAGGUUUdTdT | A-120573.1 | AAACCUUCCUUUUUCCAGAdTdT |
| AD-59649.1 | A-120542.1 | UUCAAGGCCAACAGGCCUUdTdT | A-120543.1 | AAGGCCUGUUGGCCUUGAAdTdT |
| AD-59650.1 | A-120558.1 | GAAGUCAAAGUUCAGCCCUdTdT | A-120559.1 | AGGGCUGAACUUUGACUUCdTdT |
| AD-59651.1 | A-120574.1 | CCAUCAAUGAGCUCACUGUdTdT | A-120575.1 | ACAGUGAGCUCAUUGAUGGdTdT |
| AD-59652.1 | A-120544.1 | CUCUGAACACUAUUAUCUUdTdT | A-120545.1 | AAGAUAAUAGUGUUCAGAGdTdT |
| AD-59653.1 | A-120560.1 | UGCUGGUUAACACCAUUUAdTdT | A-120561.1 | UAAAUGGUGUUAACCAGCAdTdT |
| AD-59654.1 | A-120546.1 | AGAGGAAAGAACCAGUUUUdTdT | A-120547.1 | AAAACUGGUUCUUUCCUCUdTdT |
| AD-59655.1 | A-120562.1 | UGCCCAGCCCUGUGGAAGAdTdT | A-120563.1 | UCUUCCACAGGGCUGGGCAdTdT |

Cell Culture and Transfections

HepG2 cells (ATCC, Manassas, Va.) were grown to near confluence at 37° C. in an atmosphere of 5% CO2 in Eagle's Minimum Essential Medium (ATCC) supplemented with 10% FBS, streptomycin, and glutamine (ATCC) before being released from the plate by trypsinization. Transfection was carried out by adding 14.8 µl of Opti-MEM plus 0.2 µl of Lipofectamine RNAiMax per well (Invitrogen, Carlsbad Calif. cat #13778-150) to 5 µl of each of the 164 siRNA duplexes to an individual well in a 96-well plate. The mixture was then incubated at room temperature for 15 minutes. 80 µl of complete growth media without antibiotic containing ~$2.5\times10^4$ HepG2 cells were then added to the siRNA mixture. Cells were incubated for 24 hours prior to RNA purification. Experiments were performed at 20 nM and included naïve cells and cells transfected with AD-1955, a luciferase targeting siRNA as negative controls.

Total RNA Isolation Using DYNABEADS mRNA Isolation Kit (Invitrogen, Part #: 610-12)

Cells were harvested and lysed in 150 µl of Lysis/Binding Buffer then mixed for 5 minute at 700 rpm on a platform shaker (the mixing speed was the same throughout the process). Ten microliters of magnetic beads and 80 µl Lysis/Binding Buffer mixture were added to a round bottom plate and mixed for 1 minute. Magnetic beads were captured using magnetic stand and the supernatant was removed without disturbing the beads. After removing supernatant, the lysed cells were added to the remaining beads and mixed for 5 minutes. After removing supernatant, magnetic beads were washed 2 times with 150 µl Wash Buffer A and mixed for 1 minute. Beads were capture again and supernatant removed. Beads were then washed with 150 µl Wash Buffer B, captured and supernatant was removed. Beads were next washed with 150 µl Elution Buffer, captured and supernatant removed. Beads were allowed to dry for 2 minutes. After drying, 50 µl of Elution Buffer was added and mixed for 5 minutes at 70° C. Beads were captured on magnet for 5 minutes. Forty µl of supernatant, containing the isolated RNA was removed and added to another 96 well plate.

cDNA Synthesis using ABI High Capacity cDNA Reverse Transcription Kit (Applied Biosystems, Foster City, Calif., Cat #4368813)

A master mix of 2 µl 10× Buffer, 0.8 µl 25× dNTPs, 2 µl Random primers, 1 µl Reverse Transcriptase, 1 µl RNase inhibitor and 3.2 µl of H2O per reaction were added into 10 µl total RNA. cDNA was generated using a Bio-Rad C-1000 or S-1000 thermal cycler (Hercules, Calif.) through the following steps: 25° C. 10 min, 37° C. 120 min, 85° C. 5 sec, 4° C. hold.

Real Time PCR

Two µl of cDNA were added to a master mix containing 0.50 human GAPDH TaqMan Probe (Applied Biosystems Cat #4326317E), 0.50 human SERPINC1 TaqMan probe (Applied Biosystems cat #Hs00892758_ml) and 50 Lightcycler 480 probe master mix (Roche Cat #04887301001) per well in a 384-well plate (Roche cat #04887301001). Real time PCR was done in an LC480 Real Time PCR machine (Roche).

To calculate relative fold change, real time data were analyzed using the ΔΔCt method and normalized to assays performed with cells transfected with 20 nM AD-1955.

Table 22 shows the results of a single dose screen in HepG2 of the indicated iRNAs.

TABLE 22[2]

20 nM single dose screen of the indicated iRNAs

| Duplex ID | 20 nM Average | Standard Deviation |
|---|---|---|
| AD1955 | 100.4 | 9.1 |
| AD-59267.1 | 9.3 | 2.7 |
| AD-59268.1 | 72.2 | 20.3 |
| AD-59269.1 | 6.9 | 0.4 |
| AD-59270.1 | 18.3 | 5.2 |
| AD-59271.1 | 27.9 | 7.6 |
| AD-59272.1 | 13.0 | 1.1 |
| AD-59273.1 | 79.4 | 10.9 |
| AD-59274.1 | 5.9 | 1.1 |
| AD-59275.1 | 16.1 | 5.5 |
| AD-59276.1 | 6.1 | 2.2 |
| AD-59277.1 | 4.4 | 0.9 |
| AD-59278.1 | 9.3 | 0.4 |
| AD-59279.1 | 12.7 | 4.7 |
| AD-59280.1 | 4.5 | 1.7 |
| AD-59281.1 | 15.7 | 5.6 |
| AD-59282.1 | 25.9 | 6.9 |
| AD-59283.1 | 27.0 | 18.9 |

TABLE 22[2]-continued 20 nM single dose screen of the indicated iRNAs

| Duplex ID | 20 nM Average | Standard Deviation |
|---|---|---|
| AD-59284.1 | 8.6 | 3.7 |
| AD-59285.1 | 11.2 | 3.7 |
| AD-59286.1 | 15.2 | 5.0 |
| AD-59287.1 | 6.9 | 1.9 |
| AD-59288.1 | 74.5 | 16.5 |
| AD-59289.1 | 3.3 | 1.3 |
| AD-59290.1 | 13.8 | 2.5 |
| AD-59291.1 | 9.4 | 2.8 |
| AD-59292.1 | 9.5 | 3.5 |
| AD-59293.1 | 2.5 | 1.1 |
| AD-59294.1 | 4.8 | 1.8 |
| AD-59295.1 | 11.8 | 7.2 |
| AD-59296.1 | 32.4 | 4.9 |
| AD-59297.1 | 78.5 | 105.0 |
| AD-59298.1 | 76.3 | 10.7 |
| AD-59299.1 | 4.4 | 0.8 |
| AD-59300.1 | 32.2 | 10.8 |
| AD-59301.1 | 48.5 | 15.2 |
| AD-59302.1 | 7.2 | 3.0 |
| AD-59303.1 | 17.0 | 2.3 |
| AD-59304.1 | 87.1 | 16.4 |
| AD-59305.1 | 4.4 | 0.9 |
| AD-59306.1 | 35.7 | 10.6 |
| AD-59307.1 | 6.3 | 0.4 |
| AD-59308.1 | 65.1 | 9.1 |
| AD-59309.1 | 7.5 | 2.0 |
| AD-59310.1 | 27.1 | 9.5 |
| AD-59311.1 | 8.1 | 1.4 |
| AD-59312.1 | 84.5 | 8.5 |
| AD-59313.1 | 17.8 | 0.2 |
| AD-59314.1 | 21.1 | 0.4 |
| AD-59315.1 | 85.5 | 29.8 |
| AD-59316.1 | 13.0 | 1.6 |
| AD-59317.1 | 64.0 | 10.7 |
| AD-59318.1 | 7.9 | 2.2 |
| AD-59319.1 | 31.8 | 4.7 |
| AD-59320.1 | 5.7 | 2.1 |
| AD-59321.1 | 3.4 | 0.0 |
| AD-59322.1 | 9.6 | 1.3 |
| AD-59323.1 | 100.1 | 4.8 |
| AD-59324.1 | 40.2 | 2.9 |
| AD-59325.1 | 5.8 | 0.7 |
| AD-59326.1 | 20.4 | 10.9 |
| AD-59327.1 | 5.0 | 2.0 |
| AD-59328.1 | 8.0 | 2.8 |
| AD-59329.1 | 54.1 | 5.9 |
| AD-59330.1 | 21.6 | 12.3 |
| AD-59331.1 | 4.3 | 2.4 |
| AD-59332.1 | 12.9 | 3.8 |
| AD-59333.1 | 26.1 | 1.0 |
| AD-59334.1 | 41.9 | 4.7 |
| AD-59335.1 | 12.5 | 1.7 |
| AD-59336.1 | 13.5 | 1.7 |
| AD-59337.1 | 78.6 | 3.6 |
| AD-59338.1 | 17.9 | 12.3 |
| AD-59339.1 | 5.8 | 4.1 |
| AD-59340.1 | 92.3 | 10.0 |
| AD-59341.1 | 8.0 | 1.8 |
| AD-59342.1 | 11.1 | 1.9 |
| AD-59343.1 | 43.6 | 4.2 |
| AD-59344.1 | 6.0 | 2.3 |
| AD-59345.1 | 23.6 | 3.6 |
| AD-59346.1 | 41.0 | 3.2 |
| AD-59347.1 | 12.2 | 1.0 |
| AD-59348.1 | 30.0 | 5.1 |
| AD-59349.1 | 14.4 | 0.9 |
| AD-59350.1 | 9.1 | 1.0 |
| AD-59351.1 | 10.7 | 1.6 |
| AD-59352.1 | 1.9 | 0.4 |
| AD-59353.1 | 4.6 | 0.8 |
| AD-59354.1 | 30.1 | 0.1 |
| AD-59355.1 | 12.2 | 2.2 |
| AD-59356.1 | 63.6 | 11.5 |
| AD-59357.1 | 112.1 | 20.6 |
| AD-59358.1 | 23.2 | 3.0 |

TABLE 22[2]-continued 20 nM single dose screen of the indicated iRNAs

| Duplex ID | 20 nM Average | Standard Deviation |
|---|---|---|
| AD-59359.1 | 7.5 | 0.8 |
| AD-59360.1 | 19.2 | 0.5 |
| AD-59587.1 | 8.4 | 2.7 |
| AD-59588.1 | 24.8 | 5.7 |
| AD-59589.1 | 4.4 | 1.7 |
| AD-59590.1 | 13.6 | 1.3 |
| AD-59591.1 | 3.1 | 0.5 |
| AD-59592.1 | 12.1 | 2.7 |
| AD-59593.1 | 7.6 | 3.5 |
| AD-59594.1 | 7.5 | 1.6 |
| AD-59595.1 | 20.1 | 2.9 |
| AD-59596.1 | 7.3 | 1.3 |
| AD-59597.1 | 61.3 | 6.8 |
| AD-59598.1 | 24.4 | 1.6 |
| AD-59599.1 | 4.3 | 0.4 |
| AD-59600.1 | 30.1 | 2.8 |
| AD-59601.1 | 11.4 | 0.8 |
| AD-59602.1 | 6.0 | 0.0 |
| AD-59603.1 | 19.4 | 2.2 |
| AD-59604.1 | 5.8 | 0.6 |
| AD-59605.1 | 6.5 | 0.3 |
| AD-59606.1 | 9.9 | 0.6 |
| AD-59607.1 | 28.0 | 2.8 |
| AD-59608.1 | 66.1 | 8.0 |
| AD-59609.1 | 84.2 | 9.0 |
| AD-59610.1 | 8.0 | 1.7 |
| AD-59611.1 | 6.6 | 1.5 |
| AD-59612.1 | 31.5 | 2.7 |
| AD-59613.1 | 27.6 | 1.7 |
| AD-59614.1 | 20.3 | 0.5 |
| AD-59615.1 | 12.8 | 1.4 |
| AD-59616.1 | 6.8 | 0.3 |
| AD-59617.1 | 13.1 | 0.9 |
| AD-59618.1 | 5.4 | 0.2 |
| AD-59619.1 | 59.1 | 5.4 |
| AD-59620.1 | 6.3 | 1.7 |
| AD-59621.1 | 18.4 | 1.8 |
| AD-59622.1 | 9.6 | 1.2 |
| AD-59623.1 | 8.7 | 2.1 |
| AD-59624.1 | 13.6 | 0.7 |
| AD-59625.1 | 12.0 | 1.5 |
| AD-59626.1 | 14.6 | 1.8 |
| AD-59627.1 | 7.7 | 6.7 |
| AD-59628.1 | 7.6 | 0.3 |
| AD-59629.1 | 55.7 | 8.2 |
| AD-59630.1 | 20.2 | 5.9 |
| AD-59631.1 | 12.3 | 0.1 |
| AD-59632.1 | 3.1 | 0.3 |
| AD-59633.1 | 20.4 | 2.1 |
| AD-59634.1 | 3.7 | 0.0 |
| AD-59635.1 | 16.1 | 1.3 |
| AD-59636.1 | 13.0 | 1.0 |
| AD-59637.1 | 14.4 | 4.8 |
| AD-59638.1 | 7.7 | 1.0 |
| AD-59639.1 | 70.4 | 5.3 |
| AD-59640.1 | 2.5 | 0.1 |
| AD-59641.1 | 18.1 | 2.1 |
| AD-59642.1 | 5.9 | 1.0 |
| AD-59643.1 | 70.7 | 17.8 |
| AD-59644.1 | 17.9 | 4.7 |
| AD-59645.1 | 2.5 | 0.1 |
| AD-59646.1 | 19.9 | 0.1 |
| AD-59647.1 | 74.8 | 12.0 |
| AD-59648.1 | 6.8 | 0.0 |
| AD-59649.1 | 95.2 | 6.2 |
| AD-59650.1 | 71.1 | 1.0 |
| AD-59651.1 | 5.0 | 0.8 |
| AD-59652.1 | 5.5 | 1.2 |
| AD-59653.1 | 15.3 | 1.0 |
| AD-59654.1 | 67.4 | 0.9 |
| AD-59655.1 | 10.8 | 1.0 |
| Naïve | 94.9 | 14.2 |

[2]Modified.

We claim:

1. A double-stranded ribonucleic acid (dsRNA) for inhibiting expression of Serpinc1, wherein said dsRNA comprises a sense strand and an antisense strand, wherein the sense strand comprises the nucleotide sequence of 5'-GfsgsUfuAfaCfaCfCfAfuUfuAfcUfuCfaAf-3' (SEQ ID NO:941) and the antisense strand comprises the nucleotide sequence of 5'-usUfsgAfaGfuAfaAfuggUfgUfuAfaCfcsasg-3' (SEQ ID NO:960), wherein a, g, c and u are 2'-O-methyl(2'-OMe) A, U, C, or G; Af, Cf, Gf or Uf are 2'-fluoro A, G, C or U; and s is a phosphorothioate linkage.

2. The dsRNA of claim 1, further comprising a ligand.

3. The dsRNA of claim 2, wherein the ligand is conjugated to the 3' end of the sense strand of the dsRNA.

4. The dsRNA of claim 2, wherein the ligand is an N-acetylgalactosamine (GalNAc) derivative.

5. The dsRNA of claim 4, wherein the ligand is

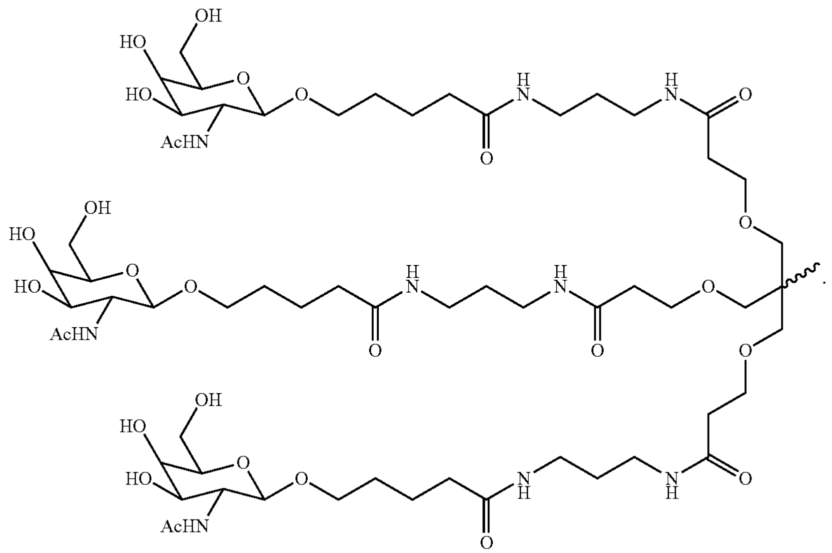 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

6. The dsRNA of claim 4, wherein the dsRNA is conjugated to the ligand as shown in the following schematic

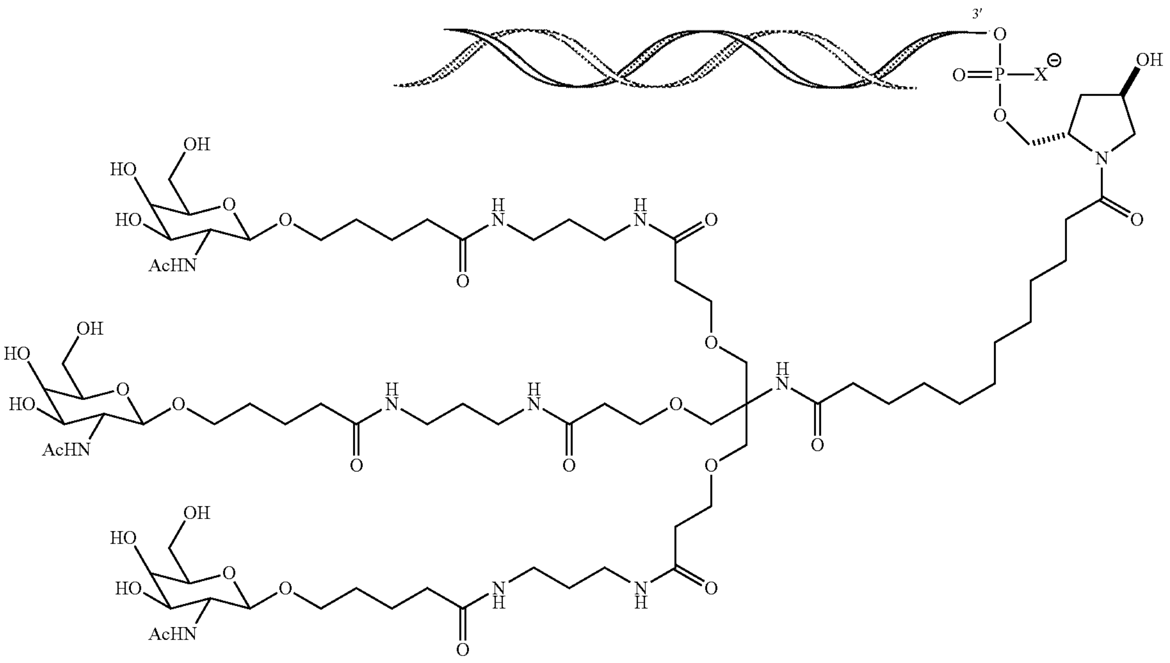

and, wherein X is O or S.

7. The dsRNA of claim 6, wherein the X is O.

8. A cell containing the dsRNA of claim 1.

9. A pharmaceutical composition for inhibiting expression of a Serpinc1 gene comprising the dsRNA of claim 1.

10. A method of inhibiting Serpinc1 expression in a cell, the method comprising:
(a) contacting the cell with the dsRNA of claim 1; and
(b) maintaining the cell produced in step (a) for a time sufficient to obtain degradation of the mRNA transcript of a Serpinc1 gene, thereby inhibiting expression of the Serpinc1 gene in the cell.

11. The method of claim 10, wherein said cell is within a subject.

12. The method of claim 11, wherein the subject is a human.

13. The method of claim 12, wherein the human subject suffers from a bleeding disorder.

14. The method of claim 13, wherein the bleeding disorder is a hemophilia.

15. The method of any one of claims 10-14, wherein the Serpinc1 expression is inhibited by at least about 30%.

16. A method of treating a subject having a disorder that would benefit from reduction in Serpinc1 expression, comprising administering to the subject a therapeutically effective amount of the dsRNA of claim 1, thereby treating said subject.

17. A method of preventing at least one symptom in a subject having a disorder that would benefit from reduction in Serpinc1 expression, comprising administering to the subject a therapeutically effective amount of the dsRNA of claim 1, thereby preventing at least one symptom in the subject having a disorder that would benefit from reduction in Serpinc1 expression.

18. The method of claim 16, wherein the disorder is a bleeding disorder.

19. The method of claim 18, wherein the bleeding disorder is a hemophilia.

20. The method of claim 16, wherein the administration of the dsRNA to the subject causes an increase in blood clotting and/or a decrease in Serpinc1 protein accumulation.

21. The method of claim 16, wherein the dsRNA is conjugated to a ligand.

22. The method of claim 21, wherein the ligand is conjugated to the 3'-end of the sense strand of the dsRNA.

23. The method of claim 22, wherein the ligand is an N-acetylgalactosamine (GalNAc) derivative.

24. The method of claim 17, wherein the dsRNA is administered at a dose of about 0.01 mg/kg to about 50 mg/kg.

25. The method of claim 24, wherein the dsRNA is administered at a dose of about 10 mg/kg to about 30 mg/kg.

26. The method of claim 24, wherein the dsRNA is administered at a dose selected from the group consisting of 0.3 mg/kg 0.5 mg/kg 1 mg/kg, 1.5 mg/kg, 3 mg/kg, 10 mg/kg, and 30 mg/kg.

27. The method of claim 25 or 26, wherein the dsRNA is administered to the subject once a week.

28. The method of claim 25 or 26, wherein the dsRNA is administered to the subject twice a month.

29. The method of claim 16, further comprising measuring thrombin levels in said subject.

30. The method of claim 17, wherein the dsRNA is administered to the subject subcutaneously at a cumulative weekly dose of about 0.5 mg/kg to about 5 mg/kg.

31. A method of inhibiting the expression of Serpinc1 in a subject, the method comprising
administering to said subject a therapeutically effective amount of the dsRNA of claim 1, thereby inhibiting the expression of Serpinc1 in said subject.

32. The method of claim 31, wherein the dsRNA is conjugated to a ligand.

33. The method of claim 32, wherein the ligand is conjugated to the 3'-end of the sense strand of the dsRNA.

34. The method of claim 33, wherein the ligand is an N-acetylgalactosamine (GalNAc) derivative.

35. The method of claim 31, wherein the dsRNA is administered at a dose of about 0.01 mg/kg to about 50 mg/kg.

36. The method of claim 35, wherein the dsRNA is administered at a dose of about 10 mg/kg to about 30 mg/kg.

37. The method of claim 35, wherein the dsRNA is administered at a dose selected from the group consisting of 1 mg/kg, 3 mg/kg, 10 mg/kg, and 30 mg/kg.

38. The method of claim 37, wherein the dsRNA is administered to the subject once a week.

39. The method of claim 37, wherein the dsRNA is administered to the subject twice a month.

40. The method of claim 31, wherein the dsRNA is administered to the subject subcutaneously at a cumulative weekly dose of about 0.5 mg/kg to about 5 mg/kg.

41. The method of claim 31, further comprising measuring thrombin levels in said subject.

42. The method of claim 21, wherein the ligand is

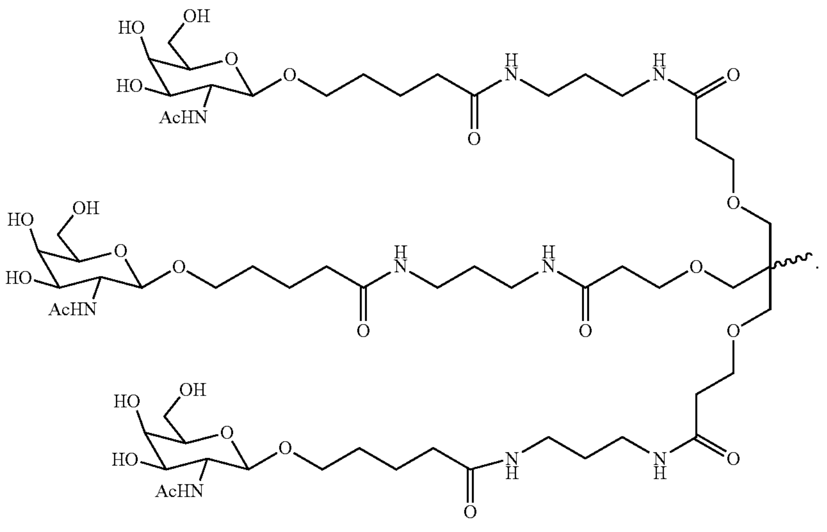 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

43. The method of claim 21, wherein the dsRNA is conjugated to the ligand as shown in the following schematic

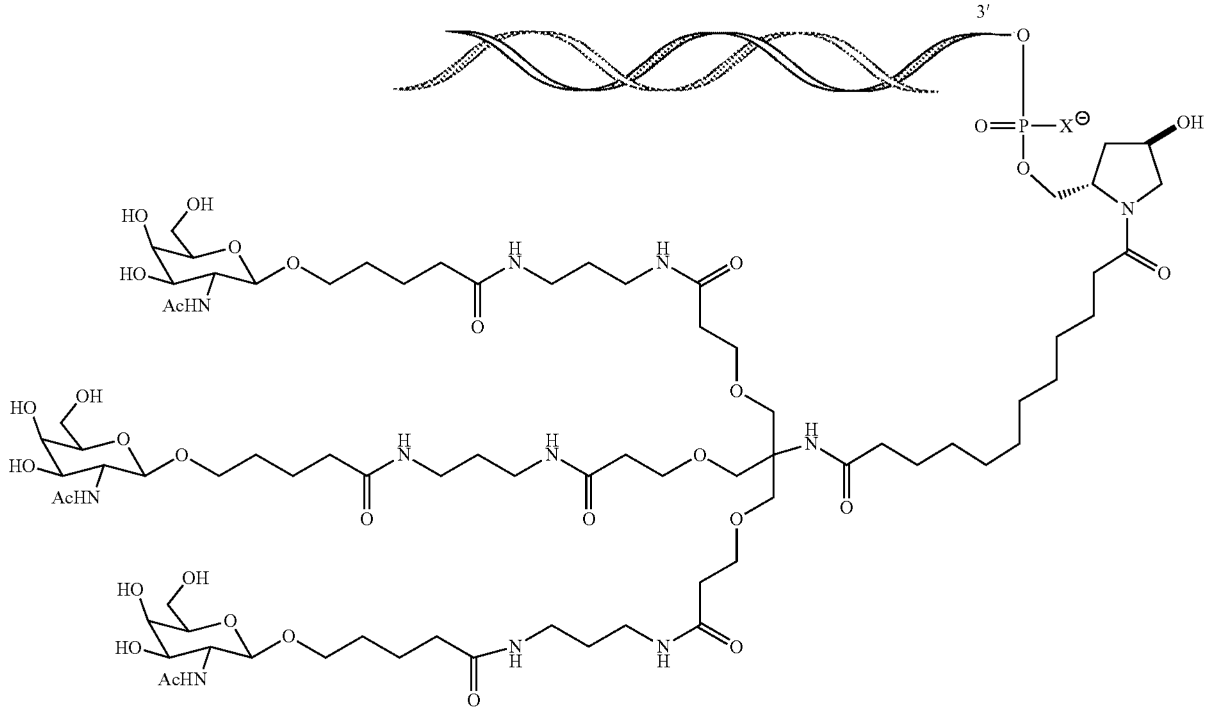

and, wherein X is O or S.

44. The dsRNA of claim 43, wherein the X is O.

45. The method of claim 16, wherein the dsRNA is administered at a dose of about 0.01 mg/kg to about 50 mg/kg.

46. The method of claim 45, wherein the dsRNA is administered at a dose of about 10 mg/kg to about 30 mg/kg.

47. The method of claim 45, wherein the dsRNA is administered at a dose selected from the group consisting of 0.3 mg/kg 0.5 mg/kg 1 mg/kg, 1.5 mg/kg, 3 mg/kg, 10 mg/kg, and 30 mg/kg.

48. The method of claim 46 or 47, wherein the dsRNA is administered to the subject once a week.

49. The method of claim 46 or 47, wherein the dsRNA is administered to the subject twice a month.

50. The method of claim 17, wherein the disorder is a bleeding disorder.

51. The method of claim 50, wherein the bleeding disorder is a hemophilia.

52. The method of claim 17, wherein the administration of the dsRNA to the subject causes an increase in blood clotting and/or a decrease in Serpinc1 protein accumulation.

53. The method of claim 17, wherein the dsRNA is conjugated to a ligand.

54. The method of claim 53, wherein the ligand is conjugated to the 3'-end of the sense strand of the dsRNA.

55. The method of claim 54, wherein the ligand is an N-acetylgalactosamine (GalNAc) derivative.

56. The method of claim 55, wherein the ligand is

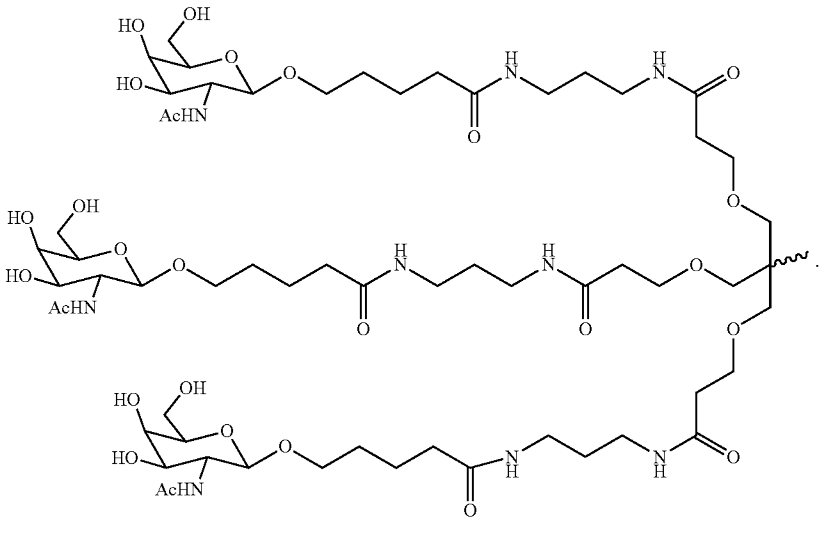 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

57. The method of claim 55, wherein the dsRNA is conjugated to the ligand as shown in the following schematic
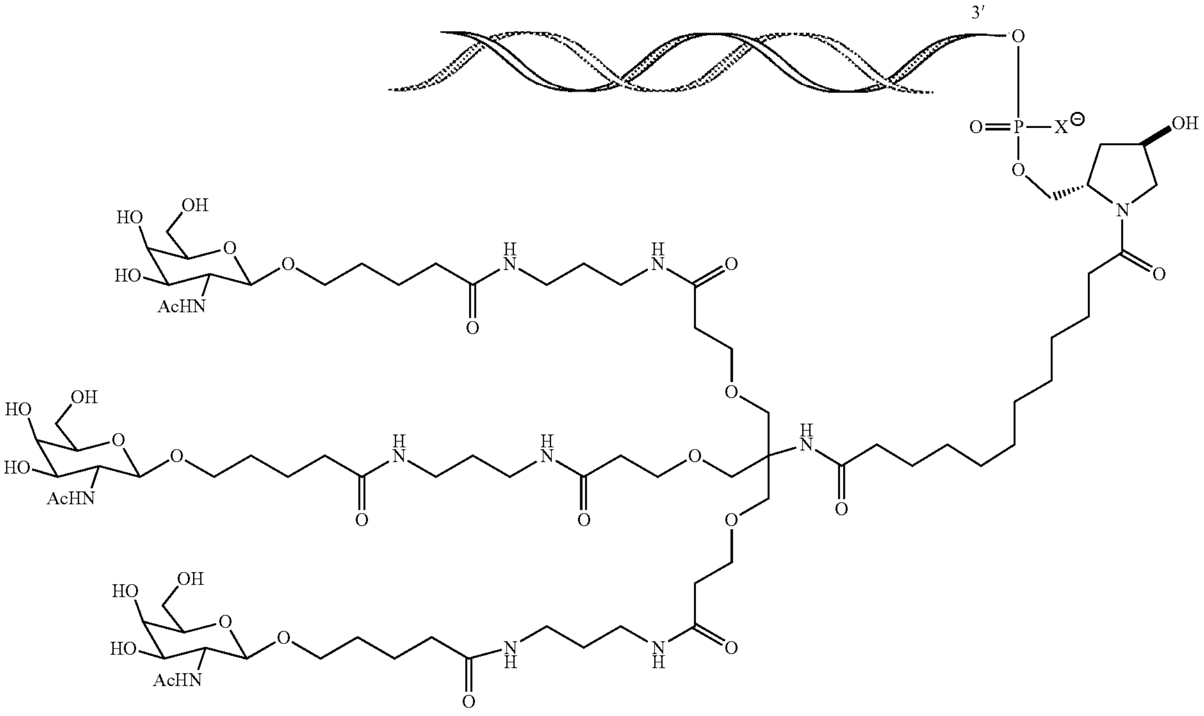
and, wherein X is O or S.
58. The method of claim 57, wherein the X is O.
59. The method of claim 17, further comprising measuring thrombin levels in said subject.
60. The method of claim 34, wherein the ligand is
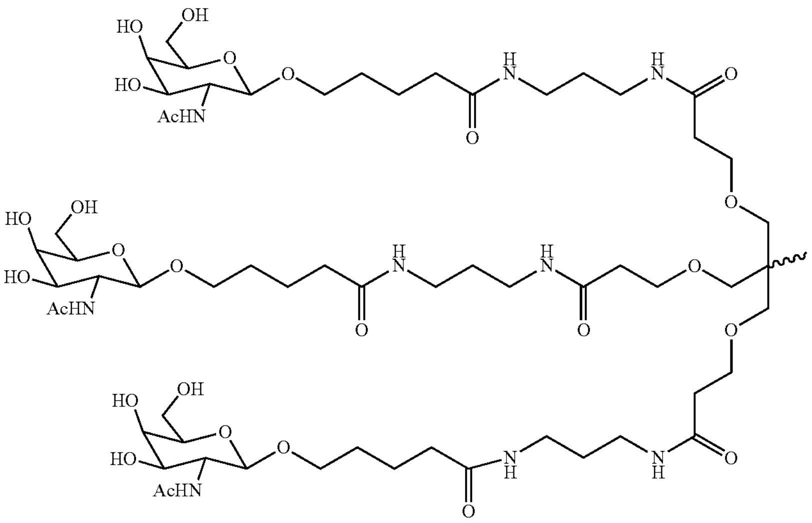
.

61. The method of claim 34, wherein the dsRNA is conjugated to the ligand as shown in the following schematic
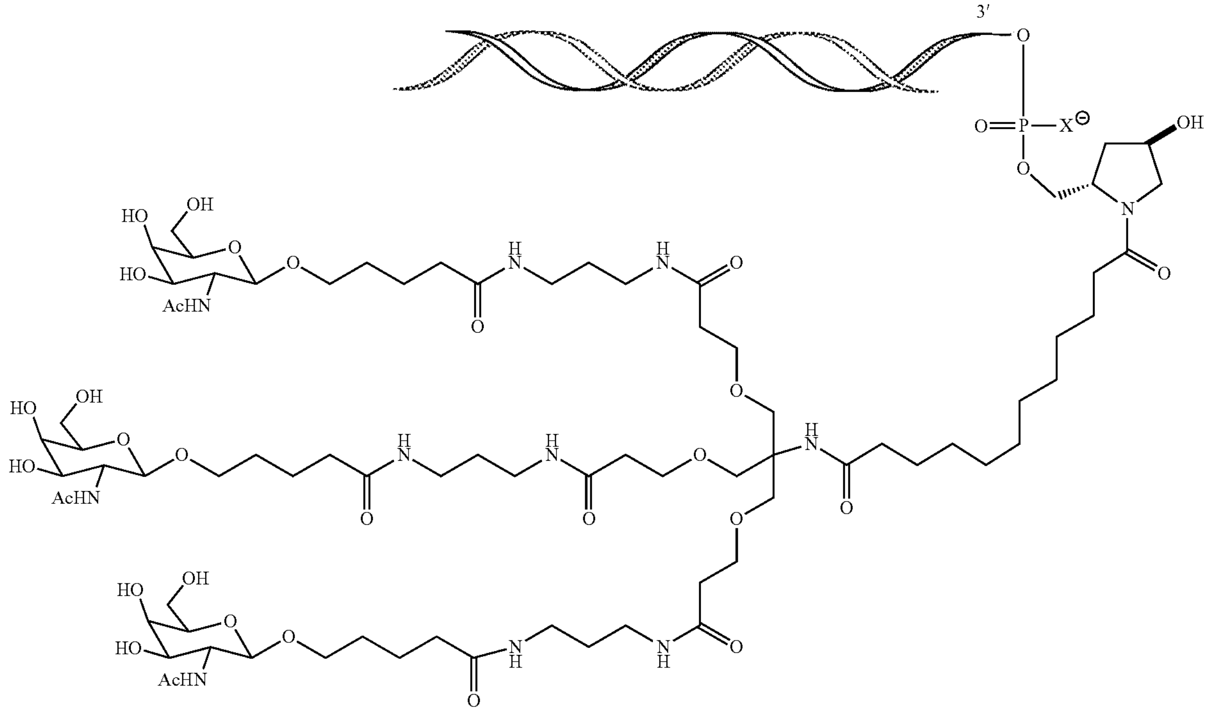
and, wherein X is O or S.
62. The method of claim 61, wherein the X is O.
* * * * *

SEQUENCE LISTING

<160> NUMBER OF SEQ ID NOS: 1630

<210> SEQ ID NO 1
<211> LENGTH: 1599
<212> TYPE: DNA
<213> ORGANISM: Homo sapiens

<400> SEQUENCE: 1

```
tctgccccac cctgtcctct ggaacctctg cgagatttag aggaaagaac cagttttcag     60
gcggattgcc tcagatcaca ctatctccac ttgcccagcc ctgtggaaga ttagcggcca    120
tgtattccaa tgtgatagga actgtaacct ctggaaaaag gaaggtttat cttttgtcct    180
tgctgctcat tggcttctgg gactgcgtga cctgtcacgg gagccctgtg gacatctgca    240
cagccaagcc gcgggacatt cccatgaatc ccatgtgcat ttaccgctcc ccggagaaga    300
aggcaactga ggatgagggc tcagaacaga agatcccgga ggccaccaac cggcgtgtct    360
gggaactgtc caaggccaat tcccgctttg ctaccacttt ctatcagcac ctggcagatt    420
ccaagaatga caatgataac attttcctgt cacccctgag tatctccacg gcttttgcta    480
tgaccaagct gggtgcctgt aatgacaccc tccagcaact gatggaggta tttaagtttg    540
acaccatatc tgagaaaaca tctgatcaga tccacttctt ctttgccaaa ctgaactgcc    600
gactctatcg aaaagccaac aaatcctcca agttagtatc agccaatcgc ctttttggag    660
acaaatccct taccttcaat gagacctacc aggacatcag tgagttggta tatggagcca    720
agctccagcc cctggacttc aaggaaaatg cagagcaatc cagagcggcc atcaacaaat    780
gggtgtccaa taagaccgaa ggccgaatca ccgatgtcat tccctcggaa gccatcaatg    840
agctcactgt tctggtgctg gttaacacca tttacttcaa gggcctgtgg aagtcaaagt    900
tcagccctga gaacacaagg aaggaactgt tctacaaggc tgatggagag tcgtgttcag    960
catctatgat gtaccaggaa ggcaagttcc gttatcggcg cgtggctgaa ggcacccagg   1020
tgcttgagtt gcccttcaaa ggtgatgaca tcaccatggt cctcatcttg cccaagcctg   1080
agaagagcct ggccaaggta gagaaggaac tcaccccaga ggtgctgcaa gagtggctgg   1140
atgaattgga ggagatgatg ctggtggtcc acatgccccg cttccgcatt gaggacggct   1200
tcagtttgaa ggagcagctg caagacatgg gccttgtcga tctgttcagc cctgaaaagt   1260
ccaaactccc aggtattgtt gcagaaggcc gagatgacct ctatgtctca gatgcattcc   1320
ataaggcatt tcttgaggta aatgaagaag gcagtgaagc agctgcaagt accgctgttg   1380
tgattgctgg ccgttcgcta aaccccaaca gggtgacttt caaggccaac aggcctttcc   1440
tggtttttat aagagaagtt cctctgaaca ctattatctt catgggcaga gtagccaacc   1500
cttgtgttaa gtaaaatgtt cttattcttt gcacctcttc ctatttttgg tttgtgaaca   1560
gaagtaaaaa taaatacaaa ctacttccat ctcacatta                          1599
```

<210> SEQ ID NO 2
<211> LENGTH: 1545
<212> TYPE: DNA
<213> ORGANISM: Macaca mulatta

<400> SEQUENCE: 2

```
ggcacgagga ccatctccac ttgcccagcc ctgtggaaga ttagcgacca tgtattccaa     60
tgtgatagga accgtagcct ctggaaaaag gaaggtttat cttctgtcct tgctgctcat    120
tggcctctgg gactgtatga cctgtcacgg gagccctgtg gacatctgca cagccaagcc    180
gcgggacatt cccatgaatc ccatgtgcat ttaccgctcc ccggagaaga aggcaactga    240
```

-continued ggatgagggc tcagaacaga agatccccga ggccaccaac cggcgcgtct gggaactgtc 300
caaggccaat tcccgctttg ctaccacttt ctatcagcac ctggcagatt ccaagaacga 360
caaggataac attttcctgt cacccctgag tgtctccacg gcttttgcta tgaccaagct 420
gggtgcctgt aatgacaccc tcaagcaact gatggaggta tttaagtttg acaccatatc 480
tgagaaaaca tctgatcaga tccacttctt ctttgccaaa ctgaactgcc gactctatcg 540
aaaagccaac aaatcctcca agttagtatc agccaatcgc ctttttggag acaaatccct 600
taccttcaat gagacctacc aggacatcag tgagttggta tacggagcca agctccagcc 660
cctggacttc aaggaaaatg cagagcaatc cagagcggcc atcaacaaat gggtgtccaa 720
taagaccgaa ggccgaatca ccgatgtcat tcccccggaa gccatcaacg agctcactgt 780
tctggtgctg gttaacacca tttacttcaa gggcctgtgg aagtcaaagt ttagccctga 840
gaacacaagg atggaaccgt tctacaaggc tgatggagag tcgtgttcag cgtctatgat 900
gtaccaggaa ggcaagttct gttatcggcg cgtggctgaa ggcacccagg tgcttgagtt 960
gcccttcaag ggtgatgaca tcaccatggt gctcatcctg cccaagcctg agaagagcct 1020
gaccaaggtg gagcaggaac tcaccccaga ggtgctgcag gagtggctgg atgagttgga 1080
ggagatgatg ctggtggttc acatgccccg cttccgcatt gaggacggct tcagtttgaa 1140
ggagcagctg caagacatgg gccttgtcga tctgttcagc cctgaaaagt ccaaactccc 1200
aggtattgtt gcagaaggcc gggatgacct ctatgtctcc gatgcattcc ataaggcatt 1260
tcttgaggta aatgaagaag gcagtgaagc agctgcaagt accgccattg ggattgctgg 1320
ccgttcgcta aaccccaaca gggtgacctt caaggccaac aggcctttcc tggtttttat 1380
aagagaagtt cctctgaaca ctattatctt catgggcaga gtagccaacc cttgtgtgag 1440
ctaaactgtt cttattcttt gtacctcttc ctattttggt ttgtgaatag aagtaaaaat 1500
aaatacaact actcccatct tacattaaaa aaaaaaaaaa aaaaa 1545

<210> SEQ ID NO 3
<211> LENGTH: 2171
<212> TYPE: DNA
<213> ORGANISM: Mus musculus

<400> SEQUENCE: 3
ataggtaatt ttagaaatag atctgatttg tatctgagac attttagtga agtggtgaga 60
tataagacat aatcagaaga catatctacc tgaagacttt aaggggagag ctccctcccc 120
cacctggcct ctggacctct cagatttagg ggaaagaacc agttttcgga gtgatcgtct 180
cagtcagcac catctctgta ggagcatcgg ccatgtattc ccctggggca ggaagtgggg 240
ctgctggtga gaggaagctt tgtctcctct ctctgctcct catcggtgcc ttgggctgtg 300
ctatctgtca cggaaaccct gtggacgaca tctgcatagc gaagccccga gacatccccg 360
tgaatccctt gtgcatttac cgctcccctg ggaagaaggc caccgaggag gatggctcag 420
agcagaaggt tccagaagcc accaaccggc gggtctggga actgtccaag gccaattcgc 480
gatttgccac taacttctac cagcacctgg cagactccaa gaatgacaac gacaacattt 540
tcctgtcacc cttgagcatc tccactgctt ttgctatgac caagctgggt gcctgtaacg 600
acactctcaa gcagctgatg gaggttttta aatttgatac catctccgag aagacatccg 660
accagatcca cttcttcttt gccaaactga actgccgact ctatcgaaaa gccaacaagt 720
cctctgactt ggtatcagcc aaccgccttt ttggagacaa atccctcacc ttcaacgaga 780

```
gctatcaaga tgttagtgag gttgtctatg gagccaagct ccagccccctg gacttcaagg    840
agaatccgga gcaatccaga gtgaccatca acaactgggt agctaataag actgaaggcc    900
gcatcaaaga tgtcatccca cagggcgcca ttaacgagct cactgccctg gttctggtta    960
acaccattta cttcaagggc ctgtggaagt caaagttcag ccctgagaac acaaggaagg   1020
aaccgttcta taaggtcgat gggcagtcat gcccagtgcc tatgatgtac caggaaggca   1080
aattcaaata ccggcgcgtg gcagagggca cccaggtgct agagctgccc ttcaaggggg   1140
atgacatcac catggtgctc atcctgccca agcctgagaa gagcctggcc aaggtggagc   1200
aggagctcac cccagagctg ctgcaggagt ggctggatga gctgtcagag actatgcttg   1260
tggtccacat gccccgcttc cgcaccgagg atggcttcag tctgaaggag cagctgcaag   1320
acatgggcct cattgatctc ttcagccctg aaaagtccca actcccaggg atcgttgctg   1380
gaggcaggga cgacctctat gtctccgacg cattccacaa agcatttctt gaggtaaatg   1440
aggaaggcag tgaagcagca gcgagtactt ctgtcgtgat tactggccgg tcactgaacc   1500
ccaatagggt gaccttcaag gccaacaggc ccttcctggt tcttataagg gaagttgcac   1560
tgaacactat tatattcatg ggagagtgg ctaatccttg tgtgaactaa aatattctta   1620
atctttgcac cttttcctac tttggtgttt gtgaatagaa gtaaaaataa atacgactgc   1680
cacctcacga gaatggactt ttccacttga agacgagaga ctggagtaca gatgctacac   1740
cacttttggg caagtgaagg gggagcagcc agccacggtg gcacaaacct atatcctggt   1800
gcttttgaag gtagaagcag ggcggtcagg agttaaggcc agttgaggct gggctgcaga   1860
gtgaaagacc atgtctcaag atggtctttc tcctccccaa agtagaaaag aaaaccataa   1920
aaacaagagg taaatatatt actatttcat cttagaggat agcaggcatc ttgaaagggt   1980
agagggacct taaattctca ttattgcccc catactacaa actaaaaaac aaacccgaat   2040
caatctccca taaagacaga gattcaaata agagtattaa acgttttatt tctcaaacca   2100
ctcacatgca taatgttctt atacacagtg tcaaaataaa gagaaatgca tttttataca   2160
aaaaaaaaaa a                                                        2171
```

<210> SEQ ID NO 4
<211> LENGTH: 1561
<212> TYPE: DNA
<213> ORGANISM: Rattus norvegicus

<400> SEQUENCE: 4

```
cggagggatt gctcagcact gtctccacgg cttctctgca gaagcgtcca ccatgtattc     60
cccgggaata ggaagtgcgg ttgctggaga gaggaagctt tgtctcctct ctctgctact    120
cattggtgcc ttgggctgtg ctgtctgtca tggaaaccct gtggacgaca tctgcatagc    180
gaagccccga gacatccccg tgaaccccat gtgcatttac cgctcccctg cgaagaaggc    240
cacggaggag gatgtcctag agcagaaggt tccggaagcc accaaccggc gggtctggga    300
actgtccaag gccaattctc gatttgccac taacttctat cagcacctgg cagactccaa    360
gaacgacaac gacaacattt tcctgtcacc cttgagcatc tccacggcgt ttgctatgac    420
caagctgggt gcttgtaata acaccctcaa gcagctgatg gaggttttta aatttgatac    480
catctccgag aagacatccg accagatcca cttcttcttt gccaaactga actgccgact    540
ctatcgaaaa gccaacaagt cctctaactt ggtgtcagcc aaccgccttt ttggagacaa    600
atcccttacc ttcaatgaga gctatcaaga cgttagtgag attgtctatg gagccaagct    660
tcagccccctg gacttcaagg agaatccgga gcaatccaga gtgaccatca acaactgggt    720
```

agctaataag actgaaggcc gcatcaaaga cgtcatcccc caaggagcca ttgatgagct 780
cactgccctg gtgctggtta acaccattta cttcaagggc ctgtggaagt caaagttcag 840
ccctgagaac acaaggaagg aaccattcca caaagttgat gggcagtcat gcctggtgcc 900
catgatgtac caggaaggca aattcaaata caggcgtgtg ggagagggta cccaggtgct 960
agagatgccc ttcaaggggg acgacatcac catggtgctc atcctgccca agcctgagaa 1020
gagcctggct aaggtggagc aggaactcac cccggagctg ctgcaggagt ggctggatga 1080
gctgtcggag gtcatgcttg tggtccacgt gccccgcttc cgcatcgagg acagcttcag 1140
tctgaaggag cagctgcaag acatgggcct tgttgatctc ttcagccctg agaagtccca 1200
actcccaggg atcattgctg aaggcaggga cgacctcttt gtctccgatg cattccacaa 1260
agcgtttctt gaggtaaatg aggaaggcag tgaagcagca gcgagtactt ctgtcgtgat 1320
tactggccgg tcactgaacc ccagtagggt gaccttcaag gccaacaggc ccttcctggt 1380
tcttataagg gaagtcgcac tgaacactat tatattcatg ggagagtgt ctaatccttg 1440 tgtgaactaa aatattctta atctttgcac cttttcctat ctcggtgttt gttaatggaa 1500
gtaaaaataa atatgactgc cacctcaaaa aaaaaaaaaa aaaaaaaaaa aaaaaaaaaa 1560
a 1561

<210> SEQ ID NO 5
<211> LENGTH: 1599
<212> TYPE: DNA
<213> ORGANISM: Homo sapiens

<400> SEQUENCE: 5
taatgtgaga tggaagtagt ttgtatttat ttttacttct gttcacaaac caaaaatagg 60
aagaggtgca aagaataaga acattttact taacacaagg gttggctact ctgcccatga 120
agataatagt gttcagagga acttctctta taaaaaccag gaaaggcctg ttggccttga 180
aagtcaccct gttggggttt agcgaacggc cagcaatcac aacagcggta cttgcagctg 240
cttcactgcc ttcttcattt acctcaagaa atgccttatg gaatgcatct gagacataga 300
ggtcatctcg gccttctgca acaatacctg ggagtttgga cttttcaggg ctgaacagat 360
cgacaaggcc catgtcttgc agctgctcct tcaaactgaa gccgtcctca atgcggaagc 420
ggggcatgtg gaccaccagc atcatctcct ccaattcatc cagccactct tgcagcacct 480
ctggggtgag ttccttctct accttggcca ggctcttctc aggcttgggc aagatgagga 540
ccatggtgat gtcatcacct ttgaagggca actcaagcac ctgggtgcct tcagccacgc 600
gccgataacg gaacttgcct tcctggtaca tcatagatgc tgaacacgac tctccatcag 660
ccttgtagaa cagttccttc cttgtgttct cagggctgaa ctttgacttc cacaggccct 720
tgaagtaaat ggtgttaacc agcaccagaa cagtgagctc attgatggct tccgagggaa 780
tgacatcggt gattcggcct tcggtcttat tggacaccca tttgttgatg gccgctctgg 840
attgctctgc attttccttg aagtccaggg gctggagctt ggctccatat accaactcac 900
tgatgtcctg gtaggtctca ttgaaggtaa gggatttgtc tccaaaaagg cgattggctg 960
atactaactt ggaggatttg ttggcttttc gatagagtcg gcagttcagt ttggcaaaga 1020
agaagtggat ctgatcagat gttttctcag atatggtgtc aaacttaaat acctccatca 1080
gttgctggag ggtgtcatta caggcaccca gcttggtcat agcaaaagcc gtggagatac 1140
tcaggggtga caggaaaatg ttatcattgt cattcttgga atctgccagg tgctgataga 1200

-continued

```
aagtggtagc aaagcgggaa ttggccttgg acagttccca gacacgccgg ttggtggcct   1260

ccgggatctt ctgttctgag ccctcatcct cagttgcctt cttctccggg gagcggtaaa   1320

tgcacatggg attcatggga atgtcccgcg gcttggctgt gcagatgtcc acagggctcc   1380

cgtgacaggt cacgcagtcc cagaagccaa tgagcagcaa ggacaaaaga taaaccttcc   1440

tttttccaga ggttacagtt cctatcacat tggaatacat ggccgctaat cttccacagg   1500

gctgggcaag tggagatagt gtgatctgag gcaatccgcc tgaaaactgg ttctttcctc   1560

taaatctcgc agaggttcca gaggacaggg tggggcaga                          1599
```

<210> SEQ ID NO 6
<211> LENGTH: 1545
<212> TYPE: DNA
<213> ORGANISM: Macaca mulatta

<400> SEQUENCE: 6

```
ttttttttt ttttttttta atgtaagatg ggagtagttg tatttatttt tacttctatt     60

cacaaaccaa aataggaaga ggtacaaaga ataagaacag tttagctcac acaagggttg    120

gctactctgc ccatgaagat aatagtgttc agaggaactt ctcttataaa aaccaggaaa    180

ggcctgttgg ccttgaaggt caccctgttg gggtttagcg aacggccagc aatcccaatg    240

gcggtacttg cagctgcttc actgccttct tcatttacct caagaaatgc cttatggaat    300

gcatcggaga catagaggtc atcccggcct tctgcaacaa tacctgggag tttggacttt    360

tcagggctga acagatcgac aaggcccatg tcttgcagct gctccttcaa actgaagccg    420

tcctcaatgc ggaagcgggg catgtgaacc accagcatca tctcctccaa ctcatccagc    480

cactcctgca gcacctctgg ggtgagttcc tgctccacct tggtcaggct cttctcaggc    540

ttgggcagga tgagcaccat ggtgatgtca tcacccttga agggcaactc aagcacctgg    600

gtgccttcag ccacgcgccg ataacagaac ttgccttcct ggtacatcat agacgctgaa    660

cacgactctc catcagcctt gtagaacggt tccatccttg tgttctcagg gctaaacttt    720

gacttccaca ggcccttgaa gtaaatggtg ttaaccagca ccagaacagt gagctcgttg    780

atggcttccg ggggaatgac atcggtgatt cggccttcgg tcttattgga cacccatttg    840

ttgatggccg ctctggattg ctctgcattt tccttgaagt ccaggggctg gagcttggct    900

ccgtatacca actcactgat gtcctggtag gtctcattga aggtaaggga tttgtctcca    960

aaaaggcgat tggctgatac taacttggag gatttgttgg cttttcgata gagtcggcag   1020

ttcagtttgg caaagaagaa gtggatctga tcagatgttt tctcagatat ggtgtcaaac   1080

ttaaatacct ccatcagttg cttgagggtg tcattacagg cacccagctt ggtcatagca   1140

aaagccgtgg agacactcag gggtgacagg aaaatgttat ccttgtcgtt cttggaatct   1200

gccaggtgct gatagaaagt ggtagcaaag cgggaattgg ccttggacag ttcccagacg   1260

cgccggttgg tggcctcggg gatcttctgt tctgagccct catcctcagt tgccttcttc   1320

tccggggagc ggtaaatgca catgggattc atgggaatgt cccgcggctt ggctgtgcag   1380

atgtccacag ggctcccgtg acaggtcata cagtcccaga ggccaatgag cagcaaggac   1440

agaagataaa ccttcctttt tccagaggct acggttccta tcacattgga atacatggtc   1500

gctaatcttc cacagggctg ggcaagtgga gatggtcctc gtgcc                   1545
```

<210> SEQ ID NO 7
<211> LENGTH: 2171
<212> TYPE: DNA
<213> ORGANISM: Mus musculus

<400> SEQUENCE: 7

```
ttttttttt ttgtataaaa atgcatttct ctttattttg acactgtgta taagaacatt      60
atgcatgtga gtggtttgag aaataaaacg tttaatactc ttatttgaat ctctgtcttt     120
atgggagatt gattcgggtt tgttttttag tttgtagtat gggggcaata atgagaattt     180
aaggtccctc taccctttca agatgcctgc tatcctctaa gatgaaatag taatatattt     240
acctcttgtt tttatggttt tcttttctac tttggggagg agaaagacca tcttgagaca     300
tggtctttca ctctgcagcc cagcctcaac tggccttaac tcctgaccgc cctgcttcta     360
ccttcaaaag caccaggata taggtttgtg ccaccgtggc tggctgctcc cccttcactt     420
gcccaaaagt ggtgtagcat ctgtactcca gtctctcgtc ttcaagtgga aaagtccatt     480
ctcgtgaggt ggcagtcgta tttattttta cttctattca caaacaccaa agtaggaaaa     540
ggtgcaaaga ttaagaatat tttagttcac acaaggatta gccactctcc ccatgaatat     600
aatagtgttc agtgcaactt cccttataag aaccaggaag ggcctgttgg ccttgaaggt     660
caccctattg gggttcagtg accggccagt aatcacgaca gaagtactcg ctgctgcttc     720
actgccttcc tcatttacct caagaaatgc tttgtggaat gcgtcggaga catagaggtc     780
gtccctgcct ccagcaacga tccctgggag ttgggacttt tcagggctga agagatcaat     840
gaggcccatg tcttgcagct gctccttcag actgaagcca tcctcggtgc ggaagcgggg     900
catgtggacc acaagcatag tctctgacag ctcatccagc cactcctgca gcagctctgg     960
ggtgagctcc tgctccacct tggccaggct cttctcaggc ttgggcagga tgagcaccat    1020
ggtgatgtca tccccccttga agggcagctc tagcacctgg gtgccctctg ccacgcgccg   1080
gtatttgaat ttgccttcct ggtacatcat aggcactggg catgactgcc catcgacctt    1140
atagaacggt tccttccttg tgttctcagg gctgaacttt gacttccaca ggcccttgaa    1200
gtaaatggtg ttaaccagaa ccagggcagt gagctcgtta atggcgccct gtgggatgac    1260
atctttgatg cggccttcag tcttattagc tacccagttg ttgatggtca ctctggattg    1320
ctccggattc tccttgaagt ccaggggctg gagcttggct ccatagacaa cctcactaac    1380
atcttgatag ctctcgttga aggtgaggga tttgtctcca aaaaggcggt tggctgatac    1440
caagtcagag gacttgttgg cttttcgata gagtcggcag ttcagtttgg caaagaagaa    1500
gtggatctgg tcggatgtct tctcggagat ggtatcaaat ttaaaaacct ccatcagctg    1560
cttgagagtg tcgttacagg cacccagctt ggtcatagca aaagcagtgg agatgctcaa    1620
gggtgacagg aaaatgttgt cgttgtcatt cttggagtct gccaggtgct ggtagaagtt    1680
agtggcaaat cgcgaattgg ccttggacag ttcccagacc cgccggttgg tggcttctgg    1740
aaccttctgc tctgagccat cctcctcggt ggccttcttc ccaggggagc ggtaaatgca    1800
caagggattc acggggatgt ctcggggctt cgctatgcag atgtcgtcca cagggtttcc    1860
gtgacagata gcacagccca aggcaccgat gaggagcaga gagaggagac aaagcttcct    1920
ctcaccagca gccccacttc ctgccccagg ggaatacatg gccgatgctc ctacagagat    1980
ggtgctgact gagacgatca ctccgaaaac tggttctttc ccctaaatct gagaggtcca    2040
gaggccaggt gggggaggga gctctcccct taaagtcttc aggtagatat gtcttctgat    2100
tatgtcttat atctcaccac ttcactaaaa tgtctcagat acaaatcaga tctatttcta    2160
aaattaccta t                                                         2171
```

<210> SEQ ID NO 8

<211> LENGTH: 1561
<212> TYPE: DNA
<213> ORGANISM: Rattus norvegicus

<400> SEQUENCE: 8 ttttttttt ttttttttt ttttttttt tttttgaggt ggcagtcata tttattttta 60
cttccattaa caaacaccga gataggaaaa ggtgcaaaga ttaagaatat tttagttcac 120
acaaggatta gacactctcc ccatgaatat aatagtgttc agtgcgactt cccttataag 180
aaccaggaag ggcctgttgg ccttgaaggt caccctactg gggttcagtg accggccagt 240
aatcacgaca gaagtactcg ctgctgcttc actgccttcc tcatttacct caagaaacgc 300
tttgtggaat gcatcggaga caaagaggtc gtccctgcct tcagcaatga tccctgggag 360
ttgggacttc tcagggctga agagatcaac aaggcccatg tcttgcagct gctccttcag 420
actgaagctg tcctcgatgc ggaagcgggg cacgtggacc acaagcatga cctccgacag 480
ctcatccagc cactcctgca gcagctccgg ggtgagttcc tgctccacct tagccaggct 540
cttctcaggc ttgggcagga tgagcaccat ggtgatgtcg tccccccttga agggcatctc 600 tagcacctgg gtaccctctc ccacacgcct gtatttgaat ttgccttcct ggtacatcat 660
gggcaccagg catgactgcc catcaacttt gtggaatggt tccttccttg tgttctcagg 720
gctgaacttt gacttccaca ggcccttgaa gtaaatggtg ttaaccagca ccagggcagt 780
gagctcatca atggctcctt gggggatgac gtctttgatg cggccttcag tcttattagc 840
tacccagttg ttgatggtca ctctggattg ctccggattc tccttgaagt ccaggggctg 900
aagcttggct ccatagacaa tctcactaac gtcttgatag ctctcattga aggtaaggga 960
tttgtctcca aaaaggcggt tggctgacac caagttagag gacttgttgg cttttcgata 1020
gagtcggcag ttcagtttgg caaagaagaa gtggatctgg tcggatgtct tctcggagat 1080
ggtatcaaat ttaaaaacct ccatcagctg cttgagggtg ttattacaag cacccagctt 1140
ggtcatagca aacgccgtgg agatgctcaa gggtgacagg aaaatgttgt cgttgtcgtt 1200
cttggagtct gccaggtgct gatagaagtt agtggcaaat cgagaattgg ccttggacag 1260
ttcccagacc cgccggttgg tggcttccgg aaccttctgc tctaggacat cctcctccgt 1320
ggccttcttc gcaggggagc ggtaaatgca catggggttc acggggatgt ctcggggctt 1380
cgctatgcag atgtcgtcca cagggtttcc atgacagaca gcacagccca aggcaccaat 1440
gagtagcaga gagaggagac aaagcttcct ctctccagca accgcacttc ctattcccgg 1500
ggaatacatg gtggacgctt ctgcagagaa gccgtggaga cagtgctgag caatccctcc 1560
g 1561

<210> SEQ ID NO 9
<211> LENGTH: 16
<212> TYPE: PRT
<213> ORGANISM: Unknown
<220> FEATURE:
<223> OTHER INFORMATION: Description of Unknown: Exemplary
hydrophobic membrane translocation peptide

<400> SEQUENCE: 9

Ala Ala Val Ala Leu Leu Pro Ala Val Leu Leu Ala Leu Leu Ala Pro
1 5 10 15

<210> SEQ ID NO 10
<211> LENGTH: 11
<212> TYPE: PRT
<213> ORGANISM: Unknown

<220> FEATURE:
<223> OTHER INFORMATION: Description of Unknown: RFGF
analogue peptide

<400> SEQUENCE: 10

```
Ala Ala Leu Leu Pro Val Leu Leu Ala Ala Pro
1               5                   10
```

<210> SEQ ID NO 11
<211> LENGTH: 13
<212> TYPE: PRT
<213> ORGANISM: Human immunodeficiency virus

<400> SEQUENCE: 11

```
Gly Arg Lys Lys Arg Arg Gln Arg Arg Arg Pro Pro Gln
1               5                   10
```

<210> SEQ ID NO 12
<211> LENGTH: 16
<212> TYPE: PRT
<213> ORGANISM: Drosophila sp.

<400> SEQUENCE: 12

```
Arg Gln Ile Lys Ile Trp Phe Gln Asn Arg Arg Met Lys Trp Lys Lys
1               5                   10                  15
```

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 13
cuuacgcuga guacuucgat t 21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 14
ucgaaguacu cagcguaagt t 21

<210> SEQ ID NO 15
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 15
cccuguggac aucugcaca 19

<210> SEQ ID NO 16
<211> LENGTH: 19

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 16
cuaccacuuu cuaucagca 19

<210> SEQ ID NO 17
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 17
cuaucgaaaa gccaacaaa 19

<210> SEQ ID NO 18
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 18
ggacuucaag gaaaaugca 19

<210> SEQ ID NO 19
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 19
guuaacacca uuuacuuca 19

<210> SEQ ID NO 20
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 20
ccugguuuuu auaagagaa 19

<210> SEQ ID NO 21
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 21
gacauuccca ugaauccca 19

<210> SEQ ID NO 22
<211> LENGTH: 19
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 22

caccuggcag auuccaaga                                                19


<210> SEQ ID NO 23
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23

cgaaaagcca acaaauccu                                                19


<210> SEQ ID NO 24
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24

gaaaaugcag agcaaucca                                                19


<210> SEQ ID NO 25
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25

ggccugugga agucaaagu                                                19


<210> SEQ ID NO 26
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26

gaaguuccuc ugaacacua                                                19


<210> SEQ ID NO 27
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27

ccaugaaucc caugugcau                                                19


<210> SEQ ID NO 28
<211> LENGTH: 19
<212> TYPE: RNA
<213> ORGANISM: Artificial Sequence
```

<220> FEATURE:
<223> OTHER INFORMATION: Description of Artificial Sequence: Synthetic
      oligonucleotide

<400> SEQUENCE: 28
caacugaugg agguauuua 19

<210> SEQ ID NO 29
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
ccaaguuagu aucagccaa 19

<210> SEQ ID NO 30
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
cggccaucaa caaaugggu 19

<210> SEQ ID NO 31
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
gaggacggcu ucaguuuga 19

<210> SEQ ID NO 32
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
ccucugaaca cuauuaucu 19

<210> SEQ ID NO 33
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
caugaauccc augugcauu 19

<210> SEQ ID NO 34
<211> LENGTH: 19
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 34
gauggaggua uuuaaguuu 19

<210> SEQ ID NO 35
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
guaucagcca aucgccuuu 19

<210> SEQ ID NO 36
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
ggguguccaa uaagaccga 19

<210> SEQ ID NO 37
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
cagcccugaa aaguccaaa 19

<210> SEQ ID NO 38
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
cccaugugca uuuaccgcu 19

<210> SEQ ID NO 39
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
guauuuaagu uugacacca 19

<210> SEQ ID NO 40
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 40
gacaaauccc uuaccuuca 19

<210> SEQ ID NO 41
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 41
cuguucuggu gcugguuaa 19

<210> SEQ ID NO 42
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 42
ccaaacuccc agguauugu 19

<210> SEQ ID NO 43
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 43
cccgcuuugc uaccacuuu 19

<210> SEQ ID NO 44
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 44
cuuaccuuca augagaccu 19

<210> SEQ ID NO 45
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 45
cuggugcugg uuaacacca 19

<210> SEQ ID NO 46
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 46
caaacuccca gguauuguu 19

<210> SEQ ID NO 47
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 47
gcuuugcuac cacuuucua 19

<210> SEQ ID NO 48
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 48
ccuaccagga caucaguga 19

<210> SEQ ID NO 49
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 49
ggugcugguu aacaccauu 19

<210> SEQ ID NO 50
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 50
gccguucgcu aaaccccaa 19

<210> SEQ ID NO 51
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 51
ggacaucagu gaguuggua 19

<210> SEQ ID NO 52
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 52
gugcugguua acaccauuu 19

<210> SEQ ID NO 53
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 53
gccuuuccug guuuuuaua 19

<210> SEQ ID NO 54
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 54
cuuuugcuau gaccaagcu 19

<210> SEQ ID NO 55
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 55
uguaccagga aggcaaguu 19

<210> SEQ ID NO 56
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 56
acuauuaucu ucaugggca 19

<210> SEQ ID NO 57
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 57
ucaugggcag aguagccaa 19

<210> SEQ ID NO 58
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 58
ccauuuacuu caagggccu 19

<210> SEQ ID NO 59
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 59
uacuucaagg gccugugga 19

<210> SEQ ID NO 60
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 60
acuucaaggg ccuguggaa 19

<210> SEQ ID NO 61
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 61
cgacucuauc gaaaagcca 19

<210> SEQ ID NO 62
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 62
aacugccgac ucuaucgaa 19

<210> SEQ ID NO 63
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 63
acugccgacu cuaucgaaa 19

<210> SEQ ID NO 64
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 64

-continued gacucuaucg aaaagccaa 19

<210> SEQ ID NO 65
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 65
ucuucuuugc caaacugaa 19

<210> SEQ ID NO 66
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 66
ugccaaacug aacugccga 19

<210> SEQ ID NO 67
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 67
ccaaacugaa cugccgacu 19

<210> SEQ ID NO 68
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 68
acugaacugc cgacucuau 19

<210> SEQ ID NO 69
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 69
gaacugccga cucuaucga 19

<210> SEQ ID NO 70
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 70
cugccgacuc uaucgaaaa 19

<210> SEQ ID NO 71
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 71
cugguuaaca ccauuuacu 19

<210> SEQ ID NO 72
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 72
ugugcagaug uccacaggg 19

<210> SEQ ID NO 73
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 73
ugcugauaga aagugguag 19

<210> SEQ ID NO 74
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 74
uuuguuggcu uuucgauag 19

<210> SEQ ID NO 75
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 75
ugcauuuucc uugaagucc 19

<210> SEQ ID NO 76
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 76
ugaaguaaau gguguuaac 19

<210> SEQ ID NO 77
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 77
uucucuuaua aaaaccagg 19

<210> SEQ ID NO 78
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 78
ugggauucau gggaauguc 19

<210> SEQ ID NO 79
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 79
ucuuggaauc ugccaggug 19

<210> SEQ ID NO 80
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 80
aggauuuguu ggcuuuucg 19

<210> SEQ ID NO 81
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 81
uggauugcuc ugcauuuuc 19

<210> SEQ ID NO 82
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 82
acuuugacuu ccacaggcc 19

<210> SEQ ID NO 83
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 83
uaguguucag aggaacuuc 19

<210> SEQ ID NO 84
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 84
augcacaugg gauucaugg 19

<210> SEQ ID NO 85
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 85
uaaauaccuc caucaguug 19

<210> SEQ ID NO 86
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 86
uuggcugaua cuaacuugg 19

<210> SEQ ID NO 87
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 87
acccauuugu ugauggccg 19

<210> SEQ ID NO 88
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 88
ucaaacugaa gccguccuc 19

<210> SEQ ID NO 89

<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 89
agauaauagu guucagagg 19

<210> SEQ ID NO 90
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 90
aaugcacaug ggauucaug 19

<210> SEQ ID NO 91
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 91
aaacuuaaau accuccauc 19

<210> SEQ ID NO 92
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 92
aaaggcgauu ggcugauac 19

<210> SEQ ID NO 93
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 93
ucggucuuau uggacaccc 19

<210> SEQ ID NO 94
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 94
uuuggacuuu ucagggcug 19

<210> SEQ ID NO 95
<211> LENGTH: 19

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 95

agcgguaaau gcacauggg                                                19


<210> SEQ ID NO 96
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 96

uggugucaaa cuuaaauac                                                19


<210> SEQ ID NO 97
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97

ugaagguaag ggauuuguc                                                19


<210> SEQ ID NO 98
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98

uuaaccagca ccagaacag                                                19


<210> SEQ ID NO 99
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99

acaauaccug ggaguuugg                                                19


<210> SEQ ID NO 100
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100

aaagugguag caaagcggg                                                19


<210> SEQ ID NO 101
<211> LENGTH: 19
<212> TYPE: RNA
```

<213> ORGANISM: Artificial Sequence
<220> FEATURE:
<223> OTHER INFORMATION: Description of Artificial Sequence: Synthetic
oligonucleotide

<400> SEQUENCE: 101
aggucucauu gaagguaag 19

<210> SEQ ID NO 102
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 102
ugguguuaac cagcaccag 19

<210> SEQ ID NO 103
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 103
aacaauaccu gggaguuug 19

<210> SEQ ID NO 104
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 104
uagaaagugg uagcaaagc 19

<210> SEQ ID NO 105
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 105
ucacugaugu ccugguagg 19

<210> SEQ ID NO 106
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 106
aaugguguua accagcacc 19

<210> SEQ ID NO 107
<211> LENGTH: 19
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 107

uugggguuua gcgaacggc                                                      19

<210> SEQ ID NO 108
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 108

uaccaacuca cugaugucc                                                      19

<210> SEQ ID NO 109
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 109

aaaugguguu aaccagcac                                                      19

<210> SEQ ID NO 110
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 110

uauaaaaacc aggaaaggc                                                      19

<210> SEQ ID NO 111
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 111

agcuugguca uagcaaaag                                                      19

<210> SEQ ID NO 112
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 112

aacuugccuu ccugguaca                                                      19

<210> SEQ ID NO 113
<211> LENGTH: 19
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 113
ugcccaugaa gauaauagu 19

<210> SEQ ID NO 114
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 114
uuggcuacuc ugcccauga 19

<210> SEQ ID NO 115
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 115
aggcccuuga aguaaaugg 19

<210> SEQ ID NO 116
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 116
uccacaggcc cuugaagua 19

<210> SEQ ID NO 117
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 117
uuccacaggc ccuugaagu 19

<210> SEQ ID NO 118
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 118
uggcuuuucg auagagucg 19

<210> SEQ ID NO 119
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 119
uucgauagag ucggcaguu 19

<210> SEQ ID NO 120
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 120
uuucgauaga gucggcagu 19

<210> SEQ ID NO 121
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 121
uuggcuuuuc gauagaguc 19

<210> SEQ ID NO 122
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 122
uucaguuugg caaagaaga 19

<210> SEQ ID NO 123
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 123
ucggcaguuc aguuuggca 19

<210> SEQ ID NO 124
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 124
agucggcagu ucaguuugg 19

<210> SEQ ID NO 125
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 125
auagagucgg caguucagu 19

<210> SEQ ID NO 126
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 126
ucgauagagu cggcaguuc 19

<210> SEQ ID NO 127
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 127
uuuucgauag agucggcag 19

<210> SEQ ID NO 128
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 128
aguaaauggu guuaaccag 19

<210> SEQ ID NO 129
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 129
cccuguggac aucugcacat t 21

<210> SEQ ID NO 130
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 130
cuaccacuuu cuaucagcat t 21

<210> SEQ ID NO 131
<211> LENGTH: 21

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 131

cuaucgaaaa gccaacaaat t                                              21


<210> SEQ ID NO 132
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 132

ggacuucaag gaaaaugcat t                                              21


<210> SEQ ID NO 133
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 133

guuaacacca uuuacuucat t                                              21


<210> SEQ ID NO 134
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 134

ccugguuuuu auaagagaat t                                              21


<210> SEQ ID NO 135
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 135

gacauuccca ugaaucccat t                                              21


<210> SEQ ID NO 136
```

<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 136
caccuggcag auuccaagat t 21

<210> SEQ ID NO 137
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 137
cgaaaagcca acaaauccut t 21

<210> SEQ ID NO 138
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 138
gaaaaugcag agcaauccat t 21

<210> SEQ ID NO 139
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 139
ggccugugga agucaaagut t 21

<210> SEQ ID NO 140
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 140
gaaguuccuc ugaacacuat t 21

<210> SEQ ID NO 141
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 141
ccaugaaucc caugugcaut t 21

<210> SEQ ID NO 142
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 142
caacugaugg agguauuuat t 21

<210> SEQ ID NO 143
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 143
ccaaguuagu aucagccaat t 21

<210> SEQ ID NO 144
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 144
cggccaucaa caaaugggut t 21

<210> SEQ ID NO 145
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 145
gaggacggcu ucaguuugat t 21

<210> SEQ ID NO 146
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 146
ccucugaaca cuauuaucut t 21

<210> SEQ ID NO 147
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 147
caugaauccc augugcauut t 21

<210> SEQ ID NO 148
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 148
gauggaggua uuuaaguuut t 21

<210> SEQ ID NO 149
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 149
guaucagcca aucgccuuut t 21

<210> SEQ ID NO 150
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 150
ggguguccaa uaagaccgat t 21

<210> SEQ ID NO 151
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 151
cagcccugaa aaguccaaat t 21

<210> SEQ ID NO 152
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 152
cccaugugca uuuaccgcut t 21

<210> SEQ ID NO 153
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 153
guauuuaagu uugacaccat t 21

<210> SEQ ID NO 154
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 154
gacaaauccc uuaccuucat t 21

<210> SEQ ID NO 155
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 155

-continued cuguucuggu gcugguuaat t 21

<210> SEQ ID NO 156
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 156
ccaaacuccc agguauugut t 21

<210> SEQ ID NO 157
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 157
cccgcuuugc uaccacuuut t 21

<210> SEQ ID NO 158
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 158
cuuaccuuca augagaccut t 21

<210> SEQ ID NO 159
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 159
cuggugcugg uuaacaccat t 21

<210> SEQ ID NO 160
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 160
caaacuccca gguauuguut t 21

<210> SEQ ID NO 161
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 161
gcuuugcuac cacuuucuat t 21

<210> SEQ ID NO 162
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 162
ccuaccagga caucagugat t 21

<210> SEQ ID NO 163
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 163
ggugcugguu aacaccauut t 21

<210> SEQ ID NO 164
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 164
gccguucgcu aaaccccaat t 21

<210> SEQ ID NO 165
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 165
ggacaucagu gaguugguat t 21

<210> SEQ ID NO 166
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 166
gugcugguua acaccauuut t 21

<210> SEQ ID NO 167
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 167
gccuuuccug guuuuuauat t 21

<210> SEQ ID NO 168
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 168
cuuuugcuau gaccaagcut t 21

<210> SEQ ID NO 169
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 169
uguaccagga aggcaaguut t 21

<210> SEQ ID NO 170
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 170
acuauuaucu ucaugggcat t 21

<210> SEQ ID NO 171
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 171
ucaugggcag aguagccaat t 21

<210> SEQ ID NO 172
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 172
ccauuuacuu caagggccut t 21

<210> SEQ ID NO 173
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 173
uacuucaagg gccuguggat t 21

<210> SEQ ID NO 174
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 174
acuucaaggg ccuguggaat t 21

<210> SEQ ID NO 175
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:

Synthetic oligonucleotide

<400> SEQUENCE: 175
cgacucuauc gaaaagccat t 21

<210> SEQ ID NO 176
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 176
aacugccgac ucuaucgaat t 21

<210> SEQ ID NO 177
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 177
acugccgacu cuaucgaaat t 21

<210> SEQ ID NO 178
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 178
gacucuaucg aaaagccaat t 21

<210> SEQ ID NO 179
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 179
ucuucuuugc caaacugaat t 21

<210> SEQ ID NO 180
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:

<223> OTHER INFORMATION: Description of Combined DNA/RNA Molecule:
      Synthetic oligonucleotide

<400> SEQUENCE: 180
ugccaaacug aacugccgat t                                              21

<210> SEQ ID NO 181
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 181
ccaaacugaa cugccgacut t                                              21

<210> SEQ ID NO 182
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 182
acugaacugc cgacucuaut t                                              21

<210> SEQ ID NO 183
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 183
gaacugccga cucuaucgat t                                              21

<210> SEQ ID NO 184
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 184
cugccgacuc uaucgaaaat t                                              21

<210> SEQ ID NO 185
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide <220> FEATURE:
<223> OTHER INFORMATION: Description of Combined DNA/RNA Molecule: Synthetic oligonucleotide

<400> SEQUENCE: 185
cugguuaaca ccauuuacut t 21

<210> SEQ ID NO 186
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 186
ugugcagaug uccacagggt t 21

<210> SEQ ID NO 187
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 187
ugcugauaga aagugguagt t 21

<210> SEQ ID NO 188
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 188
uuuguuggcu uuucgauagt t 21

<210> SEQ ID NO 189
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 189
ugcauuuucc uugaagucct t 21

<210> SEQ ID NO 190
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:
Synthetic oligonucleotide

<400> SEQUENCE: 190
ugaaguaaau gguguuaact t 21

<210> SEQ ID NO 191
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 191
uucucuuaua aaaaccaggt t 21

<210> SEQ ID NO 192
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 192
ugggauucau gggaauguct t 21

<210> SEQ ID NO 193
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 193
ucuuggaauc ugccaggugt t 21

<210> SEQ ID NO 194
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 194
aggauuuguu ggcuuuucgt t 21

<210> SEQ ID NO 195
<211> LENGTH: 21
<212> TYPE: DNA
<213> ORGANISM: Artificial Sequence
<220> FEATURE:

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 195
uggauugcuc ugcauuuuct t 21

<210> SEQ ID NO 196
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 196
acuuugacuu ccacaggcct t 21

<210> SEQ ID NO 197
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 197
uaguguucag aggaacuuct t 21

<210> SEQ ID NO 198
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 198
augcacaugg gauucauggt t 21

<210> SEQ ID NO 199
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 199
uaaauaccuc caucaguugt t 21

<210> SEQ ID NO 200
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 200
uuggcugaua cuaacuuggt t 21

<210> SEQ ID NO 201
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 201
acccauuugu ugauggccgt t 21

<210> SEQ ID NO 202
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 202
ucaaacugaa gccguccuct t 21

<210> SEQ ID NO 203
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 203
agauaauagu guucagaggt t 21

<210> SEQ ID NO 204
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 204
aaugcacaug ggauucaugt t 21

<210> SEQ ID NO 205
<211> LENGTH: 21
<212> TYPE: DNA

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 205
aaacuuaaau accuccauct t 21

<210> SEQ ID NO 206
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 206
aaaggcgauu ggcugauact t 21

<210> SEQ ID NO 207
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 207
ucggucuuau uggacaccct t 21

<210> SEQ ID NO 208
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 208
uuuggacuuu ucagggcugt t 21

<210> SEQ ID NO 209
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 209
agcgguaaau gcacaugggt t 21

<210> SEQ ID NO 210
<211> LENGTH: 21

<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 210
uggugucaaa cuuaaauact t 21

<210> SEQ ID NO 211
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 211
ugaagguaag ggauuuguct t 21

<210> SEQ ID NO 212
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 212
uuaaccagca ccagaacagt t 21

<210> SEQ ID NO 213
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 213
acaauaccug ggaguuuggt t 21

<210> SEQ ID NO 214
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 214
aaagugguag caaagcgggt t 21

<210> SEQ ID NO 215

<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 215
aggucucauu gaagguaagt t 21

<210> SEQ ID NO 216
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 216
ugguguuaac cagcaccagt t 21

<210> SEQ ID NO 217
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 217
aacaauaccu gggaguuugt t 21

<210> SEQ ID NO 218
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 218
uagaaagugg uagcaaagct t 21

<210> SEQ ID NO 219
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 219
ucacugaugu ccugguaggt t 21

```
<210> SEQ ID NO 220
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 220

aaugguguua accagcacct t                                              21

<210> SEQ ID NO 221
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 221

uugggguuua gcgaacggct t                                              21

<210> SEQ ID NO 222
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 222

uaccaacuca cugaugucct t                                              21

<210> SEQ ID NO 223
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 223

aaaugguguu aaccagcact t                                              21

<210> SEQ ID NO 224
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 224

uauaaaaacc aggaaaggct t                                              21
```

<210> SEQ ID NO 225
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 225
agcuugguca uagcaaaagt t 21

<210> SEQ ID NO 226
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 226
aacuugccuu ccugguacat t 21

<210> SEQ ID NO 227
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 227
ugcccaugaa gauaauagut t 21

<210> SEQ ID NO 228
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 228
uuggcuacuc ugcccaugat t 21

<210> SEQ ID NO 229
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 229
aggcccuuga aguaaauggt t 21

<210> SEQ ID NO 230
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 230
uccacaggcc cuugaaguat t 21

<210> SEQ ID NO 231
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 231
uuccacaggc ccuugaagut t 21

<210> SEQ ID NO 232
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 232
uggcuuuucg auagagucgt t 21

<210> SEQ ID NO 233
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 233
uucgauagag ucggcaguut t 21

<210> SEQ ID NO 234
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 234
uuucgauaga gucggcagut t 21

<210> SEQ ID NO 235
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 235
uuggcuuuuc gauagaguct t 21

<210> SEQ ID NO 236
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 236
uucaguuugg caaagaagat t 21

<210> SEQ ID NO 237
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 237
ucggcaguuc aguuuggcat t 21

<210> SEQ ID NO 238
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 238
agucggcagu ucaguuuggt t 21

<210> SEQ ID NO 239
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 239
auagagucgg caguucagut t 21

<210> SEQ ID NO 240
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 240
ucgauagagu cggcaguuct t 21

<210> SEQ ID NO 241
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 241
uuuucgauag agucggcagt t 21

<210> SEQ ID NO 242
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 242
aguaaauggu guuaaccagt t 21

<210> SEQ ID NO 243
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 243
cuaucgaaaa gccaacaaat t 21

<210> SEQ ID NO 244
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 244
cuaucgaaaa gccaacaaat t 21

<210> SEQ ID NO 245
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 245
cuaucgaaaa gccaacaaat t 21

<210> SEQ ID NO 246
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 246
cuaucgaaaa gccaacaaat t 21

<210> SEQ ID NO 247
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 247
cuaucgaaaa gccaacaaat t 21

<210> SEQ ID NO 248
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 248
cuaucgaaaa gccaacaaat t 21

<210> SEQ ID NO 249
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 249
cuaucgaaaa gccaacaaat t 21

<210> SEQ ID NO 250
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 250
cuaucgaaaa gccaacaaat t 21

<210> SEQ ID NO 251
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 251
cuaucgaaaa gccaacaaat t 21

<210> SEQ ID NO 252
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 252
cuaucgaaaa gccaacaaat t 21

<210> SEQ ID NO 253
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 253
cuaucgaaaa gccaacaaat t 21

<210> SEQ ID NO 254
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:

-continued

Synthetic oligonucleotide

<400> SEQUENCE: 254
cuaucgaaaa gccaacaaat t 21

<210> SEQ ID NO 255
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 255
cuaucgaaaa gccaacaaat t 21

<210> SEQ ID NO 256
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 256
ccaugaaucc caugugcaut t 21

<210> SEQ ID NO 257
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 257
ccaugaaucc caugugcaut t 21

<210> SEQ ID NO 258
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 258
ccaugaaucc caugugcaut t 21

<210> SEQ ID NO 259
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:

<223> OTHER INFORMATION: Description of Combined DNA/RNA Molecule: Synthetic oligonucleotide

<400> SEQUENCE: 259
ccaugaaucc caugugcaut t 21

<210> SEQ ID NO 260
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 260
ccaugaaucc caugugcaut t 21

<210> SEQ ID NO 261
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 261
ccaugaaucc caugugcaut t 21

<210> SEQ ID NO 262
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 262
ccaugaaucc caugugcaut t 21

<210> SEQ ID NO 263
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 263
ccaugaaucc caugugcaut t 21

<210> SEQ ID NO 264
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 264
ccaugaaucc caugugcaut t 21

<210> SEQ ID NO 265
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 265
ccaugaaucc caugugcaut t 21

<210> SEQ ID NO 266
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 266
ccaugaaucc caugugcaut t 21

<210> SEQ ID NO 267
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 267
ccaugaaucc caugugcaut t 21

<210> SEQ ID NO 268
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 268
ccaugaaucc caugugcaut t 21

<210> SEQ ID NO 269
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:
Synthetic oligonucleotide

<400> SEQUENCE: 269
cugccgacuc uaucgaaaat t 21

<210> SEQ ID NO 270
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 270
cugccgacuc uaucgaaaat t 21

<210> SEQ ID NO 271
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 271
cugccgacuc uaucgaaaat t 21

<210> SEQ ID NO 272
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 272
cugccgacuc uaucgaaaat t 21

<210> SEQ ID NO 273
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 273
cugccgacuc uaucgaaaat t 21

<210> SEQ ID NO 274
<211> LENGTH: 21
<212> TYPE: DNA
<213> ORGANISM: Artificial Sequence
<220> FEATURE:

<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 274
cugccgacuc uaucgaaaat t 21

<210> SEQ ID NO 275
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 275
cugccgacuc uaucgaaaat t 21

<210> SEQ ID NO 276
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 276
cugccgacuc uaucgaaaat t 21

<210> SEQ ID NO 277
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 277
cugccgacuc uaucgaaaat t 21

<210> SEQ ID NO 278
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 278
cugccgacuc uaucgaaaat t 21

<210> SEQ ID NO 279
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 279
cugccgacuc uaucgaaaat t 21

<210> SEQ ID NO 280
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 280
cugccgacuc uaucgaaaat t 21

<210> SEQ ID NO 281
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 281
cugccgacuc uaucgaaaat t 21

<210> SEQ ID NO 282
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 282
ucuucuuugc caaacugaat t 21

<210> SEQ ID NO 283
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 283
ucuucuuugc caaacugaat t 21

<210> SEQ ID NO 284
<211> LENGTH: 21
<212> TYPE: DNA

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 284
ucuucuuugc caaacugaat t 21

<210> SEQ ID NO 285
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 285
ucuucuuugc caaacugaat t 21

<210> SEQ ID NO 286
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 286
ucuucuuugc caaacugaat t 21

<210> SEQ ID NO 287
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 287
ucuucuuugc caaacugaat t 21

<210> SEQ ID NO 288
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 288
ucuucuuugc caaacugaat t 21

<210> SEQ ID NO 289
<211> LENGTH: 21

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 289

ucuucuuugc caaacugaat t                                                21


<210> SEQ ID NO 290
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 290

ucuucuuugc caaacugaat t                                                21


<210> SEQ ID NO 291
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 291

ucuucuuugc caaacugaat t                                                21


<210> SEQ ID NO 292
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 292

ucuucuuugc caaacugaat t                                                21


<210> SEQ ID NO 293
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 293

ucuucuuugc caaacugaat t                                                21


<210> SEQ ID NO 294
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 294

gguuaacacc auuuacuuca a                                              21


<210> SEQ ID NO 295
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 295

uaguaucagc caaucgccuu u                                              21


<210> SEQ ID NO 296
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 296

cgcuuugcua ccacuuucua u                                              21


<210> SEQ ID NO 297
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 297

cuuugcuacc acuuucuauc a                                              21


<210> SEQ ID NO 298
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 298

aucgaaaagc caacaaaucc u                                              21


<210> SEQ ID NO 299
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 299

ucccaugaau cccaugugca u                                              21


<210> SEQ ID NO 300
<211> LENGTH: 21
```

<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 300
uaaggcauuu cuugagguaa a 21

<210> SEQ ID NO 301
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 301
gcaacugaug gagguauuua a 21

<210> SEQ ID NO 302
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 302
uuuaaguuug acaccauauc u 21

<210> SEQ ID NO 303
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 303
ccaugaaucc caugugcauu u 21

<210> SEQ ID NO 304
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 304
ugcugguuaa caccauuuac u 21

<210> SEQ ID NO 305
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 305
ucuaucgaaa agccaacaaa u 21

<210> SEQ ID NO 306
<211> LENGTH: 21
<212> TYPE: RNA

<213> ORGANISM: Artificial Sequence
<220> FEATURE:
<223> OTHER INFORMATION: Description of Artificial Sequence: Synthetic
      oligonucleotide

<400> SEQUENCE: 306
uucccgcuuu gcuaccacuu u                                              21

<210> SEQ ID NO 307
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 307
gauggaggua uuuaaguuug a                                              21

<210> SEQ ID NO 308
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 308
agacaaaucc cuuaccuuca a                                              21

<210> SEQ ID NO 309
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 309
ugcuaccacu uucuaucagc a                                              21

<210> SEQ ID NO 310
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 310
uguauuccaa ugugauagga a                                              21

<210> SEQ ID NO 311
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 311
aacugccgac ucuaucgaaa a                                              21

<210> SEQ ID NO 312
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 312
gccgacucua ucgaaaagcc a 21

<210> SEQ ID NO 313
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 313
uauuuaaguu ugacaccaua u 21

<210> SEQ ID NO 314
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 314
ugggccuugu cgaucuguuc a 21

<210> SEQ ID NO 315
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 315
caaaucccuu accuucaaug a 21

<210> SEQ ID NO 316
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 316
uccaaacucc cagguauugu u 21

<210> SEQ ID NO 317
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 317
gaacugccga cucuaucgaa a 21

<210> SEQ ID NO 318
<211> LENGTH: 21
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 318
ucaacaaaug gguguccaau a 21

<210> SEQ ID NO 319
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 319
cacuguucug gugcugguua a 21

<210> SEQ ID NO 320
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 320
ggacggcuuc aguuugaagg a 21

<210> SEQ ID NO 321
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 321
cuggacuuca aggaaaaugc a 21

<210> SEQ ID NO 322
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 322
agguauuuaa guuugacacc a 21

<210> SEQ ID NO 323
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 323
uuacuucaag ggccugugga a 21

<210> SEQ ID NO 324
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 324
uuuuuggaga caaaucccuu a 21

<210> SEQ ID NO 325
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 325
gauugcuggc cguucgcuaa a 21

<210> SEQ ID NO 326
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 326
ccgacucuau cgaaaagcca a 21

<210> SEQ ID NO 327
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 327
caccauuuac uucaagggcc u 21

<210> SEQ ID NO 328
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 328
caagcugggu gccuguaaug a 21

<210> SEQ ID NO 329
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 329
acacuauuau cuucaugggc a 21

<210> SEQ ID NO 330
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 330
aggaaaaugc agagcaaucc a 21

<210> SEQ ID NO 331
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 331
ucuggugcug guuaacacca u 21

<210> SEQ ID NO 332
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 332
agcccugugg acaucugcac a 21

<210> SEQ ID NO 333
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 333
cuucuucuuu gccaaacuga a 21

<210> SEQ ID NO 334
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 334
ucuccacggc uuuugcuaug a 21

<210> SEQ ID NO 335
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 335
gcaccuggca gauuccaaga a 21

<210> SEQ ID NO 336
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 336
cuucaugggc agaguagcca a 21

<210> SEQ ID NO 337
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 337
cuccaaguua guaucagcca a 21

<210> SEQ ID NO 338
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 338
gguuaacacc auuuacuuca a 21

<210> SEQ ID NO 339
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 339
gguuaacacc auuuacuuca a 21

<210> SEQ ID NO 340
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 340
gguuaacacc auuuacuuca a 21

<210> SEQ ID NO 341
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 341
gguuaacacc auuuacuuca a 21

<210> SEQ ID NO 342
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 342
gguuaacacc auuuacuuca a 21

<210> SEQ ID NO 343
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 343
gguuaacacc auuuacuuca a 21

<210> SEQ ID NO 344
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 344
gguuaacacc auuuacuuca a 21

<210> SEQ ID NO 345
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 345
gguuaacacc auuuacuuca a 21

<210> SEQ ID NO 346
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 346
gguuaacacc auuuacuuca a 21

<210> SEQ ID NO 347
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 347
gguuaacacc auuuacuuca a 21

<210> SEQ ID NO 348
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 348
gguuaacacc auuuacuuca a 21

<210> SEQ ID NO 349
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 349
gguuaacacc auuuacuuca a 21

<210> SEQ ID NO 350
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 350
gguuaacacc auuuacuuca a 21

<210> SEQ ID NO 351
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 351
gguuaacacc auuuacuuca a 21

<210> SEQ ID NO 352
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 352
gguuaacacc auuuacuuca a 21

<210> SEQ ID NO 353
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 353
gguuaacacc auuuacuuca a 21

<210> SEQ ID NO 354
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 354
gguuaacacc auuuacuuca a 21

<210> SEQ ID NO 355
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 355
gguuaacacc auuuacuuca a 21

<210> SEQ ID NO 356
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 356
gguuaacacc auuuacuuca a 21

<210> SEQ ID NO 357
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 357
gguuaacacc auuuacuuca a 21

<210> SEQ ID NO 358
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 358
gguuaacacc auuuacuuca a 21

<210> SEQ ID NO 359
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 359
gguuaacacc auuuacuuca a 21

<210> SEQ ID NO 360
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 360
gguuaacacc auuuacuuca a 21

<210> SEQ ID NO 361
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 361
gguuaacacc auuuacuuca a 21

<210> SEQ ID NO 362
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 362
gguuaacacc auuuacuuca a 21

<210> SEQ ID NO 363
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 363
gguuaacacc auuuacuuca a 21

<210> SEQ ID NO 364
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 364
gguuaacacc auuuacuuca a 21

<210> SEQ ID NO 365
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 365
gguuaacacc auuuacuuca a 21

<210> SEQ ID NO 366
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 366
gguuaacacc auuuacuuca a 21

<210> SEQ ID NO 367
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 367
gguuaacacc auuuacuuca a 21

<210> SEQ ID NO 368
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 368
gguuaacacc auuuacuuca a 21

<210> SEQ ID NO 369
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 369
gguuaacacc auuuacuuca a 21

<210> SEQ ID NO 370
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 370
gguuaacacc auuuacuuca a 21

<210> SEQ ID NO 371
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 371
gguuaacacc auuuacuuca a 21

<210> SEQ ID NO 372
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 372
gguuaacacc auuuacuuca a 21

<210> SEQ ID NO 373

<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 373
gguuaacacc auuuacuuca a 21

<210> SEQ ID NO 374
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 374
gguuaacacc auuuacuuca a 21

<210> SEQ ID NO 375
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 375
gguuaacacc auuuacuuca a 21

<210> SEQ ID NO 376
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 376
gguuaacacc auuuacuuca a 21

<210> SEQ ID NO 377
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 377
gguuaacacc auuuacuuca a 21

<210> SEQ ID NO 378
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 378
gguuaacacc auuuacuuca a 21

<210> SEQ ID NO 379
<211> LENGTH: 21

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 379
gguuaacacc auuuacuuca a                                              21

<210> SEQ ID NO 380
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 380
gguuaacacc auuuacuuca a                                              21

<210> SEQ ID NO 381
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 381
gguuaacacc auuuacuuca a                                              21

<210> SEQ ID NO 382
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 382
gguuaacacc auuuacuuca a                                              21

<210> SEQ ID NO 383
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 383
gguuaacacc auuuacuuca a                                              21

<210> SEQ ID NO 384
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 384
gguuaacacc auuuacuuca a                                              21

<210> SEQ ID NO 385
<211> LENGTH: 21
<212> TYPE: RNA

<213> ORGANISM: Artificial Sequence
<220> FEATURE:
<223> OTHER INFORMATION: Description of Artificial Sequence: Synthetic
      oligonucleotide

<400> SEQUENCE: 385
gguuaacacc auuuacuuca a 21

<210> SEQ ID NO 386
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 386
gguuaacacc auuuacuuca a 21

<210> SEQ ID NO 387
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 387
gguuaacacc auuuacuuca a 21

<210> SEQ ID NO 388
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 388
gguuaacacc auuuacuuca a 21

<210> SEQ ID NO 389
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 389
gguuaacacc auuuacuuca a 21

<210> SEQ ID NO 390
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 390
gguuaacacc auuuacuuca a 21

<210> SEQ ID NO 391
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 391
gguuaacacc auuuacuuca a 21

<210> SEQ ID NO 392
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 392
gguuaacacc auuuacuuca a 21

<210> SEQ ID NO 393
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 393
gguuaacacc auuuacuuca a 21

<210> SEQ ID NO 394
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 394
gguuaacacc auuuacuuca a 21

<210> SEQ ID NO 395
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 395
gguuaacacc auuuacuuca a 21

<210> SEQ ID NO 396
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 396
gguuaacacc auuuacuuca a 21

<210> SEQ ID NO 397
<211> LENGTH: 21
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 397
gguuaacacc auuuacuuca a 21

<210> SEQ ID NO 398
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 398
gguuaacacc auuuacuuca a 21

<210> SEQ ID NO 399
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 399
gguuaacacc auuuacuuca a 21

<210> SEQ ID NO 400
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 400
gguuaacacc auuuacuuca a 21

<210> SEQ ID NO 401
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 401
gguuaacacc auuuacuuca a 21

<210> SEQ ID NO 402
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 402
gguuaacacc auuuacuuca a 21

<210> SEQ ID NO 403
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 403
gguuaacacc auuuacuuca a 21

<210> SEQ ID NO 404
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 404
gguuaacacc auuuacuuca a 21

<210> SEQ ID NO 405
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 405
gguuaacacc auuuacuuca a 21

<210> SEQ ID NO 406
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 406
gguuaacacc auuuacuuca a 21

<210> SEQ ID NO 407
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 407
gguuaacacc auuuacuuca a 21

<210> SEQ ID NO 408
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 408
gguuaacacc auuuacuuca a 21

<210> SEQ ID NO 409
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 409
gguuaacacc auuuacuuca a 21

<210> SEQ ID NO 410
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 410
gguuaacacc auuuacuuca a 21

<210> SEQ ID NO 411
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 411
gguuaacacc auuuacuuca a 21

<210> SEQ ID NO 412
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 412
gguuaacacc auuuacuuca a 21

<210> SEQ ID NO 413
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 413
gguuaacacc auuuacuuca a 21

<210> SEQ ID NO 414
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 414
gguuaacacc auuuacuuca a 21

<210> SEQ ID NO 415
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 415
gguuaacacc auuuacuuca a 21

<210> SEQ ID NO 416
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 416
gguuaacacc auuuacuuca a 21

<210> SEQ ID NO 417
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 417
gguuaacacc auuuacuuca a 21

<210> SEQ ID NO 418
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 418
gguuaacacc auuuacuuca a 21

<210> SEQ ID NO 419
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 419
gguuaacacc auuuacuuca a 21

<210> SEQ ID NO 420
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 420
gguuaacacc auuuacuuca a 21

<210> SEQ ID NO 421
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 421
gguuaacacc auuuacuuca a 21

<210> SEQ ID NO 422
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 422
gguuaacacc auuuacuuca a 21

<210> SEQ ID NO 423
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 423
gguuaacacc auuuacuuca a 21

<210> SEQ ID NO 424
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 424
gguuaacacc auuuacuuca a 21

<210> SEQ ID NO 425
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 425
gguuaacacc auuuacuuca a 21

<210> SEQ ID NO 426
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 426
gguuaacacc auuuacuuca a 21

<210> SEQ ID NO 427
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 427
gguuaacacc auuuacuuca a 21

<210> SEQ ID NO 428
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 428
gguuaacacc auuuacuuca a 21

<210> SEQ ID NO 429
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 429
gguuaacacc auuuacuuca a 21

<210> SEQ ID NO 430
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 430
gguuaacacc auuuacuuca a 21

<210> SEQ ID NO 431
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 431
gguuaacacc auuuacuuca a 21

<210> SEQ ID NO 432
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 432
gguuaacacc auuuacuuca a 21

<210> SEQ ID NO 433
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 433
gguuaacacc auuuacuuca a 21

<210> SEQ ID NO 434
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 434
gguuaacacc auuuacuuca a 21

<210> SEQ ID NO 435
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 435
gguuaacacc auuuacuuca a 21

<210> SEQ ID NO 436
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 436
gguuaacacc auuuacuuca a 21

<210> SEQ ID NO 437
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 437
gguuaacacc auuuacuuca a 21

<210> SEQ ID NO 438
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 438
gguuaacacc auuuacuuca a 21

<210> SEQ ID NO 439
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 439
gguuaacacc auuuacuuca a 21

<210> SEQ ID NO 440
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 440
gguuaacacc auuuacuuca a 21

<210> SEQ ID NO 441
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 441
gguuaacacc auuuacuuca a 21

<210> SEQ ID NO 442
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 442
gguuaacacc auuuacuuca a 21

<210> SEQ ID NO 443
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 443
gguuaacacc auuuacuuca a 21

<210> SEQ ID NO 444
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 444
gguuaacacc auuuacuuca a 21

<210> SEQ ID NO 445
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 445
gguuaacacc auuuacuuca a 21

<210> SEQ ID NO 446
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 446
gguuaacacc auuuacuuca a 21

<210> SEQ ID NO 447
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 447
gguuaacacc auuuacuuca a 21

<210> SEQ ID NO 448
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 448
gguuaacacc auuuacuuca a 21

<210> SEQ ID NO 449
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 449
gguuaacacc auuuacuuca a 21

<210> SEQ ID NO 450
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 450
gguuaacacc auuuacuuca a 21

<210> SEQ ID NO 451
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 451
gguuaacacc auuuacuuca a 21

<210> SEQ ID NO 452

<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 452
gguuaacacc auuuacuuca a 21

<210> SEQ ID NO 453
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 453
gguuaacacc auuuacuuca a 21

<210> SEQ ID NO 454
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 454
gguuaacacc auuuacuuca a 21

<210> SEQ ID NO 455
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 455
gguuaacacc auuuacuuca a 21

<210> SEQ ID NO 456
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 456
gguuaacacc auuuacuuca a 21

<210> SEQ ID NO 457
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 457
gguuaacacc auuuacuuca a 21

<210> SEQ ID NO 458
<211> LENGTH: 21

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 458
gguuaacacc auuuacuuca a 21

<210> SEQ ID NO 459
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 459
gguuaacacc auuuacuuca a 21

<210> SEQ ID NO 460
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 460
gguuaacacc auuuacuuca a 21

<210> SEQ ID NO 461
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 461
gguuaacacc auuuacuuca a 21

<210> SEQ ID NO 462
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 462
gguuaacacc auuuacuuca a 21

<210> SEQ ID NO 463
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 463
gguuaacacc auuuacuuca a 21

<210> SEQ ID NO 464
<211> LENGTH: 21
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 464
gguuaacacc auuuacuuca a 21

<210> SEQ ID NO 465
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 465
gguuaacacc auuuacuuca a 21

<210> SEQ ID NO 466
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 466
gguuaacacc auuuacuuca a 21

<210> SEQ ID NO 467
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 467
gguuaacacc auuuacuuca a 21

<210> SEQ ID NO 468
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 468
gguuaacacc auuuacuuca a 21

<210> SEQ ID NO 469
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 469
gguuaacacc auuuacuuca a 21

<210> SEQ ID NO 470
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 470
gguuaacacc auuuacuuca a 21

<210> SEQ ID NO 471
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 471
gguuaacacc auuuacuuca a 21

<210> SEQ ID NO 472
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 472
gguuaacacc auuuacuuca a 21

<210> SEQ ID NO 473
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 473
gguuaacacc auuuacuuca a 21

<210> SEQ ID NO 474
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 474
gguuaacacc auuuacuuca a 21

<210> SEQ ID NO 475
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 475
gguuaacauc auuuacuuca a 21

<210> SEQ ID NO 476
<211> LENGTH: 21
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 476
gguuaacaac auuuacuuca a 21

<210> SEQ ID NO 477
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 477
gguuaacacu auuuacuuca a 21

<210> SEQ ID NO 478
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 478
gguuaacaca auuuacuuca a 21

<210> SEQ ID NO 479
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 479
gguuaacacc auuuacuuca a 21

<210> SEQ ID NO 480
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 480
gguuaacacc auuuacuuca a 21

<210> SEQ ID NO 481
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 481
gguuaacacc auuuacuuca a 21

<210> SEQ ID NO 482
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 482
gguuaacacc auuuacuuca a 21

<210> SEQ ID NO 483
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 483
uuaacaccau uuacuucaa 19

<210> SEQ ID NO 484
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 484
uuaacaccau uuacuucaa 19

<210> SEQ ID NO 485
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 485
uuaacaccau uuacuucaa 19

<210> SEQ ID NO 486
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 486
uuaacaccau uuacuucaa 19

<210> SEQ ID NO 487
<211> LENGTH: 17
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 487
aacaccauuu acuucaa 17

<210> SEQ ID NO 488
<211> LENGTH: 17
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 488
aacaccauuu acuucaa 17

<210> SEQ ID NO 489
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 489
gguuaacacc auuuacuuca a 21

<210> SEQ ID NO 490
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 490
gguuaacacc auuuacuuca a 21

<210> SEQ ID NO 491
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 491
gguuaacacc auuuacuuca a 21

<210> SEQ ID NO 492
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 492
gguuaacacc auuuacuuca a 21

<210> SEQ ID NO 493
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 493
gguuaacacc auuuacuuca a 21

<210> SEQ ID NO 494
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 494
gguuaacacc auuuacuuca a 21

<210> SEQ ID NO 495
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 495
gguuaacacc auuuacuuca a 21

<210> SEQ ID NO 496
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 496
gguuaacacc auuuacuuca a 21

<210> SEQ ID NO 497
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 497
gguuaacacc auuuacuuca a 21

<210> SEQ ID NO 498
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 498
gguuaacacc auuuacuuca a 21

<210> SEQ ID NO 499
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 499
gguuaacacc auuuacuuca a 21

<210> SEQ ID NO 500
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 500
gguuaacacc auuuacuuca a 21

<210> SEQ ID NO 501
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 501
gguuaacacc auuuacuuca a 21

<210> SEQ ID NO 502
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 502
gguuaacacc auuuacuuca a 21

<210> SEQ ID NO 503
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 503
gguuaacacc auuuacuuca a 21

<210> SEQ ID NO 504
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 504
gguuaacacc auuuacutca a 21

<210> SEQ ID NO 505
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 505
gguuaacacc auuuacutca a 21

<210> SEQ ID NO 506
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 506
ggutaacacc auuuacutca a 21

<210> SEQ ID NO 507
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 507
ggutaacacc auuuacutca a 21

<210> SEQ ID NO 508
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 508
ggutaacacc auutacutca a 21

<210> SEQ ID NO 509
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 509
ggutaacacc atutacutca a 21

<210> SEQ ID NO 510
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 510
ggutaacacc atutacutca a 21

<210> SEQ ID NO 511
<211> LENGTH: 21
<212> TYPE: DNA

<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 511
uuuguuggcu uuucgauagt t 21

<210> SEQ ID NO 512
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 512
uuuguuggcu uuucgauagt t 21

<210> SEQ ID NO 513
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 513
uuuguuggcu uuucgauagt t 21

<210> SEQ ID NO 514
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 514
uuuguuggcu uuucgauagt t 21

<210> SEQ ID NO 515
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 515
uuuguuggcu uuucgauagt t 21

<210> SEQ ID NO 516
<211> LENGTH: 21

<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 516
uuuguuggcu uuucgauagt t 21

<210> SEQ ID NO 517
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 517
uuuguuggcu uuucgauagt t 21

<210> SEQ ID NO 518
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 518
uuuguuggcu uuucgauagt t 21

<210> SEQ ID NO 519
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 519
uuuguuggcu uuucgauagt t 21

<210> SEQ ID NO 520
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 520
uuuguuggcu uuucgauagt t 21

<210> SEQ ID NO 521

<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 521
uuuguuggcu uuucgauagt t 21

<210> SEQ ID NO 522
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 522
uuuguuggcu uuucgauagt t 21

<210> SEQ ID NO 523
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 523
uuuguuggcu uuucgauagt t 21

<210> SEQ ID NO 524
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 524
augcacaugg gauucauggt t 21

<210> SEQ ID NO 525
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 525
augcacaugg gauucauggt t 21

```
<210> SEQ ID NO 526
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 526

augcacaugg gauucauggt t                                              21


<210> SEQ ID NO 527
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 527

augcacaugg gauucauggt t                                              21


<210> SEQ ID NO 528
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 528

augcacaugg gauucauggt t                                              21


<210> SEQ ID NO 529
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 529

augcacaugg gauucauggt t                                              21


<210> SEQ ID NO 530
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 530

augcacaugg gauucauggt t                                              21
```

<210> SEQ ID NO 531
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 531
augcacaugg gauucauggt t 21

<210> SEQ ID NO 532
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 532
augcacaugg gauucauggt t 21

<210> SEQ ID NO 533
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 533
augcacaugg gauucauggt t 21

<210> SEQ ID NO 534
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 534
augcacaugg gauucauggt t 21

<210> SEQ ID NO 535
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 535
augcacaugg gauucauggt t 21

<210> SEQ ID NO 536
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 536
augcacaugg gauucauggt t 21

<210> SEQ ID NO 537
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 537
uuuucgauag agucggcagt t 21

<210> SEQ ID NO 538
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 538
uuuucgauag agucggcagt t 21

<210> SEQ ID NO 539
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 539
uuuucgauag agucggcagt t 21

<210> SEQ ID NO 540
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 540
uuuucgauag agucggcagt t 21

<210> SEQ ID NO 541
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 541
uuuucgauag agucggcagt t 21

<210> SEQ ID NO 542
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 542
uuuucgauag agucggcagt t 21

<210> SEQ ID NO 543
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 543
uuuucgauag agucggcagt t 21

<210> SEQ ID NO 544
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 544
uuuucgauag agucggcagt t 21

<210> SEQ ID NO 545
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 545
uuuucgauag agucggcagt t 21

<210> SEQ ID NO 546
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 546
uuuucgauag agucggcagt t 21

<210> SEQ ID NO 547
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 547
uuuucgauag agucggcagt t 21

<210> SEQ ID NO 548
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 548
uuuucgauag agucggcagt t 21

<210> SEQ ID NO 549
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 549
uuuucgauag agucggcagt t 21

<210> SEQ ID NO 550
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 550
uucaguuugg caaagaagat t 21

<210> SEQ ID NO 551
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 551
uucaguuugg caaagaagat t 21

<210> SEQ ID NO 552
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 552
uucaguuugg caaagaagat t 21

<210> SEQ ID NO 553
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 553
uucaguuugg caaagaagat t 21

<210> SEQ ID NO 554
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 554
uucaguuugg caaagaagat t 21

<210> SEQ ID NO 555
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 555
uucaguuugg caaagaagat t 21

<210> SEQ ID NO 556
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 556
uucaguuugg caaagaagat t 21

<210> SEQ ID NO 557
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 557
uucaguuugg caaagaagat t 21

<210> SEQ ID NO 558
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 558
uucaguuugg caaagaagat t 21

<210> SEQ ID NO 559
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 559
uucaguuugg caaagaagat t 21

<210> SEQ ID NO 560
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:

Synthetic oligonucleotide

<400> SEQUENCE: 560
uucaguuugg caaagaagat t 21

<210> SEQ ID NO 561
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 561
uucaguuugg caaagaagat t 21

<210> SEQ ID NO 562
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 562
uugaaguaaa ugguguuaac cag 23

<210> SEQ ID NO 563
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 563
aaaggcgauu ggcugauacu aac 23

<210> SEQ ID NO 564
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 564
auagaaagug guagcaaagc ggg 23

<210> SEQ ID NO 565
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 565
ugauagaaag ugguagcaaa gcg 23

<210> SEQ ID NO 566
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 566
aggauuuguu ggcuuuucga uag 23

<210> SEQ ID NO 567
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 567
augcacaugg gauucauggg aau 23

<210> SEQ ID NO 568
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 568
uuuaccucaa gaaaugccuu aug 23

<210> SEQ ID NO 569
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 569
uuaaauaccu ccaucaguug cug 23

<210> SEQ ID NO 570
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 570
agauauggug ucaaacuuaa aua 23

<210> SEQ ID NO 571
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 571
aaaugcacau gggauucaug gga 23

<210> SEQ ID NO 572
<211> LENGTH: 23
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 572
aguaaauggu guuaaccagc acc 23

<210> SEQ ID NO 573
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 573
auuuguuggc uuuucgauag agu 23

<210> SEQ ID NO 574
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 574
aaagugguag caaagcggga auu 23

<210> SEQ ID NO 575
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 575
ucaaacuuaa auaccuccau cag 23

<210> SEQ ID NO 576
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 576
uugaagguaa gggauuuguc ucc 23

<210> SEQ ID NO 577
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 577
ugcugauaga aagugguagc aaa 23

<210> SEQ ID NO 578
<211> LENGTH: 23
<212> TYPE: RNA
<213> ORGANISM: Artificial Sequence
<220> FEATURE:
<223> OTHER INFORMATION: Description of Artificial Sequence: Synthetic

```
                   oligonucleotide

<400> SEQUENCE: 578

uuccuaucac auuggaauac aug                                         23

<210> SEQ ID NO 579
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 579

uuuucgauag agucggcagu uca                                         23

<210> SEQ ID NO 580
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 580

uggcuuuucg auagagucgg cag                                         23

<210> SEQ ID NO 581
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 581

auaugguguc aaacuuaaau acc                                         23

<210> SEQ ID NO 582
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 582

ugaacagauc gacaaggccc aug                                         23

<210> SEQ ID NO 583
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 583

ucauugaagg uaagggauuu guc                                         23

<210> SEQ ID NO 584
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
```

<400> SEQUENCE: 584
aacaauaccu gggaguuugg acu 23

<210> SEQ ID NO 585
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 585
uuucgauaga gucggcaguu cag 23

<210> SEQ ID NO 586
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 586
uauuggacac ccauuuguug aug 23

<210> SEQ ID NO 587
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 587
uuaaccagca ccagaacagu gag 23

<210> SEQ ID NO 588
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 588
uccuucaaac ugaagccguc cuc 23

<210> SEQ ID NO 589
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 589
ugcauuuucc uugaagucca ggg 23

<210> SEQ ID NO 590
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 590
uggugucaaa cuuaaauacc ucc 23

<210> SEQ ID NO 591
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 591
uuccacaggc ccuugaagua aau 23

<210> SEQ ID NO 592
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 592
uaagggauuu gucuccaaaa agg 23

<210> SEQ ID NO 593
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 593
uuuagcgaac ggccagcaau cac 23

<210> SEQ ID NO 594
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 594
uuggcuuuuc gauagagucg gca 23

<210> SEQ ID NO 595
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 595
aggcccuuga aguaaauggu guu 23

<210> SEQ ID NO 596
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 596
ucauuacagg cacccagcuu ggu 23

<210> SEQ ID NO 597
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 597
ugcccaugaa gauaauagug uuc 23

<210> SEQ ID NO 598
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 598
uggauugcuc ugcauuuucc uug 23

<210> SEQ ID NO 599
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 599
augguguuaa ccagcaccag aac 23

<210> SEQ ID NO 600
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 600
ugugcagaug uccacagggc ucc 23

<210> SEQ ID NO 601
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 601
uucaguuugg caaagaagaa gug 23

<210> SEQ ID NO 602
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 602

-continued

```
ucauagcaaa agccguggag aua                                              23


<210> SEQ ID NO 603
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 603

uucuuggaau cugccaggug cug                                              23


<210> SEQ ID NO 604
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 604

uuggcuacuc ugcccaugaa gau                                              23


<210> SEQ ID NO 605
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 605

uuggcugaua cuaacuugga gga                                              23


<210> SEQ ID NO 606
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 606

uugaaguaaa ugguguuaac cag                                              23


<210> SEQ ID NO 607
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 607

uugaaguaaa ugguguuaac cag                                              23


<210> SEQ ID NO 608
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 608

uugaaguaaa ugguguuaac cag                                              23
```

<210> SEQ ID NO 609
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 609
uugaaguaaa ugguguuaac cag 23

<210> SEQ ID NO 610
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 610
uugaaguaaa ugguguuaac cag 23

<210> SEQ ID NO 611
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 611
uugaaguaaa ugguguuaac cag 23

<210> SEQ ID NO 612
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 612
uugaaguaaa ugguguuaac cag 23

<210> SEQ ID NO 613
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 613
uugaaguaaa ugguguuaac cag 23

<210> SEQ ID NO 614
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 614
uugaaguaaa ugguguuaac cag 23

<210> SEQ ID NO 615
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 615
uugaaguaaa ugguguuaac cag 23

<210> SEQ ID NO 616
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 616
uugaaguaaa ugguguuaac cag 23

<210> SEQ ID NO 617
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 617
uugaaguaaa ugguguuaac cag 23

<210> SEQ ID NO 618
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 618
uugaaguaaa ugguguuaac cag 23

<210> SEQ ID NO 619
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 619
uugaaguaaa ugguguuaac cag 23

<210> SEQ ID NO 620
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 620
uugaaguaaa ugguguuaac cag 23

<210> SEQ ID NO 621
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 621
uugaaguaaa ugguguuaac cag 23

<210> SEQ ID NO 622
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 622
uugaaguaaa ugguguuaac cag 23

<210> SEQ ID NO 623
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 623
uugaaguaaa ugguguuaac cag 23

<210> SEQ ID NO 624
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 624
uugaaguaaa ugguguuaac cag 23

<210> SEQ ID NO 625
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 625
uugaaguaaa ugguguuaac cag 23

<210> SEQ ID NO 626
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 626
uugaaguaaa ugguguuaac cag 23

<210> SEQ ID NO 627

<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 627
uugaaguaaa ugguguuaac cag 23

<210> SEQ ID NO 628
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 628
uugaaguaaa ugguguuaac cag 23

<210> SEQ ID NO 629
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 629
uugaaguaaa ugguguuaac cag 23

<210> SEQ ID NO 630
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 630
uugaaguaaa ugguguuaac cag 23

<210> SEQ ID NO 631
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 631
uugaaguaaa ugguguuaac cag 23

<210> SEQ ID NO 632
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 632
uugaaguaaa ugguguuaac cag 23

<210> SEQ ID NO 633
<211> LENGTH: 23

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 633
uugaaguaaa ugguguuaac cag 23

<210> SEQ ID NO 634
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 634
uugaaguaaa ugguguuaac cag 23

<210> SEQ ID NO 635
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 635
uugaaguaaa ugguguuaac cag 23

<210> SEQ ID NO 636
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 636
uugaaguaaa ugguguuaac cag 23

<210> SEQ ID NO 637
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 637
uugaaguaaa ugguguuaac cag 23

<210> SEQ ID NO 638
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 638
uugaaguaaa ugguguuaac cag 23

<210> SEQ ID NO 639
<211> LENGTH: 23
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 639
uugaaguaaa ugguguuaac cag 23

<210> SEQ ID NO 640
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 640
uugaaguaaa ugguguuaac cag 23

<210> SEQ ID NO 641
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 641
uugaaguaaa ugguguuaac cag 23

<210> SEQ ID NO 642
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 642
uugaaguaaa ugguguuaac cag 23

<210> SEQ ID NO 643
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 643
uugaaguaaa ugguguuaac cag 23

<210> SEQ ID NO 644
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 644
uugaaguaaa ugguguuaac cag 23

<210> SEQ ID NO 645
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 645
uugaaguaaa ugguguuaac cag 23

<210> SEQ ID NO 646
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 646
uugaaguaaa ugguguuaac cag 23

<210> SEQ ID NO 647
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 647
uugaaguaaa ugguguuaac cag 23

<210> SEQ ID NO 648
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 648
uugaaguaaa ugguguuaac cag 23

<210> SEQ ID NO 649
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 649
uugaaguaaa ugguguuaac cag 23

<210> SEQ ID NO 650
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 650
uugaaguaaa ugguguuaac cag 23

<210> SEQ ID NO 651
<211> LENGTH: 23
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 651
uugaaguaaa ugguguuaac cag 23

<210> SEQ ID NO 652
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 652
uugaaguaaa ugguguuaac cag 23

<210> SEQ ID NO 653
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 653
uugaaguaaa ugguguuaac cag 23

<210> SEQ ID NO 654
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 654
uugaaguaaa ugguguuaac cag 23

<210> SEQ ID NO 655
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 655
uugaaguaaa ugguguuaac cag 23

<210> SEQ ID NO 656
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 656
uugaaguaaa ugguguuaac cag 23

<210> SEQ ID NO 657
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 657
uugaaguaaa ugguguuaac cag 23

<210> SEQ ID NO 658
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 658
uugaaguaaa ugguguuaac cag 23

<210> SEQ ID NO 659
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 659
uugaaguaaa ugguguuaac cag 23

<210> SEQ ID NO 660
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 660
uugaaguaaa ugguguuaac cag 23

<210> SEQ ID NO 661
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 661
uugaaguaaa ugguguuaac cag 23

<210> SEQ ID NO 662
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 662
uugaaguaaa ugguguuaac cag 23

<210> SEQ ID NO 663
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 663
uugaaguaaa ugguguuaac cag 23

<210> SEQ ID NO 664
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 664
uugaaguaaa ugguguuaac cag 23

<210> SEQ ID NO 665
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 665
uugaaguaaa ugguguuaac cag 23

<210> SEQ ID NO 666
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 666
uugaaguaaa ugguguuaac cag 23

<210> SEQ ID NO 667
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 667
uugaaguaaa ugguguuaac cag 23

<210> SEQ ID NO 668
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 668
uugaaguaaa ugguguuaac cag 23

<210> SEQ ID NO 669
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 669
uugaaguaaa ugguguuaac cag 23

<210> SEQ ID NO 670
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 670
uugaaguaaa ugguguuaac cag 23

<210> SEQ ID NO 671
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 671
uugaaguaaa ugguguuaac cag 23

<210> SEQ ID NO 672
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 672
uugaaguaaa ugguguuaac cag 23

<210> SEQ ID NO 673
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 673
uugaaguaaa ugguguuaac cag 23

<210> SEQ ID NO 674
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 674
uugaaguaaa ugguguuaac cag 23

<210> SEQ ID NO 675
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 675
uugaaguaaa ugguguuaac cag 23

<210> SEQ ID NO 676
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 676
uugaaguaaa ugguguuaac cag 23

<210> SEQ ID NO 677
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 677
uugaaguaaa ugguguuaac cag 23

<210> SEQ ID NO 678
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 678
uugaaguaaa ugguguuaac cag 23

<210> SEQ ID NO 679
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 679
uugaaguaaa ugguguuaac cag 23

<210> SEQ ID NO 680
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 680
uugaaguaaa ugguguuaac cag 23

<210> SEQ ID NO 681
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 681
uugaaguaaa ugguguuaac cag 23

<210> SEQ ID NO 682
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 682
uugaaguaaa ugguguuaac cag 23

<210> SEQ ID NO 683
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 683
uugaaguaaa ugguguuaac cag 23

<210> SEQ ID NO 684
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 684
uugaaguaaa ugguguuaac cag 23

<210> SEQ ID NO 685
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 685
uugaaguaaa ugguguuaac cag 23

<210> SEQ ID NO 686
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 686
uugaaguaaa ugguguuaac cag 23

<210> SEQ ID NO 687
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 687
uugaaguaaa ugguguuaac cag 23

<210> SEQ ID NO 688
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 688
uugaaguaaa ugguguuaac cag 23

<210> SEQ ID NO 689
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 689
uugaaguaaa ugguguuaac cag 23

<210> SEQ ID NO 690
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 690
uugaaguaaa ugguguuaac cag 23

<210> SEQ ID NO 691
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 691
uugaaguaaa ugguguuaac cag 23

<210> SEQ ID NO 692
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 692
uugaaguaaa ugguguuaac cag 23

<210> SEQ ID NO 693
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 693
uugaaguaaa ugguguuaac cag 23

<210> SEQ ID NO 694
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 694
uugaaguaaa ugguguuaac cag 23

<210> SEQ ID NO 695
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 695
uugaaguaaa ugguguuaac cag 23

<210> SEQ ID NO 696
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 696
uugaaguaaa ugguguuaac cag 23

<210> SEQ ID NO 697
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 697
uugaaguaaa ugguguuaac cag 23

<210> SEQ ID NO 698
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 698
uugaaguaaa ugguguuaac cag 23

<210> SEQ ID NO 699
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 699
uugaaguaaa ugguguuaac cag 23

<210> SEQ ID NO 700
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 700
uugaaguaaa ugguguuaac cag 23

<210> SEQ ID NO 701
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 701
uugaaguaaa ugguguuaac cag 23

<210> SEQ ID NO 702
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 702
uugaaguaaa ugguguuaac cag 23

<210> SEQ ID NO 703
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 703
uugaaguaaa ugguguuaac cag 23

<210> SEQ ID NO 704
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 704
uugaaguaaa ugguguuaac cag 23

<210> SEQ ID NO 705
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 705
uugaaguaaa ugguguuaac cag 23

<210> SEQ ID NO 706

<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 706
uugaaguaaa ugguguuaac cag 23

<210> SEQ ID NO 707
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 707
uugaaguaaa ugguguuaac cag 23

<210> SEQ ID NO 708
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 708
uugaaguaaa ugguguuaac cag 23

<210> SEQ ID NO 709
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 709
uugaaguaaa ugguguuaac cag 23

<210> SEQ ID NO 710
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 710
uugaaguaaa ugguguuaac cag 23

<210> SEQ ID NO 711
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 711
uugaaguaaa ugguguuaac cag 23

<210> SEQ ID NO 712
<211> LENGTH: 23

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 712
uugaaguaaa ugguguuaac cag 23

<210> SEQ ID NO 713
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 713
uugaaguaaa ugguguuaac cag 23

<210> SEQ ID NO 714
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 714
uugaaguaaa ugguguuaac cag 23

<210> SEQ ID NO 715
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 715
uugaaguaaa ugguguuaac cag 23

<210> SEQ ID NO 716
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 716
uugaaguaaa ugguguuaac cag 23

<210> SEQ ID NO 717
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 717
uugaaguaaa ugguguuaac cag 23

<210> SEQ ID NO 718
<211> LENGTH: 23
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 718
uugaaguaaa ugguguuaac cag 23

<210> SEQ ID NO 719
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 719
uugaaguaaa ugguguuaac cag 23

<210> SEQ ID NO 720
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 720
uugaaguaaa ugguguuaac cag 23

<210> SEQ ID NO 721
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 721
uugaaguaaa ugguguuaac cag 23

<210> SEQ ID NO 722
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 722
uugaaguaaa ugguguuaac cag 23

<210> SEQ ID NO 723
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 723
uugaaguaaa ugguguuaac cag 23

<210> SEQ ID NO 724
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 724
uugaaguaaa ugguguuaac cag 23

<210> SEQ ID NO 725
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 725
uugaaguaaa ugguguuaac cag 23

<210> SEQ ID NO 726
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 726
uugaaguaaa ugguguuaac cag 23

<210> SEQ ID NO 727
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 727
uugaaguaaa ugguguuaac cag 23

<210> SEQ ID NO 728
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 728
uugaaguaaa ugguguuaac cag 23

<210> SEQ ID NO 729
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 729
uugaaguaaa ugguguuaac cag 23

<210> SEQ ID NO 730
<211> LENGTH: 23
<212> TYPE: RNA
<213> ORGANISM: Artificial Sequence
<220> FEATURE:

<223> OTHER INFORMATION: Description of Artificial Sequence: Synthetic oligonucleotide

<400> SEQUENCE: 730
uugaaguaaa ugguguuaac cag 23

<210> SEQ ID NO 731
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 731
uugaaguaaa ugguguuaac cag 23

<210> SEQ ID NO 732
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 732
uugaaguaaa ugguguuaac cag 23

<210> SEQ ID NO 733
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 733
uugaaguaaa ugguguuaac cag 23

<210> SEQ ID NO 734
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 734
uugaaguaaa ugguguuaac cag 23

<210> SEQ ID NO 735
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 735
uugaaguaaa ugguguuaac cag 23

<210> SEQ ID NO 736
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 736
uugaaguaaa ugguguuaac cag 23

<210> SEQ ID NO 737
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 737
uugaaguaaa ugguguuaac cag 23

<210> SEQ ID NO 738
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 738
uugaaguaaa ugguguuaac cag 23

<210> SEQ ID NO 739
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 739
uugaaguaaa ugguguuaac cag 23

<210> SEQ ID NO 740
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 740
uugaaguaaa ugguguuaac cag 23

<210> SEQ ID NO 741
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 741
uugaaguaaa ugguguuaac cag 23

<210> SEQ ID NO 742
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 742
uugaaguaaa ugguguuaac cag 23

<210> SEQ ID NO 743
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 743
uugaaguaaa ugguguuaac cag 23

<210> SEQ ID NO 744
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 744
uugaaguaaa ugguguuaac cag 23

<210> SEQ ID NO 745
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 745
uugaaguaaa ugguguuaac cag 23

<210> SEQ ID NO 746
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 746
uugaaguaaa ugguguuaac cag 23

<210> SEQ ID NO 747
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 747
uugaaguaaa ugguguuaac c 21

<210> SEQ ID NO 748
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 748
uugaaguaaa ugguguuaac c 21

<210> SEQ ID NO 749
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 749
uugaaguaaa ugguguuaac c 21

<210> SEQ ID NO 750
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 750
uugaaguaaa ugguguuaac c 21

<210> SEQ ID NO 751
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 751
uugaaguaaa ugguguuaac c 21

<210> SEQ ID NO 752
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 752
uugaaguaaa ugguguuaa 19

<210> SEQ ID NO 753
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 753
uugaaguaaa ugguguuaa 19

<210> SEQ ID NO 754
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 754
uugaaguaaa ugguguuaa 19

<210> SEQ ID NO 755
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 755
uugaaguaaa ugguguuaa 19

<210> SEQ ID NO 756
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 756
uugaaguaaa ugguguuaa 19

<210> SEQ ID NO 757
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 757
uugaaguaaa ugguguuaac cag 23

<210> SEQ ID NO 758
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 758
uugaaguaaa ugguguuaac cag 23

<210> SEQ ID NO 759
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 759
uugaaguaaa ugguguuaac cag 23

<210> SEQ ID NO 760
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 760
uugaaguaaa ugguguuaac cag 23

<210> SEQ ID NO 761
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 761
uugaaguaaa ugguguuaac cag 23

<210> SEQ ID NO 762
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 762
uugaaguaaa uggtguuaac cag 23

<210> SEQ ID NO 763
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 763
uugaaguaaa ugguguuaac cag 23

<210> SEQ ID NO 764
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 764
uugaaguaaa uggugtuaac cag 23

<210> SEQ ID NO 765
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 765
uugaaguaaa uggugutaac cag 23

<210> SEQ ID NO 766
<211> LENGTH: 23

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 766
uugaaguaaa ugguguuaac cag 23

<210> SEQ ID NO 767
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 767
uugaaguaaa ugguguuaac cag 23

<210> SEQ ID NO 768
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 768
uugaaguaaa ugguguuaac cag 23

<210> SEQ ID NO 769
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 769
uugaaguaaa ugguguuaac cag 23

<210> SEQ ID NO 770
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 770
uugaaguaaa ugguguuaac cag 23

<210> SEQ ID NO 771
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 771
uugaaguaaa tgguguuaa 19

<210> SEQ ID NO 772
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 772
uugaaguaaa ugguguuaac cag 23

<210> SEQ ID NO 773
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 773
uugaaguaaa ugguguuaac cag 23

<210> SEQ ID NO 774
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 774
uugaaguaaa ugguguuaac cag 23

<210> SEQ ID NO 775
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 775
uugaaguaaa ugguguuaac cag 23

<210> SEQ ID NO 776
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 776
uugaaguaaa ugguguuaac cag 23

<210> SEQ ID NO 777
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 777
uugaaguaaa ugguguuaac cag 23

<210> SEQ ID NO 778

```
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 778

uugaaguaaa ugguguuaac cag                                              23


<210> SEQ ID NO 779
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 779

gguuaacacc auuuacuuca a                                                21


<210> SEQ ID NO 780
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 780

gguuaacacc auuuacuuca a                                                21


<210> SEQ ID NO 781
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 781

gguuaacacc auuuacuuca a                                                21


<210> SEQ ID NO 782
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 782

gguuaacacc auuuacuuca a                                                21


<210> SEQ ID NO 783
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 783

gguuaacacc auuuacuuca a                                                21


<210> SEQ ID NO 784
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 784

gguuaacacc auuuacuuca a                                                21


<210> SEQ ID NO 785
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 785

gguuaacacc auuuacuuca a                                                21


<210> SEQ ID NO 786
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 786

gguuaacacc auuuacuuca a                                                21


<210> SEQ ID NO 787
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 787

gguuaacacc auuuacuuca a                                                21


<210> SEQ ID NO 788
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 788

gguuaacacc auuuacuuca a                                                21


<210> SEQ ID NO 789
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 789

gguuaacacc auuuacuuca a                                                21


<210> SEQ ID NO 790
<211> LENGTH: 21
<212> TYPE: RNA
```

<213> ORGANISM: Artificial Sequence
<220> FEATURE:
<223> OTHER INFORMATION: Description of Artificial Sequence: Synthetic
oligonucleotide

<400> SEQUENCE: 790
gguuaacacc auuuacuuca a 21

<210> SEQ ID NO 791
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 791
gguuaacacc auuuacuuca a 21

<210> SEQ ID NO 792
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 792
gguuaacacc auuuacuuca a 21

<210> SEQ ID NO 793
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 793
gguuaacacc auuuacuuca a 21

<210> SEQ ID NO 794
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 794
gguuaacacc auuuacuuca a 21

<210> SEQ ID NO 795
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 795
ggutaacacc auuuacutca a 21

<210> SEQ ID NO 796

<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 796
ggutaacacc auutacutca a 21

<210> SEQ ID NO 797
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 797
ggutaacacc auuuacutca a 21

<210> SEQ ID NO 798
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 798
ggutaacacc auutacutca a 21

<210> SEQ ID NO 799
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 799
ggutaacacc auuuacutca a 21

<210> SEQ ID NO 800
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 800
gguuaacacc auuuacutca a 21

<210> SEQ ID NO 801
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 801
ggutaacacc auuuacutca a 21

<210> SEQ ID NO 802
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 802
gguuaacacc auuuacuuca a 21

<210> SEQ ID NO 803
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 803
gguuaacacc auuuacuuca a 21

<210> SEQ ID NO 804
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 804
gguuaacacc auuuacutca a 21

<210> SEQ ID NO 805
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 805
gguuaacacc auuuacuuca a 21

<210> SEQ ID NO 806
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 806
gguuaacacc auuuacuuca a 21

<210> SEQ ID NO 807
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 807
gguuaacacc auuuacuuca a 21

<210> SEQ ID NO 808
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 808
gguuaacacc auuuacuuca a 21

<210> SEQ ID NO 809
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 809
uugaaguaaa ugguguuaac cag 23

<210> SEQ ID NO 810
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 810
uugaaguaaa ugguguuaac cag 23

<210> SEQ ID NO 811
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 811
uugaaguaaa ugguguuaac cag 23

<210> SEQ ID NO 812
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 812
uugaaguaaa ugguguuaac cag 23

<210> SEQ ID NO 813
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 813
uugaaguaaa ugguguuaac cag 23

<210> SEQ ID NO 814
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 814
uugaaguaaa ugguguuaac cag 23

<210> SEQ ID NO 815
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 815
uugaaguaaa ugguguuaac cag 23

<210> SEQ ID NO 816
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 816
uugaaguaaa ugguguuaac cag 23

<210> SEQ ID NO 817
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 817
uugaaguaaa ugguguuaac cag 23

<210> SEQ ID NO 818
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 818

-continued uugaaguaaa ugguguuaac cag 23

<210> SEQ ID NO 819
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 819
uugaaguaaa ugguguuaac cag 23

<210> SEQ ID NO 820
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 820
uugaaguaaa ugguguuaac cag 23

<210> SEQ ID NO 821
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 821
uugaaguaaa ugguguuaac cag 23

<210> SEQ ID NO 822
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 822
uugaaguaaa ugguguuaac cag 23

<210> SEQ ID NO 823
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 823
uugaaguaaa ugguguuaac c 21

<210> SEQ ID NO 824
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 824
uugaaguaaa ugguguuaac cag 23

<210> SEQ ID NO 825
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 825
uugaaguaaa ugguguuaac cag 23

<210> SEQ ID NO 826
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 826
uugaaguaaa ugguguuaac cag 23

<210> SEQ ID NO 827
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 827
uugaaguaaa ugguguuaac cag 23

<210> SEQ ID NO 828
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 828
uugaaguaaa ugguguuaac cag 23

<210> SEQ ID NO 829
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 829
uugaaguaaa ugguguuaac cag 23

<210> SEQ ID NO 830
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 830
uugaaguaaa ugguguuaac cag 23

<210> SEQ ID NO 831
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 831
uugaaguaaa ugguguuaac cag 23

<210> SEQ ID NO 832
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 832
uugaaguaaa ugguguuaac cag 23

<210> SEQ ID NO 833
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 833
uugaaguaaa ugguguuaac cag 23

<210> SEQ ID NO 834
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 834
uugaaguaaa ugguguuaac cag 23

<210> SEQ ID NO 835
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 835
uugaaguaaa ugguguuaac cag 23

<210> SEQ ID NO 836
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 836
uugaaguaaa ugguguuaac cag 23

<210> SEQ ID NO 837
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 837
uugaaguaaa ugguguuaac cag 23

<210> SEQ ID NO 838
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 838
uugaaguaaa ugguguuaac cag 23

<210> SEQ ID NO 839
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 839
gguuaacacc auuuacuuca a 21

<210> SEQ ID NO 840
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 840
gguuaacacc auuuacutca a 21

<210> SEQ ID NO 841
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 841
ggutaacacc auutacutca a 21

<210> SEQ ID NO 842
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 842
gguuaacacc auuuacuuca a 21

<210> SEQ ID NO 843
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 843
gguuaacacc auuuacuuca a 21

<210> SEQ ID NO 844
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 844
ggutaacacc auuuacutca a 21

<210> SEQ ID NO 845
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 845
gguuaacacc auuuacuuca a 21

<210> SEQ ID NO 846
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 846
gguuaacacc auuuacuuca a 21

<210> SEQ ID NO 847
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 847
ggutaacacc auutacutca a 21

<210> SEQ ID NO 848
<211> LENGTH: 21
<212> TYPE: RNA

<213> ORGANISM: Artificial Sequence
<220> FEATURE:
<223> OTHER INFORMATION: Description of Artificial Sequence: Synthetic
      oligonucleotide

<400> SEQUENCE: 848
gguuaacacc auuuacuuca a 21

<210> SEQ ID NO 849
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 849
gguuaacacc auuuacuuca a 21

<210> SEQ ID NO 850
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 850
ggutaacacc auuuacutca a 21

<210> SEQ ID NO 851
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 851
gguuaacacc auuuacuuca a 21

<210> SEQ ID NO 852
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 852
gguuaacacc auuuacuuca a 21

<210> SEQ ID NO 853
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 853
gguuaacacc auuuacutca a 21

<210> SEQ ID NO 854
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 854
ggutaacacc auuuacutca a 21

<210> SEQ ID NO 855
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 855
gguuaacacc auuuacuuca a 21

<210> SEQ ID NO 856
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 856
gguuaacacc auuuacuuca a 21

<210> SEQ ID NO 857
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 857
gguuaacacc auuuacuuca a 21

<210> SEQ ID NO 858
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 858
gguuaacacc auuuacuuca a 21

<210> SEQ ID NO 859
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 859
gguuaacacc auuuacuuca a 21

<210> SEQ ID NO 860
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 860
gguuaacacc auuuacuuca a 21

<210> SEQ ID NO 861
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 861
gguuaacacc auuuacuuca a 21

<210> SEQ ID NO 862
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 862
gguuaacacc auuuacuuca a 21

<210> SEQ ID NO 863
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 863
gguuaacacc auuuacuuca a 21

<210> SEQ ID NO 864
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 864
gguuaacacc auuuacuuca a 21

<210> SEQ ID NO 865
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 865
gguuaacacc auuuacuuca a 21

<210> SEQ ID NO 866
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 866
gguuaacacc auuuacuuca a 21

<210> SEQ ID NO 867
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 867
ggutaacacc auuuacutca a 21

<210> SEQ ID NO 868
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 868
gguuaacacc auuuacuuca a 21

<210> SEQ ID NO 869
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 869
uugaaguaaa ugguguuaac cag 23

<210> SEQ ID NO 870
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 870
uugaaguaaa ugguguuaac cag 23

<210> SEQ ID NO 871
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 871
uugaaguaaa ugguguuaac cag 23

<210> SEQ ID NO 872
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 872
uugaaguaaa ugguguuaac cag 23

<210> SEQ ID NO 873
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 873
uugaaguaaa ugguguuaac cag 23

<210> SEQ ID NO 874
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 874
uugaaguaaa ugguguuaac cag 23

<210> SEQ ID NO 875
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 875
uugaaguaaa ugguguuaac cag 23

<210> SEQ ID NO 876
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 876
uugaaguaaa ugguguuaac cag 23

<210> SEQ ID NO 877
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 877
uugaaguaaa ugguguuaac cag 23

<210> SEQ ID NO 878
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 878
uugaaguaaa ugguguuaac cag 23

<210> SEQ ID NO 879
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 879
uugaaguaaa ugguguuaac cag 23

<210> SEQ ID NO 880
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 880
uugaaguaaa ugguguuaac cag 23

<210> SEQ ID NO 881
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 881
uugaaguaaa ugguguuaac cag 23

<210> SEQ ID NO 882
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 882
uugaaguaaa ugguguuaac cag 23

<210> SEQ ID NO 883
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 883
uugaaguaaa ugguguuaac cag 23

<210> SEQ ID NO 884
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 884
uugaaguaaa ugguguuaac cag 23

<210> SEQ ID NO 885
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 885
uugaaguaaa ugguguuaac cag 23

<210> SEQ ID NO 886
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 886
uugaaguaaa ugguguuaac cag 23

<210> SEQ ID NO 887
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 887
uugaaguaaa ugguguuaac cag 23

<210> SEQ ID NO 888
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 888
uugaaguaaa ugguguuaac cag 23

<210> SEQ ID NO 889
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 889
uugaaguaaa ugguguuaac cag 23

<210> SEQ ID NO 890
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 890
uugaaguaaa ugguguuaac cag 23

<210> SEQ ID NO 891
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 891
uugaaguaaa ugguguuaac cag 23

<210> SEQ ID NO 892
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 892
uugaaguaaa ugguguuaac cag 23

<210> SEQ ID NO 893
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 893
uugaaguaaa ugguguuaac cag 23

<210> SEQ ID NO 894
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 894
uugaaguaaa ugguguuaac cag 23

<210> SEQ ID NO 895
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 895
uugaaguaaa ugguguuaac cag 23

-continued

<210> SEQ ID NO 896
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 896
uugaaguaaa ugguguuaac c 21

<210> SEQ ID NO 897
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 897
uugaaguaaa ugguguuaac cag 23

<210> SEQ ID NO 898
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 898
uugaaguaaa ugguguuaac cag 23

<210> SEQ ID NO 899
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 899
gguuaacacc auuuacuuca a 21

<210> SEQ ID NO 900
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 900
gguuaacacc auuuacuuca a 21

<210> SEQ ID NO 901
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 901
ggutaacacc auutacutca a 21

<210> SEQ ID NO 902
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 902
gguuaacacc auuuacuuca a 21

<210> SEQ ID NO 903
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 903
gguuaacacc auuuacutca a 21

<210> SEQ ID NO 904
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 904
ggutaacacc auuuacutca a 21

<210> SEQ ID NO 905
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 905
ggutaacacc auutacutca a 21

<210> SEQ ID NO 906
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 906
gguuaacacc auuuacuuca a 21

<210> SEQ ID NO 907
<211> LENGTH: 21

<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 907
ggutaacacc auuuacutca a 21

<210> SEQ ID NO 908
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 908
gguuaacacc auuuacuuca a 21

<210> SEQ ID NO 909
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 909
gguuaacacc auuuacuuca a 21

<210> SEQ ID NO 910
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 910
ggutaacacc auuuacutca a 21

<210> SEQ ID NO 911
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 911
gguuaacacc auuuacutca a 21

<210> SEQ ID NO 912
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 912
guuaacacca uuuacuucaa 20

<210> SEQ ID NO 913
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 913
gguuaacacc auutacuuca a 21

<210> SEQ ID NO 914
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 914
ggutaacacc auutacutca a 21

<210> SEQ ID NO 915
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 915
aacugccgac ucuaucgaaa a 21

<210> SEQ ID NO 916
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 916
gguuaacacc autuactuca a 21

<210> SEQ ID NO 917
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 917
guuaacacca uuuacuucaa 20

<210> SEQ ID NO 918
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 918
gguuaacacc auuuacuuca a 21

<210> SEQ ID NO 919
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 919
ggutaacacc auuuacutca a 21

<210> SEQ ID NO 920
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 920
uugaaguaaa ugguguuaac cag 23

<210> SEQ ID NO 921
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 921
uugaaguaaa ugguguuaac cag 23

<210> SEQ ID NO 922
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 922
uugaaguaaa ugguguuaac cag 23

<210> SEQ ID NO 923
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 923

-continued uugaaguaaa ugguguuaac cag 23

<210> SEQ ID NO 924
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 924
uugaaguaaa ugguguuaac cag 23

<210> SEQ ID NO 925
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 925
uugaaguaaa ugguguuaac cag 23

<210> SEQ ID NO 926
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 926
uugaaguaaa ugguguuaac cag 23

<210> SEQ ID NO 927
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 927
uugaaguaaa ugguguuaac cag 23

<210> SEQ ID NO 928
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 928
uugaaguaaa ugguguuaac cag 23

<210> SEQ ID NO 929
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 929
uugaaguaaa ugguguuaac cag 23

<210> SEQ ID NO 930
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 930
uugaaguaaa ugguguuaac cag 23

<210> SEQ ID NO 931
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 931
uugaaguaaa ugguguuaac cag 23

<210> SEQ ID NO 932
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 932
uugaaguaaa ugguguuaac cag 23

<210> SEQ ID NO 933
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 933
uugaaguaaa ugguguuaac ca 22

<210> SEQ ID NO 934
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 934
utgaagtaaa uggtguuaac cag 23

<210> SEQ ID NO 935
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 935
uugaaguaaa ugguguuaac cag 23

<210> SEQ ID NO 936
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 936
uuuucgauag agucggcagu uca 23

<210> SEQ ID NO 937
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 937
utgaagtaaa uggtguuaac cag 23

<210> SEQ ID NO 938
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 938
uugaaguaaa ugguguuaac ca 22

<210> SEQ ID NO 939
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 939
uugaaguaaa ugguguuaac cag 23

<210> SEQ ID NO 940
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 940
uugaaguaaa ugguguuaac cag 23

<210> SEQ ID NO 941
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 941
gguuaacacc auuuacuuca a 21

<210> SEQ ID NO 942
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 942
gguuaacacc auuuacuuca a 21

<210> SEQ ID NO 943
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 943
gguuaacacc auuuacuuca a 21

<210> SEQ ID NO 944
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 944
gguuaacacc auuuacuuca a 21

<210> SEQ ID NO 945
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 945
gguuaacacc auuuacuuca a 21

<210> SEQ ID NO 946
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 946
gguuaacacc auuuacuuca a 21

<210> SEQ ID NO 947
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:

<223> OTHER INFORMATION: Description of Combined DNA/RNA Molecule: Synthetic oligonucleotide

<400> SEQUENCE: 947
ggutaacacc auutacutca a 21

<210> SEQ ID NO 948
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 948
gguuaacacc auuuacuuca a 21

<210> SEQ ID NO 949
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 949
gguuaacacc auuuacuuca a 21

<210> SEQ ID NO 950
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 950
gguuaacacc auuuacuuca a 21

<210> SEQ ID NO 951
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 951
gguuaacacc auuuacuuca a 21

<210> SEQ ID NO 952
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 952
gguuaacacc auuuacuuca a 21

<210> SEQ ID NO 953
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 953
gguuaacacc auuuacuuca a 21

<210> SEQ ID NO 954
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 954
ggutaacacc auutacutca a 21

<210> SEQ ID NO 955
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 955
gguuaacacc auuuacuuca a 21

<210> SEQ ID NO 956
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 956
gguuaacacc auuuacuuca a 21

<210> SEQ ID NO 957
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 957
gguuaacacc auuuacuuca a 21

<210> SEQ ID NO 958
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 958
gguuaacacc auuuacuuca a 21

<210> SEQ ID NO 959
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 959
gguuaacacc auuuacuuca a 21

<210> SEQ ID NO 960
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 960
uugaaguaaa ugguguuaac cag 23

<210> SEQ ID NO 961
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 961
uugaaguaaa ugguguuaac cag 23

<210> SEQ ID NO 962
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 962
uugaaguaaa ugguguuaac cag 23

<210> SEQ ID NO 963
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 963
uugaaguaaa ugguguuaac cag 23

<210> SEQ ID NO 964
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 964
uugaaguaaa ugguguuaac cag 23

<210> SEQ ID NO 965
<211> LENGTH: 23
<212> TYPE: RNA
<213> ORGANISM: Artificial Sequence
<220> FEATURE:

-continued

<223> OTHER INFORMATION: Description of Artificial Sequence: Synthetic
      oligonucleotide

<400> SEQUENCE: 965
uugaaguaaa ugguguuaac cag 23

<210> SEQ ID NO 966
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 966
uugaaguaaa ugguguuaac cag 23

<210> SEQ ID NO 967
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 967
uugaaguaaa ugguguuaac cag 23

<210> SEQ ID NO 968
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 968
uugaaguaaa ugguguuaac cag 23

<210> SEQ ID NO 969
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 969
uugaaguaaa ugguguuaac cag 23

<210> SEQ ID NO 970
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 970
uugaaguaaa ugguguuaac cag 23

<210> SEQ ID NO 971
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 971
uugaaguaaa ugguguuaac cag 23

<210> SEQ ID NO 972
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 972
uugaaguaaa ugguguuaac cag 23

<210> SEQ ID NO 973
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 973
uugaaguaaa ugguguuaac cag 23

<210> SEQ ID NO 974
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 974
uugaaguaaa ugguguuaac cag 23

<210> SEQ ID NO 975
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 975
uugaaguaaa ugguguuaac cag 23

<210> SEQ ID NO 976
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 976
uugaaguaaa ugguguuaac cag 23

<210> SEQ ID NO 977
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 977
uugaaguaaa ugguguuaac cag 23

<210> SEQ ID NO 978
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 978
uugaaguaaa ugguguuaac cag 23

<210> SEQ ID NO 979
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 979
ggagaagaag gcaacugag 19

<210> SEQ ID NO 980
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 980
ugaccaagcu gggugccug 19

<210> SEQ ID NO 981
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 981
gguuaacacc auuuacuuc 19

<210> SEQ ID NO 982
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 982
gcugguuaac accauuuac 19

<210> SEQ ID NO 983
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 983
uaaugacacc cuccagcaa 19

<210> SEQ ID NO 984
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 984
cguguucagc aucuaugau 19

<210> SEQ ID NO 985
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 985
uugaggacgg cuucaguuu 19

<210> SEQ ID NO 986
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 986
cggcgugucu gggaacugu 19

<210> SEQ ID NO 987
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 987
uuaacaccau uuacuucaa 19

<210> SEQ ID NO 988
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 988
cccugaaaag uccaaacuc 19

<210> SEQ ID NO 989
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 989
cgagaugacc ucuaugucu 19

<210> SEQ ID NO 990
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 990
ucuacaaggc ugauggaga 19

<210> SEQ ID NO 991
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 991
agcucacugu ucuggugcu 19

<210> SEQ ID NO 992
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 992
aggagcagcu gcaagacau 19

<210> SEQ ID NO 993
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 993
gccaccaacc ggcgugucu 19

<210> SEQ ID NO 994
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 994
cagaacagaa gaucccgga 19

<210> SEQ ID NO 995
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 995
ccuugucgau cuguucagc 19

<210> SEQ ID NO 996
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 996
aggcaaguuc cguuaucgg 19

<210> SEQ ID NO 997
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 997
uuuuguccuu gcugcucau 19

<210> SEQ ID NO 998
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 998
agaccuacca ggacaucag 19

<210> SEQ ID NO 999
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 999
aacugaacug ccgacucua 19

<210> SEQ ID NO 1000
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1000
cauuuacuuc aagggccug 19

<210> SEQ ID NO 1001
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1001
cccuggacuu caaggaaaa 19

<210> SEQ ID NO 1002
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1002
agcugcaagu accgcuguu 19

<210> SEQ ID NO 1003
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1003
acacaaggaa ggaacuguu 19

<210> SEQ ID NO 1004
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1004
gcaacugagg augagggcu 19

<210> SEQ ID NO 1005
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1005
guagccaacc cuuguguua 19

<210> SEQ ID NO 1006
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1006
guuugugaac agaaguaaa 19

<210> SEQ ID NO 1007
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1007
gggugacuuu caaggccaa 19

<210> SEQ ID NO 1008
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1008
uuaucggcgc guggcugaa 19

<210> SEQ ID NO 1009
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1009
ccacuucuuc uuugccaaa 19

<210> SEQ ID NO 1010
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1010
aacaccauuu acuucaagg 19

<210> SEQ ID NO 1011
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1011
gauggagagu cguguucag 19

<210> SEQ ID NO 1012
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1012
caccauuuac uucaagggc 19

<210> SEQ ID NO 1013
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1013
uuuacuucaa gggccugug 19

<210> SEQ ID NO 1014
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1014
uaagagaagu uccucugaa 19

<210> SEQ ID NO 1015
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1015
gcgggacauu cccaugaau 19

<210> SEQ ID NO 1016
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1016
ugccccaccc uguccucug 19

<210> SEQ ID NO 1017
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1017
ugguuaacac cauuuacuu 19

<210> SEQ ID NO 1018
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1018
cggauugccu cagaucaca 19

<210> SEQ ID NO 1019
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1019
ccaggacauc agugaguug 19

<210> SEQ ID NO 1020

-continued

<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1020
ccaguuuuca ggcggauug 19

<210> SEQ ID NO 1021
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1021
caccauaucu gagaaaaca 19

<210> SEQ ID NO 1022
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1022
aaguaaaaau aaauacaaa 19

<210> SEQ ID NO 1023
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1023
gcacccaggu gcuugaguu 19

<210> SEQ ID NO 1024
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1024
uaacaccauu uacuucaag 19

<210> SEQ ID NO 1025
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1025
ccuucaaagg ugaugacau 19

<210> SEQ ID NO 1026
<211> LENGTH: 19

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1026
caaggccaau ucccgcuuu 19

<210> SEQ ID NO 1027
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1027
ucaguuugaa ggagcagcu 19

<210> SEQ ID NO 1028
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1028
gggacugcgu gaccuguca 19

<210> SEQ ID NO 1029
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1029
ucagccaauc gccuuuuug 19

<210> SEQ ID NO 1030
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1030
ccucggaagc caucaauga 19

<210> SEQ ID NO 1031
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1031
gacaaugaua acauuuucc 19

<210> SEQ ID NO 1032
<211> LENGTH: 19
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 1032
cuuauucuuu gcaccucuu 19

<210> SEQ ID NO 1033
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1033
auugcuggcc guucgcuaa 19

<210> SEQ ID NO 1034
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1034
aaaugaagaa ggcagugaa 19

<210> SEQ ID NO 1035
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1035
ugaguuggua uauggagcc 19

<210> SEQ ID NO 1036
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1036
uccagcaacu gauggaggu 19

<210> SEQ ID NO 1037
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1037
aacuguaacc ucuggaaaa 19

<210> SEQ ID NO 1038
<211> LENGTH: 19
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 1038

ucaacaaaug gguguccaa                                                 19

<210> SEQ ID NO 1039
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1039

gauuagcggc cauguauuc                                                 19

<210> SEQ ID NO 1040
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1040

gugcuugagu ugcccuuca                                                 19

<210> SEQ ID NO 1041
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1041

ugcagaaggc cgagaugac                                                 19

<210> SEQ ID NO 1042
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1042

cuauuuuugg uuugugaac                                                 19

<210> SEQ ID NO 1043
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1043

cagugaagca gcugcaagu                                                 19

<210> SEQ ID NO 1044
<211> LENGTH: 19
<212> TYPE: RNA
<213> ORGANISM: Artificial Sequence
<220> FEATURE:
```

<223> OTHER INFORMATION: Description of Artificial Sequence: Synthetic
oligonucleotide

<400> SEQUENCE: 1044
guguccaaua agaccgaag 19

<210> SEQ ID NO 1045
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1045
augaauugga ggagaugau 19

<210> SEQ ID NO 1046
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1046
aucuaugaug uaccaggaa 19

<210> SEQ ID NO 1047
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1047
ccauaaggca uuucuugag 19

<210> SEQ ID NO 1048
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1048
augcauucca uaaggcauu 19

<210> SEQ ID NO 1049
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1049
uggugcuggu uaacaccau 19

<210> SEQ ID NO 1050
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1050
aucuguucag cccugaaaa 19

<210> SEQ ID NO 1051
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1051
agaugaugcu gguggucca 19

<210> SEQ ID NO 1052
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1052
auauggagcc aagcuccag 19

<210> SEQ ID NO 1053
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1053
ccgaaucacc gaugucauu 19

<210> SEQ ID NO 1054
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1054
gcagagcaau ccagagcgg 19

<210> SEQ ID NO 1055
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1055
acaccauuua cuucaaggg 19

<210> SEQ ID NO 1056
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1056
guaccaggaa ggcaaguuc 19

<210> SEQ ID NO 1057
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1057
ugcccaagcc ugagaagag 19

<210> SEQ ID NO 1058
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1058
uucuuugcca aacugaacu 19

<210> SEQ ID NO 1059
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1059
uggccaaggu agagaagga 19

<210> SEQ ID NO 1060
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1060
ugcugcaaga guggcugga 19

<210> SEQ ID NO 1061
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1061
ccaugugcau uuaccgcuc 19

<210> SEQ ID NO 1062
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1062
agacaugggc cuugucgau 19

<210> SEQ ID NO 1063
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1063
uuuuggagac aaaucccuu 19

<210> SEQ ID NO 1064
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1064
ggaugagggc ucagaacag 19

<210> SEQ ID NO 1065
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1065
cggcuuuugc uaugaccaa 19

<210> SEQ ID NO 1066
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1066
agcuccagcc ccuggacuu 19

<210> SEQ ID NO 1067
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1067
cugaucagau ccacuucuu 19

<210> SEQ ID NO 1068
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1068
ugcugguggu ccacaugcc 19

<210> SEQ ID NO 1069
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1069
gcgagauuua gaggaaaga 19

<210> SEQ ID NO 1070
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1070
cugcucauug gcuucuggg 19

<210> SEQ ID NO 1071
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1071
ccuucaauga gaccuacca 19

<210> SEQ ID NO 1072
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1072
accauuuacu ucaagggcc 19

<210> SEQ ID NO 1073
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1073
gcaccucuuc cuauuuuug 19

<210> SEQ ID NO 1074
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1074
guggcugaag gcacccagg 19

<210> SEQ ID NO 1075
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1075
uccgcauuga ggacggcuu 19

<210> SEQ ID NO 1076
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1076
uggacaucug cacagccaa 19

<210> SEQ ID NO 1077
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1077
guccaaacuc ccagguauu 19

<210> SEQ ID NO 1078
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1078
agaaggaacu caccccaga 19

<210> SEQ ID NO 1079
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1079
ucuugaggua aaugaagaa 19

<210> SEQ ID NO 1080
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1080
agcccugugg acaucugca 19

<210> SEQ ID NO 1081
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1081
cagagcggcc aucaacaaa 19

<210> SEQ ID NO 1082
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1082
auuuaaguuu gacaccaua 19

<210> SEQ ID NO 1083
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1083
ugagaagagc cuggccaag 19

<210> SEQ ID NO 1084
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1084
ucaccauggu ccucaucuu 19

<210> SEQ ID NO 1085
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1085
ggaaggaacu guucuacaa 19

<210> SEQ ID NO 1086
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1086
cugguuuuua uaagagaag 19

<210> SEQ ID NO 1087
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1087
cugggugccu guaaugaca 19

<210> SEQ ID NO 1088
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1088
guaccgcugu ugugauugc 19

<210> SEQ ID NO 1089
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1089
ucuaucagca ccuggcaga 19

<210> SEQ ID NO 1090
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1090
cuggcagauu ccaagaaug 19

<210> SEQ ID NO 1091
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1091
cgaugucauu cccucggaa 19

<210> SEQ ID NO 1092
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1092
gcuucuggga cugcgugac 19

-continued

<210> SEQ ID NO 1093
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1093
ccugucacgg gagcccugu 19

<210> SEQ ID NO 1094
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1094
auuuacuuca agggccugu 19

<210> SEQ ID NO 1095
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1095
ugcuaccacu uucuaucag 19

<210> SEQ ID NO 1096
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1096
ggaacugucc aaggccaau 19

<210> SEQ ID NO 1097
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1097
acaaauccuc caaguuagu 19

<210> SEQ ID NO 1098
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1098
auuuaccgcu ccccggaga 19

<210> SEQ ID NO 1099

<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1099
accccugagu aucuccacg 19

<210> SEQ ID NO 1100
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1100
cacuaucucc acuugccca 19

<210> SEQ ID NO 1101
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1101
aaauacaaac uacuuccau 19

<210> SEQ ID NO 1102
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1102
cugguuaaca ccauuuacu 19

<210> SEQ ID NO 1103
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1103
ucaucuugcc caagccuga 19

<210> SEQ ID NO 1104
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1104
ccucagauca cacuaucuc 19

<210> SEQ ID NO 1105
<211> LENGTH: 19

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1105
cuguccucug gaaccucug 19

<210> SEQ ID NO 1106
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1106
cccuguggaa gauuagcgg 19

<210> SEQ ID NO 1107
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1107
aucuccacgg cuuuugcua 19

<210> SEQ ID NO 1108
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1108
guggcuggau gaauuggag 19

<210> SEQ ID NO 1109
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1109
caaguuagua ucagccaau 19

<210> SEQ ID NO 1110
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1110
gugaugacau caccauggu 19

<210> SEQ ID NO 1111
<211> LENGTH: 19
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 1111
uuccaagaau gacaaugau 19

<210> SEQ ID NO 1112
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1112
ugauggaggu auuuaaguu 19

<210> SEQ ID NO 1113
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1113
guauuccaau gugauagga 19

<210> SEQ ID NO 1114
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1114
cagccaagcc gcgggacau 19

<210> SEQ ID NO 1115
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1115
caugccccgc uuccgcauu 19

<210> SEQ ID NO 1116
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1116
augugauagg aacuguaac 19

<210> SEQ ID NO 1117
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1117
acaaaucccu uaccuucaa 19

<210> SEQ ID NO 1118
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1118
agguuuaucu uuuguccuu 19

<210> SEQ ID NO 1119
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1119
agaucccgga ggccaccaa 19

<210> SEQ ID NO 1120
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1120
acauuuuccu gucaccccu 19

<210> SEQ ID NO 1121
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1121
ggccuuuccu gguuuuuau 19

<210> SEQ ID NO 1122
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1122
uuguguuaag uaaaauguu 19

<210> SEQ ID NO 1123
<211> LENGTH: 19
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 1123
caaggaaaau gcagagcaa 19

<210> SEQ ID NO 1124
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1124
cugagaaaac aucugauca 19

<210> SEQ ID NO 1125
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1125
uuacuucaag ggccugugg 19

<210> SEQ ID NO 1126
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1126
accccaacag ggugacuuu 19

<210> SEQ ID NO 1127
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1127
ccagguauug uugcagaag 19

<210> SEQ ID NO 1128
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1128
gccuguggaa gucaaaguu 19

<210> SEQ ID NO 1129
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1129
uggaaccucu gcgagauuu 19

<210> SEQ ID NO 1130
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1130
agcccugaga acacaagga 19

<210> SEQ ID NO 1131
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1131
cucuaugucu cagaugcau 19

<210> SEQ ID NO 1132
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1132
aagaccgaag gccgaauca 19

<210> SEQ ID NO 1133
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1133
uaaaauguuc uuauucuuu 19

<210> SEQ ID NO 1134
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1134
ucuggaaaaa ggaagguuu 19

<210> SEQ ID NO 1135
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1135
uucaaggcca acaggccuu 19

<210> SEQ ID NO 1136
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1136
gaagucaaag uucagcccu 19

<210> SEQ ID NO 1137
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1137
ccaucaauga gcucacugu 19

<210> SEQ ID NO 1138
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1138
cucugaacac uauuaucuu 19

<210> SEQ ID NO 1139
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1139
ugcugguuaa caccauuua 19

<210> SEQ ID NO 1140
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1140
agaggaaaga accaguuuu 19

<210> SEQ ID NO 1141
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1141
ugcccagccc uguggaaga 19

<210> SEQ ID NO 1142
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1142
cucaguugcc uucuucucc 19

<210> SEQ ID NO 1143
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1143
caggcaccca gcuugguca 19

<210> SEQ ID NO 1144
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1144
gaaguaaaug guguuaacc 19

<210> SEQ ID NO 1145
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1145
guaaauggug uuaaccagc 19

<210> SEQ ID NO 1146
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1146
uugcuggagg gugucauua 19

<210> SEQ ID NO 1147
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1147
aucauagaug cugaacacg 19

<210> SEQ ID NO 1148
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1148
aaacugaagc cguccucaa 19

<210> SEQ ID NO 1149
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1149
acaguuccca gacacgccg 19

<210> SEQ ID NO 1150
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1150
uugaaguaaa ugguguuaa 19

<210> SEQ ID NO 1151
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1151
gaguuuggac uuuucaggg 19

<210> SEQ ID NO 1152
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1152
agacauagag gucaucucg 19

<210> SEQ ID NO 1153
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1153

```
ucuccaucag ccuuguaga                                                19
```

<210> SEQ ID NO 1154
<211> LENGTH: 19
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 1154

```
agcaccagaa cagugagcu                                                19
```

<210> SEQ ID NO 1155
<211> LENGTH: 19
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 1155

```
augucuugca gcugcuccu                                                19
```

<210> SEQ ID NO 1156
<211> LENGTH: 19
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 1156

```
agacacgccg guugguggc                                                19
```

<210> SEQ ID NO 1157
<211> LENGTH: 19
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 1157

```
uccgggaucu ucuguucug                                                19
```

<210> SEQ ID NO 1158
<211> LENGTH: 19
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 1158

```
gcugaacaga ucgacaagg                                                19
```

<210> SEQ ID NO 1159
<211> LENGTH: 19
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 1159

```
ccgauaacgg aacuugccu                                                19
```

<210> SEQ ID NO 1160
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1160
augagcagca aggacaaaa 19

<210> SEQ ID NO 1161
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1161
cugauguccu gguaggucu 19

<210> SEQ ID NO 1162
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1162
uagagucggc aguucaguu 19

<210> SEQ ID NO 1163
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1163
caggcccuug aaguaaaug 19

<210> SEQ ID NO 1164
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1164
uuuuccuuga aguccaggg 19

<210> SEQ ID NO 1165
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1165
aacagcggua cuugcagcu 19

<210> SEQ ID NO 1166
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1166
aacaguuccu uccuugugu 19

<210> SEQ ID NO 1167
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1167
agcccucauc cucaguugc 19

<210> SEQ ID NO 1168
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1168
uaacacaagg guuggcuac 19

<210> SEQ ID NO 1169
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1169
uuuacuucug uucacaaac 19

<210> SEQ ID NO 1170
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1170
uuggccuuga aagucaccc 19

<210> SEQ ID NO 1171
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1171
uucagccacg cgccgauaa 19

<210> SEQ ID NO 1172
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1172
uuuggcaaag aagaagugg 19

<210> SEQ ID NO 1173
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1173
ccuugaagua aaugguguu 19

<210> SEQ ID NO 1174
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1174
cugaacacga cucuccauc 19

<210> SEQ ID NO 1175
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1175
gcccuugaag uaaauggug 19

<210> SEQ ID NO 1176
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1176
cacaggcccu ugaaguaaa 19

<210> SEQ ID NO 1177
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1177
uucagaggaa cuucucuua 19

<210> SEQ ID NO 1178

<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1178
auucauggga augucccgc 19

<210> SEQ ID NO 1179
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1179
cagaggacag gguggggca 19

<210> SEQ ID NO 1180
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1180
aaguaaaugg uguuaacca 19

<210> SEQ ID NO 1181
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1181
ugugaucuga ggcaauccg 19

<210> SEQ ID NO 1182
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1182
caacucacug auguccugg 19

<210> SEQ ID NO 1183
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1183
caauccgccu gaaaacugg 19

<210> SEQ ID NO 1184
<211> LENGTH: 19

<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1184
uguuuucuca gauauggug 19

<210> SEQ ID NO 1185
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1185
uuuguauuua uuuuuacuu 19

<210> SEQ ID NO 1186
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1186
aacucaagca ccugggugc 19

<210> SEQ ID NO 1187
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1187
cuugaaguaa augguguua 19

<210> SEQ ID NO 1188
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1188
augucaucac cuuugaagg 19

<210> SEQ ID NO 1189
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1189
aaagcgggaa uuggccuug 19

<210> SEQ ID NO 1190
<211> LENGTH: 19
<212> TYPE: RNA

-continued

<213> ORGANISM: Artificial Sequence
<220> FEATURE:
<223> OTHER INFORMATION: Description of Artificial Sequence: Synthetic
      oligonucleotide

<400> SEQUENCE: 1190
agcugcuccu ucaaacuga 19

<210> SEQ ID NO 1191
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1191
ugacagguca cgcaguccc 19

<210> SEQ ID NO 1192
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1192
caaaaaggcg auuggcuga 19

<210> SEQ ID NO 1193
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1193
ucauugaugg cuuccgagg 19

<210> SEQ ID NO 1194
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1194
ggaaaauguu aucauuguc 19

<210> SEQ ID NO 1195
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1195
aagaggugca aagaauaag 19

<210> SEQ ID NO 1196
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1196
uuagcgaacg gccagcaau 19

<210> SEQ ID NO 1197
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1197
uucacugccu ucuucauuu 19

<210> SEQ ID NO 1198
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1198
ggcuccauau accaacuca 19

<210> SEQ ID NO 1199
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1199
accuccauca guugcugga 19

<210> SEQ ID NO 1200
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1200
uuuuccagag guuacaguu 19

<210> SEQ ID NO 1201
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1201
uuggacaccc auuuguuga 19

<210> SEQ ID NO 1202
<211> LENGTH: 19
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 1202
gaauacaugg ccgcuaauc 19

<210> SEQ ID NO 1203
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1203
ugaagggcaa cucaagcac 19

<210> SEQ ID NO 1204
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1204
gucaucucgg ccuucugca 19

<210> SEQ ID NO 1205
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1205
guucacaaac caaaaauag 19

<210> SEQ ID NO 1206
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1206
acuugcagcu gcuucacug 19

<210> SEQ ID NO 1207
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1207
cuucggucuu auuggacac 19

<210> SEQ ID NO 1208
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1208
aucaucuccu ccaauucau 19

<210> SEQ ID NO 1209
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1209
uuccugguac aucauagau 19

<210> SEQ ID NO 1210
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1210
cucaagaaau gccuuaugg 19

<210> SEQ ID NO 1211
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1211
aaugccuuau ggaaugcau 19

<210> SEQ ID NO 1212
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1212
augguguuaa ccagcacca 19

<210> SEQ ID NO 1213
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1213
uuuucagggc ugaacagau 19

<210> SEQ ID NO 1214
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1214
uggaccacca gcaucaucu 19

<210> SEQ ID NO 1215
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1215
cuggagcuug gcuccauau 19

<210> SEQ ID NO 1216
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1216
aaugacaucg gugauucgg 19

<210> SEQ ID NO 1217
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1217
ccgcucugga uugcucugc 19

<210> SEQ ID NO 1218
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1218
cccuugaagu aaauggugu 19

<210> SEQ ID NO 1219
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1219
gaacuugccu uccugguac 19

<210> SEQ ID NO 1220
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1220
cucuucucag gcuugggca 19

<210> SEQ ID NO 1221
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1221
aguucaguuu ggcaaagaa 19

<210> SEQ ID NO 1222
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1222
uccuucucua ccuuggcca 19

<210> SEQ ID NO 1223
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1223
uccagccacu cuugcagca 19

<210> SEQ ID NO 1224
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1224
gagcgguaaa ugcacaugg 19

<210> SEQ ID NO 1225
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1225
aucgacaagg cccaugucu 19

<210> SEQ ID NO 1226
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1226
aagggauuug ucuccaaaa 19

<210> SEQ ID NO 1227
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1227
cuguucugag cccucaucc 19

<210> SEQ ID NO 1228
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1228
uuggucauag caaaagccg 19

<210> SEQ ID NO 1229
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1229
aaguccaggg gcuggagcu 19

<210> SEQ ID NO 1230
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1230
aagaagugga ucugaucag 19

<210> SEQ ID NO 1231
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1231
ggcaugugga ccaccagca 19

<210> SEQ ID NO 1232
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1232
ucuuuccucu aaaucucgc 19

<210> SEQ ID NO 1233
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1233
cccagaagcc aaugagcag 19

<210> SEQ ID NO 1234
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1234
ugguaggucu cauugaagg 19

<210> SEQ ID NO 1235
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1235
ggcccuugaa guaaauggu 19

<210> SEQ ID NO 1236
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1236
caaaaauagg aagaggugc 19

<210> SEQ ID NO 1237
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1237
ccugggugcc uucagccac 19

<210> SEQ ID NO 1238
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1238
aagccguccu caaugcgga 19

<210> SEQ ID NO 1239
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1239
uuggcugugc agaugucca 19

<210> SEQ ID NO 1240
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1240
aauaccuggg aguuuggac 19

<210> SEQ ID NO 1241
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1241 ucuggggluga guuccuucu 19

<210> SEQ ID NO 1242
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1242
uucuucauuu accucaaga 19

<210> SEQ ID NO 1243
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1243
ugcagauguc cacagggcu 19

<210> SEQ ID NO 1244
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1244
uuuguugaug gccgcucug 19

<210> SEQ ID NO 1245
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1245 uauggguguca aacuuaaau 19

<210> SEQ ID NO 1246
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1246
cuuggccagg cucuucuca 19

<210> SEQ ID NO 1247
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1247
aagaugagga ccaugguga 19

<210> SEQ ID NO 1248
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1248
uuguagaaca guuccuucc 19

<210> SEQ ID NO 1249
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1249
cuucucuuau aaaaaccag 19

<210> SEQ ID NO 1250
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1250
ugucauuaca ggcacccag 19

<210> SEQ ID NO 1251
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1251
gcaaucacaa cagcgguac 19

<210> SEQ ID NO 1252
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1252
ucugccaggu gcugauaga 19

<210> SEQ ID NO 1253
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1253
cauucuugga aucugccag 19

<210> SEQ ID NO 1254
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1254
uuccgaggga augacaucg 19

<210> SEQ ID NO 1255
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1255
gucacgcagu cccagaagc 19

<210> SEQ ID NO 1256
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1256
acagggcucc cgugacagg 19

<210> SEQ ID NO 1257

-continued

<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1257
acaggcccuu gaaguaaau 19

<210> SEQ ID NO 1258
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1258
cugauagaaa gugguagca 19

<210> SEQ ID NO 1259
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1259
auuggccuug gacaguucc 19

<210> SEQ ID NO 1260
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1260
acuaacuugg aggauuugu 19

<210> SEQ ID NO 1261
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1261
ucuccgggga gcgguaaau 19

<210> SEQ ID NO 1262
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1262
cguggagaua cucaggggu 19

<210> SEQ ID NO 1263
<211> LENGTH: 19

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1263
ugggcaagug gagauagug 19

<210> SEQ ID NO 1264
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1264
auggaaguag uuuguauuu 19

<210> SEQ ID NO 1265
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1265
aguaaauggu guuaaccag 19

<210> SEQ ID NO 1266
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1266
ucaggcuugg gcaagauga 19

<210> SEQ ID NO 1267
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1267
gagauagugu gaucugagg 19

<210> SEQ ID NO 1268
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1268
cagagguucc agaggacag 19

<210> SEQ ID NO 1269
<211> LENGTH: 19
<212> TYPE: RNA

<213> ORGANISM: Artificial Sequence
<220> FEATURE:
<223> OTHER INFORMATION: Description of Artificial Sequence: Synthetic oligonucleotide

<400> SEQUENCE: 1269
ccgcuaaucu uccacaggg 19

<210> SEQ ID NO 1270
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1270
uagcaaaagc cguggagau 19

<210> SEQ ID NO 1271
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1271
cuccaauuca uccagccac 19

<210> SEQ ID NO 1272
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1272
auuggcugau acuaacuug 19

<210> SEQ ID NO 1273
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1273
accaugguga ugucaucac 19

<210> SEQ ID NO 1274
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1274
aucauuguca uucuuggaa 19

<210> SEQ ID NO 1275
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1275
aacuuaaaua ccuccauca 19

<210> SEQ ID NO 1276
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1276
uccuaucaca uuggaauac 19

<210> SEQ ID NO 1277
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1277
augucccgcg gcuuggcug 19

<210> SEQ ID NO 1278
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1278
aaugcggaag cggggcaug 19

<210> SEQ ID NO 1279
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1279
guuacaguuc cuaucacau 19

<210> SEQ ID NO 1280
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1280
uugaagguaa gggauuugu 19

<210> SEQ ID NO 1281
<211> LENGTH: 19
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 1281
aaggacaaaa gauaaaaccu 19

<210> SEQ ID NO 1282
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1282
uugguggccu ccgggaucu 19

<210> SEQ ID NO 1283
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1283
aggggugaca ggaaaaugu 19

<210> SEQ ID NO 1284
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1284
auaaaaacca ggaaaggcc 19

<210> SEQ ID NO 1285
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1285
aacauuuuac uuaacacaa 19

<210> SEQ ID NO 1286
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1286
uugcucugca uuuuccuug 19

<210> SEQ ID NO 1287
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1287
ugaucagaug uuuucucag 19

<210> SEQ ID NO 1288
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1288
ccacaggccc uugaaguaa 19

<210> SEQ ID NO 1289
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1289
aaagucaccc uguuggggu 19

<210> SEQ ID NO 1290
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1290
cuucugcaac aauaccugg 19

<210> SEQ ID NO 1291
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1291
aacuuugacu uccacaggc 19

<210> SEQ ID NO 1292
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1292
aaaucucgca gagguucca 19

<210> SEQ ID NO 1293
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1293
uccuuguguu cucagggcu 19

<210> SEQ ID NO 1294
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1294
augcaucuga gacauagag 19

<210> SEQ ID NO 1295
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1295
ugauucggcc uucggucuu 19

<210> SEQ ID NO 1296
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1296
aaagaauaag aacauuuua 19

<210> SEQ ID NO 1297
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1297
aaaccuuccu uuuuccaga 19

<210> SEQ ID NO 1298
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1298
aaggccuguu ggccuugaa 19

<210> SEQ ID NO 1299
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1299
agggcugaac uuugacuuc 19

<210> SEQ ID NO 1300
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1300
acagugagcu cauugaugg 19

<210> SEQ ID NO 1301
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1301
aagauaauag uguucagag 19

<210> SEQ ID NO 1302
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1302
uaaauggugu uaaccagca 19

<210> SEQ ID NO 1303
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1303
aaaacugguu cuuuccucu 19

<210> SEQ ID NO 1304
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1304
ucuuccacag ggcugggca 19

<210> SEQ ID NO 1305
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:

Synthetic oligonucleotide

<400> SEQUENCE: 1305
ggagaagaag gcaacugagt t 21

<210> SEQ ID NO 1306
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1306
ugaccaagcu gggugccugt t 21

<210> SEQ ID NO 1307
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1307
gguuaacacc auuuacuuct t 21

<210> SEQ ID NO 1308
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1308
gcugguuaac accauuuact t 21

<210> SEQ ID NO 1309
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1309
uaaugacacc cuccagcaat t 21

<210> SEQ ID NO 1310
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:

<223> OTHER INFORMATION: Description of Combined DNA/RNA Molecule: Synthetic oligonucleotide

<400> SEQUENCE: 1310
cguguucagc aucuaugaut t 21

<210> SEQ ID NO 1311
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1311
uugaggacgg cuucaguuut t 21

<210> SEQ ID NO 1312
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1312
cggcgugucu gggaacugut t 21

<210> SEQ ID NO 1313
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1313
uuaacaccau uuacuucaat t 21

<210> SEQ ID NO 1314
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1314
cccugaaaag uccaaacuct t 21

<210> SEQ ID NO 1315
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:
Synthetic oligonucleotide

<400> SEQUENCE: 1315
cgagaugacc ucuaugucut t 21

<210> SEQ ID NO 1316
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1316
ucuacaaggc ugauggagat t 21

<210> SEQ ID NO 1317
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1317
agcucacugu ucuggugcut t 21

<210> SEQ ID NO 1318
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1318
aggagcagcu gcaagacaut t 21

<210> SEQ ID NO 1319
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1319
gccaccaacc ggcgugucut t 21

<210> SEQ ID NO 1320
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1320
cagaacagaa gaucccggat t 21

<210> SEQ ID NO 1321
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1321
ccuugucgau cuguucagct t 21

<210> SEQ ID NO 1322
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1322
aggcaaguuc cguuaucggt t 21

<210> SEQ ID NO 1323
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1323
uuuuguccuu gcugcucaut t 21

<210> SEQ ID NO 1324
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1324
agaccuacca ggacaucagt t 21

<210> SEQ ID NO 1325
<211> LENGTH: 21
<212> TYPE: DNA
<213> ORGANISM: Artificial Sequence
<220> FEATURE:

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1325
aacugaacug ccgacucuat t 21

<210> SEQ ID NO 1326
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1326
cauuuacuuc aagggccugt t 21

<210> SEQ ID NO 1327
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1327
cccuggacuu caaggaaaat t 21

<210> SEQ ID NO 1328
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1328
agcugcaagu accgcuguut t 21

<210> SEQ ID NO 1329
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1329
acacaaggaa ggaacuguut t 21

<210> SEQ ID NO 1330
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1330
gcaacugagg augagggcut t 21

<210> SEQ ID NO 1331
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1331
guagccaacc cuuguguuat t 21

<210> SEQ ID NO 1332
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1332
guuugugaac agaaguaaat t 21

<210> SEQ ID NO 1333
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1333
gggugacuuu caaggccaat t 21

<210> SEQ ID NO 1334
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1334
uuaucggcgc guggcugaat t 21

<210> SEQ ID NO 1335
<211> LENGTH: 21
<212> TYPE: DNA

<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1335
ccacuucuuc uuugccaaat t 21

<210> SEQ ID NO 1336
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1336
aacaccauuu acuucaaggt t 21

<210> SEQ ID NO 1337
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1337
gauggagagu cguguucagt t 21

<210> SEQ ID NO 1338
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1338
caccauuuac uucaagggct t 21

<210> SEQ ID NO 1339
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1339
uuuacuucaa gggccugugt t 21

<210> SEQ ID NO 1340
<211> LENGTH: 21

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1340

uaagagaagu uccucugaat t                                              21


<210> SEQ ID NO 1341
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1341

gcgggacauu cccaugaaut t                                              21


<210> SEQ ID NO 1342
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1342

ugccccaccc uguccucugt t                                              21


<210> SEQ ID NO 1343
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1343

ugguuaacac cauuuacuut t                                              21


<210> SEQ ID NO 1344
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1344

cggauugccu cagaucacat t                                              21


<210> SEQ ID NO 1345
```

<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1345
ccaggacauc agugaguugt t 21

<210> SEQ ID NO 1346
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1346
ccaguuuuca ggcggauugt t 21

<210> SEQ ID NO 1347
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1347
caccauaucu gagaaaacat t 21

<210> SEQ ID NO 1348
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1348
aaguaaaaau aaauacaaat t 21

<210> SEQ ID NO 1349
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1349
gcacccaggu gcuugaguut t 21

-continued

<210> SEQ ID NO 1350
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1350
uaacaccauu uacuucaagt t 21

<210> SEQ ID NO 1351
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1351
ccuucaaagg ugaugacaut t 21

<210> SEQ ID NO 1352
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1352
caaggccaau ucccgcuuut t 21

<210> SEQ ID NO 1353
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1353
ucaguuugaa ggagcagcut t 21

<210> SEQ ID NO 1354
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1354
gggacugcgu gaccugucat t 21

<210> SEQ ID NO 1355
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1355
ucagccaauc gccuuuuugt t 21

<210> SEQ ID NO 1356
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1356
ccucggaagc caucaaugat t 21

<210> SEQ ID NO 1357
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1357
gacaaugaua acauuuucct t 21

<210> SEQ ID NO 1358
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1358
cuuauucuuu gcaccucuut t 21

<210> SEQ ID NO 1359
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1359
auugcuggcc guucgcuaat t 21

<210> SEQ ID NO 1360
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1360
aaaugaagaa ggcagugaat t 21

<210> SEQ ID NO 1361
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1361
ugaguuggua uauggagcct t 21

<210> SEQ ID NO 1362
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1362
uccagcaacu gauggaggut t 21

<210> SEQ ID NO 1363
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1363
aacuguaacc ucuggaaaat t 21

<210> SEQ ID NO 1364
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1364
ucaacaaaug ggugucccaat t 21

<210> SEQ ID NO 1365
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1365
gauuagcggc cauguauuct t 21

<210> SEQ ID NO 1366
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1366
gugcuugagu ugcccuucat t 21

<210> SEQ ID NO 1367
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1367
ugcagaaggc cgagaugact t 21

<210> SEQ ID NO 1368
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1368
cuauuuuugg uuugugaact t 21

<210> SEQ ID NO 1369
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1369
cagugaagca gcugcaagut t 21

<210> SEQ ID NO 1370
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1370
guguccaaua agaccgaagt t 21

<210> SEQ ID NO 1371
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1371
augaauugga ggagaugaut t 21

<210> SEQ ID NO 1372
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1372
aucuaugaug uaccaggaat t 21

<210> SEQ ID NO 1373
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1373
ccauaaggca uuucuugagt t 21

<210> SEQ ID NO 1374
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1374
augcauucca uaaggcauut t 21

<210> SEQ ID NO 1375
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1375
uggugcuggu uaacaccaut t 21

<210> SEQ ID NO 1376
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1376
aucuguucag cccugaaaat t 21

<210> SEQ ID NO 1377
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1377
agaugaugcu ggugguccat t 21

<210> SEQ ID NO 1378
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1378
auauggagcc aagcuccagt t 21

<210> SEQ ID NO 1379
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1379
ccgaaucacc gaugucauut t 21

<210> SEQ ID NO 1380
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1380
gcagagcaau ccagagcggt t 21

<210> SEQ ID NO 1381
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1381
acaccauuua cuucaagggt t 21

<210> SEQ ID NO 1382
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1382
guaccaggaa ggcaaguuct t 21

<210> SEQ ID NO 1383
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1383
ugcccaagcc ugagaagagt t 21

<210> SEQ ID NO 1384
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:

Synthetic oligonucleotide

<400> SEQUENCE: 1384
uucuuugcca aacugaacut t 21

<210> SEQ ID NO 1385
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1385
uggccaaggu agagaaggat t 21

<210> SEQ ID NO 1386
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1386
ugcugcaaga guggcuggat t 21

<210> SEQ ID NO 1387
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1387
ccaugugcau uuaccgcuct t 21

<210> SEQ ID NO 1388
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1388
agacaugggc cuugucgaut t 21

<210> SEQ ID NO 1389
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:

<223> OTHER INFORMATION: Description of Combined DNA/RNA Molecule: Synthetic oligonucleotide

<400> SEQUENCE: 1389
uuuuggagac aaaucccuut t 21

<210> SEQ ID NO 1390
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1390
ggaugagggc ucagaacagt t 21

<210> SEQ ID NO 1391
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1391
cggcuuuugc uaugaccaat t 21

<210> SEQ ID NO 1392
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1392
agcuccagcc ccuggacuut t 21

<210> SEQ ID NO 1393
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1393
cugaucagau ccacuucuut t 21

<210> SEQ ID NO 1394
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:
Synthetic oligonucleotide

<400> SEQUENCE: 1394
ugcugguggu ccacaugcct t 21

<210> SEQ ID NO 1395
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1395
gcgagauuua gaggaaagat t 21

<210> SEQ ID NO 1396
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1396
cugcucauug gcuucugggt t 21

<210> SEQ ID NO 1397
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1397
ccuucaauga gaccuaccat t 21

<210> SEQ ID NO 1398
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1398
accauuuacu ucaagggcct t 21

<210> SEQ ID NO 1399
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:
Synthetic oligonucleotide

<400> SEQUENCE: 1399
gcaccucuuc cuauuuuugt t 21

<210> SEQ ID NO 1400
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1400
guggcugaag gcacccaggt t 21

<210> SEQ ID NO 1401
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1401
uccgcauuga ggacggcuut t 21

<210> SEQ ID NO 1402
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1402
uggacaucug cacagccaat t 21

<210> SEQ ID NO 1403
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1403
guccaaacuc ccagguauut t 21

<210> SEQ ID NO 1404
<211> LENGTH: 21
<212> TYPE: DNA
<213> ORGANISM: Artificial Sequence
<220> FEATURE:

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1404
agaaggaacu caccccagat t 21

<210> SEQ ID NO 1405
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1405
ucuugaggua aaugaagaat t 21

<210> SEQ ID NO 1406
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1406
agcccugugg acaucugcat t 21

<210> SEQ ID NO 1407
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1407
cagagcggcc aucaacaaat t 21

<210> SEQ ID NO 1408
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1408
auuuaaguuu gacaccauat t 21

<210> SEQ ID NO 1409
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1409
ugagaagagc cuggccaagt t 21

<210> SEQ ID NO 1410
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1410
ucaccauggu ccucaucuut t 21

<210> SEQ ID NO 1411
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1411
ggaaggaacu guucuacaat t 21

<210> SEQ ID NO 1412
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1412
cugguuuuua uaagagaagt t 21

<210> SEQ ID NO 1413
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1413
cugggugccu guaaugacat t 21

<210> SEQ ID NO 1414
<211> LENGTH: 21
<212> TYPE: DNA

<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1414
guaccgcugu ugugauugct t 21

<210> SEQ ID NO 1415
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1415
ucuaucagca ccuggcagat t 21

<210> SEQ ID NO 1416
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1416
cuggcagauu ccaagaaugt t 21

<210> SEQ ID NO 1417
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1417
cgaugucauu cccucggaat t 21

<210> SEQ ID NO 1418
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1418
gcuucuggga cugcgugact t 21

<210> SEQ ID NO 1419
<211> LENGTH: 21

<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1419
ccugucacgg gagcccugut t 21

<210> SEQ ID NO 1420
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1420
auuuacuuca agggccugut t 21

<210> SEQ ID NO 1421
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1421
ugcuaccacu uucuaucagt t 21

<210> SEQ ID NO 1422
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1422
ggaacugucc aaggccaaut t 21

<210> SEQ ID NO 1423
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1423
acaaauccuc caaguuagut t 21

<210> SEQ ID NO 1424

<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1424
auuuaccgcu ccccggagat t 21

<210> SEQ ID NO 1425
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1425
accccugagu aucuccacgt t 21

<210> SEQ ID NO 1426
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1426
cacuaucucc acuugcccat t 21

<210> SEQ ID NO 1427
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1427
aaauacaaac uacuuccaut t 21

<210> SEQ ID NO 1428
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1428
cugguuaaca ccauuuacut t 21

<210> SEQ ID NO 1429
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1429
ucaucuugcc caagccugat t 21

<210> SEQ ID NO 1430
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1430
ccucagauca cacuaucuct t 21

<210> SEQ ID NO 1431
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1431
cuguccucug gaaccucugt t 21

<210> SEQ ID NO 1432
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1432
cccuguggaa gauuagcggt t 21

<210> SEQ ID NO 1433
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1433
aucuccacgg cuuuugcuat t 21

<210> SEQ ID NO 1434
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1434
guggcuggau gaauuggagt t 21

<210> SEQ ID NO 1435
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1435
caaguuagua ucagccaaut t 21

<210> SEQ ID NO 1436
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1436
gugaugacau caccauggut t 21

<210> SEQ ID NO 1437
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1437
uuccaagaau gacaaugaut t 21

<210> SEQ ID NO 1438
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1438
ugauggaggu auuuaaguut t 21

<210> SEQ ID NO 1439
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1439
guauuccaau gugauaggat t 21

<210> SEQ ID NO 1440
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1440
cagccaagcc gcgggacaut t 21

<210> SEQ ID NO 1441
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1441
caugccccgc uuccgcauut t 21

<210> SEQ ID NO 1442
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1442
augugauagg aacuguaact t 21

<210> SEQ ID NO 1443
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1443
acaaaucccu uaccuucaat t 21

<210> SEQ ID NO 1444
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1444
agguuuaucu uuuguccuut t 21

<210> SEQ ID NO 1445
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1445
agaucccgga ggccaccaat t 21

<210> SEQ ID NO 1446
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1446
acauuuuccu gucaccccut t 21

<210> SEQ ID NO 1447
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1447
ggccuuuccu gguuuuuaut t 21

<210> SEQ ID NO 1448
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1448
uuguguuaag uaaaauguut t 21

<210> SEQ ID NO 1449
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1449
caaggaaaau gcagagcaat t 21

<210> SEQ ID NO 1450
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1450
cugagaaaac aucugaucat t 21

<210> SEQ ID NO 1451
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1451
uuacuucaag ggccuguggt t 21

<210> SEQ ID NO 1452
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1452
accccaacag ggugacuuut t 21

<210> SEQ ID NO 1453
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1453
ccagguauug uugcagaagt t 21

<210> SEQ ID NO 1454
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1454
gccuguggaa gucaaaguut t 21

<210> SEQ ID NO 1455
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1455
uggaaccucu gcgagauuut t 21

<210> SEQ ID NO 1456
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1456
agcccugaga acacaaggat t 21

<210> SEQ ID NO 1457
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1457
cucuaugucu cagaugcaut t 21

<210> SEQ ID NO 1458
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1458
aagaccgaag gccgaaucat t 21

<210> SEQ ID NO 1459
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1459
uaaaauguuc uuauucuuut t 21

<210> SEQ ID NO 1460
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1460
ucuggaaaaa ggaagguuut t 21

<210> SEQ ID NO 1461
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1461
uucaaggcca acaggccuut t 21

<210> SEQ ID NO 1462
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1462
gaagucaaag uucagcccut t 21

<210> SEQ ID NO 1463
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:

Synthetic oligonucleotide

<400> SEQUENCE: 1463
ccaucaauga gcucacugut t 21

<210> SEQ ID NO 1464
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1464
cucugaacac uauuaucuut t 21

<210> SEQ ID NO 1465
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1465
ugcugguuaa caccauuuat t 21

<210> SEQ ID NO 1466
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1466
agaggaaaga accaguuuut t 21

<210> SEQ ID NO 1467
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1467
ugcccagccc uguggaagat t 21

<210> SEQ ID NO 1468
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:

<223> OTHER INFORMATION: Description of Combined DNA/RNA Molecule:
Synthetic oligonucleotide

<400> SEQUENCE: 1468
cucaguugcc uucuucucct t 21

<210> SEQ ID NO 1469
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1469
caggcaccca gcuuggucat t 21

<210> SEQ ID NO 1470
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1470
gaaguaaaug guguuaacct t 21

<210> SEQ ID NO 1471
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1471
guaaauggug uuaaccagct t 21

<210> SEQ ID NO 1472
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1472
uugcuggagg gugucauuat t 21

<210> SEQ ID NO 1473
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide <220> FEATURE:
<223> OTHER INFORMATION: Description of Combined DNA/RNA Molecule:
Synthetic oligonucleotide

<400> SEQUENCE: 1473
aucauagaug cugaacacgt t 21

<210> SEQ ID NO 1474
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1474
aaacugaagc cguccucaat t 21

<210> SEQ ID NO 1475
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1475
acaguuccca gacacgccgt t 21

<210> SEQ ID NO 1476
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1476
uugaaguaaa ugguguuaat t 21

<210> SEQ ID NO 1477
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1477
gaguuuggac uuuucagggt t 21

<210> SEQ ID NO 1478
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1478
agacauagag gucaucucgt t 21

<210> SEQ ID NO 1479
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1479
ucuccaucag ccuuguagat t 21

<210> SEQ ID NO 1480
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1480
agcaccagaa cagugagcut t 21

<210> SEQ ID NO 1481
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1481
augucuugca gcugcuccut t 21

<210> SEQ ID NO 1482
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1482
agacacgccg guugguggct t 21

<210> SEQ ID NO 1483
<211> LENGTH: 21
<212> TYPE: DNA
<213> ORGANISM: Artificial Sequence
<220> FEATURE:

<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1483
uccgggaucu ucuguucugt t 21

<210> SEQ ID NO 1484
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1484
gcugaacaga ucgacaaggt t 21

<210> SEQ ID NO 1485
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1485
ccgauaacgg aacuugccut t 21

<210> SEQ ID NO 1486
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1486
augagcagca aggacaaaat t 21

<210> SEQ ID NO 1487
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1487
cugauguccu gguaggucut t 21

<210> SEQ ID NO 1488
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1488
uagagucggc aguucaguut t 21

<210> SEQ ID NO 1489
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1489
caggcccuug aaguaaaugt t 21

<210> SEQ ID NO 1490
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1490
uuuuccuuga aguccagggt t 21

<210> SEQ ID NO 1491
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1491
aacagcggua cuugcagcut t 21

<210> SEQ ID NO 1492
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1492
aacaguuccu uccuugugut t 21

<210> SEQ ID NO 1493
<211> LENGTH: 21
<212> TYPE: DNA

<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1493
agcccucauc cucaguugct t 21

<210> SEQ ID NO 1494
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1494
uaacacaagg guuggcuact t 21

<210> SEQ ID NO 1495
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1495
uuuacuucug uucacaaact t 21

<210> SEQ ID NO 1496
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1496
uuggccuuga aagucaccct t 21

<210> SEQ ID NO 1497
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1497
uucagccacg cgccgauaat t 21

<210> SEQ ID NO 1498
<211> LENGTH: 21

<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1498
uuuggcaaag aagaaguggt t 21

<210> SEQ ID NO 1499
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1499
ccuugaagua aaugguguut t 21

<210> SEQ ID NO 1500
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1500
cugaacacga cucuccauct t 21

<210> SEQ ID NO 1501
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1501
gcccuugaag uaaauggugt t 21

<210> SEQ ID NO 1502
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1502
cacaggcccu ugaaguaaat t 21

<210> SEQ ID NO 1503

<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1503
uucagaggaa cuucucuuat t 21

<210> SEQ ID NO 1504
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1504
auucauggga augucccgct t 21

<210> SEQ ID NO 1505
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1505
cagaggacag gguggggcat t 21

<210> SEQ ID NO 1506
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1506
aaguaaaugg uguuaaccat t 21

<210> SEQ ID NO 1507
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1507
ugugaucuga ggcaauccgt t 21

<210> SEQ ID NO 1508
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1508
caacucacug auguccuggt t 21

<210> SEQ ID NO 1509
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1509
caauccgccu gaaaacuggt t 21

<210> SEQ ID NO 1510
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1510
uguuuucuca gauauggugt t 21

<210> SEQ ID NO 1511
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1511
uuuguauuua uuuuuacuut t 21

<210> SEQ ID NO 1512
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1512
aacucaagca ccugggugct t 21

<210> SEQ ID NO 1513
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1513
cuugaaguaa augguguuat t 21

<210> SEQ ID NO 1514
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1514
augucaucac cuuugaaggt t 21

<210> SEQ ID NO 1515
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1515
aaagcgggaa uuggccuugt t 21

<210> SEQ ID NO 1516
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1516
agcugcuccu ucaaacugat t 21

<210> SEQ ID NO 1517
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1517
ugacagguca cgcaguccct t 21

<210> SEQ ID NO 1518
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1518
caaaaaggcg auuggcugat t 21

<210> SEQ ID NO 1519
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1519
ucauugaugg cuuccgaggt t 21

<210> SEQ ID NO 1520
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1520
ggaaaauguu aucauuguct t 21

<210> SEQ ID NO 1521
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1521
aagaggugca aagaauaagt t 21

<210> SEQ ID NO 1522
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1522

-continued uuagcgaacg gccagcaaut t 21

<210> SEQ ID NO 1523
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1523
uucacugccu ucuucauuut t 21

<210> SEQ ID NO 1524
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1524
ggcuccauau accaacucat t 21

<210> SEQ ID NO 1525
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1525
accuccauca guugcuggat t 21

<210> SEQ ID NO 1526
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1526
uuuuccagag guuacaguut t 21

<210> SEQ ID NO 1527
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1527
uuggacaccc auuuguugat t 21

<210> SEQ ID NO 1528
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1528
gaauacaugg ccgcuaauct t 21

<210> SEQ ID NO 1529
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1529
ugaagggcaa cucaagcact t 21

<210> SEQ ID NO 1530
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1530
gucaucucgg ccuucugcat t 21

<210> SEQ ID NO 1531
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1531
guucacaaac caaaaauagt t 21

<210> SEQ ID NO 1532
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1532
acuugcagcu gcuucacugt t 21

<210> SEQ ID NO 1533
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1533
cuucggucuu auuggacact t 21

<210> SEQ ID NO 1534
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1534
aucaucuccu ccaauucaut t 21

<210> SEQ ID NO 1535
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1535
uuccugguac aucauagaut t 21

<210> SEQ ID NO 1536
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1536
cucaagaaau gccuuauggt t 21

<210> SEQ ID NO 1537
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1537
aaugccuuau ggaaugcaut t 21

<210> SEQ ID NO 1538
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1538
augguguuaa ccagcaccat t 21

<210> SEQ ID NO 1539
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1539
uuuucagggc ugaacagaut t 21

<210> SEQ ID NO 1540
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1540
uggaccacca gcaucaucut t 21

<210> SEQ ID NO 1541
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1541
cuggagcuug gcuccauaut t 21

<210> SEQ ID NO 1542
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:

Synthetic oligonucleotide

<400> SEQUENCE: 1542
aaugacaucg gugauucggt t 21

<210> SEQ ID NO 1543
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1543
ccgcucugga uugcucugct t 21

<210> SEQ ID NO 1544
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1544
cccuugaagu aaauggugut t 21

<210> SEQ ID NO 1545
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1545
gaacuugccu uccugguact t 21

<210> SEQ ID NO 1546
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1546
cucuucucag gcuugggcat t 21

<210> SEQ ID NO 1547
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:

-continued

<223> OTHER INFORMATION: Description of Combined DNA/RNA Molecule: Synthetic oligonucleotide

<400> SEQUENCE: 1547
aguucaguuu ggcaaagaat t 21

<210> SEQ ID NO 1548
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1548
uccuucucua ccuuggccat t 21

<210> SEQ ID NO 1549
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1549
uccagccacu cuugcagcat t 21

<210> SEQ ID NO 1550
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1550
gagcgguaaa ugcacauggt t 21

<210> SEQ ID NO 1551
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1551
aucgacaagg cccaugucut t 21

<210> SEQ ID NO 1552
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:
Synthetic oligonucleotide

<400> SEQUENCE: 1552
aagggauuug ucuccaaaat t 21

<210> SEQ ID NO 1553
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1553
cuguucugag cccucaucct t 21

<210> SEQ ID NO 1554
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1554
uuggucauag caaaagccgt t 21

<210> SEQ ID NO 1555
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1555
aaguccaggg gcuggagcut t 21

<210> SEQ ID NO 1556
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1556
aagaagugga ucugaucagt t 21

<210> SEQ ID NO 1557
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1557
ggcaugugga ccaccagcat t 21

<210> SEQ ID NO 1558
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1558
ucuuuccucu aaaucucgct t 21

<210> SEQ ID NO 1559
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1559
cccagaagcc aaugagcagt t 21

<210> SEQ ID NO 1560
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1560
ugguaggucu cauugaaggt t 21

<210> SEQ ID NO 1561
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1561
ggcccuugaa guaaauggut t 21

<210> SEQ ID NO 1562
<211> LENGTH: 21
<212> TYPE: DNA
<213> ORGANISM: Artificial Sequence
<220> FEATURE:

<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1562
caaaaauagg aagaggugct t 21

<210> SEQ ID NO 1563
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1563
ccugggugcc uucagccact t 21

<210> SEQ ID NO 1564
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1564
aagccguccu caaugcggat t 21

<210> SEQ ID NO 1565
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1565
uuggcugugc agauguccat t 21

<210> SEQ ID NO 1566
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1566
aauaccuggg aguuuggact t 21

<210> SEQ ID NO 1567
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1567
ucugggguga guuccuucut t 21

<210> SEQ ID NO 1568
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1568
uucuucauuu accucaagat t 21

<210> SEQ ID NO 1569
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1569
ugcagauguc cacagggcut t 21

<210> SEQ ID NO 1570
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1570
uuuguugaug gccgcucugt t 21

<210> SEQ ID NO 1571
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1571
uaugguguca aacuuaaaut t 21

<210> SEQ ID NO 1572
<211> LENGTH: 21
<212> TYPE: DNA

<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1572
cuuggccagg cucuucucat t 21

<210> SEQ ID NO 1573
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1573
aagaugagga ccauggugat t 21

<210> SEQ ID NO 1574
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1574
uuguagaaca guuccuucct t 21

<210> SEQ ID NO 1575
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1575
cuucucuuau aaaaaccagt t 21

<210> SEQ ID NO 1576
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1576
ugucauuaca ggcacccagt t 21

<210> SEQ ID NO 1577
<211> LENGTH: 21

<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1577
gcaaucacaa cagcgguact t 21

<210> SEQ ID NO 1578
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1578
ucugccaggu gcugauagat t 21

<210> SEQ ID NO 1579
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1579
cauucuugga aucugccagt t 21

<210> SEQ ID NO 1580
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1580
uuccgaggga augacaucgt t 21

<210> SEQ ID NO 1581
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1581
gucacgcagu cccagaagct t 21

<210> SEQ ID NO 1582

<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1582
acagggcucc cgugacaggt t 21

<210> SEQ ID NO 1583
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1583
acaggcccuu gaaguaaaut t 21

<210> SEQ ID NO 1584
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1584
cugauagaaa gugguagcat t 21

<210> SEQ ID NO 1585
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1585
auuggccuug gacaguucct t 21

<210> SEQ ID NO 1586
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1586
acuaacuugg aggauuugut t 21

<210> SEQ ID NO 1587
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1587
ucuccgggga gcgguaaaut t 21

<210> SEQ ID NO 1588
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1588
cguggagaua cucaggggut t 21

<210> SEQ ID NO 1589
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1589
ugggcaagug gagauagugt t 21

<210> SEQ ID NO 1590
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1590
auggaaguag uuuguauuut t 21

<210> SEQ ID NO 1591
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1591
aguaaauggu guuaaccagt t 21

<210> SEQ ID NO 1592
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1592
ucaggcuugg gcaagaugat t 21

<210> SEQ ID NO 1593
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1593
gagauagugu gaucugaggt t 21

<210> SEQ ID NO 1594
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1594
cagagguucc agaggacagt t 21

<210> SEQ ID NO 1595
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1595
ccgcuaaucu uccacagggt t 21

<210> SEQ ID NO 1596
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1596
uagcaaaagc cguggagaut t 21

<210> SEQ ID NO 1597
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1597
cuccaauuca uccagccact t 21

<210> SEQ ID NO 1598
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1598
auuggcugau acuaacuugt t 21

<210> SEQ ID NO 1599
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1599
accaugguga ugucaucact t 21

<210> SEQ ID NO 1600
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1600
aucauuguca uucuuggaat t 21

<210> SEQ ID NO 1601
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1601
aacuuaaaua ccuccaucat t 21

<210> SEQ ID NO 1602
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1602
uccuaucaca uuggaauact t 21

<210> SEQ ID NO 1603
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1603
augucccgcg gcuuggcugt t 21

<210> SEQ ID NO 1604
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1604
aaugcggaag cggggcaugt t 21

<210> SEQ ID NO 1605
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1605
guuacaguuc cuaucacaut t 21

<210> SEQ ID NO 1606
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1606
uugaagguaa gggauuugut t 21

<210> SEQ ID NO 1607
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1607
aaggacaaaa gauaaaccut t 21

<210> SEQ ID NO 1608
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1608
uugguggccu ccgggaucut t 21

<210> SEQ ID NO 1609
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1609
aggggugaca ggaaaaugut t 21

<210> SEQ ID NO 1610
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1610
auaaaaacca ggaaaggcct t 21

<210> SEQ ID NO 1611
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1611
aacauuuuac uuaacacaat t 21

<210> SEQ ID NO 1612
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1612
uugcucugca uuuuccuugt t 21

<210> SEQ ID NO 1613
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1613
ugaucagaug uuuucucagt t 21

<210> SEQ ID NO 1614
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1614
ccacaggccc uugaaguaat t 21

<210> SEQ ID NO 1615
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1615
aaagucaccc uguuggggut t 21

<210> SEQ ID NO 1616
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1616
cuucugcaac aauaccuggt t 21

<210> SEQ ID NO 1617
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1617
aacuuugacu uccacaggct t 21

<210> SEQ ID NO 1618
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1618
aaaucucgca gagguuccat t 21

<210> SEQ ID NO 1619
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1619
uccuuguguu cucagggcut t 21

<210> SEQ ID NO 1620
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1620
augcaucuga gacauagagt t 21

<210> SEQ ID NO 1621
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:

Synthetic oligonucleotide

<400> SEQUENCE: 1621
ugauucggcc uucggucuut t 21

<210> SEQ ID NO 1622
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1622
aaagaauaag aacauuuuat t 21

<210> SEQ ID NO 1623
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1623
aaaccuuccu uuuuccagat t 21

<210> SEQ ID NO 1624
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1624
aaggccuguu ggccuugaat t 21

<210> SEQ ID NO 1625
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1625
agggcugaac uuugacuuct t 21

<210> SEQ ID NO 1626
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:

-continued

<223> OTHER INFORMATION: Description of Combined DNA/RNA Molecule: Synthetic oligonucleotide

<400> SEQUENCE: 1626
acagugagcu cauugauggt t 21

<210> SEQ ID NO 1627
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1627
aagauaauag uguucagagt t 21

<210> SEQ ID NO 1628
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1628
uaaauggugu uaaccagcat t 21

<210> SEQ ID NO 1629
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1629
aaaacugguu cuuuccucut t 21

<210> SEQ ID NO 1630
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1630
ucuuccacag ggcugggcat t 21